US012398177B2

(12) United States Patent
Andrabi et al.

(10) Patent No.: US 12,398,177 B2
(45) Date of Patent: Aug. 26, 2025

(54) SIV ENVELOPE TRIMER

(71) Applicant: The Scripps Research Institute, La Jolla, CA (US)

(72) Inventors: Raiees Andrabi, La Jolla, CA (US); Dennis Burton, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 788 days.

(21) Appl. No.: 17/231,415

(22) Filed: Apr. 15, 2021

(65) Prior Publication Data

US 2021/0324003 A1 Oct. 21, 2021

Related U.S. Application Data

(63) Continuation-in-part of application No. PCT/US2019/056867, filed on Oct. 18, 2019.

(60) Provisional application No. 62/747,650, filed on Oct. 18, 2018.

(51) Int. Cl.
| | |
|---|---|
| C07K 5/08 | (2006.01) |
| A61K 9/127 | (2006.01) |
| A61K 9/51 | (2006.01) |
| A61K 39/00 | (2006.01) |
| A61K 39/21 | (2006.01) |
| A61K 39/39 | (2006.01) |
| A61K 47/08 | (2006.01) |
| A61K 47/10 | (2017.01) |
| A61P 31/18 | (2006.01) |
| C12N 7/00 | (2006.01) |
| C12N 15/86 | (2006.01) |
| G01N 33/569 | (2006.01) |

(52) U.S. Cl.
CPC .............. *C07K 5/08* (2013.01); *A61K 9/127* (2013.01); *A61K 9/51* (2013.01); *A61K 39/21* (2013.01); *A61K 39/39* (2013.01); *A61K 47/08* (2013.01); *A61K 47/10* (2013.01); *A61P 31/18* (2018.01); *C12N 7/00* (2013.01); *C12N 15/86* (2013.01); *G01N 33/56988* (2013.01); *A61K 2039/545* (2013.01); *A61K 2039/55505* (2013.01); *A61K 2039/55555* (2013.01); *A61K 2039/55566* (2013.01); *C12N 2740/15022* (2013.01); *C12N 2740/15034* (2013.01); *C12N 2750/14143* (2013.01)

(58) Field of Classification Search
CPC ........... C07K 5/08; A61P 31/18; A61K 9/127; A61K 9/51; A61K 39/21; A61K 39/39; A61K 47/08; A61K 47/10; A61K 2039/545; A61K 2039/55505; A61K 2039/55555; A61K 2039/55566; C12N 7/00; C12N 15/86; C12N 2740/15022; C12N 2740/15034; C12N 2750/14143; G01N 33/56988

See application file for complete search history.

(56) References Cited

U.S. PATENT DOCUMENTS

| | | | | |
|---|---|---|---|---|
| 10,400,015 | B2 * | 9/2019 | Kwong | C07K 16/1063 |
| 11,555,196 | B2 * | 1/2023 | Meyers | C12N 15/8258 |
| 2004/0191260 | A1 | 9/2004 | Reiter et al. | |
| 2021/0309753 | A1 * | 10/2021 | Munoz-Olaya | C07K 16/18 |
| 2021/0363194 | A1 * | 11/2021 | Tokatlian | C12N 7/00 |
| 2024/0261388 | A1 * | 8/2024 | Weiner | A61P 31/18 |

OTHER PUBLICATIONS

Dondelinger, M., Filée, P., Sauvage, E., Quinting, B., Muyldermans, S., Galleni, M., and Vandevenne, M.S. (2018). Understanding the Significance and Implications of Antibody Numbering and Antigen-Binding Surface/Residue Definition. Frontiers in Immunology, 9(2278). (Year: 2018).*
Bowie, J. U., Reidhaar-Olson, J. F., Lim, W. A., & Sauer, R. T. (1990). Deciphering the Message in Protein Sequences: Tolerance to Amino Acid Substitutions. Science (American Association for the Advancement of Science), 247(4948), 1306-1310. (Year: 1990).*
Winkler, K., Kramer, A., Kuttner, G., Seifert, M., Scholz, C., Wessner, H., Schneider-Mergener, J., & Hohne, W. (2000). Changing the Antigen Binding Specificity by Single Point Mutations of an Anti-p24 (HIV-1) Antibody. The Journal of Immunology (1950), 165(8), 4505-4514. (Year: 2000).*
Chen, Z., Wang, J., Bao, L., Guo, L., Zhang, W., Xue, Y., Zhou, H., Xiao, Y., Wang, J., Wu, F., Deng, Y., Qin, C., & Jin, Q. (2015). Human monoclonal antibodies targeting the haemagglutinin glycoprotein can neutralize H7N9 influenza virus. Nature communications, 6, 6714. (Year: 2015).*
Sela-Culang, I., Kunik, V., & Ofran, Y. (2013). The Structural Basis of Antibody-Antigen Recognition. Frontiers in Immunology, 4, 302-302. (Year: 2013).*

(Continued)

*Primary Examiner* — Janet L Anders
*Assistant Examiner* — Carey Alexander Stuart
(74) *Attorney, Agent, or Firm* — Duane Morris LLP; Thomas J. Kowalski

(57) ABSTRACT

The present application relates to epitope-targeted SIV and HIV vaccines. The invention provides novel envelope glycoproteins which may be utilized as HIV-1 vaccine immunogens, antigens for crystallization, and for identification of broadly neutralizing antibodies. The invention encompasses preparation and purification of immunogenic compositions which are formulated into vaccines of the present invention.

18 Claims, 62 Drawing Sheets
(57 of 62 Drawing Sheet(s) Filed in Color)
Specification includes a Sequence Listing.

(56) References Cited

OTHER PUBLICATIONS

Tsuchiya, Y., & Mizuguchi, K. (2016). The diversity of H3 loops determines the antigen-binding tendencies of antibody CDR loops. Protein science : a publication of the Protein Society, 25(4), 815-825. (Year: 2016).*

Collis, A. V., Brouwer, A. P., & Martin, A. C. (2003). Analysis of the antigen combining site: correlations between length and sequence composition of the hypervariable loops and the nature of the antigen. Journal of molecular biology, 325(2), 337-354. (Year: 2003).*

Dondelinger, M., Filée, P., Sauvage, E., Quinting, B., Muyldermans, S., Galleni, M., & Vandevenne, M. S. (2018). Understanding the Significance and Implications of Antibody Numbering and Antigen-Binding Surface/Residue Definition. Frontiers in Immunology, 9, 2278-2278. (Year: 2018).*

Griffith, S. A., & McCoy, L. E. (2021). To bnAb or Not to bnAb: Defining Broadly Neutralising Antibodies Against HIV-1. Frontiers in immunology, 12, 708227. (Year: 2021).*

Andrabi, R. et al. (2019). The Chimpanzee SIV Envelope Trimer: Structure and Deployment as an HIV Vaccine Template. Cell Reports, 27(8), 2426-2441.e6. (Year: 2019).*

R. Andrabi, et al. Identification of Common Features in Prototype Broadly Neutralizing Antibodies to HIV Envelope V2 Apex to Facilitate Vaccine Design. Immunity (Nov. 17, 2015) vol. 43, No. 5, pp. 959-973.

P. Wang, Anti-HIV Passive Immunization in Animal Models, J. Hiv Retrovirus (Feb. 26, 2018) vol. 4, No. 1:4.

International Search Report and Written Opinion dated Apr. 14, 2020 issued in Int'l Application PCT/US2019/056867.

Brandon F. Keele, et al., Chimpanzee Reservoirs of Pandemic and Nonpandemic HIV-1, Science, Jul. 28, 2006) vol. 313 pp. 523-526.

Jason S. McLellan, et al., Structure of HIV-1 gp120 VI/V2 domain with broadly neutralizing antibody PG9, Nature (Dec. 15, 2011) vol. 480, pp. 336-343.

EMBL Accession No. DQ373066—Simian immunodeficiency virus isolate SIVcpzMT145, complete genome (Jun. 3, 2006).

Supplementary EP Search Report issued Jun. 2, 2022 in counterpart EP Application No. 19872424.7.

* cited by examiner

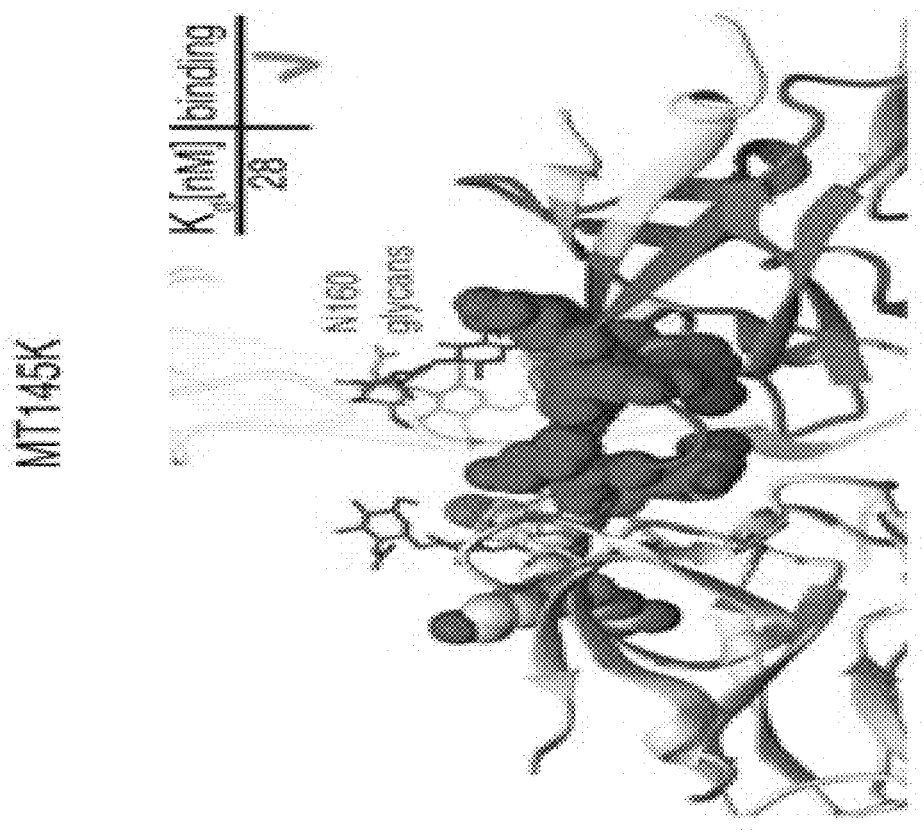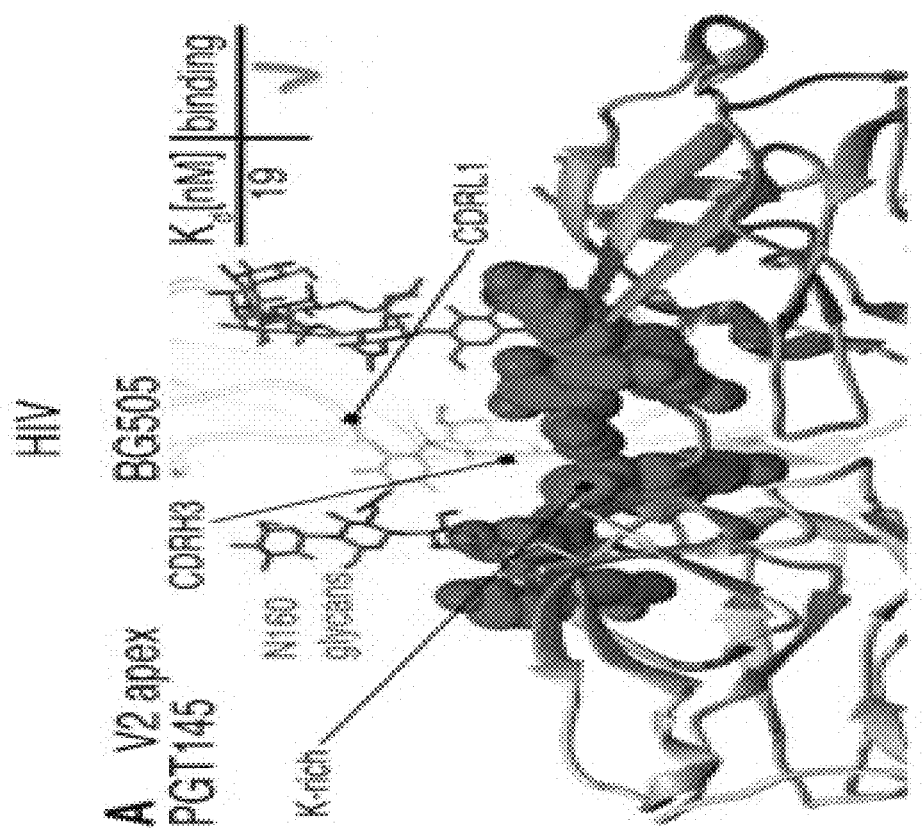
Fig.5A

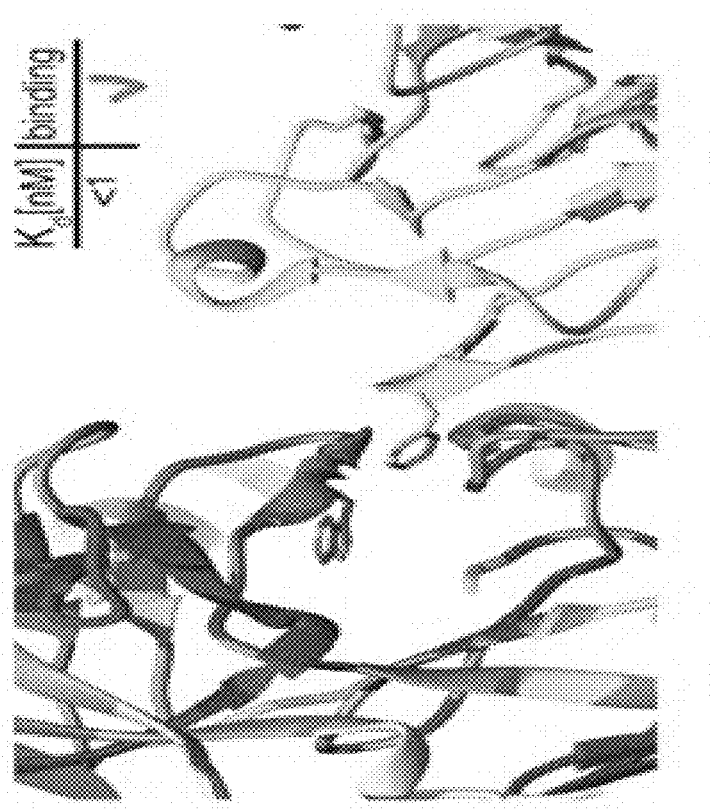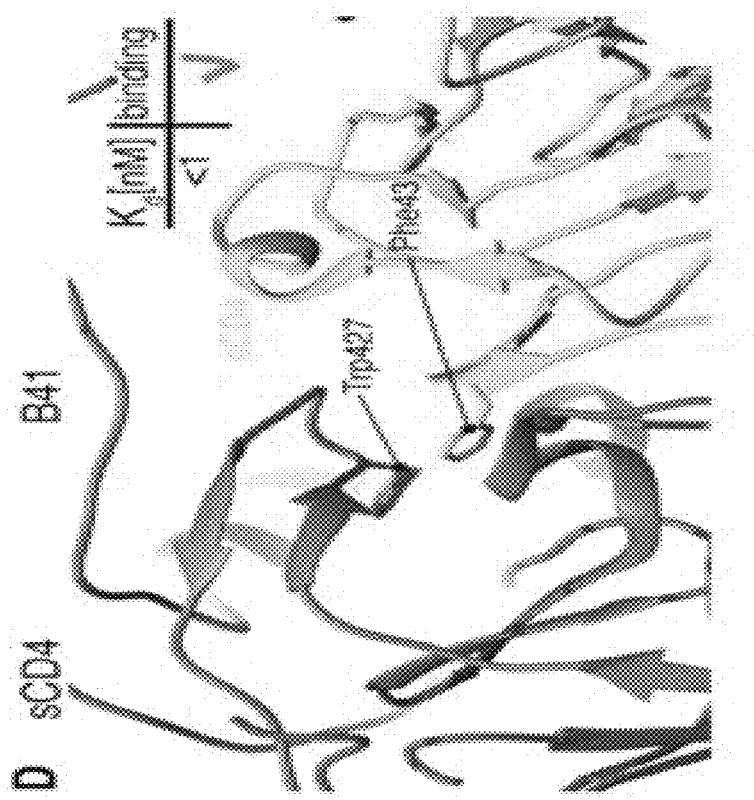
Fig. 5D

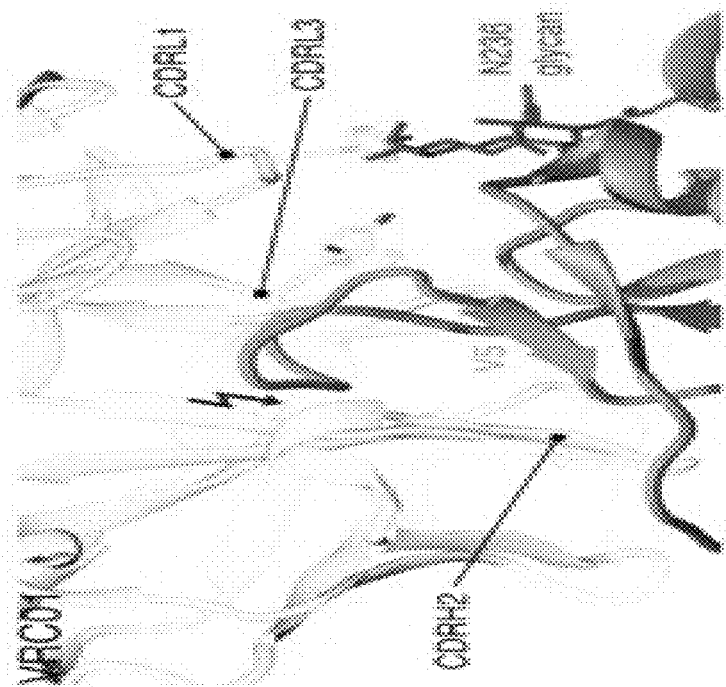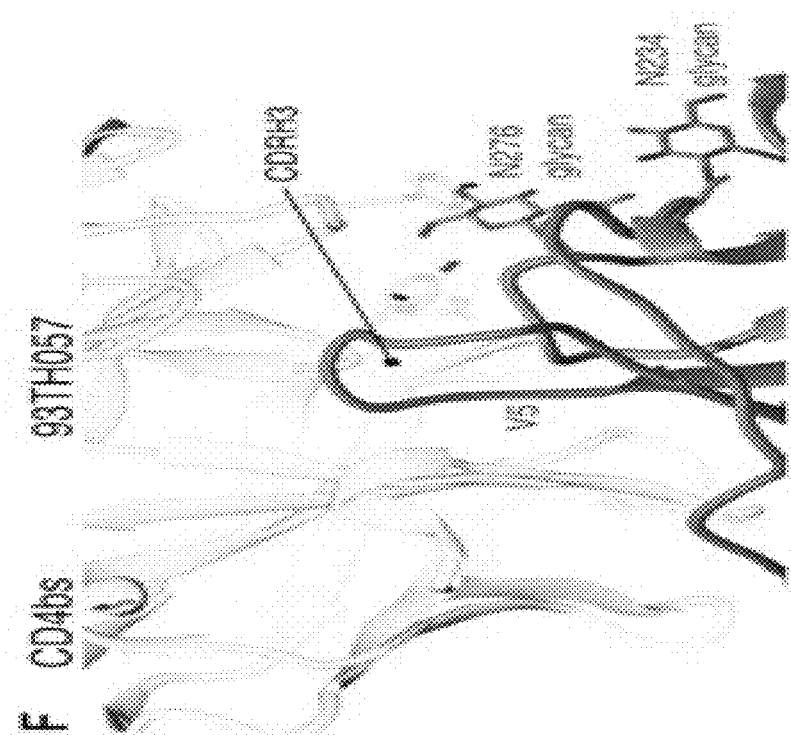
Fig. 5F

MT145-WT group

| Virus/mutant | Pre-bleed | | | | | Bleed #1 | | | | | Bleed #2 | | | | |
|---|---|---|---|---|---|---|---|---|---|---|---|---|---|---|---|
| | 13315 | 13316 | 13317 | 13318 | 13319 | 13315 | 13316 | 13317 | 13318 | 13319 | 13315 | 13316 | 13317 | 13318 | 13319 |
| MT145K | <100 | <100 | <100 | <100 | <100 | <100 | <100 | <100 | <100 | <100 | <100 | <100 | <100 | <100 | <100 |
| MT145K N160A | <100 | <100 | <100 | <100 | <100 | <100 | <100 | <100 | <100 | <100 | <100 | <100 | <100 | <100 | <100 |
| MT145-WT | <100 | 150 | <100 | <100 | <100 | <100 | <100 | <100 | <100 | <100 | <100 | <100 | <100 | <100 | <100 |
| Q23_17 | <100 | <100 | <100 | <100 | <100 | <100 | <100 | <100 | <100 | 100 | <100 | <100 | <100 | <100 | <100 |

MT145K group

| Virus/mutant | Pre-bleed | | | | | Bleed #1 | | | | | Bleed #2 | | | | |
|---|---|---|---|---|---|---|---|---|---|---|---|---|---|---|---|
| | 13200 | 13201 | 13202 | 13300 | 13301 | 13200 | 13201 | 13202 | 13300 | 13301 | 13200 | 13201 | 13202 | 13300 | 13301 |
| MT145K | <100 | <100 | <100 | <100 | <100 | 100 | <100 | <100 | <100 | <100 | 100 | 42 | <100 | 185 | 576 |
| MT145K N160A | <100 | <100 | <100 | <100 | <100 | <100 | <100 | <100 | <100 | <100 | <100 | <100 | <100 | <100 | <100 |
| MT145-WT | <100 | <100 | <100 | <100 | <100 | 383 | 145 | <100 | 369 | 427 | 197 | 635 | 260 | <100 | <100 |
| Q23_17 | <100 | <100 | <100 | <100 | <100 | <100 | <100 | <100 | <100 | <100 | <100 | <100 | <100 | 1897 | <100 |

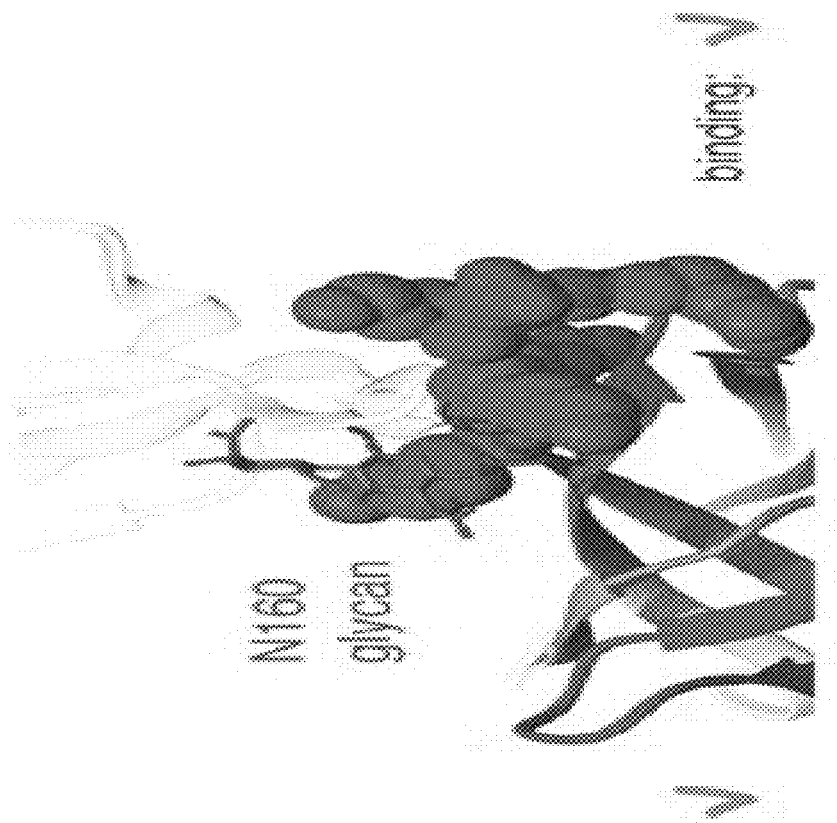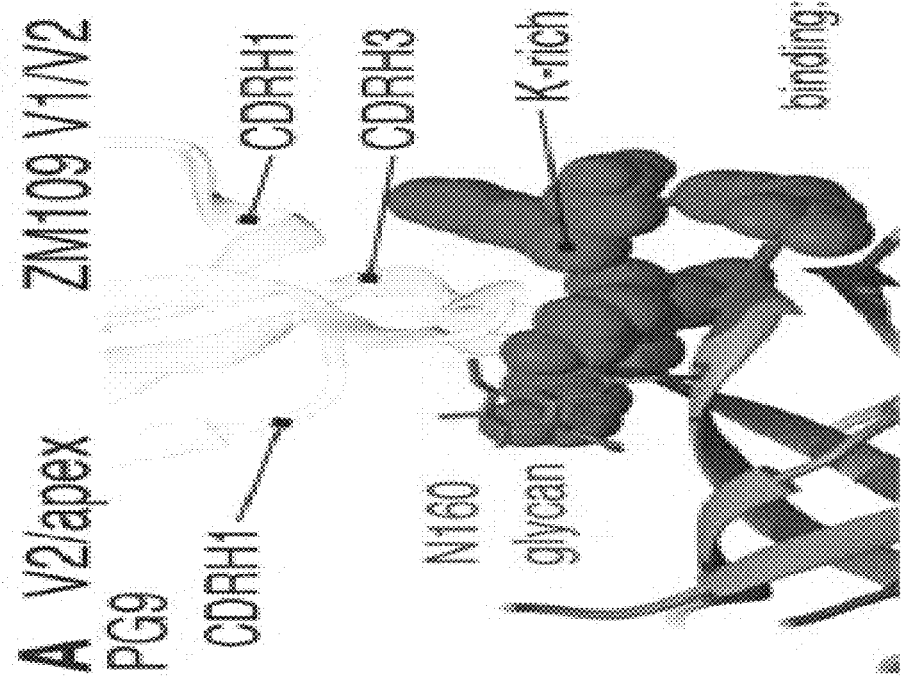
Fig. 17A

>MT145K_dV5_SOSIP.664
MDAMKRGLCCVLLLCGAVFVSPSQEIHARFRRGAR
ENWWTVTVYGVPVWREAKTTLFCASDAKSYSTEAHNIWATQACVPTDPTPQEVLLPNVTEEFNM
WENYMVDQMQEDIISLWEQSLKPCVKLTPLCVTLTCNNPTNTSCTNSTDDRLGDMRNCSFNVTT
ELRDKKRKVYSLFYVEDITAIGNNSTYRLINCNTTAITQACPKTSFEPIPIHYCAPAGFALLKC
NDIDYKGNETCKNVSTVHCTHGIKPVATTQLILNGSTADNQTVARIDPSENLAIIQLKDPVKIT
CRRPGNNTRGQIQIGPAMTFYNIENVVGDTRKAYCEINGTQWAKALNETKEVLRNILRKNISFM
VPSGGDPEVTNHHFNCGGEFFYCNTSEIINITKINKTENMTIIPCRIRQIVNSWMRVGKGIFAP
PIRGNITCTSNITGMLLEIHKDQNNTYVCLTGGNMKDIWRSELYKYKIVEIQPLGVAPTKCRRY
AVEKQHHRRRRALGLGALFLGFLGAAGSTMGAASVVLTVQARQLLTGIVQQQNNLLRAPEAQ
QHLLQLSVWGIKQLQARVLAVERYLRDQQLLGLWGCTGKTICCTAVRWNKTWGNISDYQVIWNN
YTWQQWDREVNNYTGLIYTLLEEANTQQEKNEKELLELD*

Fig. 19

B. ELISA binding

| MT145KdV5 | MT145KdV5 SOSIP | | | | | |
|---|---|---|---|---|---|---|
| | rh2686 | rh2688 | rh2689 | rh2690 | rh2691 | rh2694 |
| PB | <30 | <30 | <30 | <30 | <30 | <30 |
| 1wk | <30 | <30 | <30 | <30 | <30 | <30 |
| 2wk | 267 | 832 | 217 | 749 | 344 | 658 |
| 4wk | 722 | 2262 | 1650 | 2897 | 2167 | 962 |
| 8wk | 240 | 1793 | 858 | 2743 | 1356 | 733 |
| 9wk | 33926 | 41971 | 58730 | 43796 | 65915 | 49644 |
| 10wk | 76452 | 83972 | 102384 | 65255 | 110291 | 69398 |

EC50 serum IgG ELISA binding titers with MT145KdV5 SOSIP

Fig. 21B

SEQUENCE LISTING

```
<160> NUMBER OF SEQ ID NOS: 359

<210> SEQ ID NO 1
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa comprises any amino acid.

<400> SEQUENCE: 1

Xaa Lys Lys Lys
1

<210> SEQ ID NO 2
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa comprises any amino acid

<400> SEQUENCE: 2

Lys Xaa Lys Lys
1

<210> SEQ ID NO 3
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa comprises any amino acid.

<400> SEQUENCE: 3

Lys Lys Xaa Lys
1

<210> SEQ ID NO 4
<211> LENGTH: 4
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (4)..(4)
<223> OTHER INFORMATION: Xaa comprises any amino acid.

<400> SEQUENCE: 4

Lys Lys Lys Xaa
1

<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Lys Lys Lys Lys
1

<210> SEQ ID NO 6
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa comprises two or three amino acids, each of
      which can be any amino acid.
<220> FEATURE:
<221> NAME/KEY: misc_feature
<222> LOCATION: (4)..(4)
<223> OTHER INFORMATION: Xaa comprises five to seven amino acids, each
      of which can be any amino acid.
<220> FEATURE:
<221> NAME/KEY: misc_feature
<222> LOCATION: (5)..(5)
<223> OTHER INFORMATION: Xaa comprises four amino acids, each of which
      can be K or R.
<220> FEATURE:
<221> NAME/KEY: misc_feature
<222> LOCATION: (6)..(6)
<223> OTHER INFORMATION: Xaa comprises any amino acid.

<400> SEQUENCE: 6

Asn Xaa Asn Xaa Xaa Xaa
1               5

<210> SEQ ID NO 7
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa comprises S, T, N, or F.
<220> FEATURE:
<221> NAME/KEY: misc_feature
<222> LOCATION: (6)..(6)
<223> OTHER INFORMATION: Xaa comprises I, V, T, Q, or M.
<220> FEATURE:
<221> NAME/KEY: misc_feature
<222> LOCATION: (7)..(7)
<223> OTHER INFORMATION: Xaa comprises S or T.
<220> FEATURE:
<221> NAME/KEY: misc_feature
<222> LOCATION: (8)..(8)
<223> OTHER INFORMATION: Xaa comprises S or T.
<220> FEATURE:
<221> NAME/KEY: misc_feature
```

-continued

```
<222> LOCATION: (9)..(9)
<223> OTHER INFORMATION: Xaa comprises S, E, or G.
<220> FEATURE:
<221> NAME/KEY: misc_feature
<222> LOCATION: (10)..(10)
<223> OTHER INFORMATION: Xaa comprises I, L, V, or F.
<220> FEATURE:
<221> NAME/KEY: misc_feature
<222> LOCATION: (11)..(11)
<223> OTHER INFORMATION: Xaa comprises K or R.
<220> FEATURE:
<221> NAME/KEY: misc_feature
<222> LOCATION: (12)..(12)
<223> OTHER INFORMATION: Xaa comprises G or D.
<220> FEATURE:
<221> NAME/KEY: misc_feature
<222> LOCATION: (13)..(13)
<223> OTHER INFORMATION: Xaa comprises K, R, E, or Q.
<220> FEATURE:
<221> NAME/KEY: misc_feature
<222> LOCATION: (14)..(14)
<223> OTHER INFORMATION: Xaa comprises K, R, E, or Q.
<220> FEATURE:
<221> NAME/KEY: misc_feature
<222> LOCATION: (15)..(15)
<223> OTHER INFORMATION: Xaa comprises K, R, E, or Q.
<220> FEATURE:
<221> NAME/KEY: misc_feature
<222> LOCATION: (16)..(16)
<223> OTHER INFORMATION: Xaa comprises K, E, or Q.
<220> FEATURE:
<221> NAME/KEY: misc_feature
<222> LOCATION: (17)..(17)
<223> OTHER INFORMATION: Xaa comprises E, T, V, I, or M.
<220> FEATURE:
<221> NAME/KEY: misc_feature
<222> LOCATION: (18)..(18)
<223> OTHER INFORMATION: Xaa comprises Y or K.
<220> FEATURE:
<221> NAME/KEY: misc_feature
<222> LOCATION: (19)..(19)
<223> OTHER INFORMATION: Xaa comprises A or S.
<220> FEATURE:
<221> NAME/KEY: misc_feature
<222> LOCATION: (20)..(20)
<223> OTHER INFORMATION: Xaa comprises F, I, or L.

<400> SEQUENCE: 7

Asn Cys Xaa Phe Asn Xaa Xaa Xaa Xaa Xaa Xaa Xaa Xaa Xaa Xaa
1               5                   10                  15

Xaa Xaa Xaa Xaa
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa comprises S, T, N, or F.
<220> FEATURE:
<221> NAME/KEY: MISC_FEATURE
<222> LOCATION: (6)..(6)
<223> OTHER INFORMATION: Xaa comprises I, V, T, Q, or M.
<220> FEATURE:
<221> NAME/KEY: MISC_FEATURE
<222> LOCATION: (7)..(7)
<223> OTHER INFORMATION: Xaa comprises S or T.
<220> FEATURE:
<221> NAME/KEY: MISC_FEATURE
<222> LOCATION: (8)..(8)
<223> OTHER INFORMATION: Xaa comprises S or T.
<220> FEATURE:
```

-continued

```
<221> NAME/KEY: MISC_FEATURE
<222> LOCATION: (9)..(9)
<223> OTHER INFORMATION: Xaa comprises S, E, or G.
<220> FEATURE:
<221> NAME/KEY: MISC_FEATURE
<222> LOCATION: (10)..(10)
<223> OTHER INFORMATION: Xaa comprises I, L, V, or F.
<220> FEATURE:
<221> NAME/KEY: MISC_FEATURE
<222> LOCATION: (11)..(11)
<223> OTHER INFORMATION: Xaa comprises K or R.
<220> FEATURE:
<221> NAME/KEY: MISC_FEATURE
<222> LOCATION: (12)..(12)
<223> OTHER INFORMATION: Xaa comprises G or D.
<220> FEATURE:
<221> NAME/KEY: MISC_FEATURE
<222> LOCATION: (13)..(13)
<223> OTHER INFORMATION: Xaa comprises K, R, E, or Q.
<220> FEATURE:
<221> NAME/KEY: MISC_FEATURE
<222> LOCATION: (13)..(16)
<223> OTHER INFORMATION: At least three of four Xaa comprise basic amino
      acids.
<220> FEATURE:
<221> NAME/KEY: MISC_FEATURE
<222> LOCATION: (14)..(14)
<223> OTHER INFORMATION: Xaa comprises K, R, E, or Q.
<220> FEATURE:
<221> NAME/KEY: MISC_FEATURE
<222> LOCATION: (15)..(15)
<223> OTHER INFORMATION: Xaa comprises K, R, E, or Q.
<220> FEATURE:
<221> NAME/KEY: MISC_FEATURE
<222> LOCATION: (16)..(16)
<223> OTHER INFORMATION: Xaa comprises K, E, or Q.
<220> FEATURE:
<221> NAME/KEY: MISC_FEATURE
<222> LOCATION: (17)..(17)
<223> OTHER INFORMATION: Xaa comprises E, T, V, I, or M.
<220> FEATURE:
<221> NAME/KEY: MISC_FEATURE
<222> LOCATION: (18)..(18)
<223> OTHER INFORMATION: Xaa comprises Y or K.
<220> FEATURE:
<221> NAME/KEY: MISC_FEATURE
<222> LOCATION: (19)..(19)
<223> OTHER INFORMATION: Xaa comprises A or S.
<220> FEATURE:
<221> NAME/KEY: MISC_FEATURE
<222> LOCATION: (20)..(20)
<223> OTHER INFORMATION: Xaa comprises F, I, or L.

<400> SEQUENCE: 8

Asn Cys Xaa Phe Asn Xaa Xaa Xaa Xaa Xaa Xaa Xaa Xaa Xaa Xaa
1               5                   10                  15

Xaa Xaa Xaa Xaa
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa comprises S, T, N, or F.
<220> FEATURE:
<221> NAME/KEY: MISC_FEATURE
<222> LOCATION: (6)..(6)
<223> OTHER INFORMATION: Xaa comprises I, V, T, Q, or M.
<220> FEATURE:
<221> NAME/KEY: MISC_FEATURE
<222> LOCATION: (7)..(7)
```

```
<223> OTHER INFORMATION: Xaa comprises S or T.
<220> FEATURE:
<221> NAME/KEY: MISC_FEATURE
<222> LOCATION: (8)..(8)
<223> OTHER INFORMATION: Xaa comprises S or T.
<220> FEATURE:
<221> NAME/KEY: MISC_FEATURE
<222> LOCATION: (9)..(9)
<223> OTHER INFORMATION: Xaa comprises S, E, or G.
<220> FEATURE:
<221> NAME/KEY: MISC_FEATURE
<222> LOCATION: (10)..(10)
<223> OTHER INFORMATION: Xaa comprises I, L, V, or F.
<220> FEATURE:
<221> NAME/KEY: MISC_FEATURE
<222> LOCATION: (11)..(11)
<223> OTHER INFORMATION: Xaa comprises K or R.
<220> FEATURE:
<221> NAME/KEY: MISC_FEATURE
<222> LOCATION: (12)..(12)
<223> OTHER INFORMATION: Xaa comprises G or D.
<220> FEATURE:
<221> NAME/KEY: MISC_FEATURE
<222> LOCATION: (13)..(13)
<223> OTHER INFORMATION: Xaa comprises K or R.
<220> FEATURE:
<221> NAME/KEY: MISC_FEATURE
<222> LOCATION: (14)..(14)
<223> OTHER INFORMATION: Xaa comprises K or R.
<220> FEATURE:
<221> NAME/KEY: MISC_FEATURE
<222> LOCATION: (15)..(15)
<223> OTHER INFORMATION: Xaa comprises K or R.
<220> FEATURE:
<221> NAME/KEY: MISC_FEATURE
<222> LOCATION: (16)..(16)
<223> OTHER INFORMATION: Xaa comprises K or R.
<220> FEATURE:
<221> NAME/KEY: MISC_FEATURE
<222> LOCATION: (17)..(17)
<223> OTHER INFORMATION: Xaa comprises E, T, V, I, or M.
<220> FEATURE:
<221> NAME/KEY: MISC_FEATURE
<222> LOCATION: (18)..(18)
<223> OTHER INFORMATION: Xaa comprises Y or K.
<220> FEATURE:
<221> NAME/KEY: MISC_FEATURE
<222> LOCATION: (19)..(19)
<223> OTHER INFORMATION: Xaa comprises A or S.
<220> FEATURE:
<221> NAME/KEY: MISC_FEATURE
<222> LOCATION: (20)..(20)
<223> OTHER INFORMATION: Xaa comprises F, I, or L.

<400> SEQUENCE: 9

Asn Cys Xaa Phe Asn Xaa Xaa Xaa Xaa Xaa Xaa Xaa Xaa Xaa Xaa
1               5                   10                  15

Xaa Xaa Xaa Xaa
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa comprises S, T, N, or F.
<220> FEATURE:
<221> NAME/KEY: MISC_FEATURE
<222> LOCATION: (6)..(6)
<223> OTHER INFORMATION: Xaa comprises I, V, T, Q, or M.
<220> FEATURE:
<221> NAME/KEY: MISC_FEATURE
```

```
<222> LOCATION: (7)..(7)
<223> OTHER INFORMATION: Xaa comprises S or T.
<220> FEATURE:
<221> NAME/KEY: MISC_FEATURE
<222> LOCATION: (8)..(8)
<223> OTHER INFORMATION: Xaa comprises S or T.
<220> FEATURE:
<221> NAME/KEY: MISC_FEATURE
<222> LOCATION: (9)..(9)
<223> OTHER INFORMATION: Xaa comprises S, E, or G.
<220> FEATURE:
<221> NAME/KEY: MISC_FEATURE
<222> LOCATION: (10)..(10)
<223> OTHER INFORMATION: Xaa comprises I, L, V, or F.
<220> FEATURE:
<221> NAME/KEY: MISC_FEATURE
<222> LOCATION: (11)..(11)
<223> OTHER INFORMATION: Xaa comprises K or R.
<220> FEATURE:
<221> NAME/KEY: MISC_FEATURE
<222> LOCATION: (12)..(12)
<223> OTHER INFORMATION: Xaa comprises G or D.
<220> FEATURE:
<221> NAME/KEY: MISC_FEATURE
<222> LOCATION: (17)..(17)
<223> OTHER INFORMATION: Xaa comprises E, T, V, I, or M.
<220> FEATURE:
<221> NAME/KEY: MISC_FEATURE
<222> LOCATION: (18)..(18)
<223> OTHER INFORMATION: Xaa comprises Y or K.
<220> FEATURE:
<221> NAME/KEY: MISC_FEATURE
<222> LOCATION: (19)..(19)
<223> OTHER INFORMATION: Xaa comprises A or S.
<220> FEATURE:
<221> NAME/KEY: MISC_FEATURE
<222> LOCATION: (20)..(20)
<223> OTHER INFORMATION: Xaa comprises F, I, or L.

<400> SEQUENCE: 10

Asn Cys Xaa Phe Asn Xaa Xaa Xaa Xaa Xaa Xaa Lys Lys Lys Lys
1               5                   10                  15

Xaa Xaa Xaa Xaa
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic

<400> SEQUENCE: 11

Asn Cys Ser Phe Asn Val Thr Thr Glu Leu Arg Asp Lys Lys Arg Gln
1               5                   10                  15

Val Tyr Ser Leu
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic

<400> SEQUENCE: 12

Asn Cys Ser Phe Asn Val Thr Thr Glu Leu Arg Asp Lys Lys Arg Lys
1               5                   10                  15

Val Tyr Ser Leu
            20
```

<210> SEQ ID NO 13
<211> LENGTH: 20
<212> TYPE: PRT
<213> ORGANISM: Artificial Sequence
<220> FEATURE:
<223> OTHER INFORMATION: Synthetic

<400> SEQUENCE: 13

Asn Cys Ser Phe Asn Val Thr Thr Glu Leu Arg Asp Lys Lys Lys
1               5                   10                  15

Glu Tyr Ser Phe
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic

<400> SEQUENCE: 14

Asn Cys Ser Phe Asn Ala Thr Thr Glu Leu Arg Asp Lys Lys Lys
1               5                   10                  15

Glu Tyr Ala Leu
            20

<210> SEQ ID NO 15
<211> LENGTH: 23
<212> TYPE: PRT
<213> ORGANISM: Artificial Sequence
<220> FEATURE:
<223> OTHER INFORMATION: Synthetic

<400> SEQUENCE: 15

Asn Cys Ser Phe Asn Val Thr Thr Glu Leu Arg Asp Lys Lys Arg Gln
1               5                   10                  15

Val Tyr Ser Leu Phe Phe Tyr
            20

<210> SEQ ID NO 16
<211> LENGTH: 22
<212> TYPE: PRT
<213> ORGANISM: Artificial Sequence
<220> FEATURE:
<223> OTHER INFORMATION: Synthetic

<400> SEQUENCE: 16

Asn Cys Ser Phe Asn Val Thr Thr Glu Leu Arg Asp Lys Lys Arg Gln
1               5                   10                  15

Val Tyr Ser Leu Phe Tyr
            20

<210> SEQ ID NO 17
<211> LENGTH: 23
<212> TYPE: PRT
<213> ORGANISM: Artificial Sequence
<220> FEATURE:
<223> OTHER INFORMATION: Synthetic

<400> SEQUENCE: 17

Asn Cys Ser Phe Asn Val Thr Thr Glu Leu Arg Asp Lys Lys Arg Lys
1               5                   10                  15

Val Tyr Ser Leu Phe Phe Tyr
            20

<210> SEQ ID NO 18
<211> LENGTH: 22
<212> TYPE: PRT
<213> ORGANISM: Artificial Sequence
<220> FEATURE:
<223> OTHER INFORMATION: Synthetic

<400> SEQUENCE: 18

Asn Cys Ser Phe Asn Val Thr Thr Glu Leu Arg Asp Lys Lys Arg Lys
1               5                   10                  15

Val Tyr Ser Leu Phe Tyr
            20

<210> SEQ ID NO 19
<211> LENGTH: 23
<212> TYPE: PRT
<213> ORGANISM: Artificial Sequence
<220> FEATURE:
<223> OTHER INFORMATION: Synthetic

<400> SEQUENCE: 19

Asn Cys Ser Phe Asn Val Thr Thr Glu Leu Arg Asp Lys Lys Lys Lys
1               5                   10                  15

Glu Tyr Ser Phe Phe Phe Tyr
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic

<400> SEQUENCE: 20

Asn Cys Ser Phe Asn Val Thr Thr Glu Leu Arg Asp Lys Lys Lys Lys
1               5                   10                  15

Glu Tyr Ser Phe Phe Tyr
            20

<210> SEQ ID NO 21
<211> LENGTH: 23
<212> TYPE: PRT
<213> ORGANISM: Artificial Sequence
<220> FEATURE:
<223> OTHER INFORMATION: Synthetic

<400> SEQUENCE: 21

Asn Cys Ser Phe Asn Ala Thr Thr Glu Leu Arg Asp Lys Lys Lys Lys
1               5                   10                  15

Glu Tyr Ala Leu Phe Phe Tyr
            20

<210> SEQ ID NO 22
<211> LENGTH: 22
<212> TYPE: PRT
<213> ORGANISM: Artificial Sequence
<220> FEATURE:
<223> OTHER INFORMATION: Synthetic

<400> SEQUENCE: 22

Asn Cys Ser Phe Asn Ala Thr Thr Glu Leu Arg Asp Lys Lys Lys Lys
1               5                   10                  15

Glu Tyr Ala Leu Phe Tyr

```
<210> SEQ ID NO 23
<211> LENGTH: 22
<212> TYPE: PRT
<213> ORGANISM: Simian immunodeficiency virus

<400> SEQUENCE: 23

Asn Cys Ser Phe Asn Ile Ser Thr Ser Ile Arg Gly Lys Val Gln Lys
1               5                   10                  15

Glu Tyr Ala Phe Phe Tyr
            20

<210> SEQ ID NO 24
<211> LENGTH: 856
<212> TYPE: PRT
<213> ORGANISM: Human immunodeficiency virus type 1

<400> SEQUENCE: 24

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
```

```
                290                 295                 300
Lys Arg Ile Arg Ile Gln Arg Gly Pro Gly Arg Ala Phe Val Thr Ile
305                 310                 315                 320
Gly Lys Ile Gly Asn Met Arg Gln Ala His Cys Asn Ile Ser Arg Ala
                325                 330                 335
Lys Trp Asn Asn Thr Leu Lys Gln Ile Ala Ser Lys Leu Arg Glu Gln
                340                 345                 350
Phe Gly Asn Asn Lys Thr Ile Ile Phe Lys Gln Ser Ser Gly Gly Asp
                355                 360                 365
Pro Glu Ile Val Thr His Ser Phe Asn Cys Gly Gly Glu Phe Phe Tyr
                370                 375                 380
Cys Asn Ser Thr Gln Leu Phe Asn Ser Thr Trp Phe Asn Ser Thr Trp
385                 390                 395                 400
Ser Thr Glu Gly Ser Asn Asn Thr Glu Gly Ser Asp Thr Ile Thr Leu
                405                 410                 415
Pro Cys Arg Ile Lys Gln Ile Ile Asn Met Trp Gln Lys Val Gly Lys
                420                 425                 430
Ala Met Tyr Ala Pro Pro Ile Ser Gly Gln Ile Arg Cys Ser Ser Asn
                435                 440                 445
Ile Thr Gly Leu Leu Leu Thr Arg Asp Gly Gly Asn Ser Asn Asn Glu
                450                 455                 460
Ser Glu Ile Phe Arg Pro Gly Gly Gly Asp Met Arg Asp Asn Trp Arg
465                 470                 475                 480
Ser Glu Leu Tyr Lys Tyr Lys Val Val Lys Ile Glu Pro Leu Gly Val
                485                 490                 495
Ala Pro Thr Lys Ala Lys Arg Arg Val Val Gln Arg Glu Lys Arg Ala
                500                 505                 510
Val Gly Ile Gly Ala Leu Phe Leu Gly Phe Leu Gly Ala Ala Gly Ser
                515                 520                 525
Thr Met Gly Ala Ala Ser Met Thr Leu Thr Val Gln Ala Arg Gln Leu
                530                 535                 540
Leu Ser Gly Ile Val Gln Gln Gln Asn Asn Leu Leu Arg Ala Ile Glu
545                 550                 555                 560
Ala Gln Gln His Leu Leu Gln Leu Thr Val Trp Gly Ile Lys Gln Leu
                565                 570                 575
Gln Ala Arg Ile Leu Ala Val Glu Arg Tyr Leu Lys Asp Gln Gln Leu
                580                 585                 590
Leu Gly Ile Trp Gly Cys Ser Gly Lys Leu Ile Cys Thr Thr Ala Val
                595                 600                 605
Pro Trp Asn Ala Ser Trp Ser Asn Lys Ser Leu Glu Gln Ile Trp Asn
                610                 615                 620
His Thr Thr Trp Met Glu Trp Asp Arg Glu Ile Asn Asn Tyr Thr Ser
625                 630                 635                 640
Leu Ile His Ser Leu Ile Glu Glu Ser Gln Asn Gln Gln Glu Lys Asn
                645                 650                 655
Glu Gln Glu Leu Leu Glu Leu Asp Lys Trp Ala Ser Leu Trp Asn Trp
                660                 665                 670
Phe Asn Ile Thr Asn Trp Leu Trp Tyr Ile Lys Leu Phe Ile Met Ile
                675                 680                 685
Val Gly Gly Leu Val Gly Leu Arg Ile Val Phe Ala Val Leu Ser Ile
                690                 695                 700
Val Asn Arg Val Arg Gln Gly Tyr Ser Pro Leu Ser Phe Gln Thr His
705                 710                 715                 720
```

```
Leu Pro Thr Pro Arg Gly Pro Asp Arg Pro Glu Gly Ile Glu Glu
            725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
            755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
            805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
            835                 840                 845

Gln Gly Leu Glu Arg Ile Leu Leu
    850                 855

<210> SEQ ID NO 25
<211> LENGTH: 678
<212> TYPE: PRT
<213> ORGANISM: Simian immunodeficiency virus

<400> SEQUENCE: 25

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ser Glu Leu Trp Val Thr Val Tyr Tyr Gly Val Pro Val
        35                  40                  45

Trp His Asp Ala Asp Pro Val Leu Phe Cys Ala Ser Asp Ala Lys Ala
    50                  55                  60

His Ser Thr Glu Ala His Asn Ile Trp Ala Thr Gln Ala Cys Val Pro
65                  70                  75                  80

Thr Asp Pro Ser Pro Gln Glu Val Phe Leu Pro Asn Val Ile Glu Ser
                85                  90                  95

Phe Asn Met Trp Lys Asn Asn Met Val Asp Gln Met His Glu Asp Ile
            100                 105                 110

Ile Ser Leu Trp Asp Gln Ser Leu Lys Pro Cys Val Lys Leu Thr Pro
        115                 120                 125

Leu Cys Val Thr Leu Gln Cys Ser Lys Ala Asn Phe Ser Gln Ala Lys
    130                 135                 140

Asn Leu Thr Asn Gln Thr Ser Ser Pro Pro Leu Glu Met Lys Asn Cys
145                 150                 155                 160

Ser Phe Asn Val Thr Thr Glu Leu Arg Asp Lys Lys Gln Val Tyr
                165                 170                 175

Ser Leu Phe Tyr Val Glu Asp Val Val Asn Leu Gly Asn Glu Asn Asn
            180                 185                 190

Thr Tyr Arg Ile Ile Asn Cys Asn Thr Thr Ala Ile Thr Gln Ala Cys
        195                 200                 205

Pro Lys Thr Ser Phe Glu Pro Ile Pro Ile His Tyr Cys Ala Pro Ala
    210                 215                 220

Gly Phe Ala Ile Leu Lys Cys Asn Asp Lys Asp Phe Ser Gly Lys Gly
```

-continued

```
            225                 230                 235                 240
Lys Cys Thr Asn Val Ser Thr His Cys Thr His Gly Ile Lys Pro
                245                 250                 255
Val Val Thr Thr Gln Leu Leu Ile Asn Gly Ser Leu Ala Glu Gly Asn
                260                 265                 270
Ile Thr Val Arg Val Glu Asn Lys Ser Lys Asn Thr Asp Val Trp Ile
                275                 280                 285
Val Gln Leu Val Glu Ala Val Ser Leu Asn Cys His Arg Pro Gly Asn
    290                 295                 300
Asn Thr Gly Arg Glu Val Gln Ile Gly Pro Gly Met Thr Phe Tyr Asn
305                 310                 315                 320
Ile Glu Asn Val Val Gly Asp Thr Arg Ser Ala Tyr Cys Lys Ile Asn
                325                 330                 335
Gly Thr Thr Trp Asn Arg Thr Val Glu Glu Val Lys Lys Ala Leu Ala
                340                 345                 350
Thr Ser Ser Asn Arg Thr Ala Ala Asn Ile Thr Leu Asn Arg Ala Ser
                355                 360                 365
Gly Gly Asp Pro Glu Val Thr His His Met Phe Asn Cys Gly Gly Glu
                370                 375                 380
Phe Phe Tyr Cys Asn Thr Ser Gln Ile Phe Thr Asp Asn Ile Thr Asn
385                 390                 395                 400
Gly Ile Ile Ile Leu Pro Cys Arg Ile Arg Gln Ile Val Ser Ser Trp
                405                 410                 415
Met Arg Val Gly Arg Gly Ile Tyr Ala Pro Pro Ile Arg Gly Asn Ile
                420                 425                 430
Thr Cys Asn Ser Asn Ile Thr Gly Leu Leu Leu Thr Ser Asp Thr Pro
                435                 440                 445
Val Thr Asn Asn Ser Gly Asn Leu Thr Phe Arg Pro Thr Gly Gly Asn
                450                 455                 460
Met Lys Asp Ile Trp Arg Ser Glu Leu Tyr Lys Tyr Lys Val Val Arg
465                 470                 475                 480
Ile Glu Pro Leu Ser Val Ala Pro Thr Lys Cys Arg Arg His Thr Val
                485                 490                 495
Ala Arg Gln Lys Asp Arg Arg Arg Arg Arg Ala Ala Phe Gly Leu
                500                 505                 510
Gly Ala Leu Phe Leu Gly Phe Leu Gly Ala Ala Gly Ser Thr Met Gly
                515                 520                 525
Ala Ala Ala Val Thr Leu Thr Val Gln Ala Arg Gln Leu Leu Ser Gly
                530                 535                 540
Ile Val Gln Gln Gln Asn Asn Leu Leu Lys Ala Pro Glu Ala Gln Gln
545                 550                 555                 560
His Leu Leu Gln Leu Ser Ile Trp Gly Val Lys Gln Leu Gln Ala Arg
                565                 570                 575
Leu Leu Ala Val Glu Arg Tyr Leu Gln Asp Gln Gln Ile Leu Gly Leu
                580                 585                 590
Trp Gly Cys Ser Gly Lys Ala Val Cys Cys Thr Thr Val Pro Trp Asn
                595                 600                 605
Asn Ser Trp Pro Gly Ser Asn Thr Asp Asp Ile Trp Gly Asn Leu
                610                 615                 620
Thr Trp Gln Gln Trp Asp Lys Leu Val Ser Asn Tyr Thr Gly Lys Ile
625                 630                 635                 640
Phe Gly Leu Leu Glu Glu Ala Gln Ser Gln Gln Glu Lys Asn Glu Arg
                645                 650                 655
```

Asp Leu Leu Glu Leu Asp Gly Ser Gly Ser Gly Gly Ser Gly His His
            660             665             670

His His His His His His
        675

<210> SEQ ID NO 26
<211> LENGTH: 669
<212> TYPE: PRT
<213> ORGANISM: Simian immunodeficiency virus

<400> SEQUENCE: 26

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ser Glu Asn Asn Leu Trp Val Thr Val Tyr Tyr Gly Val
        35                  40                  45

Pro Val Trp Lys Glu Ala Lys Thr Thr Leu Phe Cys Ala Ser Asp Ala
    50                  55                  60

Lys Ala Gln Ile Ala Glu Ala His Asn Ile Trp Ala Ser Gln Ala Cys
65                  70                  75                  80

Val Pro Thr Asp Pro Asn Pro Glu Glu Ile Thr Leu Glu Asn Val Thr
                85                  90                  95

Glu Glu Phe Asp Ala Trp Asn Asn Met Val Asp Gln Met Gln Glu
            100                 105                 110

Asp Leu Ile Ser Leu Trp Asp Gln Ser Leu Lys Pro Cys Val Lys Leu
            115                 120                 125

Thr Pro Leu Cys Val Thr Leu Asn Cys Ser Asn Thr Thr Thr Glu
    130                 135                 140

Ala Ser Gln Val Gln Tyr Asn Cys Ser Phe Asn Val Thr Thr Glu Leu
145                 150                 155                 160

Arg Asp Lys Lys Lys Gln Val Tyr Ser Leu Phe Tyr Arg Glu Asp Ile
                165                 170                 175

Thr Ser Leu Asp Ser Asn Lys Thr Val Lys Asn Gly Thr Tyr Arg Leu
            180                 185                 190

Ile Asn Cys Asn Thr Thr Ala Ile Thr Gln Ala Cys Pro Lys Thr Ser
        195                 200                 205

Phe Glu Pro Ile Pro Ile Tyr Tyr Cys Ala Pro Ala Gly Phe Ala Leu
    210                 215                 220

Leu Lys Cys Asn Asp Gln Asn Phe Lys Gly Lys Gly Thr Cys Arg Asn
225                 230                 235                 240

Val Ser Thr Val His Cys Thr His Gly Ile Lys Pro Val Val Ser Thr
                245                 250                 255

Gln Phe Leu Leu Asn Gly Ser Leu Ala Glu Gly Asn Lys Thr Val Val
            260                 265                 270

Arg Val Arg Ser Lys Ser Asn Thr Glu Thr Ile Ile Val Gln Leu Ala
        275                 280                 285

Thr Ala Ile Tyr Ile Asn Cys Thr Arg Leu Gly Asn Lys Thr Ile Glu
    290                 295                 300

Gly Ile Pro Ile Gly Pro Gly Gln Ile Phe Tyr Arg Thr Lys Thr Val
305                 310                 315                 320

Val Gly Asp Thr Arg Gly Ala Glu Cys Arg Ile Asn Gly Thr Ala Trp
                325                 330                 335

Asn Glu Thr Leu Arg Gln Val Lys Glu Ala Leu Asn Asn Thr Tyr Arg

```
                340             345             350
Asn Leu Asn Leu Ser Leu Thr Glu Ile Asn Phe Glu Gly Ala Ser Gly
            355             360             365
Gly Asp Leu Glu Val Thr Thr His Tyr Phe Asn Cys Gly Gly Glu Phe
370             375             380
Phe Tyr Cys Asn Thr Ser Asn Leu Phe Asn Gln Ser Thr Ile Asn Asn
385             390             395             400
Ile Thr His Ile Pro Cys Arg Ile Arg Gln Ile Val Asn Gln Trp Gln
                405             410             415
Gly Val Gly Lys Gly Ile Phe Ala Pro Pro Ile Arg Gly Thr Ile Gln
            420             425             430
Cys Asn Ser Thr Ile Thr Gly Leu Leu Leu Thr Arg Asp Gly Lys Asn
            435             440             445
Glu Thr Glu Thr Phe Arg Pro Thr Gly Gly Asp Met Arg Asn Asn Trp
        450             455             460
Arg Ser Glu Leu Tyr Lys Tyr Lys Val Val Lys Ile Glu Pro Leu Gly
465             470             475             480
Leu Ala Pro Thr Lys Cys Lys Arg Arg Thr Val Gln Arg Arg Arg Arg
                485             490             495
Arg Arg Ala Val Gly Leu Gly Val Met Phe Leu Gly Phe Met Gly Ala
                500             505             510
Ala Gly Ser Thr Met Gly Ala Ala Leu Thr Leu Thr Val Gln Ala
            515             520             525
Arg Asn Leu Leu Ser Gly Ile Val Gln Gln Gln Ser Asn Leu Leu Lys
            530             535             540
Ala Pro Glu Ala Gln Gln His Leu Leu Gln Leu Ser Val Trp Gly Ile
545             550             555             560
Lys Gln Leu Gln Ala Arg Val Leu Ala Val Glu Arg Tyr Leu Lys Asp
                565             570             575
Gln Gln Leu Leu Gly Leu Trp Gly Cys Ser Gly Lys Leu Ile Cys Cys
            580             585             590
Thr Asn Val Pro Trp Asn Asn Thr Trp Ser Lys Lys Leu Gly Thr Asn
            595             600             605
Leu Ser Phe Trp Asp Asn Met Thr Trp Met Gln Trp Glu Lys Glu Ile
        610             615             620
Asp Asn Tyr Thr Glu Thr Ile Tyr Glu Leu Leu Thr Arg Ser Gln Asn
625             630             635             640
Gln Gln Glu Val Asn Glu Gln Glu Leu Leu Ala Leu Asp Gly Ser Gly
                645             650             655
Ser Gly Gly Ser Gly His His His His His His
            660             665
```

<210> SEQ ID NO 27
<211> LENGTH: 665
<212> TYPE: PRT
<213> ORGANISM: Simian immunodeficiency virus

<400> SEQUENCE:

-continued

```
Trp His Asp Ala Glu Thr Val Leu Phe Cys Ala Ser Asp Ala Lys Ala
 50              55                  60

His Ser Thr Glu Ala His Asn Ile Trp Ala Thr Gln Ala Cys Val Pro
 65              70                  75                  80

Thr Asp Pro Asn Pro Gln Glu Val Leu Ile Pro Asn Val Thr Glu Arg
                 85                  90                  95

Phe Asp Met Trp Lys Asn Asn Met Val Asp Gln Met Gln Glu Asp Ile
            100                 105                 110

Ile Ser Leu Trp Glu Gln Ser Leu Lys Pro Cys Val Lys Leu Thr Pro
            115                 120                 125

Leu Cys Val Thr Leu Ser Cys Ser Ser Trp Arg Ser Val Asn Asn Ser
130                 135                 140

Val Asn Gln Thr Asn His Val Gln Met Gln Asn Cys Ser Phe Asn Val
145                 150                 155                 160

Thr Thr Glu Leu Arg Asp Lys Lys Lys Gln Val Tyr Ser Leu Phe Tyr
                165                 170                 175

Met Gly Asp Ile Ile Pro Leu Asp Thr Asn Ser Ser Gly Asn Asn
            180                 185                 190

Ser Gln Tyr Arg Leu Ile Asn Cys Asn Thr Thr Ala Val Thr Gln Ala
            195                 200                 205

Cys Pro Lys Ile Ser Phe Glu Pro Ile Pro Ile Tyr Tyr Cys Ala Pro
210                 215                 220

Pro Gly Phe Ala Ile Ile Lys Cys Asn Asp Gln Asp Phe Asn Gly Thr
225                 230                 235                 240

Gly Glu Cys Asn Asn Val Ser Thr Val Gln Cys Thr His Gly Ile Lys
                245                 250                 255

Pro Val Ile Ser Thr Gln Leu Ile Leu Asn Gly Ser Leu Ala Thr Ser
            260                 265                 270

Asn Ile Val Ile Arg Asn Asn Ser Lys Asp Thr Leu Leu Val Gln Leu
            275                 280                 285

Asn Glu Ser Ile Pro Ile Asn Cys Thr Arg Pro Gly Asn Lys Thr Arg
290                 295                 300

Gly Gln Val Gln Ile Gly Pro Gly Met Thr Phe Tyr Asn Ile Glu Asn
305                 310                 315                 320

Ile Ile Gly Asp Thr Arg Gln Ala Tyr Cys Glu Val Asn Arg Thr Trp
                325                 330                 335

Glu Gln Ile Trp Asn Thr Thr Lys Gln Ile Ile Asn Asn Arg Lys
            340                 345                 350

Asn Ile Thr Phe Ile Pro Asn Pro Gly Gly Asp Leu Glu Val Thr Asn
            355                 360                 365

Leu Met Ile Asn Cys Gly Gly Glu Phe Phe Tyr Cys Asn Thr Ser Gln
370                 375                 380

Leu Phe Thr Lys Gln Asn Gly Asn Thr Thr Gly Asn Ile Thr Leu Gln
385                 390                 395                 400

Cys Arg Ile Arg Gln Ile Val Asn Leu Trp Thr Arg Val Gly Lys Gly
                405                 410                 415

Ile Tyr Ala Pro Pro Ile Lys Gly Pro Ile Asn Cys Leu Ser Asn Ile
            420                 425                 430

Thr Gly Ile Ile Leu Asp Tyr Thr Lys Ser Gly Thr Glu Lys Tyr Thr
            435                 440                 445

Ile Tyr Pro Thr Gly Gly Asp Met Thr Asn Leu Trp Arg Gln Glu Leu
450                 455                 460

Tyr Lys Tyr Lys Val Val Ser Ile Glu Pro Ile Gly Val Ala Pro Gly
```

```
            465                 470                 475                 480
Lys Cys Lys Arg His Thr Val Thr Arg Arg Arg Arg Arg Ala Ala
                    485                 490                 495

Phe Gly Leu Gly Ala Leu Phe Leu Gly Phe Leu Gly Ala Ala Gly Ser
                500                 505                 510

Thr Met Gly Ala Ala Ser Ile Thr Leu Thr Val Gln Ala Arg Lys Leu
                515                 520                 525

Leu Ser Gly Ile Val Gln Gln Gln Asn Asn Leu Leu Arg Ala Pro Glu
                530                 535                 540

Ala Gln Gln His Leu Leu Gln Leu Ser Val Trp Gly Ile Lys Gln Leu
545                 550                 555                 560

Gln Ala Arg Val Leu Ala Ile Glu Arg Tyr Leu Arg Asp Gln Gln Ile
                565                 570                 575

Leu Gly Leu Trp Gly Cys Ser Gly Lys Ser Val Cys Cys Thr Asn Val
                580                 585                 590

Pro Trp Asn Thr Thr Trp Ser Asn Asn Ser Tyr Asp Thr Ile Trp
                595                 600                 605

Gly Asn Met Thr Trp Gln Asn Trp Asp Glu Gln Val Arg Asn Tyr Ser
                610                 615                 620

Gly Val Ile Phe Gly Leu Leu Glu Gln Ala Gln Glu Gln Ser Ile
625                 630                 635                 640

Asn Glu Lys Ser Leu Leu Glu Leu Asp Gly Ser Gly Ser Gly Gly Ser
                645                 650                 655

Gly His His His His His His His
                660                 665

<210> SEQ ID NO 28
<211> LENGTH: 675
<212> TYPE: PRT
<213> ORGANISM: Simian immunodeficiency virus

<400> SEQUENCE: 28

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ser Glu Trp Trp Val Thr Val Tyr Tyr Gly Val Pro Val
            35                  40                  45

Trp Arg Glu Ala Lys Thr Thr Leu Phe Cys Ala Ser Asp Ala Lys Ser
        50                  55                  60

Tyr Ser Thr Glu Ala His Asn Ile Trp Ala Thr Gln Ala Cys Val Pro
65                  70                  75                  80

Thr Asp Pro Thr Pro Gln Glu Val Leu Leu Pro Asn Val Thr Glu Glu
                85                  90                  95

Phe Asn Met Trp Glu Asn Tyr Met Val Asp Gln Met Gln Glu Asp Ile
                100                 105                 110

Ile Ser Leu Trp Glu Gln Ser Leu Lys Pro Cys Val Lys Leu Thr Pro
            115                 120                 125

Leu Cys Val Thr Leu Thr Cys Asn Asn Pro Thr Asn Thr Ser Cys Thr
        130                 135                 140

Asn Ser Thr Asp Asp Arg Leu Gly Asp Arg Met Asn Cys Ser Phe Asn
145                 150                 155                 160

Val Thr Thr Glu Leu Arg Asp Lys Lys Lys Gln Val Tyr Ser Leu Phe
                165                 170                 175
```

-continued

```
Tyr Val Glu Asp Ile Thr Ala Ile Gly Asn Asn Ser Thr Tyr Arg Leu
                180                 185                 190

Ile Asn Cys Asn Thr Thr Ala Ile Thr Gln Ala Cys Pro Lys Thr Ser
            195                 200                 205

Phe Glu Pro Ile Pro Ile His Tyr Cys Ala Pro Ala Gly Phe Ala Leu
210                 215                 220

Leu Lys Cys Asn Asp Ile Asp Tyr Lys Gly Asn Glu Thr Cys Lys Asn
225                 230                 235                 240

Val Ser Thr Val His Cys Thr His Gly Ile Lys Pro Val Ala Thr Thr
                245                 250                 255

Gln Leu Ile Leu Asn Gly Ser Thr Ala Asp Asn Gln Thr Val Ala Arg
                260                 265                 270

Ile Asp Pro Ser Glu Asn Leu Ala Ile Ile Gln Leu Lys Asp Pro Val
                275                 280                 285

Lys Ile Thr Cys Arg Arg Pro Gly Asn Asn Thr Arg Gly Gln Ile Gln
                290                 295                 300

Ile Gly Pro Ala Met Thr Phe Tyr Asn Ile Glu Asn Val Val Gly Asp
305                 310                 315                 320

Thr Arg Lys Ala Tyr Cys Glu Ile Asn Gly Thr Gln Trp Ala Lys Ala
                325                 330                 335

Leu Asn Glu Thr Lys Glu Val Leu Arg Asn Ile Leu Arg Lys Asn Ile
                340                 345                 350

Ser Phe Met Val Pro Ser Gly Gly Asp Pro Glu Val Thr Asn His His
                355                 360                 365

Phe Asn Cys Gly Gly Glu Phe Phe Tyr Cys Asn Thr Ser Asp Ile Ile
                370                 375                 380

Asn Ile Thr Lys Ile Asn Lys Thr Glu Asn Met Thr Ile Ile Pro Cys
385                 390                 395                 400

Arg Ile Arg Gln Ile Val Asn Ser Trp Met Arg Val Gly Lys Gly Ile
                405                 410                 415

Phe Ala Pro Pro Ile Arg Gly Asn Ile Thr Cys Thr Ser Asn Ile Thr
                420                 425                 430

Gly Met Leu Leu Glu Ile His Lys Asn Arg Glu Asp Gln Gly Glu Asp
            435                 440                 445

Gln Asp Gln Asn Asn Thr Tyr Val Cys Leu Thr Gly Gly Asn Met Lys
450                 455                 460

Asp Ile Trp Arg Ser Glu Leu Tyr Lys Tyr Lys Ile Val Glu Ile Gln
465                 470                 475                 480

Pro Leu Gly Val Ala Pro Thr Lys Cys Arg Arg Tyr Ala Val Glu Lys
                485                 490                 495

Gln His His Arg Arg Arg Arg Arg Ala Leu Gly Leu Gly Ala Leu
                500                 505                 510

Phe Leu Gly Phe Leu Gly Ala Ala Gly Ser Thr Met Gly Ala Ala Ser
            515                 520                 525

Val Val Leu Thr Val Gln Ala Arg Gln Leu Leu Thr Gly Ile Val Gln
            530                 535                 540

Gln Gln Asn Asn Leu Leu Arg Ala Pro Glu Ala Gln Gln His Leu Leu
545                 550                 555                 560

Gln Leu Ser Val Trp Gly Ile Lys Gln Leu Gln Ala Arg Val Leu Ala
                565                 570                 575

Val Glu Arg Tyr Leu Arg Asp Gln Gln Leu Leu Gly Leu Trp Gly Cys
                580                 585                 590

Thr Gly Lys Thr Ile Cys Cys Thr Ala Val Arg Trp Asn Lys Thr Trp
```

```
                    595                 600                 605
Gly Asn Ile Ser Asp Tyr Gln Val Ile Trp Asn Asn Tyr Thr Trp Gln
            610                 615                 620

Gln Trp Asp Arg Glu Val Asn Asn Tyr Thr Gly Leu Ile Tyr Thr Leu
625                 630                 635                 640

Leu Glu Glu Ala Asn Thr Gln Gln Lys Asn Glu Lys Glu Leu Leu
                    645                 650                 655

Glu Leu Asp Gly Ser Gly Ser Gly Gly Ser His His His His
            660                 665                 670

His His His
        675

<210> SEQ ID NO 29
<211> LENGTH: 98
<212> TYPE: PRT
<213> ORGANISM: Homo sapiens

<400> SEQUENCE: 29

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 30
<211> LENGTH: 136
<212> TYPE: PRT
<213> ORGANISM: Homo sapiens

<400> SEQUENCE: 30

Gln Arg Leu Val Glu Ser Gly Gly Gly Val Val Gln Pro Gly Ser Ser
1               5                   10                  15

Leu Arg Leu Ser Cys Ala Ala Ser Gly Phe Asp Phe Ser Arg Gln Gly
            20                  25                  30

Met His Trp Val Arg Gln Ala Pro Gly Gln Gly Leu Glu Trp Val Ala
        35                  40                  45

Phe Ile Lys Tyr Asp Gly Ser Glu Lys Tyr His Ala Asp Ser Val Trp
    50                  55                  60

Gly Arg Leu Ser Ile Ser Arg Asp Asn Ser Lys Asp Thr Leu Tyr Leu
65                  70                  75                  80

Gln Met Asn Ser Leu Arg Val Glu Asp Thr Ala Thr Tyr Phe Cys Val
                85                  90                  95

Arg Glu Ala Gly Gly Pro Asp Tyr Arg Asn Gly Tyr Asn Tyr Tyr Asp
            100                 105                 110

Phe Tyr Asp Gly Tyr Tyr Asn Tyr His Tyr Met Asp Val Trp Gly Lys
        115                 120                 125

Gly Thr Thr Val Thr Val Ser Ser
    130                 135
```

```
<210> SEQ ID NO 31
<211> LENGTH: 137
<212> TYPE: PRT
<213> ORGANISM: unknown
<220> FEATURE:
<223> OTHER INFORMATION: synthetic sequence

<400> SEQUENCE: 31

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Gly Gly Pro Asp Tyr Arg Asn Gly Tyr Asn Tyr Tyr
            100                 105                 110

Asp Phe Tyr Asp Gly Tyr Tyr Asn Tyr His Tyr Met Asp Val Trp Gly
        115                 120                 125

Lys Gly Thr Thr Val Thr Val Ser Ser
    130                 135

<210> SEQ ID NO 32
<211> LENGTH: 137
<212> TYPE: PRT
<213> ORGANISM: unknown
<220> FEATURE:
<223> OTHER INFORMATION: synthetic sequence

<400> SEQUENCE: 32

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Gly Gly Pro Asp Tyr Arg Asn Gly Tyr Asn Tyr Tyr
            100                 105                 110

Asp Phe Trp Ser Gly Tyr Tyr Tyr Tyr Tyr Met Asp Val Trp Gly
        115                 120                 125

Lys Gly Thr Thr Val Thr Val Ser Ser
    130                 135

<210> SEQ ID NO 33
<211> LENGTH: 5
<212> TYPE: PRT
```

```
<213> ORGANISM: Homo sapiens

<400> SEQUENCE: 33

Ser Tyr Gly Met His
1               5

<210> SEQ ID NO 34
<211> LENGTH: 17
<212> TYPE: PRT
<213> ORGANISM: Homo sapiens

<400> SEQUENCE: 34

Val Ile Ser Tyr Asp Gly Ser Asn Lys Tyr Tyr Ala Asp Ser Val Lys
1               5                   10                  15

Gly

<210> SEQ ID NO 35
<211> LENGTH: 28
<212> TYPE: PRT
<213> ORGANISM: Homo sapiens

<400> SEQUENCE: 35

Glu Ala Gly Gly Pro Asp Tyr Arg Asn Gly Tyr Asn Tyr Tyr Asp Phe
1               5                   10                  15

Trp Ser Gly Tyr Tyr Tyr Tyr Tyr Met Asp Val
            20                  25

<210> SEQ ID NO 36
<211> LENGTH: 20
<212> TYPE: PRT
<213> ORGANISM: unknown
<220> FEATURE:
<223> OTHER INFORMATION: synthetic sequence

<400> SEQUENCE: 36

Tyr Tyr Tyr Tyr Tyr Tyr Met Asp Val Trp Gly Lys Gly Thr Thr Val
1               5                   10                  15

Thr Val Ser Ser
            20

<210> SEQ ID NO 37
<211> LENGTH: 10
<212> TYPE: PRT
<213> ORGANISM: unknown
<220> FEATURE:
<223> OTHER INFORMATION: synthetic sequence

<400> SEQUENCE: 37

Tyr Tyr Asp Phe Trp Ser Gly Tyr Tyr Thr
1               5                   10

<210> SEQ ID NO 38
<211> LENGTH: 99
<212> TYPE: PRT
<213> ORGANISM: homo sapiens

<400> SEQUENCE: 38

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45
```

```
Met Ile Tyr Glu Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu

<210> SEQ ID NO 39
<211> LENGTH: 110
<212> TYPE: PRT
<213> ORGANISM: unknown
<220> FEATURE:
<223> OTHER INFORMATION: synthetic sequence

<400> SEQUENCE: 39

Gln Ser Ala Leu Thr Gln Pro Ala Ser Val Ser Gly Ser Pro Gly Gln
 1               5                  10                  15

Ser Ile Thr Ile Ser Cys Asn Gly Thr Ser Asn Asp Val Gly Gly Tyr
                 20                  25                  30

Glu Ser Val Ser Trp Tyr Gln Gln His Pro Gly Lys Ala Pro Lys Val
             35                  40                  45

Val Ile Tyr Asp Val Ser Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Gly Asp Tyr Tyr Cys Lys Ser Leu Thr Ser Thr
                 85                  90                  95

Arg Arg Arg Val Phe Gly Thr Gly Thr Lys Leu Thr Val Leu
            100                 105                 110

<210> SEQ ID NO 40
<211> LENGTH: 110
<212> TYPE: PRT
<213> ORGANISM: unknown
<220> FEATURE:
<223> OTHER INFORMATION: synthetic sequence

<400> SEQUENCE: 40

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Glu Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu Val Phe Gly Thr Gly Thr Lys Leu Thr Val Leu
            100                 105                 110

<210> SEQ ID NO 41
<211> LENGTH: 110
<212> TYPE: PRT
<213> ORGANISM: unknown
```

<220> FEATURE:
<223> OTHER INFORMATION: synthetic sequence

<400> SEQUENCE: 41

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110

<210> SEQ ID NO 42
<211> LENGTH: 14
<212> TYPE: PRT
<213> ORGANISM: Homo sapiens

<400> SEQUENCE: 42

Thr Gly Thr Ser Ser Asp Val Gly Gly Tyr Asn Tyr Val Ser
1               5                   10

<210> SEQ ID NO 43
<211> LENGTH: 7
<212> TYPE: PRT
<213> ORGANISM: Homo sapiens

<400> SEQUENCE: 43

Glu Val Ser Asn Arg Pro Ser
1               5

<210> SEQ ID NO 44
<211> LENGTH: 10
<212> TYPE: PRT
<213> ORGANISM: Homo sapiens

<400> SEQUENCE: 44

Ser Ser Tyr Thr Ser Ser Ser Thr Trp Val
1               5                   10

<210> SEQ ID NO 45
<211> LENGTH: 12
<212> TYPE: PRT
<213> ORGANISM: unknown
<220> FEATURE:
<223> OTHER INFORMATION: synthetic sequence

<400> SEQUENCE: 45

Trp Val Phe Gly Gly Gly Thr Lys Leu Thr Val Leu
1               5                   10

<210> SEQ ID NO 46
<211> LENGTH: 98
<212> TYPE: PRT
<213> ORGANISM: homo sapiens

<400> SEQUENCE: 46

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
            85                  90                  95

Ala Arg

<210> SEQ ID NO 47
<211> LENGTH: 133
<212> TYPE: PRT
<213> ORGANISM: homo sapiens

<400> SEQUENCE: 47

Glu Val Gln Leu Val Glu Ser Gly Ala Asn Val Val Arg Pro Gly Gly
1               5                   10                  15

Ser Leu Arg Leu Ser Cys Lys Ala Ser Gly Phe Ile Phe Glu Asn Phe
            20                  25                  30

Gly Phe Ser Trp Val Arg Gln Ala Pro Gly Lys Gly Leu Gln Trp Val
        35                  40                  45

Ala Gly Leu Asn Trp Asn Gly Gly Asp Thr Arg Tyr Ala Asp Ser Val
50                  55                  60

Lys Gly Arg Phe Arg Met Ser Arg Asp Asn Ser Arg Asn Phe Val Tyr
65                  70                  75                  80

Leu Asp Met Asp Lys Val Gly Val Asp Thr Ala Phe Tyr Tyr Cys
            85                  90                  95

Ala Arg Gly Thr Asp Tyr Thr Ile Asp Asp Ala Gly Ile His Tyr Gln
            100                 105                 110

Gly Ser Gly Thr Phe Trp Tyr Phe Asp Leu Trp Arg Gly Thr Leu
        115                 120                 125

Val Ser Val Ser Ser
    130

<210> SEQ ID NO 48
<211> LENGTH: 133
<212> TYPE: PRT
<213> ORGANISM: unknown
<220> FEATURE:
<223> OTHER INFORMATION: synthetic sequence

<400> SEQUENCE: 48

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Leu Tyr His Cys
                85                  90                  95

Ala Arg Gly Thr Asp Tyr Thr Ile Asp Asp Ala Gly Ile His Tyr Gln
                100                 105                 110

Gly Ser Gly Thr Phe Trp Tyr Phe Asp Leu Trp Gly Arg Gly Thr Leu
                115                 120                 125

Val Ser Val Ser Ser
                130

<210> SEQ ID NO 49
<211> LENGTH: 133
<212> TYPE: PRT
<213> ORGANISM: unknown
<220> FEATURE:
<223> OTHER INFORMATION: synthetic sequence

<400> SEQUENCE: 49

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
                35                  40                  45

Ser Gly Ile Asn Trp Asn Gly Gly Ser Thr Gly Tyr Ala Asp Ser Val
                50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Thr Asp Tyr Thr Ile Asp Asp Ala Gly Ile His Tyr Tyr
                100                 105                 110

Gly Ser Gly Ser Tyr Trp Tyr Phe Asp Leu Trp Gly Arg Gly Thr Leu
                115                 120                 125

Val Thr Val Ser Ser
                130

<210> SEQ ID NO 50
<211> LENGTH: 5
<212> TYPE: PRT
<213> ORGANISM: Homo sapiens

<400> SEQUENCE: 50

Asp Tyr Gly Met Ser
1               5

<210> SEQ ID NO 51
<211> LENGTH: 17
<212> TYPE: PRT
<213> ORGANISM: Homo sapiens

<400> SEQUENCE: 51

Gly Ile Asn Trp Asn Gly Gly Ser Thr Gly Tyr Ala Asp Ser Val Lys
1               5                   10                  15

Gly

<210> SEQ ID NO 52
<211> LENGTH: 24
<212> TYPE: PRT
```

<213> ORGANISM: Homo sapiens

<400> SEQUENCE: 52

Gly Thr Asp Tyr Thr Ile Asp Asp Ala Gly Ile His Tyr Tyr Gly Ser
1               5                   10                  15

Gly Ser Tyr Trp Tyr Phe Asp Leu
            20

<210> SEQ ID NO 53
<211> LENGTH: 17
<212> TYPE: PRT
<213> ORGANISM: unknown
<220> FEATURE:
<223> OTHER INFORMATION: synthetic sequence

<400> SEQUENCE: 53

Tyr Trp Tyr Phe Asp Leu Trp Gly Arg Gly Thr Leu Val Thr Val Ser
1               5                   10                  15

Ser

<210> SEQ ID NO 54
<211> LENGTH: 10
<212> TYPE: PRT
<213> ORGANISM: unknown
<220> FEATURE:
<223> OTHER INFORMATION: synthetic sequence

<400> SEQUENCE: 54

Tyr Tyr Tyr Gly Ser Gly Ser Tyr Tyr Asn
1               5                   10

<210> SEQ ID NO 55
<211> LENGTH: 97
<212> TYPE: PRT
<213> ORGANISM: homo sapiens

<400> SEQUENCE: 55

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Cys Gln Gln Tyr Gly Ser Ser
                85                  90                  95

Pro

<210> SEQ ID NO 56
<211> LENGTH: 109
<212> TYPE: PRT
<213> ORGANISM: homo sapiens

<400> SEQUENCE: 56

Glu Ile Val Leu Ala Gln Ser Pro Gly Thr Leu Ser Leu Ser Pro Gly
1               5                   10                  15

Glu Arg Ala Thr Leu Ser Cys Arg Ala Ser His Asn Val His Pro Lys
            20                  25                  30

```
Tyr Phe Ala Trp Tyr Gln Gln Lys Pro Gly Gln Ser Pro Arg Leu Leu
            35                  40                  45

Ile Tyr Gly Gly Ser Thr Arg Ala Ala Gly Ile Pro Gly Lys Phe Ser
 50                  55                  60

Gly Ser Gly Ser Gly Thr Asp Phe Thr Leu Thr Ile Ser Arg Val Asp
 65                  70                  75                  80

Pro Glu Asp Phe Ala Val Tyr Tyr Cys Cys Gln Gln Tyr Gly Gly Ser
                 85                  90                  95

Pro Tyr Thr Phe Gly Gln Gly Thr Lys Val Glu Ile Lys
            100                 105
```

<210> SEQ ID NO 57
<211> LENGTH: 109
<212> TYPE: PRT
<213> ORGANISM: unknown
<220> FEATURE:
<223> OTHER INFORMATION: synthetic sequence

<400> SEQUENCE: 57

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Cys Gln Gln Tyr Gly Ser Ser
                 85                  90                  95

Pro Tyr Thr Phe Gly Gln Gly Thr Lys Val Glu Ile Lys
            100                 105
```

<210> SEQ ID NO 58
<211> LENGTH: 109
<212> TYPE: PRT
<213> ORGANISM: unknown
<220> FEATURE:
<223> OTHER INFORMATION: synthetic sequence

<400> SEQUENCE: 58

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Cys Gln Gln Tyr Gly Ser Ser
                 85                  90                  95

Pro Trp Thr Phe Gly Gln Gly Thr Lys Val Glu Ile Lys
            100                 105
```

```
<210> SEQ ID NO 59
<211> LENGTH: 12
<212> TYPE: PRT
<213> ORGANISM: Homo sapiens

<400> SEQUENCE: 59

Arg Ala Ser Gln Ser Val Ser Ser Ser Tyr Leu Ala
1               5                   10

<210> SEQ ID NO 60
<211> LENGTH: 7
<212> TYPE: PRT
<213> ORGANISM: Homo sapiens

<400> SEQUENCE: 60

Gly Ala Ser Ser Arg Ala Thr
1               5

<210> SEQ ID NO 61
<211> LENGTH: 9
<212> TYPE: PRT
<213> ORGANISM: Homo sapiens

<400> SEQUENCE: 61

Gln Gln Tyr Gly Ser Ser Pro Trp Thr
1               5

<210> SEQ ID NO 62
<211> LENGTH: 12
<212> TYPE: PRT
<213> ORGANISM: unknown
<220> FEATURE:
<223> OTHER INFORMATION: synthetic sequence

<400> SEQUENCE: 62

Trp Thr Phe Gly Gln Gly Thr Lys Val Glu Ile Lys
1               5                   10

<210> SEQ ID NO 63
<211> LENGTH: 20
<212> TYPE: PRT
<213> ORGANISM: Human immunodeficiency virus type 1

<400> SEQUENCE: 63

Asn Cys Ser Phe Asn Ile Ser Thr Ser Ile Arg Gly Lys Val Gln Lys
1               5                   10                  15

Glu Tyr Ala Phe
            20

<210> SEQ ID NO 64
<211> LENGTH: 33
<212> TYPE: PRT
<213> ORGANISM: Human immunodeficiency virus type 1

<400> SEQUENCE: 64

Gly Lys Ile Gly Asn Met Arg Gln Ala His Cys Asn Ile Ser Arg Ala
1               5                   10                  15

Lys Trp Asn Asn Thr Leu Lys Gln Ile Ala Ser Lys Leu Arg Glu Gln
            20                  25                  30

Phe

<210> SEQ ID NO 65
<211> LENGTH: 39
<212> TYPE: PRT
```

<213> ORGANISM: Human immunodeficiency virus type 1

<400> SEQUENCE: 65

Glu Gly Ser Asp Thr Ile Thr Leu Pro Cys Arg Ile Lys Gln Ile
1               5                   10                  15
Asn Met Trp Gln Lys Val Gly Lys Ala Met Tyr Ala Pro Pro Ile Ser
            20                  25                  30
Gly Gln Ile Arg Cys Ser Ser
        35

<210> SEQ ID NO 66
<211> LENGTH: 36
<212> TYPE: PRT
<213> ORGANISM: Human immunodeficiency virus type 1

<400> SEQUENCE: 66

Ser Thr Gln Leu Leu Leu Asn Gly Ser Leu Ala Glu Glu Val Val
1               5                   10                  15
Ile Arg Ser Val Asn Phe Thr Asp Asn Ala Lys Thr Ile Ile Val Gln
            20                  25                  30
Leu Asn Thr Ser
        35

<210> SEQ ID NO 67
<211> LENGTH: 18
<212> TYPE: PRT
<213> ORGANISM: Human immunodeficiency virus type 1

<400> SEQUENCE: 67

Cys Asn Asn Lys Thr Phe Asn Gly Thr Gly Pro Cys Thr Asn Val Ser
1               5                   10                  15
Thr Val

<210> SEQ ID NO 68
<211> LENGTH: 12
<212> TYPE: PRT
<213> ORGANISM: Human immunodeficiency virus type 1

<400> SEQUENCE: 68

Asn Ile Thr Gly Leu Leu Leu Thr Arg Asp Gly Gly
1               5                   10

<210> SEQ ID NO 69
<211> LENGTH: 10
<212> TYPE: PRT
<213> ORGANISM: Human immunodeficiency virus type 1

<400> SEQUENCE: 69

Val Val Leu Val Asn Val Thr Glu Asn Phe
1               5                   10

<210> SEQ ID NO 70
<211> LENGTH: 8
<212> TYPE: PRT
<213> ORGANISM: Human immunodeficiency virus type 1

<400> SEQUENCE: 70

Asn Ile Thr Gly Leu Leu Leu Thr
1               5

<210> SEQ ID NO 71
<211> LENGTH: 28

```
<212> TYPE: PRT
<213> ORGANISM: Human immunodeficiency virus type 1

<400> SEQUENCE: 71

Gln Arg Glu Lys Arg Ala Val Gly Ile Gly Ala Leu Phe Leu Gly Phe
1               5                   10                  15

Leu Gly Ala Ala Gly Ser Thr Met Gly Ala Ala Ser
            20                  25

<210> SEQ ID NO 72
<211> LENGTH: 10
<212> TYPE: PRT
<213> ORGANISM: Human immunodeficiency virus type 1

<400> SEQUENCE: 72

Thr Thr Ala Val Pro Trp Asn Ala Ser Trp
1               5                   10

<210> SEQ ID NO 73
<211> LENGTH: 26
<212> TYPE: PRT
<213> ORGANISM: Human immunodeficiency virus type 1

<400> SEQUENCE: 73

Gln Ile Trp Asn His Thr Thr Trp Met Glu Trp Asp Arg Glu Ile Asn
1               5                   10                  15

Asn Tyr Thr Ser Leu Ile His Ser Leu Ile
            20                  25

<210> SEQ ID NO 74
<211> LENGTH: 20
<212> TYPE: PRT
<213> ORGANISM: Simian immunodeficiency virus

<400> SEQUENCE: 74

Asn Cys Ser Phe Asn Val Thr Thr Glu Leu Arg Asp Lys Lys Arg Gln
1               5                   10                  15

Val Tyr Ser Leu
            20

<210> SEQ ID NO 75
<211> LENGTH: 34
<212> TYPE: PRT
<213> ORGANISM: Simian immunodeficiency virus

<400> SEQUENCE: 75

Glu Asn Val Val Gly Asp Thr Arg Lys Ala Tyr Cys Glu Ile Asn Gly
1               5                   10                  15

Thr Gln Trp Ala Lys Ala Leu Asn Glu Thr Lys Glu Val Leu Arg Asn
            20                  25                  30

Ile Leu

<210> SEQ ID NO 76
<211> LENGTH: 39
<212> TYPE: PRT
<213> ORGANISM: Simian immunodeficiency virus

<400> SEQUENCE: 76

Lys Thr Glu Asn Met Thr Ile Ile Pro Cys Arg Ile Arg Gln Ile Val
1               5                   10                  15

Asn Ser Trp Met Arg Val Gly Lys Gly Ile Phe Ala Pro Pro Ile Arg
            20                  25                  30
```

Gly Asn Ile Thr Cys Thr Ser
        35

<210> SEQ ID NO 77
<211> LENGTH: 33
<212> TYPE: PRT
<213> ORGANISM: Simian immunodeficiency virus

<400> SEQUENCE: 77

Thr Thr Gln Leu Ile Leu Asn Gly Ser Thr Ala Asp Asn Gln Thr Val
1               5                   10                  15

Ala Arg Ile Asp Pro Ser Glu Asn Leu Ala Ile Ile Gln Leu Lys Asp
            20                  25                  30

Pro

<210> SEQ ID NO 78
<211> LENGTH: 18
<212> TYPE: PRT
<213> ORGANISM: Simian immunodeficiency virus

<400> SEQUENCE: 78

Cys Asn Asp Ile Asp Tyr Lys Gly Asn Glu Thr Cys Lys Asn Val Ser
1               5                   10                  15

Thr Val

<210> SEQ ID NO 79
<211> LENGTH: 17
<212> TYPE: PRT
<213> ORGANISM: Simian immunodeficiency virus

<400> SEQUENCE: 79

Asn Ile Thr Gly Met Leu Leu Glu Ile His Lys Asn Arg Glu Asp Gln
1               5                   10                  15

Gly

<210> SEQ ID NO 80
<211> LENGTH: 10
<212> TYPE: PRT
<213> ORGANISM: Simian immunodeficiency virus

<400> SEQUENCE: 80

Val Leu Leu Pro Asn Val Thr Glu Glu Phe
1               5                   10

<210> SEQ ID NO 81
<211> LENGTH: 8
<212> TYPE: PRT
<213> ORGANISM: Simian immunodeficiency virus

<400> SEQUENCE: 81

Asn Ile Thr Gly Met Leu Leu Glu
1               5

<210> SEQ ID NO 82
<211> LENGTH: 28
<212> TYPE: PRT
<213> ORGANISM: Simian immunodeficiency virus

<400> SEQUENCE: 82

His Arg Glu Lys Arg Ala Leu Gly Leu Gly Ala Leu Phe Leu Gly Phe
1               5                   10                  15

```
Leu Gly Ala Ala Gly Ser Thr Met Gly Ala Ala Ser
            20                  25

<210> SEQ ID NO 83
<211> LENGTH: 10
<212> TYPE: PRT
<213> ORGANISM: Simian immunodeficiency virus

<400> SEQUENCE: 83

Pro Thr Ala Val Arg Trp Asn Lys Thr Trp
1               5                   10

<210> SEQ ID NO 84
<211> LENGTH: 26
<212> TYPE: PRT
<213> ORGANISM: Simian immunodeficiency virus

<400> SEQUENCE: 84

Val Ile Trp Asn Asn Tyr Thr Trp Gln Gln Trp Asp Arg Glu Val Asn
1               5                   10                  15

Asn Tyr Thr Gly Leu Ile Tyr Thr Leu Leu
            20                  25

<210> SEQ ID NO 85
<211> LENGTH: 20
<212> TYPE: PRT
<213> ORGANISM: Simian immunodeficiency virus

<400> SEQUENCE: 85

Asn Cys Ser Phe Asn Val Thr Thr Glu Leu Arg Asp Lys Lys Lys Gln
1               5                   10                  15

Val Tyr Ser Leu
            20

<210> SEQ ID NO 86
<211> LENGTH: 34
<212> TYPE: PRT
<213> ORGANISM: Simian immunodeficiency virus

<400> SEQUENCE: 86

Lys Thr Val Val Gly Asp Thr Arg Gly Ala Glu Cys Arg Ile Asn Gly
1               5                   10                  15

Thr Ala Trp Asn Glu Thr Leu Arg Gln Val Lys Glu Ala Leu Gln His
            20                  25                  30

Ile Ser

<210> SEQ ID NO 87
<211> LENGTH: 39
<212> TYPE: PRT
<213> ORGANISM: Simian immunodeficiency virus

<400> SEQUENCE: 87

Thr Ile Asn Asn Ile Thr His Ile Pro Cys Arg Ile Arg Gln Ile Val
1               5                   10                  15

Asn Gln Trp Gln Gly Val Gly Lys Gly Ile Phe Ala Pro Pro Ile Arg
            20                  25                  30

Gly Thr Ile Gln Cys Asn Ser
                35

<210> SEQ ID NO 88
<211> LENGTH: 36
<212> TYPE: PRT
```

<213> ORGANISM: Simian immunodeficiency virus

<400> SEQUENCE: 88

Ser Thr Gln Phe Leu Leu Asn Gly Ser Leu Ala Glu Gly Asn Lys Thr
1               5                   10                  15

Val Val Arg Val Arg Ser Lys Ser Asn Thr Glu Thr Ile Ile Val Gln
            20                  25                  30

Leu Ala Thr Ala
        35

<210> SEQ ID NO 89
<211> LENGTH: 18
<212> TYPE: PRT
<213> ORGANISM: Simian immunodeficiency virus

<400> SEQUENCE: 89

Cys Asn Asp Gln Asn Phe Lys Gly Lys Gly Thr Cys Arg Asn Val Ser
1               5                   10                  15

Thr Val

<210> SEQ ID NO 90
<211> LENGTH: 11
<212> TYPE: PRT
<213> ORGANISM: Simian immunodeficiency virus

<400> SEQUENCE: 90

Thr Ile Thr Gly Leu Leu Leu Thr Arg Asp Gly
1               5                   10

<210> SEQ ID NO 91
<211> LENGTH: 10
<212> TYPE: PRT
<213> ORGANISM: Simian immunodeficiency virus

<400> SEQUENCE: 91

Ile Thr Leu Glu Asn Val Thr Glu Glu Phe
1               5                   10

<210> SEQ ID NO 92
<211> LENGTH: 8
<212> TYPE: PRT
<213> ORGANISM: Simian immunodeficiency virus

<400> SEQUENCE: 92

Thr Ile Thr Gly Leu Leu Leu Thr
1               5

<210> SEQ ID NO 93
<211> LENGTH: 28
<212> TYPE: PRT
<213> ORGANISM: Simian immunodeficiency virus

<400> SEQUENCE: 93

Gln Arg Glu Lys Arg Ala Val Gly Leu Gly Val Met Phe Leu Gly Phe
1               5                   10                  15

Met Gly Ala Ala Gly Ser Thr Met Gly Ala Ala Ala
            20                  25

<210> SEQ ID NO 94
<211> LENGTH: 10
<212> TYPE: PRT
<213> ORGANISM: Simian immunodeficiency virus

```
<400> SEQUENCE: 94

Thr Thr Asn Val Pro Trp Asn Asn Thr Trp
1               5                   10

<210> SEQ ID NO 95
<211> LENGTH: 25
<212> TYPE: PRT
<213> ORGANISM: Simian immunodeficiency virus

<400> SEQUENCE: 95

Phe Trp Asp Asn Met Thr Trp Met Gln Trp Glu Lys Glu Ile Asp Asn
1               5                   10                  15

Tyr Thr Glu Thr Ile Tyr Glu Leu Leu
            20                  25

<210> SEQ ID NO 96
<211> LENGTH: 20
<212> TYPE: PRT
<213> ORGANISM: Simian immunodeficiency virus

<400> SEQUENCE: 96

Asn Cys Ser Phe Asn Thr Thr Thr Glu Leu Arg Asp Lys Lys Lys Gln
1               5                   10                  15

Thr Tyr Ser Leu
            20

<210> SEQ ID NO 97
<211> LENGTH: 34
<212> TYPE: PRT
<213> ORGANISM: Simian immunodeficiency virus

<400> SEQUENCE: 97

Glu Thr Val Val Gly Asp Thr Arg Glu Ala His Cys Glu Ile Asn Gln
1               5                   10                  15

Thr His Trp Tyr Lys Ile Leu Asn Gln Val Lys Arg Glu Leu Thr Thr
            20                  25                  30

Val Phe

<210> SEQ ID NO 98
<211> LENGTH: 39
<212> TYPE: PRT
<213> ORGANISM: Simian immunodeficiency virus

<400> SEQUENCE: 98

Thr Leu His Asn Asn Leu Thr Leu Pro Cys Arg Ile Arg Gln Ile Val
1               5                   10                  15

Asn Leu Trp Leu Arg Val Gly Lys Gly Ile Phe Ala Pro Pro Ile Arg
            20                  25                  30

Gly Asn Ile Arg Cys Asn Ser
        35

<210> SEQ ID NO 99
<211> LENGTH: 31
<212> TYPE: PRT
<213> ORGANISM: Simian immunodeficiency virus

<400> SEQUENCE: 99

Ser Thr Gln Leu Ile Leu Asn Gly Ser Leu Ala Glu Glu Lys Ile Met
1               5                   10                  15

Ile Arg Tyr Lys Ala Asp Lys Val Leu Val Gln Leu Asn Thr Ser
            20                  25                  30
```

<210> SEQ ID NO 100
<211> LENGTH: 18
<212> TYPE: PRT
<213> ORGANISM: Simian immunodeficiency virus

<400> SEQUENCE: 100

Cys Asn Asn Lys Thr Tyr Asn Gly Ser Gly Pro Cys Asn Asn Val Ser
1               5                   10                  15

Thr Val

<210> SEQ ID NO 101
<211> LENGTH: 8
<212> TYPE: PRT
<213> ORGANISM: Simian immunodeficiency virus

<400> SEQUENCE: 101

Thr Ile Thr Gly Leu Ile Leu Glu
1               5

<210> SEQ ID NO 102
<211> LENGTH: 10
<212> TYPE: PRT
<213> ORGANISM: Simian immunodeficiency virus

<400> SEQUENCE: 102

Ile Glu Leu Ser Asn Val Thr Glu Asn Phe
1               5                   10

<210> SEQ ID NO 103
<211> LENGTH: 8
<212> TYPE: PRT
<213> ORGANISM: Simian immunodeficiency virus

<400> SEQUENCE: 103

Thr Ile Thr Gly Leu Ile Leu Glu
1               5

<210> SEQ ID NO 104
<211> LENGTH: 28
<212> TYPE: PRT
<213> ORGANISM: Simian immunodeficiency virus

<400> SEQUENCE: 104

Asp Arg Glu Lys Arg Ala Ala Gly Leu Gly Val Phe Phe Leu Gly Phe
1               5                   10                  15

Leu Gly Ala Ala Gly Ser Thr Met Gly Ala Ala Ser
            20                  25

<210> SEQ ID NO 105
<211> LENGTH: 10
<212> TYPE: PRT
<213> ORGANISM: Simian immunodeficiency virus

<400> SEQUENCE: 105

Thr Thr Ser Val Pro Trp Asn Arg Thr Trp
1               5                   10

<210> SEQ ID NO 106
<211> LENGTH: 26
<212> TYPE: PRT
<213> ORGANISM: Simian immunodeficiency virus

<400> SEQUENCE: 106

```
Asp Ile Trp Asn Asn Leu Thr Trp Gln Gln Trp Asp Lys Leu Ile Thr
1               5                   10                  15

Asn Tyr Thr Gly Thr Ile Phe Gly Leu Leu
            20                  25
```

<210> SEQ ID NO 107
<211> LENGTH: 20
<212> TYPE: PRT
<213> ORGANISM: Simian immunodeficiency virus

<400> SEQUENCE: 107

```
Asn Cys Thr Phe Asn Thr Thr Thr Glu Leu Arg Asp Lys Lys Lys Gln
1               5                   10                  15

Val Tyr Ser Leu
            20
```

<210> SEQ ID NO 108
<211> LENGTH: 34
<212> TYPE: PRT
<213> ORGANISM: Simian immunodeficiency virus

<400> SEQUENCE: 108

```
Asp His Ile Phe Gly Asp Thr Arg Lys Ala Phe Cys Glu Leu Asn Gly
1               5                   10                  15

Thr Thr Trp Asn Glu Thr Leu Gln Lys Val Arg Glu Ser Leu Ile Lys
            20                  25                  30

Glu Ile
```

<210> SEQ ID NO 109
<211> LENGTH: 39
<212> TYPE: PRT
<213> ORGANISM: Simian immunodeficiency virus

<400> SEQUENCE: 109

```
Pro Phe His Glu Asn Met Thr Ile Pro Cys Arg Ile Arg Gln Ile Val
1               5                   10                  15

Asn Ser Trp Met Arg Val Gly Arg Gly Ile Tyr Ala Pro Pro Ile Pro
            20                  25                  30

Gly His Ile Thr Cys Asn Ser
            35
```

<210> SEQ ID NO 110
<211> LENGTH: 36
<212> TYPE: PRT
<213> ORGANISM: Simian immunodeficiency virus

<400> SEQUENCE: 110

```
Thr Thr Gln Leu Ile Ile Asn Gly Ser Leu Ala Thr Glu Asn Ile Thr
1               5                   10                  15

Val Arg Val Asn Asn Ala Ser Lys Asn Thr His Asp Trp Ile Val Gln
            20                  25                  30

Leu Ser Thr Ala
            35
```

<210> SEQ ID NO 111
<211> LENGTH: 18
<212> TYPE: PRT
<213> ORGANISM: Simian immunodeficiency virus

<400> SEQUENCE: 111

```
Cys Asn Asp Val Asn Phe Ser Gly Lys Gly Lys Cys Arg Asn Val Ser
1               5                   10                  15

Thr Val

<210> SEQ ID NO 112
<211> LENGTH: 12
<212> TYPE: PRT
<213> ORGANISM: Simian immunodeficiency virus

<400> SEQUENCE: 112

Leu Ile Thr Gly Leu Ile Leu Thr Arg Asp His Val
1               5                   10

<210> SEQ ID NO 113
<211> LENGTH: 10
<212> TYPE: PRT
<213> ORGANISM: Simian immunodeficiency virus

<400> SEQUENCE: 113

Val Val Leu His Asn Val Thr Glu Asp Phe
1               5                   10

<210> SEQ ID NO 114
<211> LENGTH: 8
<212> TYPE: PRT
<213> ORGANISM: Simian immunodeficiency virus

<400> SEQUENCE: 114

Leu Ile Thr Gly Leu Ile Leu Thr
1               5

<210> SEQ ID NO 115
<211> LENGTH: 29
<212> TYPE: PRT
<213> ORGANISM: Simian immunodeficiency virus

<400> SEQUENCE: 115

Arg Arg Gln Lys Arg Ala Ala Phe Gly Leu Gly Ala Leu Phe Leu Gly
1               5                   10                  15

Phe Leu Gly Ala Ala Gly Ser Thr Met Gly Ala Ala Ala
            20                  25

<210> SEQ ID NO 116
<211> LENGTH: 10
<212> TYPE: PRT
<213> ORGANISM: Simian immunodeficiency virus

<400> SEQUENCE: 116

Tyr Thr Thr Val Pro Trp Asn Lys Thr Trp
1               5                   10

<210> SEQ ID NO 117
<211> LENGTH: 26
<212> TYPE: PRT
<213> ORGANISM: Simian immunodeficiency virus

<400> SEQUENCE: 117

Asp Ile Trp Asn Asn Leu Thr Trp Gln Gln Trp Asp Lys Leu Ile Thr
1               5                   10                  15

Asn Tyr Thr Gly Thr Ile Phe Gly Leu Leu
            20                  25

<210> SEQ ID NO 118
```

-continued

```
<211> LENGTH: 20
<212> TYPE: PRT
<213> ORGANISM: Simian immunodeficiency virus

<400> SEQUENCE: 118

Asn Cys Ser Phe Asn Val Thr Thr Glu Leu Arg Asp Lys Lys Gln
1               5                   10                  15

Val Tyr Ser Leu
            20

<210> SEQ ID NO 119
<211> LENGTH: 33
<212> TYPE: PRT
<213> ORGANISM: Simian immunodeficiency virus

<400> SEQUENCE: 119

Glu Asn Val Val Gly Asp Thr Arg Ser Ala Tyr Cys Lys Ile Asn Gly
1               5                   10                  15

Thr Thr Trp Asn Arg Thr Val Glu Glu Val Lys Gly Phe Ser Asn Leu
            20                  25                  30

Ile

<210> SEQ ID NO 120
<211> LENGTH: 39
<212> TYPE: PRT
<213> ORGANISM: Simian immunodeficiency virus

<400> SEQUENCE: 120

Ile Thr Asn Gly Ile Ile Ile Leu Pro Cys Arg Ile Arg Gln Ile Val
1               5                   10                  15

Ser Ser Trp Met Arg Val Gly Arg Gly Ile Tyr Ala Pro Pro Ile Arg
            20                  25                  30

Gly Asn Ile Thr Cys Asn Ser
            35

<210> SEQ ID NO 121
<211> LENGTH: 36
<212> TYPE: PRT
<213> ORGANISM: Simian immunodeficiency virus

<400> SEQUENCE: 121

Thr Thr Gln Leu Leu Ile Asn Gly Ser Leu Ala Glu Gly Asn Ile Thr
1               5                   10                  15

Val Arg Val Glu Asn Lys Ser Lys Asn Thr Asp Val Trp Ile Val Gln
            20                  25                  30

Leu Val Glu Ala
            35

<210> SEQ ID NO 122
<211> LENGTH: 18
<212> TYPE: PRT
<213> ORGANISM: Simian immunodeficiency virus

<400> SEQUENCE: 122

Cys Asn Asp Lys Asp Phe Ser Gly Lys Gly Lys Cys Thr Asn Val Ser
1               5                   10                  15

Thr Val

<210> SEQ ID NO 123
<211> LENGTH: 12
<212> TYPE: PRT
```

<213> ORGANISM: Simian immunodeficiency virus

<400> SEQUENCE: 123

Asn Ile Thr Gly Leu Leu Leu Thr Ser Asp Thr Pro
1               5                   10

<210> SEQ ID NO 124
<211> LENGTH: 10
<212> TYPE: PRT
<213> ORGANISM: Simian immunodeficiency virus

<400> SEQUENCE: 124

Val Phe Leu Pro Asn Val Ile Glu Ser Phe
1               5                   10

<210> SEQ ID NO 125
<211> LENGTH: 8
<212> TYPE: PRT
<213> ORGANISM: Simian immunodeficiency virus

<400> SEQUENCE: 125

Asn Ile Thr Gly Leu Leu Leu Thr
1               5

<210> SEQ ID NO 126
<211> LENGTH: 29
<212> TYPE: PRT
<213> ORGANISM: Simian immunodeficiency virus

<400> SEQUENCE: 126

Asp Arg Gln Lys Arg Ala Ala Phe Gly Leu Gly Ala Leu Phe Leu Gly
1               5                   10                  15
Phe Leu Gly Ala Ala Gly Ser Thr Met Gly Ala Ala Ala
            20                  25

<210> SEQ ID NO 127
<211> LENGTH: 10
<212> TYPE: PRT
<213> ORGANISM: Simian immunodeficiency virus

<400> SEQUENCE: 127

Tyr Thr Thr Val Pro Trp Asn Asn Ser Trp
1               5                   10

<210> SEQ ID NO 128
<211> LENGTH: 26
<212> TYPE: PRT
<213> ORGANISM: Simian immunodeficiency virus

<400> SEQUENCE: 128

Asp Ile Trp Gly Asn Leu Thr Trp Gln Gln Trp Asp Lys Leu Val Ser
1               5                   10                  15
Asn Tyr Thr Gly Lys Ile Phe Gly Leu Leu
            20                  25

<210> SEQ ID NO 129
<211> LENGTH: 20
<212> TYPE: PRT
<213> ORGANISM: Simian immunodeficiency virus

<400> SEQUENCE: 129

Asn Cys Ser Phe Asn Ala Thr Thr Glu Leu Arg Asp Arg Lys Lys Gln
1               5                   10                  15

```
Val Tyr Ser Leu
        20

<210> SEQ ID NO 130
<211> LENGTH: 34
<212> TYPE: PRT
<213> ORGANISM: Simian immunodeficiency virus

<400> SEQUENCE: 130

Glu Thr Val Ile Gly Asp Thr Arg Gln Ala Phe Cys Gln Leu Asn Lys
1               5                   10                  15

Thr Val Trp Thr Asn Thr Phe Lys Lys Val Arg His Ala Leu Asn Glu
            20                  25                  30

Thr Tyr

<210> SEQ ID NO 131
<211> LENGTH: 39
<212> TYPE: PRT
<213> ORGANISM: Simian immunodeficiency virus

<400> SEQUENCE: 131

Thr Lys Asp Asp Asn Ile Thr Ile Pro Cys Arg Ile Arg Gln Ile Val
1               5                   10                  15

Arg Leu Trp Gln Arg Val Gly Arg Gly Ile Phe Leu Pro Pro Ile Arg
            20                  25                  30

Gly Thr Ile Asn Cys Ile Ser
        35

<210> SEQ ID NO 132
<211> LENGTH: 35
<212> TYPE: PRT
<213> ORGANISM: Simian immunodeficiency virus

<400> SEQUENCE: 132

Ser Thr Gln Phe Leu Leu Asn Gly Thr Leu Glu Glu Lys Val Thr Val
1               5                   10                  15

Leu Asp Arg Asn Val Ser Asn Asp Met Asp Thr Ile Ile Val Lys Leu
            20                  25                  30

Asn Glu Thr
        35

<210> SEQ ID NO 133
<211> LENGTH: 18
<212> TYPE: PRT
<213> ORGANISM: Simian immunodeficiency virus

<400> SEQUENCE: 133

Cys Asn Asp Lys Asn Phe Thr Gly Ile Gly Gln Cys Lys Asn Val Ser
1               5                   10                  15

Thr Val

<210> SEQ ID NO 134
<211> LENGTH: 10
<212> TYPE: PRT
<213> ORGANISM: Simian immunodeficiency virus

<400> SEQUENCE: 134

Asn Ile Thr Gly Ile Leu Phe Ala Gln Gln
1               5                   10

<210> SEQ ID NO 135
```

```
<211> LENGTH: 10
<212> TYPE: PRT
<213> ORGANISM: Simian immunodeficiency virus

<400> SEQUENCE: 135

Ile Glu Leu Thr Asn Val Thr Glu Tyr Phe
1               5                   10

<210> SEQ ID NO 136
<211> LENGTH: 8
<212> TYPE: PRT
<213> ORGANISM: Simian immunodeficiency virus

<400> SEQUENCE: 136

Asn Ile Thr Gly Ile Leu Phe Ala
1               5

<210> SEQ ID NO 137
<211> LENGTH: 29
<212> TYPE: PRT
<213> ORGANISM: Simian immunodeficiency virus

<400> SEQUENCE: 137

His Arg Glu Lys Arg Ala Ala Val Gly Leu Gly Ala Leu Phe Leu Gly
1               5                   10                  15

Phe Leu Gly Ala Ala Gly Ser Thr Met Gly Ala Ala Ser
            20                  25

<210> SEQ ID NO 138
<211> LENGTH: 10
<212> TYPE: PRT
<213> ORGANISM: Simian immunodeficiency virus

<400> SEQUENCE: 138

Thr Thr Ser Val Pro Trp Asn Thr Thr Trp
1               5                   10

<210> SEQ ID NO 139
<211> LENGTH: 26
<212> TYPE: PRT
<213> ORGANISM: Simian immunodeficiency virus

<400> SEQUENCE: 139

Asp Ile Trp Tyr Asn Met Thr Trp Met Gln Trp Asp Lys Glu Val Ser
1               5                   10                  15

Asn Tyr Thr Asp Val Ile Tyr Asn Leu Leu
            20                  25

<210> SEQ ID NO 140
<211> LENGTH: 12
<212> TYPE: PRT
<213> ORGANISM: Simian immunodeficiency virus

<400> SEQUENCE: 140

Asn Cys Thr Phe Asn Val Thr Thr Glu Leu Arg Gly
1               5                   10

<210> SEQ ID NO 141
<211> LENGTH: 34
<212> TYPE: PRT
<213> ORGANISM: Simian immunodeficiency virus

<400> SEQUENCE: 141

Glu Asn Ile Val Gly Asn Thr Arg Lys Ala Phe Cys Lys Val Asn Gly
```

```
                1               5                   10                  15
Ser Gln Trp Trp Asn Met Lys Gln Asn Ile Ile Gln Arg Phe Lys Ala
                20                  25                  30

Glu His

<210> SEQ ID NO 142
<211> LENGTH: 39
<212> TYPE: PRT
<213> ORGANISM: Simian immunodeficiency virus

<400> SEQUENCE: 142

Lys Thr Asn Ile Thr Ile Ile Leu Pro Cys Lys Ile Arg Gln Ile Val
1               5                   10                  15

Asn Ser Trp Met Arg Val Gly Lys Gly Ile Tyr Ala Pro Pro Ile Arg
                20                  25                  30

Gly Asn Leu Ser Cys Asn Ser
                35

<210> SEQ ID NO 143
<211> LENGTH: 35
<212> TYPE: PRT
<213> ORGANISM: Simian immunodeficiency virus

<400> SEQUENCE: 143

Thr Thr Gln Leu Ile Leu Asn Gly Ser Ile Gln Gln Ile Met Ile
1               5                   10                  15

Arg Ser Lys Asn Ile Ser Ser Asn Ser Phe Asn Ile Ile Val Gln Phe
                20                  25                  30

Asn Glu Thr
        35

<210> SEQ ID NO 144
<211> LENGTH: 18
<212> TYPE: PRT
<213> ORGANISM: Simian immunodeficiency virus

<400> SEQUENCE: 144

Cys Asn Glu Glu Asn Ser Gln Glu Met Gly Tyr Cys Glu Asn Val Ser
1               5                   10                  15

Thr Val

<210> SEQ ID NO 145
<211> LENGTH: 12
<212> TYPE: PRT
<213> ORGANISM: Simian immunodeficiency virus

<400> SEQUENCE: 145

Asn Ile Thr Gly Leu Leu Leu Thr Arg Asp Gly Pro
1               5                   10

<210> SEQ ID NO 146
<211> LENGTH: 10
<212> TYPE: PRT
<213> ORGANISM: Simian immunodeficiency virus

<400> SEQUENCE: 146

Val Phe Leu Lys Asn Val Lys Glu Asn Phe
1               5                   10

<210> SEQ ID NO 147
<211> LENGTH: 8
```

```
<212> TYPE: PRT
<213> ORGANISM: Simian immunodeficiency virus

<400> SEQUENCE: 147

Asn Ile Thr Gly Leu Leu Leu Thr
1               5

<210> SEQ ID NO 148
<211> LENGTH: 18
<212> TYPE: PRT
<213> ORGANISM: Simian immunodeficiency virus

<400> SEQUENCE: 148

His Arg Ala Lys Arg Ala Ala Phe Ala Ala Gly Ser Thr Met Gly Ala
1               5                   10                  15

Ala Ala

<210> SEQ ID NO 149
<211> LENGTH: 10
<212> TYPE: PRT
<213> ORGANISM: Simian immunodeficiency virus

<400> SEQUENCE: 149

Tyr Thr Asn Val Pro Trp Asn Arg Asn Trp
1               5                   10

<210> SEQ ID NO 150
<211> LENGTH: 26
<212> TYPE: PRT
<213> ORGANISM: Simian immunodeficiency virus

<400> SEQUENCE: 150

Glu Ile Trp Asn Asn Leu Thr Trp Asn Glu Trp Asp Lys Gln Val Ser
1               5                   10                  15

Asn Tyr Thr Thr Glu Ile Phe Lys Ala Leu
            20                  25

<210> SEQ ID NO 151
<211> LENGTH: 20
<212> TYPE: PRT
<213> ORGANISM: Simian immunodeficiency virus

<400> SEQUENCE: 151

Asn Cys Ser Phe Asn Val Thr Thr Glu Leu Arg Asp Lys Lys Lys Gln
1               5                   10                  15

Val Tyr Ser Leu
            20

<210> SEQ ID NO 152
<211> LENGTH: 34
<212> TYPE: PRT
<213> ORGANISM: Simian immunodeficiency virus

<400> SEQUENCE: 152

Glu Asn Val Val Gly Asp Thr Arg Lys Ala Tyr Cys Thr Leu Asn Gly
1               5                   10                  15

Ser Asn Trp Glu Glu Ala Met Ser Lys Val Lys Glu Leu Glu Lys
            20                  25                  30

Ile Thr

<210> SEQ ID NO 153
<211> LENGTH: 39
```

```
<212> TYPE: PRT
<213> ORGANISM: Simian immunodeficiency virus

<400> SEQUENCE: 153

Asn Lys Ser Glu Glu Ile Ile Leu Pro Cys Arg Ile Lys Gln Ile Val
1               5                   10                  15

Asn Leu Trp Thr Arg Val Gly Lys Gly Ile Tyr Ala Pro Pro Ile Arg
            20                  25                  30

Gly Asn Ile Ser Cys Lys Ser
        35

<210> SEQ ID NO 154
<211> LENGTH: 36
<212> TYPE: PRT
<213> ORGANISM: Simian immunodeficiency virus

<400> SEQUENCE: 154

Thr Thr Gln Leu Ile Leu Asn Gly Ser Leu Ala Glu Gly Asn Val Thr
1               5                   10                  15

Ile Arg Val Lys Asn Ala Ser Ser Asn Ser Gly Asn Tyr Ile Val Gln
            20                  25                  30

Leu Ala Arg Ser
        35

<210> SEQ ID NO 155
<211> LENGTH: 18
<212> TYPE: PRT
<213> ORGANISM: Simian immunodeficiency virus

<400> SEQUENCE: 155

Cys Asn Asp Thr Asn Tyr Leu Gly Thr Gly Lys Cys His Asn Val Ser
1               5                   10                  15

Thr Val

<210> SEQ ID NO 156
<211> LENGTH: 12
<212> TYPE: PRT
<213> ORGANISM: Simian immunodeficiency virus
<220> FEATURE:
<221> NAME/KEY: MISC_FEATURE
<222> LOCATION: (10)..(10)
<223> OTHER INFORMATION: Xaa can be any naturally occurring amino acid

<400> SEQUENCE: 156

Asn Ile Thr Gly Ile Leu Leu Ala Arg Xaa Glu Gly
1               5                   10

<210> SEQ ID NO 157
<211> LENGTH: 10
<212> TYPE: PRT
<213> ORGANISM: Simian immunodeficiency virus

<400> SEQUENCE: 157

Val Phe Leu Pro Asn Val Thr Glu Asn Phe
1               5                   10

<210> SEQ ID NO 158
<211> LENGTH: 8
<212> TYPE: PRT
<213> ORGANISM: Simian immunodeficiency virus

<400> SEQUENCE: 158

Asn Ile Thr Gly Ile Leu Leu Ala
1               5
```

```
<210> SEQ ID NO 159
<211> LENGTH: 29
<212> TYPE: PRT
<213> ORGANISM: Simian immunodeficiency virus

<400> SEQUENCE: 159

Lys Arg Gln Lys Arg Ala Ala Phe Gly Leu Gly Ala Leu Phe Leu Gly
1               5                   10                  15

Phe Leu Gly Ala Ala Gly Ser Thr Met Gly Ala Ala Ala
            20                  25

<210> SEQ ID NO 160
<211> LENGTH: 10
<212> TYPE: PRT
<213> ORGANISM: Simian immunodeficiency virus

<400> SEQUENCE: 160

Tyr Thr Thr Val Pro Trp Asn Lys Thr Trp
1               5                   10

<210> SEQ ID NO 161
<211> LENGTH: 26
<212> TYPE: PRT
<213> ORGANISM: Simian immunodeficiency virus

<400> SEQUENCE: 161

Tyr Ile Trp Asn Asn Leu Thr Trp Glu Gln Trp Asp Val His Val Ser
1               5                   10                  15

Asn Tyr Thr Gly Val Ile Phe Gly Leu Leu
            20                  25

<210> SEQ ID NO 162
<211> LENGTH: 20
<212> TYPE: PRT
<213> ORGANISM: Simian immunodeficiency virus

<400> SEQUENCE: 162

Asn Cys Thr Phe Asn Met Thr Thr Glu Val Arg Asp Lys Glu Lys Lys
1               5                   10                  15

Val Tyr Ser Leu
            20

<210> SEQ ID NO 163
<211> LENGTH: 34
<212> TYPE: PRT
<213> ORGANISM: Simian immunodeficiency virus

<400> SEQUENCE: 163

Glu Asn Ile Val Gly Asp Thr Arg Arg Ala Tyr Cys Gln Ile Asn Arg
1               5                   10                  15

Thr Val Trp Asp Glu Arg Leu Asn Glu Thr Gly Gln Ala Leu Arg Glu
            20                  25                  30

Leu Phe

<210> SEQ ID NO 164
<211> LENGTH: 39
<212> TYPE: PRT
<213> ORGANISM: Simian immunodeficiency virus

<400> SEQUENCE: 164
```

```
Lys Gly Asp Asn Thr Thr Phe Phe Pro Cys Arg Ile Arg Gln Ile Val
1               5                   10                  15

Asn Ser Trp Met Arg Val Gly Lys Gly Ile Tyr Ala Pro Pro Ile Arg
            20                  25                  30

Gly Val Ile Ser Cys Thr Ser
            35

<210> SEQ ID NO 165
<211> LENGTH: 31
<212> TYPE: PRT
<213> ORGANISM: Simian immunodeficiency virus
<220> FEATURE:
<221> NAME/KEY: MISC_FEATURE
<222> LOCATION: (23)..(23)
<223> OTHER INFORMATION: Xaa can be any naturally occurring amino acid
<220> FEATURE:
<221> NAME/KEY: MISC_FEATURE
<222> LOCATION: (26)..(26)
<223> OTHER INFORMATION: Xaa can be any naturally occurring amino acid
<220> FEATURE:
<221> NAME/KEY: MISC_FEATURE
<222> LOCATION: (30)..(30)
<223> OTHER INFORMATION: Xaa can be any naturally occurring amino acid
<220> FEATURE:
<221> NAME/KEY: MISC_FEATURE
<222> LOCATION: (31)..(31)
<223> OTHER INFORMATION: Xaa can be any naturally occurring amino acid

<400> SEQUENCE: 165

Thr Thr Gln Leu Ile Leu Asn Gly Ser Val Ala Glu Asn Lys Thr Ile
1               5                   10                  15

Ala Arg Arg Asn Gly Tyr Xaa Phe Leu Xaa Gln Phe Gln Xaa Xaa
            20                  25                  30

<210> SEQ ID NO 166
<211> LENGTH: 20
<212> TYPE: PRT
<213> ORGANISM: Simian immunodeficiency virus

<400> SEQUENCE: 166

Cys Asn Met Pro Asn Phe Asn Gly Thr Gly Thr Gly Arg Cys Asn Asn
1               5                   10                  15

Ile Ser Thr Val
            20

<210> SEQ ID NO 167
<211> LENGTH: 12
<212> TYPE: PRT
<213> ORGANISM: Simian immunodeficiency virus

<400> SEQUENCE: 167

Asn Val Thr Gly Ile Ile Leu Glu Thr Gly His Gly
1               5                   10

<210> SEQ ID NO 168
<211> LENGTH: 10
<212> TYPE: PRT
<213> ORGANISM: Simian immunodeficiency virus

<400> SEQUENCE: 168

Val Gln Ile Pro Asn Val Thr Glu Asn Phe
1               5                   10

<210> SEQ ID NO 169
<211> LENGTH: 8
<212> TYPE: PRT
```

<213> ORGANISM: Simian immunodeficiency virus

<400> SEQUENCE: 169

Asn Val Thr Gly Ile Ile Leu Glu
1               5

<210> SEQ ID NO 170
<211> LENGTH: 29
<212> TYPE: PRT
<213> ORGANISM: Simian immunodeficiency virus

<400> SEQUENCE: 170

Ser Arg Glu Lys Arg Ala Ala Phe Gly Leu Gly Ala Leu Phe Leu Gly
1               5                   10                  15

Phe Leu Gly Ala Ala Gly Ser Thr Met Gly Ala Ala Ser
            20                  25

<210> SEQ ID NO 171
<211> LENGTH: 10
<212> TYPE: PRT
<213> ORGANISM: Simian immunodeficiency virus

<400> SEQUENCE: 171

Tyr Thr Thr Val Pro Trp Asn Asn Thr Trp
1               5                   10

<210> SEQ ID NO 172
<211> LENGTH: 26
<212> TYPE: PRT
<213> ORGANISM: Simian immunodeficiency virus

<400> SEQUENCE: 172

Glu Ile Trp Asn Asn Leu Thr Trp Gln Asp Trp Asp Lys Arg Val Lys
1               5                   10                  15

Asn Tyr Ser Gly Val Ile Phe Ser Leu Ile
            20                  25

<210> SEQ ID NO 173
<211> LENGTH: 20
<212> TYPE: PRT
<213> ORGANISM: Simian immunodeficiency virus

<400> SEQUENCE: 173

Asn Cys Ser Phe Asn Gln Thr Thr Glu Phe Arg Asp Lys Lys Lys Gln
1               5                   10                  15

Ile Tyr Ser Leu
            20

<210> SEQ ID NO 174
<211> LENGTH: 34
<212> TYPE: PRT
<213> ORGANISM: Simian immunodeficiency virus

<400> SEQUENCE: 174

Glu Asn Val Val Gly Asp Thr Arg Lys Ala Tyr Cys His Val Asn Ala
1               5                   10                  15

Thr Leu Trp Asp Gln Ser Leu Ser Arg Ala Met Glu Ala Ile Asn Lys
            20                  25                  30

Thr Leu

<210> SEQ ID NO 175
<211> LENGTH: 39

-continued

```
<212> TYPE: PRT
<213> ORGANISM: Simian immunodeficiency virus

<400> SEQUENCE: 175

His Arg Asn Gly Thr Leu Val Ala Pro Cys Arg Leu Arg Gln Ile Val
1               5                   10                  15

Asn His Trp Gly Ile Val Ser Lys Gly Ile Tyr Leu Pro Pro Arg Arg
            20                  25                  30

Gly Thr Leu Lys Cys Asn Ser
        35

<210> SEQ ID NO 176
<211> LENGTH: 35
<212> TYPE: PRT
<213> ORGANISM: Simian immunodeficiency virus

<400> SEQUENCE: 176

Ala Thr Ala Leu His Leu Asn Gly Thr Leu Glu Glu Asn Glu Thr Lys
1               5                   10                  15

Ala Tyr Phe Ala Asp Val Asn Val Asn Pro Pro Leu Leu Val Lys Phe
            20                  25                  30

Asn Glu Ser
        35

<210> SEQ ID NO 177
<211> LENGTH: 18
<212> TYPE: PRT
<213> ORGANISM: Simian immunodeficiency virus

<400> SEQUENCE: 177

Cys Asn Asp Gln Gly Tyr Thr Gly Asn Gly Thr Cys Ser Asn Val Thr
1               5                   10                  15

Val Val

<210> SEQ ID NO 178
<211> LENGTH: 12
<212> TYPE: PRT
<213> ORGANISM: Simian immunodeficiency virus

<400> SEQUENCE: 178

Asn Ile Thr Gly Leu Ile Met Thr Ala Glu Lys Gly
1               5                   10

<210> SEQ ID NO 179
<211> LENGTH: 10
<212> TYPE: PRT
<213> ORGANISM: Simian immunodeficiency virus

<400> SEQUENCE: 179

Val Pro Leu Ala Asn Val Ser Ile Asp Phe
1               5                   10

<210> SEQ ID NO 180
<211> LENGTH: 8
<212> TYPE: PRT
<213> ORGANISM: Simian immunodeficiency virus

<400> SEQUENCE: 180

Asn Ile Thr Gly Leu Ile Met Thr
1               5

<210> SEQ ID NO 181
```

```
<211> LENGTH: 28
<212> TYPE: PRT
<213> ORGANISM: Simian immunodeficiency virus

<400> SEQUENCE: 181

Thr Arg Ser Arg Arg Asp Val Gly Ile Gly Leu Leu Phe Leu Gly Phe
1               5                   10                  15

Leu Ser Ala Ala Gly Ser Thr Met Gly Ala Ala Ser
            20                  25

<210> SEQ ID NO 182
<211> LENGTH: 10
<212> TYPE: PRT
<213> ORGANISM: Simian immunodeficiency virus

<400> SEQUENCE: 182

His Ser Ser Val Pro Trp Asn Leu Ser Trp
1               5                   10

<210> SEQ ID NO 183
<211> LENGTH: 26
<212> TYPE: PRT
<213> ORGANISM: Simian immunodeficiency virus

<400> SEQUENCE: 183

Cys Ile Trp Asn Asn Leu Thr Trp Gln Glu Trp Asp Arg Leu Val Gln
1               5                   10                  15

Asn Ala Ser Glu Thr Ile Tyr Ser Leu Leu
            20                  25

<210> SEQ ID NO 184
<211> LENGTH: 20
<212> TYPE: PRT
<213> ORGANISM: Simian immunodeficiency virus

<400> SEQUENCE: 184

Asn Cys Ser Phe Gln Gln Thr Thr Glu Phe Arg Asp Lys Lys Lys Gln
1               5                   10                  15

Ile Tyr Ser Leu
            20

<210> SEQ ID NO 185
<211> LENGTH: 33
<212> TYPE: PRT
<213> ORGANISM: Simian immunodeficiency virus

<400> SEQUENCE: 185

Glu Asn Val Val Gly Asp Thr Arg Lys Ala Tyr Cys Trp Val Asn Ala
1               5                   10                  15

Thr Leu Trp Tyr Lys Ser Leu Asp Asn Ala Trp Arg Leu Pro Lys His
            20                  25                  30

Arg

<210> SEQ ID NO 186
<211> LENGTH: 40
<212> TYPE: PRT
<213> ORGANISM: Simian immunodeficiency virus

<400> SEQUENCE: 186

Ala Leu Asn Lys Thr His Leu Leu Ala Gln Cys Arg Leu Arg Gln Ile
1               5                   10                  15

Val Asn His Trp Gly Ile Val Ser Lys Gly Ile Tyr Leu Pro Pro Arg
```

```
              20                  25                  30

Lys Gly His Ile Lys Cys Val Ser
        35                  40

<210> SEQ ID NO 187
<211> LENGTH: 35
<212> TYPE: PRT
<213> ORGANISM: Simian immunodeficiency virus

<400> SEQUENCE: 187

Ala Thr Ala Leu His Leu Asn Gly Thr Leu Glu Glu Lys Glu Thr Lys
1               5                   10                  15

Ala Tyr Phe Val Asn Ala Thr Asn Asn Pro Pro Leu Leu Val Lys Phe
            20                  25                  30

Asn Glu Ser
        35

<210> SEQ ID NO 188
<211> LENGTH: 18
<212> TYPE: PRT
<213> ORGANISM: Simian immunodeficiency virus

<400> SEQUENCE: 188

Cys Lys Asp Gln Asn Tyr Thr Gly Asn Gly Ile Cys Tyr Asn Val Thr
1               5                   10                  15

Val Val

<210> SEQ ID NO 189
<211> LENGTH: 12
<212> TYPE: PRT
<213> ORGANISM: Simian immunodeficiency virus

<400> SEQUENCE: 189

Asn Ile Thr Gly Leu Ile Met Thr Ala Glu Gly Gly
1               5                   10

<210> SEQ ID NO 190
<211> LENGTH: 10
<212> TYPE: PRT
<213> ORGANISM: Simian immunodeficiency virus

<400> SEQUENCE: 190

Val Pro Ile Ala Asn Val Ser Ile Lys Phe
1               5                   10

<210> SEQ ID NO 191
<211> LENGTH: 8
<212> TYPE: PRT
<213> ORGANISM: Simian immunodeficiency virus

<400> SEQUENCE: 191

Asn Ile Thr Gly Leu Ile Met Thr
1               5

<210> SEQ ID NO 192
<211> LENGTH: 28
<212> TYPE: PRT
<213> ORGANISM: Simian immunodeficiency virus

<400> SEQUENCE: 192

Thr Arg Ser Arg Arg Asp Val Gly Ile Gly Leu Leu Phe Leu Gly Phe
1               5                   10                  15
```

Leu Ser Ala Ala Gly Ser Thr Met Gly Ala Ala Ser
            20                  25

<210> SEQ ID NO 193
<211> LENGTH: 10
<212> TYPE: PRT
<213> ORGANISM: Simian immunodeficiency virus

<400> SEQUENCE: 193

His Ser Ser Val Pro Trp Asn Leu Ser Trp
1               5                   10

<210> SEQ ID NO 194
<211> LENGTH: 26
<212> TYPE: PRT
<213> ORGANISM: Simian immunodeficiency virus

<400> SEQUENCE: 194

Cys Ile Trp Asn Asn Leu Thr Trp Gln Glu Trp Asp Lys Leu Val Gln
1               5                   10                  15

Asn Ser Ser Glu Thr Ile Tyr Ser Leu Leu
            20                  25

<210> SEQ ID NO 195
<211> LENGTH: 20
<212> TYPE: PRT
<213> ORGANISM: Simian immunodeficiency virus

<400> SEQUENCE: 195

Asn Cys Ser Phe Asn Gln Thr Thr Glu Phe Arg Asp Lys Lys Lys Gln
1               5                   10                  15

Ile Tyr Ser Leu
            20

<210> SEQ ID NO 196
<211> LENGTH: 34
<212> TYPE: PRT
<213> ORGANISM: Simian immunodeficiency virus

<400> SEQUENCE: 196

Glu Asn Val Val Gly Asp Thr Arg Lys Ala Tyr Cys Ser Val Asn Ala
1               5                   10                  15

Thr Thr Trp Tyr Arg Asn Leu Asp Trp Ala Met Ala Ala Ile Asn Thr
            20                  25                  30

Thr Met

<210> SEQ ID NO 197
<211> LENGTH: 39
<212> TYPE: PRT
<213> ORGANISM: Simian immunodeficiency virus

<400> SEQUENCE: 197

Asn Thr His Gly Thr Leu Val Ala Pro Cys Arg Leu Arg Gln Ile Val
1               5                   10                  15

Asn His Trp Gly Ile Val Ser Lys Gly Val Tyr Leu Pro Pro Arg Arg
            20                  25                  30

Gly Thr Val Lys Cys His Ser
        35

<210> SEQ ID NO 198
<211> LENGTH: 35
<212> TYPE: PRT

<213> ORGANISM: Simian immunodeficiency virus

<400> SEQUENCE: 198

Ala Thr Ala Leu His Leu Asn Gly Ser Leu Glu Glu Glu Thr Lys
1               5                   10                  15

Ala Tyr Phe Val Asn Thr Ser Val Asn Thr Pro Leu Leu Val Lys Phe
            20                  25                  30

Asn Val Ser
        35

<210> SEQ ID NO 199
<211> LENGTH: 18
<212> TYPE: PRT
<213> ORGANISM: Simian immunodeficiency virus

<400> SEQUENCE: 199

Cys Arg Asp Gln Asn Phe Thr Gly Lys Gly Gln Cys Ser Asn Val Ser
1               5                   10                  15

Val Val

<210> SEQ ID NO 200
<211> LENGTH: 12
<212> TYPE: PRT
<213> ORGANISM: Simian immunodeficiency virus

<400> SEQUENCE: 200

Asn Ile Thr Gly Leu Ile Met Thr Ala Glu Lys Asp
1               5                   10

<210> SEQ ID NO 201
<211> LENGTH: 10
<212> TYPE: PRT
<213> ORGANISM: Simian immunodeficiency virus

<400> SEQUENCE: 201

Val Thr Leu Ala Asn Val Ser Ile Arg Phe
1               5                   10

<210> SEQ ID NO 202
<211> LENGTH: 8
<212> TYPE: PRT
<213> ORGANISM: Simian immunodeficiency virus

<400> SEQUENCE: 202

Asn Ile Thr Gly Leu Ile Met Thr
1               5

<210> SEQ ID NO 203
<211> LENGTH: 28
<212> TYPE: PRT
<213> ORGANISM: Simian immunodeficiency virus

<400> SEQUENCE: 203

Thr Arg Ser Arg Arg Asp Val Gly Ile Gly Leu Leu Phe Leu Gly Phe
1               5                   10                  15

Leu Ser Ala Ala Gly Ser Thr Met Gly Ala Ala Ser
            20                  25

<210> SEQ ID NO 204
<211> LENGTH: 10
<212> TYPE: PRT
<213> ORGANISM: Simian immunodeficiency virus

```
<400> SEQUENCE: 204

His Ser Ser Val Pro Trp Asn Leu Thr Trp
1               5                   10

<210> SEQ ID NO 205
<211> LENGTH: 26
<212> TYPE: PRT
<213> ORGANISM: Simian immunodeficiency virus

<400> SEQUENCE: 205

Cys Ile Trp Asn Asn Leu Thr Trp Gln Glu Trp Asp Arg Leu Val Glu
1               5                   10                  15

Asn Ser Thr Gly Thr Ile Tyr Ser Leu Leu
            20                  25

<210> SEQ ID NO 206
<211> LENGTH: 20
<212> TYPE: PRT
<213> ORGANISM: Simian immunodeficiency virus

<400> SEQUENCE: 206

Lys Cys Ser Phe Asn Gln Thr Thr Glu Phe Arg Asp Lys Lys Lys Gln
1               5                   10                  15

Ile Tyr Ser Leu
            20

<210> SEQ ID NO 207
<211> LENGTH: 34
<212> TYPE: PRT
<213> ORGANISM: Simian immunodeficiency virus

<400> SEQUENCE: 207

Glu Asn Val Val Gly Asp Thr Arg Lys Ala Phe Cys Ile Val Asn Ala
1               5                   10                  15

Thr Glu Trp Ser Asn Ala Leu Asn Glu Ser Lys Ile Ala Ile Asn Glu
            20                  25                  30

Thr Leu

<210> SEQ ID NO 208
<211> LENGTH: 39
<212> TYPE: PRT
<213> ORGANISM: Simian immunodeficiency virus

<400> SEQUENCE: 208

Gly Lys Asn Gly Ser Ile Val Ala Gln Cys Arg Leu Arg Gln Ile Val
1               5                   10                  15

Asn His Trp Gly Ile Val Ser Lys Gly Ile Tyr Leu Pro Pro Arg Arg
            20                  25                  30

Gly Thr Ile Lys Cys Thr Ser
            35

<210> SEQ ID NO 209
<211> LENGTH: 35
<212> TYPE: PRT
<213> ORGANISM: Simian immunodeficiency virus

<400> SEQUENCE: 209

Ala Thr Ala Leu His Leu Asn Gly Thr Leu Glu Glu Asn Lys Thr Thr
1               5                   10                  15

Ala Tyr Phe Ala Asp Ser Thr His Asn Gln Pro Leu Leu Val Lys Phe
            20                  25                  30
```

His Lys Ala
         35

<210> SEQ ID NO 210
<211> LENGTH: 18
<212> TYPE: PRT
<213> ORGANISM: Simian immunodeficiency virus

<400> SEQUENCE: 210

Cys Lys Asp Gln Asn Phe Thr Gly Lys Gly Pro Cys Ser Asn Val Ser
1               5                   10                  15

Val Val

<210> SEQ ID NO 211
<211> LENGTH: 12
<212> TYPE: PRT
<213> ORGANISM: Simian immunodeficiency virus

<400> SEQUENCE: 211

Asn Ile Thr Gly Leu Ile Leu Thr Ala Glu Gly Gly
1               5                   10

<210> SEQ ID NO 212
<211> LENGTH: 10
<212> TYPE: PRT
<213> ORGANISM: Simian immunodeficiency virus

<400> SEQUENCE: 212

Val Pro Leu Ala Asn Met Thr Val Asp Phe
1               5                   10

<210> SEQ ID NO 213
<211> LENGTH: 8
<212> TYPE: PRT
<213> ORGANISM: Simian immunodeficiency virus

<400> SEQUENCE: 213

Asn Ile Thr Gly Leu Ile Leu Thr
1               5

<210> SEQ ID NO 214
<211> LENGTH: 28
<212> TYPE: PRT
<213> ORGANISM: Simian immunodeficiency virus

<400> SEQUENCE: 214

Thr Arg Ser Lys Arg Asp Val Gly Ile Gly Leu Leu Phe Leu Gly Phe
1               5                   10                  15

Leu Ser Ala Ala Gly Ser Thr Met Gly Ala Ala Ser
            20                  25

<210> SEQ ID NO 215
<211> LENGTH: 10
<212> TYPE: PRT
<213> ORGANISM: Simian immunodeficiency virus

<400> SEQUENCE: 215

His Ser Ser Val Pro Trp Asn Ile Thr Trp
1               5                   10

<210> SEQ ID NO 216
<211> LENGTH: 26
<212> TYPE: PRT

<213> ORGANISM: Simian immunodeficiency virus

<400> SEQUENCE: 216

Cys Ile Trp Asn Asn Leu Thr Trp Gln Glu Trp Asp Lys Leu Val Lys
1               5                   10                  15

Asn Ser Ser Glu Thr Ile Tyr Ser Leu Leu
            20                  25

<210> SEQ ID NO 217
<211> LENGTH: 20
<212> TYPE: PRT
<213> ORGANISM: Simian immunodeficiency virus

<400> SEQUENCE: 217

Asn Cys Ser Phe Asn Gln Thr Thr Glu Phe Arg Asp Lys Lys Lys Gln
1               5                   10                  15

Ile Tyr Ser Leu
            20

<210> SEQ ID NO 218
<211> LENGTH: 34
<212> TYPE: PRT
<213> ORGANISM: Simian immunodeficiency virus

<400> SEQUENCE: 218

Glu Asn Ile Val Gly Asn Thr Arg Lys Ala Tyr Cys Thr Val Asn Tyr
1               5                   10                  15

Gln Glu Trp Ser His Ala Ile Gly Glu Ala Lys Lys Val Ala Glu Glu
            20                  25                  30

Ala Leu

<210> SEQ ID NO 219
<211> LENGTH: 39
<212> TYPE: PRT
<213> ORGANISM: Simian immunodeficiency virus

<400> SEQUENCE: 219

Asn Ser Ser Arg Pro Leu Val Ala Pro Cys Lys Leu Arg Gln Ile Val
1               5                   10                  15

Asn His Trp Gly Ile Val Ser Lys Gly Ile Tyr Leu Pro Pro Arg Arg
            20                  25                  30

Gly Asn Leu Thr Cys Arg Ser
            35

<210> SEQ ID NO 220
<211> LENGTH: 35
<212> TYPE: PRT
<213> ORGANISM: Simian immunodeficiency virus

<400> SEQUENCE: 220

Ala Thr Ala Leu His Leu Asn Gly Thr Leu Glu Lys His Asn Thr Thr
1               5                   10                  15

Ala Tyr Phe Ala Thr Pro Thr His Asn Lys Pro Leu Leu Ile Lys Phe
            20                  25                  30

Asn Lys Ser
        35

<210> SEQ ID NO 221
<211> LENGTH: 18
<212> TYPE: PRT
<213> ORGANISM: Simian immunodeficiency virus

<400> SEQUENCE: 221

Cys Asn Ser Ala Asn Phe Thr Gly Val Gly Thr Cys Asn Asn Val Ser
1               5                   10                  15

Val Val

<210> SEQ ID NO 222
<211> LENGTH: 10
<212> TYPE: PRT
<213> ORGANISM: Simian immunodeficiency virus

<400> SEQUENCE: 222

Asn Ile Thr Gly Phe Ile Thr Thr Trp Asp
1               5                   10

<210> SEQ ID NO 223
<211> LENGTH: 10
<212> TYPE: PRT
<213> ORGANISM: Simian immunodeficiency virus

<400> SEQUENCE: 223

Val Pro Leu Ser Asn Val Ser Val Asp Phe
1               5                   10

<210> SEQ ID NO 224
<211> LENGTH: 8
<212> TYPE: PRT
<213> ORGANISM: Simian immunodeficiency virus

<400> SEQUENCE: 224

Asn Ile Thr Gly Phe Ile Thr Thr
1               5

<210> SEQ ID NO 225
<211> LENGTH: 28
<212> TYPE: PRT
<213> ORGANISM: Simian immunodeficiency virus

<400> SEQUENCE: 225

Thr Arg Ser Lys Arg Asp Val Gly Ile Gly Leu Leu Phe Leu Gly Phe
1               5                   10                  15

Leu Ser Ala Ala Gly Ser Thr Met Gly Ala Ala Ser
            20                  25

<210> SEQ ID NO 226
<211> LENGTH: 10
<212> TYPE: PRT
<213> ORGANISM: Simian immunodeficiency virus

<400> SEQUENCE: 226

His Ser Asn Val Val Trp Asn Met Thr Trp
1               5                   10

<210> SEQ ID NO 227
<211> LENGTH: 26
<212> TYPE: PRT
<213> ORGANISM: Simian immunodeficiency virus

<400> SEQUENCE: 227

Cys Ile Trp Asn Asn Leu Thr Trp Gln Gln Trp Glu Lys Leu Val Ala
1               5                   10                  15

Asn Ser Thr Glu Glu Ile Tyr Thr Leu Leu
            20                  25

<210> SEQ ID NO 228
<211> LENGTH: 20
<212> TYPE: PRT
<213> ORGANISM: Simian immunodeficiency virus

<400> SEQUENCE: 228

Asn Cys Ser Phe Asn Gln Thr Thr Glu Phe Arg Asp Lys Lys Lys Asn
1               5                   10                  15

Ile Tyr Ser Leu
            20

<210> SEQ ID NO 229
<211> LENGTH: 34
<212> TYPE: PRT
<213> ORGANISM: Simian immunodeficiency virus

<400> SEQUENCE: 229

Glu Asn Ile Phe Gly Asp Thr Arg Lys Ala Phe Cys Tyr Val Asn Ala
1               5                   10                  15

Thr Glu Trp Arg Arg Thr Leu Glu Met Ala Lys Thr Ala Leu Arg Glu
            20                  25                  30

Ala Thr

<210> SEQ ID NO 230
<211> LENGTH: 39
<212> TYPE: PRT
<213> ORGANISM: Simian immunodeficiency virus

<400> SEQUENCE: 230

Thr Asp Gln Thr Asn Leu Val Ala Pro Cys Arg Leu Arg Gln Ile Val
1               5                   10                  15

Asn His Trp Gly Ile Val Ala Lys Ala Ile Tyr Leu Pro Pro Arg Arg
            20                  25                  30

Gly Thr Val Lys Cys Val Ser
        35

<210> SEQ ID NO 231
<211> LENGTH: 35
<212> TYPE: PRT
<213> ORGANISM: Simian immunodeficiency virus

<400> SEQUENCE: 231

Ala Ser Trp Leu His Leu Asn Gly Thr Tyr Glu Lys Glu Lys Thr Lys
1               5                   10                  15

Val Tyr His Thr Asn Val Thr Asn Asn Pro Pro Leu Leu Val Lys Phe
            20                  25                  30

Asn Glu Thr
        35

<210> SEQ ID NO 232
<211> LENGTH: 18
<212> TYPE: PRT
<213> ORGANISM: Simian immunodeficiency virus

<400> SEQUENCE: 232

Cys Asn Asp Ala Asn Phe Thr Gly Ala Gly Glu Cys Thr Asn Val Ser
1               5                   10                  15

Val Val

```
<210> SEQ ID NO 233
<211> LENGTH: 8
<212> TYPE: PRT
<213> ORGANISM: Simian immunodeficiency virus

<400> SEQUENCE: 233

Asn Ile Thr Gly Phe Leu Met Thr
1               5

<210> SEQ ID NO 234
<211> LENGTH: 10
<212> TYPE: PRT
<213> ORGANISM: Simian immunodeficiency virus

<400> SEQUENCE: 234

Val Pro Leu Pro Asn Val Ser Ile Glu Phe
1               5                   10

<210> SEQ ID NO 235
<211> LENGTH: 8
<212> TYPE: PRT
<213> ORGANISM: Simian immunodeficiency virus

<400> SEQUENCE: 235

Asn Ile Thr Gly Phe Leu Met Thr
1               5

<210> SEQ ID NO 236
<211> LENGTH: 28
<212> TYPE: PRT
<213> ORGANISM: Simian immunodeficiency virus

<400> SEQUENCE: 236

Thr Arg Ser Lys Arg Asp Val Gly Ile Gly Leu Leu Phe Leu Gly Phe
1               5                   10                  15

Leu Ser Ala Ala Gly Ser Thr Met Gly Ala Ala Ser
            20                  25

<210> SEQ ID NO 237
<211> LENGTH: 10
<212> TYPE: PRT
<213> ORGANISM: Simian immunodeficiency virus

<400> SEQUENCE: 237

His Ser Thr Val Val Trp Asn Asp Thr Trp
1               5                   10

<210> SEQ ID NO 238
<211> LENGTH: 26
<212> TYPE: PRT
<213> ORGANISM: Simian immunodeficiency virus

<400> SEQUENCE: 238

Cys Ile Trp Gln Asn Leu Thr Trp Gln Gln Trp Ser Glu Leu Val Asp
1               5                   10                  15

Asn Ser Thr Asp Thr Ile Tyr Thr Leu Leu
            20                  25

<210> SEQ ID NO 239
<211> LENGTH: 20
<212> TYPE: PRT
<213> ORGANISM: Simian immunodeficiency virus

<400> SEQUENCE: 239
```

-continued

Glu Cys Phe Phe Asn Gln Thr Thr Glu Phe Arg Asp Lys Lys Lys Gln
1               5                   10                  15

Ile Tyr Ser Leu
            20

<210> SEQ ID NO 240
<211> LENGTH: 35
<212> TYPE: PRT
<213> ORGANISM: Simian immunodeficiency virus

<400> SEQUENCE: 240

Arg Asn Val Ile Gly Asp Thr Arg Lys Ala Phe Cys Tyr Val Asn Lys
1               5                   10                  15

Thr Leu Trp Glu Asn Ala Leu Arg Gln Gln Lys Gln Thr Lys Leu Leu
            20                  25                  30

Lys Thr Pro
        35

<210> SEQ ID NO 241
<211> LENGTH: 39
<212> TYPE: PRT
<213> ORGANISM: Simian immunodeficiency virus

<400> SEQUENCE: 241

Glu Ile Asp Gly Met Leu Ile Ala Pro Cys Arg Leu Arg Gln Ile Val
1               5                   10                  15

Asn His Trp Gly Ile Val Ser Arg Gly Ile Tyr Leu Pro Pro Arg Glu
            20                  25                  30

Gly Gln Val Lys Cys Val Ser
        35

<210> SEQ ID NO 242
<211> LENGTH: 35
<212> TYPE: PRT
<213> ORGANISM: Simian immunodeficiency virus

<400> SEQUENCE: 242

Ala Thr Ala Leu His Leu Asn Gly Ser Val Glu Glu Gly Glu Thr Lys
1               5                   10                  15

Ala Tyr Tyr Val Glu Ala Lys His Asn Ala Pro Leu Leu Ile Lys Phe
            20                  25                  30

Asn Lys Ala
        35

<210> SEQ ID NO 243
<211> LENGTH: 18
<212> TYPE: PRT
<213> ORGANISM: Simian immunodeficiency virus

<400> SEQUENCE: 243

Cys Lys Asp Glu Asn Phe Arg Gly Lys Gly Asn Cys Thr Thr Val Arg
1               5                   10                  15

Ile Val

<210> SEQ ID NO 244
<211> LENGTH: 8
<212> TYPE: PRT
<213> ORGANISM: Simian immunodeficiency virus

<400> SEQUENCE: 244

Ser Ile Thr Gly Phe Ile Met Thr

<210> SEQ ID NO 245
<211> LENGTH: 9
<212> TYPE: PRT
<213> ORGANISM: Simian immunodeficiency virus

<400> SEQUENCE: 245

Ile Pro Ile Asn Ile Thr Thr Glu Phe
1               5

<210> SEQ ID NO 246
<211> LENGTH: 8
<212> TYPE: PRT
<213> ORGANISM: Simian immunodeficiency virus

<400> SEQUENCE: 246

Ser Ile Thr Gly Phe Ile Met Thr
1               5

<210> SEQ ID NO 247
<211> LENGTH: 28
<212> TYPE: PRT
<213> ORGANISM: Simian immunodeficiency virus

<400> SEQUENCE: 247

Ser Arg Ser Lys Arg Glu Ile Gly Met Gly Met Ile Phe Met Gly Phe
1               5                   10                  15

Leu Ser Ala Ala Gly Ser Thr Met Gly Ala Ala Ser
            20                  25

<210> SEQ ID NO 248
<211> LENGTH: 10
<212> TYPE: PRT
<213> ORGANISM: Simian immunodeficiency virus

<400> SEQUENCE: 248

His Ser Ser Leu Glu Trp Asn Ser Ser Trp
1               5                   10

<210> SEQ ID NO 249
<211> LENGTH: 26
<212> TYPE: PRT
<213> ORGANISM: Simian immunodeficiency virus

<400> SEQUENCE: 249

Cys Ile Trp Ser Gln Tyr Thr Trp Gln Gln Trp Asp Glu Glu Ile Arg
1               5                   10                  15

Asn Ile Ser Asp Val Ile Tyr Leu Ser Leu
            20                  25

<210> SEQ ID NO 250
<211> LENGTH: 20
<212> TYPE: PRT
<213> ORGANISM: Simian immunodeficiency virus

<400> SEQUENCE: 250

Glu Cys Asn Phe Asn Gln Ser Thr Gly Phe Lys Asp Lys Lys Gln Lys
1               5                   10                  15

Met Lys Ala Ile
            20

<210> SEQ ID NO 251

```
<211> LENGTH: 34
<212> TYPE: PRT
<213> ORGANISM: Simian immunodeficiency virus

<400> SEQUENCE: 251

Glu Ile Ala Thr Gly Asp Thr Arg Lys Ala Phe Cys Thr Val Asn Lys
1               5                   10                  15

Thr Leu Trp Glu Gln Ala Arg Asn Lys Thr Glu His Val Leu Ala Glu
            20                  25                  30

His Trp

<210> SEQ ID NO 252
<211> LENGTH: 39
<212> TYPE: PRT
<213> ORGANISM: Simian immunodeficiency virus

<400> SEQUENCE: 252

Ile Thr Asn Gly Ala Leu Ile Ala His Cys Arg Ile Lys Gln Ile Val
1               5                   10                  15

Asn His Trp Gly Ile Val Ser Lys Gly Ile Tyr Leu Ala Pro Arg Arg
            20                  25                  30

Gly Asn Val Ser Cys Thr Ser
        35

<210> SEQ ID NO 253
<211> LENGTH: 32
<212> TYPE: PRT
<213> ORGANISM: Simian immunodeficiency virus

<400> SEQUENCE: 253

Ala Thr Trp Leu Leu Leu Asn Gly Thr Tyr Gln Thr Asn Thr Ser Val
1               5                   10                  15

Val Met Asn Gly Ala Lys Met Asn Leu Cys Leu Asp Leu Glu Lys Asn
            20                  25                  30

<210> SEQ ID NO 254
<211> LENGTH: 18
<212> TYPE: PRT
<213> ORGANISM: Simian immunodeficiency virus

<400> SEQUENCE: 254

Cys Glu Asp Glu Asp Phe Thr Gly Val Gly Met Cys Lys Asn Val Ser
1               5                   10                  15

Val Val

<210> SEQ ID NO 255
<211> LENGTH: 9
<212> TYPE: PRT
<213> ORGANISM: Simian immunodeficiency virus

<400> SEQUENCE: 255

Ser Ile Thr Gly Ile Met Leu Glu Gly
1               5

<210> SEQ ID NO 256
<211> LENGTH: 9
<212> TYPE: PRT
<213> ORGANISM: Simian immunodeficiency virus

<400> SEQUENCE: 256

Val Arg Leu Asn Thr Ser Val Trp Phe
1               5
```

<210> SEQ ID NO 257
<211> LENGTH: 8
<212> TYPE: PRT
<213> ORGANISM: Simian immunodeficiency virus

<400> SEQUENCE: 257

Ser Ile Thr Gly Ile Met Leu Glu
1               5

<210> SEQ ID NO 258
<211> LENGTH: 28
<212> TYPE: PRT
<213> ORGANISM: Simian immunodeficiency virus

<400> SEQUENCE: 258

Ser Arg Gln Lys Arg Gly Ile Gly Ile Gly Leu Phe Phe Leu Gly Leu
1               5                   10                  15

Leu Ser Ala Ala Gly Ser Thr Met Gly Ala Ala Ser
            20                  25

<210> SEQ ID NO 259
<211> LENGTH: 10
<212> TYPE: PRT
<213> ORGANISM: Simian immunodeficiency virus

<400> SEQUENCE: 259

His Thr Thr Val Pro Trp Asn Asn Ser Trp
1               5                   10

<210> SEQ ID NO 260
<211> LENGTH: 26
<212> TYPE: PRT
<213> ORGANISM: Simian immunodeficiency virus

<400> SEQUENCE: 260

Cys Ile Trp Glu Asn Met Thr Trp Gln Glu Trp Asp Arg Leu Val Gln
1               5                   10                  15

Asn Ser Thr Gly Gln Ile Tyr Asn Ile Leu
            20                  25

<210> SEQ ID NO 261
<211> LENGTH: 20
<212> TYPE: PRT
<213> ORGANISM: Simian immunodeficiency virus

<400> SEQUENCE: 261

Asn Cys Thr Phe Asn Thr Thr Thr Glu Leu Arg Asp Lys Lys Gln Gln
1               5                   10                  15

Ile Tyr Ser Leu
            20

<210> SEQ ID NO 262
<211> LENGTH: 34
<212> TYPE: PRT
<213> ORGANISM: Simian immunodeficiency virus

<400> SEQUENCE: 262

Glu Ala Leu Ile Gly Asn Pro Arg Lys Ala Ser Cys His Leu Asn Gly
1               5                   10                  15

Thr Leu Trp Asn Asn Ile Leu Asn Arg Ile Lys Gln Lys Ile Lys Asn
            20                  25                  30

Ser Thr

<210> SEQ ID NO 263
<211> LENGTH: 39
<212> TYPE: PRT
<213> ORGANISM: Simian immunodeficiency virus

<400> SEQUENCE: 263

Ser Asp Thr Ser Glu Tyr Ile Leu Pro Cys Lys Ile Arg Gln Val Val
1               5                   10                  15

Asn Ser Trp Met Arg Val Gly Lys Gly Ile Phe Ala Pro Pro Arg Arg
            20                  25                  30

Gly Thr Ile Thr Cys Asn Ser
        35

<210> SEQ ID NO 264
<211> LENGTH: 39
<212> TYPE: PRT
<213> ORGANISM: Simian immunodeficiency virus

<400> SEQUENCE: 264

Thr Thr Gln Leu Ile Leu Asn Gly Ser Leu Ala Glu Glu Glu Val
1               5                   10                  15

Val Phe Arg Thr Lys Asn Met Thr Ala Pro Gly Leu Ser Asp Thr Val
            20                  25                  30

Ile Val Gln Leu Lys Arg Ala
        35

<210> SEQ ID NO 265
<211> LENGTH: 18
<212> TYPE: PRT
<213> ORGANISM: Simian immunodeficiency virus

<400> SEQUENCE: 265

Cys Asn Asp Lys Asp Tyr Pro Gly Lys Gly Lys Cys Lys Asn Val Ser
1               5                   10                  15

Thr Val

<210> SEQ ID NO 266
<211> LENGTH: 12
<212> TYPE: PRT
<213> ORGANISM: Simian immunodeficiency virus

<400> SEQUENCE: 266

Thr Ile Thr Gly Leu Leu Leu Glu Val Gln Asn Gly
1               5                   10

<210> SEQ ID NO 267
<211> LENGTH: 10
<212> TYPE: PRT
<213> ORGANISM: Simian immunodeficiency virus

<400> SEQUENCE: 267

Val Ile Leu Ile Asn Val Thr Glu Glu Phe
1               5                   10

<210> SEQ ID NO 268
<211> LENGTH: 8
<212> TYPE: PRT
<213> ORGANISM: Simian immunodeficiency virus

<400> SEQUENCE: 268

Thr Ile Thr Gly Leu Leu Leu Glu
1               5

<210> SEQ ID NO 269
<211> LENGTH: 29
<212> TYPE: PRT
<213> ORGANISM: Simian immunodeficiency virus

<400> SEQUENCE: 269

Asp Arg Ser Lys Arg Ala Ala Phe Gly Leu Gly Ala Leu Phe Leu Gly
1               5                   10                  15

Phe Leu Gly Ala Ala Gly Ser Thr Met Gly Ala Ala Ser
            20                  25

<210> SEQ ID NO 270
<211> LENGTH: 10
<212> TYPE: PRT
<213> ORGANISM: Simian immunodeficiency virus

<400> SEQUENCE: 270

Tyr Ser Thr Val Pro Trp Asn Thr Ser Trp
1               5                   10

<210> SEQ ID NO 271
<211> LENGTH: 26
<212> TYPE: PRT
<213> ORGANISM: Simian immunodeficiency virus

<400> SEQUENCE: 271

Asp Ile Trp Ser Asn Leu Thr Trp Gln Gln Trp Asp Lys Leu Val Glu
1               5                   10                  15

Asn His Thr Gly Thr Ile Phe Gln Leu Leu
            20                  25

<210> SEQ ID NO 272
<211> LENGTH: 20
<212> TYPE: PRT
<213> ORGANISM: Simian immunodeficiency virus

<400> SEQUENCE: 272

Asn Cys Ser Phe Asn Val Thr Thr Glu Leu Arg Asp Lys Lys Lys Gln
1               5                   10                  15

Val Tyr Ser Leu
            20

<210> SEQ ID NO 273
<211> LENGTH: 31
<212> TYPE: PRT
<213> ORGANISM: Simian immunodeficiency virus

<400> SEQUENCE: 273

Glu Asn Ile Ile Gly Asp Thr Arg Gln Ala Tyr Cys Glu Val Asn Arg
1               5                   10                  15

Thr Trp Glu Gln Ile Trp Asn Thr Lys Gln Ile Ile Ile Asn
            20                  25                  30

<210> SEQ ID NO 274
<211> LENGTH: 39
<212> TYPE: PRT
<213> ORGANISM: Simian immunodeficiency virus

<400> SEQUENCE: 274

Asn Thr Thr Gly Asn Ile Thr Leu Gln Cys Arg Ile Arg Gln Ile Val

```
                1               5                  10                  15
Asn Leu Trp Thr Arg Val Gly Lys Gly Ile Tyr Ala Pro Pro Ile Lys
                20                  25                  30
Gly Pro Ile Asn Cys Leu Ser
            35

<210> SEQ ID NO 275
<211> LENGTH: 32
<212> TYPE: PRT
<213> ORGANISM: Simian immunodeficiency virus

<400> SEQUENCE: 275

Ser Thr Gln Leu Ile Leu Asn Gly Ser Leu Ala Thr Ser Asn Ile Val
1               5                   10                  15
Ile Arg Asn Asn Ser Lys Asp Thr Leu Leu Val Gln Leu Asn Glu Ser
                20                  25                  30

<210> SEQ ID NO 276
<211> LENGTH: 18
<212> TYPE: PRT
<213> ORGANISM: Simian immunodeficiency virus

<400> SEQUENCE: 276

Cys Asn Asp Gln Asp Phe Asn Gly Thr Gly Glu Cys Asn Asn Val Ser
1               5                   10                  15
Thr Val

<210> SEQ ID NO 277
<211> LENGTH: 10
<212> TYPE: PRT
<213> ORGANISM: Simian immunodeficiency virus

<400> SEQUENCE: 277

Asn Ile Thr Gly Ile Ile Leu Asp Tyr Thr
1               5                   10

<210> SEQ ID NO 278
<211> LENGTH: 10
<212> TYPE: PRT
<213> ORGANISM: Simian immunodeficiency virus

<400> SEQUENCE: 278

Val Leu Ile Pro Asn Val Thr Glu Arg Phe
1               5                   10

<210> SEQ ID NO 279
<211> LENGTH: 8
<212> TYPE: PRT
<213> ORGANISM: Simian immunodeficiency virus

<400> SEQUENCE: 279

Asn Ile Thr Gly Ile Ile Leu Asp
1               5

<210> SEQ ID NO 280
<211> LENGTH: 29
<212> TYPE: PRT
<213> ORGANISM: Simian immunodeficiency virus

<400> SEQUENCE: 280

Thr Arg Gln Lys Arg Ala Ala Phe Gly Leu Gly Ala Leu Phe Leu Gly
1               5                   10                  15
```

Phe Leu Gly Ala Ala Gly Ser Thr Met Gly Ala Ala Ser
            20                  25

<210> SEQ ID NO 281
<211> LENGTH: 10
<212> TYPE: PRT
<213> ORGANISM: Simian immunodeficiency virus

<400> SEQUENCE: 281

Tyr Thr Asn Val Pro Trp Asn Thr Thr Trp
1               5                   10

<210> SEQ ID NO 282
<211> LENGTH: 26
<212> TYPE: PRT
<213> ORGANISM: Simian immunodeficiency virus

<400> SEQUENCE: 282

Thr Ile Trp Gly Asn Met Thr Trp Gln Asn Trp Asp Glu Gln Val Arg
1               5                   10                  15

Asn Tyr Ser Gly Val Ile Phe Gly Leu Leu
            20                  25

<210> SEQ ID NO 283
<211> LENGTH: 20
<212> TYPE: PRT
<213> ORGANISM: Simian immunodeficiency virus

<400> SEQUENCE: 283

Asn Cys Thr Phe Asn Met Thr Thr Glu Val Arg Asp Lys Lys Lys Glu
1               5                   10                  15

Val Tyr Ser Leu
            20

<210> SEQ ID NO 284
<211> LENGTH: 34
<212> TYPE: PRT
<213> ORGANISM: Simian immunodeficiency virus

<400> SEQUENCE: 284

Glu Asn Ile Val Gly Asp Pro Arg Gln Ala His Cys Asn Val Ser Lys
1               5                   10                  15

Ala Gln Trp Met Lys Lys Leu Asn Glu Thr Ala Leu Ala Ile Ala Lys
            20                  25                  30

Tyr Asp

<210> SEQ ID NO 285
<211> LENGTH: 39
<212> TYPE: PRT
<213> ORGANISM: Simian immunodeficiency virus

<400> SEQUENCE: 285

Ser Asp Asn Ser Thr Leu Thr Ile Ser Cys Arg Ile Arg Gln Ile Val
1               5                   10                  15

Asn Ser Trp Met Arg Val Gly Lys Gly Ile Tyr Ala Pro Pro Ile Arg
            20                  25                  30

Gly Asn Ile Thr Cys Ile Ser
                35

<210> SEQ ID NO 286
<211> LENGTH: 35
<212> TYPE: PRT

<213> ORGANISM: Simian immunodeficiency virus

<400> SEQUENCE: 286

Thr Thr Gln Val Ile Leu Asn Gly Ser Leu Ala Glu Glu Gly Pro Ala
1               5                   10                  15

Val Ala Arg Ser Glu Asp Leu Arg His Lys Ile Ile Ile Gln Phe
            20                  25                  30

Lys Glu Gly
        35

<210> SEQ ID NO 287
<211> LENGTH: 18
<212> TYPE: PRT
<213> ORGANISM: Simian immunodeficiency virus

<400> SEQUENCE: 287

Cys Asn Asp Gln Lys Phe Asn Gly Thr Gly Pro Cys Thr Asn Ile Ser
1               5                   10                  15

Thr Val

<210> SEQ ID NO 288
<211> LENGTH: 11
<212> TYPE: PRT
<213> ORGANISM: Simian immunodeficiency virus

<400> SEQUENCE: 288

Asn Ile Thr Gly Leu Leu Leu Glu Ala Gly Gly
1               5                   10

<210> SEQ ID NO 289
<211> LENGTH: 10
<212> TYPE: PRT
<213> ORGANISM: Simian immunodeficiency virus

<400> SEQUENCE: 289

Val Tyr Met Pro Asn Val Ser Glu Ser Phe
1               5                   10

<210> SEQ ID NO 290
<211> LENGTH: 8
<212> TYPE: PRT
<213> ORGANISM: Simian immunodeficiency virus

<400> SEQUENCE: 290

Asn Ile Thr Gly Leu Leu Leu Glu
1               5

<210> SEQ ID NO 291
<211> LENGTH: 29
<212> TYPE: PRT
<213> ORGANISM: Simian immunodeficiency virus

<400> SEQUENCE: 291

Ala Arg Glu Lys Arg Ala Ala Phe Gly Leu Gly Ala Leu Phe Leu Gly
1               5                   10                  15

Phe Leu Gly Ala Ala Gly Ser Thr Met Gly Ala Ala Ser
            20                  25

<210> SEQ ID NO 292
<211> LENGTH: 10
<212> TYPE: PRT
<213> ORGANISM: Simian immunodeficiency virus

```
<400> SEQUENCE: 292

Tyr Thr Thr Val Pro Trp Asn Ala Thr Trp
1               5                  10

<210> SEQ ID NO 293
<211> LENGTH: 26
<212> TYPE: PRT
<213> ORGANISM: Simian immunodeficiency virus

<400> SEQUENCE: 293

Glu Ile Trp Asn Asn Leu Thr Trp Gln Asp Trp Asp Lys Lys Val Lys
1               5                  10                  15

Asn Tyr Ser Gly Val Ile Phe Ser Leu Ile
            20                  25

<210> SEQ ID NO 294
<211> LENGTH: 20
<212> TYPE: PRT
<213> ORGANISM: Simian immunodeficiency virus

<400> SEQUENCE: 294

Asn Cys Ser Phe Asn Ile Thr Thr Glu Leu Arg Asp Lys Lys Lys Gln
1               5                  10                  15

Val Tyr Ser Leu
            20

<210> SEQ ID NO 295
<211> LENGTH: 34
<212> TYPE: PRT
<213> ORGANISM: Simian immunodeficiency virus

<400> SEQUENCE: 295

Pro Lys Ile Val Gly Asp Val Arg Glu Ala His Cys Asn Ile Ser Lys
1               5                  10                  15

Leu Thr Trp Glu Lys Gln Arg Lys Tyr Thr Leu Glu Ile Ile Lys Lys
            20                  25                  30

Glu Ala

<210> SEQ ID NO 296
<211> LENGTH: 39
<212> TYPE: PRT
<213> ORGANISM: Simian immunodeficiency virus

<400> SEQUENCE: 296

Thr Asp Asn Thr Thr Ile Thr Leu Lys Cys Arg Ile Arg Gln Ile Val
1               5                  10                  15

Asn Gln Trp Met Arg Val Gly Lys Gly Ile Phe Ala Pro Pro Ile Lys
            20                  25                  30

Gly Val Leu Ser Cys Asn Ser
            35

<210> SEQ ID NO 297
<211> LENGTH: 33
<212> TYPE: PRT
<213> ORGANISM: Simian immunodeficiency virus

<400> SEQUENCE: 297

Thr Thr Gln Leu Ile Ile Asn Gly Ser Leu Ala Thr Lys Asn Val Thr
1               5                  10                  15

Val Arg Ser Lys Asn Phe Ala Asp Ile Ile Leu Val Gln Phe Ser Glu
            20                  25                  30
```

Gly

<210> SEQ ID NO 298
<211> LENGTH: 18
<212> TYPE: PRT
<213> ORGANISM: Simian immunodeficiency virus

<400> SEQUENCE: 298

Cys Asn Glu Lys Asp Phe Lys Gly Lys Gly Glu Cys Lys Asn Val Ser
1               5                   10                  15

Thr Val

<210> SEQ ID NO 299
<211> LENGTH: 11
<212> TYPE: PRT
<213> ORGANISM: Simian immunodeficiency virus

<400> SEQUENCE: 299

Asn Ile Thr Gly Met Phe Leu Thr Ala Ala Gln
1               5                   10

<210> SEQ ID NO 300
<211> LENGTH: 10
<212> TYPE: PRT
<213> ORGANISM: Simian immunodeficiency virus

<400> SEQUENCE: 300

Val His Leu Pro Asn Val Thr Glu Lys Phe
1               5                   10

<210> SEQ ID NO 301
<211> LENGTH: 8
<212> TYPE: PRT
<213> ORGANISM: Simian immunodeficiency virus

<400> SEQUENCE: 301

Asn Ile Thr Gly Met Phe Leu Thr
1               5

<210> SEQ ID NO 302
<211> LENGTH: 29
<212> TYPE: PRT
<213> ORGANISM: Simian immunodeficiency virus

<400> SEQUENCE: 302

Lys Arg Glu Lys Arg Ala Ala Phe Gly Leu Gly Ala Leu Phe Leu Gly
1               5                   10                  15

Phe Leu Gly Ala Ala Gly Ser Thr Met Gly Ala Ala Ser
            20                  25

<210> SEQ ID NO 303
<211> LENGTH: 10
<212> TYPE: PRT
<213> ORGANISM: Simian immunodeficiency virus

<400> SEQUENCE: 303

Tyr Thr Thr Val Pro Trp Asn Asp Thr Trp
1               5                   10

<210> SEQ ID NO 304
<211> LENGTH: 26
<212> TYPE: PRT
<213> ORGANISM: Simian immunodeficiency virus -continued

```
<400> SEQUENCE: 304

Ala Ile Trp Gly Asn Leu Thr Trp Gln Glu Trp Asp Arg Lys Val Arg
1               5                   10                  15

Asn Tyr Ser Gly Thr Ile Phe Ser Leu Ile
            20                  25

<210> SEQ ID NO 305
<211> LENGTH: 20
<212> TYPE: PRT
<213> ORGANISM: Simian immunodeficiency virus

<400> SEQUENCE: 305

Lys Cys Phe Phe Asn Met Thr Thr Glu Leu Arg Asp Lys Gln Lys Gln
1               5                   10                  15

Val Tyr Ser Leu
            20

<210> SEQ ID NO 306
<211> LENGTH: 34
<212> TYPE: PRT
<213> ORGANISM: Simian immunodeficiency virus
<220> FEATURE:
<221> NAME/KEY: MISC_FEATURE
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (23)..(23)
<223> OTHER INFORMATION: Xaa can be any naturally occurring amino acid
<220> FEATURE:
<221> NAME/KEY: MISC_FEATURE
<222> LOCATION: (24)..(24)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Xaa can be any naturally occurring amino acid

<400> SEQUENCE: 306

Glu Asn Ile Ile Gly Asp Thr Arg Gln Ala Tyr Cys Asn Xaa Ser Ala
1               5                   10                  15

Ala Glu Trp Glu Gln Arg Xaa Xaa Asp Thr Xaa Arg Ala Ile Lys Ser
            20                  25                  30

Leu Lys

<210> SEQ ID NO 307
<211> LENGTH: 39
<212> TYPE: PRT
<213> ORGANISM: Simian immunodeficiency virus

<400> SEQUENCE: 307

Ile Asn Ser Ser Asn Ile Ile Ile Asn Cys Arg Ile Arg Gln Ile Val
1               5                   10                  15

Asn Ser Trp Met Arg Val Gly Lys Gly Ile Tyr Ala Pro Pro Ile Arg
            20                  25                  30

Gly Thr Ile Ser Cys Thr Ser
        35

<210> SEQ ID NO 308
<211> LENGTH: 36
<212> TYPE: PRT
<213> ORGANISM: Simian immunodeficiency virus
<220> FEATURE:
<221> NAME/KEY: MISC_FEATURE
```

```
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (17)..(17)
<223> OTHER INFORMATION: Xaa can be any naturally occurring amino acid
<220> FEATURE:
<221> NAME/KEY: MISC_FEATURE
<222> LOCATION: (21)..(21)
<223> OTHER INFORMATION: Xaa can be any naturally occurring amino acid
<220> FEATURE:
<221> NAME/KEY: MISC_FEATURE
<222> LOCATION: (23)..(23)
<223> OTHER INFORMATION: Xaa can be any naturally occurring amino acid
<220> FEATURE:
<221> NAME/KEY: MISC_FEATURE
<222> LOCATION: (24)..(24)
<223> OTHER INFORMATION: Xaa can be any naturally occurring amino acid
<220> FEATURE:
<221> NAME/KEY: MISC_FEATURE
<222> LOCATION: (27)..(27)
<223> OTHER INFORMATION: Xaa can be any naturally occurring amino acid

<400> SEQUENCE: 308

Thr Thr Gln Leu Ile Leu Asn Gly Ser Leu Ala Glu Asn Ser Thr Xaa
1               5                   10                  15

Xaa Arg Thr Glu Xaa Met Xaa Xaa Met Asp Xaa Thr Ile Ile Val Gln
            20                  25                  30

Phe His Lys Arg
        35

<210> SEQ ID NO 309
<211> LENGTH: 18
<212> TYPE: PRT
<213> ORGANISM: Simian immunodeficiency virus

<400> SEQUENCE: 309

Cys Asn Glu Pro Asp Phe Asn Gly Thr Gly Lys Cys Arg Asn Ile Ser
1               5                   10                  15

Thr Val

<210> SEQ ID NO 310
<211> LENGTH: 15
<212> TYPE: PRT
<213> ORGANISM: Simian immunodeficiency virus

<400> SEQUENCE: 310

Asn Ile Thr Gly Leu Leu Leu Glu Leu Asp Arg Gly Leu Pro Arg
1               5                   10                  15

<210> SEQ ID NO 311
<211> LENGTH: 10
<212> TYPE: PRT
<213> ORGANISM: Simian immunodeficiency virus

<400> SEQUENCE: 311

Val His Val Pro Asn Ile Thr Glu Thr Phe
1               5                   10

<210> SEQ ID NO 312
<211> LENGTH: 8
<212> TYPE: PRT
<213> ORGANISM: Simian immunodeficiency virus

<400> SEQUENCE: 312

Asn Ile Thr Gly Leu Leu Leu Glu
1               5
```

<210> SEQ ID NO 313
<211> LENGTH: 29
<212> TYPE: PRT
<213> ORGANISM: Simian immunodeficiency virus

<400> SEQUENCE: 313

Thr Arg Glu Lys Arg Ala Ala Phe Gly Leu Gly Ala Leu Phe Leu Gly
1               5                   10                  15

Phe Leu Gly Ala Ala Gly Ser Thr Met Gly Ala Ala Ser
            20                  25

<210> SEQ ID NO 314
<211> LENGTH: 10
<212> TYPE: PRT
<213> ORGANISM: Simian immunodeficiency virus

<400> SEQUENCE: 314

Tyr Thr Thr Val Pro Trp Asn Ser Thr Trp
1               5                   10

<210> SEQ ID NO 315
<211> LENGTH: 26
<212> TYPE: PRT
<213> ORGANISM: Simian immunodeficiency virus

<400> SEQUENCE: 315

Glu Ile Trp Asn Asn Leu Thr Trp Gln Asp Trp Asp Lys Arg Val Lys
1               5                   10                  15

Asn Tyr Ser Gly Val Ile Phe Asp Leu Ile
            20                  25

<210> SEQ ID NO 316
<211> LENGTH: 650
<212> TYPE: PRT
<213> ORGANISM: Simian immunodeficiency virus

<400> SEQUENCE: 316

Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg Arg
            20                  25                  30

Gly Ala Arg Glu Asn Trp Trp Val Thr Val Tyr Tyr Gly Val Pro Val
                35                  40                  45

Trp Arg Glu Ala Lys Thr Thr Leu Phe Cys Ala Ser Asp Ala Lys Ser
    50                  55                  60

Tyr Ser Thr Glu Ala His Asn Ile Trp Ala Thr Gln Ala Cys Val Pro
65                  70                  75                  80

Thr Asp Pro Thr Pro Gln Glu Val Leu Leu Pro Asn Val Thr Glu Glu
                85                  90                  95

Phe Asn Met Trp Glu Asn Tyr Met Val Asp Gln Met Gln Glu Asp Ile
            100                 105                 110

Ile Ser Leu Trp Glu Gln Ser Leu Lys Pro Cys Val Lys Leu Thr Pro
        115                 120                 125

Leu Cys Val Thr Leu Thr Cys Asn Asn Pro Thr Asn Thr Ser Cys Thr
    130                 135                 140

Asn Ser Thr Asp Asp Arg Leu Gly Asp Met Arg Asn Cys Ser Phe Asn
145                 150                 155                 160

Val Thr Thr Glu Leu Arg Asp Lys Lys Arg Lys Val Tyr Ser Leu Phe

```
                    165                 170                 175
Tyr Val Glu Asp Ile Thr Ala Ile Gly Asn Asn Ser Thr Tyr Arg Leu
                180                 185                 190

Ile Asn Cys Asn Thr Thr Ala Ile Thr Gln Ala Cys Pro Lys Thr Ser
                195                 200                 205

Phe Glu Pro Ile Pro Ile His Tyr Cys Ala Pro Ala Gly Phe Ala Leu
                210                 215                 220

Leu Lys Cys Asn Asp Ile Asp Tyr Lys Gly Asn Glu Thr Cys Lys Asn
225                 230                 235                 240

Val Ser Thr Val His Cys Thr His Gly Ile Lys Pro Val Ala Thr Thr
                245                 250                 255

Gln Leu Ile Leu Asn Gly Ser Thr Ala Asp Asn Gln Thr Val Ala Arg
                260                 265                 270

Ile Asp Pro Ser Glu Asn Leu Ala Ile Ile Gln Leu Lys Asp Pro Val
                275                 280                 285

Lys Ile Thr Cys Arg Arg Pro Gly Asn Asn Thr Arg Gly Gln Ile Gln
                290                 295                 300

Ile Gly Pro Ala Met Thr Phe Tyr Asn Ile Glu Asn Val Val Gly Asp
305                 310                 315                 320

Thr Arg Lys Ala Tyr Cys Glu Ile Asn Gly Thr Gln Trp Ala Lys Ala
                325                 330                 335

Leu Asn Glu Thr Lys Glu Val Leu Arg Asn Ile Leu Arg Lys Asn Ile
                340                 345                 350

Ser Phe Met Val Pro Ser Gly Gly Asp Pro Glu Val Thr Asn His His
                355                 360                 365

Phe Asn Cys Gly Gly Glu Phe Phe Tyr Cys Asn Thr Ser Glu Ile Ile
                370                 375                 380

Asn Ile Thr Lys Ile Asn Lys Thr Glu Asn Met Thr Ile Ile Pro Cys
385                 390                 395                 400

Arg Ile Arg Gln Ile Val Asn Ser Trp Met Arg Val Gly Lys Gly Ile
                405                 410                 415

Phe Ala Pro Pro Ile Arg Gly Asn Ile Thr Cys Thr Ser Asn Ile Thr
                420                 425                 430

Gly Met Leu Leu Glu Ile His Lys Asp Gln Asn Asn Thr Tyr Val Cys
                435                 440                 445

Leu Thr Gly Gly Asn Met Lys Asp Ile Trp Arg Ser Glu Leu Tyr Lys
                450                 455                 460

Tyr Lys Ile Val Glu Ile Gln Pro Leu Gly Val Ala Pro Thr Lys Cys
465                 470                 475                 480

Arg Arg Tyr Ala Val Glu Lys Gln His His Arg Arg Arg Arg Arg Arg
                485                 490                 495

Ala Leu Gly Leu Gly Ala Leu Phe Leu Gly Phe Leu Gly Ala Ala Gly
                500                 505                 510

Ser Thr Met Gly Ala Ala Ser Val Val Leu Thr Val Gln Ala Arg Gln
                515                 520                 525

Leu Leu Thr Gly Ile Val Gln Gln Gln Asn Asn Leu Leu Arg Ala Pro
                530                 535                 540

Glu Ala Gln Gln His Leu Leu Gln Leu Ser Val Trp Gly Ile Lys Gln
545                 550                 555                 560

Leu Gln Ala Arg Val Leu Ala Val Glu Arg Tyr Leu Arg Asp Gln Gln
                565                 570                 575

Leu Leu Gly Leu Trp Gly Cys Thr Gly Lys Thr Ile Cys Cys Thr Ala
                580                 585                 590
```

```
Val Arg Trp Asn Lys Thr Trp Gly Asn Ile Ser Asp Tyr Gln Val Ile
        595                 600                 605

Trp Asn Asn Tyr Thr Trp Gln Gln Trp Asp Arg Glu Val Asn Asn Tyr
        610                 615                 620

Thr Gly Leu Ile Tyr Thr Leu Leu Glu Glu Ala Asn Thr Gln Gln Glu
625                 630                 635                 640

Lys Asn Glu Lys Glu Leu Leu Glu Leu Asp
                645                 650

<210> SEQ ID NO 317
<211> LENGTH: 836
<212> TYPE: PRT
<213> ORGANISM: Simian immunodeficiency virus

<400> SEQUENCE: 317

Met Lys Val Met Glu Lys Lys Arg Leu Trp Leu Ser Tyr Cys Leu
1               5                   10                  15

Leu Ser Ser Leu Ile Ile Pro Gly Leu Ser Ser Leu Trp Ala Thr Val
                20                  25                  30

Tyr Tyr Gly Val Pro Val Trp Arg Asp Val Glu Thr Thr Leu Phe Cys
                35                  40                  45

Ala Ser Asp Ala Lys Ala Tyr Lys Gln Glu Ala His Asn Ile Trp Ala
50                  55                  60

Thr Gln Ala Cys Val Pro Thr Asp Pro Asn Pro Gln Glu Val His Leu
65                  70                  75                  80

Pro Asn Val Thr Glu Lys Phe Asp Met Trp Glu Asn Asn Met Ala Glu
                85                  90                  95

Gln Met Gln Glu Asp Ile Ile Ser Leu Trp Asp Gln Ser Leu Lys Pro
                100                 105                 110

Cys Ile Lys Leu Thr Pro Leu Cys Val Thr Met Thr Cys Leu Asn Pro
                115                 120                 125

Asp Ser Asn Ser Ser Ala Val Asn Thr Thr Asp Ile Met Arg Asn Cys
                130                 135                 140

Ser Phe Asn Ile Thr Thr Glu Leu Arg Asp Lys Lys Lys Gln Val Tyr
145                 150                 155                 160

Ser Leu Phe Tyr Val Asp Asp Leu Ala His Ile Asn Asn Asn Thr Tyr
                165                 170                 175

Arg Leu Ile Asn Cys Asn Thr Thr Ala Ile Thr Gln Ala Cys Pro Lys
                180                 185                 190

Thr Ser Phe Glu Pro Ile Pro Ile His Tyr Cys Ala Pro Pro Gly Phe
                195                 200                 205

Ala Ile Leu Lys Cys Asn Glu Lys Asp Phe Lys Gly Lys Gly Glu Cys
210                 215                 220

Lys Asn Val Ser Thr Val Gln Cys Thr His Gly Ile Lys Pro Val Val
225                 230                 235                 240

Thr Thr Gln Leu Ile Ile Asn Gly Ser Leu Ala Thr Lys Asn Val Thr
                245                 250                 255

Val Arg Ser Lys Asn Phe Ala Asp Ile Ile Leu Val Gln Phe Ser Glu
                260                 265                 270

Gly Val Asn Met Thr Cys Ile Arg Pro Gly Asn Asn Thr Val Gly Asn
                275                 280                 285

Val Gln Leu Gly Pro Gly Met Thr Phe Tyr Asn Ile Pro Lys Ile Val
                290                 295                 300

Gly Asp Val Arg Glu Ala His Cys Asn Ile Ser Lys Leu Thr Trp Glu
```

```
            305                 310                 315                 320
Lys Gln Arg Lys Tyr Thr Leu Glu Ile Ile Lys Lys Glu Ala Asn Leu
                    325                 330                 335

Thr Lys Val Glu Leu Ile Pro Asn Ala Gly Gly Asp Pro Glu Val Val
                340                 345                 350

Asn Met Met Leu Asn Cys Gly Gly Glu Phe Phe Tyr Cys Asn Thr Ile
            355                 360                 365

Pro Leu Phe Asn Met Thr Tyr Asn Asn Thr Asp Asn Thr Thr Ile Thr
        370                 375                 380

Leu Lys Cys Arg Ile Arg Gln Ile Val Asn Gln Trp Met Arg Val Gly
385                 390                 395                 400

Lys Gly Ile Phe Ala Pro Pro Ile Lys Gly Val Leu Ser Cys Asn Ser
                405                 410                 415

Asn Ile Thr Gly Met Ile Leu Asp Ile Ser Ile Ser Ala Val Asn Asn
            420                 425                 430

Asp Ser Arg Asn Ile Thr Val Met Pro Thr Gly Gly Asp Met Thr Ala
        435                 440                 445

Leu Trp Lys Asn Glu Leu His Lys Tyr Lys Val Val Ser Ile Glu Pro
    450                 455                 460

Ile Gly Val Ala Pro Gly Lys Ala Lys Arg His Thr Val Lys Arg Glu
465                 470                 475                 480

Lys Arg Ala Ala Phe Gly Leu Gly Ala Leu Phe Leu Gly Phe Leu Gly
                485                 490                 495

Ala Ala Gly Ser Thr Met Gly Ala Ala Ser Val Val Leu Thr Val Gln
            500                 505                 510

Ala Arg Gln Leu Leu Ser Gly Ile Val Gln Gln Asn Asn Leu Leu
        515                 520                 525

Arg Ala Ile Glu Ala Gln Gln His Leu Leu Gln Leu Ser Val Trp Gly
    530                 535                 540

Ile Lys Gln Leu Gln Ala Arg Val Leu Ala Val Glu Arg Tyr Leu Lys
545                 550                 555                 560

Asp Gln Gln Ile Leu Gly Leu Trp Gly Cys Ser Gly Lys Thr Ile Cys
                565                 570                 575

Tyr Thr Thr Val Pro Trp Asn Asp Thr Trp Ser Asn Asn Leu Ser Tyr
            580                 585                 590

Asp Ala Ile Trp Gly Asn Leu Thr Trp Gln Glu Trp Asp Arg Lys Val
        595                 600                 605

Arg Asn Tyr Ser Gly Thr Ile Phe Ser Leu Ile Glu Gln Ala Gln Glu
    610                 615                 620

Gln Gln Asn Thr Asn Glu Lys Ser Leu Leu Glu Leu Asp Gln Trp Ser
625                 630                 635                 640

Ser Leu Trp Asn Trp Phe Asp Ile Thr Asn Trp Leu Trp Tyr Ile Lys
                645                 650                 655

Ile Phe Leu Ile Val Val Ala Ser Leu Val Gly Ile Arg Ile Val Gly
            660                 665                 670

Val Ile Phe Ser Leu Val Ala Lys Val Arg Gln Gly Tyr Ser Pro Leu
        675                 680                 685

Ser Leu Gln Thr Leu Phe Pro Thr Thr Arg Glu Pro Asp Arg Pro Glu
    690                 695                 700

Gly Thr Glu Glu Gly Ala Gly Lys Thr Asp Asn Val Arg Ser Thr Arg
705                 710                 715                 720

Leu Val Ser Gly Phe Leu Ala Leu Val Trp Glu Asp Leu Arg Asn Leu
                725                 730                 735
```

```
Leu Ile Phe Leu Tyr His Arg Leu Glu Asp Leu Leu Leu Ile Leu Arg
            740                 745                 750

Arg Thr Val Gln Ile Leu Gly Gln Asn Ile Asn Lys Gly Leu Gln Leu
        755                 760                 765

Leu Asn Glu Leu Arg Ala Arg Cys Trp Gly Val Ile Ala Tyr Trp Ala
    770                 775                 780

Arg Glu Leu Lys Val Ser Ala Thr Ser Leu Leu Asp Thr Thr Ala Ile
785                 790                 795                 800

Ala Val Ala Glu Gly Thr Asp Arg Ile Ile Glu Leu Thr Arg Arg Leu
                805                 810                 815

Phe Leu Gly Ile Ile His Ile Pro Arg Arg Ile Arg Gln Gly Leu Glu
            820                 825                 830

Arg Ser Leu Leu
        835

<210> SEQ ID NO 318
<211> LENGTH: 859
<212> TYPE: PRT
<213> ORGANISM: Simian immunodeficiency virus
<220> FEATURE:
<221> NAME/KEY: MISC_FEATURE
<222> LOCATION: (154)..(154)
<223> OTHER INFORMATION: Xaa can be any naturally occurring amino acid.
<220> FEATURE:
<221> NAME/KEY: MISC_FEATURE
<222> LOCATION: (284)..(284)
<223> OTHER INFORMATION: Xaa can be any naturally occurring amino acid.
<220> FEATURE:
<221> NAME/KEY: MISC_FEATURE
<222> LOCATION: (287)..(287)
<223> OTHER INFORMATION: Xaa can be any naturally occurring amino acid.
<220> FEATURE:
<221> NAME/KEY: MISC_FEATURE
<222> LOCATION: (291)..(291)
<223> OTHER INFORMATION: Xaa can be any naturally occurring amino acid.
<220> FEATURE:
<221> NAME/KEY: misc_feature
<222> LOCATION: (292)..(292)
<223> OTHER INFORMATION: Xaa can be any naturally occurring amino acid
<220> FEATURE:
<221> NAME/KEY: MISC_FEATURE
<222> LOCATION: (303)..(303)
<223> OTHER INFORMATION: Xaa can be any naturally occurring amino acid.

<400> SEQUENCE: 318

Met Lys Val Met Glu Lys Ile Lys Gly Ser Leu Ile Glu Lys Tyr Met
1               5                   10                  15

Phe Met Gly Leu Ile Ile Pro Cys Leu Thr Gly Ser Asp Gln Leu Trp
            20                  25                  30

Ala Thr Val Tyr Tyr Gly Val Pro Val Trp Lys Glu Ala Asp Thr Thr
        35                  40                  45

Leu Phe Cys Ala Ser Glu Ala Ser Ala Leu Asn Lys Glu Ala His Asn
    50                  55                  60

Ile Trp Ala Ser Gln Ala Cys Val Pro Thr Asp Pro Asn Pro Gln Glu
65                  70                  75                  80

Val Gln Ile Pro Asn Val Thr Glu Asn Phe Asn Met Trp Asn Asn Thr
                85                  90                  95

Met Ala Glu Gln Met Asn Thr Asp Ile Ile Ser Leu Trp Asp Gln Ser
            100                 105                 110

Leu Lys Pro Cys Val Lys Leu Thr Pro Ile Cys Val Thr Met Glu Cys
        115                 120                 125

Arg Lys Val Thr Phe Asn Ser Thr Ser Asn Arg Asn Lys Thr Ser Thr
```

```
            130                 135                 140
Met Thr Thr Asn Ser Pro Asn Glu Lys Xaa Asp Ser Thr Val Lys Asn
145                 150                 155                 160

Cys Thr Phe Asn Met Thr Thr Glu Val Arg Asp Lys Glu Lys Lys Val
                165                 170                 175

Tyr Ser Leu Phe Tyr Val Asp Asp Leu Val Leu Ile Asp Asn Asp Thr
            180                 185                 190

Asp Thr Tyr Arg Leu Ile Asn Cys Asn Thr Thr Ala Ile Thr Gln Ala
                195                 200                 205

Cys Pro Lys Thr Ser Phe Glu Pro Ile Pro Ile His Tyr Cys Ala Thr
210                 215                 220

Pro Gly Tyr Ala Ile Met Lys Cys Asn Met Pro Asn Phe Asn Gly Thr
225                 230                 235                 240

Gly Thr Gly Arg Cys Asn Asn Ile Ser Thr Val Gln Cys Thr His Gly
                245                 250                 255

Ile Arg Pro Val Val Thr Thr Gln Leu Ile Leu Asn Gly Ser Val Ala
                260                 265                 270

Glu Asn Lys Thr Ile Ala Arg Arg Asn Gly Tyr Xaa Phe Leu Xaa Gln
                275                 280                 285

Phe Gln Xaa Xaa Val Ser Ile Asn Cys Thr Arg Pro Gly Asn Xaa Ser
            290                 295                 300

Arg Gly Gln Ile Gln Ile Gly Pro Gly Met Thr Phe Tyr Asn Ile Glu
305                 310                 315                 320

Asn Ile Val Gly Asp Thr Arg Arg Ala Tyr Cys Gln Ile Asn Arg Thr
                325                 330                 335

Val Trp Asp Glu Arg Leu Asn Glu Thr Gly Gln Ala Leu Arg Glu Leu
                340                 345                 350

Phe Thr Asn Leu Thr Gln Val Asn Phe Thr Val Ser Pro Gly Gly Asp
            355                 360                 365

Pro Glu Val Thr Asn Met Met Phe Asn Cys Gly Gly Glu Phe Phe Tyr
370                 375                 380

Cys Asn Thr Thr Thr Leu Phe Asn Tyr Thr Trp Lys Asn Asn Asn Ile
385                 390                 395                 400

Thr Lys Gly Asp Asn Thr Thr Phe Phe Pro Cys Arg Ile Arg Gln Ile
                405                 410                 415

Val Asn Ser Trp Met Arg Val Gly Lys Gly Ile Tyr Ala Pro Pro Ile
                420                 425                 430

Arg Gly Val Ile Ser Cys Thr Ser Asn Val Thr Gly Ile Ile Leu Glu
                435                 440                 445

Thr Gly His Gly Ile Asn Asn Ser Ile Thr Asn Ile Thr Leu Tyr Pro
                450                 455                 460

Thr Gly Gly Asn Met Val Asp Leu Trp Arg Leu Glu Leu His Lys Tyr
465                 470                 475                 480

Lys Val Val Ser Ile Glu Pro Ile Gly Val Ala Pro Ser Lys Ala Lys
                485                 490                 495

Arg His Thr Val Ser Arg Glu Lys Arg Ala Ala Phe Gly Leu Gly Ala
                500                 505                 510

Leu Phe Leu Gly Phe Leu Gly Ala Ala Gly Ser Thr Met Gly Ala Ala
            515                 520                 525

Ser Val Val Leu Thr Val Gln Ala Arg Gln Leu Leu Ser Gly Ile Val
        530                 535                 540

Gln Gln Gln Asn Asn Leu Leu Arg Ala Ile Glu Ala Gln Gln His Leu
545                 550                 555                 560
```

Leu Gln Leu Ser Val Trp Gly Ile Lys Gln Leu Gln Ala Arg Val Leu
            565                 570                 575

Ala Val Glu Arg Tyr Leu Arg Asp Gln Gln Ile Leu Gly Leu Trp Gly
            580                 585                 590

Cys Ser Gly Lys Ala Ile Cys Tyr Thr Thr Val Pro Trp Asn Asn Thr
            595                 600                 605

Trp Ser Ala Asn Thr Ser Phe Asp Glu Ile Trp Asn Asn Leu Thr Trp
        610                 615                 620

Gln Asp Trp Asp Lys Arg Val Lys Asn Tyr Ser Gly Val Ile Phe Ser
625                 630                 635                 640

Leu Ile Glu Gln Ala Gln Glu Gln Gln Asn Thr Asn Glu Lys Ser Leu
            645                 650                 655

Leu Glu Leu Asp Gln Trp Ser Ser Leu Trp Asn Trp Phe Asp Ile Thr
            660                 665                 670

Arg Trp Leu Trp Tyr Ile Lys Leu Phe Ile Met Ile Val Ala Gly Leu
        675                 680                 685

Val Gly Ile Arg Ile Val Gly Ala Ile Ile Ser Phe Val Ala Lys Val
        690                 695                 700

Arg Gln Gly Tyr Ser Pro Leu Ser Leu Gln Thr Leu Ile Pro Thr Thr
705                 710                 715                 720

Arg Glu Pro Asp Arg Pro Gly Gly Thr Glu Glu Asp Val Gly Glu Pro
            725                 730                 735

Gly Lys Gly Arg Ser Ile Arg Leu Val Ser Gly Phe Leu Ala Leu Ile
            740                 745                 750

Trp Glu Asp Leu Arg Asn Leu Leu Phe Cys Tyr His Arg Leu Arg
        755                 760                 765

Asp Leu Leu Leu Ile Leu Gly Arg Thr Leu Glu Asn Leu Gly Gln Ser
        770                 775                 780

Leu Asn Lys Gly Leu Gln Gln Leu Arg Asn Phe Ser Arg Tyr Leu Trp
785                 790                 795                 800

Gly Val Ile Thr Tyr Trp Gly Arg Glu Leu Gln Thr Ser Ala Ile Ser
            805                 810                 815

Leu Leu Asp Ala Thr Ala Ile Ala Val Ala Glu Gly Thr Asp Arg Ile
            820                 825                 830

Leu Glu Val Ala Gln Ile Ile Gly Arg Gly Ile Leu His Ile Pro Arg
            835                 840                 845

Arg Ile Arg Gln Gly Leu Glu Arg Ser Leu Leu
    850                 855

<210> SEQ ID NO 319
<211> LENGTH: 856
<212> TYPE: PRT
<213> ORGANISM: Simian immunodeficiency virus

<400> SEQUENCE: 319

Met Lys Val Met Gly Lys Thr Arg Arg Trp Gln Pro Tyr Cys Ile
1               5                   10                  15

Ile Met Ala Leu Ile Ile Pro Cys Leu Lys Thr Glu Ser Asp Gln Trp
20 25 30

Trp Val Thr Val Tyr Tyr Gly Val Pro Val Trp Lys Glu Ala Thr Thr
35 40 45

Pro Leu Phe Cys Ala Ala Asn Ala Thr Ala Leu Lys Glu Glu Pro His
50 55 60

Asn Ile Trp Ala Thr Gln Ala Cys Val Pro Thr Asp Pro Ser Pro Glu

```
            65                  70                  75                  80
        Glu Val Ile Leu Ile Asn Val Thr Glu Glu Phe Asn Val Trp Asp Asn
                            85                  90                  95
        Ala Met Val Glu Gln Met Gln Glu Asp Ile Thr Ser Leu Trp Asp Gln
                            100                 105                 110
        Ser Leu Arg Pro Cys Val Lys Leu Asn Pro Leu Cys Val Gln Leu Thr
                            115                 120                 125
        Cys Thr Ser Ile Asn Ala Thr Gly Asn Glu Thr Asn Ala Thr Gly Asn
                            130                 135                 140
        Gly Ile Glu Lys Asp Gly Leu Ala Gln Asp Met Arg Asn Cys Thr Phe
        145                 150                 155                 160
        Asn Thr Thr Thr Glu Leu Arg Asp Lys Lys Gln Gln Ile Tyr Ser Leu
                            165                 170                 175
        Phe Trp Lys Asn Asp Leu Val Gly Thr Asn Asn Thr Phe Arg Leu Ile
                            180                 185                 190
        Asn Cys Asn Thr Thr Ala Ile Thr Gln Ala Cys Pro Lys Thr Ser Phe
                            195                 200                 205
        Glu Pro Ile Pro Ile His Tyr Cys Ala Pro Ala Gly Phe Ala Leu Leu
                            210                 215                 220
        Lys Cys Asn Asp Lys Asp Tyr Pro Gly Lys Gly Lys Cys Lys Asn Val
        225                 230                 235                 240
        Ser Thr Val His Cys Thr His Gly Ile Lys Pro Thr Val Thr Thr Gln
                            245                 250                 255
        Leu Ile Leu Asn Gly Ser Leu Ala Glu Glu Glu Val Val Phe Arg
                            260                 265                 270
        Thr Lys Asn Met Thr Ala Pro Gly Leu Ser Asp Thr Val Ile Val Gln
                            275                 280                 285
        Leu Lys Arg Ala Ile Pro Ile Asn Cys Ser Arg Pro Gly Asn Asn Thr
                            290                 295                 300
        Gly Arg Ala Ile Asn Leu Ser Pro Gly Thr Thr Phe Phe Asn Thr Glu
        305                 310                 315                 320
        Ala Leu Ile Gly Asn Pro Arg Lys Ala Ser Cys His Leu Asn Gly Thr
                            325                 330                 335
        Leu Trp Asn Asn Ile Leu Asn Arg Ile Lys Gln Lys Ile Lys Asn Ser
                            340                 345                 350
        Thr Thr Trp His Arg Gly Asp Ile Thr Phe Thr Lys His Pro Gly Gly
                            355                 360                 365
        Asp Pro Glu Val Val Asn Phe Met Phe Asn Cys Gly Gly Glu Phe Phe
        370                 375                 380
        Tyr Cys Asn Thr Ser Arg Leu Ile Thr Cys Asn Ser Ser Asp Thr Ser
        385                 390                 395                 400
        Glu Tyr Ile Leu Pro Cys Lys Ile Arg Gln Val Val Asn Ser Trp Met
                            405                 410                 415
        Arg Val Gly Lys Gly Ile Phe Ala Pro Pro Arg Arg Gly Thr Ile Thr
                            420                 425                 430
        Cys Asn Ser Thr Ile Thr Gly Leu Leu Leu Glu Val Gln Asn Gly Thr
                            435                 440                 445
        Gly Asn Asn Thr Glu Val Tyr Leu Ser Gly Gly Asp Met Arg Asp Ile
                            450                 455                 460
        Trp Arg Ser Glu Leu Tyr Lys Tyr Lys Ile Val Lys Ile Glu Pro Leu
        465                 470                 475                 480
        Gly Val Ala Pro Thr Lys Ala Lys Arg Tyr Thr Val Ala Lys Ala Leu
                            485                 490                 495
```

```
Asp Arg Ser Lys Arg Ala Ala Phe Gly Leu Gly Ala Leu Phe Leu Gly
            500                 505                 510

Phe Leu Gly Ala Ala Gly Ser Thr Met Gly Ala Ala Ser Val Met Leu
            515                 520                 525

Thr Val Gln Ala Arg Asn Leu Leu Ser Gly Ile Val Gln Gln Gln Asn
            530                 535                 540

Asn Leu Leu Arg Ala Ile Glu Ala Gln Gln His Leu Leu Gln Leu Ser
545                 550                 555                 560

Val Trp Gly Ile Lys Gln Leu Gln Ala Arg Val Leu Ala Val Glu Arg
                565                 570                 575

Tyr Leu Lys Asp Gln Gln Val Leu Ala Leu Trp Gly Cys Ser Gly Lys
            580                 585                 590

Thr Val Cys Tyr Ser Thr Val Pro Trp Asn Thr Ser Trp Asn Ser Asn
            595                 600                 605

Lys Ser Tyr Glu Asp Ile Trp Ser Asn Leu Thr Trp Gln Gln Trp Asp
            610                 615                 620

Lys Leu Val Glu Asn His Thr Gly Thr Ile Phe Gln Leu Leu Gln Arg
625                 630                 635                 640

Ala His Glu Gln Gln Asn Ser Asn Glu Lys Glu Leu Leu Glu Leu Asp
                645                 650                 655

Gln Trp Ser Ser Leu Trp Asn Trp Phe Asp Ile Thr Asn Trp Leu Trp
            660                 665                 670

Tyr Ile Lys Met Phe Ile Ile Leu Val Gly Val Ile Gly Leu Arg
            675                 680                 685

Ile Val Ile Gly Val Val Asn Ile Ile Arg Arg Ser Arg Gln Gly Tyr
            690                 695                 700

Ser Pro Leu Ser Phe Gln Thr Leu Ile Pro Ala Thr Gly Gly Pro Glu
705                 710                 715                 720

Val Pro Glu Gly Ile Gly Gly Gly Gly Glu Gln Asp Arg Gly Arg
                725                 730                 735

Ser Val Arg Leu Val Ser Gly Phe Leu Ala Leu Cys Trp Asp Asp Ile
            740                 745                 750

Arg Asn Leu Thr Ile Phe Leu Tyr Arg Leu Leu Arg Asp Cys Leu Ser
            755                 760                 765

Val Leu Trp Ser Leu Leu Glu Gln Leu Gly Gln Gln Val Leu Arg Gly
            770                 775                 780

Leu Arg Leu Leu Arg Glu Leu Leu Ser Gln Leu Lys Gly Ile Gly Gln
785                 790                 795                 800

Tyr Trp Leu Gln Glu Leu Arg Thr Ser Ala Ile Ser Leu Leu Asp Thr
                805                 810                 815

Thr Ala Ile Ile Val Ala Glu Arg Thr Asp Thr Ile Ile Glu Val Ala
            820                 825                 830

Thr Arg Ile Gly Arg Gly Ile Leu His Ile Pro Arg Arg Ile Arg Gln
            835                 840                 845

Gly Leu Glu Arg Ala Leu Leu Glu
        850                 855

<210> SEQ ID NO 320
<211> LENGTH: 871
<212> TYPE: PRT
<213> ORGANISM: Simian immunodeficiency virus

<400> SEQUENCE: 320

Met Lys Asn Leu Ile Gly Ile Thr Leu Ile Leu Ile Ile Thr Ile Leu
```

-continued

```
1               5                   10                  15
Gly Ile Gly Phe Ser Thr Tyr Tyr Thr Thr Val Phe Tyr Gly Val Pro
            20                  25                  30

Val Trp Lys Glu Ala Gln Pro Thr Leu Phe Cys Ala Ser Asp Ala Asp
        35                  40                  45

Ile Thr Ser Arg Asp Lys His Asn Ile Trp Ala Thr His Asn Cys Val
    50                  55                  60

Pro Leu Asp Pro Asn Pro Tyr Glu Val Thr Leu Ala Asn Val Ser Ile
65                  70                  75                  80

Arg Phe Asn Met Glu Glu Asn Tyr Met Val Gln Glu Met Lys Glu Asp
                85                  90                  95

Ile Leu Ser Leu Phe Gln Gln Ser Phe Lys Pro Cys Val Lys Leu Thr
            100                 105                 110

Pro Phe Cys Ile Lys Met Thr Cys Thr Met Thr Asn Thr Thr Asn Lys
        115                 120                 125

Thr Leu Asn Ser Ala Thr Thr Thr Leu Thr Pro Thr Val Asn Leu Ser
    130                 135                 140

Ser Ile Pro Asn Tyr Glu Val Tyr Asn Cys Ser Phe Asn Gln Thr Thr
145                 150                 155                 160

Glu Phe Arg Asp Lys Lys Lys Gln Ile Tyr Ser Leu Phe Tyr Arg Glu
                165                 170                 175

Asp Ile Val Lys Glu Asp Gly Asn Asn Asn Ser Tyr Tyr Leu His Asn
            180                 185                 190

Cys Asn Thr Ser Val Ile Thr Gln Glu Cys Asp Lys Ser Thr Phe Glu
        195                 200                 205

Pro Ile Pro Ile Arg Tyr Cys Ala Pro Ala Gly Phe Ala Leu Leu Lys
    210                 215                 220

Cys Arg Asp Gln Asn Phe Thr Gly Lys Gly Gln Cys Ser Asn Val Ser
225                 230                 235                 240

Val Val His Cys Thr His Gly Ile Tyr Pro Met Ile Ala Thr Ala Leu
                245                 250                 255

His Leu Asn Gly Ser Leu Glu Glu Glu Thr Lys Ala Tyr Phe Val
            260                 265                 270

Asn Thr Ser Val Asn Thr Pro Leu Leu Val Lys Phe Asn Val Ser Ile
        275                 280                 285

Asn Leu Thr Cys Glu Arg Thr Gly Asn Asn Thr Arg Gly Gln Val Gln
    290                 295                 300

Ile Gly Pro Gly Met Thr Phe Tyr Asn Ile Glu Asn Val Val Gly Asp
305                 310                 315                 320

Thr Arg Lys Ala Tyr Cys Ser Val Asn Ala Thr Thr Trp Tyr Arg Asn
                325                 330                 335

Leu Asp Trp Ala Met Ala Ala Ile Asn Thr Thr Met Arg Ala Arg Asn
            340                 345                 350

Glu Thr Val Gln Gln Thr Phe Gln Trp Gln Arg Asp Gly Asp Pro Glu
        355                 360                 365

Val Thr Ser Phe Trp Phe Asn Cys Gln Gly Glu Phe Phe Tyr Cys Asn
    370                 375                 380

Leu Thr Asn Trp Thr Asn Thr Trp Thr Ala Asn Arg Thr Asn Asn Thr
385                 390                 395                 400

His Gly Thr Leu Val Ala Pro Cys Arg Leu Arg Gln Ile Val Asn His
                405                 410                 415

Trp Gly Ile Val Ser Lys Gly Val Tyr Leu Pro Pro Arg Gly Thr
            420                 425                 430
```

```
Val Lys Cys His Ser Asn Ile Thr Gly Leu Ile Met Thr Ala Glu Lys
        435                 440                 445

Asp Asn Asn Ser Tyr Thr Pro Gln Phe Ser Ala Val Val Glu Asp
450                 455                 460

Tyr Trp Lys Val Glu Leu Ala Arg Tyr Lys Val Val Glu Ile Gln Pro
465                 470                 475                 480

Leu Ser Val Ala Pro Arg Pro Gly Lys Arg Pro Glu Ile Lys Ala Asn
                485                 490                 495

His Thr Arg Ser Arg Arg Asp Val Gly Ile Gly Leu Leu Phe Leu Gly
                500                 505                 510

Phe Leu Ser Ala Ala Gly Ser Thr Met Gly Ala Ala Ser Ile Ala Leu
                515                 520                 525

Thr Ala Gln Ala Arg Gly Leu Leu Ser Gly Ile Val Gln Gln Gln Gln
                530                 535                 540

Asn Leu Leu Gln Ala Ile Glu Ala Gln Gln His Leu Leu Gln Leu Ser
545                 550                 555                 560

Val Trp Gly Ile Lys Gln Leu Gln Ala Arg Met Leu Ala Val Glu Lys
                565                 570                 575

Tyr Ile Arg Asp Gln Gln Leu Leu Ser Leu Trp Gly Cys Ala Asn Lys
                580                 585                 590

Leu Val Cys His Ser Ser Val Pro Trp Asn Leu Thr Trp Ala Glu Asp
                595                 600                 605

Ser Thr Lys Cys Asn His Ser Asp Ala Lys Tyr Tyr Asp Cys Ile Trp
                610                 615                 620

Asn Asn Leu Thr Trp Gln Glu Trp Asp Arg Leu Val Glu Asn Ser Thr
625                 630                 635                 640

Gly Thr Ile Tyr Ser Leu Leu Glu Lys Ala Gln Thr Gln Gln Glu Lys
                645                 650                 655

Asn Lys Gln Glu Leu Leu Glu Leu Asp Lys Trp Ser Ser Leu Trp Asp
                660                 665                 670

Trp Phe Asp Ile Thr Gln Trp Leu Trp Tyr Ile Lys Ile Ala Ile Ile
                675                 680                 685

Ile Val Ala Gly Leu Val Gly Leu Arg Ile Leu Met Phe Ile Val Asn
                690                 695                 700

Val Val Lys Gln Val Arg Gln Gly Tyr Thr Pro Leu Phe Ser Gln Ile
705                 710                 715                 720

Pro Thr Gln Ala Glu Gln Asp Pro Glu Gln Pro Gly Gly Ile Ala Gly
                725                 730                 735

Gly Gly Gly Gly Arg Asp Asn Ile Arg Trp Thr Pro Ser Pro Ala Gly
                740                 745                 750

Phe Phe Ser Ile Val Trp Glu Asp Leu Arg Asn Leu Leu Ile Trp Ile
                755                 760                 765

Tyr Gln Thr Phe Gln Asn Phe Ile Trp Ile Leu Trp Ile Ser Leu Gln
                770                 775                 780

Ala Leu Lys Gln Gly Ile Ile Ser Leu Ala His Ser Leu Val Ile Val
785                 790                 795                 800

His Arg Thr Ile Ile Val Gly Val Arg Gln Ile Glu Trp Ser Ser
                805                 810                 815

Asn Thr Tyr Ala Ser Leu Arg Val Leu Leu Ile Gln Ala Ile Asp Arg
                820                 825                 830

Leu Ala Asn Phe Thr Gly Trp Trp Thr Asp Leu Ile Ile Glu Gly Val
                835                 840                 845
```

Val Tyr Ile Ala Arg Gly Ile Arg Asn Ile Pro Arg Ile Arg Gln
            850                 855                 860

Gly Leu Glu Leu Ala Leu Asn
865                 870

<210> SEQ ID NO 321
<211> LENGTH: 865
<212> TYPE: PRT
<213> ORGANISM: Simian immunodeficiency virus

<400> SEQUENCE: 321

Met Lys Ala Met Glu Arg Lys Lys Leu Asn Trp Ile Ile Cys Tyr Met
1               5                   10                  15

Leu Met Gly Leu Ile Thr Pro Cys Leu Thr Gly His Glu Trp Trp Ala
            20                  25                  30

Thr Val Tyr Tyr Gly Val Pro Val Trp Lys Glu Ala Glu Thr Thr Leu
        35                  40                  45

Phe Cys Ala Ser Glu Ala Ser Ala Leu Asn Lys Glu Ala His Asn Ile
    50                  55                  60

Trp Ala Ser Gln Ala Cys Val Pro Val Asp Pro Asn Pro Gln Glu Val
65                  70                  75                  80

Tyr Met Pro Asn Val Ser Glu Ser Phe Asn Met Trp Lys Asn Asn Met
                85                  90                  95

Ala Glu Gln Met Gln Glu Asp Ile Ser Ser Leu Trp Asp Gln Ser Leu
            100                 105                 110

Lys Pro Cys Val Lys Leu Thr Pro Ile Cys Val Thr Met Gln Cys Thr
        115                 120                 125

Thr Leu Lys Asn Ile Ser Thr Thr Asn Thr Asn Ser Thr Glu Leu Lys
    130                 135                 140

Asn Ile Lys Glu Ile Met Lys Asn Cys Thr Phe Asn Met Thr Thr Glu
145                 150                 155                 160

Val Arg Asp Lys Lys Lys Glu Val Tyr Ser Leu Phe Tyr Val Asp Asp
                165                 170                 175

Ile Val Pro Ile Gly Gly Asn Lys Ser Asn Asp Thr Tyr Arg Leu Ile
            180                 185                 190

Asn Cys Asn Thr Thr Thr Val Thr Gln Ala Cys Pro Lys Thr Ser Phe
        195                 200                 205

Glu Pro Ile Pro Ile His Tyr Cys Ala Pro Pro Gly Phe Ala Ile Met
    210                 215                 220

Lys Cys Asn Asp Gln Lys Phe Asn Gly Thr Gly Pro Cys Thr Asn Ile
225                 230                 235                 240

Ser Thr Val Gln Cys Thr His Gly Ile Arg Pro Val Val Thr Thr Gln
                245                 250                 255

Val Ile Leu Asn Gly Ser Leu Ala Glu Gly Pro Ala Val Ala Arg
            260                 265                 270

Ser Glu Asp Leu Arg His Lys Ile Ile Ile Gln Phe Lys Glu Gly
        275                 280                 285

Ile Asn Ile Ile Cys Met Arg Pro Gly Asn Asn Ser Arg Gly Gln Leu
    290                 295                 300

Gln Ile Gly Pro Gly Val Ser Phe Tyr Asn Ile Glu Asn Ile Val Gly
305                 310                 315                 320

Asp Pro Arg Gln Ala His Cys Asn Val Ser Lys Ala Gln Trp Met Lys
                325                 330                 335

Lys Leu Asn Glu Thr Ala Leu Ala Ile Ala Lys Tyr Asp Lys Ser Ile
            340                 345                 350

```
Ala Lys Val Thr Phe Thr Pro Asn Pro Gly Gly Asp Pro Glu Ile Thr
        355                 360                 365

Asn Met Met Phe Asn Cys Gly Gly Glu Phe Phe Tyr Cys Asn Thr Thr
        370                 375                 380

Pro Leu Phe Asn Lys Phe Asn Tyr Thr Cys Asp Asn Gln Asn Asn Cys
385                 390                 395                 400

Thr Arg Asn Asn Thr Asn Asp Thr Asn Ser Asp Asn Ser Thr Leu Thr
                405                 410                 415

Ile Ser Cys Arg Ile Arg Gln Ile Val Asn Ser Trp Met Arg Val Gly
                420                 425                 430

Lys Gly Ile Tyr Ala Pro Pro Ile Arg Gly Asn Ile Thr Cys Ile Ser
                435                 440                 445

Asn Ile Thr Gly Leu Leu Leu Glu Ala Gly Gly Lys Trp Glu Asn Asn
        450                 455                 460

Thr Ile Thr Val Tyr Pro Ser Gly Gly Glu Met Arg Asp Leu Trp Arg
465                 470                 475                 480

Leu Glu Leu Asn Arg Tyr Lys Val Val Ser Ile Glu Pro Ile Gly Val
                485                 490                 495

Ala Pro Thr Lys Ala Lys Arg His Thr Val Ala Arg Glu Lys Arg Ala
        500                 505                 510

Ala Phe Gly Leu Gly Ala Leu Phe Leu Gly Phe Leu Gly Ala Ala Gly
        515                 520                 525

Ser Thr Met Gly Ala Ala Ser Val Val Leu Thr Val Gln Ala Arg His
        530                 535                 540

Leu Leu Ser Gly Ile Val Gln Gln Gln Asn Asn Leu Leu Arg Ala Ile
545                 550                 555                 560

Glu Ala Gln Gln His Leu Leu Gln Leu Ser Val Trp Gly Ile Lys Gln
                565                 570                 575

Leu Gln Ala Arg Val Leu Ala Val Glu Arg Tyr Leu Lys Asp Gln Gln
                580                 585                 590

Ile Leu Ser Leu Trp Gly Cys Ser Gly Lys Ala Ile Cys Tyr Thr Thr
                595                 600                 605

Val Pro Trp Asn Ala Thr Trp Ser Ala Asn Thr Ser Tyr Asp Glu Ile
        610                 615                 620

Trp Asn Asn Leu Thr Trp Gln Asp Trp Asp Lys Lys Val Lys Asn Tyr
625                 630                 635                 640

Ser Gly Val Ile Phe Ser Leu Ile Glu Gln Ala Gln Glu Gln Gln Asn
                645                 650                 655

Thr Asn Glu Lys Asp Leu Leu Glu Leu Asp Gln Trp Ser Ser Leu Trp
                660                 665                 670

Ser Trp Phe Asn Ile Thr Gln Trp Leu Trp Tyr Ile Lys Ile Phe Leu
                675                 680                 685

Ile Val Val Ala Gly Leu Ile Gly Phe Arg Leu Ile Gly Ile Val Met
        690                 695                 700

Ser Val Ile Ala Lys Val Arg Gln Gly Tyr Ser Pro Leu Ser Leu Gln
705                 710                 715                 720

Thr Leu Ile Pro Thr Thr Arg Glu Pro Asp Arg Arg Gly Gly Thr Glu
                725                 730                 735

Glu Asp Gly Gly Glu Pro Gly Arg Gly Arg Ser Thr Arg Leu Val Ser
                740                 745                 750

Gly Phe Leu Ala Leu Val Trp Glu Asp Leu Arg Asn Leu Leu Ile Phe
                755                 760                 765
```

Phe Tyr His Arg Leu Ile Asp Leu Leu Ser Ile Leu Trp Arg Thr Val
    770                 775                 780

Gln Ile Leu Gly Gln Ser Ile Asn Lys Gly Leu Gln Gln Leu Lys Asp
785                 790                 795                 800

Phe Ser Thr Tyr Leu Lys Gly Val Leu Thr Tyr Trp Gly Arg Glu Ile
                805                 810                 815

Gln Ile Ser Ala Thr Ser Leu Leu Asp Thr Thr Ala Ile Ala Val Ala
            820                 825                 830

Asn Gly Thr Asp Arg Ile Ile Glu Phe Val Gln Ile Val Gly Arg Gly
        835                 840                 845

Ile Leu His Ile Pro Arg Arg Ile Arg Gln Gly Leu Glu Arg Ser Leu
    850                 855                 860

Leu
865

<210> SEQ ID NO 322
<211> LENGTH: 864
<212> TYPE: PRT
<213> ORGANISM: Simian immunodeficiency virus

<400> SEQUENCE: 322

Met Lys Val Met Glu Glu Arg Lys Arg Ser Phe Asn Gly Phe Tyr Met
1               5                   10                  15

Thr Met Thr Ile Cys Met Ala Leu Leu Ile Pro Cys Leu Thr Ser Asp
            20                  25                  30

Glu Trp Val Thr Val Tyr Tyr Gly Val Pro Val Trp Arg Glu Val Asn
        35                  40                  45

Thr Val Leu Phe Cys Ala Ser Asp Ala Lys Ala His Ser Thr Glu Ala
    50                  55                  60

His Asn Ile Trp Ala Thr His Ala Cys Val Pro Thr Asp Pro Asn Pro
65                  70                  75                  80

Gln Glu Val Val Leu His Asn Val Thr Glu Asp Phe Asn Met Trp Asn
                85                  90                  95

Asn Gln Met Val Glu Gln Met Gln Glu Asp Ile Ser Ser Leu Trp Asp
            100                 105                 110

Gln Ser Leu Lys Pro Cys Val Lys Leu Thr Pro Leu Cys Val Thr Met
        115                 120                 125

Lys Cys Ser Asn Val Thr Arg Gln Asn Ser Thr Ser Asn Ser Asn Asn
    130                 135                 140

Asn Pro Thr Leu Lys Asn Asn Thr Ser Gly Lys Asn Glu Thr Gly Val
145                 150                 155                 160

Leu Gln Met Lys Asn Cys Thr Phe Asn Thr Thr Thr Glu Leu Arg Asp
                165                 170                 175

Lys Lys Lys Gln Val Tyr Ser Leu Phe Tyr Val Asp Asp Leu Gln Ser
            180                 185                 190

Leu Gly Ser Gly Thr Gly Asp Thr Tyr Thr Met Ile Asn Cys Asn Thr
        195                 200                 205

Thr Ala Ile Thr Gln Ala Cys Pro Lys Val Ser Phe Glu Pro Ile Pro
    210                 215                 220

Ile His Tyr Cys Ala Pro Ala Gly Phe Ala Ile Leu Lys Cys Asn Asp
225                 230                 235                 240

Val Asn Phe Ser Gly Lys Gly Lys Cys Arg Asn Val Ser Thr Val His
                245                 250                 255

Cys Thr His Gly Ile Lys Pro Val Val Thr Thr Gln Leu Ile Ile Asn
            260                 265                 270

```
Gly Ser Leu Ala Thr Glu Asn Ile Thr Val Arg Val Asn Asn Ala Ser
            275                 280                 285

Lys Asn Thr His Asp Trp Ile Val Gln Leu Ser Thr Ala Val Asn Leu
    290                 295                 300

Thr Cys Lys Arg Val Gly Asn Asn Thr Arg Gly Lys Val Gln Ile Gly
305                 310                 315                 320

Pro Gly Met Thr Phe Tyr Asn Met Asp His Ile Phe Gly Asp Thr Arg
                325                 330                 335

Lys Ala Phe Cys Glu Leu Asn Gly Thr Thr Trp Asn Glu Thr Leu Gln
            340                 345                 350

Lys Val Arg Glu Ser Leu Ile Lys Glu Ile Lys Ala Asn Ala Asn Gly
        355                 360                 365

Thr Tyr Asn Ile Thr Phe Glu Pro Ser Ser Gly Gly Asp Pro Glu Ile
    370                 375                 380

Ala Asn His Met Phe Asn Cys Gly Gly Glu Phe Phe Tyr Cys Asp Thr
385                 390                 395                 400

Arg Lys Met Phe Asn Glu Ser Glu Pro Phe His Glu Asn Met Thr Ile
                405                 410                 415

Pro Cys Arg Ile Arg Gln Ile Val Asn Ser Trp Met Arg Val Gly Arg
            420                 425                 430

Gly Ile Tyr Ala Pro Pro Ile Pro Gly His Ile Thr Cys Asn Ser Leu
        435                 440                 445

Ile Thr Gly Leu Ile Leu Thr Arg Asp His Val Asn Asn Thr Asn Asn
    450                 455                 460

Thr Phe Arg Pro Ile Gly Gly Asp Met Lys Asn Ile Trp Arg Ser Glu
465                 470                 475                 480

Leu Tyr Lys Tyr Lys Val Val Arg Ile Glu Pro Leu Ser Val Ala Pro
                485                 490                 495

Thr Lys Ala Lys Arg His Thr Val Gly Glu Arg Arg Gln Lys Arg Ala
            500                 505                 510

Ala Phe Gly Leu Gly Ala Leu Phe Leu Gly Phe Leu Gly Ala Ala Gly
        515                 520                 525

Ser Thr Met Gly Ala Ala Ala Val Thr Leu Thr Val Gln Ala Arg Gln
    530                 535                 540

Leu Leu Ser Gly Ile Val Gln Gln Gln Asn Asn Leu Leu Arg Ala Ile
545                 550                 555                 560

Glu Ala Gln Gln His Leu Leu Gln Leu Thr Val Trp Gly Val Lys Gln
                565                 570                 575

Leu Gln Ala Arg Leu Leu Ala Val Glu Arg Tyr Leu Gln Asp Gln Gln
            580                 585                 590

Ile Leu Gly Leu Trp Gly Cys Ser Gly Lys Ser Ile Cys Tyr Thr Thr
        595                 600                 605

Val Pro Trp Asn Lys Thr Trp Ser Gly Lys Ser Met Ser Asp Ile Trp
    610                 615                 620

Asn Asn Leu Thr Trp Gln Gln Trp Asp Lys Leu Ile Thr Asn Tyr Thr
625                 630                 635                 640

Gly Thr Ile Phe Gly Leu Leu Glu Glu Ala Gln Ser Gln Gln Glu Lys
                645                 650                 655

Asn Glu Lys Asp Leu Leu Glu Leu Asp Gln Trp Ala Ser Leu Trp Asn
            660                 665                 670

Trp Phe Asp Ile Thr Asn Trp Leu Trp Tyr Ile Lys Ile Phe Leu Met
        675                 680                 685
```

```
Ala Val Gly Gly Ile Ile Gly Leu Arg Ile Ile Met Ser Val Val Ser
        690                 695                 700

Val Ile Arg Arg Val Arg Gln Gly Tyr Ser Pro Leu Ser Leu Gln Thr
705                 710                 715                 720

Leu Ile Pro Ala Gln Arg Glu Pro Gly Thr Leu Gly Glu Thr Gly Gly
            725                 730                 735

Glu Gly Gly Glu Pro Gly Ser Gly Arg Ser Val Arg Leu Val Thr Gly
        740                 745                 750

Cys Trp Pro Leu Ile Trp Asp Asp Leu Arg Asn Leu Val Ile Trp Ser
            755                 760                 765

Tyr Arg Ser Leu Thr Ser Leu Ala Cys Ile Val Trp Arg Gln Leu Glu
770                 775                 780

Lys Leu Gly Gln Leu Leu Ile Asn Ile Leu Arg Leu Ile Gln Glu Lys
785                 790                 795                 800

Leu Thr Leu Leu Arg Gly Ile Gln Tyr Trp Gly Arg Glu Leu Arg
            805                 810                 815

Thr Ser Ala Thr Ser Leu Leu Asp Ala Thr Ala Ile Ala Val Gly Glu
        820                 825                 830

Gly Thr Asp Arg Ile Ile Arg Ala Val Gln Ile Val Phe Arg Ile Ile
        835                 840                 845

Gly Asn Ile Pro Arg Arg Ile Arg Gln Gly Leu Glu Arg Thr Leu Leu
850                 855                 860

<210> SEQ ID NO 323
<211> LENGTH: 880
<212> TYPE: PRT
<213> ORGANISM: Simian immunodeficiency virus

<400> SEQUENCE: 323

Met Lys Ala Met Glu Thr Gln Arg Asn Cys Arg Thr Leu Ser Leu Lys
1               5                   10                  15

Glu Ile Ile Leu Cys Thr Leu Val Leu Gly Ile Ile Gly Ile Ile Lys
            20                  25                  30

Cys Glu Asp Asn Met Trp Val Thr Val Tyr Tyr Gly Val Pro Val Trp
        35                  40                  45

Arg Glu Ala Asp Thr Thr Leu Phe Cys Ala Ser Asp Ala Lys Ala Gln
50                  55                  60

Asn Pro Glu Val His Asn Val Trp Ala Ser Gln Ala Cys Val Ser Thr
65                  70                  75                  80

Asn Pro Asn Pro Glu Glu Ile Glu Leu Thr Asn Val Thr Glu Tyr Phe
            85                  90                  95

Asn Ala Trp Glu Asn Asn Met Val Glu Gln Met His Glu Asp Ile Val
        100                 105                 110

Asn Leu Trp Asp Gln Ser Val Lys Pro Cys Val Lys Leu Ile Pro Leu
            115                 120                 125

Cys Val Thr Leu Asn Cys Ser Leu Phe Lys Cys Ile Lys Glu Asn Gly
        130                 135                 140

Asn Thr Thr Asn Cys Thr Val Gln Ile Ser Thr Gly Asn Asp Ser Thr
145                 150                 155                 160

Ala Asn Asn Ile Thr Val Gly Thr Ile Asp Met Tyr Asn Cys Ser Phe
            165                 170                 175

Asn Ala Thr Thr Glu Leu Arg Asp Arg Lys Lys Gln Val Tyr Ser Leu
        180                 185                 190

Phe Tyr Arg Gln Asp Leu Glu Pro Leu Glu Gly Asn Lys Pro Pro Glu
        195                 200                 205
```

```
Gly Asp Lys Asn Ala Leu Tyr Arg Leu Tyr Asn Cys Asn Thr Thr Ala
    210                 215                 220

Met Thr Gln Ala Cys Ser Lys Val Ser Leu Glu Pro Ile Pro Ile His
225                 230                 235                 240

Tyr Cys Ala Pro Ala Gly Phe Ala Leu Leu Lys Cys Asn Asp Lys Asn
                245                 250                 255

Phe Thr Gly Ile Gly Gln Cys Lys Asn Val Ser Thr Val His Cys Thr
            260                 265                 270

His Gly Ile Arg Pro Val Val Ser Thr Gln Phe Leu Leu Asn Gly Thr
        275                 280                 285

Leu Glu Glu Lys Val Thr Val Leu Asp Arg Asn Val Ser Asn Asp Met
290                 295                 300

Asp Thr Ile Ile Val Lys Leu Asn Glu Thr Val Arg Leu Asn Cys Thr
305                 310                 315                 320

Arg Thr Gly Asn Asn Thr Ile Lys Gly Ile Pro Ile Gly Pro Ser Gln
                325                 330                 335

Ile Phe Tyr Gly Ile Glu Thr Val Ile Gly Asp Thr Arg Gln Ala Phe
            340                 345                 350

Cys Gln Leu Asn Lys Thr Val Trp Thr Asn Thr Phe Lys Lys Val Arg
        355                 360                 365

His Ala Leu Asn Glu Thr Tyr Lys Gly Tyr Leu Gly Asn Glu Thr Ile
370                 375                 380

Thr Phe Gly Pro Ser Thr Gly Gly Asp Leu Glu Val Thr Asn Leu His
385                 390                 395                 400

Leu Ile Cys Gly Gly Glu Phe Phe Tyr Cys Asn Thr Ser Ile Leu Phe
                405                 410                 415

Asn Thr Ser Ile Ile Phe Asn Glu Thr Lys Asp Asp Asn Ile Thr Ile
            420                 425                 430

Pro Cys Arg Ile Arg Gln Ile Val Arg Leu Trp Gln Arg Val Gly Arg
        435                 440                 445

Gly Ile Phe Leu Pro Pro Ile Arg Gly Thr Ile Asn Cys Ile Ser Asn
450                 455                 460

Ile Thr Gly Ile Leu Phe Ala Gln Gln Lys Thr Asp Arg Met Asn Lys
465                 470                 475                 480

Ser Ala Met Phe Thr Pro Val Gly Gly Glu Met Arg Asn Asn Trp Arg
                485                 490                 495

Ser Glu Leu Tyr Lys Tyr Lys Val Val Arg Ile Glu Pro Leu Gly Val
            500                 505                 510

Ala Pro Thr Lys Ala Lys Arg Arg Thr Val His Arg Glu Lys Arg Ala
        515                 520                 525

Ala Val Gly Leu Gly Ala Leu Phe Leu Gly Phe Leu Gly Ala Ala Gly
530                 535                 540

Ser Thr Met Gly Ala Ala Ser Leu Thr Leu Thr Val Gln Ala Arg Gln
545                 550                 555                 560

Leu Leu Ser Gly Ile Val Gln Gln Ser Asn Leu Leu Arg Ala Ile
                565                 570                 575

Glu Ala Gln Gln His Leu Leu Gln Leu Ser Val Trp Gly Ile Lys Gln
            580                 585                 590

Leu Gln Ala Arg Val Leu Ala Val Glu Arg Tyr Leu Lys Asp Gln Gln
        595                 600                 605

Leu Leu Gly Leu Trp Gly Cys Ser Gly Lys Leu Ile Cys Thr Thr Ser
610                 615                 620
```

Val Pro Trp Asn Thr Thr Trp Thr Asn Lys Ser Tyr Asp Asp Ile Trp
625                 630                 635                 640

Tyr Asn Met Thr Trp Met Gln Trp Asp Lys Glu Val Ser Asn Tyr Thr
            645                 650                 655

Asp Val Ile Tyr Asn Leu Leu Glu Lys Ala Gln Thr Gln Gln Glu Asn
        660                 665                 670

Asn Glu Lys Glu Leu Leu Glu Leu Asp Lys Trp Ala Ser Leu Trp Asn
    675                 680                 685

Trp Phe Asp Ile Thr Ser Trp Leu Trp Tyr Ile Lys Ile Phe Ile Ile
690                 695                 700

Ile Val Gly Gly Leu Ile Gly Leu Arg Ile Val Phe Ala Leu Leu Ser
705                 710                 715                 720

Ile Val Asn Arg Val Arg Gln Gly Tyr Ser Pro Leu Ser Phe Gln Thr
            725                 730                 735

Leu Ile Pro Ala Arg Arg Asp Arg Asp Arg Pro Glu Glu Ile Glu Glu
        740                 745                 750

Gly Gly Gly Glu Pro Asp Asn Val Arg Ser Ile Arg Leu Val Ser Gly
    755                 760                 765

Phe Leu Ala Leu Ala Trp Asn Asp Leu Arg Asp Leu Cys Leu Phe Leu
770                 775                 780

Tyr His Arg Leu Arg Asp Leu Leu Ile Val Leu Arg Thr Leu Glu
785                 790                 795                 800

Leu Val Gly Gln Thr Leu Leu Lys Gly Leu Arg Arg Gly Arg Glu Ala
            805                 810                 815

Leu Ile His Leu Arg Gly Ile Leu Gln Tyr Trp Gly Gln Glu Leu Lys
        820                 825                 830

Thr Ser Ala Ile Ser Leu Leu Asp Thr Thr Ala Ile Ala Val Ala Glu
    835                 840                 845

Gly Thr Asp Arg Ile Ile Glu Ile Ala Gln Arg Phe Gly Arg Gly Ile
850                 855                 860

Leu Asn Ile Pro Arg Arg Ile Arg Gln Gly Leu Glu Arg Ala Leu Leu
865                 870                 875                 880

<210> SEQ ID NO 324
<211> LENGTH: 845
<212> TYPE: PRT
<213> ORGANISM: Simian immunodeficiency virus

<400> SEQUENCE: 324

Met Arg Val Lys Gly Thr Trp Thr Ser Cys Met Pro Tyr Tyr Val Val
1               5                   10                  15

Gly Ile Leu Ser Leu Cys Ser Leu Ile Ile Ser Ser Thr Lys Asn Glu
            20                  25                  30

Asn Leu Trp Val Thr Val Tyr Tyr Gly Val Pro Val Trp Lys Glu Ala
        35                  40                  45

Glu Ala Thr Leu Phe Cys Ala Ser Asp Ala Lys Ala Gln Lys Ala Glu
    50                  55                  60

Ala His Asn Ile Trp Ala Ser Gln Ala Cys Val Pro Thr Asp Pro Asp
65                  70                  75                  80

Pro Lys Ala Ile Glu Leu Ser Asn Val Thr Glu Asn Phe Asn Met Trp
                85                  90                  95

Thr Asn Ala Met Val Asn Gln Met Gln Gln Asp Val Ile Ser Leu Trp
            100                 105                 110

Asp Gln Ser Leu Lys Pro Cys Ile Lys Leu Thr Pro Leu Cys Val Thr
        115                 120                 125

-continued

```
Leu His Cys Ser Ile Pro Lys Phe Asp Asn Ser Ser Ile Asn Ser Ser
    130                 135                 140

Asn Glu Thr Met Lys Asn Cys Ser Phe Asn Thr Thr Thr Glu Leu Arg
145                 150                 155                 160

Asp Lys Lys Gln Thr Tyr Ser Leu Phe Tyr Val Asp Asp Leu Thr
                165                 170                 175

Gln Ile Asn Lys Thr Thr Glu Ser Tyr Lys Leu Ile Asn Cys Asn Thr
                180                 185                 190

Thr Ala Ile Thr Gln Ala Cys Pro Lys Ile Ser Phe Glu Pro Ile Pro
        195                 200                 205

Ile His Tyr Cys Ala Pro Ala Gly Phe Ala Leu Leu Arg Cys Asn Asn
    210                 215                 220

Lys Thr Tyr Asn Gly Ser Gly Pro Cys Asn Asn Val Ser Thr Val His
225                 230                 235                 240

Cys Thr His Gly Ile Lys Pro Val Ile Ser Thr Gln Leu Ile Leu Asn
                245                 250                 255

Gly Ser Leu Ala Glu Glu Lys Ile Met Ile Arg Tyr Lys Ala Asp Lys
                260                 265                 270

Val Leu Val Gln Leu Asn Thr Ser Ile His Ile Asn Cys Thr Arg Val
        275                 280                 285

Gly Asn Lys Thr Ile Lys Gly Ile Pro Leu Gly Pro Gly Gln Leu Phe
    290                 295                 300

Tyr Gly Thr Glu Thr Val Val Gly Asp Thr Arg Glu Ala His Cys Glu
305                 310                 315                 320

Ile Asn Gln Thr His Trp Tyr Lys Ile Leu Asn Gln Val Lys Arg Glu
                325                 330                 335

Leu Thr Thr Val Phe Asn Glu Ser Asn Lys Thr Val His Phe Ala Asn
                340                 345                 350

Ser Ser Gly Gly Asp Pro Glu Val Ala Asn Leu His Phe Asn Cys Gly
        355                 360                 365

Gly Glu Phe Phe Tyr Cys Asn Thr Ser Ala Leu Phe Asn Asp Thr Leu
    370                 375                 380

Leu Arg Asn Lys Thr Leu Leu Asn Glu Thr Leu His Asn Asn Leu Thr
385                 390                 395                 400

Leu Pro Cys Arg Ile Arg Gln Ile Val Asn Leu Trp Leu Arg Val Gly
                405                 410                 415

Lys Gly Ile Phe Ala Pro Pro Ile Arg Gly Asn Ile Arg Cys Asn Ser
                420                 425                 430

Thr Ile Thr Gly Leu Ile Leu Glu Lys His Thr Asn Thr Asp Asn Ile
        435                 440                 445

Thr Phe Arg Pro Ile Gly Gly Asp Met Thr Asp Ile Trp Arg Ser Glu
    450                 455                 460

Leu Tyr Asn Tyr Lys Ile Val Lys Ile Glu Pro Leu Gly Val Ala Pro
465                 470                 475                 480

Thr Arg Ala Arg Arg Thr Val Asp Arg Glu Lys Arg Ala Ala Gly
                485                 490                 495

Leu Gly Val Phe Phe Leu Gly Phe Leu Gly Ala Ala Gly Ser Thr Met
                500                 505                 510

Gly Ala Ala Ser Leu Thr Leu Thr Val Gln Ala Arg Gln Leu Leu Thr
        515                 520                 525

Gly Ile Val Gln Gln Gln Ser Asn Leu Leu Arg Ala Ile Glu Ala Gln
    530                 535                 540
```

Gln His Leu Leu Gln Leu Ser Val Trp Gly Ile Lys Gln Leu Gln Ala
545 550 555 560

Arg Val Leu Ala Ile Glu Arg Tyr Leu Lys Asp Gln Gln Leu Leu Gly
565 570 575

Ile Trp Gly Cys Ser Gly Lys Leu Ile Cys Thr Thr Ser Val Pro Trp
580 585 590

Asn Arg Thr Trp Ser Asn Lys Thr Tyr Asn Glu Ile Trp Asp Asn Met
595 600 605

Thr Trp Met Glu Trp Asp Arg Glu Val Arg Asn Tyr Thr Glu Ile Ile
610 615 620

Tyr Gly Leu Ile Glu Gln Ala Gln Asp Gln Gln Glu Asn Asn Glu Lys
625 630 635 640

Lys Leu Leu Glu Leu Asp His Trp Thr Ser Leu Trp Asn Trp Phe Asp
645 650 655

Ile Ser His Trp Leu Trp Tyr Ile Lys Ile Phe Ile Met Ile Ile Gly
660 665 670

Gly Leu Ile Val Cys Arg Ile Ile Phe Ala Val Leu Ala Ile Val Asn
675 680 685

Arg Val Arg Gln Gly Tyr Ser Pro Leu Ser Phe Gln Thr Leu Ser Pro
690 695 700

Ile Pro Arg Gly Leu Ala Gln Pro Gly Gly Thr Glu Glu Glu Gly Gly
705 710 715 720

Glu Gln Gly Thr Asp Arg Ser Val Arg Leu Leu Asp Gly Phe Leu Ala
725 730 735

Leu Ala Trp Asn Asp Leu Arg Asp Leu Cys Leu Phe Leu Tyr His Arg
740 745 750

Leu Thr Asp Leu Val Leu Ile Ala Arg Arg Thr Leu Glu Ile Val Gly
755 760 765

Gln Tyr Thr Leu Lys Gly Leu Arg Leu Val Trp Glu Ala Leu Leu Tyr
770 775 780

Leu Gln Gly Ile Leu Gln Tyr Trp Gly Lys Glu Leu Lys Thr Ser Ala
785 790 795 800

Thr Ser Leu Leu Asp Thr Thr Ala Ile Ala Val Ala Glu Gly Thr Asp
805 810 815

Arg Ile Ile Glu Ile Val Gln Arg Ile Gly Arg Gly Ile Leu His Ile
820 825 830

Pro Arg Arg Ile Arg Gln Gly Phe Glu Arg Ala Leu Leu
835 840 845

<210> SEQ ID NO 325
<211> LENGTH: 835
<212> TYPE: PRT
<213> ORGANISM: Simian immunodeficiency virus

<400> SEQUENCE: 325

Met Lys Val Thr Glu Met Gln Lys Asn Trp Leu Ile Cys Cys Leu Leu
1 5 10 15

Ile Gly Leu Ile Lys Ile Ile Gly Ser Glu Leu Trp Val Thr Val Tyr
20 25 30

Tyr Gly Val Pro Val Trp Arg Asp Ala Glu Thr Val Leu Phe Cys Ala
35 40 45

Ser Asp Ala Lys Ala His Ser Thr Glu Ala His Asn Ile Trp Ala Thr
50 55 60

Gln Ala Cys Val Pro Thr Asp Pro Asn Pro Gln Glu Val Leu Ile Pro
65 70 75 80

```
Asn Val Thr Glu Arg Phe Asp Met Trp Lys Asn Asn Met Val Asp Gln
                85                  90                  95

Met Gln Glu Asp Ile Ile Ser Leu Trp Glu Gln Ser Leu Lys Pro Cys
            100                 105                 110

Val Lys Leu Thr Pro Leu Cys Val Thr Leu Ser Cys Ser Ser Trp Arg
        115                 120                 125

Ser Val Asn Asn Ser Val Asn Gln Thr Asn His Val Gln Met Gln Asn
    130                 135                 140

Cys Ser Phe Asn Val Thr Thr Glu Leu Arg Asp Lys Lys Gln Val
145                 150                 155                 160

Tyr Ser Leu Phe Tyr Met Gly Asp Ile Ile Pro Leu Asp Thr Asn Asn
                165                 170                 175

Ser Ser Gly Asn Asn Ser Gln Tyr Arg Leu Ile Asn Cys Asn Thr Thr
            180                 185                 190

Ala Val Thr Gln Ala Cys Pro Lys Ile Ser Phe Glu Pro Ile Pro Ile
        195                 200                 205

Tyr Tyr Cys Ala Pro Pro Gly Phe Ala Ile Ile Lys Cys Asn Asp Gln
    210                 215                 220

Asp Phe Asn Gly Thr Gly Glu Cys Asn Asn Val Ser Thr Val Gln Cys
225                 230                 235                 240

Thr His Gly Ile Lys Pro Val Ile Ser Thr Gln Leu Ile Leu Asn Gly
                245                 250                 255

Ser Leu Ala Thr Ser Asn Ile Val Ile Arg Asn Asn Ser Lys Asp Thr
            260                 265                 270

Leu Leu Val Gln Leu Asn Glu Ser Ile Pro Ile Asn Cys Thr Arg Pro
        275                 280                 285

Gly Asn Lys Thr Arg Gly Gln Val Gln Ile Gly Pro Gly Met Thr Phe
    290                 295                 300

Tyr Asn Ile Glu Asn Ile Ile Gly Asp Thr Arg Gln Ala Tyr Cys Glu
305                 310                 315                 320

Val Asn Arg Thr Trp Glu Gln Ile Trp Asn Thr Thr Lys Gln Ile Ile
                325                 330                 335

Ile Asn Asn Arg Lys Asn Ile Thr Phe Ile Pro Asn Pro Gly Gly Asp
            340                 345                 350

Leu Glu Val Thr Asn Leu Met Ile Asn Cys Gly Gly Glu Phe Phe Tyr
        355                 360                 365

Cys Asn Thr Ser Gln Leu Phe Thr Asn Gln Asn Gly Asn Thr Thr Gly
    370                 375                 380

Asn Ile Thr Leu Gln Cys Arg Ile Arg Gln Ile Val Asn Leu Trp Thr
385                 390                 395                 400

Arg Val Gly Lys Gly Ile Tyr Ala Pro Pro Ile Lys Gly Pro Ile Asn
                405                 410                 415

Cys Leu Ser Asn Ile Thr Gly Ile Ile Leu Asp Tyr Thr Lys Ser Gly
            420                 425                 430

Thr Glu Lys Tyr Thr Ile Tyr Pro Thr Gly Gly Asp Met Thr Asn Leu
        435                 440                 445

Trp Arg Gln Glu Leu Tyr Lys Tyr Lys Val Val Ser Ile Glu Pro Ile
    450                 455                 460

Gly Val Ala Pro Gly Lys Ala Lys Arg His Thr Val Thr Arg Gln Lys
465                 470                 475                 480

Arg Ala Ala Phe Gly Leu Gly Ala Leu Phe Leu Gly Phe Leu Gly Ala
                485                 490                 495
```

```
Ala Gly Ser Thr Met Gly Ala Ala Ser Ile Thr Leu Thr Val Gln Ala
            500                 505                 510

Arg Lys Leu Leu Ser Gly Ile Val Gln Gln Gln Asn Asn Leu Leu Arg
        515                 520                 525

Ala Ile Glu Ala Gln Gln His Leu Leu Gln Leu Ser Val Trp Gly Ile
    530                 535                 540

Lys Gln Leu Gln Ala Arg Val Leu Ala Ile Glu Arg Tyr Leu Arg Asp
545                 550                 555                 560

Gln Gln Ile Leu Gly Leu Trp Gly Cys Ser Gly Lys Ser Val Cys Tyr
                565                 570                 575

Thr Asn Val Pro Trp Asn Thr Thr Trp Ser Asn Asn Ser Tyr Asp
            580                 585                 590

Thr Ile Trp Gly Asn Met Thr Trp Gln Asn Trp Asp Glu Gln Val Arg
                595                 600                 605

Asn Tyr Ser Gly Val Ile Phe Gly Leu Leu Glu Gln Ala Gln Glu Gln
        610                 615                 620

Gln Ser Ile Asn Glu Lys Ser Leu Leu Glu Leu Asp Gln Trp Ser Ser
625                 630                 635                 640

Leu Trp Asn Trp Phe Asp Ile Thr Lys Trp Leu Trp Tyr Ile Lys Ile
                645                 650                 655

Phe Ile Met Val Val Ala Gly Ile Val Gly Ile Arg Ile Ile Ser Ile
            660                 665                 670

Ile Met Ser Met Val Ala Arg Val Arg Gln Gly Tyr Ser Pro Leu Ser
                675                 680                 685

Leu Gln Thr Leu Ile Pro Thr Thr Arg Gly Pro Asp Arg Pro Glu Arg
        690                 695                 700

Thr Glu Glu Asp Ala Gly Glu Leu Asp Asn Gly Arg Ser Val Arg Leu
705                 710                 715                 720

Val Ser Gly Phe Leu Ala Leu Ala Trp Glu Asp Phe Arg Asn Leu Leu
                725                 730                 735

Leu Phe Leu Tyr His Arg Leu Thr Asp Cys Leu Ser Ile Leu Arg Arg
            740                 745                 750

Thr Leu Glu Leu Leu Arg Gln Asn Ile His Lys Gly Leu Gln Leu Leu
                755                 760                 765

Asn Glu Leu Arg Ile Tyr Leu Trp Gly Ile Ile Ala Tyr Trp Gly Arg
        770                 775                 780

Glu Leu Lys Ile Ser Ala Ile Asn Leu Leu Asp Thr Thr Ala Val Ala
785                 790                 795                 800

Val Ala Glu Gly Thr Asp Arg Ile Ile Glu Leu Val Gln Arg Ile Gly
                805                 810                 815

Arg Gly Ile Leu His Ile Pro Arg Arg Ile Arg Gln Gly Leu Glu Arg
            820                 825                 830

Ala Leu Leu
        835

<210> SEQ ID NO 326
<211> LENGTH: 855
<212> TYPE: PRT
<213> ORGANISM: Simian immunodeficiency virus

<400> SEQUENCE: 326

Met Lys Val Met Gly Met Lys Tyr Tyr Trp Trp Arg Asn Ser Cys Arg
1               5                   10                  15

Ser Ile Ser Ile Lys Leu Ile Leu Ile Gly Trp Ile Ala Ser Cys Phe
            20

```
Gly Glu Glu Asn Trp Trp Val Thr Val Tyr Tyr Gly Val Pro Val Trp
        35                  40                  45

Arg Glu Ala Lys Thr Thr Leu Phe Cys Ala Ser Asp Ala Lys Ser Tyr
    50                  55                  60

Ser Thr Glu Ala His Asn Ile Trp Ala Thr Gln Ala Cys Val Pro Thr
65                  70                  75                  80

Asp Pro Thr Pro Gln Glu Val Leu Leu Pro Asn Val Thr Glu Phe
                85                  90                  95

Asn Met Trp Glu Asn Tyr Met Val Asp Gln Met Gln Glu Asp Ile Ile
                100                 105                 110

Ser Leu Trp Glu Gln Ser Leu Lys Pro Cys Val Lys Leu Thr Pro Leu
        115                 120                 125

Cys Val Thr Leu Thr Cys Asn Asn Pro Thr Asn Thr Ser Cys Thr Asn
        130                 135                 140

Ser Thr Asp Asp Arg Leu Gly Asp Met Arg Asn Cys Ser Phe Asn Val
145                 150                 155                 160

Thr Thr Glu Leu Arg Asp Lys Lys Arg Gln Val Tyr Ser Leu Phe Tyr
                165                 170                 175

Val Glu Asp Ile Thr Ala Ile Gly Asn Asn Ser Thr Tyr Arg Leu Ile
        180                 185                 190

Asn Cys Asn Thr Thr Ala Ile Thr Gln Ala Cys Pro Lys Thr Ser Phe
        195                 200                 205

Glu Pro Ile Pro Ile His Tyr Cys Ala Pro Ala Gly Phe Ala Leu Leu
    210                 215                 220

Lys Cys Asn Asp Ile Asp Tyr Lys Gly Asn Glu Thr Cys Lys Asn Val
225                 230                 235                 240

Ser Thr Val His Cys Thr His Gly Ile Lys Pro Val Ala Thr Gln
                245                 250                 255

Leu Ile Leu Asn Gly Ser Thr Ala Asp Asn Gln Thr Val Ala Arg Ile
        260                 265                 270

Asp Pro Ser Glu Asn Leu Ala Ile Ile Gln Leu Lys Asp Pro Val Lys
    275                 280                 285

Ile Thr Cys Arg Arg Pro Gly Asn Asn Thr Arg Gly Gln Ile Gln Ile
    290                 295                 300

Gly Pro Ala Met Thr Phe Tyr Asn Ile Glu Asn Val Val Gly Asp Thr
305                 310                 315                 320

Arg Lys Ala Tyr Cys Glu Ile Asn Gly Thr Gln Trp Ala Lys Ala Leu
                325                 330                 335

Asn Glu Thr Lys Glu Val Leu Arg Asn Ile Leu Arg Lys Asn Ile Ser
        340                 345                 350

Phe Met Val Pro Ser Gly Gly Asp Pro Glu Val Thr Asn His His Phe
        355                 360                 365

Asn Cys Gly Gly Glu Phe Phe Tyr Cys Asn Thr Ser Glu Ile Ile Asn
    370                 375                 380

Ile Thr Lys Ile Asn Lys Thr Glu Asn Met Thr Ile Ile Pro Cys Arg
385                 390                 395                 400

Ile Arg Gln Ile Val Asn Ser Trp Met Arg Val Gly Lys Gly Ile Phe
                405                 410                 415

Ala Pro Pro Ile Arg Gly Asn Ile Thr Cys Thr Ser Asn Ile Thr Gly
            420                 425                 430

Met Leu Leu Glu Ile His Lys Asn Arg Glu Asp Gln Gly Glu Asp Gln
        435                 440                 445
```

```
Asp Gln Asn Asn Thr Tyr Val Cys Leu Thr Gly Gly Asn Met Lys Asp
    450                 455                 460

Ile Trp Arg Ser Glu Leu Tyr Lys Tyr Lys Ile Val Glu Ile Gln Pro
465                 470                 475                 480

Leu Gly Val Ala Pro Thr Lys Ser Arg Arg Tyr Ala Val Glu Lys Gln
                485                 490                 495

His His Arg Glu Lys Arg Ala Leu Gly Leu Gly Ala Leu Phe Leu Gly
                500                 505                 510

Phe Leu Gly Ala Ala Gly Ser Thr Met Gly Ala Ala Ser Val Val Leu
            515                 520                 525

Thr Val Gln Ala Arg Gln Leu Leu Thr Gly Ile Val Gln Gln Gln Asn
    530                 535                 540

Asn Leu Leu Arg Ala Ile Glu Ala Gln Gln His Leu Leu Gln Leu Ser
545                 550                 555                 560

Val Trp Gly Ile Lys Gln Leu Gln Ala Arg Val Leu Ala Val Glu Arg
                565                 570                 575

Tyr Leu Arg Asp Gln Gln Leu Leu Gly Leu Trp Gly Cys Thr Gly Lys
            580                 585                 590

Thr Ile Cys Pro Thr Ala Val Arg Trp Asn Lys Thr Trp Gly Asn Ile
    595                 600                 605

Ser Asp Tyr Gln Val Ile Trp Asn Asn Tyr Thr Trp Gln Gln Trp Asp
610                 615                 620

Arg Glu Val Asn Asn Tyr Thr Gly Leu Ile Tyr Thr Leu Leu Glu Glu
625                 630                 635                 640

Ala Asn Thr Gln Gln Glu Lys Asn Glu Lys Glu Leu Leu Glu Leu Asp
                645                 650                 655

Ser Trp Ala Asn Leu Trp Ser Trp Phe Asp Ile Thr Asn Trp Leu Trp
            660                 665                 670

Tyr Ile Lys Met Phe Leu Ile Val Val Gly Ile Ile Gly Leu Arg
    675                 680                 685

Ile Cys Phe Ala Ile Gly Ser Leu Ile Asn Arg Val Arg Lys Gly Tyr
    690                 695                 700

Ser Pro Leu Ser Leu Gln Thr Leu Ile Pro Ala Asn Gln Gly Pro Asp
705                 710                 715                 720

Gly Leu Gly Glu Thr Glu Lys Gly Gly Gly Glu Asn Val Arg Gly Arg
                725                 730                 735

Ser Ile Arg Leu Val Ser Gly Phe Leu Pro Leu Val Trp Glu Asp Leu
            740                 745                 750

Arg Asn Leu Leu Ser Phe Leu Tyr His Gln Leu Arg Asp Cys Ala Ser
    755                 760                 765

Leu Ile Trp Arg Leu Leu Glu Ile Leu Gly Gln Tyr Ser Leu Arg Gly
    770                 775                 780

Val Gln Gln Ile Gly Thr Leu His Gln Leu Arg Gly Thr Leu Gln
785                 790                 795                 800

Tyr Trp Thr Thr Glu Ile Lys Asn Ser Ala Ile Ser Leu Leu Asp Thr
                805                 810                 815

Thr Ala Ile Ala Val Gly Glu Gly Thr Asp Arg Ile Leu Glu Ala Ile
            820                 825                 830

Thr Arg Leu Gly Arg Gly Ile Leu His Ile Pro Arg Arg Ile Arg Gln
    835                 840                 845

Gly Leu Glu Arg Ala Leu Leu
850                 855
```

-continued

```
<210> SEQ ID NO 327
<211> LENGTH: 876
<212> TYPE: PRT
<213> ORGANISM: Simian immunodeficiency virus

<400> SEQUENCE: 327

Met Arg Asn Leu Ile Gly Thr Thr Leu Thr Leu Ile Ile Ile Ile Leu
1               5                   10                  15

Gly Ile Gly Ser Lys Glu Tyr Tyr Thr Thr Val Phe Tyr Gly Val Pro
            20                  25                  30

Ile Trp Lys Glu Ala Thr Pro Ser Leu Phe Cys Ala Ser Asn Ala Asp
        35                  40                  45

Ile Ala Ser Arg Asp Lys His Asn Ile Trp Ala Thr His Asn Cys Val
    50                  55                  60

Pro Leu Asp Pro Asn Pro Tyr Glu Val Pro Leu Ala Asn Val Ser Ile
65                  70                  75                  80

Asp Phe Asp Met Glu Lys Asn Tyr Met Val Glu Glu Met Lys Glu Asp
                85                  90                  95

Leu Leu Ser Leu Phe Gln Gln Ser Phe Lys Pro Cys Val Lys Leu Thr
            100                 105                 110

Pro Phe Cys Val Thr Met Lys Cys Thr Val Val Asn Thr Thr Val Val
        115                 120                 125

Asn Ala Thr Ala Pro Thr Pro Lys Val Ser Ala Thr Val Ala Thr Thr
    130                 135                 140

Pro Thr Ile Asn Leu Thr Asn Ile Lys Glu Tyr Glu Ile Phe Asn Cys
145                 150                 155                 160

Ser Phe Asn Gln Thr Thr Glu Phe Arg Asp Lys Lys Lys Gln Ile Tyr
                165                 170                 175

Ser Leu Phe Tyr Arg Glu Asp Ile Met Lys Val Gly Ser Glu Ser Thr
            180                 185                 190

Lys Asn Thr Asp Tyr Tyr Leu His Asn Cys Asn Thr Ser Ala Ile Thr
        195                 200                 205

Gln Glu Cys Asp Lys Ser Thr Phe Glu Pro Ile Pro Ile Arg Tyr Cys
    210                 215                 220

Ala Pro Ala Gly Phe Ala Met Leu Lys Cys Asn Asp Gln Gly Tyr Thr
225                 230                 235                 240

Gly Asn Gly Thr Cys Ser Asn Val Thr Val Val His Cys Thr His Gly
                245                 250                 255

Ile Phe Pro Met Ile Ala Thr Ala Leu His Leu Asn Gly Thr Leu Glu
            260                 265                 270

Glu Asn Glu Thr Lys Ala Tyr Phe Ala Asp Val Asn Val Asn Pro Pro
        275                 280                 285

Leu Leu Val Lys Phe Asn Glu Ser Val Ser Leu Thr Cys Glu Arg Thr
    290                 295                 300

Gly Asn Asn Thr Arg Gly Gln Val Gln Ile Gly Pro Gly Met Thr Phe
305                 310                 315                 320

Tyr Asn Ile Glu Asn Val Val Gly Asp Thr Arg Lys Ala Tyr Cys His
                325                 330                 335

Val Asn Ala Thr Leu Trp Asp Gln Ser Leu Ser Arg Ala Met Glu Ala
            340                 345                 350

Ile Asn Lys Thr Leu Ala Leu Tyr Asn Lys Ala Val Asn Glu Lys Phe
        355                 360                 365

Glu Trp Ser Lys Gly Asp Pro Glu Val Ser Ser Phe Trp Phe Asn Cys
    370                 375                 380
```

```
Gln Gly Glu Phe Phe Tyr Cys Asn Leu Thr Gly Trp Thr Asn Pro Trp
385                 390                 395                 400

Asn Asn Thr Asn His Arg Asn Gly Thr Leu Val Ala Pro Cys Arg Leu
            405                 410                 415

Arg Gln Ile Val Asn His Trp Gly Ile Val Ser Lys Gly Ile Tyr Leu
        420                 425                 430

Pro Pro Arg Arg Gly Thr Leu Lys Cys Asn Ser Asn Ile Thr Gly Leu
    435                 440                 445

Ile Met Thr Ala Glu Lys Gly Gly Asn Asn Thr Val Pro Thr Phe Ser
450                 455                 460

Gly Lys Val Glu Asp Tyr Trp Lys Val Glu Leu Ala Arg Tyr Lys Val
465                 470                 475                 480

Val Glu Ile Gln Pro Leu Ser Val Ala Pro Arg Pro Gly Lys Arg Pro
                485                 490                 495

Glu Ile Lys Ala Asn His Thr Arg Ser Arg Arg Asp Val Gly Ile Gly
                500                 505                 510

Leu Leu Phe Leu Gly Phe Leu Ser Ala Ala Gly Ser Thr Met Gly Ala
            515                 520                 525

Ala Ser Ile Ala Leu Thr Ala Gln Ala Arg Gly Leu Leu Ser Asp Ile
        530                 535                 540

Val Gln Gln Gln Asn Leu Leu Gln Ala Ile Glu Ala Gln Gln His
545                 550                 555                 560

Leu Leu Gln Leu Ser Val Trp Gly Ile Lys Gln Leu Gln Ala Arg Met
                565                 570                 575

Leu Ala Val Glu Lys Tyr Ile Arg Asp Gln Gln Tyr Leu Ser Ile Trp
            580                 585                 590

Gly Cys Ala Asn Lys Leu Val Cys His Ser Ser Val Pro Trp Asn Leu
        595                 600                 605

Ser Trp Ala Glu Asp Ser Gln Lys Cys Asn Ser Thr Asn Thr Lys Tyr
    610                 615                 620

Tyr Glu Cys Ile Trp Asn Asn Leu Thr Trp Gln Glu Trp Asp Arg Leu
625                 630                 635                 640

Val Gln Asn Ala Ser Glu Thr Ile Tyr Ser Leu Leu Glu Ile Ala Gln
                645                 650                 655

Thr Gln Gln Glu Lys Asn Lys Gln Glu Leu Leu Glu Leu Asp Lys Trp
                660                 665                 670

Ser Ser Leu Trp Asp Trp Phe Asp Ile Thr Gln Trp Leu Trp Tyr Ile
            675                 680                 685

Arg Leu Ala Ile Ile Ile Val Ala Gly Leu Val Gly Leu Arg Ile Leu
        690                 695                 700

Met Phe Ile Val Asn Val Val Lys Lys Val Arg Gln Gly Tyr Met Pro
705                 710                 715                 720

Leu Phe Ser Gln Thr Pro Thr Gln Ala Gln Gln Asp Pro Glu Gln Pro
                725                 730                 735

Gly Gly Ile Ala Glu Gly Gly Gly Arg Gly Asn Ile Arg Trp Thr
                740                 745                 750

Pro Ser Pro Thr Gly Phe Phe Ser Ile Val Trp Glu Asp Leu Arg Asn
            755                 760                 765

Leu Leu Ile Trp Leu Tyr Gln Thr Cys Arg Asn Phe Ile Trp Val Leu
        770                 775                 780

Trp Thr Ile Leu Gln Ala Leu Lys Gln Gly Thr Ile Ser Leu Ala Asn
785                 790                 795                 800

Asn Leu Val Ile Val His Arg Tyr Ile Val Val Lys Ile Arg Gln Ile
```

805 810 815

Ile Glu Trp Cys His Asn Thr Tyr Ala Ser Leu Arg Ala Ser Leu Ile
820 825 830

His Ala Ile Asp Arg Leu Ala Asp Phe Thr Gly Trp Trp Thr Asp Leu
835 840 845

Ile Ile Glu Gly Ile Thr Tyr Ile Gly Arg Gly Ile Arg Asn Ile Pro
850 855 860

Arg Arg Ile Arg Gln Gly Leu Glu Ile Ala Leu Asn
865 870 875

<210> SEQ ID NO 328
<211> LENGTH: 896
<212> TYPE: PRT
<213> ORGANISM: Simian immunodeficiency virus

<400> SEQUENCE: 328

Met Lys Met Arg Asn Leu Ile Gly Ile Thr Leu Ile Leu Ile Ile Leu
1 5 10 15

Thr Leu Gly Ile Gly Ser Arg Asp Tyr Tyr Thr Thr Val Phe Tyr Gly
20 25 30

Val Pro Ile Trp Lys Asp Ala Thr Pro Ser Leu Phe Cys Ala Ser Asp
35 40 45

Ala Asp Val Thr Ser Arg Glu Lys His Asn Ile Trp Ala Thr His Asn
50 55 60

Cys Val Pro Leu Asp Pro Asn Pro Tyr Glu Val Pro Ile Ala Asn Val
65 70 75 80

Ser Ile Lys Phe Asn Met Glu Glu Asn Tyr Met Val Lys Glu Met Lys
85 90 95

Glu Asp Leu Leu Ser Leu Phe Gln Gln Ser Phe Lys Pro Cys Val Lys
100 105 110

Leu Thr Pro Phe Cys Val Val Met Asn Cys Thr Lys Ser Gln Asn Val
115 120 125

Thr Thr Pro Ala Ser Thr Ser Thr Ala Ala Pro Val Asn Ala Thr Thr
130 135 140

Ile Pro Val Asn Leu Thr Asp Ile Pro Asn Tyr Glu Leu Phe Asn Cys
145 150 155 160

Ser Phe Gln Gln Thr Thr Glu Phe Arg Asp Lys Lys Lys Gln Ile Tyr
165 170 175

Ser Leu Phe Tyr Arg Glu Asp Ile Met Lys Asp Asn Arg Ser Met Gln
180 185 190

Asp Asn Arg Ser Asn Ser Ser Lys Lys Ser Asn Asn Ser Asn Asn Ser
195 200 205

Gly Tyr Tyr Leu His Asn Cys Asn Thr Ser Ala Ile Thr Gln Glu Cys
210 215 220

Asp Lys Ser Thr Phe Glu Pro Ile Pro Ile Arg Tyr Cys Ala Pro Ala
225 230 235 240

Gly Tyr Ala Met Leu Lys Cys Lys Asp Gln Asn Tyr Thr Gly Asn Gly
245 250 255

Ile Cys Tyr Asn Val Thr Val Val His Cys Thr His Gly Ile Phe Pro
260 265 270

Met Ile Ala Thr Ala Leu His Leu Asn Gly Thr Leu Glu Glu Lys Glu
275 280 285

Thr Lys Ala Tyr Phe Val Asn Ala Thr Asn Asn Pro Pro Leu Leu Val
290 295 300

```
Lys Phe Asn Glu Ser Val Pro Leu Thr Cys Gly Arg Thr Gly Asn Asn
305                 310                 315                 320

Val Arg Gly Gln Val Gln Ile Gly Pro Gly Met Thr Phe Tyr Asn Thr
            325                 330                 335

Glu Asn Val Val Gly Asp Thr Arg Lys Ala Tyr Cys Trp Val Asn Ala
                340                 345                 350

Thr Leu Trp Tyr Lys Ser Leu Asp Asn Ala Met Glu Ala Ile Thr Lys
        355                 360                 365

Thr Leu Lys Lys Ser Gly Leu Asn Val Thr Arg Arg Phe Asp Trp His
    370                 375                 380

Lys Gly Asp Leu Glu Val Gln Asn Phe Trp Phe Asn Cys Gln Gly
385                 390                 395                 400

Glu Phe Phe Tyr Cys Asn Leu Thr Thr Trp Thr Gly Asn Trp Thr Arg
                405                 410                 415

Asn Arg Thr His Gln Thr Ser Ala Leu Asn Lys Thr His Leu Leu Ala
            420                 425                 430

Gln Cys Arg Leu Arg Gln Ile Val Asn His Trp Gly Ile Val Ser Lys
        435                 440                 445

Gly Ile Tyr Leu Pro Pro Arg Lys Gly His Ile Lys Cys Val Ser Asn
450                 455                 460

Ile Thr Gly Leu Ile Met Thr Ala Glu Gly Gly Asn Ser Asn Arg Thr
465                 470                 475                 480

Pro Thr Phe Ser Ser Lys Val Glu Asp Tyr Trp Lys Val Glu Leu Ala
                485                 490                 495

Arg Tyr Lys Val Val Glu Ile Gln Pro Leu Ser Val Ala Pro Arg Pro
        500                 505                 510

Gly Lys Arg Pro Glu Ile Lys Ala Asn His Thr Arg Ser Arg Arg Asp
    515                 520                 525

Val Gly Ile Gly Leu Leu Phe Leu Gly Phe Leu Ser Ala Ala Gly Ser
530                 535                 540

Thr Met Gly Ala Ala Ser Leu Ala Leu Thr Ala Gln Ala Arg Gly Leu
545                 550                 555                 560

Leu Ser Gly Ile Val Gln Gln Gln Asn Leu Leu Gln Ala Ile Glu
                565                 570                 575

Ala Gln Gln His Leu Leu Gln Leu Ser Val Trp Gly Ile Lys Gln Leu
            580                 585                 590

Gln Ala Arg Met Leu Ala Val Glu Lys Tyr Ile Arg Asp Gln Gln Tyr
        595                 600                 605

Leu Ser Ile Trp Gly Cys Ala Asn Lys Leu Val Cys His Ser Ser Val
    610                 615                 620

Pro Trp Asn Leu Ser Trp Ala Gly Thr Ser Ser Lys Cys Asn Tyr Thr
625                 630                 635                 640

Gly Ala Lys Tyr Tyr Glu Cys Ile Trp Asn Asn Leu Thr Trp Gln Glu
                645                 650                 655

Trp Asp Lys Leu Val Gln Asn Ser Ser Glu Thr Ile Tyr Ser Leu Leu
            660                 665                 670

Glu Thr Ala Gln Thr Gln Gln Glu Arg Asn Lys Gln Glu Leu Leu Glu
        675                 680                 685

Leu Asp Lys Trp Ser Ser Leu Trp Asp Trp Phe Asp Ile Thr Gln Trp
    690                 695                 700

Leu Trp Tyr Ile Lys Ile Ala Ile Ile Val Ala Gly Leu Val Gly
705                 710                 715                 720

Leu Arg Ile Leu Met Phe Ile Val Asn Val Val Lys Lys Val Arg Gln
```

```
                725                 730                 735

Gly Tyr Met Pro Leu Phe Ser Gln Thr Pro Thr Gln Ala Glu Gln Asp
            740                 745                 750

Pro Glu Gln Pro Gly Gly Thr Ala Gly Gly Gly Gly Gly Gly Gly Asn
        755                 760                 765

Phe Arg Trp Thr Pro Ser Pro Thr Gly Phe Phe Ser Ile Val Trp Glu
    770                 775                 780

Asp Leu Arg Asn Leu Leu Ile Trp Ile Tyr Gln Thr Cys Gln Asn Phe
785                 790                 795                 800

Ile Trp Val Leu Trp Thr Ile Leu Gln Ala Leu Lys Gln Gly Thr Ile
                805                 810                 815

Ser Leu Ala His Asn Leu Val Ile Val His Arg Tyr Ile Ile Val Arg
            820                 825                 830

Val Arg Gln Thr Ile Glu Trp Cys Gly Asn Thr Tyr Ala Ser Leu Arg
        835                 840                 845

Ala Ser Leu Ile His Ala Ile Asp Arg Leu Ala Asp Phe Thr Gly Trp
    850                 855                 860

Trp Thr Asp Leu Leu Ile Glu Gly Val Val Tyr Ile Ala Arg Gly Ile
865                 870                 875                 880

Arg Asn Ile Pro Arg Arg Ile Arg Gln Gly Leu Glu Ile Ala Leu Asn
                885                 890                 895

<210> SEQ ID NO 329
<211> LENGTH: 871
<212> TYPE: PRT
<213> ORGANISM: Simian immunodeficiency virus

<400> SEQUENCE: 329

Met Lys Asn Leu Ile Gly Ile Thr Leu Ile Leu Ile Ile Thr Ile Leu
1               5                   10                  15

Gly Ile Gly Phe Ser Thr Tyr Tyr Thr Thr Val Phe Tyr Gly Val Pro
            20                  25                  30

Val Trp Lys Glu Ala Gln Pro Thr Leu Phe Cys Ala Ser Asp Ala Asp
        35                  40                  45

Ile Thr Ser Arg Asp Lys His Asn Ile Trp Ala Thr His Asn Cys Val
    50                  55                  60

Pro Leu Asp Pro Asn Pro Tyr Glu Val Thr Leu Ala Asn Val Ser Ile
65                  70                  75                  80

Arg Phe Asn Met Glu Glu Asn Tyr Met Val Gln Glu Met Lys Glu Asp
                85                  90                  95

Ile Leu Ser Leu Phe Gln Gln Ser Phe Lys Pro Cys Val Lys Leu Thr
            100                 105                 110

Pro Phe Cys Ile Lys Met Thr Cys Thr Met Thr Asn Thr Thr Asn Lys
        115                 120                 125

Thr Leu Asn Ser Ala Thr Thr Thr Leu Thr Pro Thr Val Asn Leu Ser
    130                 135                 140

Ser Ile Pro Asn Tyr Glu Val Tyr Asn Cys Ser Phe Asn Gln Thr Thr
145                 150                 155                 160

Glu Phe Arg Asp Lys Lys Lys Gln Ile Tyr Ser Leu Phe Tyr Arg Glu
                165                 170                 175

Asp Ile Val Lys Glu Asp Gly Asn Asn Asn Ser Tyr Tyr Leu His Asn
            180                 185                 190

Cys Asn Thr Ser Val Ile Thr Gln Glu Cys Asp Lys Ser Thr Phe Glu
        195                 200                 205
```

```
Pro Ile Pro Ile Arg Tyr Cys Ala Pro Ala Gly Phe Ala Leu Leu Lys
    210                 215                 220

Cys Arg Asp Gln Asn Phe Thr Gly Lys Gly Gln Cys Ser Asn Val Ser
225                 230                 235                 240

Val Val His Cys Thr His Gly Ile Tyr Pro Met Ile Ala Thr Ala Leu
            245                 250                 255

His Leu Asn Gly Ser Leu Glu Glu Glu Thr Lys Ala Tyr Phe Val
            260                 265                 270

Asn Thr Ser Val Asn Thr Pro Leu Leu Val Lys Phe Asn Val Ser Ile
        275                 280                 285

Asn Leu Thr Cys Glu Arg Thr Gly Asn Thr Arg Gly Gln Val Gln
290                 295                 300

Ile Gly Pro Gly Met Thr Phe Tyr Asn Ile Glu Asn Val Val Gly Asp
305                 310                 315                 320

Thr Arg Lys Ala Tyr Cys Ser Val Asn Ala Thr Thr Trp Tyr Arg Asn
                325                 330                 335

Leu Asp Trp Ala Met Ala Ala Ile Asn Thr Thr Met Arg Ala Arg Asn
                340                 345                 350

Glu Thr Val Gln Gln Thr Phe Gln Trp Gln Arg Asp Gly Asp Pro Glu
            355                 360                 365

Val Thr Ser Phe Trp Phe Asn Cys Gln Gly Glu Phe Phe Tyr Cys Asn
370                 375                 380

Leu Thr Asn Trp Thr Asn Thr Trp Thr Ala Asn Arg Thr Asn Asn Thr
385                 390                 395                 400

His Gly Thr Leu Val Ala Pro Cys Arg Leu Arg Gln Ile Val Asn His
                405                 410                 415

Trp Gly Ile Val Ser Lys Gly Val Tyr Leu Pro Pro Arg Arg Gly Thr
            420                 425                 430

Val Lys Cys His Ser Asn Ile Thr Gly Leu Ile Met Thr Ala Glu Lys
        435                 440                 445

Asp Asn Asn Asn Ser Tyr Thr Pro Gln Phe Ser Ala Val Val Glu Asp
    450                 455                 460

Tyr Trp Lys Val Glu Leu Ala Arg Tyr Lys Val Val Glu Ile Gln Pro
465                 470                 475                 480

Leu Ser Val Ala Pro Arg Pro Gly Lys Arg Pro Glu Ile Lys Ala Asn
                485                 490                 495

His Thr Arg Ser Arg Arg Asp Val Gly Ile Gly Leu Leu Phe Leu Gly
            500                 505                 510

Phe Leu Ser Ala Ala Gly Ser Thr Met Gly Ala Ala Ser Ile Ala Leu
        515                 520                 525

Thr Ala Gln Ala Arg Gly Leu Leu Ser Gly Ile Val Gln Gln Gln Gln
    530                 535                 540

Asn Leu Leu Gln Ala Ile Glu Ala Gln Gln His Leu Leu Gln Leu Ser
545                 550                 555                 560

Val Trp Gly Ile Lys Gln Leu Gln Ala Arg Met Leu Ala Val Glu Lys
                565                 570                 575

Tyr Ile Arg Asp Gln Gln Leu Leu Ser Leu Trp Gly Cys Ala Asn Lys
            580                 585                 590

Leu Val Cys His Ser Ser Val Pro Trp Asn Leu Thr Trp Ala Glu Asp
        595                 600                 605

Ser Thr Lys Cys Asn His Ser Asp Ala Lys Tyr Tyr Asp Cys Ile Trp
610                 615                 620

Asn Asn Leu Thr Trp Gln Glu Trp Asp Arg Leu Val Glu Asn Ser Thr
```

```
                625                 630                 635                 640
        Gly Thr Ile Tyr Ser Leu Leu Glu Lys Ala Gln Thr Gln Gln Glu Lys
                        645                 650                 655

Asn Lys Gln Glu Leu Leu Glu Leu Asp Lys Trp Ser Ser Leu Trp Asp
                        660                 665                 670

Trp Phe Asp Ile Thr Gln Trp Leu Trp Tyr Ile Lys Ile Ala Ile Ile
                        675                 680                 685

Ile Val Ala Gly Leu Val Gly Leu Arg Ile Leu Met Phe Ile Val Asn
                        690                 695                 700

Val Val Lys Gln Val Arg Gln Gly Tyr Thr Pro Leu Phe Ser Gln Ile
        705                 710                 715                 720

Pro Thr Gln Ala Glu Gln Asp Pro Glu Gln Pro Gly Ile Ala Gly
                        725                 730                 735

Gly Gly Gly Gly Arg Asp Asn Ile Arg Trp Thr Pro Ser Pro Ala Gly
                        740                 745                 750

Phe Phe Ser Ile Val Trp Glu Asp Leu Arg Asn Leu Leu Ile Trp Ile
                        755                 760                 765

Tyr Gln Thr Phe Gln Asn Phe Ile Trp Ile Leu Trp Ile Ser Leu Gln
                        770                 775                 780

Ala Leu Lys Gln Gly Ile Ile Ser Leu Ala His Ser Leu Val Ile Val
        785                 790                 795                 800

His Arg Thr Ile Ile Val Gly Val Arg Gln Ile Ile Glu Trp Ser Ser
                        805                 810                 815

Asn Thr Tyr Ala Ser Leu Arg Val Leu Leu Ile Gln Ala Ile Asp Arg
                        820                 825                 830

Leu Ala Asn Phe Thr Gly Trp Trp Thr Asp Leu Ile Ile Glu Gly Val
                        835                 840                 845

Val Tyr Ile Ala Arg Gly Ile Arg Asn Ile Pro Arg Arg Ile Arg Gln
                        850                 855                 860

Gly Leu Glu Leu Ala Leu Asn
        865                 870

<210> SEQ ID NO 330
<211> LENGTH: 876
<212> TYPE: PRT
<213> ORGANISM: Simian immunodeficiency virus
<220> FEATURE:
<221> NAME/KEY: MISC_FEATURE
<222> LOCATION: (81)..(81)
<223> OTHER INFORMATION: Xaa can be any naturally occurring amino acid
<220> FEATURE:
<221> NAME/KEY: MISC_FEATURE
<222> LOCATION: (91)..(91)
<223> OTHER INFORMATION: Xaa can be any naturally occurring amino acid
<220> FEATURE:
<221> NAME/KEY: MISC_FEATURE
<222> LOCATION: (179)..(179)
<223> OTHER INFORMATION: Xaa can be any naturally occurring amino acid
<220> FEATURE:
<221> NAME/KEY: MISC_FEATURE
<222> LOCATION: (428)..(428)
<223> OTHER INFORMATION: Xaa can be any naturally occurring amino acid

<400> SEQUENCE: 330

Met Arg Asn Leu Ile Gly Thr Thr Leu Thr Leu Ile Ile Ile Ile Leu
1               5                   10                  15

Gly Ile Gly Ser Lys Glu Tyr Tyr Thr Thr Val Phe Tyr Gly Val Pro
                20                  25                  30

Ile Trp Lys Glu Ala Thr Pro Ser Leu Phe Cys Ala Ser Asn Ala Asp
            35                  40                  45
```

```
Ile Ala Ser Arg Asp Lys His Asn Ile Trp Ala Thr His Asn Cys Val
 50                  55                  60

Pro Leu Asp Pro Asn Pro Tyr Glu Val Pro Leu Ala Asn Val Ser Ile
 65                  70                  75                  80

Xaa Phe Asp Met Glu Lys Asn Tyr Met Val Xaa Glu Met Lys Glu Asp
                 85                  90                  95

Leu Leu Ser Leu Phe Gln Gln Ser Phe Lys Pro Cys Val Lys Leu Thr
                100                 105                 110

Pro Phe Cys Val Thr Met Lys Cys Thr Val Val Asn Thr Thr Val Val
            115                 120                 125

Asn Ala Thr Ala Pro Thr Pro Lys Val Ser Ala Thr Val Ala Thr Thr
        130                 135                 140

Pro Thr Ile Asn Leu Thr Asn Ile Lys Glu Tyr Glu Ile Phe Asn Cys
145                 150                 155                 160

Ser Phe Asn Gln Thr Thr Glu Phe Arg Asp Lys Lys Gln Ile Tyr
                165                 170                 175

Ser Leu Xaa Tyr Arg Glu Asp Ile Met Lys Val Gly Ser Glu Ser Thr
            180                 185                 190

Lys Asn Thr Asp Tyr Tyr Leu His Asn Cys Asn Thr Ser Ala Ile Thr
        195                 200                 205

Gln Glu Cys Asp Lys Ser Thr Phe Glu Pro Ile Pro Ile Arg Tyr Cys
    210                 215                 220

Ala Pro Ala Gly Phe Ala Met Leu Lys Cys Asn Asp Gln Gly Tyr Thr
225                 230                 235                 240

Gly Asn Gly Thr Cys Ser Asn Val Thr Val Val His Cys Thr His Gly
                245                 250                 255

Ile Phe Pro Met Ile Ala Thr Ala Leu His Leu Asn Gly Thr Leu Glu
            260                 265                 270

Glu Asn Glu Thr Lys Ala Tyr Phe Ala Asp Val Asn Val Asn Pro Pro
        275                 280                 285

Leu Leu Val Lys Phe Asn Glu Ser Val Ser Leu Thr Cys Glu Arg Thr
    290                 295                 300

Gly Asn Asn Thr Arg Gly Gln Val Gln Ile Gly Pro Gly Met Thr Phe
305                 310                 315                 320

Tyr Asn Ile Glu Asn Val Val Gly Asp Thr Arg Lys Ala Tyr Cys His
                325                 330                 335

Val Asn Ala Thr Leu Trp Asp Gln Ser Leu Ser Arg Ala Met Glu Ala
            340                 345                 350

Ile Asn Lys Thr Leu Ala Leu Tyr Asn Lys Ala Val Asn Glu Lys Phe
        355                 360                 365

Glu Trp Ser Lys Gly Asp Pro Glu Val Ser Ser Phe Trp Phe Asn Cys
    370                 375                 380

Gln Gly Glu Phe Phe Tyr Cys Asn Leu Thr Gly Trp Thr Asn Pro Trp
385                 390                 395                 400

Asn Asn Thr Asn His Arg Asn Gly Thr Leu Val Ala Pro Cys Arg Leu
                405                 410                 415

Arg Gln Ile Val Asn His Trp Gly Ile Val Ser Xaa Gly Ile Tyr Leu
            420                 425                 430

Pro Pro Arg Arg Gly Thr Leu Lys Cys Asn Ser Asn Ile Thr Gly Leu
        435                 440                 445

Ile Met Thr Ala Glu Lys Gly Gly Asn Asn Thr Val Pro Thr Phe Ser
450                 455                 460
```

```
Gly Lys Val Glu Asp Tyr Trp Lys Val Glu Leu Ala Arg Tyr Lys Val
465                 470                 475                 480

Val Glu Ile Gln Pro Leu Ser Val Ala Pro Arg Pro Gly Lys Arg Pro
            485                 490                 495

Glu Ile Lys Ala Asn His Thr Arg Ser Arg Arg Asp Val Gly Ile Gly
            500                 505                 510

Leu Leu Phe Leu Gly Phe Leu Ser Ala Ala Gly Ser Thr Met Gly Ala
            515                 520                 525

Ala Ser Ile Ala Leu Thr Ala Gln Ala Arg Gly Leu Leu Ser Asp Ile
            530                 535                 540

Val Gln Gln Gln Asn Leu Leu Gln Ala Ile Glu Ala Gln Gln His
545                 550                 555                 560

Leu Leu Gln Leu Ser Val Trp Gly Ile Lys Gln Leu Gln Ala Arg Met
            565                 570                 575

Leu Ala Val Glu Lys Tyr Ile Arg Asp Gln Gln Tyr Leu Ser Ile Trp
            580                 585                 590

Gly Cys Ala Asn Lys Leu Val Cys His Ser Ser Val Pro Trp Asn Leu
            595                 600                 605

Ser Trp Ala Glu Asp Ser Gln Lys Cys Asn Ser Thr Asn Thr Lys Tyr
610                 615                 620

Tyr Glu Cys Ile Trp Asn Asn Leu Thr Trp Gln Gln Trp Asp Arg Leu
625                 630                 635                 640

Val Gln Asn Ala Ser Glu Thr Ile Tyr Ser Leu Leu Glu Ile Ala Gln
            645                 650                 655

Thr Gln Gln Glu Lys Asn Lys Gln Glu Leu Leu Glu Leu Asp Lys Trp
            660                 665                 670

Ser Ser Leu Trp Asp Trp Phe Asp Ile Thr Gln Trp Leu Trp Tyr Ile
            675                 680                 685

Arg Leu Ala Ile Ile Ile Val Ala Gly Leu Val Gly Leu Arg Ile Leu
            690                 695                 700

Met Phe Ile Val Asn Val Val Lys Lys Val Arg Gln Gly Tyr Met Pro
705                 710                 715                 720

Leu Phe Ser Gln Thr Pro Thr Gln Ala Gln Gln Asp Pro Glu Gln Pro
            725                 730                 735

Gly Gly Ile Ala Glu Gly Gly Gly Arg Gly Asn Ile Arg Trp Thr
            740                 745                 750

Pro Ser Pro Thr Gly Phe Phe Ser Ile Val Trp Glu Asp Leu Arg Asn
            755                 760                 765

Leu Leu Ile Trp Leu Tyr Gln Thr Cys Arg Asn Phe Ile Trp Val Leu
            770                 775                 780

Trp Thr Ile Leu Gln Ala Leu Lys Gln Gly Thr Ile Ser Leu Ala Asn
785                 790                 795                 800

Asn Leu Val Ile Val His Arg Tyr Ile Val Lys Ile Arg Gln Ile
            805                 810                 815

Ile Glu Trp Cys His Asn Thr Tyr Ala Ser Leu Arg Ala Ser Leu Ile
            820                 825                 830

His Ala Ile Asp Arg Leu Ala Asp Phe Thr Gly Trp Trp Thr Asp Leu
            835                 840                 845

Ile Ile Glu Gly Ile Thr Tyr Ile Gly Arg Gly Ile Arg Asn Ile Pro
            850                 855                 860

Arg Arg Ile Arg Gln Gly Leu Glu Ile Ala Leu Asn
865                 870                 875
```

```
<210> SEQ ID NO 331
<211> LENGTH: 896
<212> TYPE: PRT
<213> ORGANISM: Simian immunodeficiency virus
<220> FEATURE:
<221> NAME/KEY: MISC_FEATURE
<222> LOCATION: (259)..(259)
<223> OTHER INFORMATION: Xaa can be any naturally occurring amino acid
<220> FEATURE:
<221> NAME/KEY: MISC_FEATURE
<222> LOCATION: (287)..(287)
<223> OTHER INFORMATION: Xaa can be any naturally occurring amino acid
<220> FEATURE:
<221> NAME/KEY: MISC_FEATURE
<222> LOCATION: (322)..(322)
<223> OTHER INFORMATION: Xaa can be any naturally occurring amino acid
<220> FEATURE:
<221> NAME/KEY: MISC_FEATURE
<222> LOCATION: (336)..(336)
<223> OTHER INFORMATION: Xaa can be any naturally occurring amino acid
<220> FEATURE:
<221> NAME/KEY: MISC_FEATURE
<222> LOCATION: (338)..(338)
<223> OTHER INFORMATION: Xaa can be any naturally occurring amino acid
<220> FEATURE:
<221> NAME/KEY: MISC_FEATURE
<222> LOCATION: (340)..(340)
<223> OTHER INFORMATION: Xaa can be any naturally occurring amino acid
<220> FEATURE:
<221> NAME/KEY: MISC_FEATURE
<222> LOCATION: (361)..(361)
<223> OTHER INFORMATION: Xaa can be any naturally occurring amino acid
<220> FEATURE:
<221> NAME/KEY: MISC_FEATURE
<222> LOCATION: (371)..(371)
<223> OTHER INFORMATION: Xaa can be any naturally occurring amino acid
<220> FEATURE:
<221> NAME/KEY: MISC_FEATURE
<222> LOCATION: (379)..(379)
<223> OTHER INFORMATION: Xaa can be any naturally occurring amino acid
<220> FEATURE:
<221> NAME/KEY: MISC_FEATURE
<222> LOCATION: (380)..(380)
<223> OTHER INFORMATION: Xaa can be any naturally occurring amino acid
<220> FEATURE:
<221> NAME/KEY: MISC_FEATURE
<222> LOCATION: (382)..(382)
<223> OTHER INFORMATION: Xaa can be any naturally occurring amino acid

<400> SEQUENCE: 331

Met Lys Met Arg Asn Leu Ile Gly Ile Thr Leu Ile Leu Ile Ile Leu
 1               5                  10                  15

Thr Leu Gly Ile Gly Ser Arg Asp Tyr Tyr Thr Val Phe Tyr Gly
            20                  25                  30

Val Pro Ile Trp Lys Asp Ala Thr Pro Ser Leu Phe Cys Ala Ser Asp
        35                  40                  45

Ala Asp Val Thr Ser Arg Glu Lys His Asn Ile Trp Ala Thr His Asn
    50                  55                  60

Cys Val Pro Leu Asp Pro Asn Pro Tyr Glu Val Pro Ile Ala Asn Val
65                  70                  75                  80

Ser Ile Lys Phe Asn Met Glu Glu Asn Tyr Met Val Lys Glu Met Lys
                85                  90                  95

Glu Asp Leu Leu Ser Leu Phe Gln Gln Ser Phe Lys Pro Cys Val Lys
            100                 105                 110

Leu Thr Pro Phe Cys Val Val Met Asn Cys Thr Lys Ser Gln Asn Val
        115                 120                 125

Thr Thr Pro Ala Ser Thr Ser Thr Ala Ala Pro Val Asn Ala Thr Thr
    130                 135                 140

Ile Pro Val Asn Leu Thr Asp Ile Pro Asn Tyr Glu Leu Phe Asn Cys
```

```
            145                 150                 155                 160
    Ser Phe Gln Gln Thr Thr Glu Phe Arg Asp Lys Lys Gln Ile Tyr
                    165                 170                 175

Ser Leu Phe Tyr Arg Glu Asp Ile Met Lys Asp Asn Arg Ser Met Gln
                180                 185                 190

Asp Asn Arg Ser Asn Ser Ser Lys Ser Asn Asn Ser Asn Asn Ser
                195                 200                 205

Gly Tyr Tyr Leu His Asn Cys Asn Thr Ser Ala Ile Thr Gln Glu Cys
            210                 215                 220

Asp Lys Ser Thr Phe Glu Pro Ile Pro Ile Arg Tyr Cys Ala Pro Ala
    225                 230                 235                 240

Gly Tyr Ala Met Leu Lys Cys Lys Asp Gln Asn Tyr Thr Gly Asn Gly
                    245                 250                 255

Ile Cys Xaa Asn Val Thr Val Val His Cys Thr His Gly Ile Phe Pro
                260                 265                 270

Met Ile Ala Thr Ala Leu His Leu Asn Gly Thr Leu Glu Glu Xaa Glu
                275                 280                 285

Thr Lys Ala Tyr Phe Val Asn Ala Thr Asn Asn Pro Pro Leu Leu Val
            290                 295                 300

Lys Phe Asn Glu Ser Val Pro Leu Thr Cys Gly Arg Thr Gly Asx Asn
    305                 310                 315                 320

Val Xaa Gly Gln Val Gln Ile Gly Pro Gly Met Thr Phe Tyr Asn Xaa
                    325                 330                 335

Glu Xaa Val Xaa Gly Asp Thr Arg Lys Ala Tyr Cys Trp Val Asn Ala
                340                 345                 350

Thr Leu Trp Tyr Lys Ser Leu Asp Xaa Ala Met Glu Ala Ile Thr Lys
                355                 360                 365

Thr Leu Xaa Lys Ser Gly Leu Asx Val Thr Xaa Xaa Phe Xaa Trp His
            370                 375                 380

Lys Gly Gly Asp Leu Glu Val Gln Asn Phe Trp Phe Asn Cys Gln Gly
    385                 390                 395                 400

Glu Phe Phe Tyr Cys Asn Leu Thr Thr Trp Thr Gly Asn Trp Thr Arg
                    405                 410                 415

Asn Arg Thr His Gln Thr Ser Ala Leu Asn Lys Thr His Leu Leu Ala
                420                 425                 430

Gln Cys Arg Leu Arg Gln Ile Val Asn His Trp Gly Ile Val Ser Lys
                435                 440                 445

Gly Ile Tyr Leu Pro Pro Arg Lys Gly His Ile Lys Cys Val Ser Asn
            450                 455                 460

Ile Thr Gly Leu Ile Met Thr Ala Glu Gly Gly Asn Ser Asn Arg Thr
    465                 470                 475                 480

Pro Thr Phe Ser Ser Lys Val Glu Asp Tyr Trp Lys Val Glu Leu Ala
                    485                 490                 495

Arg Tyr Lys Val Val Glu Ile Gln Pro Leu Ser Val Ala Pro Arg Pro
                500                 505                 510

Gly Lys Arg Pro Glu Ile Lys Ala Asn His Thr Arg Ser Arg Arg Asp
            515                 520                 525

Val Gly Ile Gly Leu Leu Phe Leu Gly Phe Leu Ser Ala Ala Gly Ser
    530                 535                 540

Thr Met Gly Ala Ala Ser Leu Ala Leu Thr Ala Gln Ala Arg Gly Leu
    545                 550                 555                 560

Leu Ser Gly Ile Val Gln Gln Gln Asn Leu Leu Gln Ala Ile Glu
                    565                 570                 575
```

```
Ala Gln Gln His Leu Leu Gln Leu Ser Val Trp Gly Ile Lys Gln Leu
            580                 585                 590

Gln Ala Arg Met Leu Ala Val Glu Lys Tyr Ile Arg Asp Gln Gln Tyr
        595                 600                 605

Leu Ser Ile Trp Gly Cys Ala Asn Lys Leu Val Cys His Ser Ser Val
610                 615                 620

Pro Trp Asn Leu Ser Trp Ala Gly Thr Ser Ser Lys Cys Asn Tyr Thr
625                 630                 635                 640

Gly Ala Lys Tyr Tyr Glu Cys Ile Trp Asn Asn Leu Thr Trp Gln Glu
                645                 650                 655

Trp Asp Lys Leu Val Gln Asn Ser Ser Glu Thr Ile Tyr Ser Leu Leu
        660                 665                 670

Glu Thr Ala Gln Thr Gln Gln Glu Arg Asn Lys Gln Glu Leu Leu Glu
            675                 680                 685

Leu Asp Lys Trp Ser Ser Leu Trp Asp Trp Phe Asp Ile Thr Gln Trp
        690                 695                 700

Leu Trp Tyr Ile Lys Ile Ala Ile Ile Ile Val Ala Gly Leu Val Gly
705                 710                 715                 720

Leu Arg Ile Leu Met Phe Ile Val Asn Val Val Lys Lys Val Arg Gln
                725                 730                 735

Gly Tyr Met Pro Leu Phe Ser Gln Thr Pro Thr Gln Ala Glu Gln Asp
        740                 745                 750

Pro Glu Gln Pro Gly Gly Thr Ala Gly Gly Gly Gly Gly Gly Gly Asn
            755                 760                 765

Phe Arg Trp Thr Pro Ser Pro Thr Gly Phe Phe Ser Ile Val Trp Glu
        770                 775                 780

Asp Leu Arg Asn Leu Leu Ile Trp Ile Tyr Gln Thr Cys Gln Asn Phe
785                 790                 795                 800

Ile Trp Val Leu Trp Thr Ile Leu Gln Ala Leu Lys Gln Gly Thr Ile
                805                 810                 815

Ser Leu Ala His Asn Leu Val Ile Val His Arg Tyr Ile Ile Val Arg
        820                 825                 830

Val Arg Gln Thr Ile Glu Trp Cys Gly Asn Thr Tyr Ala Ser Leu Arg
            835                 840                 845

Ala Ser Leu Ile His Ala Ile Asp Arg Leu Ala Asp Phe Thr Gly Trp
        850                 855                 860

Trp Thr Asp Leu Leu Ile Glu Gly Val Val Tyr Ile Ala Arg Gly Ile
865                 870                 875                 880

Arg Asn Ile Pro Arg Arg Ile Arg Gln Gly Leu Glu Ile Ala Leu Asn
                885                 890                 895

<210> SEQ ID NO 332
<211> LENGTH: 852
<212> TYPE: PRT
<213> ORGANISM: Simian immunodeficiency virus
<220> FEATURE:
<221> NAME/KEY: MISC_FEATURE
<222> LOCATION: (174)..(174)
<223> OTHER INFORMATION: Xaa can be any naturally occurring amino acid
<220> FEATURE:
<221> NAME/KEY: MISC_FEATURE
<222> LOCATION: (178)..(178)
<223> OTHER INFORMATION: Xaa can be any naturally occurring amino acid
<220> FEATURE:
<221> NAME/KEY: MISC_FEATURE
<222> LOCATION: (179)..(179)
<223> OTHER INFORMATION: Xaa can be any naturally occurring amino acid
<220> FEATURE:
```

```
<221> NAME/KEY: MISC_FEATURE
<222> LOCATION: (261)..(261)
<223> OTHER INFORMATION: Xaa can be any naturally occurring amino acid
<220> FEATURE:
<221> NAME/KEY: MISC_FEATURE
<222> LOCATION: (262)..(262)
<223> OTHER INFORMATION: Xaa can be any naturally occurring amino acid
<220> FEATURE:
<221> NAME/KEY: MISC_FEATURE
<222> LOCATION: (266)..(266)
<223> OTHER INFORMATION: Xaa can be any naturally occurring amino acid
<220> FEATURE:
<221> NAME/KEY: MISC_FEATURE
<222> LOCATION: (268)..(268)
<223> OTHER INFORMATION: Xaa can be any naturally occurring amino acid
<220> FEATURE:
<221> NAME/KEY: MISC_FEATURE
<222> LOCATION: (269)..(269)
<223> OTHER INFORMATION: Xaa can be any naturally occurring amino acid
<220> FEATURE:
<221> NAME/KEY: MISC_FEATURE
<222> LOCATION: (272)..(272)
<223> OTHER INFORMATION: Xaa can be any naturally occurring amino acid
<220> FEATURE:
<221> NAME/KEY: MISC_FEATURE
<222> LOCATION: (322)..(322)
<223> OTHER INFORMATION: Xaa can be any naturally occurring amino acid
<220> FEATURE:
<221> NAME/KEY: MISC_FEATURE
<222> LOCATION: (331)..(331)
<223> OTHER INFORMATION: Xaa can be any naturally occurring amino acid
<220> FEATURE:
<221> NAME/KEY: misc_feature
<222> LOCATION: (332)..(332)
<223> OTHER INFORMATION: Xaa can be any naturally occurring amino acid
<220> FEATURE:
<221> NAME/KEY: MISC_FEATURE
<222> LOCATION: (335)..(335)
<223> OTHER INFORMATION: Xaa can be any naturally occurring amino acid

<400> SEQUENCE: 332

Met Arg Val Met Glu Arg Ile Arg Gly Ser Leu Trp Leu Met Gly Leu
1               5                   10                  15

Ile Ile Pro Cys Leu Thr Gly Ser Asp Gln Leu Trp Ala Thr Val Tyr
            20                  25                  30

Tyr Gly Val Pro Val Trp Lys Asp Ala Glu Thr Thr Leu Phe Cys Ala
        35                  40                  45

Ala Asp Ala Ser Ala Leu Asn Lys Glu Ala His Asn Ile Trp Ala Ser
    50                  55                  60

Gln Ala Cys Val Pro Thr Asp Pro Asn Pro Gln Glu Val His Val Pro
65                  70                  75                  80

Asn Ile Thr Glu Thr Phe Asp Met Trp Glu Asn Asn Met Val Glu Gln
                85                  90                  95

Met Gln Thr Asp Ile Ile Ser Leu Trp Asp Gln Ser Leu Lys Pro Cys
            100                 105                 110

Val Lys Leu Thr Pro Leu Cys Val Thr Met His Cys Ile Pro Tyr Asn
        115                 120                 125

Ile Ser Ser Thr Gly Asn Asp Thr Arg Asn Ser Ser Thr Ser Gln Met
    130                 135                 140

Val Lys Lys Cys Phe Phe Asn Met Thr Glu Leu Arg Asp Lys Gln
145                 150                 155                 160

Lys Gln Val Tyr Ser Leu Phe Tyr Val Asp Asp Ile Val Xaa Ile Asn
                165                 170                 175

Gly Xaa Xaa Ser Tyr Arg Leu Ile Asn Cys Asn Thr Thr Ala Ile Thr
            180                 185                 190

Gln Ala Cys Pro Lys Thr Ser Phe Glu Pro Ile Pro Ile His Tyr Cys
```

```
            195                 200                 205
Ala Pro Pro Gly Phe Ala Ile Met Lys Cys Asn Glu Pro Asp Phe Asn
210                 215                 220

Gly Thr Gly Lys Cys Arg Asn Ile Ser Thr Val Gln Cys Thr His Gly
225                 230                 235                 240

Ile Lys Pro Val Val Thr Thr Gln Leu Ile Leu Asn Gly Ser Leu Ala
                245                 250                 255

Glu Asn Ser Thr Xaa Xaa Arg Thr Glu Xaa Met Xaa Xaa Met Asp Xaa
                260                 265                 270

Thr Ile Ile Val Gln Phe His Lys Arg Val Gln Met Thr Cys Ile Arg
            275                 280                 285

Pro Gly Asn Asn Ser Arg Gly Gln Ile Gln Ile Gly Pro Ala Met Ser
        290                 295                 300

Phe Tyr Asn Leu Glu Asn Ile Ile Gly Asp Thr Arg Gln Ala Tyr Cys
305                 310                 315                 320

Asn Xaa Ser Ala Ala Glu Trp Glu Gln Arg Xaa Xaa Asp Thr Xaa Arg
                325                 330                 335

Ala Ile Lys Ser Leu Lys Pro Gly Ser Asn Ile Thr Phe Thr Asp Gln
            340                 345                 350

Gln Gly Gly Asp Pro Glu Ile Val Asn Met Met Phe Asn Cys Gly Gly
        355                 360                 365

Glu Phe Phe Tyr Cys Asn Thr Thr Pro Leu Phe Asn Asn Ser Trp Thr
370                 375                 380

Asn Thr Thr Ser Ser Asp Ile Asn Ser Ser Asn Ile Ile Ile Asn Cys
385                 390                 395                 400

Arg Ile Arg Gln Ile Val Asn Ser Trp Met Arg Val Gly Lys Gly Ile
                405                 410                 415

Tyr Ala Pro Pro Ile Arg Gly Thr Ile Ser Cys Thr Ser Asn Ile Thr
            420                 425                 430

Gly Leu Leu Leu Glu Leu Asp Arg Gly Leu Pro Arg Asn Gly Thr Asn
        435                 440                 445

Thr Asn Asn Lys Leu Thr Leu Tyr Pro Thr Gly Gly Glu Met Arg Asp
450                 455                 460

Leu Trp Arg Leu Glu Leu His Lys Tyr Lys Val Val Ser Ile Glu Pro
465                 470                 475                 480

Ile Gly Val Ala Pro Ser Lys Ala Lys Arg His Thr Val Thr Arg Glu
                485                 490                 495

Lys Arg Ala Ala Phe Gly Leu Gly Ala Leu Phe Leu Gly Phe Leu Gly
            500                 505                 510

Ala Ala Gly Ser Thr Met Gly Ala Ala Ser Leu Thr Leu Thr Val Gln
        515                 520                 525

Ala Arg Gln Leu Leu Ser Gly Ile Val Gln Gln Asn Asn Leu Leu
530                 535                 540

Arg Ala Ile Glu Ala Gln Gln His Leu Leu Gln Leu Ser Val Trp Gly
545                 550                 555                 560

Ile Lys Gln Leu Gln Ala Arg Val Leu Ala Val Glu Arg Tyr Leu Lys
                565                 570                 575

Asp Gln Gln Ile Leu Gly Leu Trp Gly Cys Ser Gly Lys Ser Ile Cys
            580                 585                 590

Tyr Thr Thr Val Pro Trp Asn Ser Thr Trp Gly Ala Asn Thr Ser Tyr
        595                 600                 605

Asp Glu Ile Trp Asn Asn Leu Thr Trp Gln Asp Trp Asp Lys Arg Val
610                 615                 620
```

```
Lys Asn Tyr Ser Gly Val Ile Phe Asp Leu Ile Glu Gln Ala Gln Glu
625                 630                 635                 640

Gln Gln Asn Thr Asn Glu Arg Ser Leu Leu Glu Leu Asp Gln Trp Ser
                645                 650                 655

Ser Leu Trp Asn Trp Phe Asp Ile Ser Asn Trp Leu Trp Tyr Ile Lys
            660                 665                 670

Ile Phe Leu Met Ala Val Ala Gly Leu Ile Gly Ile Arg Ile Val Gly
        675                 680                 685

Val Ile Met Ser Leu Ile Ala Lys Val Arg Gln Gly Tyr Ser Pro Leu
690                 695                 700

Ser Leu Gln Thr Leu Ile Pro Thr Thr Arg Gly Pro Asp Arg Pro Gly
705                 710                 715                 720

Gly Thr Glu Glu Glu Gly Gly Glu Pro Gly Arg Gly Thr Ser Thr Arg
                725                 730                 735

Leu Val Ser Gly Phe Leu Ala Leu Ala Trp Asp Asp Leu Arg Asn Leu
            740                 745                 750

Leu Leu Phe Leu Tyr His Arg Leu Ile Asp Leu Leu Ser Ile Leu Arg
        755                 760                 765

Arg Thr Leu Glu Ile Leu Gly Gln Asn Ile Asn Lys Gly Leu Gln Trp
770                 775                 780

Leu Arg Asp Ile Ser Arg His Leu Trp Gly Val Ile Ala Tyr Trp Gly
785                 790                 795                 800

Arg Glu Leu Gln Ile Ser Ala Thr Ser Leu Leu Asp Thr Thr Ala Ile
                805                 810                 815

Ala Val Ala Glu Gly Thr Asp Arg Ile Ile Glu Val Val Gln Arg Ile
            820                 825                 830

Gly Arg Gly Ile Leu His Ile Pro Arg Arg Ile Arg Gln Gly Leu Glu
        835                 840                 845

Arg Ser Leu Leu
    850

<210> SEQ ID NO 333
<211> LENGTH: 844
<212> TYPE: PRT
<213> ORGANISM: Simian immunodeficiency virus

<400> SEQUENCE: 333

Met Lys Val Met Gly Thr Gln Arg Ser Trp Lys Gln Phe Leu Ser Leu
1               5                   10                  15

Arg Ile Val Met Cys Leu Trp Leu Leu Gly Val Ile Arg Ser Glu Asn
                20                  25                  30

Asn Leu Trp Val Thr Val Tyr Tyr Gly Val Pro Val Trp Lys Glu Ala
            35                  40                  45

Lys Thr Thr Leu Phe Cys Ala Ser Asp Ala Lys Ala Gln Ile Ala Glu
        50                  55                  60

Ala His Asn Ile Trp Ala Ser Gln Ala Cys Val Pro Thr Asp Pro Asn
65                  70                  75                  80

Pro Glu Glu Ile Thr Leu Glu Asn Val Thr Glu Glu Phe Asp Ala Trp
                85                  90                  95

Asn Asn Asn Met Val Asp Gln Met Gln Glu Asp Leu Ile Ser Leu Trp
            100                 105                 110

Asp Gln Ser Leu Lys Pro Cys Val Lys Leu Thr Pro Leu Cys Val Thr
        115                 120                 125

Leu Asn Cys Ser Thr Asn Thr Thr Glu Ala Ser Gln Val Gln Tyr
```

-continued

```
            130                 135                 140
Asn Cys Ser Phe Asn Val Thr Thr Glu Leu Arg Asp Lys Lys Gln
145                 150                 155                 160

Val Tyr Ser Leu Phe Tyr Arg Glu Asp Ile Thr Ser Leu Asp Ser Asn
                    165                 170                 175

Lys Thr Val Lys Asn Gly Thr Tyr Arg Leu Ile Asn Cys Asn Thr Thr
                180                 185                 190

Ala Ile Thr Gln Ala Cys Pro Lys Thr Ser Phe Glu Pro Ile Pro Ile
            195                 200                 205

Tyr Tyr Cys Ala Pro Ala Gly Phe Ala Leu Leu Lys Cys Asn Asp Gln
        210                 215                 220

Asn Phe Lys Gly Lys Gly Thr Cys Arg Asn Val Ser Thr Val His Cys
225                 230                 235                 240

Thr His Gly Ile Lys Pro Val Val Ser Thr Gln Phe Leu Leu Asn Gly
                    245                 250                 255

Ser Leu Ala Glu Gly Asn Lys Thr Val Val Arg Val Arg Ser Lys Ser
                260                 265                 270

Asn Thr Glu Thr Ile Ile Val Gln Leu Ala Thr Ala Ile Tyr Ile Asn
            275                 280                 285

Cys Thr Arg Leu Gly Asn Lys Thr Ile Glu Gly Ile Pro Ile Gly Pro
        290                 295                 300

Gly Gln Ile Phe Tyr Arg Thr Lys Thr Val Val Gly Asp Thr Arg Gly
305                 310                 315                 320

Ala Glu Cys Arg Ile Asn Gly Thr Ala Trp Asn Glu Thr Leu Arg Gln
                    325                 330                 335

Val Lys Glu Ala Leu Asn Asn Thr Tyr Arg Asn Leu Asn Leu Ser Leu
                340                 345                 350

Thr Glu Ile Asn Phe Glu Gly Ala Ser Gly Gly Asp Leu Glu Val Thr
            355                 360                 365

Thr His Tyr Phe Asn Cys Gly Gly Glu Phe Phe Tyr Cys Asn Thr Ser
        370                 375                 380

Asn Leu Phe Asn Gln Ser Thr Ile Asn Asn Ile Thr His Ile Pro Cys
385                 390                 395                 400

Arg Ile Arg Gln Ile Val Asn Gln Trp Gln Gly Val Gly Lys Gly Ile
                    405                 410                 415

Phe Ala Pro Pro Ile Arg Gly Thr Ile Gln Cys Asn Ser Thr Ile Thr
                420                 425                 430

Gly Leu Leu Leu Thr Arg Asp Gly Lys Asn Glu Thr Glu Thr Phe Arg
            435                 440                 445

Pro Thr Gly Gly Asp Met Arg Asn Asn Trp Arg Ser Glu Leu Tyr Lys
        450                 455                 460

Tyr Lys Val Val Lys Ile Glu Pro Leu Gly Leu Ala Pro Thr Lys Ala
465                 470                 475                 480

Lys Arg Arg Thr Val Gln Arg Glu Lys Arg Ala Val Gly Leu Gly Val
                    485                 490                 495

Met Phe Leu Gly Phe Met Gly Ala Ala Gly Ser Thr Met Gly Ala Ala
                500                 505                 510

Ala Leu Thr Leu Thr Val Gln Ala Arg Asn Leu Leu Ser Gly Ile Val
            515                 520                 525

Gln Gln Gln Ser Asn Leu Leu Lys Ala Ile Glu Ala Gln Gln His Leu
        530                 535                 540

Leu Gln Leu Ser Val Trp Gly Ile Lys Gln Leu Gln Ala Arg Val Leu
545                 550                 555                 560
```

```
Ala Val Glu Arg Tyr Leu Lys Asp Gln Gln Leu Leu Gly Leu Trp Gly
            565                 570                 575

Cys Ser Gly Lys Leu Ile Cys Thr Thr Asn Val Pro Trp Asn Asn Thr
        580                 585                 590

Trp Ser Lys Lys Leu Gly Thr Asn Leu Ser Phe Trp Asp Asn Met Thr
    595                 600                 605

Trp Met Gln Trp Glu Lys Glu Ile Asp Asn Tyr Thr Glu Thr Ile Tyr
610                 615                 620

Glu Leu Leu Thr Arg Ser Gln Asn Gln Gln Glu Val Asn Glu Gln Glu
625                 630                 635                 640

Leu Leu Ala Leu Asp Lys Trp Ser Ser Leu Trp Asn Trp Phe Asp Ile
            645                 650                 655

Thr Gln Trp Leu Trp Tyr Ile Lys Leu Phe Val Met Ile Val Gly Gly
        660                 665                 670

Leu Ile Gly Ile Arg Ile Val Phe Ala Met Leu Ser Ile Val Asn Arg
    675                 680                 685

Val Arg Gln Gly Tyr Ser Pro Leu Ser Phe Gln Thr Pro Phe Pro Val
690                 695                 700

Arg Arg Asp Pro Asp Arg Pro Glu Gly Ile Glu Glu Gly Gly Gly Glu
705                 710                 715                 720

Asn Asp Asn Val Arg Ser Val Arg Leu Val Ser Gly Phe Leu Ala Leu
            725                 730                 735

Ala Trp Asp Asp Leu Arg Asn Leu Cys Leu Phe Ser Tyr His Arg Leu
        740                 745                 750

Arg Asp Leu Leu Trp Ile Val Arg Thr Leu Glu Ile Val Gly Gln
    755                 760                 765

Lys Phe Leu Ala Gly Leu Arg Leu Val Trp Glu Thr Leu Thr Tyr Leu
770                 775                 780

Lys Ser Ile Leu Gln Tyr Trp Gly Gln Glu Leu Lys Thr Ser Ala Ile
785                 790                 795                 800

Ser Leu Leu Asp Ala Thr Ala Ile Ala Val Ala Glu Gly Thr Asp Arg
            805                 810                 815

Ile Ile Glu Ile Ala Gln Arg Val Gly Arg Gly Ile Leu His Ile Pro
        820                 825                 830

Arg Arg Ile Arg Gln Gly Leu Glu Arg Ala Leu Leu
    835                 840

<210> SEQ ID NO 334
<211> LENGTH: 867
<212> TYPE: PRT
<213> ORGANISM: Simian immunodeficiency virus
<220> FEATURE:
<221> NAME/KEY: MISC_FEATURE
<222> LOCATION: (86)..(86)
<223> OTHER INFORMATION: Xaa can be any naturally occurring amino acid
<220> FEATURE:
<221> NAME/KEY: MISC_FEATURE
<222> LOCATION: (141)..(141)
<223> OTHER INFORMATION: Xaa can be any naturally occurring amino acid
<220> FEATURE:
<221> NAME/KEY: MISC_FEATURE
<222> LOCATION: (554)..(554)
<223> OTHER INFORMATION: Xaa can be any naturally occurring amino acid

<400> SEQUENCE: 334

Met Arg Asp Met Arg Ala Met Arg Lys Lys Gln Leu Asn Leu Trp Lys
1               5                   10                  15

Gly Val Met Ser Leu Gly Leu Ile Leu Thr Cys Ile Glu Ala Thr His
```

-continued

Tyr Ala Thr Val Tyr Tyr Gly Val Pro Val Trp Gln Glu Ala Asn Val
                20                  25                  30

Thr Leu Phe Cys Ala Ala Asp Ala Asn Tyr Val Ser Gln Glu Gln His
     35                  40                  45

Asn Ile Trp Ala Thr Gln Ala Cys Val Pro Thr Asp Pro Ser Pro Ile
 50                  55                  60

Glu Phe Pro Leu Glu Xaa Val Thr Glu Thr Phe Asp Ile Trp Asn Asn
 65                  70                  75                  80

Asn Met Val Asp Gln Met Gln Asp Ile Ile Ser Leu Trp Asp Gln
                 85                  90                  95

Ser Leu Lys Pro Cys Val Lys Leu Thr Val Met Cys Val Thr Leu Asn
                100                 105                 110

Cys Thr Lys Thr Thr Glu Thr Thr Gln Thr Asn Xaa Thr Asn Thr
                115                 120                 125

Thr Ile Pro Pro Tyr Ile Pro Gln Leu Asp Ile Tyr Asn Cys Ser Phe
                130                 135                 140

Asn Val Thr Thr Val Leu Lys Asp Lys Lys Thr Lys Gln Gln Ala Leu
145                 150                 155                 160

Phe Tyr Lys Gln Asp Ile Ile Lys Thr Asp Glu Thr Asn Glu Thr Lys
                165                 170                 175

Glu Tyr Ser Glu Tyr Arg Leu Ile Asn Cys Asn Thr Ser Thr Ile Ser
                180                 185                 190

Gln Ala Cys Pro Lys Val Ser Phe Glu Pro Leu Pro Ile Gln Tyr Cys
                195                 200                 205

Ala Pro Ala Gly Tyr Ala Leu Met Lys Cys Asn Asp Lys Gln Phe Asn
                210                 215                 220

Gly Thr Gly Glu Cys Lys Asn Val Ser Ile Val His Cys Thr His Gly
225                 230                 235                 240

Ile Arg Pro Thr Val Ser Thr Gln Leu Ile Leu Asn Gly Thr Leu Ala
                245                 250                 255

Lys Glu His Ala Thr Ile Ile Ser Lys Asn Ser Thr Asp Ser Gly Lys
                260                 265                 270

Asp Ile Ile Val Lys Leu Ala Arg Ser Val Glu Ile Thr Cys Glu Arg
                275                 280                 285

Thr Ser Asn Asn Thr Arg Gly Gln Ile Gln Val Gly Pro Met Thr Ile
290                 295                 300

Tyr Asn Ser Glu Asn Ile Val Gly Asn Thr Arg Lys Ala Phe Cys Lys
                305                 310                 315                 320

Tyr Asn Lys Thr Asn Trp Gln Asn Ala Leu Lys Asp Thr Val Arg Ala
                325                 330                 335

Leu Lys Ala Asn Gln Ile Arg Phe Gln Asn Ser Ser Gly Gly Asp Pro
                340                 345                 350

Glu Val Thr Phe Leu His Phe Asn Cys His Gly Glu Phe Phe Tyr Cys
                355                 360                 365

Asp Thr Thr Lys Met Phe Asn Tyr Asn Cys Thr Lys Glu Ser Cys Asp
                370                 375                 380

Cys Ile Thr Gly Asn Cys Thr Asn Tyr Ile Pro Cys His Leu Lys Gln
385                 390                 395                 400

Val Val Met Ser Trp Met Arg Val Gly Ser Gly Leu Phe Ala Pro Pro
                405                 410                 415

Ile Arg Gly Thr Leu Arg Cys Lys Ser Asn Ile Thr Gly Ile Ile Leu
                420                 425                 430
                435                 440                 445

```
Gln Arg Asp Val Pro Leu Asn Lys Thr Asn Glu Asn Ser Thr Asp Tyr
    450                 455                 460

Asn Thr Leu Arg Pro Ile Gly Gly Asp Met Thr Asn Ile Trp Arg Ser
465                 470                 475                 480

Glu Leu Tyr Pro Tyr Lys Val Val Lys Val Lys Ala Leu Ser Val Ala
                485                 490                 495

Pro Thr Lys Ala Arg Arg Pro Val Ile Ser His Asn Arg Glu Lys Arg
                500                 505                 510

Ala Ala Gly Leu Gly Met Leu Phe Leu Gly Phe Met Ser Ala Ala Gly
            515                 520                 525

Ser Thr Met Gly Ala Ala Val Thr Leu Thr Val Gln Ala Arg Gln
            530                 535                 540

Val Leu His Gly Ile Val Gln Gln Xaa Asn Met Leu Arg Ala Ile
545                 550                 555                 560

Ala Ala Gln Gln Glu Leu Leu Arg Leu Ser Val Trp Gly Ile Arg Gln
                565                 570                 575

Leu Arg Ala Arg Leu Leu Ala Ile Glu Thr Tyr Leu Arg Asp Gln Gln
                580                 585                 590

Leu Leu Gly Leu Trp Gly Cys Thr Gly Arg Leu Ile Cys Tyr Thr Asn
            595                 600                 605

Val Pro Trp Asn Lys Thr Trp Thr Gly Lys Asn Glu Thr Glu Leu Asp
610                 615                 620

Asp Ile Trp Gly Asn Met Thr Trp Gln Gln Trp Asp Lys Leu Val Asp
625                 630                 635                 640

Asn Tyr Thr Asp Thr Ile Phe Leu Glu Ile Gln Lys Ala Gln Glu Gln
                645                 650                 655

Gln Glu Val Asn Glu Lys Ala Leu Leu Glu Leu Asp Lys Trp Ala Asp
                660                 665                 670

Leu Trp Ser Trp Leu Asp Ile Thr Gln Trp Leu Trp Tyr Ile Lys Ile
            675                 680                 685

Phe Ile Met Ile Ile Ala Gly Leu Val Gly Leu Arg Ile Leu Met Ala
690                 695                 700

Ile Ile Asn Met Cys His Arg Val Arg Gln Gly Tyr Ser Pro Leu Ser
705                 710                 715                 720

Phe Gln Ile Leu Ala Arg Asn Gln Val Pro Ala Gly Ile Val Pro Glu
                725                 730                 735

Ile Gly Glu Glu Gly Gly Arg Ala Asp Ser Asp Arg Ser Ile Arg Leu
            740                 745                 750

Leu Ala Gly Phe Leu Pro Leu Ile Trp Asp Asp Leu Arg Thr Leu Ile
            755                 760                 765

Val Trp Ile Tyr Arg Thr Leu Val Ile Leu Leu Ser Gly Ile Lys Glu
770                 775                 780

Ile Thr Leu Ser Leu Ile Glu His Leu Thr Arg Leu Leu Arg Arg Val
785                 790                 795                 800

Asn Asn Leu Thr Arg Asp Cys Phe Ala Phe Ile Ala Tyr Trp Gly Gln
                805                 810                 815

Glu Leu Lys Gln Ser Ala Ile Ser Leu Leu Asp Cys Val Ala Val Trp
                820                 825                 830

Thr Ala Asp Trp Thr Asp Gln Val Ile Ala Ile Ala Gln Arg Ile Gly
            835                 840                 845

Arg Gly Ile Leu Asn Ile Pro Arg Arg Ile Arg Gln Gly Leu Glu Arg
            850                 855                 860
```

Ser Leu Leu
865

<210> SEQ ID NO 335
<211> LENGTH: 872
<212> TYPE: PRT
<213> ORGANISM: Simian immunodeficiency virus

<400> SEQUENCE: 335

Met Arg Asp Met Arg Ala Met Arg Lys Lys Gln Leu Asn Leu Trp Lys
1               5                   10                  15

Trp Val Met Ser Leu Gly Leu Ile Leu Thr Cys Ile Glu Ala Thr His
            20                  25                  30

Tyr Ala Thr Val Tyr Tyr Gly Val Pro Val Trp Arg Glu Ala Asn Val
        35                  40                  45

Thr Leu Phe Cys Ala Ala Asp Ala Asn Tyr Val Ser Lys Glu Gln His
    50                  55                  60

Asn Ile Trp Ala Thr Gln Ala Cys Val Pro Thr Asp Pro Arg Pro Thr
65                  70                  75                  80

Glu Phe Pro Leu Glu Asn Val Thr Glu Thr Phe Asn Ile Trp Lys Asn
                85                  90                  95

Tyr Met Val Asp Gln Met Gln Asp Asp Ile Val Ser Leu Trp Asp Gln
            100                 105                 110

Ser Leu Lys Pro Cys Val Lys Leu Thr Val Met Cys Val Thr Leu Asn
        115                 120                 125

Cys Thr Gln Leu Asn Thr Thr Asn Thr Thr Gln Thr Glu Met Thr Asn
    130                 135                 140

Thr Thr Ile Pro Pro His Thr Thr Ile Pro Pro His Ile Pro Gln Leu
145                 150                 155                 160

Asp Ile Tyr Asn Cys Ser Phe Asn Val Thr Thr Val Leu Lys Asp Lys
                165                 170                 175

Thr Thr Lys Gln Gln Ala Leu Phe Tyr Arg Gln Asp Ile Ile Glu Thr
            180                 185                 190

Gly Glu Thr Gly Thr Asn Gly Ile Lys Gly Tyr Arg Leu Ile Asn Cys
        195                 200                 205

Asn Thr Ser Thr Ile Ser Gln Ala Cys Pro Lys Val Ser Phe Glu Pro
    210                 215                 220

Leu Pro Ile Gln Tyr Cys Ala Pro Ala Gly Tyr Ala Leu Met Lys Cys
225                 230                 235                 240

Asn Asp Ile Gln Phe Asn Gly Thr Gly Glu Cys Arg Asn Val Ser Ile
                245                 250                 255

Val His Cys Thr His Gly Ile Arg Pro Thr Val Ser Thr Gln Leu Ile
            260                 265                 270

Leu Asn Gly Thr Leu Ala Glu Gly Asn Ala Thr Ile Ile Ser Lys Asn
        275                 280                 285

Ser Ser Asp Ser Gly Lys Asp Ile Ile Val Lys Leu Ala Arg Pro Val
    290                 295                 300

Glu Ile Thr Cys Glu Arg Thr Gly Asn Asn Thr Arg Gly Gln Ile Gln
305                 310                 315                 320

Ile Gly Pro Met Thr Ile Tyr Asn Ser Glu Asn Ile Val Gly Asn Thr
                325                 330                 335

Arg Lys Ala Phe Cys Lys Tyr Asn Glu Thr Asn Trp Gln Gly Ala Leu
            340                 345                 350

Lys Asp Thr Val Gln Ala Leu Asn Glu Ser Leu Ile His Phe Arg Asn
        355                 360                 365

```
Ser Ser Gly Gly Asp Ser Glu Val Thr Phe Leu His Phe Asn Cys His
    370             375             380

Gly Glu Phe Phe Tyr Cys Asn Thr Thr Lys Met Phe Ser Tyr Asn Cys
385             390             395                 400

Thr Thr Glu Gly Cys Asn Thr Thr Glu Thr Ser Asn Thr Thr Glu Thr
            405             410             415

Thr Lys Tyr Ile Pro Cys His Leu Lys Gln Val Val Arg Ser Trp Met
            420             425             430

Arg Val Gly Ser Gly Leu Phe Ala Pro Pro Ile Arg Gly Thr Leu Arg
        435             440             445

Cys Ile Ser Asn Ile Thr Gly Ile Ile Leu Gln Arg Asp Ala Pro Leu
    450             455             460

Lys Thr Asp Glu Asn Ser Thr Leu Arg Pro Ile Gly Gly Asp Met Thr
465             470             475             480

Asn Ile Trp Arg Ser Glu Leu Tyr Pro Tyr Lys Val Val Arg Val Lys
            485             490             495

Ala Leu Thr Val Ala Pro Thr Lys Ala Lys Arg Pro Val Ile Gly His
            500             505             510

Asn Arg Glu Lys Arg Ala Ala Gly Leu Gly Met Leu Phe Leu Gly Phe
        515             520             525

Met Ser Ala Ala Gly Ser Thr Met Gly Ala Ala Val Thr Leu Thr
530             535             540

Val Gln Ala Arg Gln Val Leu His Gly Ile Val Gln Gln Asn Asn
545             550             555             560

Met Leu Arg Ala Ile Ala Ala Gln Gln Glu Leu Leu Arg Leu Ser Val
                565             570             575

Trp Gly Ile Arg Gln Leu Arg Ala Arg Leu Leu Ala Ile Glu Thr Tyr
            580             585             590

Leu Arg Asp Gln Gln Leu Leu Gly Leu Trp Gly Cys Thr Gly Arg Leu
        595             600             605

Ile Cys Tyr Thr Asn Val Pro Trp Asn Lys Thr Trp Thr Gly Lys Asn
    610             615             620

Asp Thr Glu Leu Asp Asp Ile Trp Gly Asn Met Thr Trp Gln Gln Trp
625             630             635             640

Asp Lys Leu Val Asp Asn Tyr Thr Asp Thr Ile Phe Leu Glu Ile Gln
            645             650             655

Arg Ala Gln Glu Gln Gln Glu Ala Asn Gly Lys Ala Leu Leu Glu Leu
            660             665             670

Asp Lys Trp Ala Asp Leu Trp Ser Trp Leu Asp Ile Thr Gln Trp Leu
        675             680             685

Trp Tyr Ile Lys Ile Phe Ile Ile Ile Ala Gly Leu Val Gly Leu
    690             695             700

Arg Ile Leu Met Ala Ile Ile Asn Met Cys His Arg Val Arg Gln Gly
705             710             715             720

Tyr Ser Pro Leu Ser Phe Gln Ile Leu Gly Arg Asn Gln Val Pro Ala
            725             730             735

Gly Ile Val Pro Glu Ile Gly Glu Gly Gly Arg Ala Asp Asn Asp
            740             745             750

Arg Ser Ile Arg Leu Leu Ala Gly Phe Leu Pro Leu Ile Trp Asp Asp
        755             760             765

Ile Arg Thr Leu Val Val Trp Ile Tyr Arg Thr Leu Val Ile Leu Leu
    770             775             780
```

```
Ser Gly Ile Lys Glu Ile Thr Leu Ser Leu Ile Glu Tyr Leu Thr Arg
785                 790                 795                 800

Leu Leu Arg Arg Val Asn Asn Leu Thr Arg Asp Cys Phe Ala Phe Ile
            805                 810                 815

Ala Tyr Trp Gly Gln Glu Leu Lys Gln Ser Ala Ile Ser Leu Leu Asp
        820                 825                 830

Cys Val Ala Val Trp Thr Ala Asn Trp Thr Asp Gln Val Ile Ala Ile
        835                 840                 845

Ala Gln Arg Ile Gly Arg Gly Ile Leu Asn Ile Pro Arg Arg Ile Arg
    850                 855                 860

Gln Gly Leu Glu Arg Ser Leu Leu
865                 870

<210> SEQ ID NO 336
<211> LENGTH: 872
<212> TYPE: PRT
<213> ORGANISM: Simian immunodeficiency virus
<220> FEATURE:
<221> NAME/KEY: MISC_FEATURE
<222> LOCATION: (630)..(630)
<223> OTHER INFORMATION: Xaa can be any naturally occurring amino acid
<220> FEATURE:
<221> NAME/KEY: misc_feature
<222> LOCATION: (633)..(633)
<223> OTHER INFORMATION: Xaa can be any naturally occurring amino acid
<220> FEATURE:
<221> NAME/KEY: MISC_FEATURE
<222> LOCATION: (634)..(634)
<223> OTHER INFORMATION: Xaa can be any naturally occurring amino acid
<220> FEATURE:
<221> NAME/KEY: MISC_FEATURE
<222> LOCATION: (666)..(666)
<223> OTHER INFORMATION: Xaa can be any naturally occurring amino acid
<220> FEATURE:
<221> NAME/KEY: MISC_FEATURE
<222> LOCATION: (696)..(696)
<223> OTHER INFORMATION: Xaa can be any naturally occurring amino acid
<220> FEATURE:
<221> NAME/KEY: MISC_FEATURE
<222> LOCATION: (697)..(697)
<223> OTHER INFORMATION: Xaa can be any naturally occurring amino acid
<220> FEATURE:
<221> NAME/KEY: MISC_FEATURE
<222> LOCATION: (728)..(728)
<223> OTHER INFORMATION: Xaa can be any naturally occurring amino acid
<220> FEATURE:
<221> NAME/KEY: MISC_FEATURE
<222> LOCATION: (808)..(808)
<223> OTHER INFORMATION: Xaa can be any naturally occurring amino acid

<400> SEQUENCE: 336

Met Arg Asp Met Arg Ala Met Arg Lys Lys Gln Leu Asn Leu Trp Lys
1               5                   10                  15

Trp Val Met Ser Leu Gly Leu Ile Leu Thr Cys Ile Glu Ala Thr His
                20                  25                  30

Tyr Ala Thr Val Tyr Tyr Gly Val Pro Val Trp Arg Glu Ala Asn Val
            35                  40                  45

Thr Leu Phe Cys Ala Ala Asp Ala Asn Tyr Val Ser Lys Glu Gln His
    50                  55                  60

Asn Ile Trp Val Thr Gln Ala Cys Val Pro Thr Asp Pro Arg Pro Thr
65                  70                  75                  80

Glu Phe Pro Leu Glu Asn Val Thr Glu Thr Phe Asn Ile Trp Lys Asn
                85                  90                  95

Tyr Met Val Asp Gln Met Gln Asp Ile Val Ser Leu Trp Asp Gln
            100                 105                 110
```

```
Ser Leu Lys Pro Cys Val Lys Leu Thr Val Met Cys Val Thr Leu Asn
            115                 120                 125

Cys Thr Gln Leu Asn Thr Thr Asn Thr Thr Gln Thr Glu Met Thr Asn
        130                 135                 140

Thr Thr Ile Pro Pro His Thr Thr Ile Pro Pro His Ile Pro Gln Leu
145                 150                 155                 160

Asp Ile Tyr Asn Cys Ser Phe Asn Val Thr Val Leu Lys Asp Lys
                165                 170                 175

Thr Thr Lys Gln Gln Ala Leu Phe Tyr Arg Gln Asp Ile Ile Glu Thr
            180                 185                 190

Gly Glu Thr Gly Thr Asn Gly Ile Lys Gly Tyr Arg Leu Ile Asn Cys
            195                 200                 205

Asn Thr Ser Thr Ile Ser Gln Ala Cys Pro Lys Val Ser Phe Glu Pro
        210                 215                 220

Leu Pro Ile Gln Tyr Cys Ala Pro Ala Gly Tyr Ala Leu Met Lys Cys
225                 230                 235                 240

Asn Asp Ile Gln Phe Asn Gly Thr Gly Glu Cys Arg Asn Val Ser Ile
                245                 250                 255

Val His Cys Thr His Gly Ile Arg Pro Thr Val Ser Thr Gln Leu Ile
            260                 265                 270

Leu Asn Gly Thr Leu Ala Glu Gly Asn Ala Thr Ile Ile Ser Lys Asn
        275                 280                 285

Ser Ser Asp Ser Gly Lys Asp Ile Ile Val Lys Leu Ala Arg Pro Val
        290                 295                 300

Glu Ile Thr Cys Glu Arg Thr Gly Asn Asn Thr Arg Gly Gln Ile Gln
305                 310                 315                 320

Ile Gly Pro Met Thr Ile Tyr Asn Ser Glu Asn Ile Val Gly Asn Thr
                325                 330                 335

Arg Lys Ala Phe Cys Lys Tyr Asn Glu Thr Asn Trp Gln Gly Ala Leu
            340                 345                 350

Lys Asp Thr Val Gln Ala Leu Asn Glu Ser Leu Ile His Phe Arg Asn
        355                 360                 365

Ser Ser Gly Gly Asp Pro Glu Val Thr Phe Leu His Phe Asn Cys His
370                 375                 380

Gly Glu Phe Phe Tyr Cys Asn Thr Thr Lys Met Phe Ser Tyr Asn Cys
385                 390                 395                 400

Thr Thr Glu Gly Cys Asn Thr Thr Glu Thr Ser Asn Thr Thr Glu Thr
                405                 410                 415

Thr Lys Tyr Ile Pro Cys His Leu Lys Gln Val Val Arg Ser Trp Met
            420                 425                 430

Arg Val Gly Ser Gly Leu Phe Ala Pro Pro Ile Arg Gly Thr Leu Arg
        435                 440                 445

Cys Ile Ser Asn Ile Thr Gly Ile Ile Leu Gln Arg Asp Ala Pro Leu
        450                 455                 460

Lys Thr Asp Glu Asn Ser Thr Leu Arg Pro Ile Gly Gly Asp Met Thr
465                 470                 475                 480

Asn Ile Trp Arg Ser Glu Leu Tyr Pro Tyr Lys Val Val Arg Val Lys
                485                 490                 495

Ala Leu Thr Val Ala Pro Thr Lys Ala Lys Arg Pro Val Ile Gly His
            500                 505                 510

Asn Arg Glu Lys Arg Ala Ala Gly Leu Gly Met Leu Phe Leu Gly Phe
        515                 520                 525

Met Ser Ala Ala Gly Ser Thr Met Gly Ala Ala Ala Val Thr Leu Thr
```

```
            530             535             540
Val Gln Ala Arg Gln Val Leu His Gly Ile Val Gln Gln Asn Asn
545                     550                     555             560

Met Leu Arg Ala Ile Ala Gln Gln Glu Leu Leu Arg Leu Ser Val
                565                     570                 575

Trp Gly Ile Arg Gln Leu Arg Ala Arg Leu Leu Ala Ile Glu Thr Tyr
                580                     585                     590

Leu Arg Asp Gln Gln Leu Leu Gly Leu Trp Gly Cys Thr Gly Arg Leu
                595                     600                 605

Ile Cys Tyr Thr Asn Val Pro Trp Asn Lys Thr Trp Thr Gly Lys Asn
        610                     615                     620

Asp Thr Glu Leu Asp Xaa Ile Trp Xaa Xaa Met Thr Trp Gln Gln Trp
625                     630                     635                 640

Asp Lys Leu Val Asp Asn Tyr Thr Asp Thr Ile Phe Leu Glu Ile Gln
                    645                     650                 655

Arg Ala Gln Glu Gln Gln Glu Ala Asn Xaa Lys Ala Leu Leu Glu Leu
                660                     665                 670

Asp Lys Trp Ala Asp Leu Trp Ser Trp Leu Asp Ile Thr Gln Trp Leu
            675                     680                     685

Trp Tyr Ile Lys Ile Phe Ile Xaa Xaa Ile Ala Gly Leu Val Gly Leu
        690                     695                     700

Arg Ile Leu Met Ala Ile Ile Asn Met Cys His Arg Val Arg Gln Gly
705                     710                     715                 720

Tyr Ser Pro Leu Ser Phe Gln Xaa Leu Gly Arg Asn Gln Val Pro Ala
                    725                     730                 735

Gly Ile Val Pro Glu Ile Gly Glu Glu Gly Gly Arg Ala Asp Asn Asp
                740                     745                 750

Arg Ser Ile Arg Leu Leu Ala Gly Phe Leu Pro Leu Ile Trp Asp Asp
            755                     760                 765

Ile Arg Thr Leu Val Val Trp Ile Tyr Arg Thr Leu Val Ile Leu Leu
        770                     775                     780

Ser Gly Ile Lys Glu Ile Thr Leu Ser Leu Ile Glx Tyr Leu Thr Arg
785                     790                     795                 800

Leu Leu Arg Arg Val Asn Asn Xaa Thr Arg Asp Cys Phe Ala Phe Ile
                    805                     810                 815

Ala Tyr Trp Gly Gln Glu Leu Lys Gln Ser Ala Ile Ser Leu Leu Asp
            820                     825                 830

Cys Val Ala Val Trp Thr Ala Asn Trp Thr Asp Gln Val Ile Ala Ile
        835                     840                     845

Ala Gln Arg Ile Gly Arg Gly Ile Leu Asn Ile Pro Arg Arg Ile Arg
    850                     855                     860

Gln Gly Leu Glu Arg Ser Leu Leu
865                 870

<210> SEQ ID NO 337
<211> LENGTH: 872
<212> TYPE: PRT
<213> ORGANISM: Simian immunodeficiency virus

<400> SEQUENCE: 337

Met Arg Asp Met Arg Ala Met Arg Lys Lys Gln Leu Asn Leu Trp Lys
1               5                   10                  15

Trp Val Met Ser Leu Gly Leu Ile Leu Thr Cys Ile Glu Ala Thr His
                20                  25                  30
```

-continued

```
Tyr Ala Thr Val Tyr Tyr Gly Val Pro Val Trp Arg Glu Ala Asn Val
             35                  40                  45

Thr Leu Phe Cys Ala Ala Asp Ala Asn Tyr Val Ser Lys Glu Gln His
 50                  55                  60

Asn Ile Trp Ala Thr Gln Ala Cys Val Pro Thr Asp Pro Arg Pro Thr
 65                  70                  75                  80

Glu Phe Pro Leu Glu Asn Val Thr Glu Thr Phe Asn Ile Trp Lys Asn
                 85                  90                  95

Tyr Met Val Asp Gln Met Gln Asp Ile Val Ser Leu Trp Asp Gln
                100                 105                 110

Ser Leu Lys Pro Cys Val Lys Leu Thr Val Met Cys Val Thr Leu Asn
            115                 120                 125

Cys Thr Gln Leu Asn Thr Thr Asn Thr Thr Gln Thr Glu Met Thr Asn
130                 135                 140

Thr Thr Ile Pro Pro His Thr Thr Ile Pro Pro His Ile Pro Gln Leu
145                 150                 155                 160

Asp Ile Tyr Asn Cys Ser Phe Asn Val Thr Thr Val Leu Lys Asp Lys
                165                 170                 175

Thr Thr Lys Gln Gln Ala Leu Phe Tyr Arg Gln Asp Ile Ile Glu Thr
            180                 185                 190

Gly Glu Thr Gly Thr Asn Gly Ile Lys Gly Tyr Arg Leu Ile Asn Cys
            195                 200                 205

Asn Thr Ser Thr Ile Ser Gln Ala Cys Pro Lys Val Ser Phe Glu Pro
    210                 215                 220

Leu Pro Ile Gln Tyr Cys Ala Pro Ala Gly Tyr Ala Leu Met Lys Cys
225                 230                 235                 240

Asn Asp Ile Gln Phe Asn Gly Thr Gly Glu Cys Arg Asn Val Ser Ile
                245                 250                 255

Val His Cys Thr His Gly Ile Arg Pro Thr Val Ser Thr Gln Leu Ile
            260                 265                 270

Leu Asn Gly Thr Leu Ala Glu Gly Asn Ala Thr Ile Ile Ser Lys Asn
            275                 280                 285

Ser Ser Asp Ser Gly Lys Asp Ile Ile Val Lys Leu Ala Arg Pro Val
    290                 295                 300

Glu Ile Thr Cys Glu Arg Thr Gly Asn Asn Thr Arg Gly Gln Ile Gln
305                 310                 315                 320

Ile Gly Pro Met Thr Ile Tyr Asn Ser Glu Asn Ile Val Gly Asn Thr
                325                 330                 335

Arg Lys Ala Phe Cys Lys Tyr Asn Glu Thr Asn Trp Gln Gly Ala Leu
            340                 345                 350

Lys Asp Thr Val Gln Ala Leu Asn Glu Ser Leu Ile His Phe Arg Asn
            355                 360                 365

Ser Ser Gly Gly Asp Pro Glu Val Thr Phe Leu His Phe Asn Cys His
    370                 375                 380

Gly Glu Phe Phe Tyr Cys Asn Thr Thr Lys Met Phe Ser Tyr Asn Cys
385                 390                 395                 400

Thr Thr Glu Gly Cys Asn Thr Thr Glu Thr Ser Asn Thr Thr Glu Thr
                405                 410                 415

Thr Lys Tyr Ile Pro Cys His Leu Lys Gln Val Val Arg Ser Trp Met
            420                 425                 430

Arg Val Gly Ser Gly Leu Phe Ala Pro Pro Ile Arg Gly Thr Leu Arg
            435                 440                 445

Cys Ile Ser Asn Ile Thr Gly Ile Ile Leu Gln Arg Asp Ala Pro Leu
```

```
              450                 455                 460
Lys Thr Asp Glu Asn Ser Thr Leu Arg Pro Ile Gly Gly Asp Met Thr
465                 470                 475                 480

Asn Ile Trp Arg Ser Glu Leu Tyr Pro Tyr Lys Val Val Arg Val Lys
                    485                 490                 495

Ala Leu Thr Val Ala Pro Thr Lys Ala Lys Arg Pro Val Ile Gly His
                500                 505                 510

Asn Arg Glu Lys Arg Ala Ala Gly Leu Gly Met Leu Phe Leu Gly Phe
            515                 520                 525

Met Ser Ala Ala Gly Ser Thr Met Gly Ala Ala Val Thr Leu Thr
        530                 535                 540

Val Gln Ala Arg Gln Val Leu His Gly Ile Val Gln Gln Gln Asn Asn
545                 550                 555                 560

Met Leu Arg Ala Ile Ala Ala Gln Gln Glu Leu Leu Arg Leu Ser Val
                565                 570                 575

Trp Gly Ile Arg Gln Leu Arg Ala Arg Leu Leu Ala Ile Glu Thr Tyr
                580                 585                 590

Leu Arg Asp Gln Gln Leu Leu Gly Leu Trp Gly Cys Thr Gly Arg Leu
            595                 600                 605

Ile Cys Tyr Thr Asn Val Pro Trp Asn Lys Thr Trp Thr Gly Lys Asn
        610                 615                 620

Asp Thr Glu Leu Asp Asp Ile Trp Gly Asn Met Thr Trp Gln Gln Trp
625                 630                 635                 640

Asp Lys Leu Val Asp Asn Tyr Thr Asp Thr Ile Phe Leu Glu Ile Gln
                645                 650                 655

Arg Ala Gln Glu Gln Gln Glu Ala Asn Glu Lys Ala Leu Leu Glu Leu
                660                 665                 670

Asp Lys Trp Ala Asp Leu Trp Ser Trp Leu Asp Ile Thr Gln Trp Leu
            675                 680                 685

Trp Tyr Ile Lys Ile Phe Ile Ile Ile Ala Gly Leu Val Gly Leu
        690                 695                 700

Arg Ile Leu Met Ala Ile Ile Asn Met Cys His Arg Val Arg Gln Gly
705                 710                 715                 720

Tyr Ser Pro Leu Ser Phe Gln Ile Leu Gly Arg Asn Gln Val Pro Ala
                725                 730                 735

Gly Ile Val Pro Glu Ile Gly Glu Gly Gly Arg Ala Asp Asn Asp
                740                 745                 750

Arg Ser Ile Arg Leu Leu Ala Gly Phe Leu Pro Leu Ile Trp Asp Asp
            755                 760                 765

Ile Arg Thr Leu Val Val Trp Ile Tyr Arg Thr Leu Val Ile Leu Leu
        770                 775                 780

Ser Gly Ile Lys Glu Ile Thr Leu Ser Leu Ile Glu Tyr Leu Thr Arg
785                 790                 795                 800

Leu Leu Arg Arg Val Asn Asn Leu Thr Arg Asp Cys Phe Ala Phe Ile
                805                 810                 815

Ala Tyr Trp Gly Gln Glu Leu Lys Gln Ser Ala Ile Ser Leu Leu Asp
                820                 825                 830

Cys Val Ala Val Trp Thr Ala Asn Trp Thr Asp Gln Val Ile Ala Ile
            835                 840                 845

Ala Gln Arg Ile Gly Arg Gly Ile Leu Asn Ile Pro Arg Arg Ile Arg
        850                 855                 860

Gln Gly Leu Glu Arg Ser Leu Leu
865                 870
```

```
<210> SEQ ID NO 338
<211> LENGTH: 876
<212> TYPE: PRT
<213> ORGANISM: Simian immunodeficiency virus
<220> FEATURE:
<221> NAME/KEY: MISC_FEATURE
<222> LOCATION: (345)..(345)
<223> OTHER INFORMATION: Xaa can be any naturally occurring amino acid
<220> FEATURE:
<221> NAME/KEY: MISC_FEATURE
<222> LOCATION: (446)..(446)
<223> OTHER INFORMATION: Xaa can be any naturally occurring amino acid
<220> FEATURE:
<221> NAME/KEY: MISC_FEATURE
<222> LOCATION: (450)..(450)
<223> OTHER INFORMATION: Xaa can be any naturally occurring amino acid
<220> FEATURE:
<221> NAME/KEY: MISC_FEATURE
<222> LOCATION: (454)..(454)
<223> OTHER INFORMATION: Xaa can be any naturally occurring amino acid
<220> FEATURE:
<221> NAME/KEY: misc_feature
<222> LOCATION: (455)..(455)
<223> OTHER INFORMATION: Xaa can be any naturally occurring amino acid
<220> FEATURE:
<221> NAME/KEY: MISC_FEATURE
<222> LOCATION: (460)..(460)
<223> OTHER INFORMATION: Xaa can be any naturally occurring amino acid
<220> FEATURE:
<221> NAME/KEY: MISC_FEATURE
<222> LOCATION: (467)..(467)
<223> OTHER INFORMATION: Xaa can be any naturally occurring amino acid
<220> FEATURE:
<221> NAME/KEY: MISC_FEATURE
<222> LOCATION: (801)..(801)
<223> OTHER INFORMATION: Xaa can be any naturally occurring amino acid
<220> FEATURE:
<221> NAME/KEY: MISC_FEATURE
<222> LOCATION: (807)..(807)
<223> OTHER INFORMATION: Xaa can be any naturally occurring amino acid

<400> SEQUENCE: 338

Met Lys Asp Met Arg Ala Met Arg Lys Lys Gln Leu Asn Leu Trp Lys
1               5                   10                  15

Gly Val Met Ser Leu Gly Leu Leu Leu Thr Cys Ile Glu Ala Lys Thr
            20                  25                  30

Glu His Tyr Ala Thr Val Tyr Tyr Gly Val Pro Val Trp Arg Glu Ala
        35                  40                  45

Lys Val Thr Leu Phe Cys Ala Ala Asp Ala Ser Phe Val Ser Lys Glu
    50                  55                  60

Gln His Asn Ile Trp Ala Thr Gln Ala Cys Val Pro Thr Asp Pro Ser
65                  70                  75                  80

Pro Thr Glu Phe Leu Leu Glu Asn Val Thr Glu Thr Phe Asp Ile Trp
                85                  90                  95

Lys Asn Tyr Met Val Glu Gln Met Gln Glu Asp Ile Ile Ser Leu Trp
            100                 105                 110

Asp Gln Ser Leu Lys Pro Cys Val Lys Leu Thr Val Met Cys Val Thr
        115                 120                 125

Met Thr Cys Ser Asn Asp Thr Lys Gly Ser Asn Lys Ser Thr Ala Thr
    130                 135                 140

Thr Thr Ser Ala Asn Thr Pro Thr Ser Thr Glu Thr Thr Ile Pro Thr
145                 150                 155                 160

Asn Ile Pro Glu Leu Asp Ile Phe Asn Cys Thr Phe Asn Val Thr Thr
                165                 170                 175

Val Leu Lys Asp Lys Lys Thr Lys Gln Gln Ala Leu Phe Tyr Lys Gln
```

-continued

```
            180                 185                 190
Asp Ile Thr Glu Thr Asp Lys Asn Glu Tyr Arg Leu Ile Asn Cys Asn
            195                 200                 205
Thr Ser Thr Ile Ser Gln Ala Cys Pro Lys Val Ser Phe Glu Pro Leu
            210                 215                 220
Pro Ile Gln Tyr Cys Ala Pro Ala Gly Tyr Pro Leu Leu Lys Cys Asn
225                 230                 235                 240
Asp Glu Gln Phe Asn Gly Thr Gly Glu Cys Asn Asn Val Ser Ile Val
                    245                 250                 255
His Cys Thr His Gly Ile Arg Pro Thr Val Ser Thr Gln Leu Ile Leu
                    260                 265                 270
Asn Gly Thr Leu Ala Lys Gly Asn Asn Ala Thr Ile Ile Ser Ser Asn
                    275                 280                 285
Ser Ser Asp Ser Ala Thr Asp Ile Ile Val Lys Leu Ala Asn Pro Val
                    290                 295                 300
Glu Ile Thr Cys Glu Arg Thr Gly Asn Asn Thr Arg Gly Gln Ile Gln
305                 310                 315                 320
Val Gly Pro Leu Thr Ile Tyr Asn Ser Glu Asn Ile Ile Gly Asn Thr
                    325                 330                 335
Arg Lys Ala Phe Cys Lys Tyr Asn Xaa Thr Ala Trp Gln Lys Ala Leu
                    340                 345                 350
Gln Ala Thr Val Arg Ala Leu Lys Thr Asn Leu Thr His Tyr Phe Asn
                    355                 360                 365
Lys Ser Ser Gly Gly Asp Pro Glu Val Thr Ser Leu His Phe Asn Cys
            370                 375                 380
His Gly Glu Phe Phe Tyr Cys Asn Thr Thr Lys Met Phe Asn Tyr Lys
385                 390                 395                 400
Cys Thr Gly Glu His Cys Asn Cys Thr Asp Lys Glu Leu Cys Asn Lys
                    405                 410                 415
Thr Ala Glu Met Glu Tyr Ile Pro Cys Arg Leu Lys Gln Val Val Asn
                    420                 425                 430
Ser Trp Met Arg Val Gly Ser Gly Leu Phe Ala Pro Pro Xaa Arg Gly
            435                 440                 445
Thr Xaa Arg Cys Ile Xaa Xaa Ile Thr Gly Ile Xaa Leu Gln Arg Asp
450                 455                 460
Thr Pro Xaa Ala Glu Asn Asn Asn Thr Thr Leu Arg Pro Leu Gly
465                 470                 475                 480
Gly Glu Met Arg Asn Ile Trp Arg Ser Glu Leu Tyr Pro Tyr Lys Val
            485                 490                 495
Val Lys Val Lys Ala Leu Ser Val Ala Pro Thr Lys Ala Lys Arg Pro
            500                 505                 510
Val Val Ser His Asn Arg Glu Lys Arg Ala Ala Gly Leu Gly Met Leu
            515                 520                 525
Phe Leu Gly Phe Met Ser Ala Ala Gly Ser Thr Met Gly Ala Ala Ala
            530                 535                 540
Ile Thr Leu Thr Val Gln Ala Arg Gln Val Leu His Gly Ile Val Gln
545                 550                 555                 560
Gln Gln Asn Asn Met Leu Arg Ala Ile Ala Ala Gln Gln Glu Leu Leu
                    565                 570                 575
Arg Leu Ser Val Trp Gly Ile Arg Gln Leu Arg Ala Arg Leu Leu Ala
                    580                 585                 590
Ile Glu Thr Tyr Leu Arg Asp Gln Gln Leu Leu Gly Leu Trp Gly Cys
            595                 600                 605
```

```
Thr Gly Lys Leu Ile Cys Tyr Thr Asn Val Pro Trp Asn Thr Thr Trp
610                 615                 620

Thr Gly Lys Ser Asp Ser Glu Leu Asp Gly Ile Trp Gly Asn Leu Thr
625                 630                 635                 640

Trp Gln Gln Trp Asp Lys Leu Val Asp Asn Tyr Thr Asp Thr Ile Phe
                645                 650                 655

Leu Glu Ile Gln Lys Ala Gln Glu Gln Glu Ala Asn Glu Lys Ala
                660                 665                 670

Leu Leu Glu Leu Asp Lys Trp Ala Asp Leu Trp Ser Trp Leu Asp Ile
            675                 680                 685

Thr Gln Trp Ile Trp Tyr Ile Arg Ile Phe Ile Ile Val Ile Ala Gly
690                 695                 700

Leu Val Gly Leu Lys Ile Leu Met Ala Ile Ile Asn Ile Cys His Arg
705                 710                 715                 720

Val Arg Gln Gly Tyr Ser Pro Leu Ser Phe Gln Ile Leu Gly Arg Asn
                725                 730                 735

Gln Val Pro Ala Gly Ile Val Pro Glu Ile Gly Glu Gly Gly Arg
                740                 745                 750

Ala Asp Ser Asp Arg Ser Ile Arg Leu Leu Ala Gly Phe Leu Pro Leu
                755                 760                 765

Ile Trp Asp Asp Leu Arg Thr Leu Val Val Trp Ile Tyr Arg Thr Leu
770                 775                 780

Val Ile Leu Leu Ser Gly Ile Lys Glu Ile Thr Leu Ser Leu Ile Glu
785                 790                 795                 800

Xaa Leu Thr Arg Leu Leu Xaa Arg Val Asn Asn Leu Thr Arg Asp Cys
                805                 810                 815

Phe Ala Phe Ile Ala Tyr Trp Gly Gln Glu Leu Lys Gln Ser Ala Ile
                820                 825                 830

Ser Leu Leu Asp Cys Val Ala Val Trp Thr Ala Asp Trp Thr Asp Gln
            835                 840                 845

Val Ile Ala Ile Ala Gln Arg Ile Gly Arg Gly Ile Leu Asn Ile Pro
850                 855                 860

Arg Arg Ile Arg Gln Gly Leu Glu Arg Ser Leu Leu
865                 870                 875

<210> SEQ ID NO 339
<211> LENGTH: 870
<212> TYPE: PRT
<213> ORGANISM: Simian immunodeficiency virus
<220> FEATURE:
<221> NAME/KEY: MISC_FEATURE
<222> LOCATION: (459)..(459)
<223> OTHER INFORMATION: Xaa can be any naturally occurring amino acid
<220> FEATURE:
<221> NAME/KEY: MISC_FEATURE
<222> LOCATION: (621)..(621)
<223> OTHER INFORMATION: Xaa can be any naturally occurring amino acid
<220> FEATURE:
<221> NAME/KEY: MISC_FEATURE
<222> LOCATION: (682)..(682)
<223> OTHER INFORMATION: Xaa can be any naturally occurring amino acid

<400> SEQUENCE: 339

Met Arg Ala Met Glu Arg Thr Lys Arg Ser Trp Asn Ile Leu Ser Arg
1               5                   10                  15

Ser Met Val Leu Leu Thr Leu Cys Leu Thr Phe Asn Val Ala Thr Asp
                20                  25                  30

Tyr Trp Val Thr Val Tyr Tyr Gly Val Pro Val Trp Lys Asp Ala Glu
```

```
            35                  40                  45
Thr Thr Leu Phe Cys Ala Ser Glu Ala Lys Pro His Ser Ser Glu Ala
 50                  55                  60

His Asn Ile Trp Ala Thr Gln Ala Cys Val Pro Ile Asp Pro Asn Pro
 65                  70                  75                  80

Glu Glu Val Phe Leu Pro Asn Val Thr Glu Asn Phe Ser Met Trp Asp
                 85                  90                  95

Asn Pro Met Val Ser Gln Met Gln Glu Asp Ile Ile Ser Leu Trp Glu
            100                 105                 110

Gln Ser Leu Lys Pro Cys Val Lys Leu Thr Pro Leu Cys Val Thr Leu
        115                 120                 125

Asn Cys Ser Thr Ala Ile Phe Arg Ala Asn Arg Thr Ser Thr Asn Thr
130                 135                 140

Thr Thr Pro Ser Thr Ile Ala Thr Ser Pro Thr Thr Asp Thr Ile Tyr
145                 150                 155                 160

Glu Met Lys Asn Cys Ser Phe Asn Val Thr Thr Glu Leu Arg Asp Lys
                165                 170                 175

Lys Lys Gln Val Tyr Ser Leu Phe Tyr Val Asp Asp Val Val Lys Leu
            180                 185                 190

Asn Asp Gly Asp Ser Thr Asn Ser Ser Thr Tyr Arg Leu Ile Asn Cys
        195                 200                 205

Asn Thr Thr Ala Ile Thr Gln Ala Cys Pro Lys Ile Ser Phe Glu Pro
210                 215                 220

Ile Pro Ile His Tyr Cys Ala Pro Ala Gly Phe Ala Ile Leu Lys Cys
225                 230                 235                 240

Asn Asp Thr Asn Tyr Leu Gly Thr Gly Lys Cys His Asn Val Ser Thr
                245                 250                 255

Val His Cys Thr His Gly Ile Arg Pro Ala Val Thr Thr Gln Leu Ile
            260                 265                 270

Leu Asn Gly Ser Leu Ala Glu Gly Asn Val Thr Ile Arg Val Lys Asn
        275                 280                 285

Ala Ser Ser Asn Ser Gly Asn Tyr Ile Val Gln Leu Ala Arg Ser Val
290                 295                 300

Glu Ile Leu Cys Arg Arg Glu Gly Asn Asn Thr Arg Gly Gln Val Gln
305                 310                 315                 320

Ile Gly Pro Ala Met Thr Phe Tyr Asn Ile Glu Asn Val Val Gly Asp
                325                 330                 335

Thr Arg Lys Ala Tyr Cys Thr Leu Asn Gly Ser Asn Trp Glu Glu Ala
            340                 345                 350

Met Ser Lys Val Lys Lys Glu Leu Glu Lys Ile Thr Asn Val Thr Asn
        355                 360                 365

Ile Thr Phe Ala Asp Gln Arg Gln Gly Ser Asp Pro Glu Val Glu Asn
370                 375                 380

His Met Phe Asn Cys Gly Gly Glu Phe Phe Tyr Cys Asn Thr Ser Lys
385                 390                 395                 400

Leu Phe Asn Asn Lys Thr Gly Arg Gly Gly Asn Lys Ser Glu Glu Ile
                405                 410                 415

Ile Leu Pro Cys Arg Ile Lys Gln Ile Val Asn Leu Trp Thr Arg Val
            420                 425                 430

Gly Lys Gly Ile Tyr Ala Pro Pro Ile Arg Gly Asn Ile Ser Cys Lys
        435                 440                 445

Ser Asn Ile Thr Gly Ile Leu Leu Ala Arg Xaa Glu Gly Lys Asp Asn
450                 455                 460
```

-continued

```
Gln Asn Asn Leu Thr Phe Arg Pro Ile Gly Gly Asn Met Glu Asp Leu
465                 470                 475                 480

Trp Arg Ser Glu Leu Tyr Lys Tyr Lys Val Arg Ile Glu Pro Leu
            485                 490                 495

Ala Val Ala Pro Ser Lys Ala Lys Arg Arg Thr Val Glu Thr Glu Lys
                500                 505                 510

Arg Gln Lys Arg Ala Ala Phe Gly Leu Gly Ala Leu Phe Leu Gly Phe
            515                 520                 525

Leu Gly Ala Ala Gly Ser Thr Met Gly Ala Ala Val Thr Leu Thr
530                 535                 540

Val Gln Ala Arg Gln Leu Leu Ser Gly Ile Val Gln Gln Gln Asn Asn
545                 550                 555                 560

Leu Leu Arg Ala Ile Glu Ala Gln Gln His Leu Leu Gln Leu Ser Ile
                565                 570                 575

Trp Gly Val Lys Gln Leu Gln Gly Arg Leu Leu Ala Val Glu Arg Tyr
            580                 585                 590

Leu Gln Asp Gln Gln Ile Leu Gly Leu Trp Gly Cys Ser Gly Lys Ala
            595                 600                 605

Ile Cys Tyr Thr Thr Val Pro Trp Asn Lys Thr Trp Xaa Gly Asn Tyr
610                 615                 620

Ser Tyr Glu Tyr Ile Trp Asn Asn Leu Thr Trp Glu Gln Trp Asp Val
625                 630                 635                 640

His Val Ser Asn Tyr Thr Gly Val Ile Phe Gly Leu Leu Glu Glu Ala
                645                 650                 655

Gln Gly Gln Gln Glu Lys Asn Glu Arg Glu Leu Leu Glu Leu Asp Lys
            660                 665                 670

Trp Ser Ser Leu Trp Ser Trp Phe Asx Xaa Thr His Trp Leu Trp Tyr
            675                 680                 685

Ile Lys Ile Phe Ile Met Val Val Ala Gly Ile Val Gly Leu Arg Ile
            690                 695                 700

Cys Met Ile Val Ile Ser Val Ile Arg Arg Val Arg Gln Gly Tyr Ser
705                 710                 715                 720

Pro Leu Ser Leu Gln Thr Leu Leu Pro Val Gln Arg Gly Pro Gly Val
                725                 730                 735

Leu Asp Gly Thr Asp Glu Glu Gly Gly Glu Gln Gly Arg Gly Arg Ser
            740                 745                 750

Val Arg Leu Val Thr Gly Cys Leu Pro Leu Ile Trp Asp Asp Leu Arg
            755                 760                 765

Ser Leu Leu Ile Trp Phe Tyr Gln Thr Leu Ser Asn Ser Ala Cys Val
            770                 775                 780

Val Gln Arg His Leu Glu Arg Leu Ile Gln Leu Ile Leu Lys Gly Leu
785                 790                 795                 800

Arg Leu Leu Trp Glu Lys Ile Arg Leu Cys Trp Gly Val Leu Gln Tyr
                805                 810                 815

Trp Lys Arg Glu Leu Lys Thr Ser Ala Ile Ser Leu Leu Asp Ala Thr
            820                 825                 830

Ala Ile Arg Val Ala Glu Gly Thr Asp Gln Ile Ile Phe Ala Ala Gln
            835                 840                 845

Arg Ile Gly Arg Gly Phe Leu Asn Ile Pro Arg Arg Ile Arg Gln Gly
            850                 855                 860

Leu Glu Arg Ala Leu Leu
865                 870
```

```
<210> SEQ ID NO 340
<211> LENGTH: 868
<212> TYPE: PRT
<213> ORGANISM: Simian immunodeficiency virus
<220> FEATURE:
<221> NAME/KEY: MISC_FEATURE
<222> LOCATION: (461)..(461)
<223> OTHER INFORMATION: Xaa can be any naturally occurring amino acid
<220> FEATURE:
<221> NAME/KEY: MISC_FEATURE
<222> LOCATION: (463)..(463)
<223> OTHER INFORMATION: Xaa can be any naturally occurring amino acid
<220> FEATURE:
<221> NAME/KEY: MISC_FEATURE
<222> LOCATION: (767)..(767)
<223> OTHER INFORMATION: Xaa can be any naturally occurring amino acid

<400> SEQUENCE: 340

Met Arg Ala Met Glu Arg Thr Lys Arg Ser Trp Asn Ile Leu Ser Arg
1               5                   10                  15

Ser Met Val Leu Leu Thr Leu Cys Leu Thr Phe Asn Val Ala Thr Glu
            20                  25                  30

Tyr Trp Val Ala Val Tyr Tyr Gly Val Pro Val Trp Lys Asp Ala Glu
        35                  40                  45

Thr Thr Leu Phe Cys Ala Ser Glu Ala Lys Pro His Ser Ser Glu Ala
    50                  55                  60

His Asn Ile Trp Ala Thr Gln Ala Cys Val Pro Ile Asp Pro Asn Pro
65                  70                  75                  80

Glu Glu Val Phe Leu Thr Asn Val Thr Glu Asn Phe Ser Met Trp Asp
                85                  90                  95

Asn Pro Met Val Ser Gln Met Gln Glu Asp Ile Ile Ser Leu Trp Glu
            100                 105                 110

Gln Ser Leu Lys Pro Cys Val Lys Leu Thr Leu Tyr Val Leu Thr Pro
        115                 120                 125

Asn Cys Ser Thr Ala Glu Phe Lys Asn Asn Thr Asn Thr Asn Thr Thr
    130                 135                 140

Thr Thr Gly Pro Ala Asn Val Thr Asn Tyr Glu Met Lys Asn Cys Ser
145                 150                 155                 160

Phe Asn Val Thr Thr Glu Leu Arg Asp Arg Lys Lys Arg Val Tyr Ser
                165                 170                 175

Leu Phe Tyr Val Asp Asp Val Glu Lys Leu Asn Asp Gly Asn Ser Thr
            180                 185                 190

Asn Ser Thr Tyr Arg Leu Ile Asn Cys Asn Thr Thr Ala Ile Thr Gln
        195                 200                 205

Ala Cys Pro Lys Ile Ser Phe Glu Pro Ile Pro Ile His Tyr Cys Ala
    210                 215                 220

Pro Ala Gly Phe Ala Ile Leu Lys Cys Asn Asp Thr Asn Tyr Ser Gly
225                 230                 235                 240

Thr Gly Lys Cys His Asn Val Ser Thr Val His Cys Thr His Gly Ile
                245                 250                 255

Met Pro Ala Val Thr Thr Gln Leu Ile Leu Asn Gly Ser Leu Ala Glu
            260                 265                 270

Gly Asn Val Thr Ile Arg Val Lys Asn Ala Ser Ser Asn Ser Gly Asn
        275                 280                 285

Phe Ile Val Gln Leu Ala Lys Pro Val Glu Ile Leu Cys Arg Arg Glu
    290                 295                 300

Gly Asn Asn Thr Arg Gly Gln Val Gln Ile Gly Pro Gly Met Thr Tyr
305                 310                 315                 320
```

-continued

```
Tyr Asn Ile Glu Asn Val Ile Gly Asn Thr Arg Lys Ala Tyr Cys Lys
                325                 330                 335

Leu Asn Arg Ser Asn Trp Glu Asp Ala Met Ser Lys Val Lys Lys Glu
            340                 345                 350

Leu Glu Lys Ile Thr Asn Val Thr Lys Val Ile Phe Ala Asn Gln Ser
        355                 360                 365

His Gly Ser Asp Pro Glu Val Glu Asn His Met Phe Asn Cys Gly Gly
    370                 375                 380

Glu Phe Phe Tyr Cys Asn Thr Ser Lys Leu Phe Asn Asn Lys Thr Gly
385                 390                 395                 400

Ile Asn Asp Thr Thr Gly Lys Gly Thr Asn Glu Ser Glu Ile Ile Leu
                405                 410                 415

Pro Cys Arg Leu Arg Gln Ile Val Asn Leu Trp Thr Arg Val Gly Lys
            420                 425                 430

Gly Ile Tyr Ala Pro Pro Ile Arg Gly Asn Ile Ser Cys Lys Ser Asn
        435                 440                 445

Ile Thr Gly Ile Leu Leu Ala Arg Glu Glu Gly Asx Xaa Asn Xaa Thr
    450                 455                 460

Asn Leu Thr Phe Lys Pro Ile Gly Gly Asn Met Glu Asp Leu Trp Arg
465                 470                 475                 480

Ser Glu Leu Tyr Lys Tyr Lys Val Val Arg Ile Glu Pro Leu Ala Val
                485                 490                 495

Ala Pro Ser Lys Ala Lys Arg Arg Thr Val Glu Thr Glu Lys Arg Gln
            500                 505                 510

Lys Arg Ala Ala Phe Gly Leu Gly Ala Leu Phe Leu Gly Phe Leu Gly
        515                 520                 525

Ala Ala Gly Ser Thr Met Gly Ala Ala Val Thr Leu Thr Val Gln
    530                 535                 540

Ala Arg Gln Leu Leu Ser Gly Ile Val Gln Gln Gln Asn Asn Leu Leu
545                 550                 555                 560

Arg Ala Ile Glu Ala Gln Gln His Leu Leu Gln Leu Ser Ile Trp Gly
                565                 570                 575

Val Lys Gln Leu Gln Gly Arg Leu Leu Ala Val Glu Arg Tyr Leu Gln
            580                 585                 590

Asp Gln Gln Ile Leu Gly Leu Trp Gly Cys Ser Gly Lys Ala Ile Cys
        595                 600                 605

Tyr Thr Thr Val Pro Trp Asn Lys Thr Trp Phe Gly Asn Tyr Ser Tyr
    610                 615                 620

Glu Tyr Ile Trp Asn Asn Leu Thr Trp Glu Gln Trp Asp Val His Val
625                 630                 635                 640

Ser Asn Tyr Thr Gly Val Ile Phe Gly Leu Leu Glu Glu Ala Gln Gly
                645                 650                 655

Gln Gln Glu Lys Asn Glu Arg Glu Leu Leu Glu Leu Asp Lys Trp Ser
            660                 665                 670

Ser Leu Trp Ser Trp Phe Asp Ile Thr His Trp Leu Trp Tyr Ile Lys
        675                 680                 685

Ile Phe Ile Met Val Val Ala Gly Ile Val Gly Leu Arg Ile Cys Met
    690                 695                 700

Ile Val Ile Ser Val Ile Arg Arg Val Arg Gln Gly Tyr Ser Pro Leu
705                 710                 715                 720

Ser Leu Gln Thr Leu Leu Pro Val Gln Arg Gly Pro Gly Val Leu Asp
                725                 730                 735
```

```
Gly Thr Asp Glu Glu Gly Glu Gln Gly Arg Gly Arg Ser Val Arg
                740                 745                 750

Leu Val Thr Gly Cys Leu Pro Leu Ile Trp Asp Asp Leu Arg Xaa Leu
            755                 760                 765

Leu Ile Trp Phe Tyr Gln Thr Leu Ser Asn Ser Ala Cys Val Val Gln
        770                 775                 780

Arg His Leu Glu Arg Leu Ile Gln Leu Ile Leu Lys Gly Leu Arg Leu
785                 790                 795                 800

Leu Trp Glu Lys Ile Arg Leu Cys Trp Gly Val Leu Gln Tyr Trp Thr
                805                 810                 815

Arg Glu Leu Lys Thr Ser Ala Ile Ser Leu Leu Asp Ala Ile Ala Ile
            820                 825                 830

Arg Val Ala Glu Gly Thr Asp Gln Ile Ile Phe Ala Ala Gln Arg Ile
        835                 840                 845

Gly Arg Gly Phe Leu Asn Ile Pro Gly Arg Ile Arg Gln Gly Leu Leu
    850                 855                 860

Arg Ala Leu Leu
865

<210> SEQ ID NO 341
<211> LENGTH: 798
<212> TYPE: PRT
<213> ORGANISM: Simian immunodeficiency virus

<400> SEQUENCE: 341

Met Arg Val Arg Glu Met Lys Lys Leu Trp Ser Phe Trp Val Leu Gly
1               5                   10                  15

Leu Gly Phe Leu Ala Leu Ser Leu Thr Ser Asp Ser Asn Trp Trp Val
                20                  25                  30

Thr Val Tyr Leu Gly Val Pro Val Trp Lys Asp Ala Glu Thr Thr Leu
            35                  40                  45

Phe Cys Ala Ser Asp Ala Lys Ala Tyr Ser Thr Glu Ala His Asn Ile
        50                  55                  60

Trp Ala Thr Gln Ala Cys Val Pro Ile Asp Pro Asn Pro Gln Glu Val
65                  70                  75                  80

Phe Leu Lys Asn Val Lys Glu Asn Phe Asn Met Trp Asp Asn Pro Met
                85                  90                  95

Val Asp Gln Met Gln Glu Asp Ile Ile Ser Leu Trp Asp Gln Ser Leu
            100                 105                 110

Lys Pro Cys Val Lys Leu Thr Pro Leu Cys Val Thr Leu Asn Cys Thr
        115                 120                 125

Asn Val Asn Ala Thr Ser Pro Thr Thr Lys Pro Pro Thr Thr Thr Pro
    130                 135                 140

Thr Thr Val Ser Thr Val Ser Thr Thr Ile Pro Leu Asn Asp Ser Ile
145                 150                 155                 160

Phe Glu Asp Met Cys Asn Cys Thr Phe Asn Val Thr Thr Glu Leu Arg
                165                 170                 175

Gly Ser Ser Asn Asn Ser Tyr Asn Ser Tyr Arg Leu Ile Asn Cys Asn
            180                 185                 190

Thr Thr Ala Ile Thr Gln Ala Cys Pro Lys Thr Ser Phe Glu Pro Ile
        195                 200                 205

Pro Ile His Tyr Cys Ala Pro Ala Gly Phe Ala Ile Leu Arg Cys Asn
    210                 215                 220

Glu Glu Asn Ser Gln Glu Met Gly Tyr Cys Asn Val Ser Thr Val
225                 230                 235                 240
```

```
His Cys Thr His Gly Ile Lys Pro Val Val Thr Gln Leu Ile Leu
            245                 250                 255

Asn Gly Ser Ile Thr Gln Gln Ile Met Ile Arg Ser Lys Asn Ile Ser
        260                 265                 270

Ser Asn Ser Phe Asn Ile Ile Val Gln Phe Asn Glu Thr Ile Pro Ile
        275                 280                 285

Lys Cys Ile Arg Pro Gly Asn Asn Thr Arg Gly Gln Ile Gln Ile Gly
        290                 295                 300

Pro Ala Met Thr Phe Tyr Asn Ile Glu Asn Ile Val Gly Asn Thr Arg
305                 310                 315                 320

Lys Ala Phe Cys Lys Val Asn Gly Ser Gln Trp Trp Asn Met Lys Gln
                325                 330                 335

Asn Ile Ile Gln Arg Phe Lys Ala Glu His Lys Leu Asn Val Thr Phe
            340                 345                 350

Asn Ser Ser Ala Gly Gly Asp Pro Glu Ile Thr Asn Phe Met Val Asn
        355                 360                 365

Cys His Gly Glu Phe Phe Tyr Cys Asn Thr Thr Pro Leu Phe Thr Gly
    370                 375                 380

Asn Lys Thr Asn Ile Thr Ile Ile Leu Pro Cys Lys Ile Arg Gln Ile
385                 390                 395                 400

Val Asn Ser Trp Met Arg Val Gly Lys Gly Ile Tyr Ala Pro Pro Ile
                405                 410                 415

Arg Gly Asn Leu Ser Cys Asn Ser Asn Ile Thr Gly Leu Leu Leu Thr
            420                 425                 430

Arg Asp Gly Pro Asp Lys Asn Ile Asn Glu Thr Glu Thr Leu Arg Pro
        435                 440                 445

Gly Gly Gly Asp Met Lys Asp Ile Trp Arg Ser Glu Leu Tyr Lys Tyr
    450                 455                 460

Lys Val Val Lys Ile Glu Pro Leu Ala Val Ala Pro Thr Lys Ala Arg
465                 470                 475                 480

Arg Tyr Thr Ile Asn Met Glu Lys His Arg Ala Lys Arg Ala Ala Phe
                485                 490                 495

Ala Ala Gly Ser Thr Met Gly Ala Ala Ala Val Thr Leu Thr Val Gln
            500                 505                 510

Ala Arg Asn Leu Leu Ser Gly Ile Val Gln Gln Gln Asn Asn Leu Leu
        515                 520                 525

Arg Ala Ile Glu Ala Gln Gln His Leu Leu Gln Leu Ser Val Trp Gly
    530                 535                 540

Val Lys Gln Leu Gln Ala Arg Leu Leu Ala Val Glu Arg Tyr Leu Lys
545                 550                 555                 560

Asp Gln Gln Ile Leu Gly Leu Trp Gly Cys Ser Gly Lys Ala Ile Cys
                565                 570                 575

Tyr Thr Asn Val Pro Trp Asn Arg Asn Trp Thr Asn Ser Ser Gln Asp
            580                 585                 590

Tyr Asn Glu Ile Trp Asn Asn Leu Thr Trp Asn Glu Trp Asp Lys Gln
        595                 600                 605

Val Ser Asn Tyr Thr Thr Glu Ile Phe Lys Ala Leu Glu Glu Ala Gln
    610                 615                 620

Gly Gln Gln Glu Lys Asn Glu Lys Glu Leu Leu Glu Leu Asp Lys Trp
625                 630                 635                 640

Ser Ser Leu Trp Ser Trp Leu Asp Ile Thr Gln Trp Leu Trp Tyr Ile
                645                 650                 655
```

-continued

```
Lys Ile Phe Leu Met Val Val Gly Ala Ile Ile Gly Leu Lys Ile Val
            660                 665                 670

Met Thr Val Val Ser Leu Ile Lys Arg Val Arg Gln Gly Tyr Ser Pro
        675                 680                 685

Leu Ser Leu Gln Thr Leu Ile Pro Ala Ala Gly Glu Arg Gly Pro Pro
    690                 695                 700

Glu Glu Lys Glu Glu Gly Val Gly Asp Asn Gly Arg Thr Arg Ser Ile
705                 710                 715                 720

Arg Leu Ala Asn Gly Phe Phe Ala Leu Phe Trp Glu Asp Leu Arg Ser
                725                 730                 735

Leu Phe Leu Phe Ser Tyr His Arg Leu Arg Asp Leu Thr Ser Ile Leu
            740                 745                 750

Ser Arg Ile Leu Gln Leu Leu Tyr Arg Gln Ala Val Thr Gly Leu Gln
        755                 760                 765

Thr Val Arg Lys Ala Leu Ser Leu Leu Lys Ala His Ile Ala Tyr Trp
    770                 775                 780

Gly Ser Glu Leu Lys Ser Ser Ala Ile Ser Leu Leu Asp Ser
785                 790                 795
```

<210> SEQ ID NO 342
<211> LENGTH: 864
<212> TYPE: PRT
<213> ORGANISM: Simian immunodeficiency virus

<400> SEQUENCE: 342

```
Met Arg Arg Leu Ile Gly Thr Ile Leu Thr Leu Ser Ile Thr Ile Leu
1               5                   10                  15

Gly Ile Gly Tyr Ser Val His Tyr Ala Thr Val Phe Tyr Gly Val Pro
            20                  25                  30

Val Trp Lys Asp Ala Lys Pro Gln Leu Phe Cys Ala Ser Asp Ala Asp
        35                  40                  45

Ile Thr Ser Arg Asp Pro His Asn Ile Trp Ala Thr His Asn Cys Val
    50                  55                  60

Pro Leu Asp Pro His Pro Tyr Glu Val Pro Leu Ser Asn Val Ser Val
65                  70                  75                  80

Asp Phe Asp Met Glu Asn Asn Tyr Met Val Glu Glu Met Lys Lys Asp
                85                  90                  95

Leu Ile Ala Leu Phe Gln Gln Ser Phe Lys Pro Cys Val Lys Leu Thr
            100                 105                 110

Pro Phe Cys Val Thr Met Asn Cys Val Lys Leu Lys Glu Thr Thr Thr
        115                 120                 125

Thr Ile Ala Thr Ile Thr Asn Pro Leu Val Asn Leu Thr Gly Ile Glu
    130                 135                 140

Asp Tyr Lys Val Tyr Asn Cys Ser Phe Asn Gln Thr Thr Glu Phe Arg
145                 150                 155                 160

Asp Lys Lys Lys Gln Ile Tyr Ser Leu Phe Tyr Arg Glu Asp Ile Met
                165                 170                 175

Lys Thr Asp Asn Asn Asp Ser Tyr Tyr Leu His Asn Cys Asn Thr Ser
            180                 185                 190

Ala Ile Thr Gln Glu Cys Glu Lys Ser Ser Phe Glu Pro Ile Pro Ile
        195                 200                 205

Arg Tyr Cys Ala Pro Ala Gly Tyr Ala Met Leu Lys Cys Asn Ser Ala
    210                 215                 220

Asn Phe Thr Gly Val Gly Thr Cys Asn Asn Val Ser Val Val His Cys
225                 230                 235                 240
```

-continued

```
Thr His Gly Ile Tyr Pro Met Ile Ala Thr Ala Leu His Leu Asn Gly
            245                 250                 255

Thr Leu Glu Lys His Asn Thr Thr Ala Tyr Phe Ala Thr Pro Thr His
            260                 265                 270

Asn Lys Pro Leu Leu Ile Lys Phe Asn Lys Ser Val Asp Met Asn Cys
            275                 280                 285

Thr Arg Thr Gly Asn Asn Ser Arg Gly Gln Val Gln Ile Gly Pro Gly
            290                 295                 300

Met Thr Phe Tyr Asn Ile Glu Asn Ile Val Gly Asn Thr Arg Lys Ala
305                 310                 315                 320

Tyr Cys Thr Val Asn Tyr Gln Glu Trp Ser His Ala Ile Gly Glu Ala
                325                 330                 335

Lys Lys Val Ala Glu Ala Leu Lys Lys Asn Ile Thr Phe Arg Trp
                340                 345                 350

Asn Gln Gly Gly Asp Leu Glu Val Thr Asn Phe Trp Phe Asn Cys Gln
                355                 360                 365

Gly Glu Phe Phe Tyr Cys Asn Leu Thr Asn Trp Thr Asn Ile Thr Trp
            370                 375                 380

Leu Glu Thr Trp Leu Lys Thr Asn Asn Ser Ser Arg Pro Leu Val Ala
385                 390                 395                 400

Pro Cys Lys Leu Arg Gln Ile Val Asn His Trp Gly Ile Val Ser Lys
                405                 410                 415

Gly Ile Tyr Leu Pro Pro Arg Arg Gly Asn Leu Thr Cys Arg Ser Asn
                420                 425                 430

Ile Thr Gly Phe Ile Thr Thr Trp Asp Asn Asp Thr Glu Asn Val Leu
                435                 440                 445

Val Thr Phe Ser Ala Lys Val Glu Asp Tyr Trp Lys Val Glu Met Ser
450                 455                 460

Arg Tyr Lys Val Val Glu Ile Gln Pro Leu Ala Ile Ala Pro Thr Thr
465                 470                 475                 480

Gly Lys Arg Pro Glu Ile Arg Ala Asn His Thr Arg Ser Lys Arg Asp
                485                 490                 495

Val Gly Ile Gly Leu Leu Phe Leu Gly Phe Leu Ser Ala Ala Gly Ser
                500                 505                 510

Thr Met Gly Ala Ala Ser Ile Ala Leu Thr Ala Gln Ala Arg Gly Leu
            515                 520                 525

Leu Ser Gly Ile Val Gln Gln Gln His Asn Leu Leu Gln Ala Ile Glu
            530                 535                 540

Ala Gln Gln His Leu Leu Gln Leu Ser Val Trp Gly Ile Lys Gln Leu
545                 550                 555                 560

Gln Ala Arg Met Leu Ala Val Glu Lys Tyr Ile Arg Asp Gln Gln Leu
                565                 570                 575

Leu Ser Val Trp Gly Cys Ala Asn Lys Leu Val Cys His Ser Asn Val
                580                 585                 590

Val Trp Asn Met Thr Trp Ala Glu Asn Gly Thr Thr Cys Pro Gln Gly
                595                 600                 605

Ser Glu Asp Tyr Tyr Asn Cys Ile Trp Asn Asn Leu Thr Trp Gln Gln
            610                 615                 620

Trp Glu Lys Leu Val Ala Asn Ser Thr Glu Glu Ile Tyr Thr Leu Leu
625                 630                 635                 640

Glu Lys Ala Gln Val Gln Gln Glu Thr Asn Lys Lys Glu Leu Phe Glu
                645                 650                 655
```

Leu Asp Lys Trp Ser Thr Leu Trp Asp Trp Phe Asp Ile Thr Gln Trp
                660                 665                 670

Leu Trp Tyr Ile Lys Ile Ala Ile Leu Ile Val Ala Gly Leu Val Gly
            675                 680                 685

Leu Arg Ile Val Met Phe Ile Val Asn Val Ile Arg Gln Val Arg Gln
        690                 695                 700

Gly Tyr Met Pro Leu Phe Ser Gln Ile Pro Thr Gln Ala His Gln Asp
705                 710                 715                 720

Pro Glu Gln Pro Glu Thr Ala Gly Gly Gly Gly Thr Gly Asn
            725                 730                 735

Val Arg Trp Thr Pro Leu His Arg Gly Phe Phe Ile Val Val Trp Glu
        740                 745                 750

Asp Leu Arg Thr Leu Leu Leu Trp Ile Tyr Gln Thr Cys Gln Asn Phe
            755                 760                 765

Gly Trp Leu Leu Trp Thr Ile Leu Lys Thr Leu Arg Gln Gly Ile Ile
770                 775                 780

Ser Leu Thr Gln Arg Leu Ile Ile Val Gln Arg Asp Ile Ile Leu Lys
785                 790                 795                 800

Ser Arg Gln Leu Phe Asp Trp Leu Ser Asn Thr Tyr Ser Ile Leu Arg
            805                 810                 815

Thr Ser Leu Ile Gln Ala Ile Asp Arg Leu Ala Asn Phe Thr Gly Trp
            820                 825                 830

Trp Thr Asp Leu Val Ile Ala Gly Val Ala Phe Val Ala Gln Gly Ile
            835                 840                 845

Arg Asn Ile Pro Arg Arg Ile Arg Gln Gly Leu Glu Ile Ala Leu Asn
850                 855                 860

<210> SEQ ID NO 343
<211> LENGTH: 875
<212> TYPE: PRT
<213> ORGANISM: Simian immunodeficiency virus

<400> SEQUENCE: 343

Met Arg Asn Leu Ile Gly Ile Thr Leu Thr Leu Ile Ile Thr Thr Leu
1 5 10 15

Gly Ile Gly Phe Ser Gln Tyr Tyr Ala Thr Val Phe Tyr Gly Val Pro
20 25 30

Ile Trp Lys Asp Ala Lys Pro Ser Leu Phe Cys Ala Ser Asp Ala Asp
35 40 45

Val Thr Ser Arg Asp Glu His Asn Ile Trp Ala Thr His Asn Cys Val
50 55 60

Pro Leu Asp Pro Asn Pro Tyr Glu Val Pro Leu Ala Asn Met Thr Val
65 70 75 80

Asp Phe Asn Met Glu Glu Asn Tyr Met Val Gln Glu Met Lys Glu Asp
85 90 95

Leu Ile Ser Leu Phe Gln Gln Ser Phe Lys Pro Cys Val Lys Leu Thr
100 105 110

Pro Phe Cys Val Ser Met Ser Cys Asn Leu Thr Val Pro Ser Thr Thr
115 120 125

Val Ser Pro Ala Thr Lys Val Ser Ser Thr Thr Lys Glu Pro Glu Ile
130 135 140

Lys Arg Leu Gly Lys Asn Ile Thr Asn Tyr Glu Val Tyr Lys Cys Ser
145 150 155 160

Phe Asn Gln Thr Thr Glu Phe Arg Asp Lys Lys Lys Gln Ile Tyr Ser
165 170 175

```
Leu Phe Tyr Lys Glu Asp Ile Met Lys Asn Asn Thr Asn Asn Asn
            180                 185                 190

Asn Ser Tyr Tyr Leu His Asn Cys Asn Thr Ser Ala Ile Thr Gln Glu
        195                 200                 205

Cys Ala Lys Ser Thr Phe Glu Pro Ile Pro Ile Arg Tyr Cys Ala Pro
    210                 215                 220

Ala Gly Phe Ala Met Leu Lys Cys Lys Asp Gln Asn Phe Thr Gly Lys
225                 230                 235                 240

Gly Pro Cys Ser Asn Val Ser Val Val His Cys Thr His Gly Ile Tyr
                245                 250                 255

Pro Met Ile Ala Thr Ala Leu His Leu Asn Gly Thr Leu Glu Glu Asn
            260                 265                 270

Lys Thr Thr Ala Tyr Phe Ala Asp Ser Thr His Asn Gln Pro Leu Leu
        275                 280                 285

Val Lys Phe His Lys Ala Val Asn Leu Thr Cys Val Arg Thr Gly Asn
    290                 295                 300

Asn Thr Arg Gly Gln Val Gln Ile Gly Pro Gly Met Thr Phe Tyr Asn
305                 310                 315                 320

Ile Glu Asn Val Val Gly Asp Thr Arg Lys Ala Phe Cys Ile Val Asn
                325                 330                 335

Ala Thr Glu Trp Ser Asn Ala Leu Asn Glu Ser Lys Ile Ala Ile Asn
            340                 345                 350

Glu Thr Leu Arg Lys Tyr Asn Lys Thr Ser Tyr Gly Asn Phe Thr Trp
        355                 360                 365

Asn Thr Gly Asp Pro Glu Val Ser Asn Phe Trp Phe Asn Cys Gln Gly
    370                 375                 380

Glu Phe Phe Tyr Cys Asn Leu Thr Asn Trp Thr Ser Pro Asp Tyr Ile
385                 390                 395                 400

Gly Lys Asn Gly Ser Ile Val Ala Gln Cys Arg Leu Arg Gln Ile Val
                405                 410                 415

Asn His Trp Gly Ile Val Ser Lys Gly Ile Tyr Leu Pro Pro Arg Arg
            420                 425                 430

Gly Thr Ile Lys Cys Thr Ser Asn Ile Thr Gly Leu Ile Leu Thr Ala
        435                 440                 445

Glu Gly Gly Asn Glu Thr Ile Thr Pro Thr Phe Ser Ser Lys Val Glu
    450                 455                 460

Asp Tyr Trp Lys Val Glu Leu Ala Arg Tyr Lys Val Val Glu Ile Gln
465                 470                 475                 480

Pro Leu Ser Val Ala Pro Arg Pro Gly Lys Arg Pro Glu Ile Lys Ala
                485                 490                 495

Asn His Thr Arg Ser Lys Arg Asp Val Gly Ile Gly Leu Leu Phe Leu
            500                 505                 510

Gly Phe Leu Ser Ala Ala Gly Ser Thr Met Gly Ala Ala Ser Ile Ala
        515                 520                 525

Leu Thr Ala Gln Ala Arg Gly Leu Leu Ser Gly Ile Val Gln Gln Gln
    530                 535                 540

Gln Asn Leu Leu Gln Ala Ile Ala Ala Gln His Leu Leu Gln Leu
545                 550                 555                 560

Ser Val Trp Gly Ile Lys Gln Leu Gln Ala Arg Met Leu Ala Ile Glu
                565                 570                 575

Lys Tyr Ile Arg Asp Gln Gln Leu Leu Ser Ile Trp Gly Cys Ala Asn
            580                 585                 590
```

Lys Leu Val Cys His Ser Ser Val Pro Trp Asn Ile Thr Trp Ala Gly
595 600 605

Asn Ser Thr Lys Cys Asn His Ser Asp Thr Met Asp Ala Lys Tyr Tyr
610 615 620

Glu Cys Ile Trp Asn Asn Leu Thr Trp Gln Glu Trp Asp Lys Leu Val
625 630 635 640

Lys Asn Ser Ser Glu Thr Ile Tyr Ser Leu Leu Glu Ile Ala Gln Thr
645 650 655

Gln Gln Glu Lys Asn Lys Gln Asp Leu Leu Glu Leu Asp Lys Trp Ser
660 665 670

Ser Leu Trp Asp Trp Phe Asp Ile Thr Gln Trp Leu Trp Tyr Ile Lys
675 680 685

Ile Ala Ile Ile Ile Val Ala Gly Leu Ile Gly Leu Arg Ile Leu Met
690 695 700

Phe Ile Ile Asn Val Val Arg Gln Val Arg Gln Gly Tyr Met Pro Leu
705 710 715 720

Phe Ser Gln Thr Pro Thr Gln Ala Glu Gln Asp Pro Glu Gln Pro Gly
725 730 735

Gly Ile Ala Glu Gly Gly Gly Gly Gly Gly Lys Leu Arg Trp Thr Pro
740 745 750

Ser Pro Ala Gly Phe Phe Thr Ile Val Trp Val Asp Leu Arg Asn Leu
755 760 765

Leu Leu Trp Ile Tyr Gln Thr Cys Arg Asn Phe Ile Trp Ile Leu Trp
770 775 780

Ser Ile Leu Gln Ala Leu Lys Gln Gly Ile Ile Ser Leu Val Asp Asn
785 790 795 800

Leu Val Ile Ile His Arg Ser Ile Val Val Gly Val Arg Gln Ala Leu
805 810 815

Glu Trp Ser Gly Asn Thr Tyr Ala Ser Ile Arg Ala Ser Leu Ile Gln
820 825 830

Ala Ile Asp Arg Leu Ala Glu Phe Thr Gly Trp Trp Thr Asp Ile Val
835 840 845

Ile Glu Ala Val Val Tyr Ile Ala Arg Gly Ile Arg Asn Ile Pro Arg
850 855 860

Arg Ile Arg Gln Gly Leu Glu Ile Ala Leu Asn
865 870 875

<210> SEQ ID NO 344
<211> LENGTH: 835
<212> TYPE: PRT
<213> ORGANISM: Simian immunodeficiency virus

<400> SEQUENCE: 344

Met Lys Val Thr Glu Met Gln Lys Asn Trp Leu Ile Cys Cys Leu Leu
1 5 10 15

Ile Gly Leu Ile Lys Ile Ile Gly Ser Glu Leu Trp Val Thr Val Tyr
20 25 30

Tyr Gly Val Pro Val Trp Arg Asp Ala Glu Thr Val Leu Phe Cys Ala
35 40 45

Ser Asp Ala Lys Ala His Ser Thr Glu Ala His Asn Ile Trp Ala Thr
50 55 60

Gln Ala Cys Val Pro Thr Asp Pro Asn Pro Gln Glu Val Leu Ile Pro
65 70 75 80

Asn Val Thr Glu Arg Phe Asp Met Trp Lys Asn Asn Met Val Asp Gln
85 90 95

```
Met Gln Glu Asp Ile Ile Ser Leu Trp Glu Gln Ser Leu Lys Pro Cys
            100                 105                 110

Val Lys Leu Thr Pro Leu Cys Val Thr Leu Ser Cys Ser Ser Trp Arg
            115                 120                 125

Ser Val Asn Asn Ser Val Asn Gln Thr Asn His Val Gln Met Gln Asn
            130                 135                 140

Cys Ser Phe Asn Val Thr Thr Glu Leu Arg Asp Lys Lys Gln Val
145                 150                 155                 160

Tyr Ser Leu Phe Tyr Met Gly Asp Ile Ile Pro Leu Asp Thr Asn Asn
                165                 170                 175

Ser Ser Gly Asn Asn Ser Gln Tyr Arg Leu Ile Asn Cys Asn Thr Thr
            180                 185                 190

Ala Val Thr Gln Ala Cys Pro Lys Ile Ser Phe Glu Pro Ile Pro Ile
            195                 200                 205

Tyr Tyr Cys Ala Pro Pro Gly Phe Ala Ile Ile Lys Cys Asn Asp Gln
            210                 215                 220

Asp Phe Asn Gly Thr Gly Glu Cys Asn Asn Val Ser Thr Val Gln Cys
225                 230                 235                 240

Thr His Gly Ile Lys Pro Val Ile Ser Thr Gln Leu Ile Leu Asn Gly
                245                 250                 255

Ser Leu Ala Thr Ser Asn Ile Val Ile Arg Asn Asn Ser Lys Asp Thr
            260                 265                 270

Leu Leu Val Gln Leu Asn Glu Ser Ile Pro Ile Asn Cys Thr Arg Pro
            275                 280                 285

Gly Asn Lys Thr Arg Gly Gln Val Gln Ile Gly Pro Gly Met Thr Phe
            290                 295                 300

Tyr Asn Ile Glu Asn Ile Ile Gly Asp Thr Arg Gln Ala Tyr Cys Glu
305                 310                 315                 320

Val Asn Arg Thr Trp Glu Gln Ile Trp Asn Thr Thr Lys Gln Ile Ile
                325                 330                 335

Ile Asn Asn Arg Lys Asn Ile Thr Phe Ile Pro Asn Pro Gly Gly Asp
            340                 345                 350

Leu Glu Val Thr Asn Leu Met Ile Asn Cys Gly Gly Glu Phe Phe Tyr
            355                 360                 365

Cys Asn Thr Ser Gln Leu Phe Thr Asn Gln Asn Gly Asn Thr Thr Gly
370                 375                 380

Asn Ile Thr Leu Gln Cys Arg Ile Arg Gln Ile Val Asn Leu Trp Thr
385                 390                 395                 400

Arg Val Gly Lys Gly Ile Tyr Ala Pro Pro Ile Lys Gly Pro Ile Asn
                405                 410                 415

Cys Leu Ser Asn Ile Thr Gly Ile Ile Leu Asp Tyr Thr Lys Ser Gly
            420                 425                 430

Thr Glu Lys Tyr Thr Ile Tyr Pro Thr Gly Gly Asp Met Thr Asn Leu
            435                 440                 445

Trp Arg Gln Glu Leu Tyr Lys Tyr Lys Val Val Ser Ile Glu Pro Ile
            450                 455                 460

Gly Val Ala Pro Gly Lys Ala Lys Arg His Thr Val Thr Arg Gln Lys
465                 470                 475                 480

Arg Ala Ala Phe Gly Leu Gly Ala Leu Phe Leu Gly Phe Leu Gly Ala
                485                 490                 495

Ala Gly Ser Thr Met Gly Ala Ala Ser Ile Thr Leu Thr Val Gln Ala
            500                 505                 510
```

```
Arg Lys Leu Leu Ser Gly Ile Val Gln Gln Asn Asn Leu Leu Arg
            515                 520                 525

Ala Ile Glu Ala Gln Gln His Leu Leu Gln Leu Ser Val Trp Gly Ile
        530                 535                 540

Lys Gln Leu Gln Ala Arg Val Leu Ala Ile Glu Arg Tyr Leu Arg Asp
545                 550                 555                 560

Gln Gln Ile Leu Gly Leu Trp Gly Cys Ser Gly Lys Ser Val Cys Tyr
                565                 570                 575

Thr Asn Val Pro Trp Asn Thr Thr Trp Ser Asn Asn Ser Tyr Asp
            580                 585                 590

Thr Ile Trp Gly Asn Met Thr Trp Gln Asn Trp Asp Glu Gln Val Arg
        595                 600                 605

Asn Tyr Ser Gly Val Ile Phe Gly Leu Leu Glu Gln Ala Gln Glu Gln
    610                 615                 620

Gln Ser Ile Asn Glu Lys Ser Leu Leu Glu Leu Asp Gln Trp Ser Ser
625                 630                 635                 640

Leu Trp Asn Trp Phe Asp Ile Thr Lys Trp Leu Trp Tyr Ile Lys Ile
                645                 650                 655

Phe Ile Met Val Val Ala Gly Ile Val Gly Ile Arg Ile Ile Ser Ile
            660                 665                 670

Ile Met Ser Met Val Ala Arg Val Arg Gln Gly Tyr Ser Pro Leu Ser
        675                 680                 685

Leu Gln Thr Leu Ile Pro Thr Thr Arg Gly Pro Asp Arg Pro Glu Arg
    690                 695                 700

Thr Glu Glu Asp Ala Gly Glu Leu Asp Asn Gly Arg Ser Val Arg Leu
705                 710                 715                 720

Val Ser Gly Phe Leu Ala Leu Ala Trp Glu Asp Phe Arg Asn Leu Leu
                725                 730                 735

Leu Phe Leu Tyr His Arg Leu Thr Asp Cys Leu Ser Ile Leu Arg Arg
            740                 745                 750

Thr Leu Glu Leu Leu Arg Gln Asn Ile His Lys Gly Leu Gln Leu Leu
        755                 760                 765

Asn Glu Leu Arg Ile Tyr Leu Trp Gly Ile Ile Ala Tyr Trp Gly Arg
    770                 775                 780

Glu Leu Lys Ile Ser Ala Ile Asn Leu Leu Asp Thr Thr Ala Val Ala
785                 790                 795                 800

Val Ala Glu Gly Thr Asp Arg Ile Ile Glu Leu Val Gln Arg Ile Gly
                805                 810                 815

Arg Gly Ile Leu His Ile Pro Arg Arg Ile Arg Gln Gly Leu Glu Arg
            820                 825                 830

Ala Leu Leu
        835

<210> SEQ ID NO 345
<211> LENGTH: 844
<212> TYPE: PRT
<213> ORGANISM: Simian immunodeficiency virus

<400> SEQUENCE: 345

Met Lys Val Met Gly Thr Gln Arg Ser Trp Lys Gln Phe Leu Ser Leu
1               5                   10                  15

Arg Ile Val Met Cys Leu Trp Leu Leu Gly Val Ile Arg Ser Glu Asn
            20                  25                  30

Asn Leu Trp Val Thr Val Tyr Tyr Gly Val Pro Val Trp Lys Glu Ala
        35                  40                  45
```

-continued

Lys Thr Thr Leu Phe Cys Ala Ser Asp Ala Lys Ala Gln Ile Ala Glu
        50                      55                      60

Ala His Asn Ile Trp Ala Ser Gln Ala Cys Val Pro Thr Asp Pro Asn
 65                      70                      75                      80

Pro Glu Glu Ile Thr Leu Glu Asn Val Thr Glu Glu Phe Asp Ala Trp
                        85                      90                      95

Asn Asn Asn Met Val Asp Gln Met Gln Glu Asp Leu Ile Ser Leu Trp
                100                     105                     110

Asp Gln Ser Leu Lys Pro Cys Val Lys Leu Thr Pro Leu Cys Val Thr
         115                     120                     125

Leu Asn Cys Ser Thr Asn Thr Thr Glu Ala Ser Gln Val Gln Tyr
 130                     135                     140

Asn Cys Ser Phe Asn Val Thr Thr Glu Leu Arg Asp Lys Lys Gln
145                      150                     155                     160

Val Tyr Ser Leu Phe Tyr Arg Glu Asp Ile Thr Ser Leu Asp Ser Asn
                165                     170                     175

Lys Thr Val Lys Asn Gly Thr Tyr Arg Leu Ile Asn Cys Asn Thr Thr
                180                     185                     190

Ala Ile Thr Gln Ala Cys Pro Lys Thr Ser Phe Glu Pro Ile Pro Ile
         195                     200                     205

Tyr Tyr Cys Ala Pro Ala Gly Phe Ala Leu Leu Lys Cys Asn Asp Gln
 210                     215                     220

Asn Phe Lys Gly Lys Gly Thr Cys Arg Asn Val Ser Thr Val His Cys
225                      230                     235                     240

Thr His Gly Ile Lys Pro Val Val Ser Thr Gln Phe Leu Leu Asn Gly
                245                     250                     255

Ser Leu Ala Glu Gly Asn Lys Thr Val Val Arg Val Arg Ser Lys Ser
         260                     265                     270

Asn Thr Glu Thr Ile Ile Val Gln Leu Ala Thr Ala Ile Tyr Ile Asn
         275                     280                     285

Cys Thr Arg Leu Gly Asn Lys Thr Ile Glu Gly Ile Pro Ile Gly Pro
 290                     295                     300

Gly Gln Ile Phe Tyr Arg Thr Lys Thr Val Val Gly Asp Thr Arg Gly
305                      310                     315                     320

Ala Glu Cys Arg Ile Asn Gly Thr Ala Trp Asn Glu Thr Leu Arg Gln
                325                     330                     335

Val Lys Glu Ala Leu Asn Asn Thr Tyr Arg Asn Leu Asn Leu Ser Leu
         340                     345                     350

Thr Glu Ile Asn Phe Glu Gly Ala Ser Gly Gly Asp Leu Glu Val Thr
         355                     360                     365

Thr His Tyr Phe Asn Cys Gly Gly Glu Phe Phe Tyr Cys Asn Thr Ser
 370                     375                     380

Asn Leu Phe Asn Gln Ser Thr Ile Asn Asn Ile Thr His Ile Pro Cys
385                      390                     395                     400

Arg Ile Arg Gln Ile Val Asn Gln Trp Gln Gly Val Gly Lys Gly Ile
                405                     410                     415

Phe Ala Pro Pro Ile Arg Gly Thr Ile Gln Cys Asn Ser Thr Ile Thr
                420                     425                     430

Gly Leu Leu Leu Thr Arg Asp Gly Lys Asn Glu Thr Glu Thr Phe Arg
         435                     440                     445

Pro Thr Gly Gly Asp Met Arg Asn Asn Trp Arg Ser Glu Leu Tyr Lys
         450                     455                     460

Tyr Lys Val Val Lys Ile Glu Pro Leu Gly Leu Ala Pro Thr Lys Ala
465                 470                 475                 480

Lys Arg Arg Thr Val Gln Arg Glu Lys Arg Ala Val Gly Leu Gly Val
            485                 490                 495

Met Phe Leu Gly Phe Met Gly Ala Ala Gly Ser Thr Met Gly Ala Ala
            500                 505                 510

Ala Leu Thr Leu Thr Val Gln Ala Arg Asn Leu Leu Ser Gly Ile Val
            515                 520                 525

Gln Gln Gln Ser Asn Leu Leu Lys Ala Ile Glu Ala Gln Gln His Leu
            530                 535                 540

Leu Gln Leu Ser Val Trp Gly Ile Lys Gln Leu Gln Ala Arg Val Leu
545                 550                 555                 560

Ala Val Glu Arg Tyr Leu Lys Asp Gln Gln Leu Leu Gly Leu Trp Gly
            565                 570                 575

Cys Ser Gly Lys Leu Ile Cys Thr Thr Asn Val Pro Trp Asn Asn Thr
            580                 585                 590

Trp Ser Lys Lys Leu Gly Thr Asn Leu Ser Phe Trp Asp Asn Met Thr
            595                 600                 605

Trp Met Gln Trp Glu Lys Glu Ile Asp Asn Tyr Thr Glu Thr Ile Tyr
610                 615                 620

Glu Leu Leu Thr Arg Ser Gln Asn Gln Gln Glu Val Asn Glu Gln Glu
625                 630                 635                 640

Leu Leu Ala Leu Asp Lys Trp Ser Ser Leu Trp Asn Trp Phe Asp Ile
            645                 650                 655

Thr Gln Trp Leu Trp Tyr Ile Lys Leu Phe Val Met Ile Val Gly Gly
            660                 665                 670

Leu Ile Gly Ile Arg Ile Val Phe Ala Met Leu Ser Ile Val Asn Arg
            675                 680                 685

Val Arg Gln Gly Tyr Ser Pro Leu Ser Phe Gln Thr Pro Phe Pro Val
            690                 695                 700

Arg Arg Asp Pro Asp Arg Pro Glu Gly Ile Glu Glu Gly Gly Gly Glu
705                 710                 715                 720

Asn Asp Asn Val Arg Ser Val Arg Leu Val Ser Gly Phe Leu Ala Leu
            725                 730                 735

Ala Trp Asp Asp Leu Arg Asn Leu Cys Leu Phe Ser Tyr His Arg Leu
            740                 745                 750

Arg Asp Leu Leu Trp Ile Val Arg Arg Thr Leu Glu Ile Val Gly Gln
            755                 760                 765

Lys Phe Leu Ala Gly Leu Arg Leu Val Trp Glu Thr Leu Thr Tyr Leu
770                 775                 780

Lys Ser Ile Leu Gln Tyr Trp Gly Gln Glu Leu Lys Thr Ser Ala Ile
785                 790                 795                 800

Ser Leu Leu Asp Ala Thr Ala Ile Ala Val Ala Glu Gly Thr Asp Arg
            805                 810                 815

Ile Ile Glu Ile Ala Gln Arg Val Gly Arg Gly Ile Leu His Ile Pro
            820                 825                 830

Arg Arg Ile Arg Gln Gly Leu Glu Arg Ala Leu Leu
            835                 840

<210> SEQ ID NO 346
<211> LENGTH: 855
<212> TYPE: PRT
<213> ORGANISM: Simian immunodeficiency virus

<400> SEQUENCE: 346

-continued

```
Met Lys Val Met Gly Met Lys Tyr Tyr Trp Trp Arg Asn Ser Cys Arg
1               5                   10                  15

Ser Ile Ser Ile Lys Leu Ile Leu Ile Gly Trp Ile Ala Ser Cys Phe
            20                  25                  30

Gly Glu Glu Asn Trp Trp Val Thr Val Tyr Tyr Gly Val Pro Val Trp
        35                  40                  45

Arg Glu Ala Lys Thr Thr Leu Phe Cys Ala Ser Asp Ala Lys Ser Tyr
    50                  55                  60

Ser Thr Glu Ala His Asn Ile Trp Ala Thr Gln Ala Cys Val Pro Thr
65                  70                  75                  80

Asp Pro Thr Pro Gln Glu Val Leu Leu Pro Asn Val Thr Glu Glu Phe
                85                  90                  95

Asn Met Trp Glu Asn Tyr Met Val Asp Gln Met Gln Glu Asp Ile Ile
            100                 105                 110

Ser Leu Trp Glu Gln Ser Leu Lys Pro Cys Val Lys Leu Thr Pro Leu
        115                 120                 125

Cys Val Thr Leu Thr Cys Asn Asn Pro Thr Asn Thr Ser Cys Thr Asn
    130                 135                 140

Ser Thr Asp Asp Arg Leu Gly Asp Met Arg Asn Cys Ser Phe Asn Val
145                 150                 155                 160

Thr Thr Glu Leu Arg Asp Lys Lys Arg Gln Val Tyr Ser Leu Phe Tyr
                165                 170                 175

Val Glu Asp Ile Thr Ala Ile Gly Asn Asn Ser Thr Tyr Arg Leu Ile
            180                 185                 190

Asn Cys Asn Thr Thr Ala Ile Thr Gln Ala Cys Pro Lys Thr Ser Phe
        195                 200                 205

Glu Pro Ile Pro Ile His Tyr Cys Ala Pro Ala Gly Phe Ala Leu Leu
    210                 215                 220

Lys Cys Asn Asp Ile Asp Tyr Lys Gly Asn Glu Thr Cys Lys Asn Val
225                 230                 235                 240

Ser Thr Val His Cys Thr His Gly Ile Lys Pro Val Ala Thr Thr Gln
                245                 250                 255

Leu Ile Leu Asn Gly Ser Thr Ala Asp Asn Gln Thr Val Ala Arg Ile
            260                 265                 270

Asp Pro Ser Glu Asn Leu Ala Ile Ile Gln Leu Lys Asp Pro Val Lys
        275                 280                 285

Ile Thr Cys Arg Arg Pro Gly Asn Asn Thr Arg Gly Gln Ile Gln Ile
    290                 295                 300

Gly Pro Ala Met Thr Phe Tyr Asn Ile Glu Asn Val Val Gly Asp Thr
305                 310                 315                 320

Arg Lys Ala Tyr Cys Glu Ile Asn Gly Thr Gln Trp Ala Lys Ala Leu
                325                 330                 335

Asn Glu Thr Lys Glu Val Leu Arg Asn Ile Leu Arg Lys Asn Ile Ser
            340                 345                 350

Phe Met Val Pro Ser Gly Gly Asp Pro Glu Val Thr Asn His His Phe
        355                 360                 365

Asn Cys Gly Gly Glu Phe Phe Tyr Cys Asn Thr Ser Glu Ile Ile Asn
    370                 375                 380

Ile Thr Lys Ile Asn Lys Thr Glu Asn Met Thr Ile Ile Pro Cys Arg
385                 390                 395                 400

Ile Arg Gln Ile Val Asn Ser Trp Met Arg Val Gly Lys Gly Ile Phe
                405                 410                 415
```

-continued

Ala Pro Pro Ile Arg Gly Asn Ile Thr Cys Thr Ser Asn Ile Thr Gly
            420                 425                 430

Met Leu Leu Glu Ile His Lys Asn Arg Glu Asp Gln Gly Glu Asp Gln
        435                 440                 445

Asp Gln Asn Asn Thr Tyr Val Cys Leu Thr Gly Gly Asn Met Lys Asp
    450                 455                 460

Ile Trp Arg Ser Glu Leu Tyr Lys Tyr Lys Ile Val Glu Ile Gln Pro
465                 470                 475                 480

Leu Gly Val Ala Pro Thr Lys Ser Arg Arg Tyr Ala Val Glu Lys Gln
                485                 490                 495

His His Arg Glu Lys Arg Ala Leu Gly Leu Gly Ala Leu Phe Leu Gly
            500                 505                 510

Phe Leu Gly Ala Ala Gly Ser Thr Met Gly Ala Ala Ser Val Val Leu
        515                 520                 525

Thr Val Gln Ala Arg Gln Leu Leu Thr Gly Ile Val Gln Gln Gln Asn
    530                 535                 540

Asn Leu Leu Arg Ala Ile Glu Ala Gln Gln His Leu Leu Gln Leu Ser
545                 550                 555                 560

Val Trp Gly Ile Lys Gln Leu Gln Ala Arg Val Leu Ala Val Glu Arg
                565                 570                 575

Tyr Leu Arg Asp Gln Gln Leu Leu Gly Leu Trp Gly Cys Thr Gly Lys
            580                 585                 590

Thr Ile Cys Pro Thr Ala Val Arg Trp Asn Lys Thr Trp Gly Asn Ile
        595                 600                 605

Ser Asp Tyr Gln Val Ile Trp Asn Asn Tyr Thr Trp Gln Gln Trp Asp
    610                 615                 620

Arg Glu Val Asn Asn Tyr Thr Gly Leu Ile Tyr Thr Leu Leu Glu Glu
625                 630                 635                 640

Ala Asn Thr Gln Gln Glu Lys Asn Glu Lys Glu Leu Leu Glu Leu Asp
                645                 650                 655

Ser Trp Ala Asn Leu Trp Ser Trp Phe Asp Ile Thr Asn Trp Leu Trp
            660                 665                 670

Tyr Ile Lys Met Phe Leu Ile Val Val Gly Gly Ile Ile Gly Leu Arg
        675                 680                 685

Ile Cys Phe Ala Ile Gly Ser Leu Ile Asn Arg Val Arg Lys Gly Tyr
    690                 695                 700

Ser Pro Leu Ser Leu Gln Thr Leu Ile Pro Ala Asn Gln Gly Pro Asp
705                 710                 715                 720

Gly Leu Gly Glu Thr Glu Lys Gly Gly Gly Glu Asn Val Arg Gly Arg
                725                 730                 735

Ser Ile Arg Leu Val Ser Gly Phe Leu Pro Leu Val Trp Glu Asp Leu
            740                 745                 750

Arg Asn Leu Leu Ser Phe Leu Tyr His Gln Leu Arg Asp Cys Ala Ser
        755                 760                 765

Leu Ile Trp Arg Leu Leu Glu Ile Leu Gly Gln Tyr Ser Leu Arg Gly
    770                 775                 780

Val Gln Gln Ile Gly Thr Leu His Gln Leu Arg Gly Thr Leu Gln
785                 790                 795                 800

Tyr Trp Thr Thr Glu Ile Lys Asn Ser Ala Ile Ser Leu Leu Asp Thr
                805                 810                 815

Thr Ala Ile Ala Val Gly Glu Gly Thr Asp Arg Ile Leu Glu Ala Ile
            820                 825                 830

Thr Arg Leu Gly Arg Gly Ile Leu His Ile Pro Arg Arg Ile Arg Gln

Gly Leu Glu Arg Ala Leu Leu
    850             855

<210> SEQ ID NO 347
<211> LENGTH: 870
<212> TYPE: PRT
<213> ORGANISM: Simian immunodeficiency virus

<400> SEQUENCE: 347

Met Lys Asn Ser Ser Gly Leu Ile Leu Thr Leu Ile Thr Thr Ile Leu
1 5 10 15

Gly Ile Gly Phe Ser Thr Tyr Tyr Ala Thr Val Phe Tyr Gly Val Pro
20 25 30

Val Trp Lys Asp Ala Thr Pro Pro Leu Phe Cys Ala Ser Asp Ala Asp
35 40 45

Val Ala Ser Thr Gln Ala His Asn Ile Trp Ala Thr His Asn Cys Val
50 55 60

Pro Leu Asp Pro His Pro Tyr Glu Val Pro Leu Pro Asn Val Ser Ile
65 70 75 80

Glu Phe Asp Met Ser Thr Asn Tyr Met Val Glu Glu Met Lys Thr Asp
85 90 95

Leu Ile Ser Leu Phe Gln Gln Ser Phe Lys Pro Cys Val Lys Leu Thr
100 105 110

Pro Phe Cys Ile Arg Met Thr Cys Ala Asn Val Thr Glu Ala Thr Thr
115 120 125

Thr Thr Pro Pro Thr Thr Ser Thr Ser Thr Thr Glu Pro Pro Thr Ser
130 135 140

Lys Thr Thr Val Asn Thr Ser Glu Ile Glu Asp Tyr Lys Val Leu Asn
145 150 155 160

Cys Ser Phe Asn Gln Thr Thr Glu Phe Arg Asp Lys Lys Lys Asn Ile
165 170 175

Tyr Ser Leu Phe Tyr Arg Glu Asp Val Met Lys Glu Ser Gln Asn Lys
180 185 190

Thr Asn Asn Ser Glu Tyr Tyr Tyr Leu His Asn Cys Asn Thr Thr Ala
195 200 205

Ile Thr Gln Ser Cys Ser Lys Ser Ser Phe Glu Pro Ile Pro Ile Arg
210 215 220

Tyr Cys Ala Pro Ala Gly Tyr Ala Met Leu Lys Cys Asn Asp Ala Asn
225 230 235 240

Phe Thr Gly Ala Gly Glu Cys Thr Asn Val Ser Val Val His Cys Thr
245 250 255

His Gly Ile Met Pro Met Ile Ala Ser Trp Leu His Leu Asn Gly Thr
260 265 270

Tyr Glu Lys Glu Lys Thr Lys Val Tyr His Thr Asn Val Thr Asn Asn
275 280 285

Pro Pro Leu Leu Val Lys Phe Asn Glu Thr Ile His Ile Thr Cys Glu
290 295 300

Arg Thr Gly Asn Asn Thr Arg Gly Gln Val Gln Ile Gly Pro Gly Met
305 310 315 320

Thr Phe Tyr Asn Arg Glu Asn Ile Phe Gly Asp Thr Arg Lys Ala Phe
325 330 335

Cys Tyr Val Asn Ala Thr Glu Trp Arg Arg Thr Leu Glu Met Ala Lys
340 345 350

```
Thr Ala Leu Arg Glu Ala Thr Lys Lys Pro Thr Leu Asn Ile Thr Arg
            355                 360                 365
Pro Lys Gly Asp Pro Glu Val Glu Asn Phe Trp Phe Asn Cys Gln Gly
    370                 375                 380
Glu Phe Phe Tyr Cys Asn Leu Thr Lys Trp Ile Asn Glu Thr Trp Leu
385                 390                 395                 400
Asn Glu Thr Asp Gln Thr Asn Leu Val Ala Pro Cys Arg Leu Arg Gln
                405                 410                 415
Ile Val Asn His Trp Gly Ile Val Lys Ala Ile Tyr Leu Pro Pro
                420                 425                 430
Arg Arg Gly Thr Val Lys Cys Val Ser Asn Ile Thr Gly Phe Leu Met
            435                 440                 445
Thr Asn Glu Glu Thr Gly Ala Thr Phe Ser Gly Lys Val Glu Asp Tyr
    450                 455                 460
Trp Arg Val Glu Leu Ala Lys Tyr Lys Ile Val Glu Ile Gln Pro Leu
465                 470                 475                 480
Ser Val Ala Pro Thr Thr Gly Lys Arg Pro Glu Ile Lys Ala Asn His
                485                 490                 495
Thr Arg Ser Lys Arg Asp Val Gly Ile Gly Leu Leu Phe Leu Gly Phe
            500                 505                 510
Leu Ser Ala Ala Gly Ser Thr Met Gly Ala Ala Ser Ile Ala Leu Val
515                 520                 525
Ala Gln Ala Arg Gly Val Leu Ser Gly Ile Val Gln Gln Gln His Asn
    530                 535                 540
Leu Leu Gln Ala Ile Glu Ala Gln Gln His Leu Leu Gln Leu Thr Val
545                 550                 555                 560
Trp Gly Val Lys Gln Leu Gln Ala Arg Leu Leu Ala Met Glu Lys Tyr
                565                 570                 575
Ile Arg Asp Gln Gln Leu Leu Ser Val Trp Gly Cys Ala Asn Lys Leu
            580                 585                 590
Val Cys His Ser Thr Val Val Trp Asn Asp Thr Trp Ala Ala Arg Lys
    595                 600                 605
Pro Cys Ser Asn Thr Ser Gly Pro Thr Asp Tyr Asp Cys Ile Trp Gln
610                 615                 620
Asn Leu Thr Trp Gln Gln Trp Ser Glu Leu Val Asp Asn Ser Thr Asp
625                 630                 635                 640
Thr Ile Tyr Thr Leu Leu Glu Val Ala Gln Ile Gln Gln Glu Lys Asn
                645                 650                 655
Lys Lys Glu Leu Leu Glu Leu Asp Lys Trp Ser Thr Leu Trp Asp Trp
            660                 665                 670
Phe Asp Ile Thr Gln Trp Leu Trp Tyr Ile Lys Leu Ala Ile Ile Ile
    675                 680                 685
Ile Ala Gly Leu Ile Gly Leu Arg Ile Leu Met Phe Ile Val Asn Val
690                 695                 700
Leu Arg Gln Val Arg Gln Gly Tyr Met Pro Leu Phe Ser Gln Ile Pro
705                 710                 715                 720
Thr Gln Ala Glu Gln Asp Pro Glu Gln Pro Gly Gly Ile Ala Glu Gly
                725                 730                 735
Gly Gly Asp Arg Gly Arg Ile Arg Trp Thr Pro Ser Pro Arg Gly Phe
            740                 745                 750
Phe Ser Ile Val Trp Glu Asp Leu Arg Asn Leu Leu Leu Trp Ile Tyr
    755                 760                 765
Gln Thr Cys Leu Asn Phe Val Trp Leu Leu Gly Thr Ile Leu Gln Ala
```

```
                770              775              780
Leu Lys Gln Gly Thr Ile Ser Phe Ile Gln Thr Ile Ile Val His
785              790              795              800

Arg Asn Leu Val Leu Lys Trp Arg Leu Phe Arg Asp Trp Leu Ala Asn
            805              810              815

Ala Tyr Val Ile Val Lys Thr Ser Phe Ile Arg Asn Leu Asp Arg Leu
            820              825              830

Ala Asn Phe Thr Ala Trp Trp Thr Asp Ile Leu Ile Glu Gly Ala Val
            835              840              845

Asn Ile Phe Arg Gly Ile Arg Asn Ile Pro Thr Arg Ile Arg Gln Gly
            850              855              860

Leu Glu Ile Ala Leu Asn
865              870

<210> SEQ ID NO 348
<211> LENGTH: 884
<212> TYPE: PRT
<213> ORGANISM: Simian immunodeficiency virus

<400> SEQUENCE: 348

Met Lys Met Ala Leu Leu Ile Gly Trp Ile Leu Thr Ile Ile Phe Cys
1               5                   10                  15

Cys Lys Leu Gly Ile Gly Thr Tyr Tyr Thr Thr Val Tyr Tyr Gly Val
                20                  25                  30

Pro Val Trp Lys Glu Ala Thr Pro Thr Leu Phe Cys Ala Ser Ser Ala
            35                  40                  45

Lys Val Ala Ser Thr Gln Pro His Asn Ile Trp Ala Thr His Asn Cys
50                  55                  60

Val Pro Leu Asp Pro Gln Pro Tyr Glu Ile Pro Ile Asn Ile Thr Thr
65                  70                  75                  80

Glu Phe Asn Met Glu Thr Asn Tyr Met Val Glu Glu Met Lys Lys Asp
                85                  90                  95

Leu Ile Ser Leu Phe Gln Gln Ser Leu Lys Pro Cys Val Lys Leu Thr
            100                 105                 110

Pro Phe Cys Val Lys Met Asn Cys Ser Glu Phe Thr Arg Asn Ser Thr
            115                 120                 125

Thr Gly Asn Asn Ala Thr Lys Asn Asn Thr Ser Leu Glu Asp Lys Ile
        130                 135                 140

Lys Ser Asn Leu Thr Ser Leu Glu Met Tyr Glu Cys Phe Phe Asn Gln
145                 150                 155                 160

Thr Thr Glu Phe Arg Asp Lys Lys Gln Ile Tyr Ser Leu Phe Tyr
                165                 170                 175

Lys Glu Asp Ile Met Lys Asp Lys Asn Asp Ser Thr Asn Thr Ser Tyr
            180                 185                 190

Tyr Leu Ile Asn Cys Asn Thr Thr Ala Ile Thr Gln Glu Cys Glu Lys
            195                 200                 205

Ser Ser Phe Glu Pro Val Pro Ile Gln Tyr Cys Ala Pro Pro Gly Tyr
    210                 215                 220

Ala Met Leu Lys Cys Lys Asp Glu Asn Phe Arg Gly Lys Gly Asn Cys
225                 230                 235                 240

Thr Thr Val Arg Ile Val His Cys Thr His Ser Ile Phe Pro Met Ile
                245                 250                 255

Ala Thr Ala Leu His Leu Asn Gly Ser Val Glu Glu Gly Glu Thr Lys
            260                 265                 270
```

-continued

```
Ala Tyr Tyr Val Glu Ala Lys His Asn Ala Pro Leu Leu Ile Lys Phe
            275                 280                 285

Asn Lys Ala Thr Val Phe Asn Ile Thr Cys Val Arg Pro Gly Asn Asn
    290                 295                 300

Thr Arg Gly Gln Val Gln Ile Gly Pro Gly Met Thr Phe Tyr Asn Ile
305                 310                 315                 320

Arg Asn Val Ile Gly Asp Thr Arg Lys Ala Phe Cys Tyr Val Asn Lys
                325                 330                 335

Thr Leu Trp Glu Asn Ala Thr Glu Ala Ala Lys Val Ala Ile Asn Glu
            340                 345                 350

Thr Leu Lys Asn Thr Thr Phe Lys Asn Thr Thr Tyr Thr Phe Arg Thr
        355                 360                 365

Asp Gly Asp Leu Lys Trp Ile Ser Gly Gly Asp Gln Glu Thr Gln Thr
370                 375                 380

His Trp Phe Asn Cys Gln Gly Glu Phe Phe Tyr Cys Asp Leu Lys Asn
385                 390                 395                 400

Trp Thr Asn Asn Gly Ile Glu Ile Asp Gly Met Leu Ile Ala Pro Cys
                405                 410                 415

Arg Leu Arg Gln Ile Val Asn His Trp Gly Ile Val Ser Arg Gly Ile
            420                 425                 430

Tyr Leu Pro Pro Arg Glu Gly Gln Val Lys Cys Val Ser Ser Ile Thr
        435                 440                 445

Gly Phe Ile Met Thr Ala Glu Thr Asn Asp Thr Asp Gly Thr Ile Thr
450                 455                 460

Pro Thr Phe Ser Ala Lys Val Glu Asp Tyr Trp Lys Val Glu Met Ser
465                 470                 475                 480

Arg Tyr Lys Val Val Glu Ile Gln Pro Leu Ser Val Ala Pro Thr Lys
                485                 490                 495

Gly Lys Arg Pro Val Val Gly Asp Pro Glu Ala Lys Ser Arg Ser Lys
            500                 505                 510

Arg Glu Ile Gly Met Gly Met Ile Phe Met Gly Phe Leu Ser Ala Ala
        515                 520                 525

Gly Ser Thr Met Gly Ala Ala Ser Ile Ala Leu Thr Val Gln Ala Arg
530                 535                 540

Gly Leu Leu Ser Gly Ile Val Gln Gln Gln Ala Asn Leu Leu Gln Ala
545                 550                 555                 560

Ile Glu Ala Gln Gln His Leu Leu Gln Leu Ser Val Trp Gly Ile Lys
                565                 570                 575

Gln Leu Gln Ala Arg Leu Leu Ala Val Glu Lys Tyr Leu Arg Asp Gln
            580                 585                 590

Gln Leu Leu Gly Leu Trp Gly Cys Ala Asn Lys Leu Ile Cys His Ser
        595                 600                 605

Ser Leu Glu Trp Asn Ser Ser Trp Leu Asn Lys Thr Leu Cys Gly Asn
610                 615                 620

Lys Thr Asn Asn Tyr Glu Asn Tyr Glu Cys Ile Trp Ser Gln Tyr
625                 630                 635                 640

Thr Trp Gln Gln Trp Asp Glu Glu Ile Arg Asn Ile Ser Asp Val Ile
                645                 650                 655

Tyr Leu Ser Leu Glu Thr Ala Gln Val Gln Gln Glu Arg Asn His Lys
            660                 665                 670

Gln Leu Leu Glu Leu Asp Lys Trp Ser Ser Leu Trp Asn Trp Phe Asp
        675                 680                 685

Ile Thr Asn Trp Leu Trp Tyr Ile Lys Ile Ala Ile Ile Val Ala
```

```
                690             695             700
Ser Leu Val Gly Leu Arg Ile Val Met Phe Ile Ile Asn Leu Val Gly
705                 710                 715                 720

Lys Leu Arg Gln Gly Tyr Ser Leu Leu Ser Pro Gln Ile Pro Ile Gln
                725                 730                 735

Thr Ala Arg Gly Pro Gly Gln Pro Glu Gly Thr Glu Glu Gly Gly Gly
                740                 745                 750

Glu Ser Gly Arg Asp Arg Trp Arg Gly Tyr Pro Val Gly Phe Leu Gln
                755                 760                 765

Leu Ile Trp Glu Asp Cys Arg Gln Leu Leu Leu Trp Ile Tyr Gln Thr
                770                 775                 780

Ser Val Asn Leu Leu Trp His Leu Trp Thr Leu Ile Lys Leu Ile His
785                 790                 795                 800

Gln Trp Ser Leu Leu Leu Trp Glu Thr Val Arg Gln Leu Leu Arg Arg
                805                 810                 815

Leu Ile His Leu Leu Thr Gln Phe Leu His Leu Leu Glu Thr Trp Gly
                820                 825                 830

Ile Leu Ile Arg Gln His Cys Ile Val Cys Ile Asp Thr Leu Ala Glu
                835                 840                 845

Phe Thr Gly Trp Trp Thr Asp Gly Val Ile Glu Ala Leu Arg Val Ala
850                 855                 860

Val Asp Ile Ile Arg His Ile Pro Thr Arg Ile Arg Gln Gly Leu Glu
865                 870                 875                 880

Ile Ala Leu Asn

<210> SEQ ID NO 349
<211> LENGTH: 912
<212> TYPE: PRT
<213> ORGANISM: Simian immunodeficiency virus
<220> FEATURE:
<221> NAME/KEY: MISC_FEATURE
<222> LOCATION: (61)..(61)
<223> OTHER INFORMATION: Xaa can be any naturally occurring amino acid
<220> FEATURE:
<221> NAME/KEY: MISC_FEATURE
<222> LOCATION: (202)..(202)
<223> OTHER INFORMATION: Xaa can be any naturally occurring amino acid
<220> FEATURE:
<221> NAME/KEY: MISC_FEATURE
<222> LOCATION: (267)..(267)
<223> OTHER INFORMATION: Xaa can be any naturally occurring amino acid
<220> FEATURE:
<221> NAME/KEY: MISC_FEATURE
<222> LOCATION: (304)..(304)
<223> OTHER INFORMATION: Xaa can be any naturally occurring amino acid
<220> FEATURE:
<221> NAME/KEY: MISC_FEATURE
<222> LOCATION: (305)..(305)
<223> OTHER INFORMATION: Xaa can be any naturally occurring amino acid
<220> FEATURE:
<221> NAME/KEY: MISC_FEATURE
<222> LOCATION: (307)..(307)
<223> OTHER INFORMATION: Xaa can be any naturally occurring amino acid
<220> FEATURE:
<221> NAME/KEY: MISC_FEATURE
<222> LOCATION: (310)..(310)
<223> OTHER INFORMATION: Xaa can be any naturally occurring amino acid
<220> FEATURE:
<221> NAME/KEY: MISC_FEATURE
<222> LOCATION: (317)..(317)
<223> OTHER INFORMATION: Xaa can be any naturally occurring amino acid

<400> SEQUENCE: 349

Met Arg Val Met Gly Thr Lys Lys Ser Cys Val Leu Tyr Tyr Cys Leu
1               5                   10                  15
```

```
Val Ile Leu Ser Leu Phe Ser Leu Thr Ile Asp Ser Lys Glu Glu Leu
            20                  25                  30

Trp Val Thr Val Tyr Tyr Gly Val Pro Val Trp Arg Asp Ala Glu Thr
            35                  40                  45

Thr Leu Phe Cys Ala Ser Asp Ala Lys Ala Gln Glu Xaa Glu Ala His
    50                  55                  60

Asn Ile Trp Ala Ser Gln Ala Cys Val Pro Thr Asp Pro Asn Pro Glu
65                  70                  75                  80

Glu Ile His Leu Pro Asn Val Thr Glu Tyr Phe Asp Met Trp Lys Asn
                85                  90                  95

Asn Met Val Glu Gln Met Gln Glu Asp Ile Ile Ser Leu Trp Asp Gln
            100                 105                 110

Ser Leu Lys Pro Cys Val Lys Leu Thr Pro Leu Cys Val Thr Leu Asn
            115                 120                 125

Cys Thr Asn Cys Ile Trp Gly Asn Gly Thr Phe Arg Glu Trp Asn Asp
    130                 135                 140

Thr Arg Glu Asp Leu Arg Asn Cys Ser Phe Asn Ala Gly Asp Ile Arg
145                 150                 155                 160

Asp Lys Lys Lys Arg Val His Ser Leu Phe Tyr Ala Glu Asp Ile Ile
                165                 170                 175

Leu Ile Asp Arg Thr Arg Thr Thr Lys Gln Gly Asn Ser Thr Gln Ala
            180                 185                 190

Pro Ala Thr Thr Pro Ile Ala Ser Thr Xaa Val Pro Asp Ser Asn Asp
            195                 200                 205

Thr Cys Ser Pro Asn Asn Thr Leu Glu Tyr Arg Leu Ile Ser Cys Asn
    210                 215                 220

Thr Ser Val Ile Thr Gln Ala Cys Pro Lys Thr Ser Phe Glu Pro Ile
225                 230                 235                 240

Pro Ile His Tyr Cys Ala Pro Ala Gly Phe Ala Leu Leu Lys Cys Asn
                245                 250                 255

Asp Thr Asn Phe Ser Gly Gln Gly Ile Cys Xaa Asn Val Ser Thr Val
            260                 265                 270

His Cys Thr His Gly Ile Arg Pro Val Val Ser Thr His Leu Leu Leu
            275                 280                 285

Asn Gly Ser Leu Ala Lys Gly Asp Ile Met Ile Arg Val Lys Asx Xaa
    290                 295                 300

Xaa Gln Xaa Thr Asp Xaa Ile Ile Val Gln Leu Asn Xaa Ser Ile Asn
305                 310                 315                 320

Ile Thr Cys Ile Arg Pro Gly Asn Asn Thr Ile Lys Gly Ile Pro Ile
                325                 330                 335

Gly Pro Gly Gln His Phe Tyr Gly Thr Glu Thr Val Val Gly Asp Thr
            340                 345                 350

Arg Lys Ala Tyr Cys Lys Ile Asn Gly Thr Gln Trp Phe Asp Thr Leu
            355                 360                 365

Lys Arg Val Ala Trp Glu Leu Lys Glu Thr Phe Asn Leu Thr Arg Val
    370                 375                 380

Thr Phe Asp Gln Ala Ser Pro Gly Asp Pro Glu Ile Gln Lys His Tyr
385                 390                 395                 400

Phe Asn Cys Gly Gly Glu Phe Phe Tyr Cys Glu Thr Ser Ser Leu Phe
                405                 410                 415

Asn Ala Thr Ile Asp Ile Thr Pro Asn Thr Thr Leu Asn Glu Thr Thr
            420                 425                 430
```

```
Trp Asp Tyr Pro Ala Glu Asn Asn Ile Asn Gln Glu Met Ile Ile His
        435                 440                 445

Cys Arg Ile Lys Gln Ile Val Ser Met Trp Gln Arg Val Gly Lys Gly
        450                 455                 460

Ile Phe Ser Pro Pro Ile Arg Gly Thr Ile Gln Cys Asn Ser Thr Ile
465                 470                 475                 480

Thr Gly Leu Leu Leu Thr Arg Asp Gly Asn Asn Lys Ala Asp Ser Glu
            485                 490                 495

Asn Lys Thr Arg Ile Glu Thr Gly Gln Asn Lys Ala Glu Glu Ile Asn
        500                 505                 510

Arg Thr Asp Ile Phe Arg Pro Ala Gly Gly Glu Met Arg Asp Asn Trp
        515                 520                 525

Arg Ser Glu Leu Tyr Arg Tyr Lys Val Val Lys Ile Glu Pro Leu Gly
        530                 535                 540

Leu Ala Pro Thr Lys Ala Lys Arg Arg Thr Val Asn Arg Glu Lys Arg
545                 550                 555                 560

Ala Pro Gly Leu Gly Leu Met Phe Leu Gly Phe Leu Gly Ala Ala Gly
            565                 570                 575

Ser Thr Met Gly Ala Ala Ser Leu Thr Leu Thr Val Gln Ala Arg Gln
        580                 585                 590

Leu Leu Thr Gly Ile Val Gln Gln Gln Ser Asn Leu Leu Arg Ala Ile
        595                 600                 605

Glu Ala Gln Gln His Leu Leu Gln Leu Ser Val Trp Gly Ile Lys Gln
        610                 615                 620

Leu Gln Ala Arg Val Leu Ala Ile Glu Arg Tyr Leu Lys Asp Gln Gln
625                 630                 635                 640

Leu Leu Gly Ile Trp Gly Cys Ser Gly Lys Leu Ile Cys Thr Thr Asp
            645                 650                 655

Val Lys Trp Asn Glu Thr Trp Ser Asn Lys Ser Tyr Asn Glu Ile Trp
        660                 665                 670

Asp Asn Met Thr Trp Met Gln Trp Asp Lys Glu Val Arg Asn Tyr Thr
        675                 680                 685

Glu Thr Ile Tyr Asp Leu Ile Glu Gln Ala Gln Asn Gln Gln Glu Tyr
        690                 695                 700

Asn Glu Lys Ser Leu Leu Glu Leu Asn Gln Trp Ala Ser Leu Trp Asn
705                 710                 715                 720

Trp Phe Asp Ile Ser Asn Trp Leu Trp Tyr Ile Lys Ile Phe Ile Met
            725                 730                 735

Ile Val Gly Gly Leu Ile Gly Cys Arg Ile Val Phe Ala Leu Leu Ser
        740                 745                 750

Ile Val Asn Arg Val Arg Gln Gly Tyr Ser Pro Leu Ser Phe Gln Thr
        755                 760                 765

Leu Phe Pro Ile Pro Arg Gly Pro Glu Gln Pro Gly Glu Thr Gly Glu
        770                 775                 780

Glu Gly Gly Glu Gln Asp Asn Val Arg Ser Ile Arg Leu Leu Asn Gly
785                 790                 795                 800

Phe Leu Pro Leu Val Trp Asn Asp Leu Arg Asp Leu Cys Arg Phe Leu
            805                 810                 815

Tyr His Arg Leu Arg Asp Phe Leu Leu Ile Ala Arg Arg Thr Leu Glu
        820                 825                 830

Leu Val Gly Gln His Leu Leu Lys Gly Leu Arg Leu Val Trp Glu Thr
        835                 840                 845

Leu Leu Tyr Leu Lys Gly Val Leu Gln Tyr Trp Gly Arg Glu Leu Lys
```

```
                    850                 855                 860
Val Ser Ala Ile Ser Leu Leu Asp Thr Thr Ala Ile Ala Val Ala Glu
865                 870                 875                 880

Gly Thr Asp Arg Ile Ile Glu Val Ala Gln Arg Phe Gly Arg Gly Ile
                    885                 890                 895

Leu Asn Ile Pro Thr Arg Ile Arg Gln Gly Leu Glu Arg Ala Leu Leu
                    900                 905                 910

<210> SEQ ID NO 350
<211> LENGTH: 889
<212> TYPE: PRT
<213> ORGANISM: Simian immunodeficiency virus
<220> FEATURE:
<221> NAME/KEY: MISC_FEATURE
<222> LOCATION: (37)..(37)
<223> OTHER INFORMATION: Xaa can be any naturally occurring amino acid

<400> SEQUENCE: 350

Met Lys Asp Met Thr Val Met Lys Lys Lys Ser Ser Leu Gly Asn
1               5                   10                  15

Trp Gly Ile Cys Leu Ala Leu Ile Ile Tyr Phe Asn Ala Ile Ser Tyr
                20                  25                  30

Val Asn Cys Thr Xaa Tyr Val Thr Val Tyr Tyr Gly Val Pro Val Trp
                35                  40                  45

Gln Asp Ala Lys Thr Thr Leu Phe Cys Ala Ala Asp Ala Asp Leu Ala
50                  55                  60

Ser Lys Glu Gln His Asn Ile Trp Ala Thr Gln Ala Cys Val Pro Leu
65                  70                  75                  80

Asp Pro Thr Pro Ile Glu Leu Lys Leu Asn Ile Thr Glu Ser Phe Asn
                85                  90                  95

Ile Trp Glu Asn Tyr Met Val Glu Gln Met Gln Glu Asp Ile Val Ser
                100                 105                 110

Leu Trp Asp Gln Ser Leu Lys Pro Cys Val Lys Leu Thr Phe Leu Cys
                115                 120                 125

Val Thr Met Asn Cys Ser Glu Tyr Lys Gly Tyr Asn Cys Ser Thr Glu
130                 135                 140

Gly Asn Thr Thr Ala Ala Pro Cys Asn Thr Thr Glu Asn Thr Thr Lys
145                 150                 155                 160

Glu Asn Ser Thr Gly Met Leu Thr Cys Asn Phe Asn Val Thr Thr Val
                165                 170                 175

Leu Lys Asp Lys Lys Glu Gln Lys Gln Ala Leu Phe Tyr Arg Glu Asp
                180                 185                 190

Leu Ala Ser Leu Glu Ser Asn Asn Ser Tyr Arg Leu Ile Asn Cys Asn
                195                 200                 205

Ser Ser Thr Ile Thr Gln Ala Cys Pro Lys Val Ser Phe Glu Pro Leu
210                 215                 220

Pro Ile Gln Tyr Cys Ala Pro Ala Gly Tyr Ala Leu Met Lys Cys Asn
225                 230                 235                 240

Arg Thr Asp Phe Asn Gly Thr Gly Thr Cys Asn Glu Thr Ser Ile Val
                245                 250                 255

His Cys Thr His Gly Ile Arg Pro Thr Val Ser Thr Gln Leu Val Leu
                260                 265                 270

Asn Gly Thr Leu Ala Lys Gly Lys Pro Leu Val Ile Thr Lys Asn Val
                275                 280                 285

Ser Glu Thr Gly Ala Pro Ile Ile Val Lys Leu Ser Ala Ser Thr Ala
                290                 295                 300
```

```
Ile Thr Cys Ile Arg Pro Gly Asn Asn Thr Arg Gly Glu Val Gln Leu
305                 310                 315                 320

Gly Pro Met Thr Trp Tyr Asn Met Arg His Tyr Ile Gly Asp Ile Arg
                325                 330                 335

Lys Ala His Cys Thr Val Ser Arg Gly Asn Trp Thr Lys Val Leu Gln
            340                 345                 350

Asn Val Ser Ala Ala Leu Trp Glu Ala Tyr Pro Ala Glu Trp Lys Asn
        355                 360                 365

Lys Thr Gln Asp Lys Asn His Thr Ile Leu Phe Arg Ala Ser Ser Gly
    370                 375                 380

Gly Asp Pro Glu Val Ala Ser Leu His Phe Asn Cys His Gly Glu Phe
385                 390                 395                 400

Phe Tyr Cys Asn Thr Ser Ala Leu Phe Asn His Ser Cys Thr Lys Asn
                405                 410                 415

Met Thr Lys Asn Glu Trp Ile Cys Thr Pro Asn Asn Ala Thr Gly Thr
                420                 425                 430

Leu Arg Leu Pro Cys Arg Leu Lys Gln Val Val Asn Ser Trp Met Arg
                435                 440                 445

Val Gly Ser Gly Leu Phe Ala Pro Pro Ile Pro Gly Ser Leu Thr Cys
450                 455                 460

Lys Ser Asn Ile Thr Gly Ile Leu Leu Glu Arg Asp Leu Pro Leu Gly
465                 470                 475                 480

Asn Met Thr Asn Thr Thr Leu Arg Pro Ile Gly Gly Asp Met Lys Asn
            485                 490                 495

Ile Trp Arg Ser Glu Leu Tyr Pro Tyr Lys Val Gln Val Lys Ala
                500                 505                 510

Leu Gly Val Ala Pro Thr Lys Ile Ser Arg Pro Thr Ile Met Gly Pro
            515                 520                 525

His Arg Glu Lys Arg Gly Ala Gly Leu Gly Met Leu Phe Leu Gly Phe
    530                 535                 540

Leu Ser Ala Ala Gly Ser Thr Met Gly Ala Ala Val Thr Leu Thr
545                 550                 555                 560

Val Gln Ala Lys Gln Leu Leu His Gly Ile Val Gln Gln Asn Asn
                565                 570                 575

Leu Leu Arg Ala Ile Gln Ala Gln Gln Glu Leu Leu Arg Leu Ser Val
            580                 585                 590

Trp Gly Ile Arg Gln Leu Arg Ala Arg Leu Leu Ala Ile Glu Thr Tyr
        595                 600                 605

Leu Lys Asp Gln Gln Leu Leu Gly Leu Trp Gly Cys Ser Gly Lys Leu
    610                 615                 620

Val Cys Tyr Thr Asn Val Pro Trp Gln Lys Asn Trp Thr Thr Tyr Gln
625                 630                 635                 640

Ser Asp Ser Gln Leu Asp Ala Ile Trp Asp Asn Leu Thr Trp Gln Glu
                645                 650                 655

Trp Asp Lys Gln Val Asn Asn Tyr Thr Asp Leu Ile Phe Leu Glu Ile
                660                 665                 670

Gln Ile Ala Gln Glu Gln Gln Glu Asn Gln Lys Lys Leu Leu Glu
            675                 680                 685

Leu Asp Gln Trp Ala Gln Leu Trp Ser Trp Leu Asp Ile Thr Gln Trp
    690                 695                 700

Leu Trp Tyr Ile Lys Ile Phe Ile Met Ile Val Gly Gly Leu Ile Gly
705                 710                 715                 720
```

```
Leu Arg Ile Phe Ile Ala Val Val Asn Val Val Lys Arg Val Arg Gln
                725                 730                 735

Gly Tyr Ser Pro Leu Ser Leu Gln Thr Leu Gly Gln Asn Arg Gly Pro
            740                 745                 750

Ala Gly Ile Ala Thr Gly Thr Asp Glu Glu Gly Gly Gly Ala Gly Ser
        755                 760                 765

Val Arg Ser Ile Arg Leu Leu Asp Gly Phe Leu Pro Leu Ile Trp Asp
    770                 775                 780

Asp Leu Lys Asn Leu Val Val Trp Ile Tyr Gln Ile Leu Val Ser Cys
785                 790                 795                 800

Ile Leu Gly Ile Lys Asp Leu Leu Ala Ile Leu Trp Ile His Leu Arg
                805                 810                 815

His Leu Leu Asn Lys Gly Leu Asn Cys Val Arg Asp Cys Leu Ala Val
            820                 825                 830

Cys Gly Tyr Trp Val Gln Glu Leu Gln Arg Ser Ala Thr Asn Leu Leu
        835                 840                 845

Asp Thr Thr Ala Val Ala Val Ala Glu Trp Thr Asp Gln Val Ile Leu
    850                 855                 860

Ile Gly Gln Arg Ile Gly Arg Gly Ile Leu Asn Ile Pro Arg Arg Ile
865                 870                 875                 880

Arg Gln Gly Leu Glu Arg Ser Leu Leu
                885
```

<210> SEQ ID NO 351
<211> LENGTH: 892
<212> TYPE: PRT
<213> ORGANISM: Simian immunodeficiency virus
<220> FEATURE:
<221> NAME/KEY: MISC_FEATURE
<222> LOCATION: (248)..(248)
<223> OTHER INFORMATION: Xaa can be any naturally occurring amino acid
<220> FEATURE:
<221> NAME/KEY: MISC_FEATURE
<222> LOCATION: (250)..(250)
<223> OTHER INFORMATION: Xaa can be any naturally occurring amino acid
<220> FEATURE:
<221> NAME/KEY: MISC_FEATURE
<222> LOCATION: (254)..(254)
<223> OTHER INFORMATION: Xaa can be any naturally occurring amino acid

<400> SEQUENCE: 351

```
Met Lys Asp Met Arg Val Met Arg Lys Lys Lys Arg Ser Leu Gly Asn
1               5                   10                  15

Trp Gly Leu Ser Leu Ala Leu Leu Ile Ile Cys Phe Asn Thr Gly Ser
            20                  25                  30

Tyr Val Met Gly Thr Arg Tyr Val Thr Val Tyr Tyr Gly Val Pro Val
        35                  40                  45

Trp Arg Glu Ala Lys Thr Thr Leu Phe Cys Ala Ala Asp Ala Asn Leu
    50                  55                  60

Ala Ser Lys Glu Gln His Asn Ile Trp Ala Thr Gln Ala Cys Val Pro
65                  70                  75                  80

Thr Asp Pro Thr Pro Ile Lys Val Lys Leu Asn Ile Ser Glu Pro Tyr
                85                  90                  95

Asn Ile Trp Glu Asn Tyr Ile Val Lys Gln Met Gln Lys Asn Ile Ile
            100                 105                 110

Ser Leu Leu Asn Gln Ser Leu Lys Pro Cys Val Lys Leu Thr Val Ile
        115                 120                 125

Cys Val Thr Ile Asn Cys Ser Lys Phe Lys Pro Ala Thr Thr Asn Thr
    130                 135                 140
```

```
Thr Ser Ala Pro Ile Asn Ala Ser Leu Gln Ser Ser Thr Thr Ala Gln
145                 150                 155                 160

Asn Asn Leu Asn Phe Tyr Asn Cys Ser Phe Asn Val Thr Thr Val Leu
            165                 170                 175

Lys Asp Lys Lys Glu Lys Lys Gln Ala Leu Phe Tyr Lys Glu Asn Leu
        180                 185                 190

Val Pro Leu Asn Gln Thr Ser Lys Glu Lys Leu Tyr Arg Leu Ile Asn
        195                 200                 205

Cys Asn Thr Thr Thr Ile Thr Gln Ala Cys Pro Lys Val Ser Phe Lys
        210                 215                 220

Pro Leu Pro Ile Gln Tyr Cys Ala Pro Ala Lys Tyr Ala Leu Ile Lys
225                 230                 235                 240

Cys Lys Gln Lys Gly Phe Asn Xaa Thr Xaa Leu Cys Asn Xaa Thr Val
            245                 250                 255

Ile Thr His Cys Thr His Gly Ile Arg Pro Thr Val Ser Thr Gln Leu
            260                 265                 270

Ile Phe Asn Gly Ser Leu Ala Glu Glu Ala Leu Val Met Ser Lys
        275                 280                 285

Asp Val Thr Ala Thr Gly Lys Asn Ile Ile Lys Leu Ser Thr Gly
        290                 295                 300

Val Asn Ile Thr Cys Ile Arg Thr Gly Asn Asn Thr Arg Gly Gln Thr
305                 310                 315                 320

Gln Ile Gly Pro Met Thr Trp Tyr Asn Ser Val Asn Tyr Ile Gly Asn
            325                 330                 335

Ile Arg Arg Ala Tyr Cys Gln Val Glu Thr Asp Trp Lys Gly Ile
            340                 345                 350

Leu Lys Asn Val Ser Lys Ala Leu Ile Lys Arg Tyr Asn Gly Lys Val
        355                 360                 365

Asn Glu Thr His Thr Phe Glu Phe Lys Asn Ala Ser Gly Gly Asp Pro
        370                 375                 380

Glu Val Thr His Leu His Phe Asn Cys His Gly Glu Phe Phe Tyr Cys
385                 390                 395                 400

Asn Thr Ser Lys Leu Phe Asn Tyr Thr Tyr Val Cys Asn Gln Thr Asp
            405                 410                 415

Gln Gly Asn Ala Asn Tyr Ser Cys His Ser Thr Ser Thr Leu Glu Asn
            420                 425                 430

Gly Thr Leu Val Ile Pro Cys Lys Leu Arg Gln Val Val Asn Ser Trp
        435                 440                 445

Met Arg Val Gly Ser Gly Leu Phe Ala Pro Pro Val Pro Gly Ser Leu
        450                 455                 460

Thr Cys His Ser Asn Ile Thr Gly Leu Ile Leu Gln Arg Asp Trp Pro
465                 470                 475                 480

Leu Asn Asn Asn Thr Thr Thr Ile Leu Arg Pro Glu Gly Gly Asp Met
            485                 490                 495

Lys Asp Ile Trp Arg Ser Glu Leu Tyr Pro Tyr Lys Val Val Gln Val
            500                 505                 510

Lys Ala Leu Ala Val Ala Pro Thr Lys Ile Ser Arg Pro Thr Ile Met
        515                 520                 525

Ala Gln Thr His Gln Arg Glu Lys Arg Gly Ala Gly Leu Gly Met Leu
        530                 535                 540

Phe Leu Gly Phe Met Ser Ala Ala Gly Ser Thr Met Gly Ala Ala Ala
545                 550                 555                 560
```

Val Thr Leu Thr Val Gln Ala Lys Gln Leu His Gly Ile Val Gln
            565                 570                 575

Gln Gln Asn Asn Leu Leu Arg Ala Ile Glu Ala Gln Gln Glu Leu Leu
        580                 585                 590

Arg Leu Ser Val Trp Gly Ile Arg Gln Leu Arg Ala Arg Leu Leu Ala
    595                 600                 605

Ile Glu Thr Tyr Leu Arg Asp Gln Gln Leu Leu Gly Leu Trp Gly Cys
610                 615                 620

Thr Gly Gln Ile Val Cys Tyr Thr Asn Val Pro Trp Asn Gln Thr Trp
625                 630                 635                 640

Thr Gly Arg Asn Asp Thr Glu Leu Asp Ser Ile Trp Asn Lys Leu Thr
            645                 650                 655

Trp Gln Glu Trp Asp Lys Leu Val Asp Asn Tyr Thr Asp Thr Ile Phe
        660                 665                 670

Val Glu Ile Gln Lys Ala Asn Glu Gln Gln Lys Glu Asn Glu Lys Lys
    675                 680                 685

Leu Leu Glu Leu Asp Gln Trp Thr Gln Leu Trp Ser Trp Phe Asp Ile
690                 695                 700

Thr Lys Trp Leu Trp Tyr Ile Lys Ile Phe Ile Met Ile Val Gly Gly
705                 710                 715                 720

Leu Ile Gly Leu Lys Phe Leu Leu Ala Ile Ile Asn Ile Val Lys Arg
            725                 730                 735

Val Arg Gln Gly Tyr Ser Pro Leu Ser Leu Gln Ile Leu Gly Leu Asn
        740                 745                 750

Arg Gly Leu Ala Gly Ile Ala Pro Gly Thr Asp Glu Glu Gly Gly Glu
    755                 760                 765

Ile Asp Asn Gly Arg Ser Ile Arg Leu Leu Asp Gly Leu Leu Pro Ile
770                 775                 780

Val Trp Asp Asp Leu Lys Asn Leu Val Val Trp Ile Tyr Arg Ile Leu
785                 790                 795                 800

Ala Thr Cys Ile Leu Gly Thr Lys Asp Leu Leu Asn Ile Leu Trp Ile
            805                 810                 815

His Leu Arg His Leu Leu Asn Lys Gly Ile Asn Cys Leu Arg Asp Cys
        820                 825                 830

Leu Ala Val Cys Gly Tyr Trp Ala Gln Glu Leu Gln Gln Ser Ala Thr
    835                 840                 845

Ser Leu Leu Asp Thr Val Ala Val Arg Val Ala Asp Trp Thr Asp Gln
850                 855                 860

Val Ile Leu Val Gly Gln Arg Ile Gly Arg Gly Ile Leu Asn Ile Pro
865                 870                 875                 880

Arg Arg Leu Arg Gln Gly Leu Glu Arg Ser Leu Leu
            885                 890

<210> SEQ ID NO 352
<211> LENGTH: 884
<212> TYPE: PRT
<213> ORGANISM: Simian immunodeficiency virus
<220> FEATURE:
<221> NAME/KEY: MISC_FEATURE
<222> LOCATION: (15)..(15)
<223> OTHER INFORMATION: Xaa can be any naturally occurring amino acid
<220> FEATURE:
<221> NAME/KEY: MISC_FEATURE
<222> LOCATION: (128)..(128)
<223> OTHER INFORMATION: Xaa can be any naturally occurring amino acid
<220> FEATURE:
<221> NAME/KEY: MISC_FEATURE
<222> LOCATION: (130)..(130)

```
<223> OTHER INFORMATION: Xaa can be any naturally occurring amino acid
<220> FEATURE:
<221> NAME/KEY: MISC_FEATURE
<222> LOCATION: (150)..(150)
<223> OTHER INFORMATION: Xaa can be any naturally occurring amino acid
<220> FEATURE:
<221> NAME/KEY: MISC_FEATURE
<222> LOCATION: (202)..(202)
<223> OTHER INFORMATION: Xaa can be any naturally occurring amino acid
<220> FEATURE:
<221> NAME/KEY: MISC_FEATURE
<222> LOCATION: (473)..(473)
<223> OTHER INFORMATION: Xaa can be any naturally occurring amino acid
<220> FEATURE:
<221> NAME/KEY: MISC_FEATURE
<222> LOCATION: (621)..(621)
<223> OTHER INFORMATION: Xaa can be any naturally occurring amino acid
<220> FEATURE:
<221> NAME/KEY: MISC_FEATURE
<222> LOCATION: (661)..(661)
<223> OTHER INFORMATION: Xaa can be any naturally occurring amino acid
<220> FEATURE:
<221> NAME/KEY: MISC_FEATURE
<222> LOCATION: (711)..(711)
<223> OTHER INFORMATION: Xaa can be any naturally occurring amino acid
<220> FEATURE:
<221> NAME/KEY: MISC_FEATURE
<222> LOCATION: (839)..(839)
<223> OTHER INFORMATION: Xaa can be any naturally occurring amino acid

<400> SEQUENCE: 352

Met Lys Val Met Lys Lys Lys Glu Lys Ser Trp Ile Leu Xaa Ile
1               5                   10                  15

Val Met Ala Phe Ile Ile Pro Cys Ser Ser Arg Pro Leu Tyr Ala
            20                  25                  30

Thr Val Tyr Tyr Gly Val Pro Val Trp Arg Asp Ala Gln Thr Thr Leu
        35                  40                  45

Phe Cys Ala Ala Asp Ala Lys Met Ala Ser Ser Glu Met His Asn Val
    50                  55                  60

Trp Ala Thr Gln Ala Cys Val Pro Thr Asp Pro Gln Pro Ile Glu Leu
65                  70                  75                  80

Lys Leu Thr Asn Val Thr Glu Thr Phe Asn Ile Trp Lys Ser Gly Met
                85                  90                  95

Val Glu Gln Met Gln Glu Asp Ile Ile Ser Leu Trp Asp Gln Ser Leu
            100                 105                 110

Lys Pro Cys Val Lys Leu Thr Val Met Cys Val Thr Met Asn Cys Xaa
        115                 120                 125

Arg Xaa Thr Pro Asn Thr Thr Thr His Ser Leu Asn Met Thr Gly Pro
    130                 135                 140

Ala Pro Arg Thr Ser Xaa Pro Thr Thr Ser Ser His Asn Met Thr Ser
145                 150                 155                 160

Thr Pro Asn Ile Pro Glu Leu Glu Val Tyr Asn Cys Thr Phe Asn Val
                165                 170                 175

Thr Thr Val Leu Lys Asp Lys Lys Ser Gln Gln Gln Ala Leu Phe Tyr
            180                 185                 190

Arg Glu Asp Leu Ser Gln Ile Gly Asp Xaa Asn Ser Thr Tyr Arg Leu
        195                 200                 205

Ile Asn Cys Asn Thr Ser Thr Ile Ser Gln Ala Cys Pro Lys Val Ser
    210                 215                 220

Phe Glu Pro Leu Pro Ile Gln Tyr Cys Ala Pro Ala Gly Tyr Ala Leu
225                 230                 235                 240

Met Lys Cys Asn Gln Ser Lys Phe Asn Gly Thr Gly Thr Cys Asn Glu
                245                 250                 255
```

```
Thr Leu Ile Thr His Cys Thr His Gly Ile Arg Pro Thr Val Ser Thr
            260                 265                 270

Gln Phe Ile Phe Asn Gly Thr Leu Glu Lys Glu Leu Leu Met Leu Ser
            275                 280                 285

Lys Asn Ile Ser Asp Ser Gly Lys Thr Ile Ile Val Lys Leu Lys Lys
290                 295                 300

Ala Val Thr Phe Lys Cys Glu Arg Thr Gly Asn Asn Thr Arg Gly Gln
305                 310                 315                 320

Ile Gln Ile Gly Pro Met Thr Ile Tyr Asn Ser Glu Asn Ile Val Gly
            325                 330                 335

Lys Thr Arg Lys Ala Tyr Cys Ala Tyr Asn Arg Thr Glu Trp Glu Gln
            340                 345                 350

Ala Leu Lys Thr Ile Ser Glu Ala Phe Ala Lys Leu Glu Asn Val Thr
            355                 360                 365

Lys Val Gln Trp Lys Asn Ser Ser Gly Gly Asp Leu Glu Val Ala Met
    370                 375                 380

Leu His Phe Asn Cys His Gly Glu Phe Phe Tyr Cys Asn Thr Thr Thr
385                 390                 395                 400

Met Phe Asn Tyr Thr Tyr Asn Cys Ser His His Ser Cys Lys Ala Gln
            405                 410                 415

Ser Lys Asn Ile Ser Glu Gly Ser Gly Asp Ser Tyr Ile Pro Cys Lys
            420                 425                 430

Leu Lys Gln Val Val Asn Ser Trp Met Arg Val Gly Ser Gly Leu Phe
        435                 440                 445

Ala Pro Pro Ile Arg Gly Thr Leu Lys Cys Met Ser Asn Ile Thr Gly
    450                 455                 460

Leu Leu Leu Glu Arg Asp Val Pro Xaa Asn Ile Thr Ala Thr Asx Arg
465                 470                 475                 480

Asn Ile Thr Leu Arg Pro Thr Gly Gly Glu Met Lys Asp Ile Trp Arg
            485                 490                 495

Ser Glu Leu Tyr Pro Tyr Lys Val Val Gln Val Lys Ala Leu Ser Val
            500                 505                 510

Ala Pro Thr Lys Ile Lys Arg Pro Ile Ile Gly Leu Asn Arg Glu Lys
            515                 520                 525

Arg Gly Ala Gly Leu Gly Met Leu Phe Leu Gly Phe Met Ser Ala Ala
    530                 535                 540

Gly Ser Thr Met Gly Ala Ala Ser Leu Thr Leu Thr Val Gln Ala Lys
545                 550                 555                 560

Gln Leu Leu His Gly Ile Val Gln Gln Gln Asn Asn Met Leu Arg Ala
            565                 570                 575

Ile Ala Ala Gln Gln Glu Leu Leu Arg Leu Ser Val Trp Gly Ile Arg
            580                 585                 590

Gln Leu Arg Ala Arg Leu Leu Ala Ile Glu Thr Tyr Leu Arg Asp Gln
            595                 600                 605

Gln Leu Leu Gly Leu Trp Gly Cys Ala Gly Lys Leu Xaa Cys Tyr Thr
    610                 615                 620

Asn Val Pro Trp Asn Asn Thr Trp Thr Asn Lys Ser Asx Thr Glu Leu
625                 630                 635                 640

Glu His Ile Trp Glu Asn Leu Thr Trp Gln Glu Trp Asp Lys Leu Val
            645                 650                 655

Asp Asn Tyr Thr Xaa Asp Ile Phe Leu Lys Ile Gln Glx Ala Asn Thr
            660                 665                 670
```

```
Gln Gln Glu Val Asn Glu Lys Lys Leu Leu Glu Leu Asp Lys Trp Ala
            675                 680                 685

Asp Leu Trp Ser Trp Phe Asp Ile Thr Lys Trp Leu Trp Tyr Ile Lys
690                 695                 700

Ile Ala Ile Met Ile Val Xaa Ala Leu Ile Gly Leu Arg Val Val Met
705                 710                 715                 720

Val Val Leu Ser Leu Val Lys Asn Ile Arg Lys Gly Tyr Gln Pro Leu
            725                 730                 735

Ser Leu Gln Thr Pro Ser Pro His Pro Thr Glu Pro Gly Thr Pro Glu
            740                 745                 750

Lys Thr Gly Gly Glu Gly Gly Glu Gly Asp Lys His Lys Trp Thr Pro
            755                 760                 765

Leu Pro Pro Gly Phe Leu His Leu Leu Tyr Leu Asp Leu Arg Thr Ile
770                 775                 780

Ile Leu Trp Ser Tyr His Leu Leu Ser Ser Leu Val Ser Arg Ile Gln
785                 790                 795                 800

Arg Ile Leu Ser Leu Leu Gly Leu Gly Leu Arg Ile Leu Gly Gln Lys
            805                 810                 815

Thr Phe Glu Ala Cys Lys Thr Leu Lys Ala Thr Ala Gln Tyr Trp Leu
            820                 825                 830

Gln Glu Leu Gln Arg Ser Xaa Thr Asn Leu Leu Asp Thr Val Ala Val
            835                 840                 845

Ala Val Ala Asn Trp Thr Asp Ser Ile Ile Leu Gly Val Gln Arg Phe
            850                 855                 860

Gly Arg Gly Ile Leu Asn Ile Pro Arg Arg Ile Arg Gln Gly Leu Glu
865                 870                 875                 880

Leu Ser Leu Leu

<210> SEQ ID NO 353
<211> LENGTH: 858
<212> TYPE: PRT
<213> ORGANISM: Simian immunodeficiency virus
<220> FEATURE:
<221> NAME/KEY: MISC_FEATURE
<222> LOCATION: (99)..(99)
<223> OTHER INFORMATION: Xaa can be any naturally occurring amino acid
<220> FEATURE:
<221> NAME/KEY: MISC_FEATURE
<222> LOCATION: (482)..(482)
<223> OTHER INFORMATION: Xaa can be any naturally occurring amino acid
<220> FEATURE:
<221> NAME/KEY: MISC_FEATURE
<222> LOCATION: (538)..(538)
<223> OTHER INFORMATION: Xaa can be any naturally occurring amino acid

<400> SEQUENCE: 353

Met Arg Lys Pro Ile His Ile Ile Trp Gly Leu Ala Leu Leu Ile Gln
1               5                   10                  15

Phe Ile Glu Lys Gly Thr Asn Glu Asp Tyr Val Thr Val Phe Tyr Gly
            20                  25                  30

Val Pro Val Trp Arg Asn Ala Thr Pro Thr Leu Phe Cys Ala Thr Asn
            35                  40                  45

Ala Ser Met Thr Ser Thr Glu Val His Asn Val Trp Ala Thr Thr Ser
50                  55                  60

Cys Val Pro Ile Asp Pro Asp Pro Ile Val Val Arg Leu Asn Thr Ser
65                  70                  75                  80

Val Trp Phe Asn Ala Tyr Lys Asn Tyr Met Val Glu Ser Met Thr Glu
            85                  90                  95
```

```
Asp Met Xaa Gln Leu Phe Gln Gln Ser His Lys Pro Cys Val Lys Leu
            100                 105                 110

Thr Pro Met Cys Ile Lys Met Asn Cys Thr Gly Tyr Asn Gly Thr Pro
        115                 120                 125

Thr Thr Pro Ser Thr Thr Thr Ser Thr Val Thr Pro Lys Thr Thr Thr
    130                 135                 140

Pro Ile Val Asp Gly Met Lys Leu Gln Glu Cys Asn Phe Asn Gln Ser
145                 150                 155                 160

Thr Gly Phe Lys Asp Lys Lys Gln Lys Met Lys Ala Ile Phe Tyr Lys
                165                 170                 175

Gly Asp Leu Met Lys Cys Gln Asp Asn Asn Glu Thr Asn Cys Tyr Tyr
            180                 185                 190

Leu Trp His Cys Asn Thr Thr Ile Thr Gln Ser Cys Glu Lys Ser
        195                 200                 205

Thr Phe Glu Pro Ile Pro Ile His Tyr Cys Ala Pro Ala Gly Tyr Ala
    210                 215                 220

Ile Leu Arg Cys Glu Asp Glu Asp Phe Thr Gly Val Gly Met Cys Lys
225                 230                 235                 240

Asn Val Ser Val Val His Cys Thr His Gly Ile Ser Pro Met Val Ala
                245                 250                 255

Thr Trp Leu Leu Leu Asn Gly Thr Tyr Gln Thr Asn Thr Ser Val Val
            260                 265                 270

Met Asn Gly Arg Lys Asn Glu Ser Val Leu Val Arg Phe Gly Lys Glu
        275                 280                 285

Phe Glu Asn Leu Thr Ile Thr Cys Ile Arg Pro Gly Asn Arg Thr Val
    290                 295                 300

Arg Asn Leu Gln Ile Gly Pro Gly Met Thr Phe Tyr Asn Val Glu Ile
305                 310                 315                 320

Ala Thr Gly Asp Thr Arg Lys Ala Phe Cys Thr Val Asn Lys Thr Leu
                325                 330                 335

Trp Glu Gln Ala Arg Asn Lys Thr Glu His Val Leu Ala Glu His Trp
            340                 345                 350

Lys Lys Val Asp Asn Lys Thr Asn Ala Lys Thr Ile Trp Thr Phe Gln
        355                 360                 365

Asp Gly Asp Pro Glu Val Lys Val His Trp Phe Asn Cys Gln Gly Glu
    370                 375                 380

Phe Phe Tyr Cys Asp Ile Thr Pro Trp Phe Asn Ala Thr Tyr Thr Gly
385                 390                 395                 400

Asn Leu Ile Thr Asn Gly Ala Leu Ile Ala His Cys Arg Ile Lys Gln
                405                 410                 415

Ile Val Asn His Trp Gly Ile Val Ser Lys Gly Ile Tyr Leu Ala Pro
            420                 425                 430

Arg Arg Gly Asn Val Ser Cys Thr Ser Ser Ile Thr Gly Ile Met Leu
        435                 440                 445

Glu Gly Gln Ile Tyr Asn Glu Thr Val Lys Val Ser Pro Ala Ala Arg
    450                 455                 460

Val Ala Asp Gln Trp Arg Ala Glu Leu Ser Arg Tyr Gln Val Val Glu
465                 470                 475                 480

Ile Xaa Pro Leu Ser Val Ala Pro Thr Thr Gly Lys Arg Pro Glu Ile
                485                 490                 495

Lys Gln His Ser Arg Gln Lys Arg Gly Ile Gly Ile Gly Leu Phe Phe
            500                 505                 510

Leu Gly Leu Leu Ser Ala Ala Gly Ser Thr Met Gly Ala Ala Ser Ile
```

-continued

```
        515                 520                 525

Ala Leu Thr Ala Gln Thr Arg Asn Leu Xaa His Gly Ile Val Gln Gln
    530                 535                 540

Gln Ala Asn Leu Leu Gln Ala Ile Glu Thr Gln Gln His Leu Leu Gln
545                 550                 555                 560

Leu Ser Val Trp Gly Val Lys Gln Leu Gln Ala Arg Met Leu Ala Val
                565                 570                 575

Glu Lys Tyr Leu Arg Asp Gln Gln Leu Leu Ser Leu Trp Gly Cys Ala
            580                 585                 590

Asp Lys Val Thr Cys His Thr Thr Val Pro Trp Asn Asn Ser Trp Val
        595                 600                 605

Asn Phe Thr Gln Thr Cys Ala Lys Asn Ser Ser Asp Ile Gln Cys Ile
    610                 615                 620

Trp Glu Asn Met Thr Trp Gln Glu Trp Asp Arg Leu Val Gln Asn Ser
625                 630                 635                 640

Thr Gly Gln Ile Tyr Asn Ile Leu Gln Ile Ala His Glu Gln Gln Glu
                645                 650                 655

Arg Asn Lys Lys Glu Leu Tyr Glu Leu Asp Lys Trp Ser Ser Leu Trp
            660                 665                 670

Asn Trp Phe Asp Ile Thr Gln Trp Leu Trp Tyr Ile Lys Ile Phe Ile
        675                 680                 685

Met Ile Val Gly Ala Ile Val Gly Leu Arg Ile Leu Leu Val Leu Val
    690                 695                 700

Ser Cys Leu Arg Lys Val Arg Gln Gly Tyr His Pro Leu Ser Phe Gln
705                 710                 715                 720

Ile Pro Thr Gln Asn Gln Gln Asp Pro Glu Gln Pro Glu Glu Ile Arg
                725                 730                 735

Glu Glu Gly Gly Arg Lys Asp Arg Ile Arg Trp Arg Ala Leu Gln His
            740                 745                 750

Gly Phe Phe Ala Leu Leu Trp Val Asp Leu Thr Ser Ile Ile Gln Trp
        755                 760                 765

Ile Tyr Gln Ile Cys Arg Thr Cys Leu Leu Asn Leu Trp Ala Val Leu
    770                 775                 780

Gln His Leu Cys Arg Ile Thr Phe Arg Leu Cys Asn His Leu Glu Asn
785                 790                 795                 800

Asn Leu Ser Thr Leu Trp Thr Ile Ile Arg Thr Glu Ile Ile Lys Asn
                805                 810                 815

Ile Asp Arg Leu Ala Ile Trp Val Gly Glu Lys Thr Asp Ser Ile Leu
            820                 825                 830

Leu Ala Leu Gln Thr Ile Val Arg Ile Ile Arg Glu Val Pro Arg Arg
        835                 840                 845

Ile Arg Gln Gly Leu Glu Ile Ala Leu Asn
    850                 855
```

<210> SEQ ID NO 354
<211> LENGTH: 854
<212> TYPE: PRT
<213> ORGANISM: Simian immunodeficiency virus

<400> SEQUENCE: 354

```
Met Lys Val Met Glu Lys Lys Lys Arg Asp Trp Asn Ser Leu Ser Ile
1               5                   10                  15

Ile Thr Ile Ile Thr Ile Ile Leu Leu Thr Pro Cys Leu Thr Ser Glu
            20                  25                  30
```

Leu Trp Val Thr Val Tyr Tyr Gly Val Pro Val Trp His Asp Ala Asp
            35                  40                  45

Pro Val Leu Phe Cys Ala Ser Asp Ala Lys Ala His Ser Thr Glu Ala
 50                  55                  60

His Asn Ile Trp Ala Thr Gln Ala Cys Val Pro Thr Asp Pro Ser Pro
 65                  70                  75                  80

Gln Glu Val Phe Leu Pro Asn Val Ile Glu Ser Phe Asn Met Trp Lys
                 85                  90                  95

Asn Asn Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
            115                 120                 125

Gln Cys Ser Lys Ala Asn Phe Ser Gln Ala Lys Asn Leu Thr Asn Gln
130                 135                 140

Thr Ser Ser Pro Pro Leu Glu Met Lys Asn Cys Ser Phe Asn Val Thr
145                 150                 155                 160

Thr Glu Leu Arg Asp Lys Lys Gln Val Tyr Ser Leu Phe Tyr Val
                165                 170                 175

Glu Asp Val Val Asn Leu Gly Asn Glu Asn Asn Thr Tyr Arg Ile Ile
            180                 185                 190

Asn Cys Asn Thr Thr Ala Ile Thr Gln Ala Cys Pro Lys Thr Ser Phe
    195                 200                 205

Glu Pro Ile Pro Ile His Tyr Cys Ala Pro Ala Gly Phe Ala Ile Leu
    210                 215                 220

Lys Cys Asn Asp Lys Asp Phe Ser Gly Lys Gly Lys Cys Thr Asn Val
225                 230                 235                 240

Ser Thr Val His Cys Thr His Gly Ile Lys Pro Val Val Thr Thr Gln
                245                 250                 255

Leu Leu Ile Asn Gly Ser Leu Ala Glu Gly Asn Ile Thr Val Arg Val
            260                 265                 270

Glu Asn Lys Ser Lys Asn Thr Asp Val Trp Ile Val Gln Leu Val Glu
            275                 280                 285

Ala Val Ser Leu Asn Cys His Arg Pro Gly Asn Asn Thr Arg Gly Glu
    290                 295                 300

Val Gln Ile Gly Pro Gly Met Thr Phe Tyr Asn Ile Glu Asn Val Val
305                 310                 315                 320

Gly Asp Thr Arg Ser Ala Tyr Cys Lys Ile Asn Gly Thr Thr Trp Asn
                325                 330                 335

Arg Thr Val Glu Glu Val Lys Lys Ala Leu Ala Thr Ser Ser Asn Arg
            340                 345                 350

Thr Ala Ala Asn Ile Thr Leu Asn Arg Ala Ser Gly Gly Asp Pro Glu
            355                 360                 365

Val Thr His His Met Phe Asn Cys Gly Gly Glu Phe Phe Tyr Cys Asn
    370                 375                 380

Thr Ser Gln Ile Phe Thr Asp Asn Ile Thr Asn Gly Ile Ile Ile Leu
385                 390                 395                 400

Pro Cys Arg Ile Arg Gln Ile Val Ser Ser Trp Met Arg Val Gly Arg
                405                 410                 415

Gly Ile Tyr Ala Pro Pro Ile Arg Gly Asn Ile Thr Cys Asn Ser Asn
            420                 425                 430

Ile Thr Gly Leu Leu Leu Thr Ser Asp Thr Pro Val Thr Asn Asn Ser
            435                 440                 445

Gly Asn Leu Thr Phe Arg Pro Thr Gly Gly Asn Met Lys Asp Ile Trp

```
                450             455             460
Arg Ser Glu Leu Tyr Lys Tyr Lys Val Val Arg Ile Glu Pro Leu Ser
465             470                 475                 480

Val Ala Pro Thr Lys Ala Arg Arg His Thr Val Ala Arg Gln Lys Asp
                485                 490                 495

Arg Gln Lys Arg Ala Ala Phe Gly Leu Gly Ala Leu Phe Leu Gly Phe
            500                 505                 510

Leu Gly Ala Ala Gly Ser Thr Met Gly Ala Ala Val Thr Leu Thr
            515                 520                 525

Val Gln Ala Arg Gln Leu Leu Ser Gly Ile Val Gln Gln Gln Asn Asn
            530                 535                 540

Leu Leu Lys Ala Ile Glu Ala Gln Gln His Leu Leu Gln Leu Ser Ile
545             550                 555                 560

Trp Gly Val Lys Gln Leu Gln Ala Arg Leu Leu Ala Val Glu Arg Tyr
                565                 570                 575

Leu Gln Asp Gln Gln Ile Leu Gly Leu Trp Gly Cys Ser Gly Lys Ala
            580                 585                 590

Val Cys Tyr Thr Thr Val Pro Trp Asn Asn Ser Trp Pro Gly Ser Asn
            595                 600                 605

Ser Thr Asp Asp Ile Trp Gly Asn Leu Thr Trp Gln Gln Trp Asp Lys
            610                 615                 620

Leu Val Ser Asn Tyr Thr Gly Lys Ile Phe Gly Leu Leu Glu Glu Ala
625             630                 635                 640

Gln Ser Gln Gln Glu Lys Asn Glu Arg Asp Leu Leu Glu Leu Asp Gln
            645                 650                 655

Trp Ala Ser Leu Trp Asn Trp Phe Asp Ile Thr Lys Trp Leu Trp Tyr
            660                 665                 670

Ile Lys Ile Phe Leu Met Ala Val Gly Gly Ile Ile Gly Leu Arg Ile
            675                 680                 685

Ile Met Thr Val Phe Ser Val Val Arg Val Arg Gln Gly Tyr Ser
            690                 695                 700

Pro Leu Ser Leu Gln Thr Leu Ile Pro Val Gln Arg Glu Gln Gly Arg
705             710                 715                 720

Leu Gly Glu Ile Asp Glu Gly Gly Gly Glu Gln Asp Arg Ser Arg Ser
            725                 730                 735

Val Arg Leu Val Glu Gly Cys Leu Pro Leu Ile Trp Asp Asp Leu Arg
            740                 745                 750

Asn Leu Gly Ile Trp Ser Tyr Gln Ser Leu Thr Ser Leu Ala Cys Asn
            755                 760                 765

Val Trp Arg Gln Leu Lys Thr Leu Gly His Leu Ile Leu His Ser Leu
770             775                 780

Arg Leu Leu Arg Glu Arg Leu Cys Leu Leu Gly Gly Ile Ile Gln Tyr
785             790                 795                 800

Trp Gly Lys Glu Leu Lys Ile Ser Ala Ile Ser Leu Leu Asp Ala Thr
            805                 810                 815

Ala Ile Ala Val Ala Glu Gly Thr Asp Arg Ile Ile Glu Ala Phe Gln
            820                 825                 830

Val Thr Leu Arg Ile Ile Arg Asn Ile Pro Arg Arg Ile Arg Gln Gly
            835                 840                 845

Leu Glu Arg Ala Leu Leu
    850

<210> SEQ ID NO 355
```

```
<211> LENGTH: 6
<212> TYPE: PRT
<213> ORGANISM: Artificial Sequence
<220> FEATURE:
<223> OTHER INFORMATION: C K-rich region

<400> SEQUENCE: 355

Arg Asp Lys Lys Gln Lys
1               5

<210> SEQ ID NO 356
<211> LENGTH: 4
<212> TYPE: PRT
<213> ORGANISM: Artificial Sequence
<220> FEATURE:
<223> OTHER INFORMATION: V3 loop protein backbone residues

<400> SEQUENCE: 356

Gly Asp Ile Arg
1

<210> SEQ ID NO 357
<211> LENGTH: 5
<212> TYPE: PRT
<213> ORGANISM: Artificial Sequence
<220> FEATURE:
<223> OTHER INFORMATION: Linker

<400> SEQUENCE: 357

Gly Gly Gly Gly Ser
1               5

<210> SEQ ID NO 358
<211> LENGTH: 4
<212> TYPE: PRT
<213> ORGANISM: Artificial Sequence
<220> FEATURE:
<223> OTHER INFORMATION: Cleavage site

<400> SEQUENCE: 358

Arg Glu Lys Arg
1

<210> SEQ ID NO 359
<211> LENGTH: 6
<212> TYPE: PRT
<213> ORGANISM: Artificial Sequence
<220> FEATURE:
<223> OTHER INFORMATION: Furin inducible R6 site

<400> SEQUENCE: 359

Arg Arg Arg Arg Arg Arg
1               5
```

SIV ENVELOPE TRIMER

RELATED APPLICATIONS AND INCORPORATION BY REFERENCE

This application is a continuation-in-part of international patent application Serial No. PCT/US2019/056867 filed Oct. 18, 2019, which published as PCT Publication No. WO 2020/081895 on Apr. 23, 2020, and which claims priority to U.S. provisional application Ser. No. 62/747,650, filed on Oct. 18, 2018.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under grant number AI100663 awarded by the National Institutes of Health. The government has certain rights in the invention.

SEQUENCE STATEMENT

The instant application contains a Sequence Listing which has been submitted electronically and is hereby incorporated by reference in its entirety. Said ASCII copy, was created Nov. 18, 2024, and amended on Nov. 20, 2024, is named Y7969_03051SL.txt and is 432,909 bytes in size.

FIELD OF THE INVENTION

The present invention relates to epitope-targeted SIV and HIV vaccines. The invention relates to epitopes that elicit antibodies that are broadly neutralizing against HIV. The invention provides epitopes that efficiently stimulate germline antibody production. The invention provides novel envelope glycoproteins which may be utilized as HIV-1 vaccine immunogens, antigens for crystallization, and for identification of broadly neutralizing antibodies. The invention encompasses preparation and purification of immunogenic compositions which are formulated into vaccines of the present invention.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-I and HIV-2, have been identified thus far, of which HIV-I is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4+ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4+T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 Jun. 1 9; 280(5371):1884-8). For fusion with its target cells, HIV-I uses a trimeric Env complex containing gp120 and gp41 subunits (Burton et al., Nat Immunol. 2004 March; 5(3): 233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 200 I; 77:195-262). In the latter case, neutralizing antibodies may bind to epitopes whose exposure is enhanced or triggered by receptor binding. However, given the potential antiviral effects of neutralizing antibodies, it is not unexpected that HIV-I has evolved multiple mechanisms to protect it from antibody binding (Johnson & Desrosiers, Annu Rev Med. 2002; 53:499-518).

Most experimental HIV-I vaccines tested in human and/or non-human primate suggests that a successful vaccine incorporate immunogens that elicit broad neutralizing antibodies (bnAbs) and robust cell-mediated immunity. HIV-I envelope glycoprotein (Env) is the main viral protein involved in the entry of the virus and is also the primary target for neutralizing antibodies, but due to immune evasion strategies and extreme sequence variability of Envs, generation of bnAbs has been a daunting task (Phogat S, Wyatt R. Curr Pharm Des. 2007; 13:213-27, Phogat S, et al. J Intern Med. 2007 262:26-43, Karlsson Hedestam G B, et al Nat Rev Microbial. 2008 6:143-55).

SUMMARY OF THE INVENTION

HIV and chimpanzee SIV Envs, the target of potentially protective neutralizing antibodies, display about 60% sequence conservation at the amino acid level, and HIV V2-apex bnAbs have been shown to neutralize certain chimpanzee SIV isolates, including the SIVcpzPtt isolate MT145, suggesting cross-species conservation of this epitope. The invention provides engineered molecules derived from SIV isolates that bind to broadly neutralizing HIV antibodies. In certain embodiments, the engineered molecules mimic structures and epitopes such as but not limited to V2 or V3.

In certain examples herein, the engineered molecules include SIVcpzPtt-based trimers including from the MT145 isolate and mutants of the MT145 isolate comprising amino acid substutions, such as Asn at position 171 by Lys, which display native trimer-like properties, and selectively binds V2 apex bnAbs. In certain embodiments, the engineered molecules are designed to bind to germline or germline-reverted antibodies. For example, molecules comprising the V2 apex epitope of MT145K are effective in activating V2-apex-specific B cell precursors.

The Applicants determined the structure of the MT145K trimer by cryo-EM at a global resolution of 4.1 Å. The overall architecture displays similarity to HIV Env trimers (Julien et al., 2013a; Lyumkis et al., 2013; Ozorowski et al., 2017; Pancera et al., 2014). In addition, the glycan shield composition of MT145K closely resembled that of HIV Env glycans but is sufficiently different in detailed positioning of the glycans to exclude binding of all HIV bnAbs except for those directed to the V2 apex. MT145K trimer immunization in a V2 apex unmutated common ancestor (UCA)-expressing knock-in mouse model reveals induction of a predominantly V2-apex-site neutralizing Ab response that is reproducible and cross-neutralizes a related set of HIV isolates.

The engineered molecules are useful as immungens in HIV vaccination strategies. In V2-apex bnAb unmutated common ancestor (UCA) H chain only knock-in mice, MT145K trimer-derived molecules reproducibly elicited Abs able to neutralize the autologous virus and several V2-apex Ab sensitive viruses. The specificities of the nAbs are dependent on the glycan at N160 and a lysine on strand C of the V2. Boosting with a cocktail of HIV Env trimers successfully recalled the V2 apex specific nAb responses and generated some enhanced heterologous neutralization.

In an aspect, the invention provides an engineered or non-naturally occurring molecule from Simian Immunodeficiency Virus (SIV) that binds to a broadly neutralizing antibody (bnAb) that binds to HIV. In an embodiment of the invention, the bnAb binds to the V2 apex region of HIV. In an embodiment, the bnAb is a germline or germline reverted HIV bnAb. In an embodiment, the bnAb comprises one, two, three, four, five, or six CDRs of a bnAB described herein, including without limitation sequences in Table 2, or comprises one or more complementarity determining regions (CDRs) of a heavy chain variable domain, and/or one or more CDRs of a light chain variable domain.

In certain embodiments, the engineered or non-naturally occurring molecule binds to a HIV bnAB which comprises an amino acid sequence at least 50% identical, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical to PG9 or to CH01 antibody.

In an embodiment of the invention, the molecule comprises a complex of gp120 and gp41. In certain embodiments, the molecules comprise all or part of a subunit, such as the Env protein of SIV. Env subunits and epitopes therefrom, particularly immunogenic epitopes are useful in the invention. Thus, in certain embodiments, the molecules comprise amino acids from SIV grafted into another protein or peptide, for example but without limitation HIV, HIV env, or other molecule capable of presenting an SIV V2 apex region and/or V2 apex epitope of the molecules herein. In an embodiment, the molecule comprises a gp140. In an embodiment, the molecule comprises a complex of gp120 and gp41. In an embodiment, the molecule comprises gp120 and gp140 that are covalently linked. In an embodiment, the molecule comprises gp120 and gp140 fusion. In an embodiment, the molecule comprises an SIV trimer. In an embodiment, the molecule comprises a chimeric trimer, such as but not limited to a chimeric trimer combining an SIV sequence within the V2 apex region that binds to a bnAb and HIV sequences elsewhere. In an embodiment, the molecule is a stabilized trimer, such as without limitation, a SOSIP, NFL, or UFO trimer.

In an embodiment, the SIV, V2 apex region, or V2 apex epitope comprises or is from SIVcpzPtt, SIVcpzPts, or SIVgor. In an embodiment, the V2 apex region, or V2 apex epitope comprises or is from the SIVcpzPtt isolate MT145 or other V2-apex sequence set forth herein. In an embodiment, the V2 apex region, or V2 apex epitope comprises one or more amino acid substitutions that improve binding to a HIV broadly neutralizing antibody (bnAb) or to a germline precursor of the HIV bnAb. In an embodiment, the V2 apex epitope is carried on an env protein or fragments altered by deletion, insertion, or substitution of amino acids to disrupt an immunogenic or immunodominant epitope other than the epitope that binds to a bnAb. I an embodiment, the V5 loop is altered. In an embodiment, one or more amino acids is substituted with a basic amino acid, e.g., arginine or lysine. In an embodiment, the amino acid corresponding to position 171 of the MT145 isolate is or is substituted with lysine.

As described herein, in certain embodiments of the invention, useful V2 apex sequences comprise two glycans, thus two glycosylated aspargine residues, and basic amino acid residues, preferably three or four basic amino acid residues, in a four-amino acid sequence, for example, without limitation, Xxx-Lys-Lys-Lys (SEQ ID NO:1), Lys-Xxx-Lys-Lys (SEQ ID NO:2), Lys-Lys-Xxx-Lys (SEQ ID NO:3), Lys-Lys-Lys-Xxx (SEQ ID NO:4), or Lys-Lys-Lys-Lys (SEQ ID NO:5). In certain embodiments, the molecule comprises Asn-Xxx$_a$-Asn-Xxx$_b$-Xxx$_c$-Xxx$_d$, wherein Xxx$_a$ comprises two or three amino acids, Xxx$_b$ comprises five to seven amino acids, and Xxx$_c$ comprises four amino acids, each of the four amino acid selected from Lys or Arg (SEQ ID NO:6).

In certain embodiments, molecules of the invention comprise the amino acid sequence N-C-$X_1$-F-N-$X_2$-$X_3$-$X_4$-$X_5$-$X_6$-$X_7$-$X_8$-$X_9$-$X_{10}$-$X_{11}$-$X_2$-$X_{13}$-$X_{14}$-$X_{15}$-$X_{16}$: wherein $X_1$ comprises S, T, N, or F; $X_2$ comprises I, V, T, Q, or M; $X_3$ comprises S or T; $X_4$ comprises S or T; $X_5$ comprises S, E, or G; $X_6$ comprises I, L, V or F; $X_7$ comprises K or R; $X_8$ comprises G or D; $X_9$ comprises K, R, E, or Q; $X_{10}$ comprises K, R, E, or Q; $X_{11}$ comprises K, R, E, or Q; $X_{12}$ comprises K, E, or Q; $X_{13}$ comprises E, T, V, I, or M; $X_{14}$ comprises Y or K; $X_{15}$ comprises A or S; and $X_{16}$ comprises F, I, or L (SEQ ID NO:7). In certain embodiments, at least three of $X_9$, $X_{10}$, $X_{11}$, and $X_{12}$ comprise basic amino acid residues (SEQ ID NO:8). In certain embodiments, all of $X_9$, $X_{10}$, $X_{11}$, and $X_{12}$ comprise basic amino acid residues (SEQ ID NO:9). In certain embodiments, $X_9$, $X_{10}$, $X_{11}$, and $X_{12}$ each comprise K (SEQ ID NO:10). In one such embodiment, the amino acid sequence comprises NCSFNVTTELRDKKRQVYSL (SEQ ID NO:11). In another embodiment, the amino acid sequence comprises NCSFNVTTELRDKKRKVYSL (SEQ ID NO:12). In another embodiment, the amino acid sequence comprises NCSFNVTTELRDKKKKEYSF (SEQ ID NO:13). In another embodiment, the amino acid sequence comprises NCSFNATTELRDKKKKEYAL (SEQ ID NO:14).

In certain embodiments, molecules of the invention comprise Asn-Cys-Ser-Phe-Asn-Val-Thr-Thr-Glu-Leu-Arg-Asp-Lys-Lys-Arg-Gln-Val-Tyr-Ser-Leu-Phe-Phe-Tyr (SEQ ID NO:15), or Asn-Cys-Ser-Phe-Asn-Val-Thr-Thr-Glu-Leu-Arg-Asp-Lys-Lys-Arg-Gln-Val-Tyr-Ser-Leu-Phe-Tyr (SEQ ID NO:16), or Asn-Cys-Ser-Phe-Asn-Val-Thr-Thr-Glu-Leu-Arg-Asp-Lys-Lys-Arg-Lys-Val-Tyr-Ser-Leu-Phe-Phe-Tyr (SEQ ID NO:17), or Asn-Cys-Ser-Phe-Asn-Val-Thr-Thr-Glu-Leu-Arg-Asp-Lys-Lys-Arg-Lys-Val-Tyr-Ser-Leu-Phe-Tyr (SEQ ID NO:18), or Asn-Cys-Ser-Phe-Asn-Val-Thr-Thr-Glu-Leu-Arg-Asp-Lys-Lys-Lys-Lys-Glu-Tyr-Ser-Phe-Phe-Phe-Tyr (SEQ ID NO:19); or Asn-Cys-Ser-Phe-Asn-Val-Thr-Thr-Glu-Leu-Arg-Asp-Lys-Lys-Lys-Lys-Glu-Tyr-Ser-Phe-Phe-Tyr (SEQ ID NO:20); or Asn-Cys-Ser-Phe-Asn-Ala-Thr-Thr-Glu-Leu-Arg-Asp-Lys-Lys-Lys-Lys-Glu-Tyr-Ala-Leu-Phe-Phe-Tyr (SEQ ID NO:21), or Asn-Cys-Ser-Phe-Asn-Ala-Thr-Thr-Glu-Leu-Arg-Asp-Lys-Lys-Lys-Lys-Glu-Tyr-Ala-Leu-Phe-Tyr (SEQ ID NO:22).

In an aspect, the invention provides a nucleic acid encoding the molecule from Simian Immunodeficiency Virus (SIV) that binds to a broadly neutralizing antibody (bnAb) that binds to HIV. In an embodiment, the nucleic acid comprises RNA. In an embodiment, the nucleic acid comprises DNA. In an embodiment, the nucleic acid is operably linked to a regulatory element operable in a cell. In certain such embodiments, the regulatory element is operable in a eukaryotic cell. In certain such embodiments, the regulatory element is operable in a prokaryotic cell. The invention further provides vectors, such as but not limited to viral vectors, comprising the nucleic acids and regulatory elements. In an embodiment of the invention, the viral vector is AAV. The invention further provides cell which comprise the nucleic acids, including cells that express the molecules of the invention.

In an aspect, the invention provides a method of eliciting an immune response in a mammal comprising administering an immunogenic composition comprising a molecule of the invention. In an embodiment, a method of stimulating an HIV bnAb is provided. In certain embodiments, the bnAb is a germline antibody or a germline reverted antibody. In an embodiment of the invention, the mammal is a human. In an embodiment, the mammal is a non-human primate, such as but not limited to a chimpanzee or gorilla. In an embodiment, the mammal is one capable of expressing one or more elements of a human immune system, for example a transgenic animal such as but not limited to a mouse. In one such embodiment, the mammal comprises and is capable of expressing a human germline or germline reverted antibody or germline or germline reverted heavy chain variable domain or light chain variable domain. In another embodiemt, the mammal comprises and is capable of expressing a repertoire of human germline genes.

In certain embodiments, a molecule of the invention is administered one time. In other embodiments, a molecule of the invention is administered multiple times, such as twice, three times, or more. In certain embodiments, more than one molecule is administered, such as two, three, four, or more molecules. When immunogenic compositions are administered at more than one time point, the molecules administered at each time can be the same or different. For example, two or more that are different molecules can be administered concurrently or sequentially. Alternatively, the same molecule can be administered on two or more occasions. Without being bound by theory, the molecules are administered in a course of immunization designed to favor production of bnAbs. bnAbs can be favored when a selected epitope that elicits bnAbs is present in multiple immunizations while other epitopes of the immunogen differ from one immunization to another.

In certain embodiments, one molecule of the invention is administered at a first time point to initiate an immune response, such as, for example, to stimulate germline antibody-expressing B cells, and again at a later time to boost an immune response. In certain embodiments, one molecule of the invention is administered at a first time point and another different molecule of the invention is administered at a later time to selectively boost the antibody response against an epitope common to both molecules that binds to a HIV bnAb.

In certain embodiments, a molecule of the invention is administered at a first time point to initiate an immune response, such as, for example, to stimulate germline antibody-expressing B cells, and an HIV molecule, antigen, or vaccine is administered at a later time point to boost the response against an HIV epitope that binds to a HIV bnAb.

In certain embodiments, the germline antibodies that are stimulated are bnAbs. In certain embodiments, the germline antibodies are precursors of bnAbs. In certain such embodiments, the germline antibodies undergo somatic hypermutation and selection during the course of an immune response to higher affinity and/or specificity bnAbs.

In certain embodiments, a molecule of the invention is administered to boost or reactivate memory B cells.

The invention provides immunogenic compostions comprising the molecules of the invention. In certain embodiments, a molecule of the invention is comprised in a composition or administered with an adjuvant. In certain embodiments, the adjuvant comprises a lecithin. In certain embodiments, the lecithin is (a) combined with an acrylic polymer, (b) in a coated oil droplet in an oil-in-water emulsion, or (c) in an acrylic polymer in an oil-in-water emulsion. In certain embodiments the adjuvant is ISCOMATRIX or Adjuplex. In certain embodiments the adjuvant comprises alum.

In certain embodiments, the immunogenic composition comprises a liposome or a nanoparticle. In certain embodiments, the molecule of the invention is fixed. In an embodiment, the fixing agent can be glutaraldehyde. In an embodiment, the trimer or immunogen comprising the trimer is quenched with glycine.

In an aspect, the invention provides a method of engineering a molecule or immunogen capable of eliciting a broadly neutralizing antibody (bnAb) directed to HIV. The method comprises identifying a viral structure such as a viral epitope of SIV or other immunodeficiency virus that is conserved in HIV, selecting or designing bnAb that binds to the epitope, and designing a molecule or immunogen that comprises the conserved epitope, optionally modified to bind to a germline or germline derived antibody precursor of the bnAb. In certain embodiments, the structure, region or epitope is that of V2 of SIV.

In an aspect of the invention, there is provided a method of identifying or selecting a broadly neutralizing component of binding pair wherein such component binds to HIV and is broadly neutralizing. The method comprises contacting a molecule of the invention with a candidate binding pair component and selecting or identifying the component as broadly neutralizing if it binds to a molecule of the invention. In certain embodiments, the broadly neutralizing component comprises a bnAb. In certain embodiments, the broadly neutralizing component comprises a germline or germline reverted bnAb. In certain embodiments, the broadly neutralizing component is a germline or germline reverted antibody that is a precursor of a bnAb.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 5A-5F. A close-up view of regions on the MT145K trimer that correspond to those recognized by HIV bnAbs on HIV trimers. A. V2 apex bnAb binding region: cryo-EM model of PGT145 bnAb (HC: transparent sandy brown; LC: transparent orchid) in complex with BG505 SOSIP trimer depicting V1V2 loops in ribbon representation ((Lee et al., 2017) PDB: 5V8L). The strand C K-rich region ($^{166}$RDKKQK$^{171}$(SEQ ID NO:355); red spheres) and the glycan N160 (forest green sticks) that form the epitope for PGT145 bnAb are indicated. The elements in the core epitope interact with the CDRL1 loop and the long CDRH3 loop that penetrates through glycans to reach the positively charged surface underneath. Both glycan N160 and the positively charged protein residues are conserved between BG505 HIV-1 and MT145K SIV Env trimers. B. V3-glycan bnAb binding region: cryo-EM model of PGT128 bnAb (HC: transparent sandy brown; LC: transparent orchid) in complex with the BG505 SOSIP trimer ((Lee et al., 2015) PDB: 5ACO). The V3 loop protein backbone residues ($^{324}$GDIR$^{327}$(SEQ ID NO:356); depicted in purple spheres) and the glycans N301 and N332 form the bnAb epitope and are shown to interact with the antibody CDR loops. The MT145K trimer has a glycan at N334 rather than N332 and the glycan points away from the expected location of the PGT128 Ab paratope. In addition, MT145K Env has glycans at two positions N412, (positioned differently on HIV Env) and N442 (absent on HIV Envs) and particularly the latter will clash with PGT128 CDRH2 and prevent it from interacting with the protein part of the epitope. C. The gp120-gp41 interface bnAb binding region: cryo-EM model of PGT151 bnAb bound to a membrane-extracted clade B JRFL Env trimer. The structure depicts PGT151 bnAb CDRs interacting with gp120 and the gp41 interface regions ((Lee et al., 2016); PDB: 5FUU). PGT151 CDRH3 interacts with the epitope formed by the protein backbone (in both gp120 and gp41) including the fusion peptide (depicted in pink) and the gp120 (N88, N448) and gp41 (N611 and N637) glycans (not shown). PGT151 Ab CDR loops interact with the FP region on the BG505 trimer. The MT145K trimer FP region (cyan) remains hidden inside the trimer. D. Cryo-EM model of 2-domain human sCD4 with B41 SOSIP trimer ((Ozorowski et al., 2017); PDB: 5VN3). The structure shows how the Phe43 residue on sCD4 stacks into the Env cavity lining Trp427. This Trp427 cavity is conserved between HIV-1 and MT145K Envs to accommodate CD4 binding. E-F. CD4bs bnAb binding region: crystal structure of VRC01 bnAb in complex with 93TH057 gp120 ((Zhou et al., 2010) PDB: 3NGB). The structure depicts VRC01 CDRH3, CDRL3 and CDRL1 loops interacting with the protein residues in loop D (HXB2: 278-282) and the glycan at N276. The MT145K trimer lacks the N276 glycan and bears glycan N236 (unique to SIV Env) in place of N234 that would clash with the VRC01 CDRL1 loop. Additionally, the MT145K Env trimer has a longer gp120-V5 loop due to a 6-amino acid insertion at HIV HXB2-456 residue that would shift the loop such that it clashes with the CDRH2 the VRC01 Ab.

FIG. 6A-6D. Immunogenicity of MT145-WT compared to MT145K trimers in CH01 UCA HC-only knock-in mice. A. Schematic showing immunization schedule of CH01 UCA "HC-only" KI mice with MT145-WT and engineered MT145K trimers. The CH01 UCA "HC-only" KI mice were immunized twice with 25 µg of the soluble trimer with GLA-SA as adjuvant. Time points for immunization and bleeds are indicated. B. ELISA binding of the MT145-WT and MT145K group trimer-immunized CH01 UCA "HC-only" KI mice serum samples (pre-bleed (Pre), two-weeks post prime (Bleed #1) and two-weeks post boost-1 (Bleed #2)) with soluble MT145K SOSIP and its glycan knock-out variant (MT145K N160K) trimers. C. Neutralization titrations of the MT145-WT and MT145K group trimer immunized CH01 UCA "HC-only" KI mice sera (pre-bleed (Pre), post prime (Bleed #1) and post boost-1 (Bleed #2)) with MT145K virus and a CH01-sensitive virus (Q23_17). 3-fold diluted sera were tested against the viruses in a TZM-bl reporter cell assay. D. $ID_{50}$ neutralization titers of the MT145-WT and MT145K group trimer-immunized CH01 UCA "HC-only" KI mice sera (pre- and post-immunization bleed time points). Neutralization was assessed against the priming immunogen-matched autologous viruses in each group (MT145-WT group: MT145-WT virus, and MT145K group: MT145K virus), the N160 glycan knock-out variant of MT145K virus (MT145K N160A) and a CH01-sensitive virus, Q23_17. The numerical values shown in the table represent the $ID_{50}$ neutralization titers of the immune serum samples and were calculated by non-linear regression method from the percent neutralizations of serum titrations with virus.

FIG. 7A-7C. Immunizations combining chimpanzee SIV MT145K trimer with HIV trimers in CH01 UCA HC-only knock-in mice. A. Schematic showing immunization schedule of CH01 UCA "HC-only" KI mice with a combination of chimpanzee SIV MT145K trimer and HIV Env-derived trimers. A group of 5 animals was immunized with two doses of MT145K trimer (prime: week-0 and boost-1: week-4) followed by further boosting (boost-2 at week-8) with an HIV Env derived 3-trimer cocktail (C108, WITO and ZM197-ZM233V1V2). The V1V2 loops on trimer cartoons are depicted in red to highlight the region is shared across HIV and SIV Env trimers. The CH01 UCA "HC-only" KI mice were immunized with 25 µg of the soluble MT145K trimer or HIV trimer cocktail (25 µg total protein) with GLA-SE as adjuvant. Time points for the immunization and the bleeds are indicated. B. Neutralization of the pre- and post-immune sera were carried out against a panel of viruses in the TZM-bl reporter cell assay. The numerical values in the table represent $ID_{50}$ neutralization titers of the pre-bleed (Pre) and post-prime (Bleed #1), post boost-1 (Bleed #2) and post boost-2 (Bleed #3) serum samples. Neutralization was assessed against the priming immunogen-matched autologous virus, MT145K, its N160 glycan knock-out variant, boosting immunogen-matched, CH01 sensitive, and global panel HIV Env-encoding viruses. The numerical values shown in the table represent the $ID_{50}$ serum neutralization titers and were calculated by non-linear regression method from the percent neutralizations of serum titrations with virus. The $IC_{50}$ neutralization titers for the CH01 mature Ab against the virus panel are shown. C. The $ID_{50}$ virus neutralization titers of the Bleed #4 serum samples collected post boost-2 immunization with an HIV three-trimer cocktail. The neutralization of the post-immune sera was assessed against the priming immunogen-matched autologous virus, MT145K, the boosting immunogen-matched, CH01 sensitive viruses, and global panel HIV Env-encoding viruses. Each filled circle in the plot represents virus $ID_{50}$ neutralization values for the individual animals; an asterisk (*) indicates that 50% neutralization was not reached at a 1:100 serum dilution.

FIG. 8A-8B. Design and purification of SIVcpzPtt envelope derived SOSIP.664 trimers. A. Amino-acid sequence alignment of 4 SIVcpzPtt envelope sequences (GAB1 (SEQ ID NO:25), MB897 (SEQ ID NO:26), EK505 (SEQ ID NO:27) and MT145 (SEQ ID NO:28)) with reference HIV-1 Env sequence, HXB2 (SEQ ID NO:24), showing SOSIP.664 trimer stabilizing modifications. The soluble SOSIP.664 trimer modifications include: (i) incorporation of a disulfide bond between residue 501 of gp120 (A501C) and residue 605 of gp41 (T605C), (ii) replacing naturally occurring gp120 and gp41 cleavage site with R6-cleavage site (shown in blue), (iii) I559P substitution in the gp41, (iv) and a truncation in the gp41 subunit at residue 664. B. Size Exclusion Chromatography (SEC) profiles of *Gallanthus nivalis* lectin (GNL) purified trimers on Superdex 200 Increase 10/300 GL column. The SEC profiles show the aggregate/trimer-dimer, trimer and monomer peaks of the GNL-purified proteins. The MT145 SOSIP.664 trimer showed substantial protein fractions that assemble as a trimer.

FIG. 10A-10B. Design of inferred germline (iGL) versions of V2 apex bnAbs, PG9 and CH01. The heavy chain (VH), light chain (VL) and the diversity (D) and the joining (J) regions in the mature antibodies were reverted to their corresponding inferred germline genes. The amino-acid reversions from mature VH (panel A) and VL (panel B) chains to germline residues are indicated by asterisks. The VH_iGL and the VL_iGL chains were paired and expressed as soluble antibodies. The GenBank accession numbers and SEQ ID NOS for the heavy and light chain inferred germline versions of PG9 and CH01 broadly neutralizing antibodies are PG9_VDJH_iGL: Accession MK825341 (SEQ ID NO:32); PG9VJL_iGL: Accession MK825342 (SEQ ID NO:41); CH01VDJH_iGL: Accession MK825343 (SEQ ID NO:49); and CH01VJL_iGL: Accession MK825344 (SEQ ID NO:58). Depicted PG9-related sequences are identified in the Sequence Listing as follows: IGHV3-33-05: SEQ ID NO:29; PG9_HC: SEQ ID NO:30; PG9VH_iGL: SEQ ID NO:31; IGHJ6-03: SEQ ID NO:36; IGHD3-3-01: SEQ ID NO:37; IGLV2-14-01: SEQ ID NO:38; PG9_LC: SEQ ID NO:39; PG9VL_iGL: SEQ ID NO:40; IGLJ3-02: SEQ ID NO:45. Depicted CH01-related sequences are identified in the Sequence Listing as follows: IGHV3-20-01: SEQ ID NO:46; CH01_HC: SEQ ID NO:47; CH01VH_iGL: SEQ ID NO:48; IGHJ2-01: SEQ ID NO:53; IGHD3-10-01: SEQ ID NO:54; IGKV3-20-01: SEQ ID NO:55; CH01_LC: SEQ ID NO:56; CH01VL iGL: SEQ ID NO:57; IGKJ1-01: SEQ ID NO:62.

FIG. 16. Antigenic profile of various MT145K Env forms with HIV Env-specific mAbs. Neutralizing and non-neutralizing HIV Env-specific mAbs targeting various epitope specificities, including V2-apex, V3-N332, linear V3, CD4bs, CD4i and gp120-gp41 interface were tested with MT145K and BG505 Env-encoding pseudoviruses in a neutralization assay and against the MT145K SOSIP trimer and MT145K gp120 monomer by ELISA. The reciprocal $IC_{50}$ neutralization titers against the MT145K and BG505 viruses and the 50% ELISA binding titers ($EC_{50}$ binding with trimer and gp120 proteins) for each mAb are shown.

FIG. 17A-17E. Molecular details of the regions on the MT145K trimer that correspond to bnAb epitopes on HIV trimers. A. Crystal structure of PG9 (PDB: 3U2S (McLellan et al., 2011)) bound to ZM109 V1V2 apex and docked onto BG505. The long CDRH3 of PG9 interacts with the K-rich region of the V2 apex and the glycans at N160. Both glycan/peptide epitope elements are conserved between MT145K and HIV-1 BG505 Env and, hence, PG9 binds strongly to both. B-C. Crystal structures of V3-N332 bnAbs PGT121 (5T3Z (Gristick et al., 2016)) and PGT135 (PDB: 4JM2 (Kong et al., 2013)) interacting with their epitopes at the base of the V3 loop. The N332 glycan required by these bnAbs is absent on MT145K Env and the N334 glycan is projecting away from the epitopes and is not a functional substitute. In addition, the glycans N412 and N442, the latter being unique to the SIV Env, would clash with the CDRs of these bnAbs, thus preventing interaction. D-E. Cryo-EM reconstruction of CD4bs bnAb 3BNC117, bound to BG505 trimer (PDB: 5V8M (Lee et al., 2017)). The lack of 3BNC117 binding with MT145K SIV Env trimer correlates with significant sequence variation in loop D and a clash of bnAb CDR loops with the N236 glycan that is unique to SIV. Moreover, a longer MT145 V5 loop would introduce a clash with 3BNC117 CDRH2.

FIG. 19. Amino-acid sequence of the Chimpanzee Simian Immunodeficiency virus (SIVcpz) envelope trimer construct, MT145K dV5 SOSIP.664 (SEQ ID NO:316), showing SOSIP.664 trimer stabilizing modifications. The soluble SOSIP.664 trimer modifications include: (i) replacement of N-terminus envelope gp120 signal peptide sequence with tissue plasminogen activator (TPA) signal sequence for higher protein expression (shown in yellow) (ii) incorporation of a disulfide bond between residue 501 of gp120 (A501C) and residue 605 of gp41 (T605C) (shown in turquoise), (iii) replacing naturally occurring gp120 and gp41 cleavage site with R6-cleavage site (shown in red), (iv) I559P substitution in the gp41 (shown in grey), (v) and a truncation in the gp41 subunit at residue 664 by inserting a stop codon (indicated by an asterisk (*)). Underlined residues (KD) indicate V5 deletion position.

FIG. 21A-21C: Immunogenicity of MT145KdV5 SOSIP trimer immunogen in non-human primate model. A. Schematic showing immunization schedule of non-human primates (NHPs) vaccinated with MT145KdV5 SOSIP trimer. A group of 6 animals was immunized twice with MT145KdV5 trimer (prime, week 0; boost-1, week 8). The NHPs were immunized with 100 ug of the soluble MT145KdV5 trimer with Alum/ISCO-MPLA adjuvants. Time points for the immunizations and the bleeds are indicated. B. ELISA binding of polyclonal serum antibodies to MT145KdV5 SOSIP trimer. EC50 binding titers of pre-bleed (PB), post prime (1 wk, 2 wk, 4 wk and 8 wk) and post boost (9 wk and 10 wk) serum samples with MT145KdV5 SOSIP trimer. C. Neutralization curves of 10 wk immune serum IgG samples against the autologous MT 145KdV5 virus. Purified IgGs from 10 wk immune serum samples were tested against the MT145KdV5 virus in TZM-bl reporter cell-based assay. IC50 virus neutralization titers for each serum IgG sample are shown. V2-apex bnAb, PGT145 was control for the neutralization assay.

DETAILED DESCRIPTION OF THE INVENTION

Figures 1A, 1B:
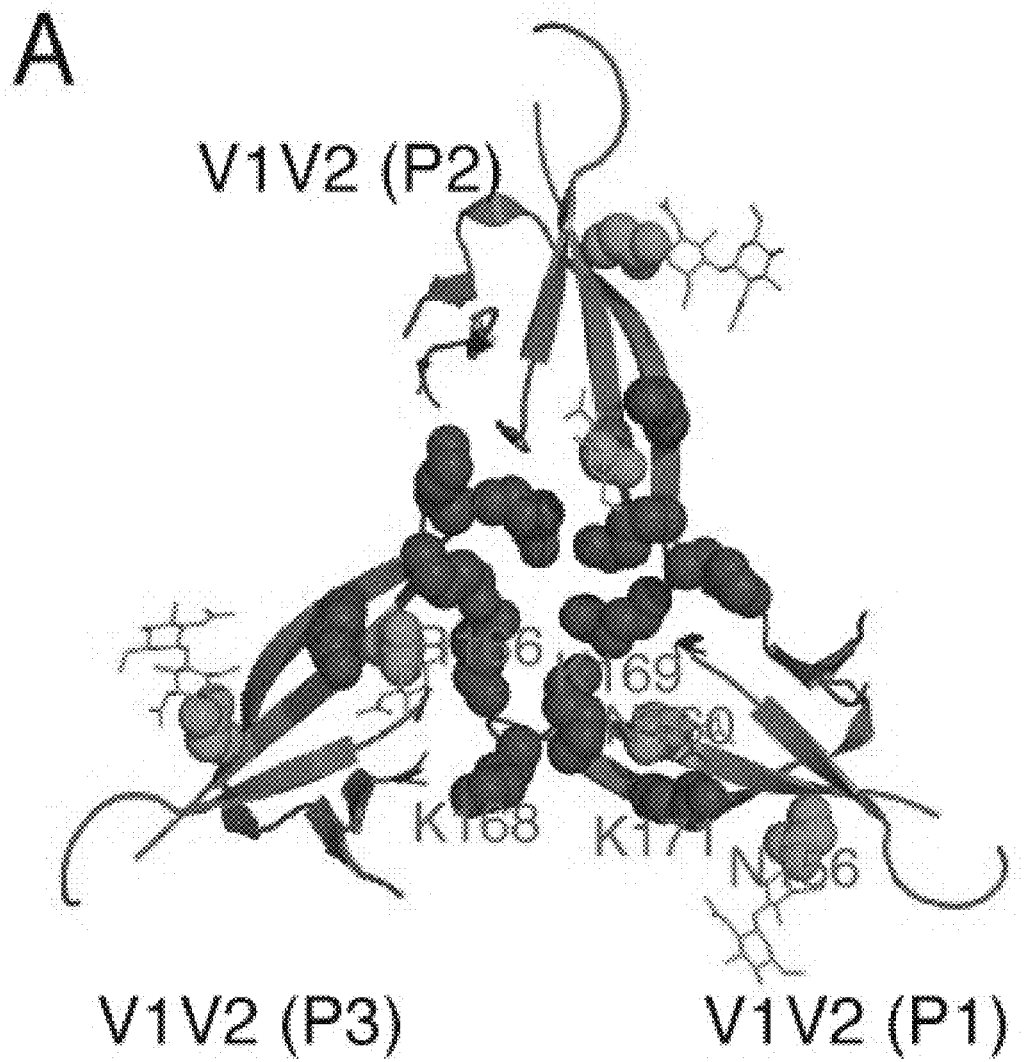
FIG. 1A-1D. Design of a chimpanzee Env-stabilized trimer and binding to V2 apex bnAb iGL Abs. A. Structural arrangement of the V2 apex bnAb core epitope region on BG505.664 soluble Env trimer (modified from (Garces et al., 2015) (PDB: 5CEZ)). The ribbon representation of V1V2 loop strands that form the trimer apex show a cluster of positively charged lysine-rich peptide regions (HXB2-R166-K171: R or K residues shown as blue spheres) and the two glycans N156 and N160 (depicted in green spheres with lines). The side chains of the positively charged residues intersperse with the side chains of residues from adjacent protomers to form a continuous positively charged surface at the tip of the trimer to provide a minimal V2 apex bnAb epitope. B. Amino-acid sequence alignment of strand B and C V2 of HXB2 (SEQ ID NO:23), HIV CRF250 (SEQ ID NO:20), CAP256. SU (SEQ ID NO:22), chimpanzee SIV MT145 WT (SEQ ID NO:16) and its V2-modified variant (Q171K), MT145K (SEQ ID NO:28). Glutamine (Q) at position 171 (shown in red) was substituted with lysine (K) in MT145 Env to gain binding to V2 apex bnAb inferred germline (iGL) Abs. C. ELISA binding of mature V2 apex bnAbs, PG9, CAP256.09 and CH01 and their iGL versions to WT MT145 (red) and MT145K SOSIP trimers. D. Octet binding curves (association: 120s (180-300) and dissociation: 240s (300-540)) of CAP256 UCA and CH01 iGL Abs and their respective mature Ab versions (CAP256.09 and CH01) to MT145K trimer, its glycan knock-out (N160K) variant, K-rich core epitope substituted variants and the corresponding monomeric gp120. The Abs were immobilized on human IgG Fc capture biosensors and 1 uM trimer or gp120 proteins used as analytes. The binding response is shown as nanometer (nm).

The invention provides molecules wich comprise regions and epitopes based on Env of various SIV isolates and advantageously bind to and are capable of stimulating production of bnAbs of HIV and display V2 apex epitopes associated with that. Virus isolates may display epitopes that are conserved across species boundaries. For example, SIV displays epitopes observed to bind to SIV and HIV antibodies, and it is theorized that such epitopes are both important for virus function and provide a means for crossing of species boundaries. Nevertheless, such epitopes may not be highly immunogenic, thus immune responses may be dominated by antibodies that bind to other more variable viral epitopes. Such variable epitopes may not be present on a broad range of viral isolates such that vaccines presenting those epitopes will not be protective against a broad range of viral isolates. Moreover, epitopes that might stimulate bnAbs may be inaccessible to antibody binding, one consequence being limited stimulation of germline B cells making antibodies capable of recognizing such epitopes. Accordingly, the invention provides engineered virus components and vaccines that display epitopes that bind to and are capable of efficiently stimulating antibodies that broadly neutralize HIV. Moreover, the invention compositions and methods of making and using immunogenic molecules that efficiently stimulate germline B cells and antibody production by those cells.

One of the Env sites that has shown great promise for vaccine targeting is the V2 apex bnAb epitope (Andrabi et al., 2015; Gorman et al., 2016; Voss et al., 2017). This bnAb epitope sits at the 3-fold axis of the trimer and is primarily formed by a patch rich in positively charged lysine residues and protected by two glycans at HXB2 HIV-1 reference positions N160 and N156/N173 that are part of the Env glycan shield. The bnAb precursors targeting this site possess a long anionic heavy-chain complementarity-determining region 3 (CDRH3) that penetrates the glycan shield to reach the protein epitope surface underneath. BnAb prototypes within this class interact with the V2 apex bnAb protein-glycan core epitope through common germline-encoded motifs and are, thus, targetable by unique trimers that bind with their germline Ab versions. Hence, the germline-priming immunogens to this site could be based directly on native-like trimer configurations. Other features of this site include: a) V2 apex bnAbs are elicited frequently in humans that make bnAbs, b) they emerge early in infection, and c) they possess relatively low levels of somatic mutation compared to most other HIV Env bnAbs.

Among the major HIV Env bnAb specificities the V2 apex site is a bnAb site that consistently exhibits cross-group neutralizing activity with virus Envs derived from HIV-1 group M, N, O and P, and in addition, V2-apex bnAbs display cross-neutralizing activity with the Simian Immunodeficiency Virus (SIV) isolates that infect chimpanzees (SIVcpzPtt [Pan troglodytes troglodytes], SIVcpzPts [Pan troglodytes *schweinfurthii*]) and gorillas (SIVgor). The sought to design molecules useful as immunogens, based on features of SIVcpzPtt Env, that could guide an immunofocused response to the HIV V2 apex bnAb epitope. The applicants elected a stable trimer as a useful format for the design of SIVcpzPtt-based molecules and immunogens. The SIV based immunogens of the invention are capable of enriching V2 apex-specific B cells, and owing to V2 apex species cross-conservation, help guide a V2-focused neutralizing Ab response when coupled with HIV trimers in a sequential prime/boost immunization strategy. In such an immunization scheme, overall Env backbone sequence diversity in combination with conservation of the V2 apex bnAb epitope in sequentially administered immunogens also reduces germinal center competition for V2 apex-specific B cells, favors a B cell recall response to the V2 apex bnAb epitope, and reduces off-target Env-specific responses.

The invention pertains to the identification, design, synthesis and isolation of molecules from SIV proteins, peptides, fragments, and mutants thereof that bind to HIV directed antibodies. The invention also pertains to molecules from SIV proteins, peptides, fragments, and mutants thereof used as immunogens to stimulate HIV directed antibodies, especially bnAbs that bind to HIV as well as nucleic acids encoding the same. The immunogens may comprise proteins, peptides, fragments, such as the various trimers disclosed herein The present invention also relates to homologues, derivatives and variants of the sequences of the mutant trimers and nucleic acids encoding the same, wherein it is preferred that the homologue, derivative or variant have at least 50%, at least 60%, at least 70%, at least 75%, at least 80%, at least 85%, at least 90%, at least 93%, at least 95%, at least 97%, at least 98% or at least 99% homology or identity with the sequence of the mutant trimers and nucleic acids encoding the same. It is noted that within this specification, homology to sequences of the mutant proteins and nucleic acids encoding the same refers to the homology of the homologue, derivative or variant to the binding site of the mutant proteins and nucleic acids encoding the same.

The invention still further relates to nucleic acid sequences expressing the proteins, peptides, fragments, trimers, and mutants disclosed herein, or homologues, variants or derivatives thereof and the epitopes presented thereon. One of skill in the art will know, recognize and understand techniques used to create such. Additionally, one of skill in the art will be able to incorporate such a nucleic acid sequence into an appropriate vector, allowing for production of the amino acid sequence of mutant proteins and nucleic acids encoding the same or a homologue, variant or derivative thereof.

The proteins, peptides, fragments, trimers, and mutants disclosed herein, or homologues, variants or derivatives thereof and the epitopes presented thereon may also be useful in screening for ligands that bind to said epitopes. Such ligands preferably block the epitopes and thus prevent infection.

Where used herein and unless specifically indicated otherwise, the following terms are intended to have the following meanings in addition to any broader (or narrower) meanings the terms might enjoy in the art:

The term "isolated" or "non-naturally occurring" is used herein to indicate that the isolated moiety (e.g. peptide or compound) exists in a physical milieu distinct from that in which it occurs in nature. For example, the isolated peptide may be substantially isolated with respect to the complex cellular milieu in which it naturally occurs. The absolute level of purity is not critical, and those skilled in the art may readily determine appropriate levels of purity according to the use to which the peptide is to be put. The term "isolating" when used a step in a process is to be interpreted accordingly.

In many circumstances, the isolated moiety will form part of a composition (for example a more or less crude extract containing many other molecules and substances), buffer system, matrix or excipient, which may for example contain other components (including proteins, such as albumin).

In other circumstances, the isolated moiety may be purified to essential homogeneity, for example as determined by PAGE or column chromatography (for example HPLC or mass spectrometry). In preferred embodiments, the isolated peptide or nucleic acid of the invention is essentially the sole peptide or nucleic acid in a given composition.

In an advantageous embodiment, a tag may be utilized for purification or biotinylation. The tag for purification may be a his tag. In another embodiment, the tag for biotinylation may be an avi-tag. Other tags are contemplated for purification, however, purification may be accomplished without a tag. In another embodiment, antibody (such as, not limited to, a broadly neutralizing antibody) affinity columns are contemplated. In anoother embodiment, lectin columns are contemplated.

Native-like soluble trimers can be made by several methods that all involve stabilizing associations between envelope protein subunits. See, e.g., P. Dosenovic et al, "Immunization for HIV-1 broadly neutralizing antibodies in human Ig knockin mice," Cell, 161:1-11, 2015; J. G. Jardine et al, "Priming a broadly neutralizing antibody response to HIV-1 using a germline targeting immunogen," Science, doi: 10.1126/science.aac5894, 2015 and R. W. Sanders et al, "HIV-1 neutralalizing antibodies induced by native-like envelope trimers," Science, doi: 10.1 126/science.aac4223, 2015.

The proteins and compounds of the invention need not be isolated in the sense defined above, however.

Compounds which have a chemical structure selected using the invention, wherein said compounds are neutralizing antibody binders, form a further aspect of the invention; and, such compounds may be used in methods of medical treatments, such as for diagnosis, preventing or treating HIV or for eliciting antibodies for diagnosis of HIV, including use in vaccines. Further, such compounds may be used in the preparation of medicaments for such treatments or prevention, or compositions for diagnostic purposes. The compounds may be employed alone or in combination with other treatments, vaccines or preventatives; and, the compounds may be used in the preparation of combination medicaments for such treatments or prevention, or in kits containing the compound and the other treatment or preventative.

The invention relates to immunogenic molecules that bind to and stimulate antibody production, particularly molecules that efficiently stimulate germline antibodies that are broadly neutralizing and/or precursors to antibodies that are broadly neutralizing against epitopes common to a variety of HIV isolates. The common epitopes may be evolutionarily selected and not especially immunogenic. Thus it can be beneficial to present antigenic molecules to the immune system that efficiently stimulate antibodies that bind to the common epitope while avoiding antibodies directed at epitopes that are not broadly neutralizing. Accordingly, the invention provides molecules engineered from SIV env regions designed to bind to and stimulate germline antibodies that are broadly neutralizing HIV antibodies or are precursors of broadly neutralizing HIV antibodies.

As described herein, in certain embodiments of the invention, useful V2 apex sequences comprise two glycans, thus two glycosylated aspargine residues, and basic amino acid residues, preferably three or four basic amino acid residues, in a four-amino acid sequence, for example, without limitation, Xxx-Lys-Lys-Lys (SEQ ID NO:1), Lys-Xxx-Lys-Lys (SEQ ID NO:2), Lys-Lys-Xxx-Lys (SEQ ID NO:3), Lys-Lys-Lys-XXX (SEQ ID NO:4), or Lys-Lys-Lys-Lys (SEQ ID NO:5). In certain embodiments, the molecule comprises Asn-$Xxx_a$-Asn-$Xxx_b$-$Xxx_c$-$Xxx_d$, wherein $Xxx_a$ comprises two or three amino acids, $Xxx_b$ comprises five to seven amino acids, and $Xxx_c$ comprises four amino acids, each of the four amino acid selected from Lys or Arg.

In certain embodiments, molecules of the invention comprise the amino acid sequence N-C-$X_1$-F-N-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$(SEQ ID NO:7): wherein $X_1$ comprises S, T, N, or F; $X_2$ comprises I, V, T, Q, or M; $X_3$ comprises S or T; $X_4$ comprises S or T; $X_5$ comprises S, E, or G; $X_6$ comprises I, L, V or F; $X_7$ comprises K or R; $X_8$ comprises G or D; $X_9$ comprises K, R, E, or Q; $X_{10}$ comprises K, R, E, or Q; $X_{11}$ comprises K, R, E, or Q; $X_{12}$ comprises K, E, or Q; $X_{13}$ comprises E, T, V, I, or M; $X_{14}$ comprises Y or K; $X_{15}$ comprises A or S; and $X_{16}$ comprises F, I, or L. In certain embodiments, at least three of $X_9$, $X_{10}$, $X_{11}$, and $X_{12}$ comprise basic amino acid residues. (SEQ ID NO: 8) In certain embodiments, all of $X_9$, $X_{10}$, $X_{11}$, and $X_{12}$ comprise basic amino acid residues. (SEQ ID NO: 9) In certain embodiments, $X_9$, $X_{10}$, $X_{11}$, and $X_{12}$ each comprise K. (SEQ ID NO: 10) In one such embodiment, the amino acid sequence comprises NCSFNVTTELRDKKRQVYSL (SEQ ID NO:11). In another embodiment, the amino acid sequence comprises NCSFNVTTELRDKKRKVYSL (SEQ ID NO:12). In another embodiment, the amino acid sequence comprises NCSFNVTTELRDKKKKEYSF (SEQ ID NO:13). In another embodiment, the amino acid sequence comprises NCSFNATTELRDKKKKEYAL (SEQ ID NO:14).

In certain embodiments, molecules of the invention comprise Asn-Cys-Ser-Phe-Asn-Val-Thr-Thr-Glu-Leu-Arg-Asp-Lys-Lys-Arg-Gln-Val-Tyr-Ser-Leu-Phe-Phe-Tyr (SEQ ID NO:15), or Asn-Cys-Ser-Phe-Asn-Val-Thr-Thr-Glu-Leu-Arg-Asp-Lys-Lys-Arg-Gln-Val-Tyr-Ser-Leu-Phe-Tyr (SEQ ID NO:16), or Asn-Cys-Ser-Phe-Asn-Val-Thr-Thr-Glu-Leu-Arg-Asp-Lys-Lys-Arg-Lys-Val-Tyr-Ser-Leu-Phe-Phe-Tyr (SEQ ID NO:17), or Asn-Cys-Ser-Phe-Asn-Val-Thr-Thr-Glu-Leu-Arg-Asp-Lys-Lys-Arg-Lys-Val-Tyr-Ser-Leu-Phe-Tyr (SEQ ID NO:18), or Asn-Cys-Ser-Phe-Asn-Val-Thr-Thr-Glu-Leu-Arg-Asp-Lys-Lys-Lys-Lys-Glu-Tyr-Ser-Phe-Phe-Phe-Tyr (SEQ ID NO:19); or Asn-Cys-Ser-Phe-Asn-Val-Thr-Thr-Glu-Leu-Arg-Asp-Lys-Lys-Lys-Lys-Glu-Tyr-Ser-Phe-Phe-Tyr (SEQ ID NO:20); or Asn-Cys-Ser-Phe-Asn-Ala-Thr-Thr-Glu-Leu-Arg-Asp-Lys-Lys-Lys-Lys-Glu-Tyr-Ala-Leu-Phe-Phe-Tyr (SEQ ID NO:21), or Asn-Cys-Ser-Phe-Asn-Ala-Thr-Thr-Glu-Leu-Arg-Asp-Lys-Lys-Lys-Lys-Glu-Tyr-Ala-Leu-Phe-Tyr (SEQ ID NO:22).

The bnAb stimulating engineered V2 apex region sequences of the invention, such as but not limited to MT145K, may be incorporated in engineered env proteins and protein fragments. Exemplary, non-limiting examples of env proteins with GenBank sequence accession numbers are set forth in the table below. See also public databases such as hiv.lanl.gov/components/sequence/HIV/search/search.html. Along with the V2 apex region sequenes, the env proteins and fragments can comprise sequences set forth in the table below (e.g., env sequences of naturally occurring SIV variants and escape mutants isolated from infected individuals) or be similar in sequence to such isolated variants. Thus, alternative embodiments of env proteins and fragments have at least 50%, at least 55%, at least 60%, at least 65%, at least 70%, at least 75%, at least 80%, at least 85%, at least 90%, at least 95%, at least 96%, at least 97%, at least 98%, at least 99% identity to the SIV env proteins in Table 1. (See hiv.lanl.gov/components/sequence/HIV/search/search.html)

TABLE 1

Exemplary SIV ENV proteins

| Patient ID | Accession | SEQ ID NO: | Name | Subtype | Country |
|---|---|---|---|---|---|
| Marylin(4288) | AF103818 | 317 | US_Marilyn | CPZ | United States |
| CAM3(4290) | AF115393 | 318 | CAM3 | CPZ | Cameroon |
| GAB2(3694) | AF382828 | 319 | SIVcpzGAB2 | CPZ | Gabon |
| Ch-06(27172) | AF447763 | 320 | TAN1 | CPZ | Tanzania |
| CAM5(4289) | AJ271369 | 321 | CAM5 | CPZ | Cameroon |
| CAM13(6922) | AY169968 | 322 | SIVcpzCAM13 | CPZ | Cameroon |
| MB66(23595) | DQ373063 | 323 | SIVcpzMB66 | CPZ | Cameroon |
| LB7(41638) | DQ373064 | 324 | SIVcpzLB7 | CPZ | Cameroon |
| EK505(50579) | DQ373065 | 325 | SIVcpzEK505 | CPZ | Cameroon |
| MT145(23809) | DQ373066 | 326 | SIVcpzMT145 | CPZ | Cameroon |
| Ch-64(3056) | DQ374657 | 327 | TAN2_69 | CPZ | Tanzania |
| CH-45(3137) | DQ374658 | 328 | TAN3_1 | CPZ | Tanzania |
| Ch-06(27172) | EF394356 | 329 | TAN1 | CPZ | Tanzania |
| Ch-64(3056) | EF394357 | 330 | TAN2 | CPZ | Tanzania |
| CH-45(3137) | EF394358 | 331 | TAN3 | CPZ | Tanzania |
| DP943(23593) | EF535993 | 332 | SIVcpzDP943 | CPZ | Cameroon |
| MB897(23594) | EF535994 | 333 | SIVcpzMB897 | CPZ | Cameroon |

TABLE 1-continued

Exemplary SIV ENV proteins

| Patient ID | Accession | SEQ ID NO: | Name | Subtype | Country |
|---|---|---|---|---|---|
| ID10(30898) | FJ424863 | 334 | SIVgorCP2135con | GOR | Cameroon |
| ID9(30899) | FJ424864 | 335 | SIVgorCP2139_1con | GOR | Cameroon |
| ID9(30899) | FJ424865 | 336 | SIVgorCP2139_2con | GOR | Cameroon |
| ID9(30899) | FJ424866 | 337 | SIVgor2139_287 | GOR | Cameroon |
| ID1(13725) | FJ424871 | 338 | SIVgorCP684con | GOR | Cameroon |
| Cam155(38651) | FR686510 | 339 | Ptt_04Cam155 | CPZ | Cameroon |
| Cam155(38651) | FR686511 | 340 | Ptt_09Cam155 | CPZ | Cameroon |
| Gab4(47562) | GQ217539 | 341 | SIVcpzGab4 | CPZ | Gabon |
| Ch-58(44459) | JN091690 | 342 | UG38 | CPZ | Tanzania |
| Ch-071(32642) | JN091691 | 343 | TAN5 | CPZ | Tanzania |
| EK505(50579) | JN835460 | 344 | SIVcpzEK505.c2 | CPZ | Cameroon |
| MB897(23594) | JN835461 | 345 | SIVcpzMB897.c2 | CPZ | Cameroon |
| MT145(23809) | JN835462 | 346 | SIVcpzMT145.c2 | CPZ | Cameroon |
| Ch-080(32641) | JQ768416 | 347 | SIVcpzTAN13 | CPZ | Tanzania |
| BF1167(32614) | JQ866001 | 348 | BF1167 | CPZ | Congo |
| LB715(41737) | JX178450 | 349 | LB715 | CPZ | Cameroon |
| BPID1(78681) | KP004989 | 350 | SIVgor-BPID1 | GOR | Cameroon |
| BPID15(78682) | KP004990 | 351 | SIVgor-BPID15 | GOR | Cameroon |
| BQID2(78683) | KP004991 | 352 | SIVgor-BQID2 | GOR | Cameroon |
| ANT(65) | U42720 | 353 | ANT | CPZ | Congo |
| GAB1(66) | X52154 | 354 | GAB1 | CPZ | Gabon |

Molecules of the invention may be further engineered to remove or reduce the immunogenicity of dominant epitopes that might otherwise interfere with a desired immune response. Such dominant env regions have been characterized and include, without limitation, epitopes located in the Vi (a.a. 111-130) and V3 (a.a. 311-330) domains and near the amino terminal part (a.a. 601-619) of the transmembrane gp36 of SIVmac251. Many immunodominant regions are similar among SIVs and HIVs (see e.g., Benichou, S. et al., 1993, Virology 194:870). As demonstrated herein, deletion of a portion of the immunodominant V5-loop from an engineered MT145K molecule results in improved induction of cross-neutralizing antibody responses compared to the parent SIV molecule.

As disclosed and exemplified herein, germline reverted antibodies can be designed by comparing the heavy and light chains of an isolated bnAb that binds to an epitope of interest to nucleotide sequences and/or the amino acid sequences potentially encoded by germline V gene segments. For example, one can obtain a germline reverted antibody starting from the amino acid sequence of an antibody directed to an antigen or epitope of choice and identifying germline encoded antibody segments (i.e., heavy chain V, D, and J gene segments and light chain V and J gene segments) close in sequence to the starting antibody. Germline variable genes are cataloged, for example at VBASE2 (Retter I, Althaus H H, Münch R, Müller W: VBASE2, an integrative V gene database. Nucleic Acids Res. 2005 Jan. 1; 33(Database issue):D671-4.). Starting from a known or preselected antibody and moving to such a database can be advantageous as the paired heavy and light chains will be compatible and likely to be well represented in the repertoire of expressed germline genes.

The invention provides germline reverted heavy and light chain variable domains, including heavy and light chain CDR regions that bind to molecules of the invention. The following are exemplary and bind to certain engineered V2 regions described herein.

TABLE 2

Germline reverted heavy and light chains and Kabat CDRs

| | SEQ ID NO: | |
|---|---|---|
| PG9_VDJH_iGL GenBank Accession: MK825341 | 32 | QVQLVESGGGVVQPGRSLRLSCAASGFTFSSYGMHWVRQAPGKGLEWVAV ISYDGSNKYYADSVKGRFTISRDNSKNTLYLQMNSLRAEDTAVYYCAREA GGPDYRNGYNYYDFWSGYYYYYYMDVWGKGTTVTVSS |
| CDR-H1 | 33 | SYGMH |
| CDR-H2 | 34 | VISYDGSNKYYADSVKG |
| CDR-H3 | 35 | EAGGPDYRNGYNYYDFWSGYYYYYYMDV |
| PG9VJL_iGL GenBank Accession: MK825342 | 41 | QSALTQPASVSGSPGQSITISCTGTSSDVGGYNYVSWYQQHPGKAPKLMI YEVSNRPSGVSNRFSGSKSGNTASLTISGLQAEDEADYYCSSYTSSSTWV FGGGTKLTVL |
| CDR-L1 | 42 | TGTSSDVGGYNYVS |
| CDR-L2 | 43 | EVSNRPS |

TABLE 2-continued

Germline reverted heavy and light chains and Kabat CDRs

| | SEQ ID NO: | |
|---|---|---|
| CDR-L3 | 44 | SSYTSSSTWV |
| CH01VDJH_iGL GenBank Accession: MK825343 | 49 | EVQLVESGGGVVRPGGSLRLSCAASGFTFDDYGMSWVRQAPGKGLEWVSG INWNGGSTGYADSVKGRFTISRDNAKNSLYLQMNSLRAEDTALYHCARGT DYTIDDAGIHYYGSGSYWYFDLWGRGTLVTVSS |
| CDR-H1 | 50 | DYGMS |
| CDR-H2 | 51 | GINWNGGSTGYADSVKG |
| CDR-H3 | 52 | GTDYTIDDAGIHYYGSGSYWYFDL |
| CH01VJL_iGL GenBank Accession: MK825344 | 58 | EIVLTQSPGTLSLSPGERATLSCRASQSVSSSYLAWYQQKPGQAPRLLIY GASSRATGIPDRFSGSGSGTDFTLTISRLEPEDFAVYYCQQYGSSPWTFG QGTKVEIK |
| CDR-L1 | 59 | RASQSVSSSYLA |
| CDR-L2 | 60 | GASSRAT |
| CDR-L3 | 61 | QQYGSSPWT |

Germline reverted antibodies such as the above provide for antibody design or selection. Using the CDRs of the germline reverted antibodies, bnAbs can be designed, or evolved by mutation and selection, that bind to the V2 apex region of HIV and SIV.

Broadly neutralizing antibodies of the invention include those set forth above and antibodies which comprise one, two, three, four, five, or all six of the CDRs set forth in Table 2, or comprise a heavy chain comprising one, two or three $V_H$ CDRs, or comprise a light chain comprising one, two or three $V_L$ CDRs. In certain embodiments, in bnAbs that bind to the V2 apex of HIV and/or SIV the CDRs, there can be conservative substitutions, as set forth elsewhere herein. The invention further includes bnAbs in which the heavy chains and/or light chains have have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity to germline reverted antibodies set forth. In certain such embodiments, variation in the CDRs is conservative.

Germline genes that bind to an epitope of interest can also be identified by screening libraries of human heavy and light chain genes, for example by phage display. Another method is by immunization and preparation of monoclonal antibodies from a mouse that expresses human antibody genes. Preferably hybridomas are prepared before there is substantial somatic mutation and selection. As mentioned, depending on the method employed, it is advantageous to select germline antibody gene segments that are well represented in the repertoire of expressed human antibodies, also taking into account compatibility of various heavy chain—light chain pairings. In certain embodiments, it is advantageous to select V-D, D-J, V-D-J (heavy chain) or V-J (light chain) combinations that are well represented.

Amino acid sequences of the V2 apex regions of many SIV isolates have been determined and can be used or compared with HIV isolates to identify useful conserved epitopes that would be bound by broadly neutralizing antibodies. FIG. 15 herein, for example provides a comparison of SIVcpz Envs with an HBX2 HIV reference. An analysis may also include modeling or determination of 3D structure to identify interactions with bnAbs. Similar analysis can be done for other HIV reference isolates and SIV counterparts based on conserved structures, regions, and epitopes of the V2 apex, as well other conserved structures, regions, and epitopes that comprise bnAb binding sites to find suitable bases for development of SIV-based molecules and immunogens that bind to and stimulate HIV antibodies.

The HIV envelope protein (Env) is the target of broadly neutralizing antibodies (bnAbs) in natural infection. Env is a membrane protein composed of a trimer of gp120 and gp41 subunits that contains a high degree of sequence diversity and a surface that is shielded by N-linked glycans. The bnAbs that target Env often have unusual features such as a long complementarity-determining region (CDR) H3, high levels of somatic hypermutation (SHM), and insertions and deletions (INDELS). Furthermore, most of the bnAbs recognize complex epitopes that are typically non-linear and have both protein and glycan components.

HIV type I (HIV-I) envelope is a noncovalent trimer of gp120-gp41 heterodimers, and its lability has hindered structural studies. SOSIP gp140 is a soluble, proteolytically mature form of the HIV-I envelope wherein gp120-gp41 interactions are stabilized via a disulfide bond and gp41 contains an additional trimer-stabilizing point mutation. The isolation of a substantially pure preparation of SOSIP gp140 trimers derived from KNH1144, a subtype A isolate was described in Iyer S P et al., AIDS Res Hum Retroviruses. 2007 June; 23(6):817-28. Following initial purification, the only significant contaminant was higher-order gp140 aggregates; however, 0.05% Tween 20 quantitatively converted these aggregates into trimers. The surfactant effect was rapid, dose dependent, and similarly effective for a subtype B SOSIP gp140.

Surfactant-treated SOSIP gp140 retained favorable antigenicity and formed compact trimers 12-13 nm in size as determined by electron microscopy. Iyer S P et al., AIDS Res Hum Retroviruses. 2007 June; 23(6):817-28 provides a description of homogeneous, cleaved HIV-I envelope trimers. These proteins may be useful as vaccine immunogens and for studying structure-function relationships within the HIV-I envelope glycoproteins.

Soluble, stabilized, proteolytically cleaved, trimeric proteins may be generated by engineering an intermolecular disulphide bond between gp120 and gp41 (SOS), combined with a single residue change, I559P, within gp41 (SOSIP). SOSIP gp140 proteins based on the subtype A HIV-I strain KNHI 144 form particularly homogenous trimers compared to a prototypic strain (JR-FL, subtype B). Described in U.S. Pat. No. 7,939,083 are the determinants of this enhanced stability which are located in the N-terminal region of KNHI 1144 gp41 and that, when substituted into heterologous Env sequences (e.g., JR-FL and Ba-L) they have a similarly beneficial effect on trimer stability. These stabilized trimers retain the epitopes for several neutralizing antibodies and related agents (CD4-IgG2, b12, 2G12, 2F5 and 4E10) and the CD4-IgG2 molecule, so that the overall antigenic structure of the gp140 protein has not been adversely impaired by the trimer-stabilizing substitutions.

The HIV-I envelope glycoprotein (Env) is a trimer of heterodimers composed of two non-covalently associated subunits; the receptor-binding gp120, and the fusion machinery-containing gp41. Each subunit is derived from a gp160 precursor glycoprotein following cleavage by cellular furins (Wyatt R & Sodroski J (1998) Science 280(5371): 1884-1888). HIV-I gp120 binds the CD4 molecule on the surface of human target T cells to initiate the viral entry process, and following co-receptor engagement, fusion is mediated by gp41 (Dalgleish A G, et al. (1984) Nature 312(5996):763-767; McDougal J S, et al. (1986) J Immunol 137(9):2937-2944; mKarlsson Hedestam G B, et al. (2008) Nat Rev Microbial 6(2):143-155). The surface-exposed HIV-I Env trimer is the sole target for antibodies capable of neutralizing the virus (Burton D R, et al. (2004) Nat Immunol 5(3):233-236). Recently, a myriad of Env-directed broadly neutralizing antibodies (bnAbs) were isolated from numerous HIV-I-infected individuals, demonstrating that the human B cell response can effectively inhibit this variable pathogen (Wu X, et al. (2010) Science 329(5993):856-861; Walker L M, et al. (2009) Science 326(5950):285-289; Walker L M, et al. (2011) Nature 477(7365):466-470; Huang J, et al. (2012) Nature 491(7424):406-412; Scharf L, et al. (2014) Antibody 8ANC195 reveals a site of broad vulnerability on the HIV-I envelope spike. Cell reports 7(3):785-795; Klein F, et al. (2012) J Exp Med 209(8):1469-1479). Infection of macaques by a chimeric model virus, SHIV, can be prevented by prior passive immunization of all bnAbs so far tested, confirming the capacity of neutralizing antibodies to prevent HIV infection (Mascola J R, et al. (1999) J Virol 73(5):4009-4018; Hessell A J, et al. (2009) PLoS Pathog 5(5):e1000433; Moldt B, et al. (2012) Proc Natl Acad Sci US A 109(46):18921-18925; Barouch D H, et al. (2013) Therapeutic efficacy of potent neutralizing HIV-I-specific monoclonal antibodies in SHIV-infected rhesus monkeys. Nature 503(7475):224-228).

Along with virus-specific T cells, an efficacious HIV-I vaccine therefore would likely need to generate bnAbs targeting Env. Although the premise is simple, in actuality, it is a tremendous challenge without precedent in the history of vaccinology. The difficulty to vaccinate against HIV arises from the extensive variability of Env present on the large number of HIV-I isolates simultaneously circulating in the human population as well as other mechanisms of immune evasion selected for by strong pressure from the human immune system.

Generally, vaccine-generated antibodies using either or both gp120 or gp41 sequences do not recognize native Env on the surface of cells or virus, do not neutralize primary isolates in vitro, and do not prevent infection in laboratory animals (Burton D R, et al. (2011) Proc Natl Acad Sci US A 108(27):11181-11186; Sundling C, et al. (2012) Science translational medicine 4(142):142ra196; Tran K, et al. (2014) Vaccine-elicited primate antibodies use a distinct approach to the HIV-I primary receptor binding site informing vaccine redesign. Proc Natl Acad Sci USA 111(7):E738-747). Non-neutralizing antibodies directed to the major variable region two (V2) of gp120 are associated with modest efficacy in a single human clinical trial (Haynes B F, et al. (2012) N Engl J Med 366(14):1275-1286; Zolla-Pazner S, et al. (2014) Vaccine-induced IgG antibodies to V1V2 regions of multiple HIV-I subtypes correlate with decreased risk of HIV-I infection. PLoS One 9(2):e87572), while, in general, Env-elicited antibodies fail to demonstrate protection in previous human clinical trials (Jones N G, et al. (2009) Vaccine 27(7):1136-1140; Rerks-Ngarm S, et al. (2009) N Engl J Med 361(23):2209-2220; Yates N L, et al. (2014) Vaccine-induced Env V1-V2 IgG3 correlates with lower HIV-I infection risk and declines soon after vaccination. Science translational medicine 6(228):228ra239).

Many Env-based trimeric candidate immunogens are engineered to eliminate cleavage between gp120 and gp41 (so called uncleaved gp140 trimers), usually generating imperfect mimetics of the functional spike based on antigenic profiling or EM analysis (Tran K, et al. (2014) Proc Natl Acad Sci US All 1(7):E738-747; Ringe R P, et al. (2013) Proc Natl Acad Sci USA 110(45):18256-18261). As a group, the defined, or presumed to be, disordered trimers (in adjuvant) generate high self-binding antibody titers. However, these vaccine-elicited antibodies do not efficiently neutralize most HIV-I primary isolates, that is, strains representative of those circulating in the human population (Sundling C, et al. (2012) Science translational medicine 4(142):142ra196; Chakrabarti B K, et al. (2013) J Virol 87(24):13239-13251; Kovacs J M, et al. (2012) Proc Natl Acad Sci US A 109(30):12111-12116; Nkolola J P, et al. (2014) Comparison of multiple adjuvants on the stability and immunogenicity of a clade C HIV-I gp140 trimer. Vaccine 32(18):2109-2116). Antibodies elicited by these immunogens target epitopes exposed only on the free gp120 and trimeric post-fusion forms of gp41 or disordered gp140s and thus are ineffective at accessing their epitopes buried within the ordered, quaternary structure achieved in the native Env spike. Applicants recently described the limitations of two CD4bs-directed non-bnAbs, (GE148 and GE136) generated following immunization of uncleaved gp140 trimers (YU2 gp140-foldon) in non-human primates (NHP). Non-bnAbs, represented by GE136 and 148, can only neutralize the sensitive so-called "tier I viruses" that are not representative of the more neutralization resistant tier 2-like primary isolates circulating in the human population. Using crystallography, EM reconstructions, paratope scanning and molecular modeling, Applicants determined that these vaccine-elicited antibodies fail to reach the CD4bs due to steric barriers imposed by quaternary packing of the native Env on neutralization resistant primary isolates, a property that Applicants use to Applicants' advantage in the negative-selection strategy presented here (Tran K, et al. (2014) Proc Natl Acad Sci US A 111(7):E738-747).

The cumulative historical data have led to the hypothesis that a more faithful mimic of the HIV-I spike that better recapitulates the native, pre-fusion form of Env, selectively displaying neutralizing determinants while occluding non-neutralizing determinants, may better elicit antibodies capable of accessing the native spike. A soluble Env mimetic, containing a disulfide linkage between gp120 and gp41 (SOS), first described in the 2000s, and further developed over the next decade, displays many of these properties, culminating in the determination of the high resolution structures of the well-ordered BG505 SOSIP trimers by crystallography and EM (Lyumkis D, et al. (2013) Science 342(6165):1484-1490; Julien J P, et al. (2013) Science 342(6165):1477-1483; Sanders R W, et al. (2013) PLoS Pathog 9(9):e1003618; Depetris R S, et al. (2012) J Biol Chem 287(29):24239-24254). A sub-nanometer EM reconstruction of KNHI 144 SOSIP is also available but does not provide atomic level details (Bartesaghi A, Merk A, Borgnia M J, Milne J L, & Subramaniam S (2013) Nat Struct Mol Biol 20(12):1352-1357). The BG505 SOSIP and KNH1144 SOSIP trimers are derived from the Env sequences of the subtype A BG505 and KNHI 144 strains. These soluble trimers possess an engineered disulfide linkage between the gp120 and gp41 (at residues 501C and 605C, respectively) and an additional mutation in the heptad repeat I (HRI) of gp41 (I559P) that facilitates trimerization (Binley J M, et al. (2000) J Virol 74(2):627-643; Sanders R W, et al. (2002) J Virol 76(17):8875-8889). A truncation of the membrane proximal external region (MPER) at residue 664 enhances expression while decreasing aggregation is incorporated into the so-called BG505 SOSIP.664 trimers (Sanders R W, et al. (2013) PLoS Pathog 9(9):e1003618; Sanders R W, et al. (2002) J Virol 76(17):8875-8889). Although SOSIP molecules based on other HIV-I primary strains were attempted over the past decade, the BG505- and KNHI 144-derived SOSIP trimers are the two limited examples of SOSIPs that yield homogeneous trimers suitable for high resolution biophysical and structural analysis. The structural explanation for the difficulty to readily transfer the SOSIP design to other HIV-I strain-derived sequences is not yet fully understood and would be valuable information to broaden the trimer design horizon.

Since the initial soluble native-like BG505 SOPIP.664 Env trimer was confirmed to adopt a near-native conformation by high-resolution structural analysis, multiple efforts to produce stable, soluble Env mimetics derived from multiple HIV-1 strains were pursued [Javiers, sanders]. Multiple solutions to this objective include the improved cleavage-independent NFL trimers, UFOs and modified SOSIPs. Both the SOSIP and NFL well-ordered trimers are efficiently recognized by broadly neutralizing antibodies (bnAbs) which arise sporadically during the course of natural infection. In some cases, including the important advances described here, have been used to isolate such bnAbs. One approach to elicit tier 2 neutralizing Abs has been to immunize the existing well-ordered trimers using prime:boosting in selected animal models. For BG505 and 16055 native-like trimers this approach does elicit tier 2 neutralizing antibodies, but of limited cross-reactive breadth (REFS).

Most cross-conserved sites on the HIV Env spike are occluded by evolved, incorporated self-N-glycans, limiting naïve B cell recognition of the underlying polypeptide surface. The exceptions are the protein surfaces of the primary receptor CD4 binding site (CD4bs) and the furin cleavage site (proximal to the gp120:41 interface). Infrequently, during the course of the natural HIV infection process, bnAbs are elicited to these aforementioned sites of vulnerability. In addition, other bnAbs directed to the V2 apex, the 332N-glycan supersite and to the fusion peptide or the high-mannose patch are elicited during the course of chronic HIV infection (REFS). However, prior to the present invention, rarely, if ever, have such bnAbs been elicited by vaccination of Env formulated with adjuvant.

After decades of development, advances in soluble HIV-1 Env mimics design permits the generation of a diverse array of native-like trimers (Ward and Wilson, 2017. The HIV-1 envelope glycoprotein structure: nailing down a moving target. Immunol Rev 275:21-32; Karlsson et al., 2017. Evolution of B cell analysis and Env trimer redesign. Immunol Rev 275:183-202). The successful development of the soluble SOSIP trimers provided proof-of-principle (Sanders et al, 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618) forming a prefusion native-like conformation (Lyumkis et al., 2013. Cryo-EM structure of a fully glycosylated soluble cleaved HIV-1 envelope trimer. Science 342:1484-1490; Julien et al, 2013. Crystal structure of a soluble cleaved HIV-1 envelope trimer. Science 342:1477-1483; Garces et al., 2015. Affinity Maturation of a Potent Family of HIV Antibodies Is Primarily Focused on Accommodating or Avoiding Glycans. Immunity 43:1053-1063; Pancera et al., 2014. Structure and immune recognition of trimeric pre-fusion HIV-1 Env. Nature 514:455-461). The SOSIP gp140 trimer is proteolytically cleaved by cellular furins to gp120 and gp41 subunits and covalently linked by an engineered intra-protomer disulfide bond A501C-T605C (SOS). These trimers also require mutation (I559P) in the gp41 heptad repeat 1 (HR1) to maintain well-ordered oligomers, as well as expression of exogenous furin for full conformational integrity (Sanders et al., 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618; Guenaga et al., 2015. Well-Ordered Trimeric HIV-1 Subtype B and C Soluble Spike Mimetics Generated by Negative Selection Display Native-like Properties. PLoS Pathog 11:e1004570; Julien et al., 2015. Design and structure of two HIV-1 clade C SOSIP.664 trimers that increase the arsenal of native-like Env immunogens. Proc Natl Acad Sci USA 112:11947-11952; de Taeye et al. 2015. Immunogenicity of Stabilized HIV-1 Envelope Trimers with Reduced Exposure of Non-neutralizing Epitopes. Cell 163:1702-1715; Pugach et al. 2015. A native-like SOSIP.664 trimer based on an HIV-1 subtype B env gene. J Virol 89:3380-3395; Ringe et al. 2013. Cleavage strongly influences whether soluble HIV-1 envelope glycoprotein trimers adopt a native-like conformation. Proc Natl Acad Sci USA 110:18256-18261; Ringe et al. 2015. Influences on the Design and Purification of Soluble, Recombinant Native-Like HIV-1 Envelope Glycoprotein Trimers. J Virol 89:12189-12210; Ringe et al. 2017. Reducing V3 Antigenicity and Immunogenicity on Soluble, Native-Like HIV-1 Env SOSIP Trimers. J Virol 91; Ahmed et al. 2017. Stabilization of a soluble, native-like trimeric form of an efficiently cleaved Indian HIV-1 clade C envelope glycoprotein. J Biol Chem 292:8236-8243; Sanders et al. 2002. Stabilization of the soluble, cleaved, trimeric form of the envelope glycoprotein complex of human immunodeficiency virus type 1. J Virol 76:8875-8889; Binley et al. 2000. A recombinant human immunodeficiency virus type 1 envelope glycoprotein complex stabilized by an intermolecular disulfide bond between the gp120 and gp41 subunits is an antigenic mimic of the trimeric virion-associated structure. J Virol 74:627-643). In the past years, Applicants developed an improved native-like trimer design, generating well-ordered soluble Env mimics that are fully cleavage-independent, termed native flexibly linked (NFL) trimers. This design uses a flexible linker (two copies of Gly4-Ser, "G4S" (SEQ ID NO:357)) to replace the natural cleavage site and sequence (Sharma et al. 2015. Cleavage-independent HIV-1 Env trimers engineered as soluble native spike mimetics for vaccine design. Cell Rep 11:539-550). The flexible linker between the natural C-terminus of gp120 and N-terminus of gp41, allows the un-cleaved trimers to achieve a native-like conformation without the need of furin for precursor processing. However, the original NFL trimer design contains the I559P mutation (Sharma et al. 2015. Cleavage-independent HIV-1 Env trimers engineered as soluble native spike mimetics for vaccine design. Cell Rep 11:539-550) that was initially identified in the SOSIP context to disfavor the post fusion state (Sanders et al. 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618). Both the original SOSIP and NFL designs do not form a high percentage of well-ordered trimers in all Env contexts. In the original NFL design, it is relatively inefficient in generating high yields of trimers derived from clade C strains, such as 16055 (Guenaga et al. 2015. Structure-Guided Redesign Increases the Propensity of HIV Env To Generate Highly Stable Soluble Trimers. J Virol 90:2806-2817). To improve trimer design, Applicants incorporated residues from BG505 (called trimer-derived (TD) residues) into 16055 NFLs, substantially improving the propensity to form native-like trimers (Guenaga et al. 2015. Structure-Guided Redesign Increases the Propensity of HIV Env To Generate Highly Stable Soluble Trimers. J Virol 90:2806-2817) and the elicitation of tier 2 clade C neutralizing antibodies (Martinez-Murillo et al., GB. 2017. Particulate Array of Well-Ordered HIV Clade C Env Trimers Elicits Neutralizing Antibodies that Display a Unique V2 Cap Approach. Immunity 46:804-817 e807; Dubrovskaya et al. 2017. Targeted N-glycan deletion at the receptor-binding site retains HIV Env NFL trimer integrity and accelerates the elicited antibody response. PLoS Pathog 13:e1006614). Further improvements on the TD design by targeted glycine substitutions at helix-to-coil transitions that disfavor the post-fusion state of Env (TD CC+, namely "TD+"), significantly improve trimer homogeneity, yield, stability and antigenicity, resulting in the first high-resolution clade C Env structure (Guenaga et al. 2017. Glycine Substitution at Helix-to-Coil Transitions Facilitates the Structural Determination of a Stabilized Subtype C HIV Envelope Glycoprotein. Immunity 46:792-803 e793).

Applicants believe that the glycine changes may lower the activation potential of the gp41 (and Env) to change conformation, and therefore results in better behaved trimers in a lower energy well from the "activation state" to spring to the next conformation. In a simple model, gp41 is essentially spring-loaded and constrained by gp120 until receptor binding. These mutations may contribute to reducing the springiness.

Assays for screening for neutralizing antibodies are known in the art. A neutralization assay approach has been described previously (Binley J M, et al., (2004). Comprehensive Cross-Clade Neutralization Analysis of a Panel of Anti-Human Immunodeficiency Virus Type 1 Monoclonal Antibodies. J Viral. 78: 13232-13252). Pseudotyped viruses may be generated by co-transfecting cells with at least two plasmids encoding the soluble Env cDNA of the present invention and the rest of the HIV genome separately. In the HIV genome encoding vector, the Env gene may be replaced by the firefly luciferase gene. Transfectant supematants containing pseudotyped virus may be co-incubated overnight with B cell supematants derived from activation of an infected donor's primary peripheral blood mononuclear cells (PBMCs). Cells stably transfected with and expressing CD4 plus the CCR5 and CXCR4 coreceptors may be added to the mixture and incubated for 3 days at 37° C. Infected cells may be quantified by luminometry.

In another embodiment of the present invention, the soluble envelope glycoproteins of the present invention may be crystallized in combination with any neutralizing antibodies, including those identified by the above methods, to determine the exact molecular surface where the soluble envelope glycoprotein binds with the neutralizing antibody to design HIV-I immunogens.

It is to be understood that this invention is not limited to particular methods, components, products or combinations described, as such methods, components, products and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of as used herein are synonymous with "including", "includes" or "containing", "contains", and are inclusive or open-ended and do not exclude additional, non-recited members, elements or method steps. It will be appreciated that the terms "comprising", "comprises" and "comprised of as used herein comprise the terms "consisting of, "consists" and "consists of, as well as the terms "consisting essentially of, "consists essentially" and "consists essentially of. It is noted that in this disclosure and particularly in the claims and/or paragraphs, terms such as "comprises", "comprised", "comprising" and the like can have the meaning attributed to it in U. S. Patent law; e.g., they can mean "includes", "included", "including", and the like; and that terms such as "consisting essentially of and "consists essentially of have the meaning ascribed to them in U. S. Patent law, e.g., they allow for elements not explicitly recited, but exclude elements that are found in the prior art or that affect a basic or novel characteristic of the invention. It may be advantageous in the practice of the invention to be in compliance with Art. 53(c) EPC and Rule 28(b) and (c) EPC. Nothing herein is intended as a promise.

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +1-5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one" or "X or more", where X is a number and understand to mean X or increases one by one of X, such as one or more or at least one member(s) or "X or more" of a group of members, is clear per se, by means of further exemplification, the term encompasses inter alia a reference to any one of said members, or to any two or more of said members, such as, e.g., any >3, >4, >5, >6 or >7 etc. of said members, and up to all said members.

All references cited in the present specification are hereby incorporated by reference in their entirety. In particular, the teachings of all references herein specifically referred to are incorporated by reference. Andrabi et al., 2019 is incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates) ("Ausubel et al. 1992"); the series Methods in Enzymology (Academic Press, Inc.); Innis et al., PCR Protocols: A Guide to Methods and Applications, Academic Press: San Diego, 1990; PCR 2: A Practical Approach (M. J. MacPherson, B. D. Hames and G. R. Taylor eds. (1995); Harlow and Lane, eds. (1988) Antibodies, a Laboratory Manual; and Animal Cell Culture (R. I. Freshney, ed. (1987). General principles of microbiology are set forth, for example, in Davis, B. D. et al., Microbiology, 3rd edition, Harper & Row, publishers, Philadelphia, Pa. (1980).

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In this description of the invention, reference is made to the accompanying drawings that form a part hereof, and in which are shown by way of illustration only of specific embodiments in which the invention may be practiced. It is to be understood that other embodiments may be utilized and structural or logical changes may be made without departing from the scope of the present invention. The description, therefore, is not to be taken in a limiting sense, and the scope of the present invention is defined by the appended claims.

Preferred statements (features) and embodiments of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous.

Unless specifically stated or obvious from context, as used herein, the term "about" is understood as within a range of normal tolerance in the art, for example within 2 standard deviations of the mean. About can be understood as within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Unless specifically stated or obvious from context, as used herein, the term "or" is understood to be inclusive. Unless specifically stated or obvious from context, as used herein, the terms "a," "an," and "the" are understood to be singular or plural.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, $F(ab')_2$, Fv and scFv which are capable of binding the epitope determinant. These antibody fragments retain some ability to selectively bind with its antigen or receptor and include, for example:

Fab, the fragment which contains a monovalent antigen-binding fragment of an antibody molecule can be produced by digestion of whole antibody with the enzyme papain to yield an intact light chain and a portion of one heavy chain;

Fab', the fragment of an antibody molecule can be obtained by treating whole antibody with pepsin, followed by reduction, to yield an intact light chain and a portion of the heavy chain; two Fab' fragments are obtained per antibody molecule;

$F(ab')_2$, the fragment of the antibody that can be obtained by treating whole antibody with the enzyme pepsin without subsequent reduction; $F(ab')_2$ is a dimer of two Fab' fragments held together by two disulfide bonds;

scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-I virus F with a neutralization index>1.5 or >2.0. Broad and potent neutralizing antibodies may neutralize greater than about 50% of HIV-I viruses (from diverse clades and different strains within a clade) in a neutralization assay. The inhibitory concentration of the monoclonal antibody may be less than about 25 mg/ml to neutralize about 50% of the input virus in the neutralization assay.

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions may generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, praline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Genart. Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448. Advantageous for use according to the present invention is the WU-BLAST (Washington University BLAST) version 2.0 software. WU-BLAST version 2.0 executable programs for several UNIX platforms can be downloaded from the Washington University BLAST website. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, intrans, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vector expressing a foreign epitope. Advantageously, the epitope is an SIV or HIV epitope or combination thereof. In an advantageous embodiment, the SIV or HIV epitope is a soluble envelope glycoprotein, however, the present invention may encompass additional HIV antigens, epitopes or immunogens. Advantageously, the additional epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971; 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709; 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615; 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997;

6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625; 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432; 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497; 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707; 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406; 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-I antigen and/or protective immunity against HIV-I, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-I immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-I566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The nucleotide sequences and vectors of the invention can be delivered to cells, for example if aim is to express and the HIV-I antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-I immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelleforming agent, and oil such as that which is commercially available under the name Provax® (IDEC Pharmaceuticals, San Diego, CA). (PEG).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from Mycobacterium tuberculosis, substances found in Cornyebacterium parvum, Bordetella pertussis, or members of the genus Brucella), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, AK. et al (2004) 22(13-14): 1791-8), and the CCR5 inhibitor CMPD167 (see Veazey, R S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-, and IFN-γ (Boyer et al., (2002) J. Liposome Res. 121:137-142; WO01/095919), immunoregulatory proteins such as CD40L (ADX40; see, for example, WO03/063899), and the CDla ligand of natural killer cells (also known as CRONY or a-galactosyl ceramide; see Green, T. D. et al, (2003) J. Virol. 77(3): 2046-2055), immunostimulatory fusion proteins such as IL-2 fused to the Fe fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate ex In an advantageous embodiment, the adjuvants may be lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).pression vectors.

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr. HIVA) or in a viral vector (e.g., MVA.RIVA). Another such HIV immunogen is RENTA (described in PCT/US2004/037699), which can also be administered as a protein, on a plasmid (e.g., pTHr. RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

The present invention will be further illustrated in the following Examples which are given for illustration purposes only and are not intended to limit the invention in any way.

Although the present invention and its advantages have been described in detail, it should be understood that various changes, substitutions and alterations can be made herein without departing from the spirit and scope of the invention as defined in the appended claims.

EXAMPLES

Example 1: Experimental Procedures

SIV Envelope Trimer Design, its Expression and Purification.

Figure 8A:
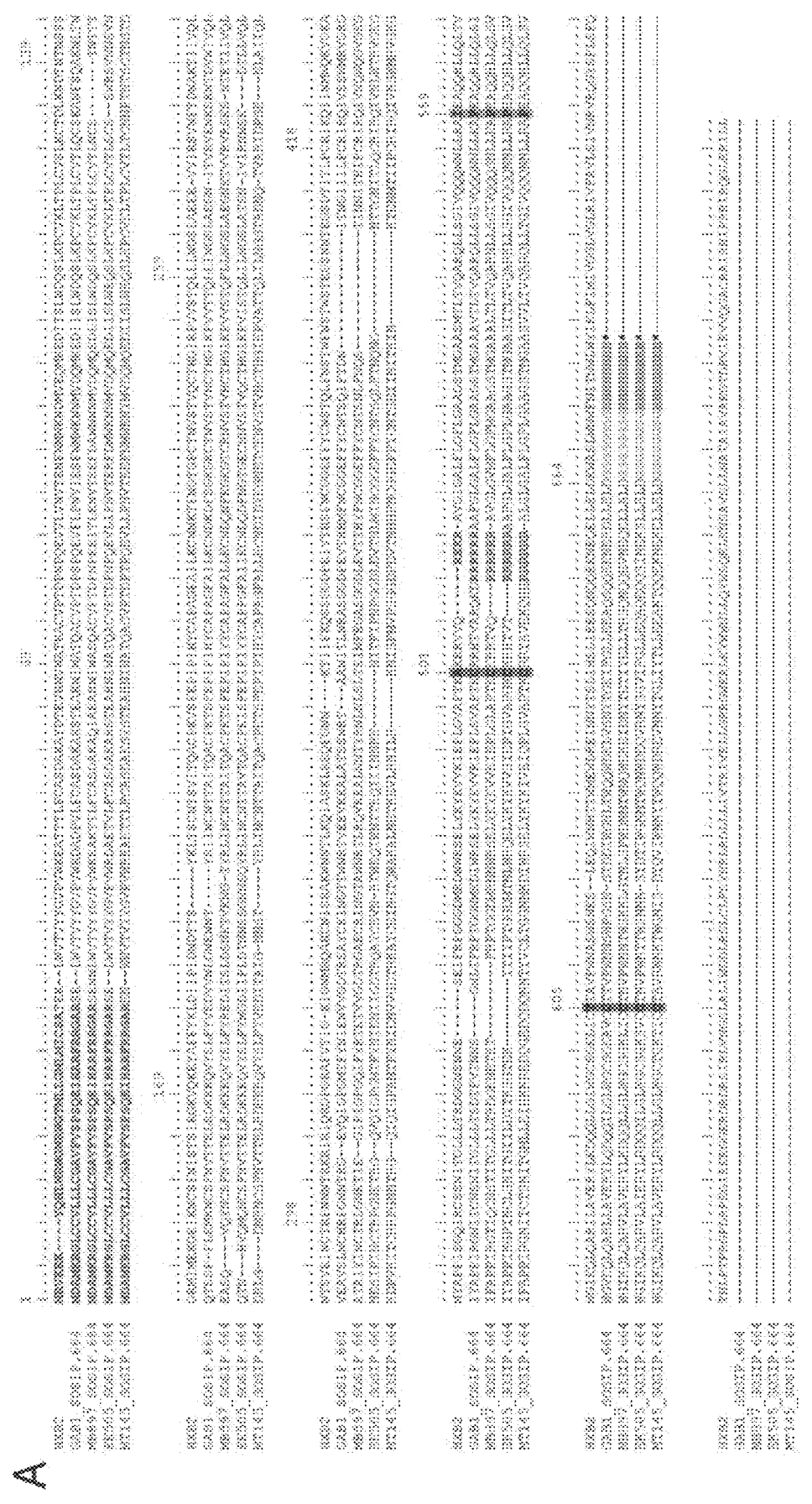
Figure 8B:
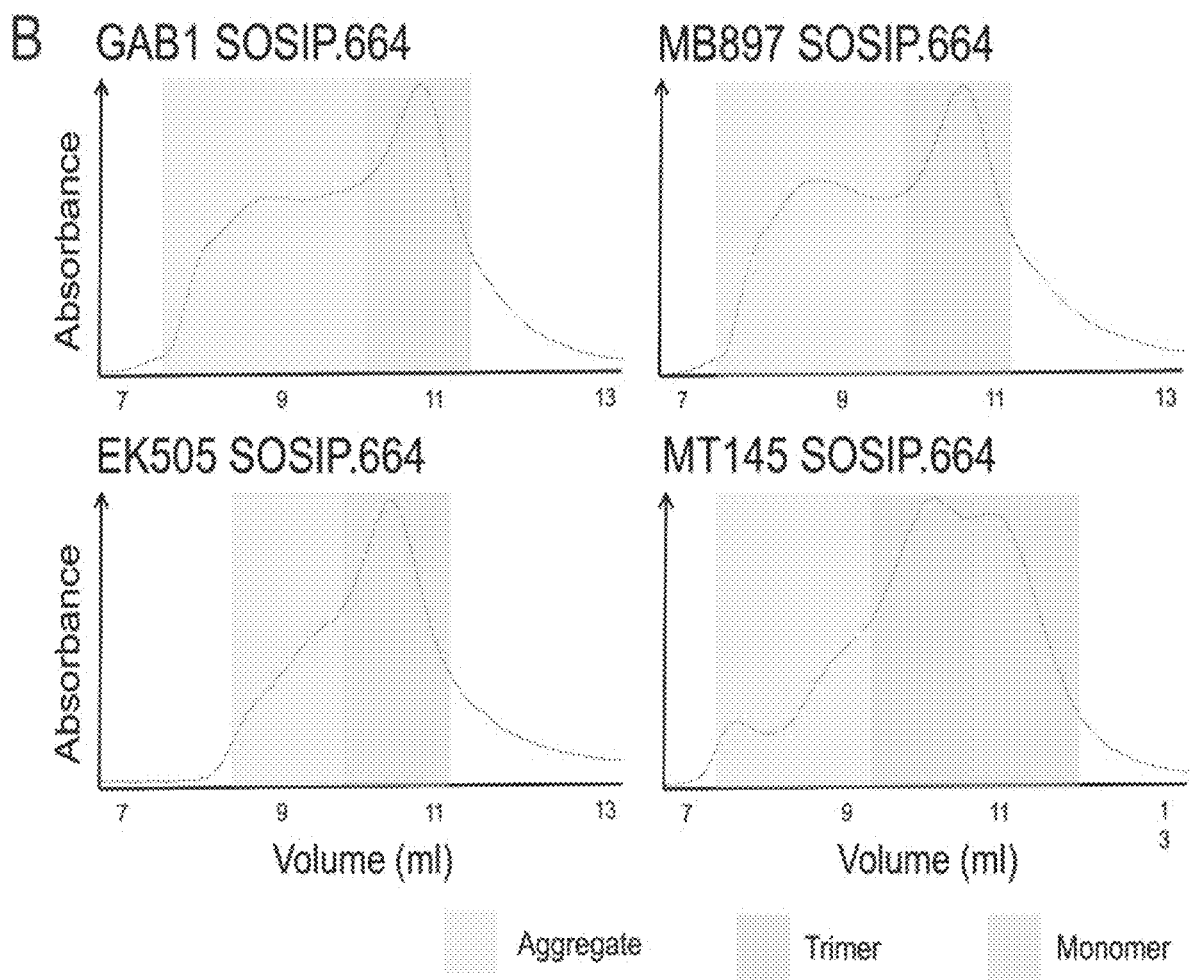
Figures 9A, 9B, 9C:
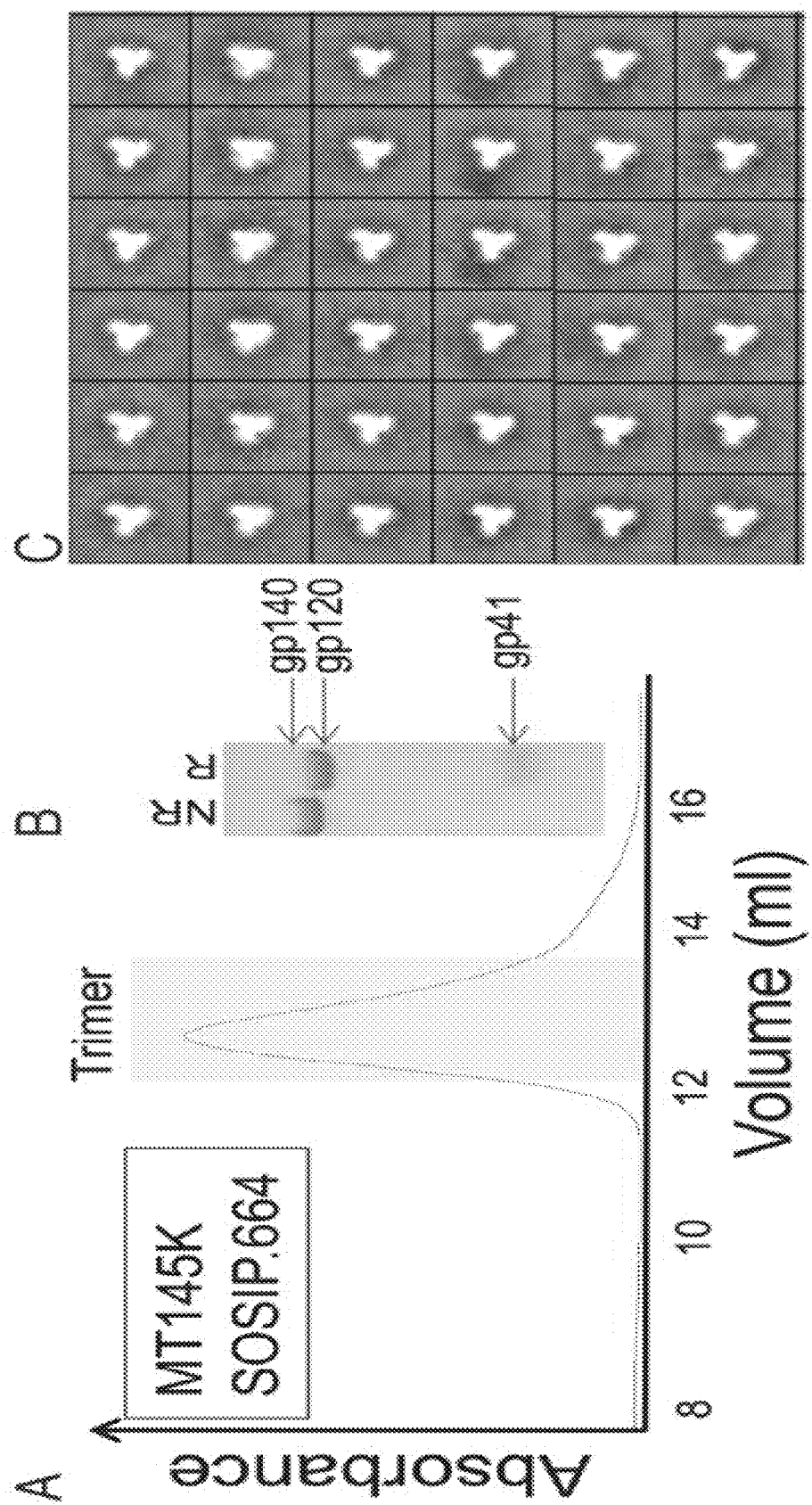
FIG. 9A-9D. MT145K SOSIP.664 forms native-like trimers that are thermostable. Size exclusion chromatography (SEC) of PGT145 antibody purified MT145K SOSIP.664 trimer reveals trimer eluting as a single peak with no aggregation. B. SDS-PAGE of MT145K trimer protein under non-reducing (NR) and reducing (R) conditions (reducing agent DTT was added). The MT145K trimer is efficiently cleaved into gp120 and gp41 subunits. C. Negative Stain Electron-Microscopy (NS-EM) of MT145K trimer: 2D class averages show that trimers adopt well-ordered, native-like conformations. D. Thermostability of the MT145K trimer. Thermal denaturation of the MT145K trimer by Differential Scanning Calorimetry (DSC) reveals a major trimer population melting at a Tm of 65.4° C.
Figure 9D:
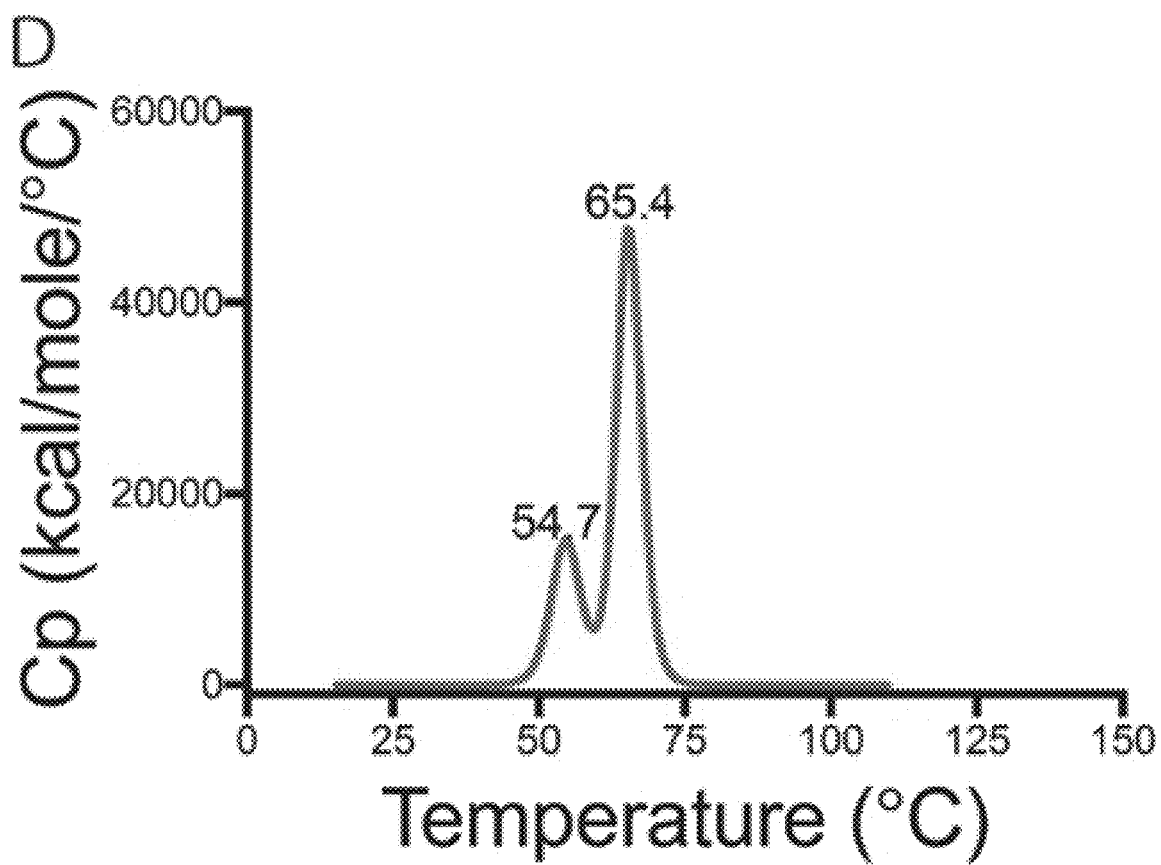
Figure 11A:
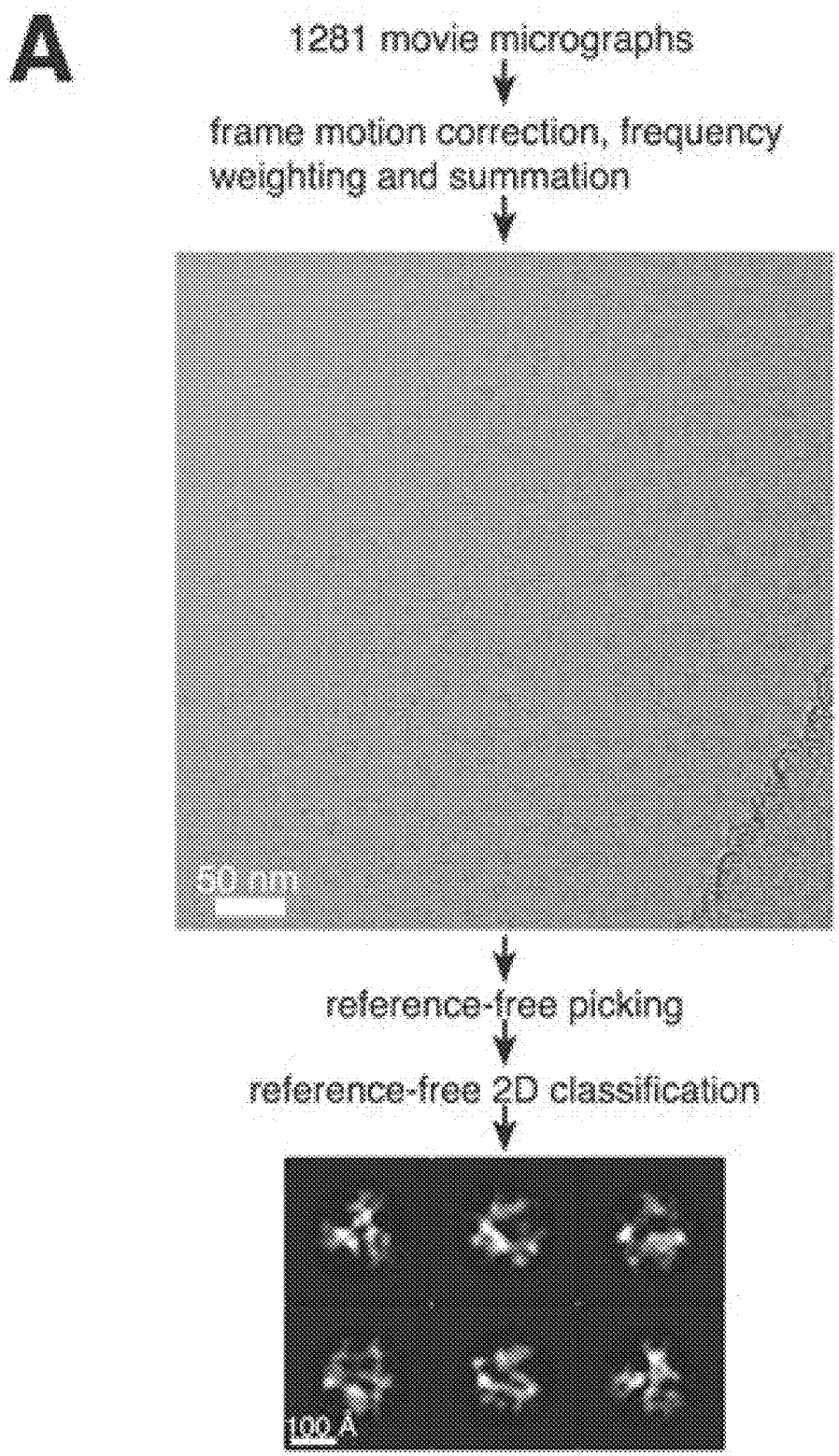
FIG. 11A-11D. Structural analysis of MT145K by cryo-electron microscopy. A. Cryo-EM data processing flow diagram resulting in a density map at ~4.1 Å global resolution. B. FSC between two independently refined data half sets. C. Local resolution in the MT145K density map. The peptide part of MT145K is resolved primarily in the 3.0-4.0 Å range, whereas the glycan shield overall is resolved to significantly lower resolutions. D. Angular distribution of the angularly refined data class giving rise to the final reconstruction.
Figure 11A:
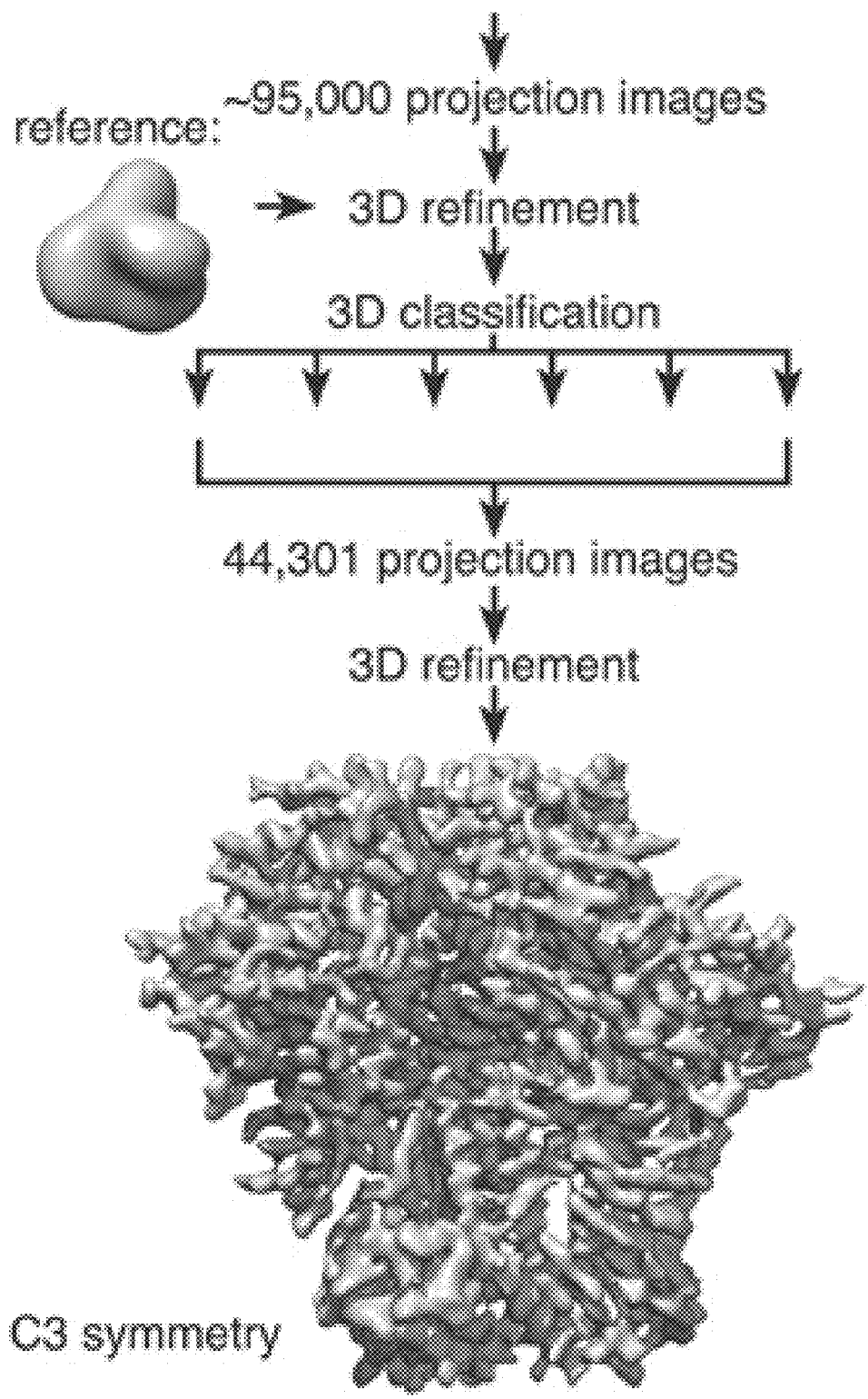
Figure 11B:
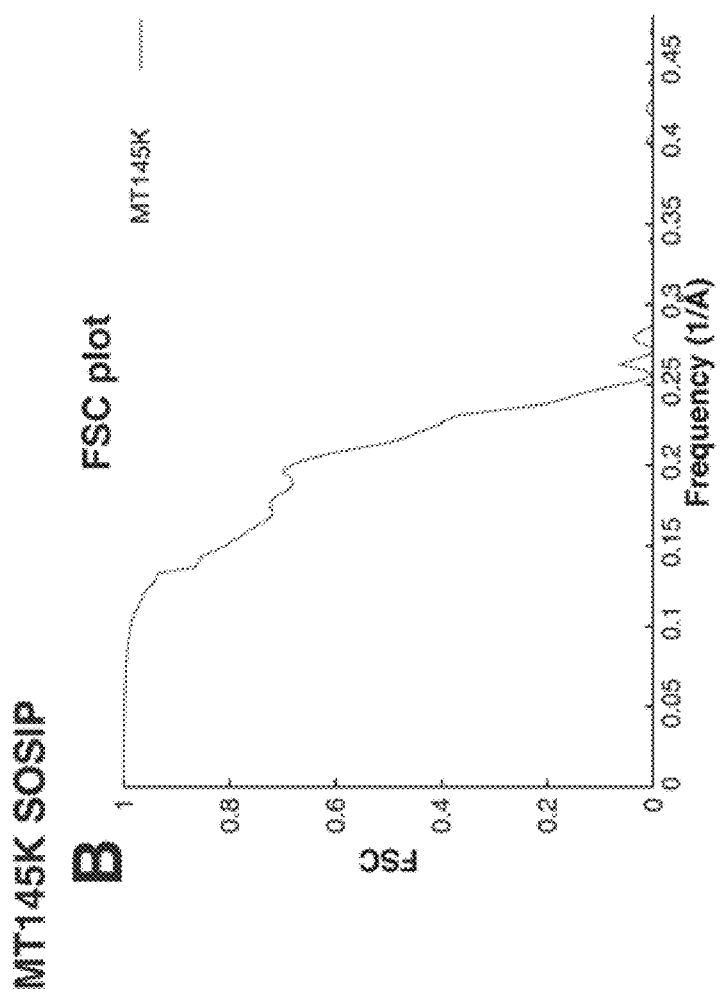
Figure 11C:
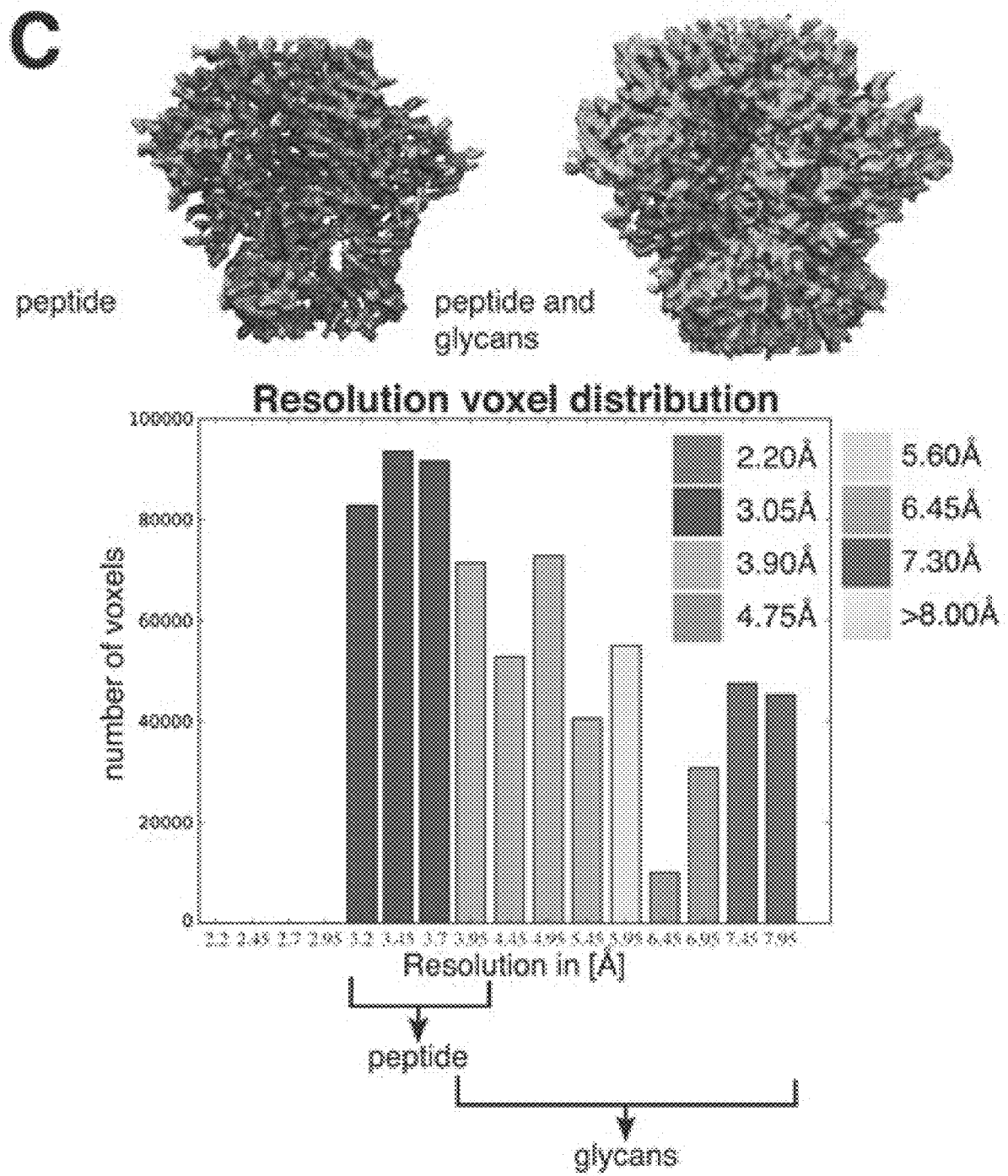
Figure 11D:
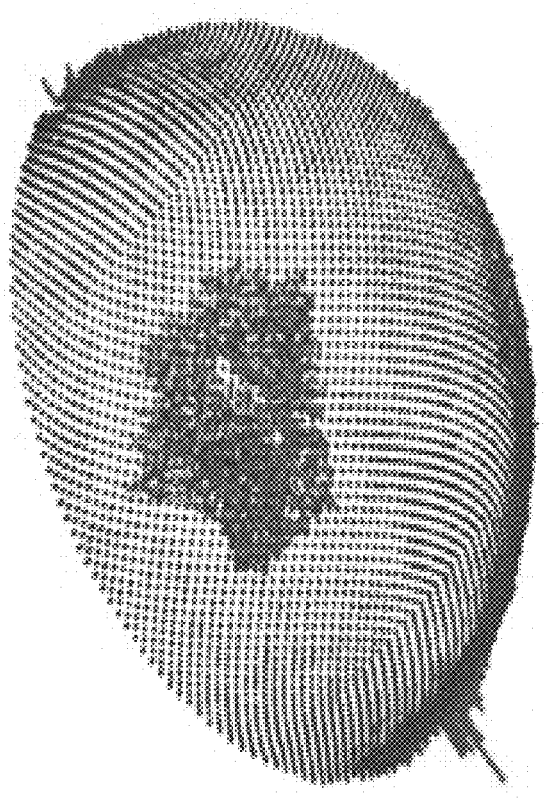

SOSIP.664 HIV-1 Env trimer design modifications were incorporated into envelope encoding sequences corresponding to four Chimpanzee (SIVcpzPtt) isolates (GAB1 [GenBank: P17281]; MB897 [GenBank: ABU53023]; EK505 [GenBank: ABD19499]; and MT145 [GenBank: ABD19508]) to express as soluble native trimers (FIG. 8A). These isolates are sensitive to the V2 apex bnAbs, PG9, PG16, and PGT145 (Barbian et al., 2015). Further characterization showed that one of these SIVcpzPtt Env sequences, MT145 SOSIP.664, could be expressed as a soluble Env trimer protein (FIG. 8B). PGT145 Ab affinity-purified MT 145 trimer was efficiently cleaved into gp120 and gp41 subunits, and revealed well-ordered native-like trimer configurations that were highly thermostable, which are all properties displayed by natively folded HIV-1 soluble trimers (FIG. 9A-D) (Pugach et al., 2015; Sanders et al., 2013; Sharma et al., 2015).

Briefly, the following modifications were incorporated into these Envs for soluble trimer expression: a) the Env leader sequence was replaced by Tissue Plasminogen Activator (TPA) signal sequence for higher protein expression; b) a disulfide bond was introduced between gp120 and gp41 subunits by substituting residues A501-C and T605-C respectively in gp120 and gp41; c) the gp120 REKR(SEQ ID NO:358) cleavage site was replaced by Furin inducible R6 site (RRRRRR)(SEQ ID NO:359) for enhancing cleavage efficiency between gp120 and gp41; and d) an I559P substitution in gp41 to stabilize the soluble trimer protein. In addition, a GS-linker and a His-tag were added to the gp41$_{ECTO}$ C-terminus at HXB2 residue 664 position. The codon-optimized SOSIP.664 gp140 gene constructs were synthesized (Geneart, Life Technologies) and cloned into the phCMV3 vector (Genlantis). Recombinant envelope proteins were expressed in HEK293F cells as described elsewhere (Sanders et al., 2013). Briefly, HIV-1 Env trimers WITO, C108, ZM197-ZM233V1V2 and the 4 chimpanzee SIV SOSIP.664 Env-encoding trimer plasmids were cotransfected with a plasmid encoding for Furin (3:1 ratio) into HEK293F cells using PEI-MAX 4000 transfection reagent (Polysciences, Inc.). The secreted soluble trimers proteins were purified from cell supernatants after 5 days using agarose-bound Gallanthus Nivalis Lectin (GNL) (Vector Labs) or CNBr-activated Sepharose 4B bead (GE Healthcare) bound PGT145 bnAb antibody affinity columns as described previously (Pugach et al., 2015). The affinity-purified proteins were size exclusion chromatography (SEC)-purified with a Superdex 200 10/300 GL column (GE Healthcare) in PBS/TBS. The purified trimers for the immunization experiments were quality control tested for antigenicity with a range of HIV-1 Env-specific neutralizing and non-neutralizing mAbs.

Example 2: Binding to bnAB Precursors

MT145K Trimer Binds Prototype V2 Apex bnAb Precursors.

Figure 1C:
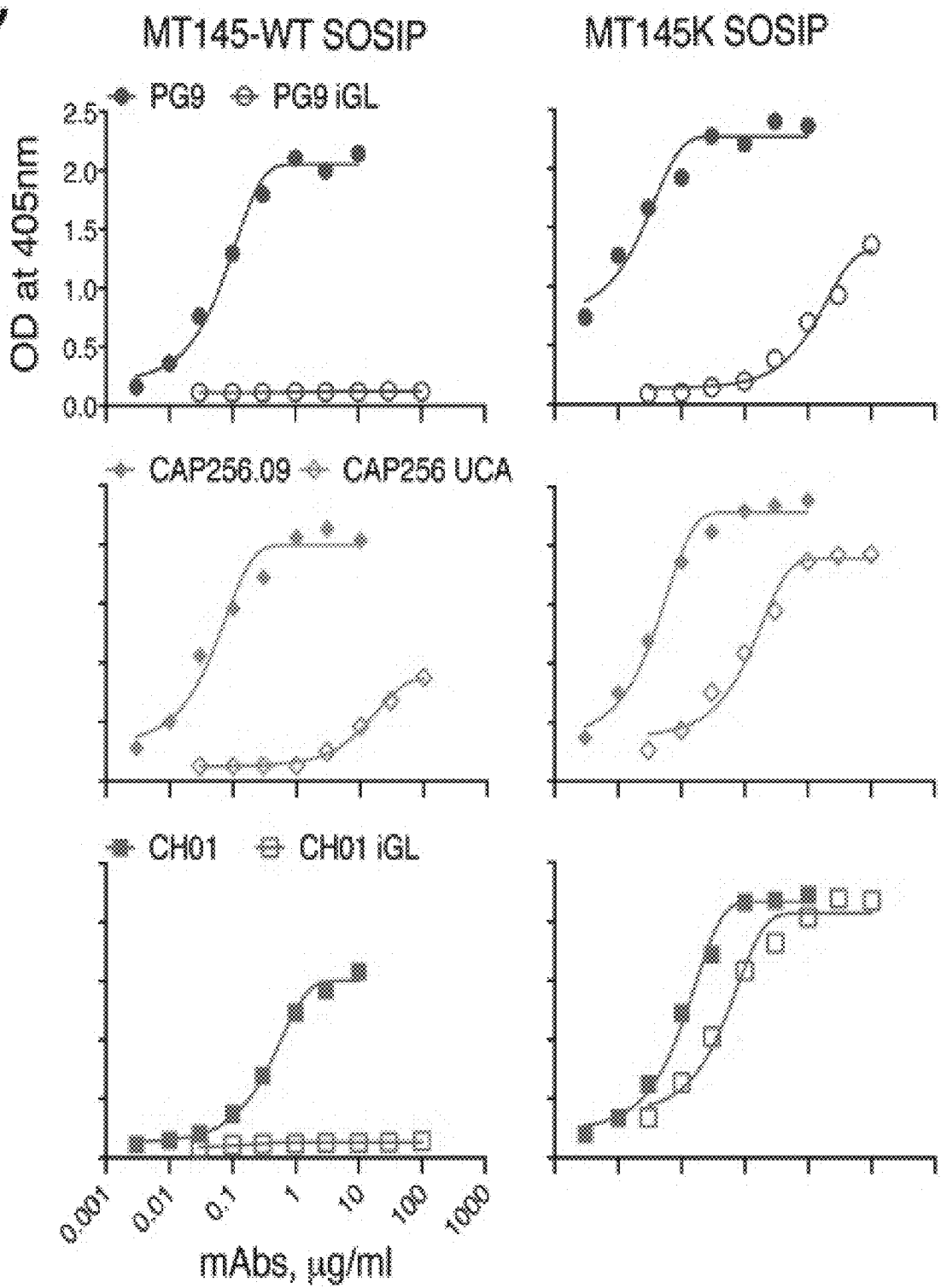
Figure 10A:
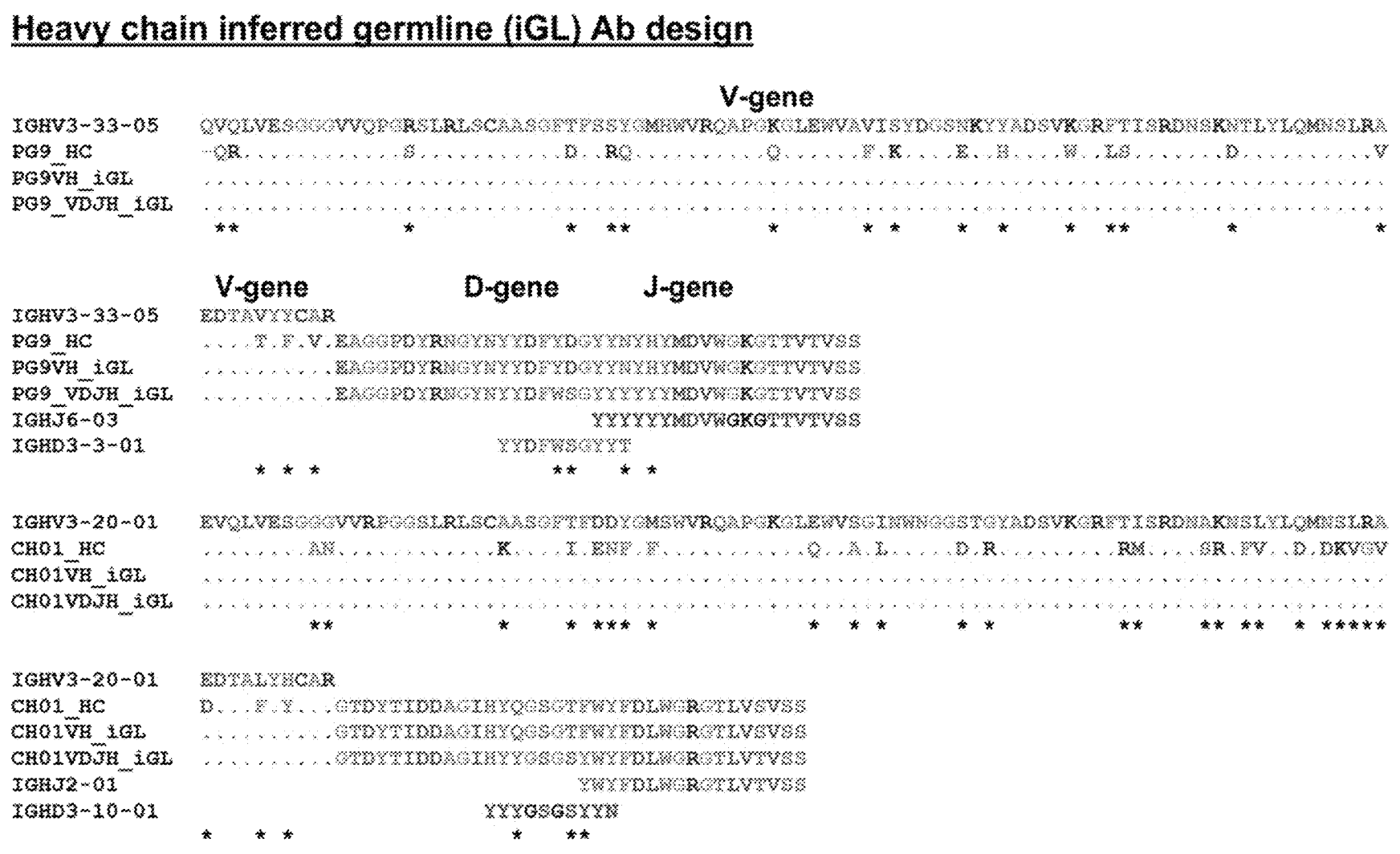
Figure 10B:
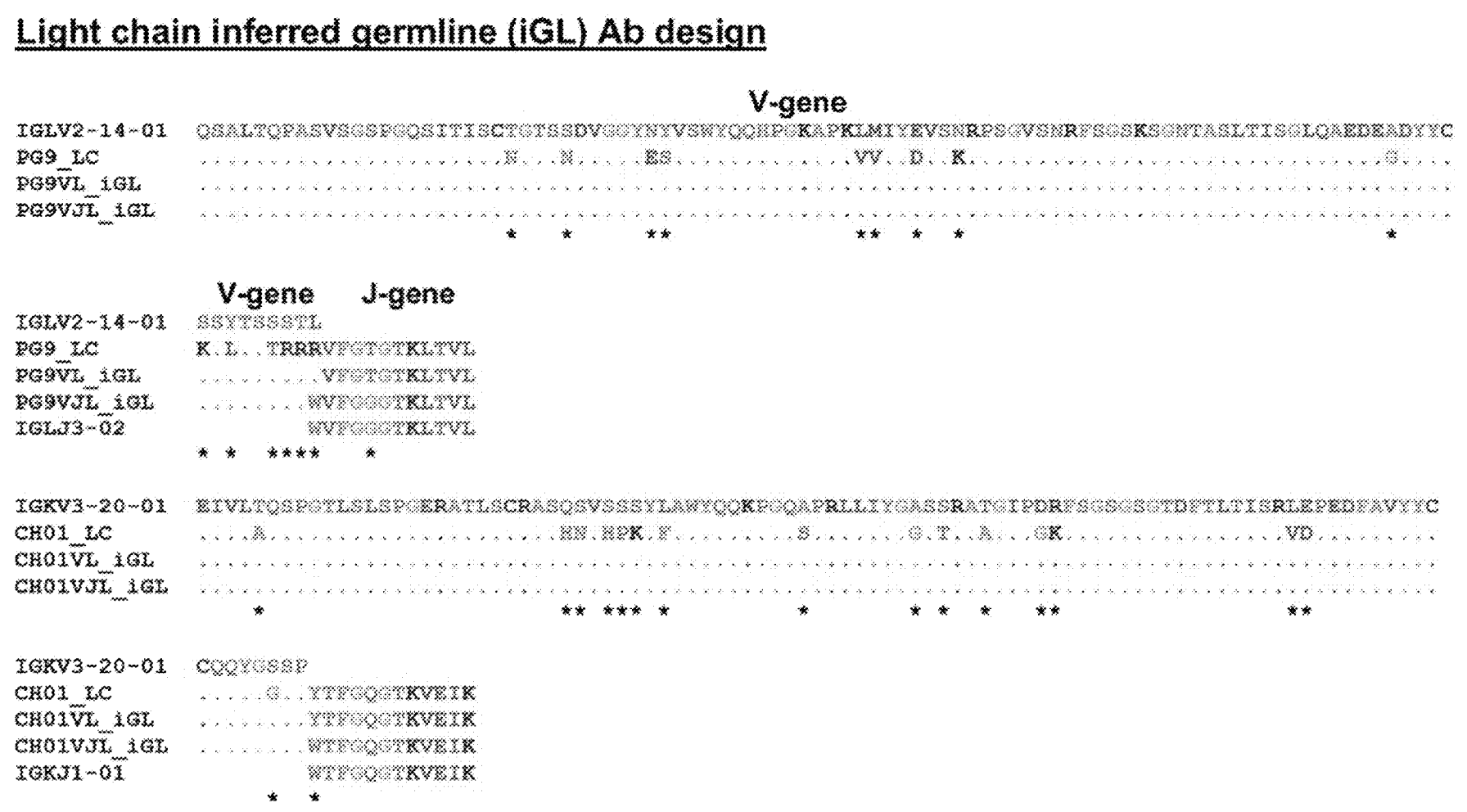

One property thought to be critical for vaccine immunogens to select rare bnAb precursors is the ability to effectively bind to UCA B cell receptors (Dosenovic et al., 2015; Escolano et al., 2016; Jardine et al., 2015; McGuire et al., 2016; Steichen et al., 2016a). Therefore, to gain or improve binding of the V2 apex bnAb inferred precursor Abs to MT145 Env trimer, glutamine (Q) was substituted with lysine (K) at residue (HXB2 position 171) in strand C of the V2 apex bnAb core epitope (FIG. 1A-B). This substitution is based on the presence of a positively charged motif (KKKK)(SEQ ID NO:5) in CRF250 and CP256. SU strand C V2 Env sequences, both of which bind V2 apex bnAb prototype precursors (Andrabi et al., 2015; Doria-Rose et al., 2014; Gorman et al., 2016). ELISA binding revealed strong binding of the mature V2 apex bnAb prototypes with the MT145-WT trimer and weak but detectable binding with one of the UCA Abs, CAP256 UCA (FIG. 1C). Strikingly, binding with a V2-engineered MT145 trimer (henceforth referred to as "MT145K") not only improved binding to CAP256 UCA Ab but also conferred binding on both PG9 and CH01 iGL Abs (FIG. 1C). The PG9 and CH01 iGL Abs used here had diversity (D; heavy chain) and joining (J; both heavy and light chains) genes reverted to their corresponding germline gene families in the CDRH3s, in addition to the VH and VL regions reported previously (FIG. 10) (Andrabi et al., 2015; Gorman et al., 2016).

Figure 1D:
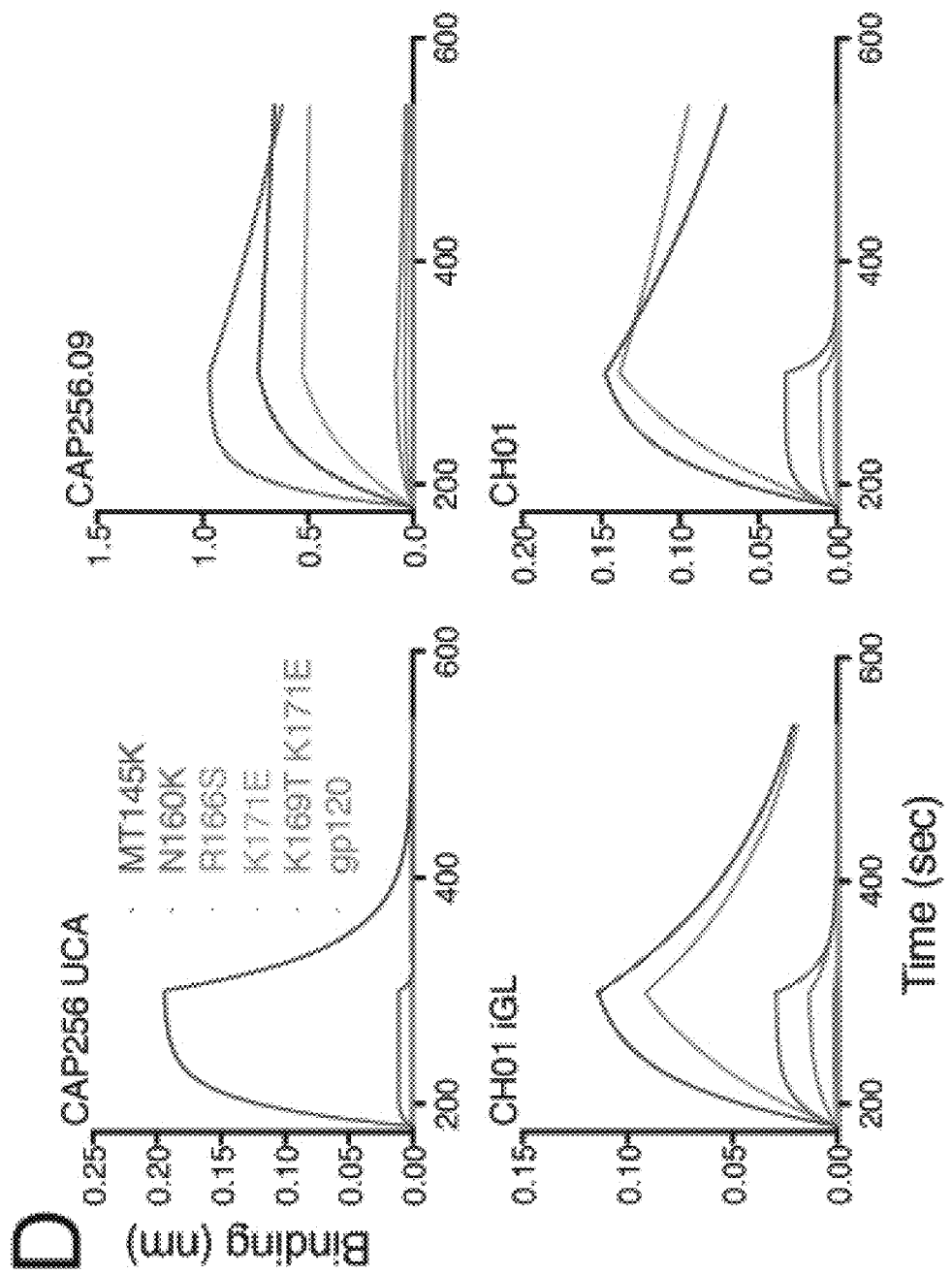

Previous mapping studies have examined the HIV core epitope recognized by mature V2 apex bnAbs (Andrabi et al., 2015; Gorman et al., 2016; Landais et al., 2017; Lee et al., 2017; McLellan et al., 2011; Pancera et al., 2013; Walker et al., 2009). To evaluate the contributions of V2 apex core epitope glycan and protein residues to binding by V2 apex bnAb inferred germline-reverted (iGL) Ab versions, MT145K strand C peptide and glycan trimer variants known to eliminate interactions of V2 apex bnAbs with the Env trimer were generated (see Andrabi et al., 2015; McLellan et al., 2011; Pancera et al., 2013). Bio-Layer Interferometry (BLI or octet) binding analyses of the iGL Abs with these trimer variants showed that glycan/peptide epitope requirements of precursor Abs were largely similar to the requirements of corresponding mature Abs (FIG. 1D), suggesting that most contacts with the MT145K V2 apex core epitope are already encoded in the germline configuration for this class of bnAbs. Notably, the mature Abs showed slightly more tolerance to changes within the core protein epitope, particularly for the CAP256.09 bnAb, suggesting that part of the affinity maturation in this class of Abs may be to accommodate variation within the bnAb V2 apex core epitope. Overall, the strand C V2-modification in the MT145 SOSIP.664 trimer conferred binding to multiple V2 apex bnAb germline prototypes.

Example 3: Structure

Architecture of the MT145K Trimer.

The structure of the MT145K trimer was solved by cryo-EM to a global resolution of ~4.1 Å (FIG. 11). Data collection methods are summarized in the following table.

| Data collection | |
| --- | --- |
| Microscope | FEI Titan Krios |
| Voltage (kV) | 300 |
| Detector | Gatan K2 Summit |
| Recording mode | Counting |
| Magnification (incl. post-magnification) | 49,020 |
| Movie micrograph pixelsize (Å) | 1.02 |
| Dose rate ($e^-$/[(camera pixel)*s]) | 10 |
| Number of frames per movie micrograph | 50 |
| Frame exposure time (ms) | 200 |
| Movie micrograph exposure time (s) | 10 |
| Total dose ($e^-/Å^2$) | 94 |
| Defocus range (μm) | 1.0-3.6 |
| EM data processing | |
| Number of movie micrographs | 1,281 |
| Number of molecular projection images in map | 44,301 |
| Symmetry | C3 |
| Map resolution (FSC 0.143; Å) | 4.1 |
| Mapsharpening B-factor ($Å^2$) | −130 |
| Structure Building and Validation | |
| Number of atoms in depositedmodel | 15,192 |
| gp120 | 3,547 |
| gp41 | 964 |
| glycans | 553 |
| MolProbity score | 1.72 (88%) |
| Clashscore | 3.55 |
| EMRinger score | 2.26 |
| Deviations from ideal | |
| Bond length outliers | 0 (0%) |
| Bond angles outliers | 0 (0%) |
| Ramachandran plot | |
| Favored (%) | 88.9 |
| Allowed(%) | 10.5 |
| Outliers (%) | 0.5 |

Figure 2A:
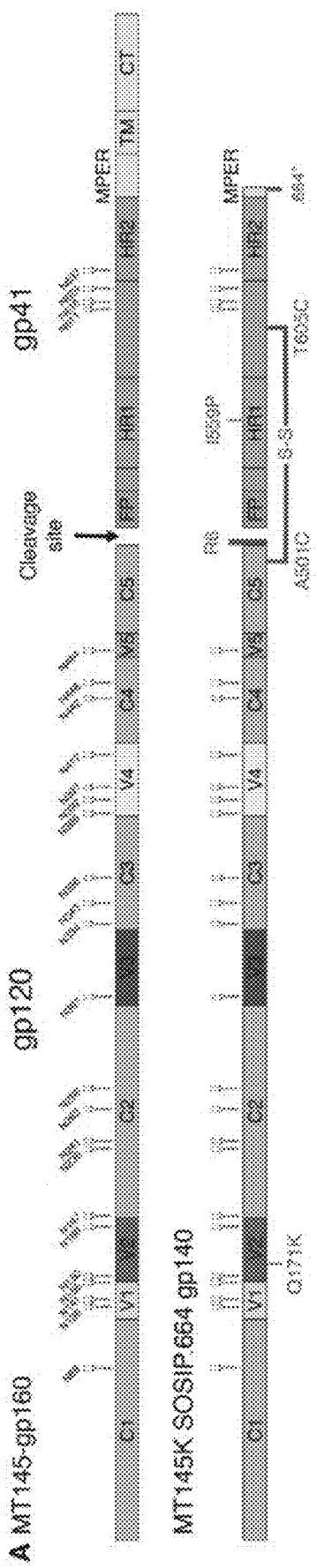
FIG. 2A-2E. Cryo-EM structure of the MT145K trimer. A. Schematic showing MT145K SOSIP soluble trimer design from its full-length gp160 Env sequence. The gp120 constant (C1-C5) and variable (V1-V5) regions and the gp41 regions (fusion peptide (FP), heptad repeat (HR1 and H1R2), membrane proximal external region (MPER), transmembrane (TM) and cytoplasmic tail (CT)) are indicated. The N-linked glycan positions for each NXT/S residue are labeled according to the HIV HXB2 numbering scheme. The SOSIP trimer stabilizingz modifications include: (i) disulfide bond: A501C-T605C, (ii) R6 cleavage site, (iii) I559P, and (iv) 664-residue truncation in gp41 MPER. The substitution to incorporate a K-residue at position 171 (Q171K) to gain binding for V2 apex iGL Abs is indicated in blue. B-C. Side and top views of the unliganded MT145K trimer model based on the cryo-EM density map at ~4.1 Å resolution. Ribbon representations of the MT145K trimer spike, in which the subunits gp120 (cornflower blue) and gp41 (orange) are depicted on one protomer. The gp120 variable loops (V1-V5) positioned to the trimer periphery are depicted in different colors (V1: khaki, V2: red, V3: magenta, V4: yellow and V5: chartreuse). The fusion peptide region of gp41 is shown in cyan. Glycan sugar residues modeled based on density are represented in forest green stick form. D. Superimposition of variable loops (V1-V5) and fusion peptide region for MT145K and unliganded HIV clade A BG505 (PDB: 4ZMJ) SOSIP trimers. The dotted lines indicate regions in the V-loops or FP for which the observed electron density was absent or unclear. E. Structural comparison of gp41 regions of MT145K (orange) and BG505 (grey) trimers. The gp41 structural elements overall show a similar arrangement except for the fusion peptide region (colored cyan on MT145K and pink on BG505), that is exposed on the BG505 trimer but remains hidden in a pocket inside the MT145K trimer.
Figure 2B:
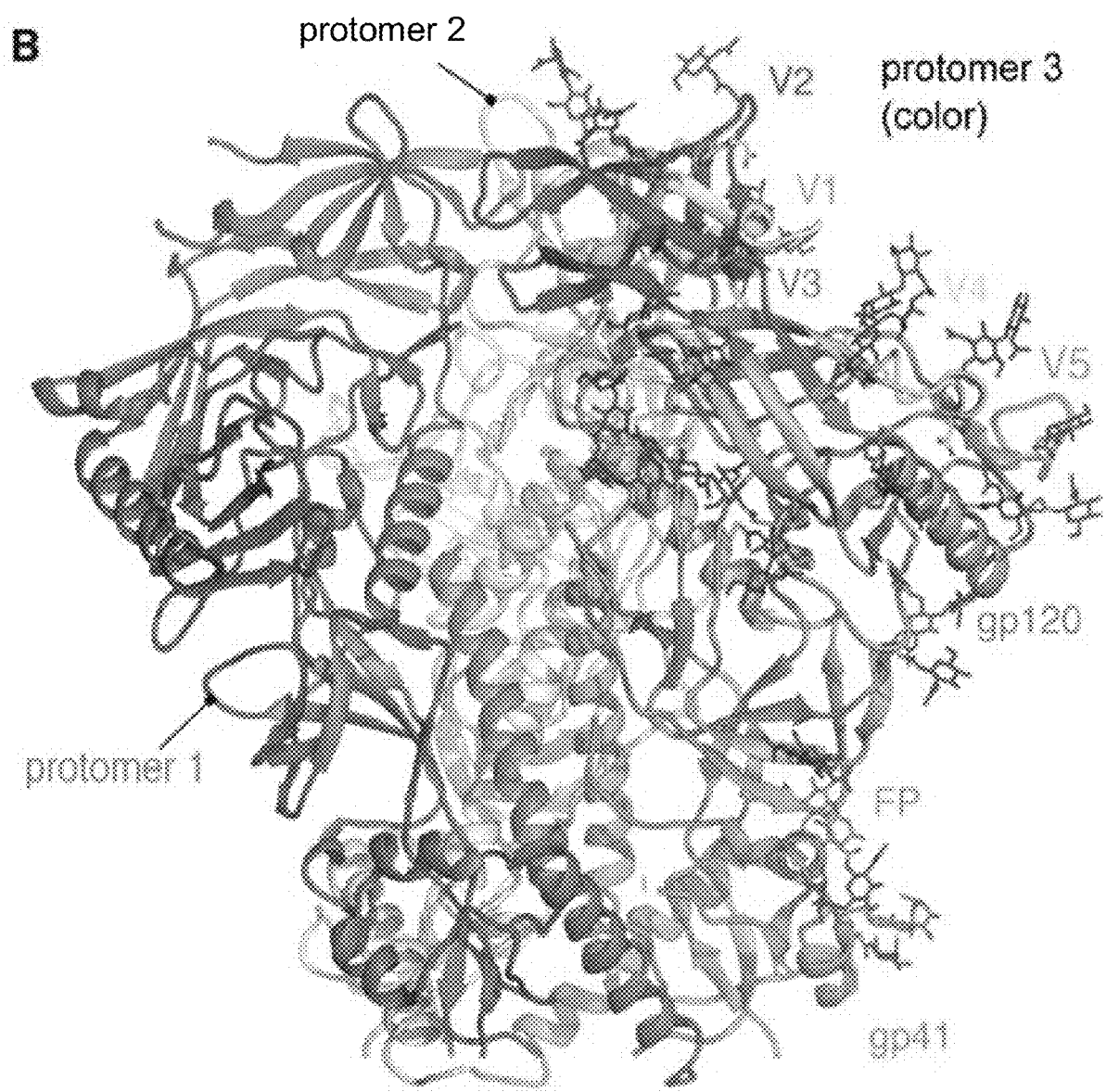
Figure 2C:
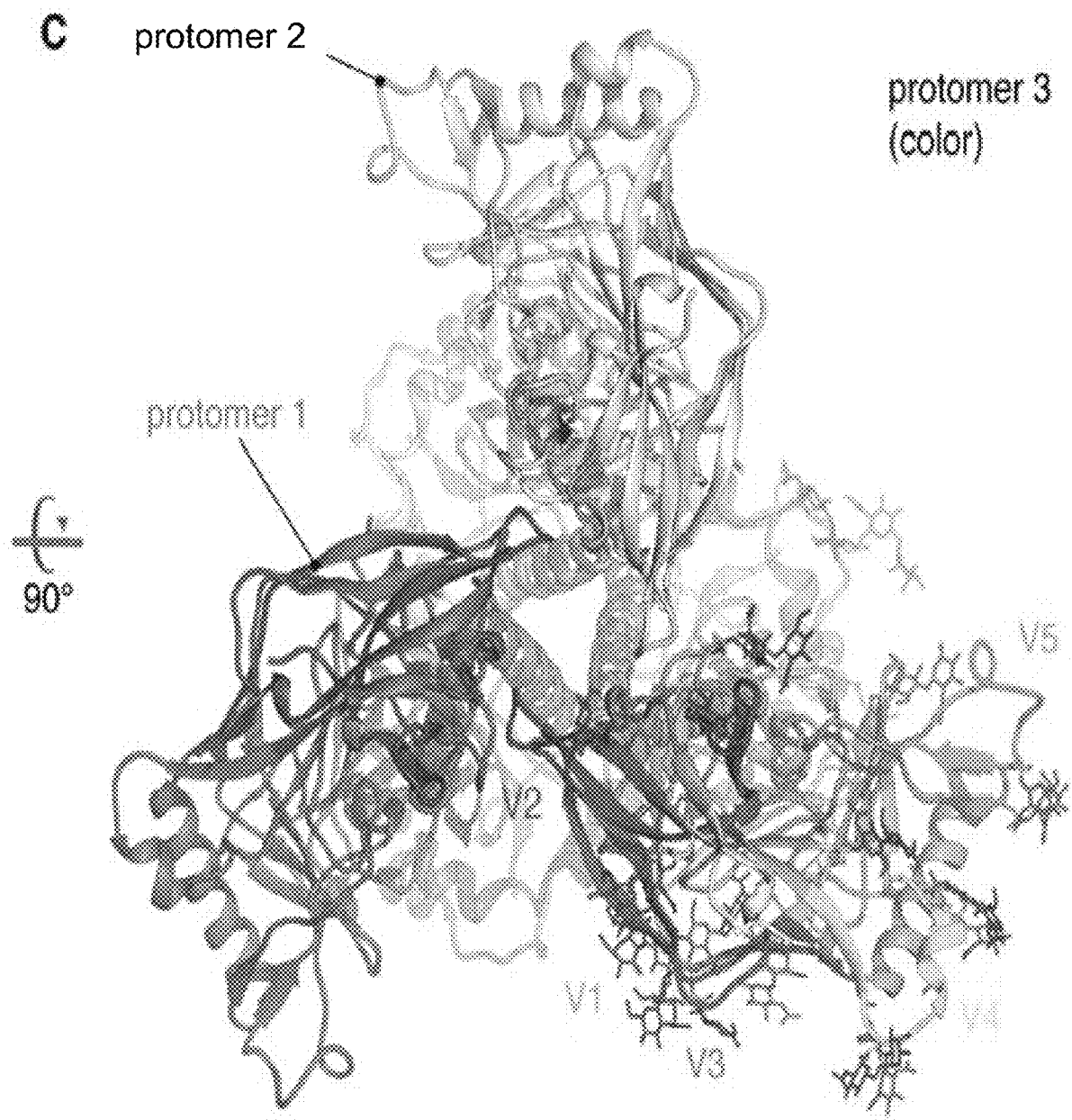
Figure 2D:
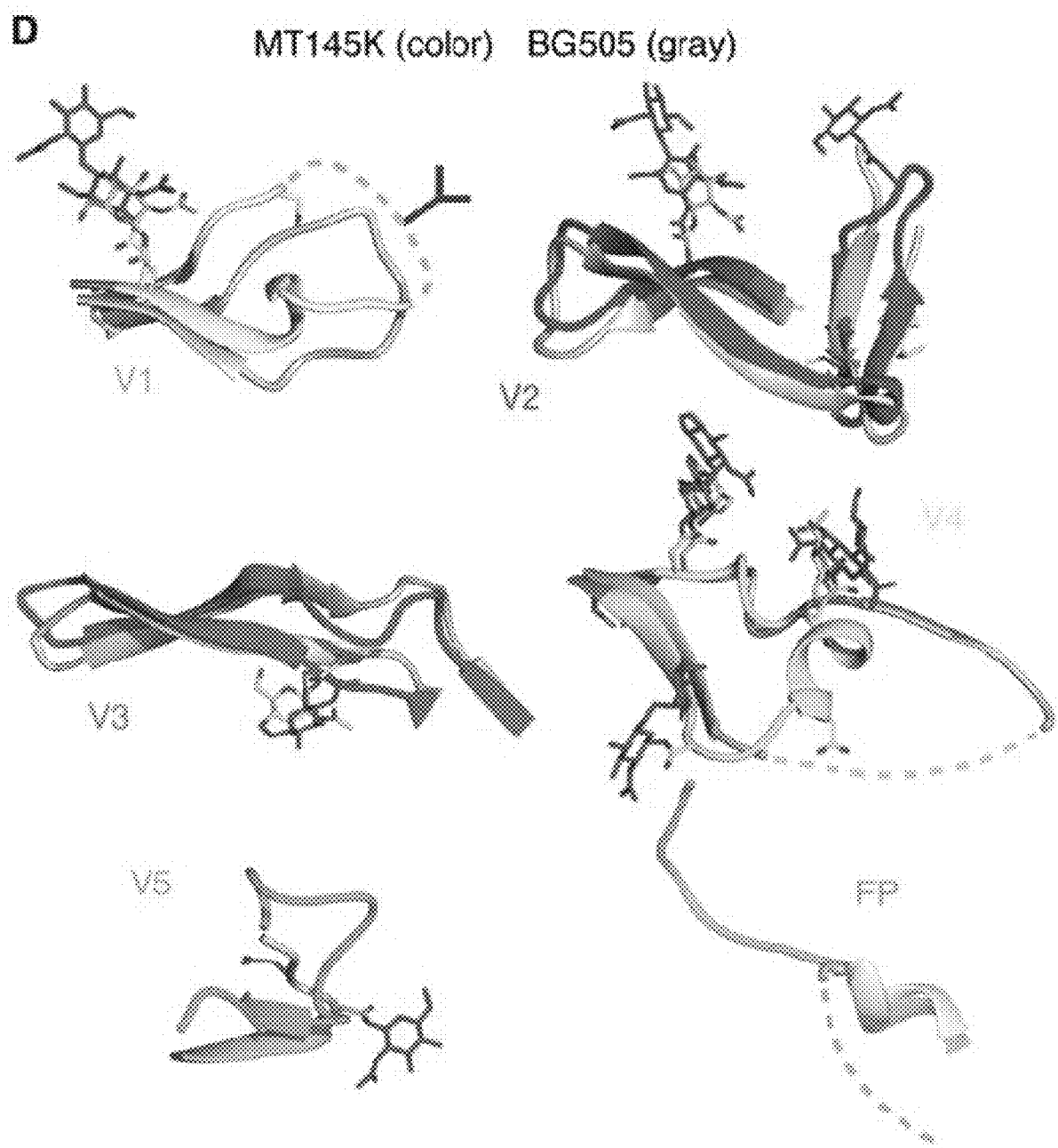
Figure 12:
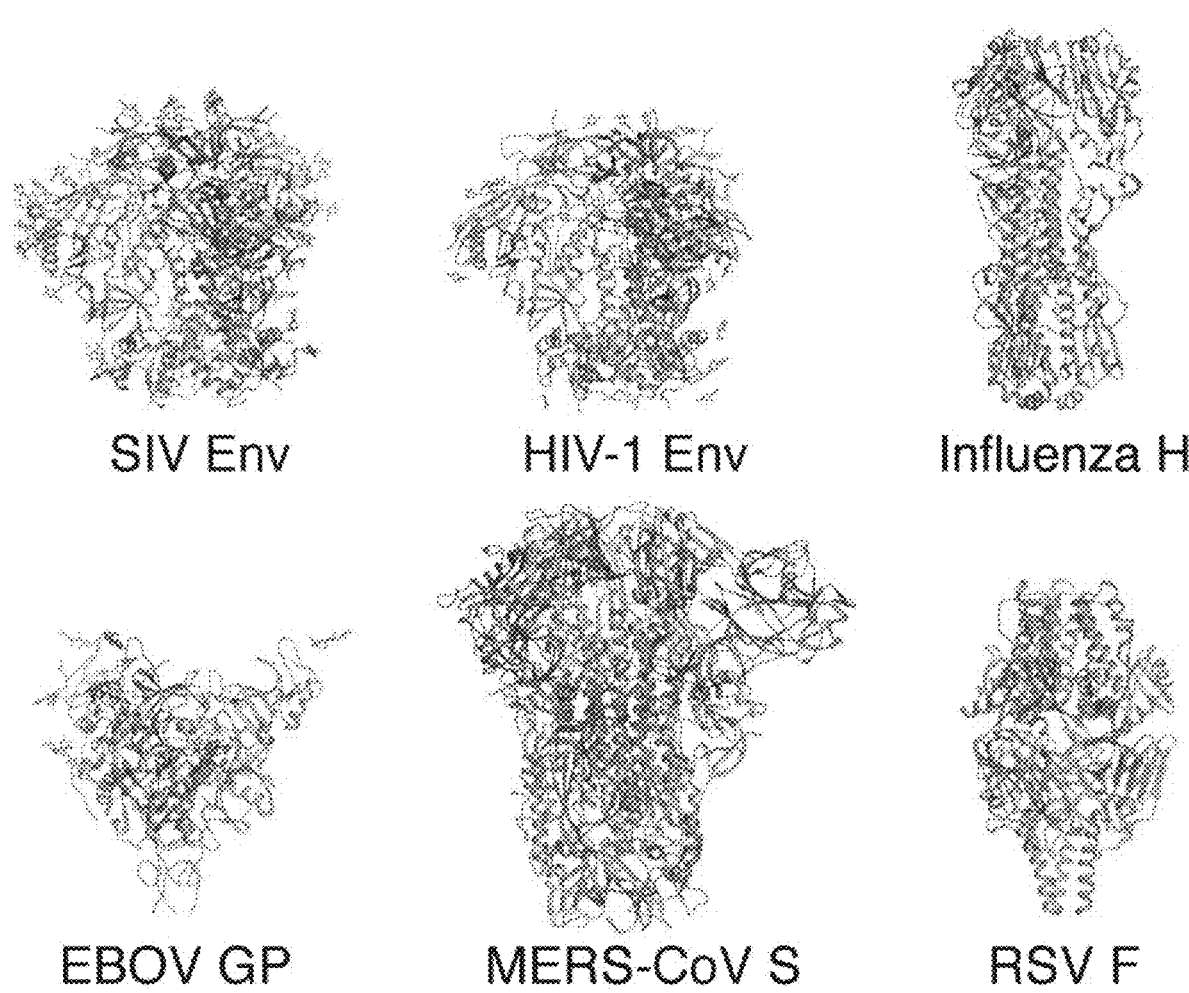
FIG. 12. Comparison of Env trimer architectures of class I fusion proteins. Prefusion SIV Env (MT145K; current study) follows an overall organization similar to other known prefusion class I fusion proteins. Fusion subunits (shown in orange) are most commonly organized membrane-proximally (RSV F deviating somewhat from this trend). Fusion subunits are largely shielded and capped by receptor-recognizing subunits (shown in cornflower blue) in the meta-stable prefusion state. SIV Env is most similar to HIV-1 Env; however, MT145K is less compact than the displayed HIV-1 Env trimer (BG505 isolate). The more open organization of MT145K may be the result of its fusion peptide being inserted into a pocket at the gp120/gp41 interface as opposed to the fusion peptide found on the outside of the HIV-1 Env trimer (MT145K: current study, HIV-1: PDB 4ZMJ (Kwon et al., 2015); Influenza A H1N1: PDB 1RD8 (Stevens et al., 2004); Ebola virus GP: PDB 5KEL (Pallesen et al., 2016); MERS-CoV S: PDB 5W9J (Pallesen et al., 2017); RSV F: PDB 4JHW (McLellan et al., 2013).

The structure represents the first atomic level structure of an SIV Env trimer. Like other class I fusion proteins, protomers (gp120 and gp41) of MT 145K trimerize to form a metastable pre-fusion Env trimer (FIGS. 2A-B, 12). The trimer architecture exhibits a mushroom-like shape with subunits gp120 and gp41 constituting the envelope-distal and proximal entities, respectively (FIG. 2B). Overall, the MT 145K trimer configuration closely resembles that of the trimeric HIV-1 Env spike, with an overall Cα root mean square deviation (rmsd) of 1.9 Å (Kwon et al., 2015). Arrangement of V-loops in the MT145K Env trimer is reminiscent of the V-loop arrangement in the HIV Env trimer and is suggestive of a similar role in immune evasion by steric occlusion of underlying conserved epitopes (Julien et al., 2013a; Pancera et al., 2014). Notably, the V1 and V2 loops are largely solvent-exposed and occlude access to the underlying V3 loop (FIG. 2C). Inaccessibility of the V3 loop is mediated by intra-protomer interactions of V1V2 to V3 and by extensive inter-protomer V1V2 trimer interactions at the apex of the spike. The SIV Env trimer exhibits well-ordered V2-V5 loops, while V1 is somewhat disordered (FIG. 2D).

Figure 2E:
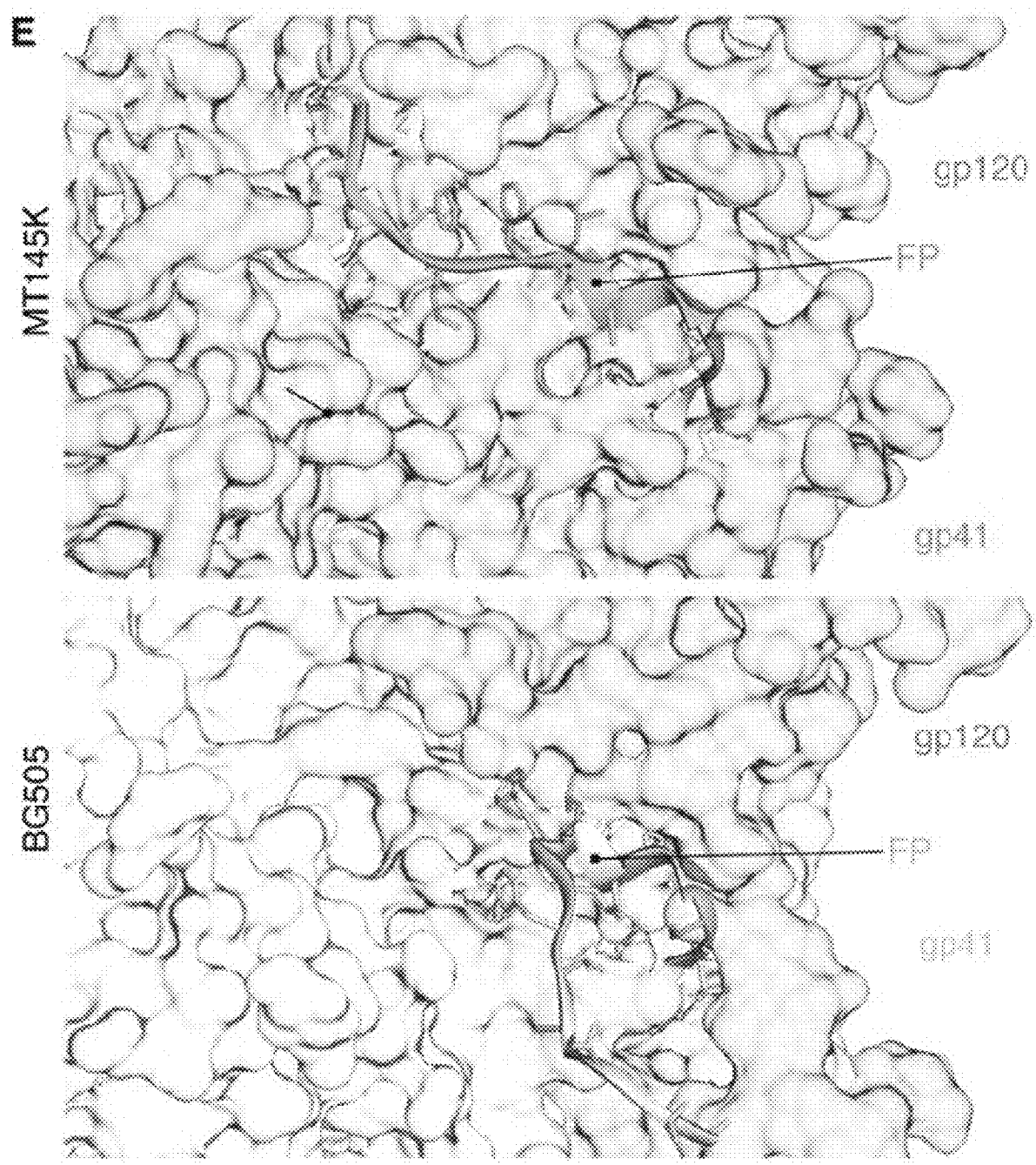

Proximal to the viral membrane is the gp4i subunit that forms the base of the trimer spike and is arranged into heptad repeat-1 (HR1), HR2 and the fusion peptide (FP) (FIG. 2B). Similar to the HIV Env trimer, the three C-terminal helices of HR1 are centrally positioned along the trimer axis perpendicular to the viral membrane (Julien et al., 2013a; Lyumkis et al., 2013; Pancera et al., 2014). Intriguingly, the FP region, which has been observed solvent-exposed on the outside of the HIV-1 Env, is positioned in a pocket inside the MT145K trimer and remains sequestered in all three protomers (FIG. 2E).

Example 4: Glycan Analysis

Conservation of the Glycan Shield on HIV and SIV Env Trimers.

Figure 3A:
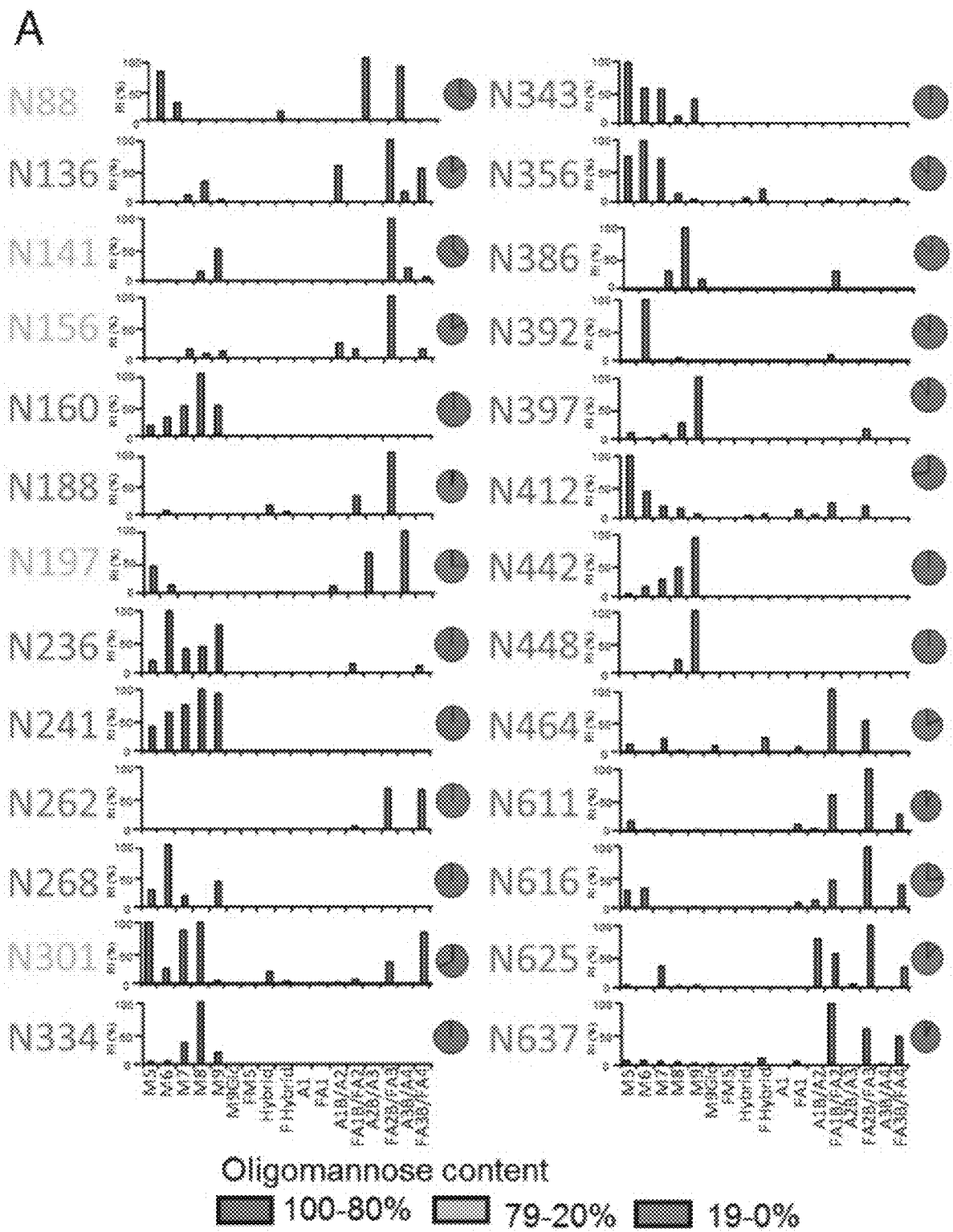
FIG. 3A-3C. Site-specific glycoform composition of MT145K trimer. A. Site-specific glycoform quantification of the MT145K SOSIP soluble trimer. MT145K trimers from transiently transfected HEK293T cell expressed supernatants were affinity purified by the quaternary trimer-specific antibody, PGT145. The purified MT145K trimers were treated separately with three proteases: trypsin, chymotrypsin and elastase and the digests were enriched for glycopeptides and analysed by LC-ESI MS. The individual glycan composition of the N-linked glycan sites (n=26) is represented by bar graphs that indicate the relative abundance of each glycoform species and are derived from the mean of two analytical replicates. The pie charts summarize the proportion of glycoforms for each site and this information is color coded; oligomannose-type (green) and complex/hybrid glycans (pink). B. HILIC-UPLC profiles of the total N-linked glycans released from MT145K trimers. The proportions of oligomannose plus hybrid glycan contents and complex-type glycans are represented in green and pink colors, respectively. C. Modeled glycan shields for MT145K and BG505 SOSIP trimers. $Man_9GlcNAc_2$ oligomannose-type glycans were docked and rigid-body-fitted at each of the corresponding Env glycan positions using the MT145K structure (determined in this study (PDB: submit)) and the unliganded BG505 SOSIP.664 trimer structure ((Kwon et al., 2015) PDB: 4ZMJ). Top and side views of the trimers are shown and the individual glycan sites are labelled and color-coded based on the content of oligomannose; green (100-80%), orange (79-20%) and pink (19-0%).
Figure 3B:
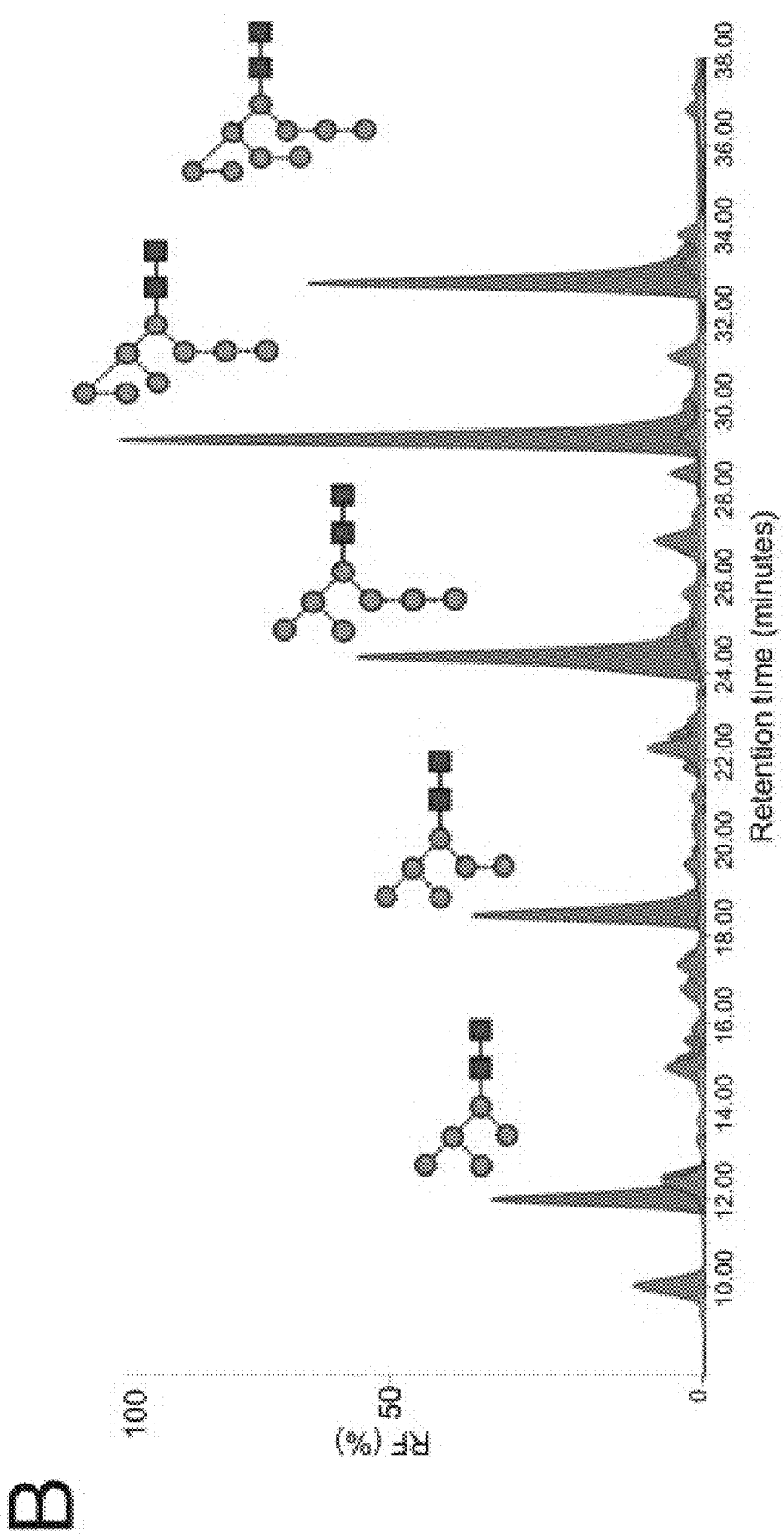
Figure 3C:
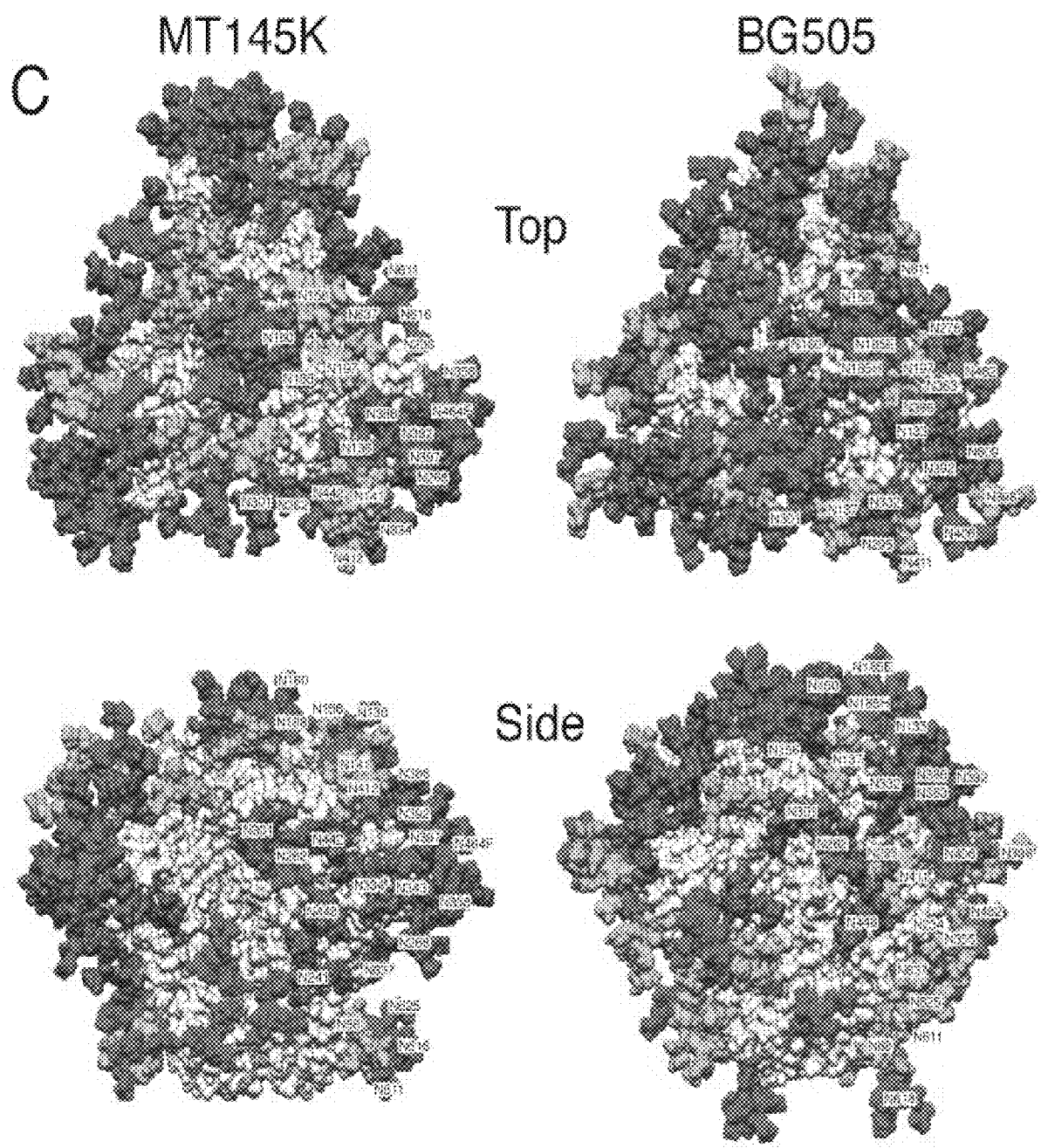
Figure 13A:
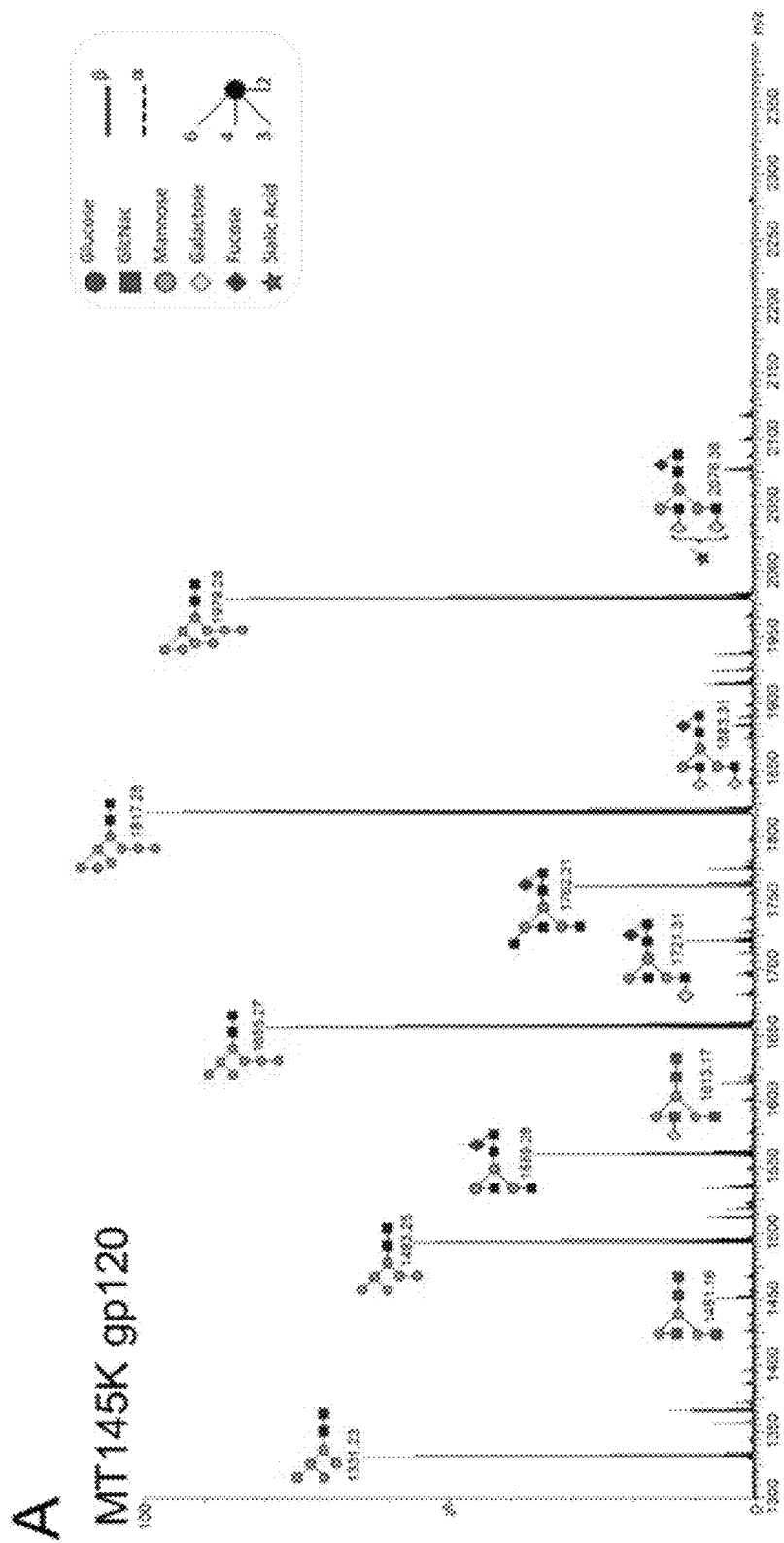
FIG. 13A-13B. Negative ion TOF MS of released glycans from Chimpanzee SIV, MT145K gp120 and gp41. A. Driftscope extracted singly charged ions of released glycans from MT145K-gp120. B. Driftscope extracted singly charged ions of released glycans from MT145K-gp41.
Figure 13B:
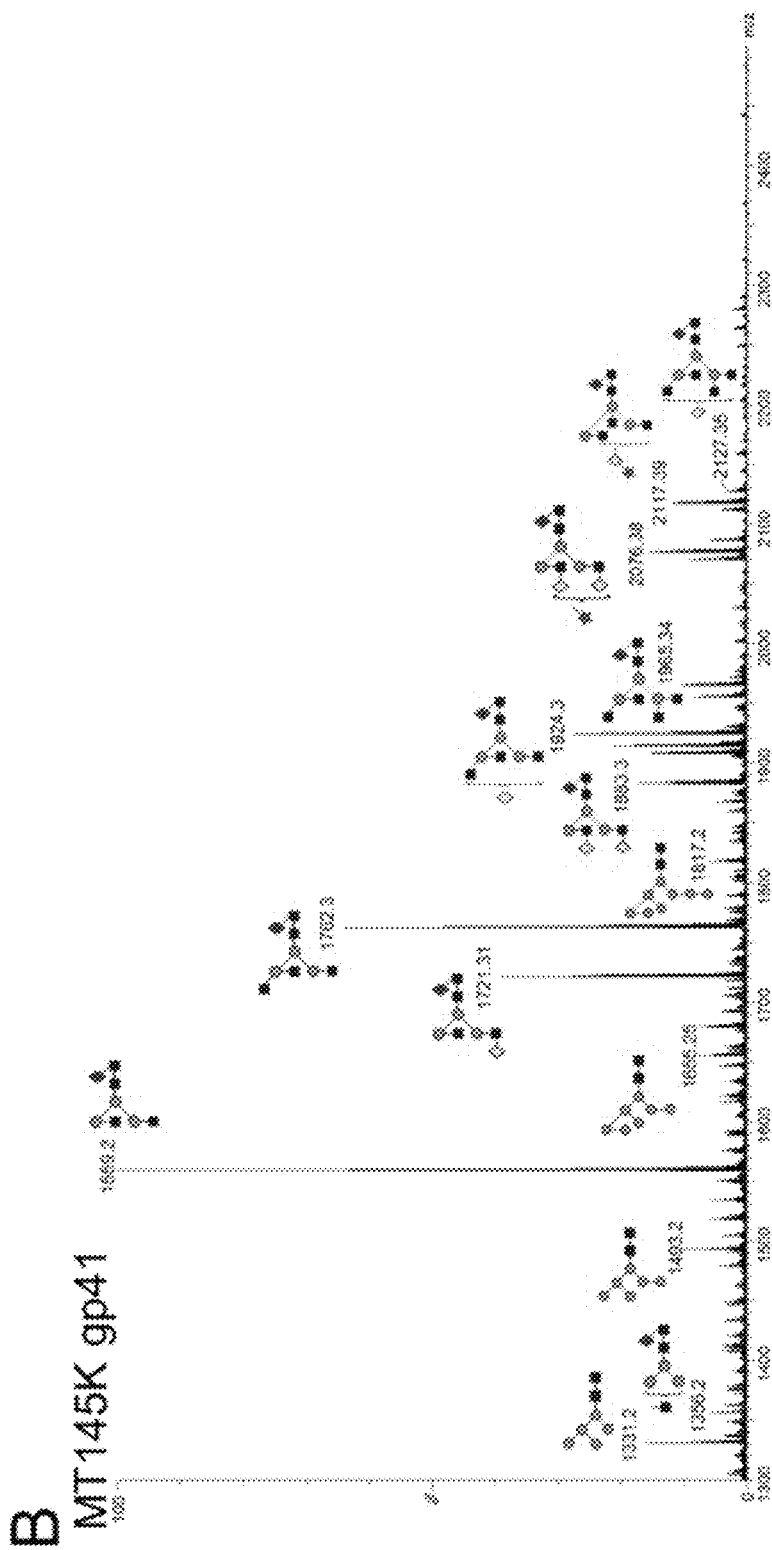

To compare the nature of the glycan shield on SIVcpzPtt Env and HIV Env, site-specific glycan analysis of the MT145K trimer was performed. The overall oligomannose content of the MT145K trimer is similar to HIV Env (FIG. 3A-B) (Panico et al., 2016; Pritchard et al., 2015). However, although the distributions differed from the HIV-1 clade A strain BG505, which is dominated by $Man_9GlcNAc_2$ oligomannose-type glycans, MT145K is predominantly $Man_8GlcNAc_2$ (Behrens et al., 2016). In addition, further processing was evident in the MT145K trimer which showed elevated $Man_{6-7}GlcNAc_2$ structures (FIG. 3B, 13). The outer domain of gp120 presents a high density of oligomannose glycans that form the intrinsic mannose patch (Bonomelli et al., 2011), which was a highly conserved feature across the two viral species. The apex of the MT145K trimer possesses oligomannose-type glycans at N160 that correspond to the trimer associated mannose patch (TAMP) also observed on HIV-1 Env (Behrens et al., 2017). As for HIV-1, glycans at the base of the trimer at N88 and on gp41 of the MT145K trimer are extensively processed (FIGS. 3A, C, 13).

Figures 14A, 14B:
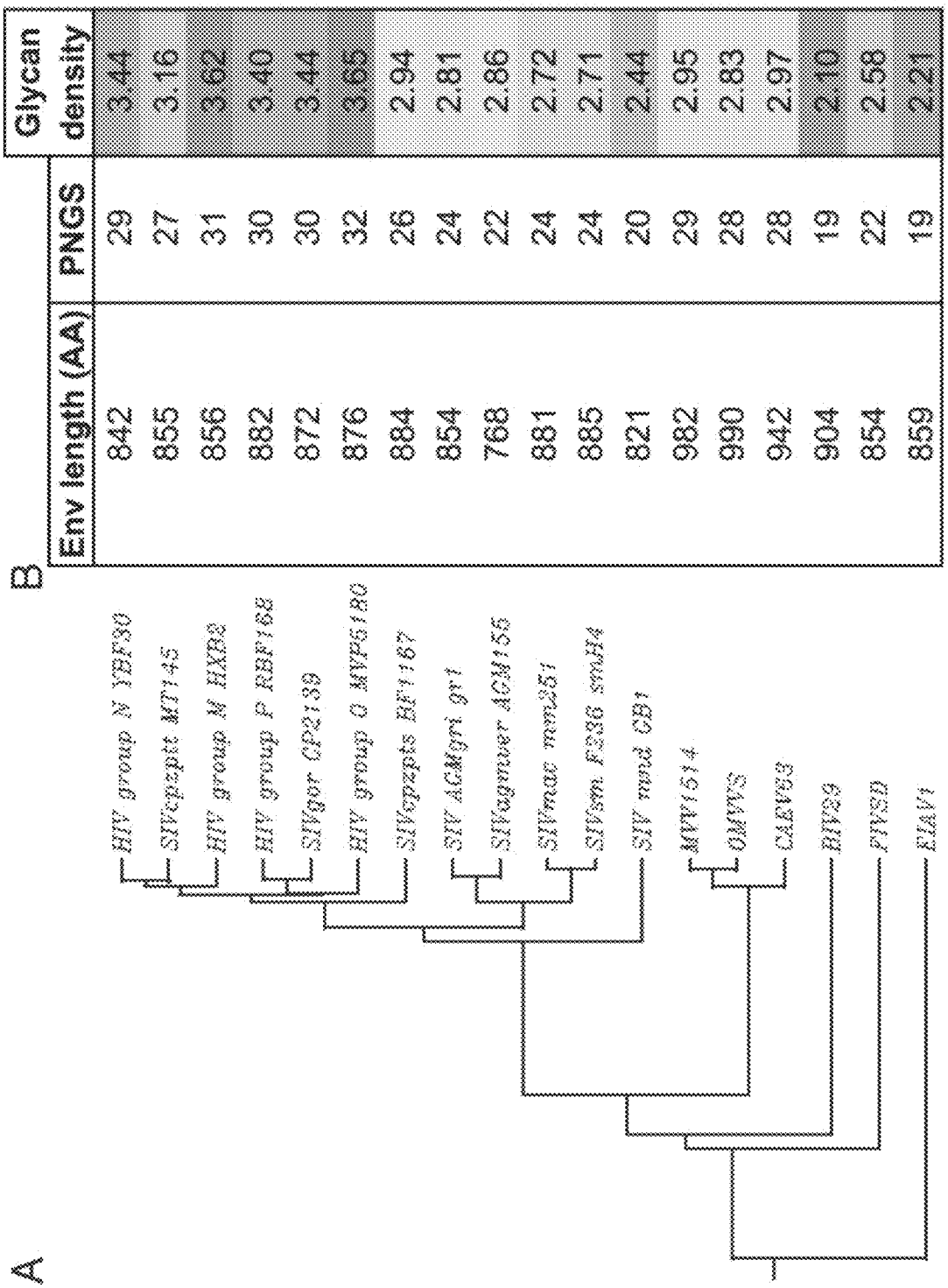
FIG. 14A-14B. Phylogeny of lentiviruses and the glycan shield density. A. Phylogenetic relationships among the envelope sequences derived from various lentiviruses; tree constructed by maximum likelihood method. These lentiviruses infect host species that include equine (EIAV), feline (FIV), bovine (BIV), caprine/ovine (CAEV, OMVVS and MVV), simian (SIV) and humans (HIV). B. The number of amino acids and the number of Potential N-linked Glycan Sites (PNGS: predicted by N-GlycoSite tool at Los Alamos HIV database) in the full-length envelopes are listed for each lentivirus. The glycan shield density for each virus is represented as % Env residues that encode PNGS motifs and was calculated by (number of PNGS/Env length×100). The glycan shield density shows a gradual increase from EIAV through CAEV, and plateaus in some of the SIV species including SIVcpzPtt, the one that has been shown to have crossed into humans.
Figure 15:
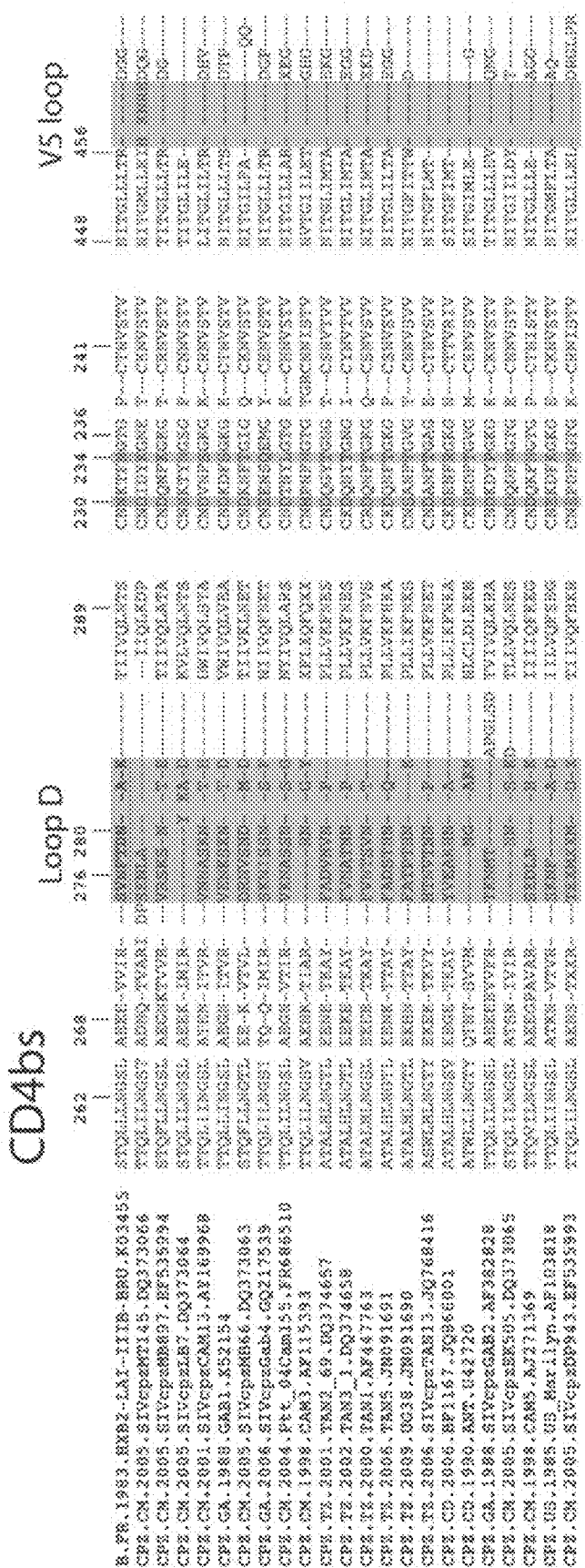
FIG. 15. Amino-acid sequence alignment of SIV envelopes with HXB2 HIV-1 Env as a reference depicting SIV Env residues equivalent to HIV bnAb epitopes. The amino-acid alignment of SIVcpzPtt envelope sequences compared to the HXB2 reference sequence. The protein residues (highlighted in grey) and the N-glycosylation sites (depicted in red) for each bnAb epitope region (V2-apex, V3-N332, CD4bs and gp120-gp41 interface) are shown. Eleven regions of 23 aligned Env isolates are depicted, indicated by amino acid numbers: i) 156-175, ii) 320-353, iii) 409-447, iv) 256-291, v) 228-245, vi) 448-467, vii) 84-93, viii) 448-455, ix) 507-534, x) 605-614, and xi) 621-646. The eleven regions of each of the 23 isolates are represented in the Sequence Listing as follows: 1) B. FR.1983. HXB2-LAI-IIIB-BRU.K03455: SEQ ID NOS: 63-73; 2) CPZ.CM.2005. SIVcpzMT145. DQ373066: SEQ ID NOS: 74-84; 3) CPZ.CM.2005. SIVcpzMB897. EF535994: SEQ ID NOS:85-95; 4) CPZ.CM.2005. SIVcpzLB7. DQ373064: SEQ ID NOS:96-106; 5) CPZ.CM.2001. SIVcpzCAM13. AY169968: SEQ ID NOS: 107-117; 6) CPZ.GA.1988. GAB1. X52154: SEQ ID NOS:118-128; 7) CPZ.CM.2005. SIVcpzMB66. DQ373063: SEQ ID NOS: 129-139; 8) CPZ.GA.2006. SIVcpzGab4. GQ217539: SEQ ID NOS: 140-150; 9) CPZ.CM.2004. Ptt_04Cam155. FR686510: SEQ ID NOS:151-161; 10) CPZ.CM.1998. CAM3. AF115393: SEQ ID NOS:162-172; 11) CPZ.TZ.2001. TAN2_69. DQ374657: SEQ ID NOS: 173-183; 12) CPZ.TZ.2002. TAN3_1. DQ374658: SEQ ID NOS:184-194; 13) CPZ.TZ.2000. TAN1. AF447763: SEQ ID NOS: 195-205; 14) CPZ.TZ.2006. TAN5. JN091691: SEQ ID NOS:206-216; 15) CPZ.TZ.2009.UG38. JN091690: SEQ ID NOS:217-227; 16) CPZ.TZ.2006. SIVcpzTAN13. JQ768416: SEQ ID NOS:228-238; 17) CPZ. CD.2006. BF1167. JQ866001: SEQ ID NOS:239-249; 18) CPZ. CD.1990. ANT.U42720: SEQ ID NOS:250-260; 19) CPZ.GA.1988. SIVcpzGAB2. AF382828: SEQ ID NOS: 261-271; 20) CPZ.CM.2005. SIVcpzEK505. DQ373065: SEQ ID NOS:272-282; 21) CPZ.CM.1998. CAM5. AJ271369: SEQ ID NOS:283-293; 22) CPZ.US.1985.US_Marilyn.AF103818: SEQ ID NOS:294-304; 23) CPZ.CM.2005. SIVcpzDP943. EF535993: SEQ ID NOS:305-315.
Figure 15:
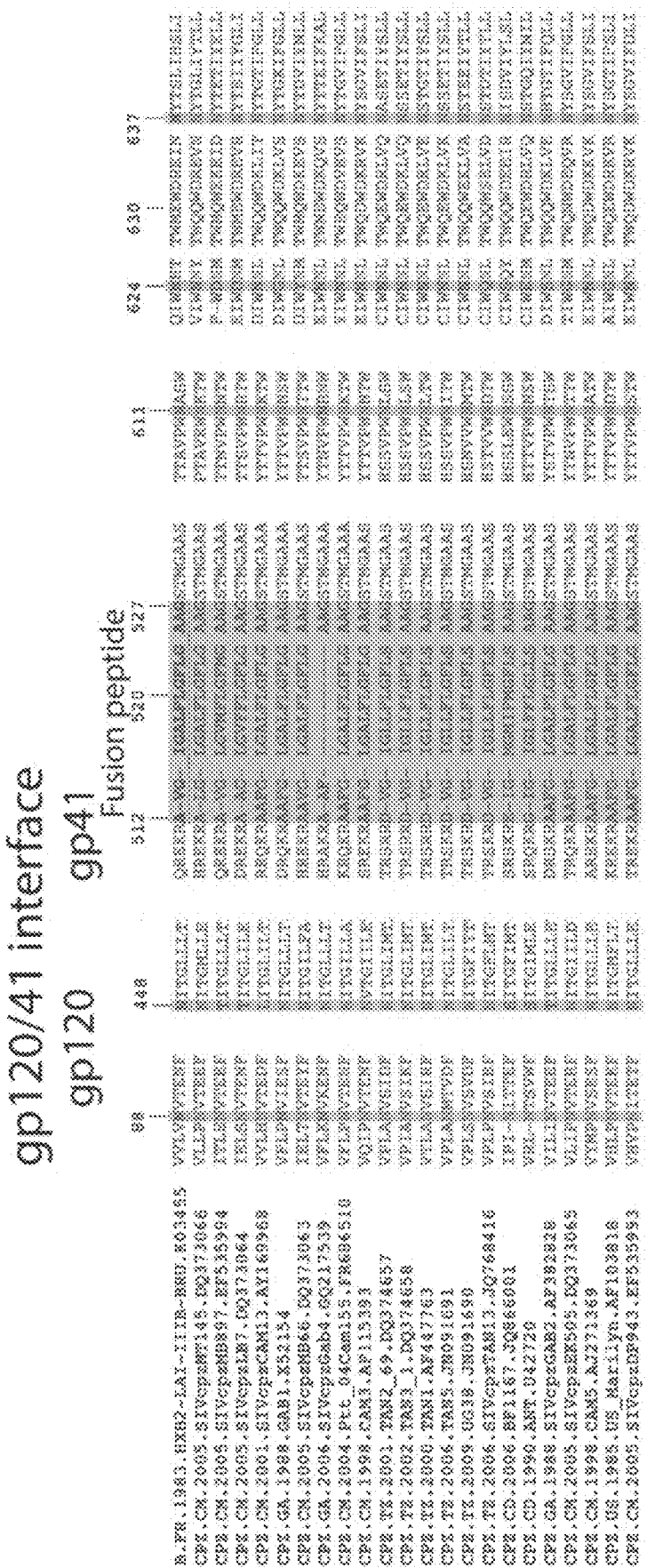
Figure 17B:
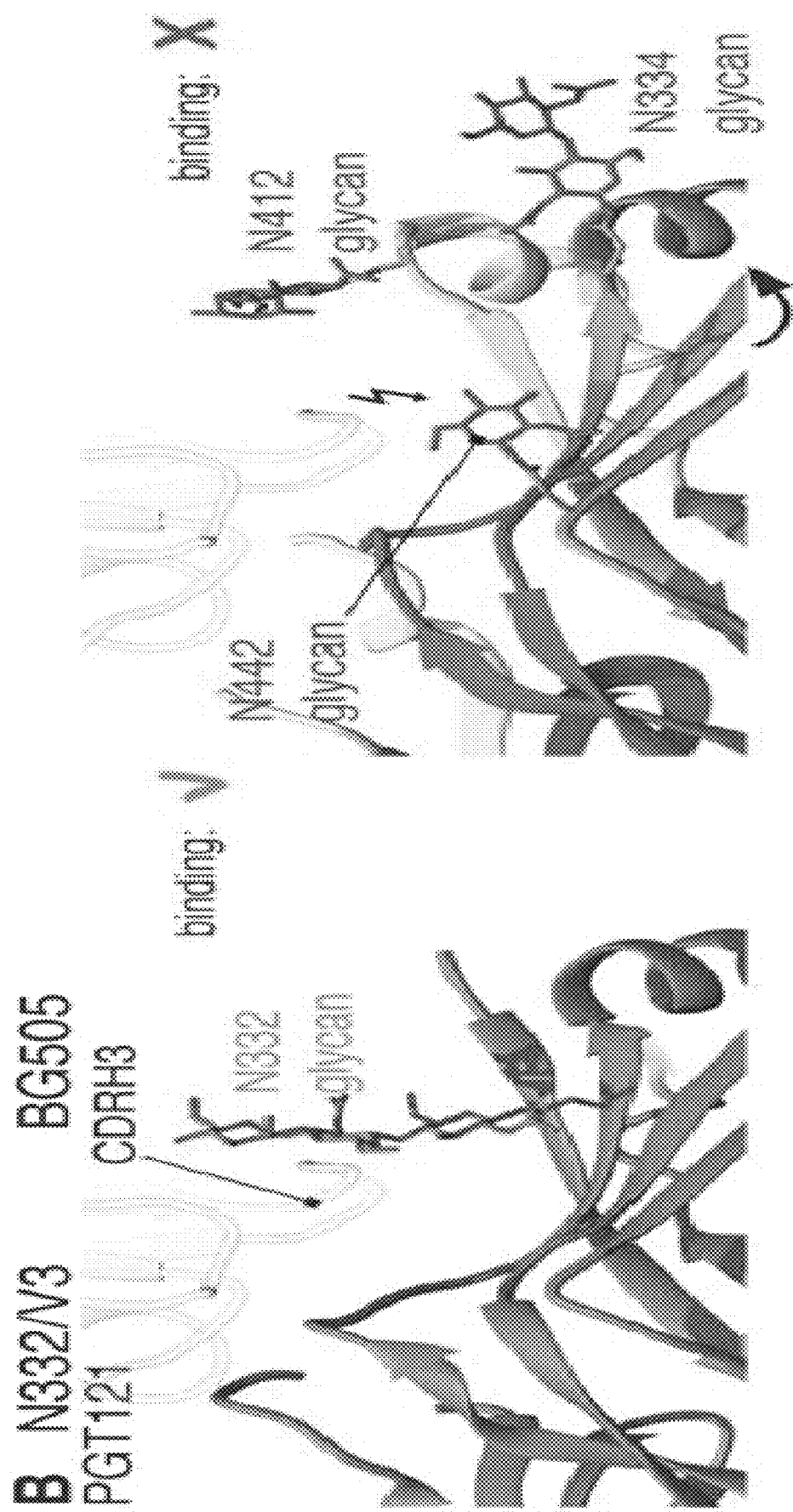
Figure 17C:
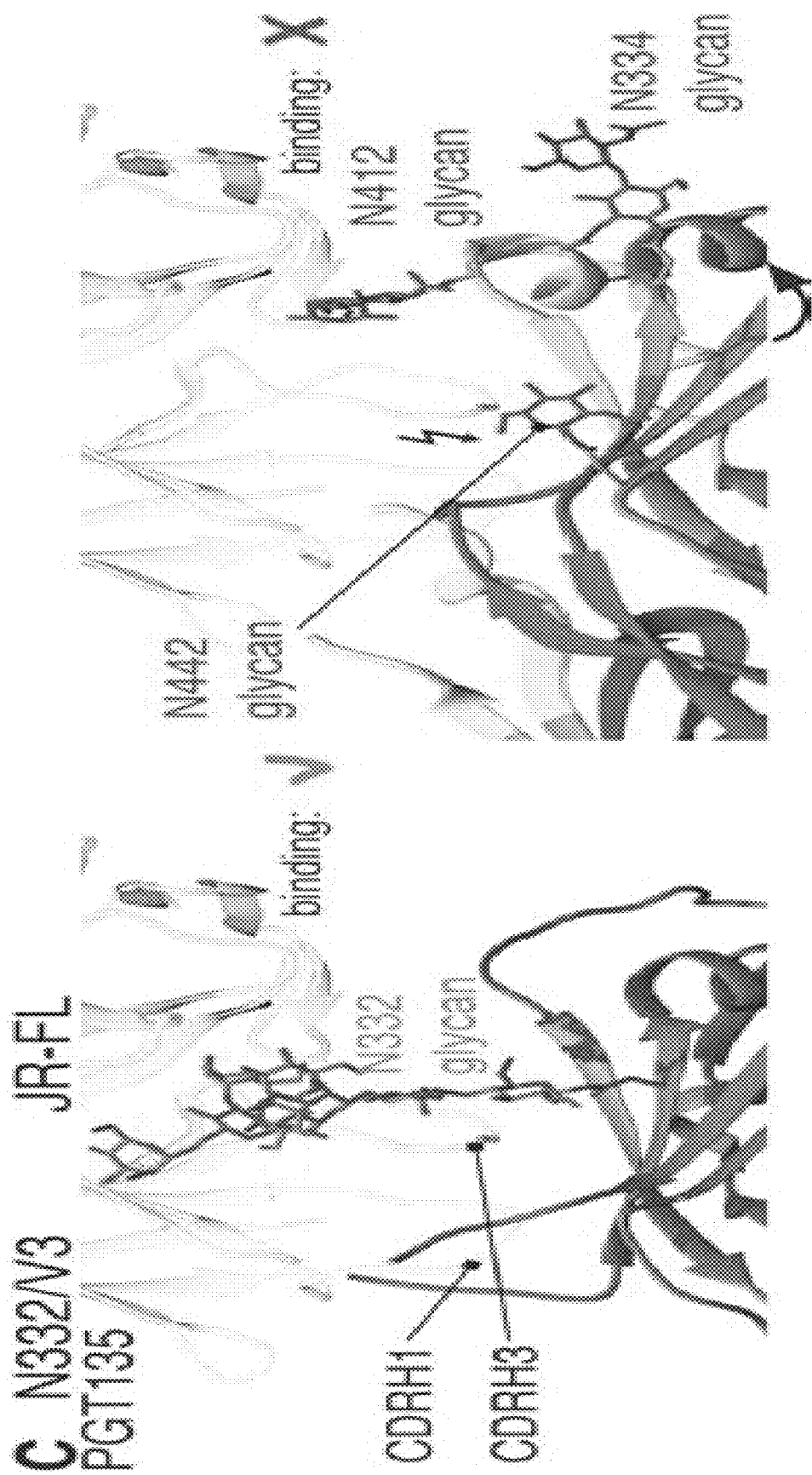
Figure 17D:
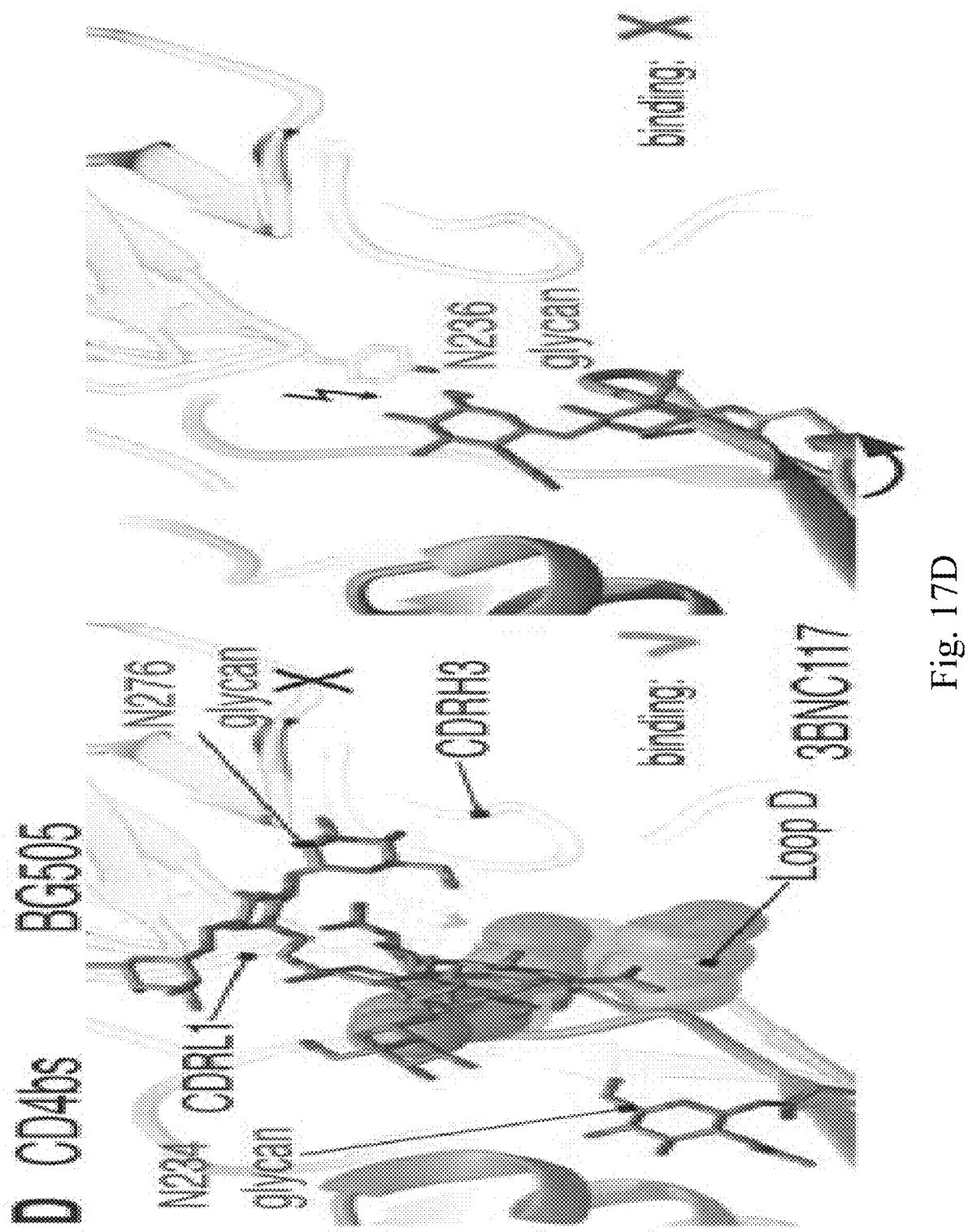
Figure 17E:
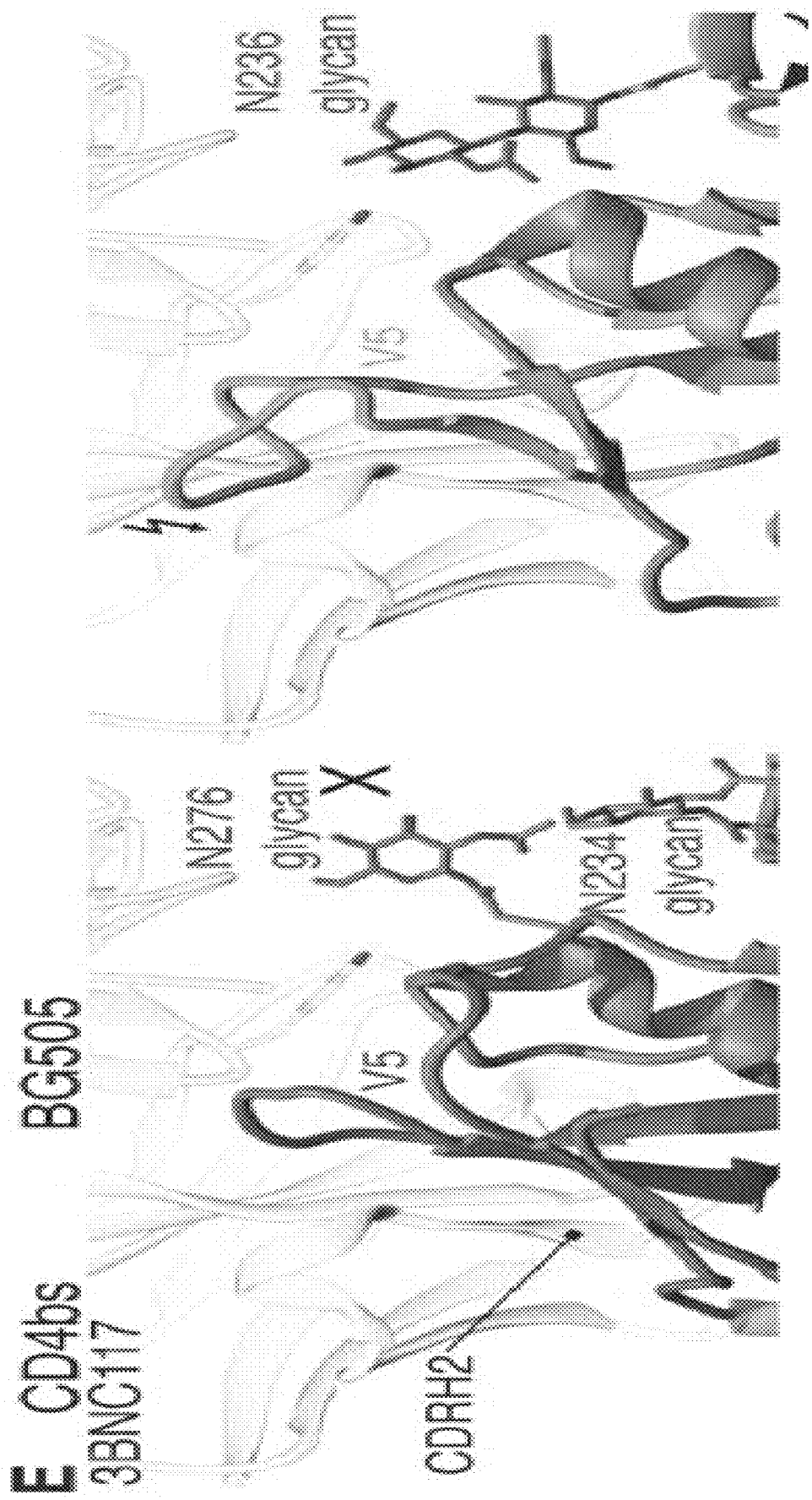

In the MT145K trimer, glycans at N156 and N262 are predominantly complex-type, whereas the corresponding glycans are oligomannose-type in HIV Env (Behrens et al., 2016). These differences may arise due to the proximity of neighbouring glycans. For instance, the HIV Env glycans at positions N295 and N332, adjacent to the N262 glycan, are absent on MT145K Env, which may lead to increased processing of N262 (FIG. 3A, C). The remarkable conservation in the overall architecture of the SIV and HIV Env glycan shield, despite sharing only ~62% of the amino-acid sequence identity, suggests that the glycan shield has an indispensable role in immune evasion and potentially maintaining functional integrity of the trimer spike. Indeed, the glycan shield is integral to all lentiviral envelopes and appears to have evolved somewhat specifically to mammalian host (FIG. 14). Over the course of lentiviral evolution, the Env glycan density shows an overall gradual progression, and likely peaked in retroviruses infecting non-human primates and plateaued in HIV Envs (FIG. 14) (Zhang et al., 2004). Therefore, the high-density Env glycan shield on HIV must have been established well before chimpanzee SIV crossed into humans. Nevertheless, several glycan positions on HIV-1 Env appear to have subtly shifted after the species cross-over that presumably resulted as an adaptation to the human immune system (FIG. 15).

Example 5: Binding Specificity

MT145K Binds V2 Apex bnAbs Almost Exclusively.

Figure 4A:
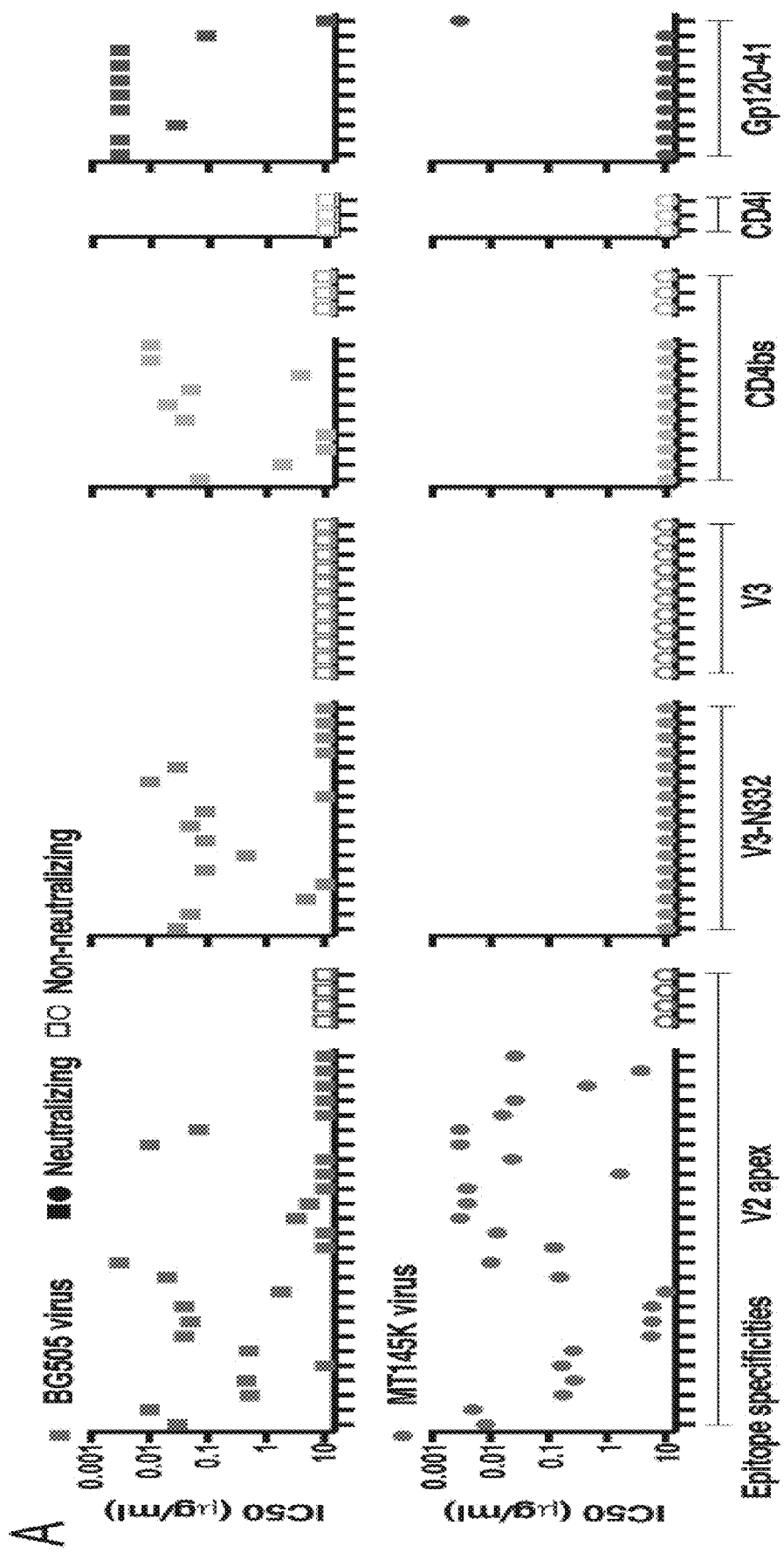
FIG. 4A-4B. Antigenic profile of the MT145K trimer. A. HIV-1 Env-specific mAbs were used to characterize the antigenicity of the MT 145K Env trimer. MAbs targeting neutralizing and non-neutralizing epitope specificities, including V2-apex, N332-V3, linear V3, CD4bs, CD4i and gp120-41 interface were tested with MT145K and BG505 Env-encoding pseudoviruses in a TZM-bl cell-based reporter assay. The reciprocal $IC_{50}$ neutralization titers for each virus are indicated as dot plots; plots for individual epitope specificities are depicted separately. The neutralization sensitivity comparison of BG505 and MT145K viruses against the mAb panel shows a selectively potent neutralization of MT145K by V2 apex bnAbs but no other bnAbs, except a single gp120-gp41 interface bnAb, 35022. BG505 virus was neutralized by bnAbs targeting diverse Env sites. B. The above mAb panel was further tested with PGT145 Ab-purified MT145K trimer and GNL-purified MT145K gp120 monomer by ELISA. The binding, represented as $EC_{50}$ binding titers, shows selective binding of MT145K by V2 apex bnAbs. Two of the gp120-gp41 interface bnAbs and a CD4i mAb also showed significant binding to MT145K trimer. Four of the non-neutralizing mAbs specific to a linear V3 epitope exhibited binding to MT145K gp120, but not to the trimer.
Figure 16:
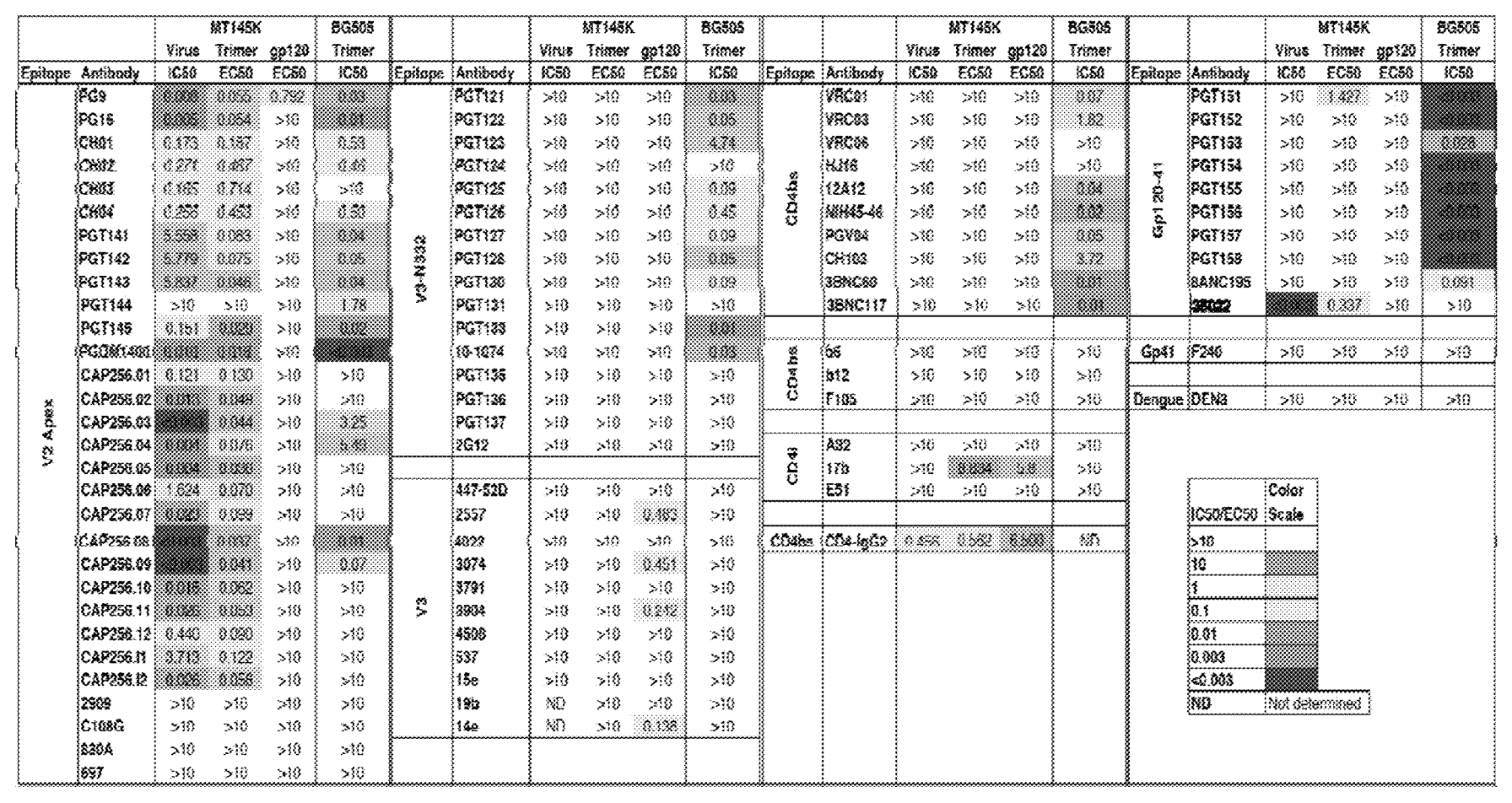

To define the overall antigenicity of the MT145K trimer, neutralization sensitivity of MT145K virus (MT145-Q171K) to a broad panel of HIV-1 Env-specific neutralizing and non-neutralizing (nnAbs) mAbs was assessed and the profiles compared to the clade A BG505 HIV virus (FIG. 4A, 16) (Sanders et al., 2013; Voss et al., 2017). Remarkably, the V2 apex bnAbs, but essentially no other bnAbs or nnAbs (except 35022 gp120-41 interface mAb), exhibited potent neutralizing activities against MT145K virus (FIG. 4A, 16). As previously observed, the BG505 isolate was sensitive to neutralization by all of the bnAbs in the panel, but none of the nnAbs (FIG. 4A FIG. 16).

Figure 4B:
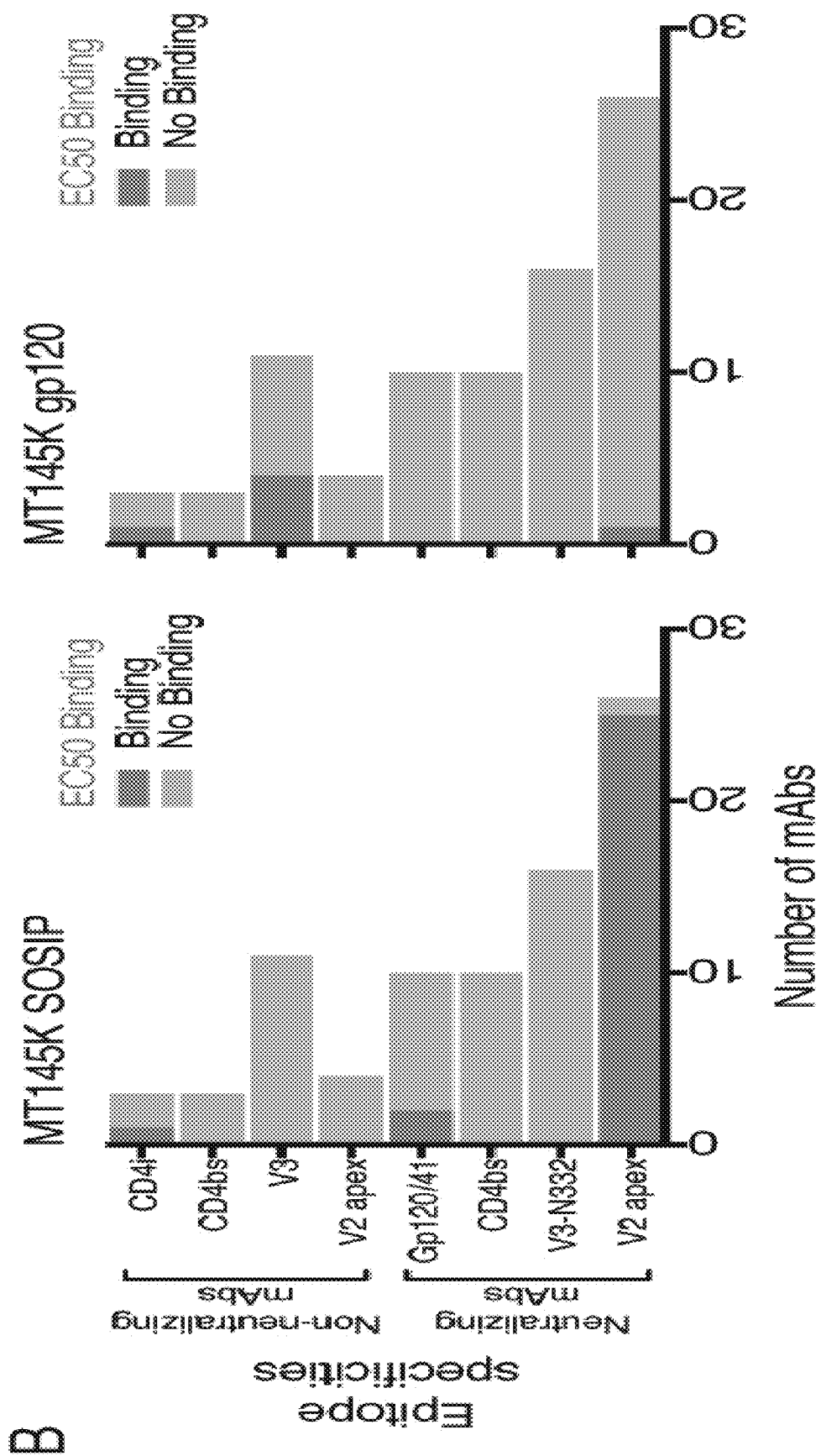

Next, binding of MT145K trimer and monomeric gp120 to a panel of mAbs was evaluated by ELISA. Consistent with the neutralization results above, bnAbs to the V2 apex site showed robust binding to the MT145K trimer (FIGS. 4B, 16), but other bnAbs and nnAbs did not bind, except for a few mAbs that displayed very weak binding (FIGS. 4B, 16). PG9, 17b and some of the linear V3-loop directed mAbs (2557, 3074, 3904 and 14e) (FIGS. 4B, 16) that bound to the MT145K gp120 monomer. The results suggest that the sequence-dependent epitopes for some of the non-neutralizing V3-loop mAbs are present on monomeric MT145K gp120, but are obscured on the MT145K trimer, as indicated by the MT145K structure. Virus neutralization and trimer binding by mAbs is strongly correlated (p=0.003), consistent with the notion that the MT145K soluble trimer adopts a native-like trimeric Env configuration and displays antigenic properties optimal for a vaccine immunogen.

Example 6: Epitope Analysis

HIV bnAb Epitopes on SIV Env.

To gain insight into the differences in the HIV-1 Env bnAb epitopes on MT145K SIV Env that may potentially explain the reactivity of V2 apex bnAbs and non-reactivity of HIV bnAbs targeting other Env epitopes, we took advantage of the previously determined structures of human HIV bnAbs in complex with various HIV Env forms and compared the corresponding epitope regions with the MT145K Env (Garces et al., 2014; Lee et al., 2017; Lee et al., 2016; Ozorowski et al., 2017; Pejchal et al., 2011; Wu et al., 2010). A lysine-rich patch in strand C of the V2 loop ($^{166}$RDKKQK$^{171}$ (SEQ ID NO:355) on BG505 Env) and two nearby glycans N160 and N156 form the core epitope for V2 apex bnAbs on HIV Envs (FIG. 5A, 17) (Gorman et al., 2016; Julien et al., 2013b; Lee et al., 2017; McLellan et al., 2011; Pancera et al., 2013). Both of these features are conserved on the MT145K trimer, thus enabling the human V2 apex bnAbs to be highly effective against the SIV Envs (FIGS. 5A, 15, 17) (Barbian et al., 2015).

Figure 5B:
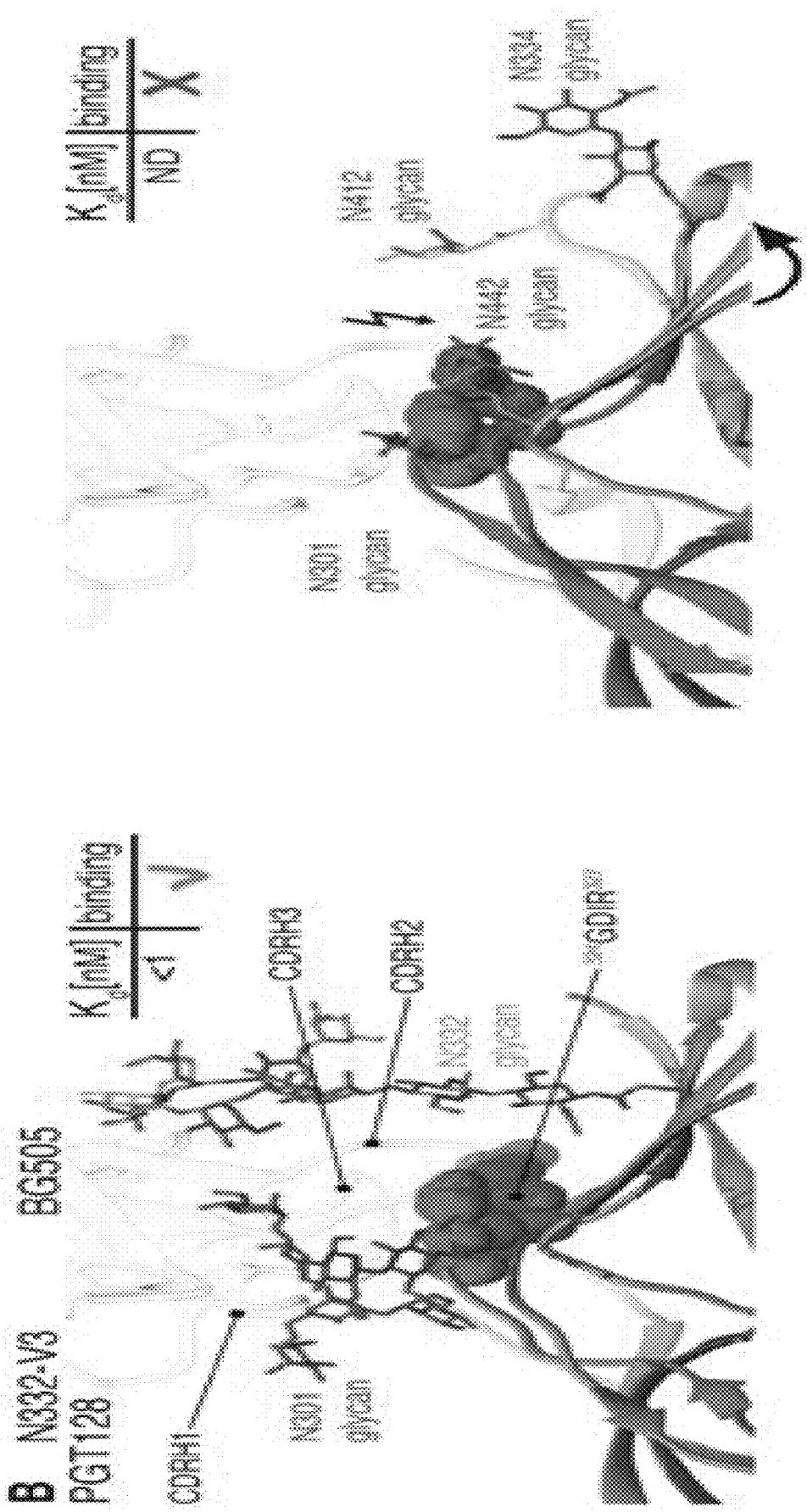

Binding of one of the N332-V3 epitope specific bnAbs, PGT128, predominantly relies on the N332 glycan and a neighboring peptide motif$^{324}$GDIR$^{327}$ (SEQ ID NO:356) at the base of the V3 loop (FIGS. 5B, 17) (Garces et al., 2014; Pejchal et al., 2011; Sok et al., 2016b). The lack of binding to the MT145K trimer by PGT128 and other bnAbs in this class can be explained by the absence of the N332 glycan on this Env. In contrast, 3 of the 4 core protein epitope residues 324G-325D-327R are conserved on MT145K trimer and, in fact, on other chimpanzee SIV Envs (FIGS. 5B, 15, 17). For the PGT128 class bnAbs, the interaction with glycan N332 can be substituted by the N295 glycan observed in some HIV isolates, but not by glycan N334 that is present on the MT145K trimer (Sok et al., 2014a). In fact, the MT145K N334 glycan points in a different direction away from the N332-V3 epitope site making it impossible to facilitate bnAb binding to this epitope. Strikingly, the majority of known SIVcpz Env sequences possess an N334 glycan in place of the more common N332 glycan on the HIV Env, which appears to be a significant glycan shift upon species cross-over as the virus established itself in humans (FIG. 15). In addition, the glycan at N412 in the gp120-V4 region of MT145K Env may obstructively interfere with bnAb binding, and, particularly, the glycan at N442, unique to the MT145K Env trimer and several other SIVcpz Envs, would clash with CDRH2 of PGT128 and other bnAbs in this class and may prevent them from accessing the epitope (FIG. 5B, 15).

Figure 5C:
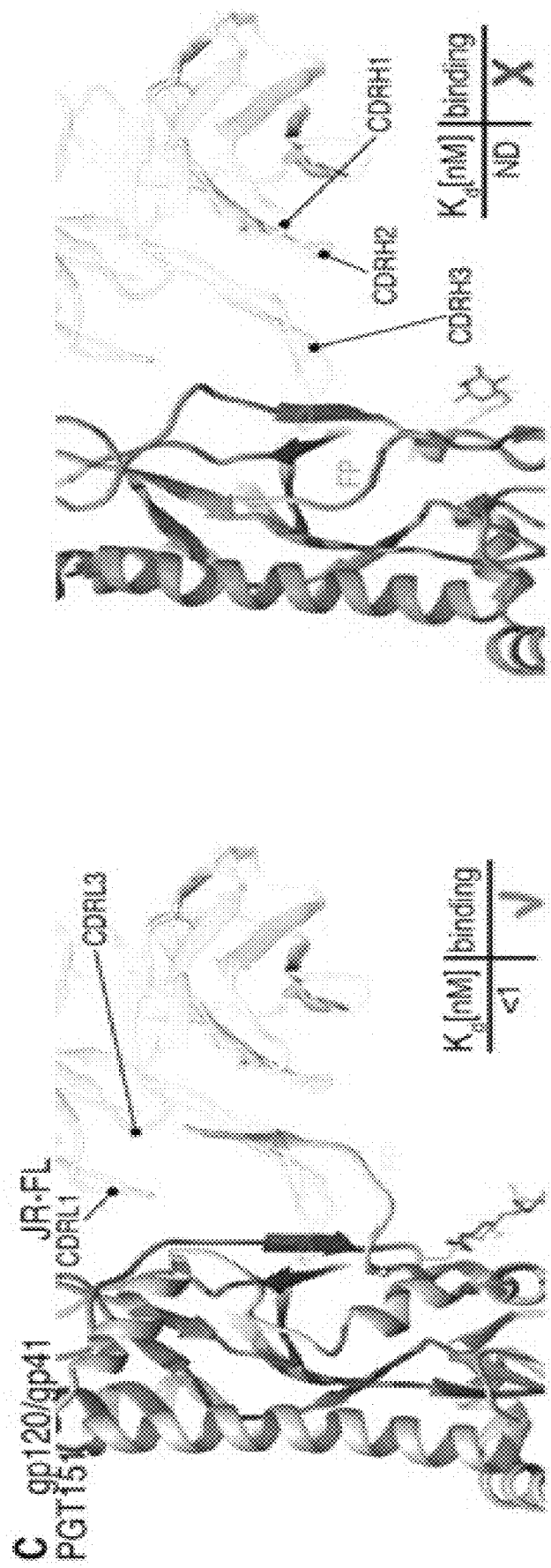

PGT151 represents another glycan-targeting bnAb class (Blattner et al., 2014; Falkowska et al., 2014; Lee et al., 2016) that recognizes several glycans on gp120 (N88, N448) and gp41 (N611 and N637) as well as the fusion peptide. All glycans and fusion peptide residues that contribute to the PGT151 epitope are conserved between HIV and SIVcpz Envs (FIG. 15). Therefore, the lack of PGT151 binding to MT145K is most likely attributable to inaccessibility of the FP on MT145K (FIG. 5C).

Figure 5E:
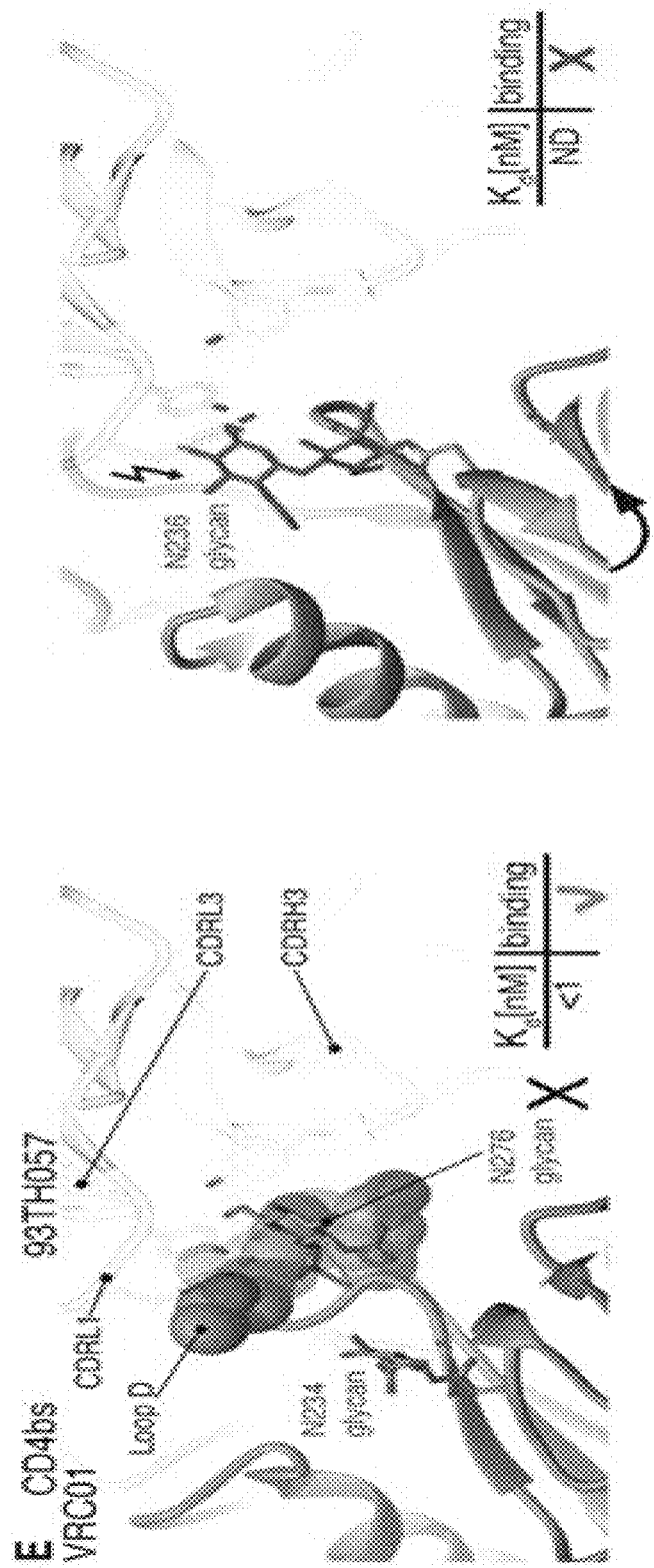

The CD4bs is conserved between HIV and SIV to the extent that there is cross-species reactivity with sCD4. Human CD4-IgG2 immunoadhesin binds well to the MT145K trimer, indicating a strong cross-species conservation of the Env CD4bs. Phe43 in domain-1 of human sCD4 would fit well inside the Trp427 Env cavity on the MT145K trimer reminiscent of its interaction with the HIV Env BG505 trimer (FIG. 5D) (Ozorowski et al., 2017). However, the MT145K trimer is nonreactive with CD4bs bnAbs. VRC01, one of the bnAbs in this class, binds to the HIV Env CD4bs bnAb epitope formed by discontinuous protein backbone elements including loop D of the gp120-C2 region and bordered by a glycan at N276 (FIG. 5E-F, 17) (Wu et al., 2010). MT145K lacks the N276 glycan and the proximal N234 glycan, present in most HIV-1 Envs, but instead has a glycan at position 236. Differences in the loop D sequence (FIG. 15) and the glycan at N236, which would clash with VRC01 CDRL1 and CDRL3 loops (FIG. 5F) on the MT145K trimer likely impose the biggest impediment to VRC01 binding. Further, the MT145K gp120-V5 loop has a 6-amino acid insertion at HXB2 position 456 compared to HIV-1 Envs that would clash with the VRC01 LC (FIG. 5F, 15).

Overall, the non-reactivity of HIV Env bnAbs with the MT145K trimer can be largely ascribed to subtle glycan shifts that have occurred in HIV-1 from chimpanzee SIV Env as the virus established itself in humans.

Example 7: Activation of B Cell Precursors

The Engineered MT145K but not the MT145-WT Trimer Activates V2 Apex UCA-Expressing B Cell Precursors In Vivo.

Figure 6A:
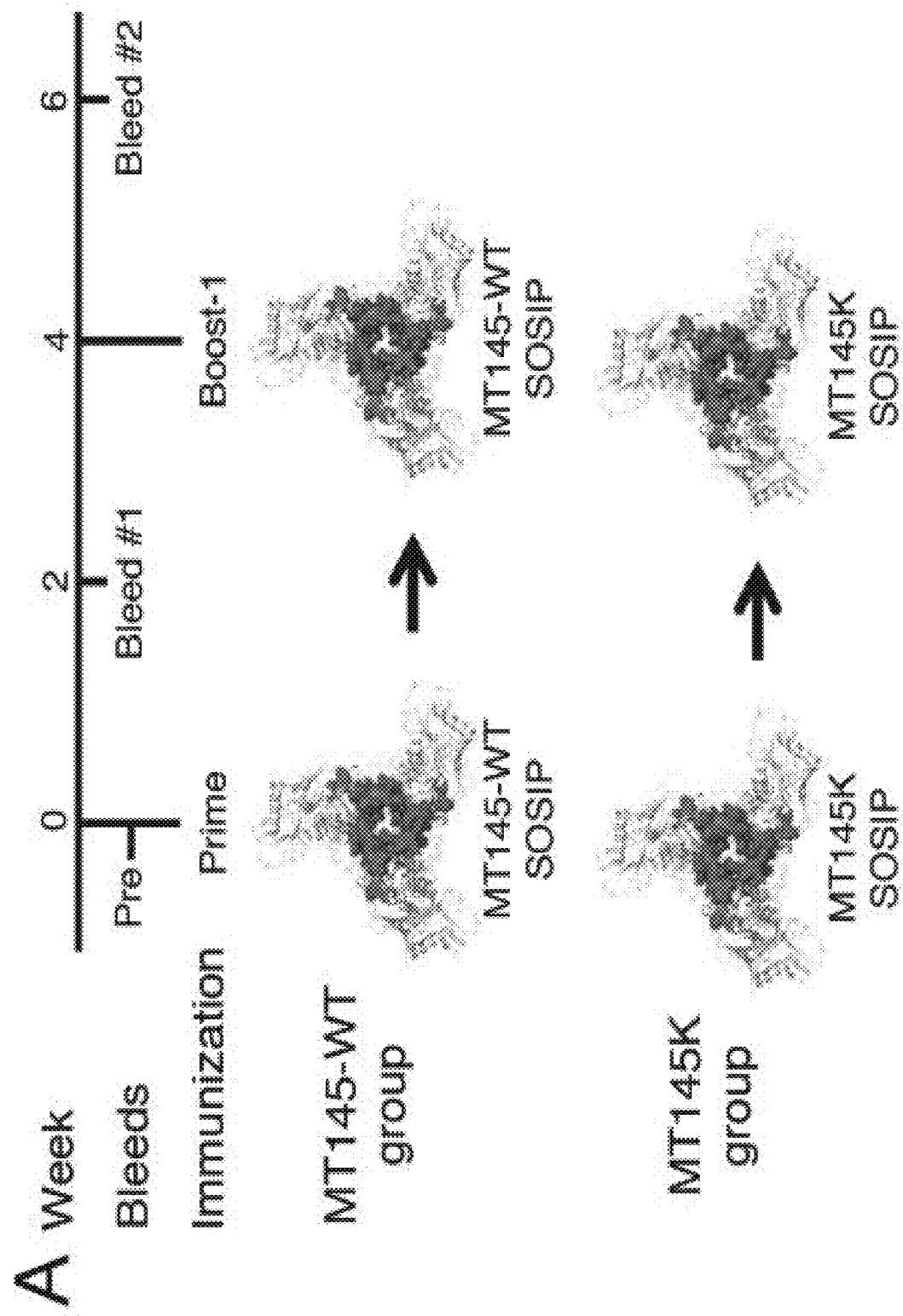
Figure 6B:
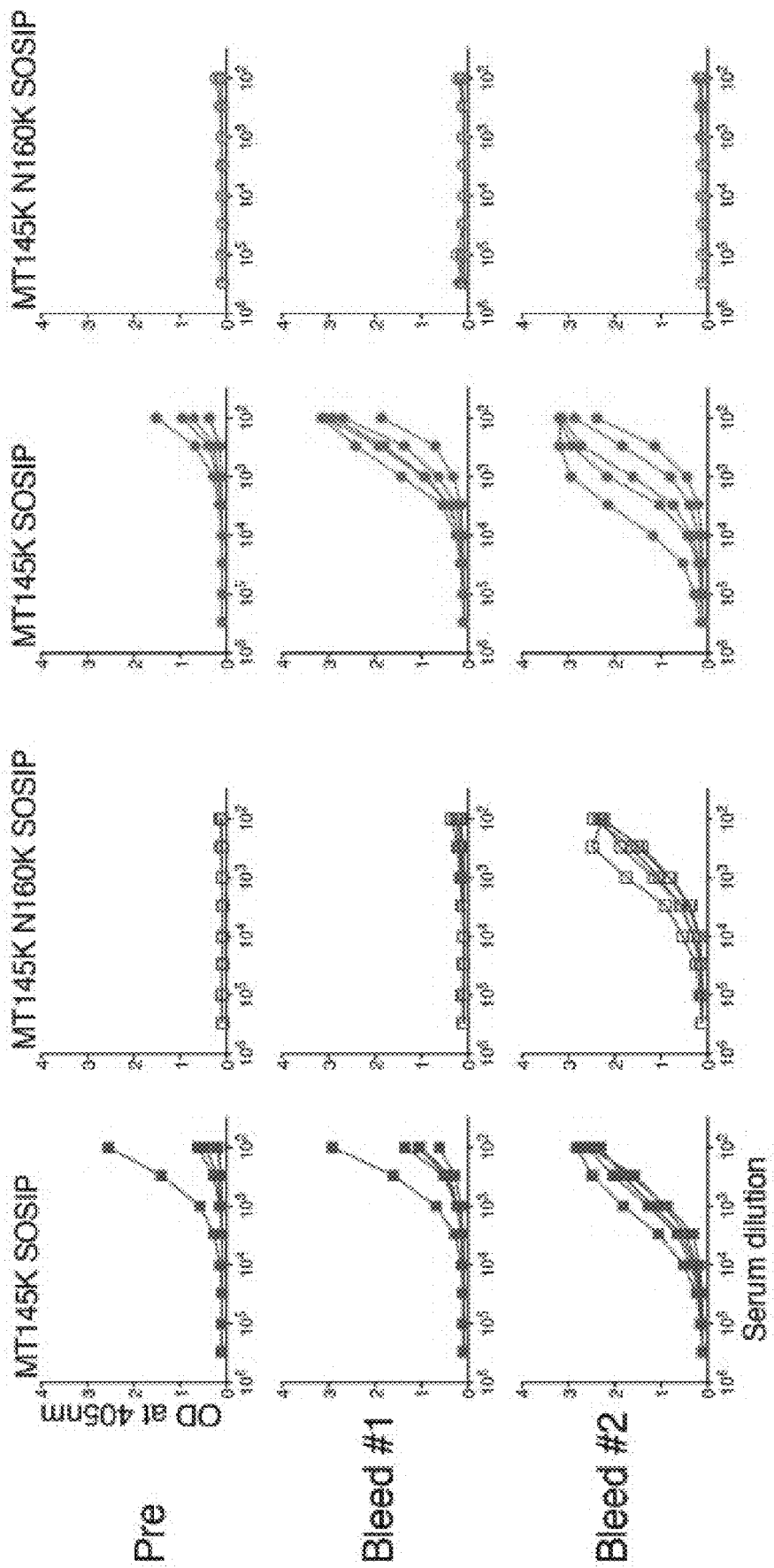

To determine whether the engineered chimpanzee MT145K trimer could efficiently activate HIV V2 apex Ab germline-encoding precursor B cells in vivo and how it compares with the MT145-WT trimer, immunization experiments were conducted in the CH01 unmutated common ancestor (UCA) "HC only" knock-in (KI) mouse model. This KI-mouse model expresses the pre-rearranged heavy chain ($V_H DDJ_H$) of the CH01 V2 apex bnAb UCA paired with WT mouse light chains. Two groups of 5 CH01 UCA "HC only" KI mice were immunized, each with two repeated doses (at week-0 and week -4) of MT145-WT or MT145K trimer (FIG. 6A). To track the development of Ab responses, ELISA assays were performed on the pre-bleed, 2-week (day 14) post prime (Bleed #1) and 2-week post boost-1 (day 42) (Bleed #2) serum samples with MT145K SOSIP trimer protein and its N160 glycan knock-out variant (MT145K N160K) (FIG. 6B). The pre-bleed serum samples in both immunization groups exhibited weak binding activity with the MT145K trimer that was dependent on the N160 glycan, consistent with the presence of CH01 UCA Abs that do show some binding to MT145K trimer as described above (FIG. 6B).

The immunogen-specific titers of the serum Ab responses post prime immunizations (Bleed #1 samples) marginally increased in the MT145K group but remained largely unchanged in the MT145-WT trimer immunized group. The serum Ab titers post boost-1 immunization (Bleed #2) increased in both the groups and were orders of magnitude higher as compared to the pre-bleed or the post prime Ab binding responses (FIG. 6B). At this immunization step, the serum Ab responses in the MT145K trimer immunized group were solely dependent on the N160 glycan while the MT145-WT trimer immunization group responses targeted the MT145 Env that were mostly independent of the N160 glycan, which forms part of the core V2 apex bnAb epitope (FIG. 6B). Therefore, we conclude that the engineered MT145K trimer but not the MT145-WT, efficiently triggers the epitope specific V2-apex bnAb UCA encoding B cell precursors in vivo. Remarkably, immunizations with Q171K substituted engineered MT145K trimer also appeared to eliminate the non-V2 apex bnAb site Env specific off-target B cell responses that were elicited in the MT145-WT trimer immunization group (FIG. 6B). The results demonstrate that the activation of the HIV Env bnAb-encoding unmutated B cell precursor by immunogens that display binding to their UCA Ab versions is critical for eliciting epitope-specific Ab responses and the findings are consistent with studies that specifically use germline-targeting immunogen molecules to kick-off the bnAb precursor encoding B cell responses in vivo (Dosenovic et al., 2015; Escolano et al., 2016; Jardine et al., 2015; McGuire et al., 2013; Sok et al., 2016a; Steichen et al., 2016b; Tian et al., 2016).

Figure 6C:
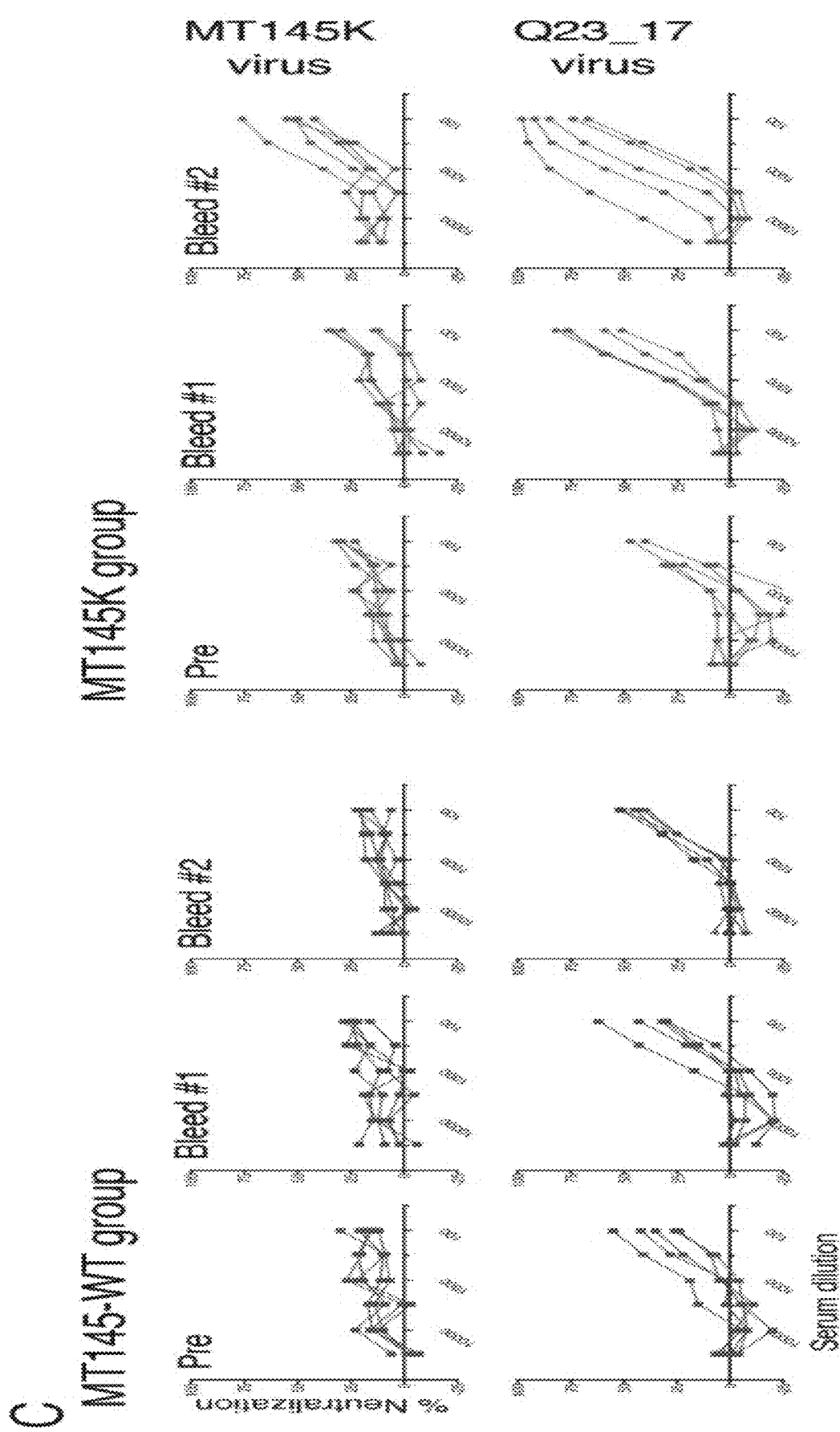

Immune sera were evaluated for neutralization of autologous and heterologous viruses. Reproducible MT145K autologous virus-specific neutralizing Ab responses were induced in the MT145K immunization group but not in the MT145-WT immunization group (FIG. 6C-D). As for the ELISA binding responses, the nAb titers in the MT145K trimer immunized group increased at 2 weeks post prime, as indicated by nAb titers against a CH01 sensitive HIV Env-encoding virus (Q23_17), and further significantly increased after the boost-1 immunization (FIG. 6C). At this point, all animals in the MT145K group developed autologous virus specific nAb responses (FIG. 6C). The nAb responses in MT145K trimer-immunized animals mapped to the glycan N160 and strand C K171 residue, both of which form part of the core epitope for V2-apex bnAbs, suggesting that the MT145K trimer successfully primed V2 apex UCA B cells in an epitope-specific manner in vivo.

Overall, we conclude that the engineered MT145K but not the MT145-WT trimer activated the V2-apex specific bnAb precursor B cells in a UCA-expressing mouse model and further drove maturation along favorable B cell pathways.

Example 8: Immunization Strategies

Combining Chimpanzee SIV MT145K Trimer with HIV Env Trimer Immunizations in the CH01 UCA Model.

Figure 7A:
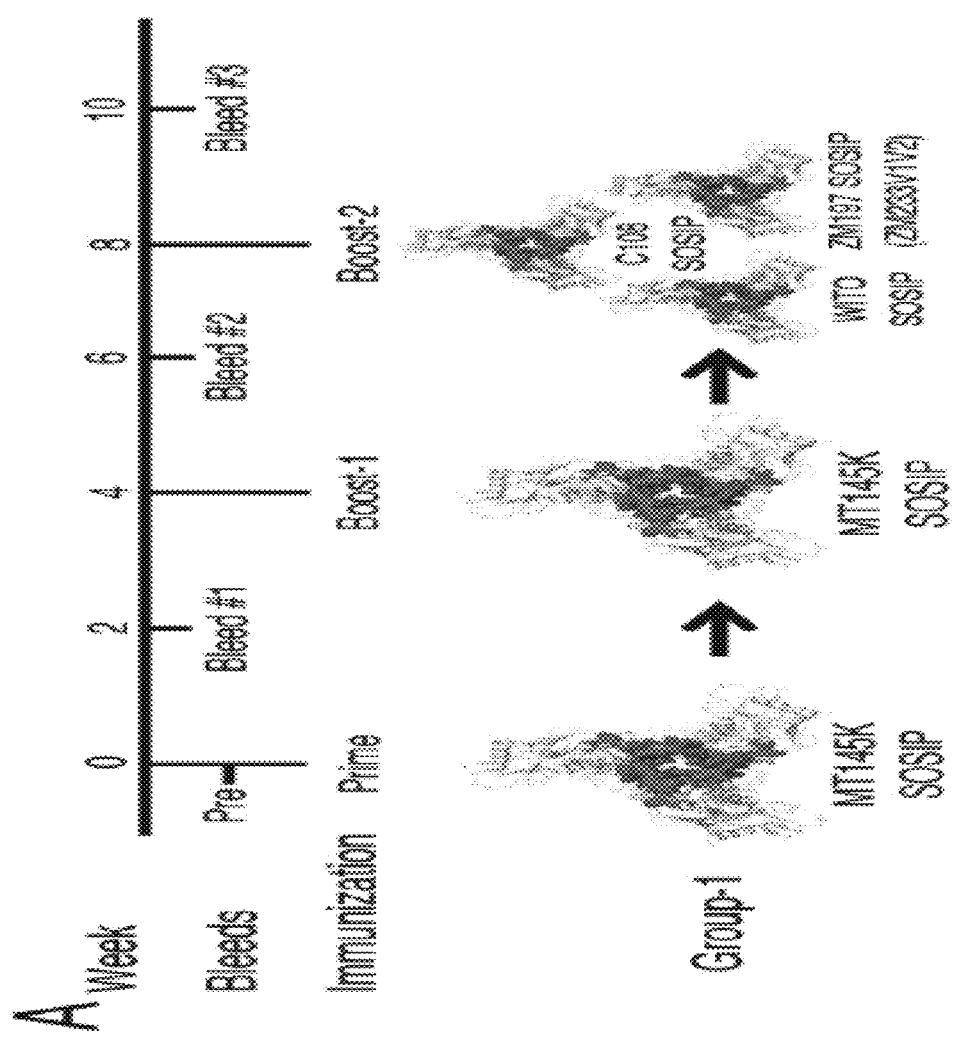
Figure 7B:
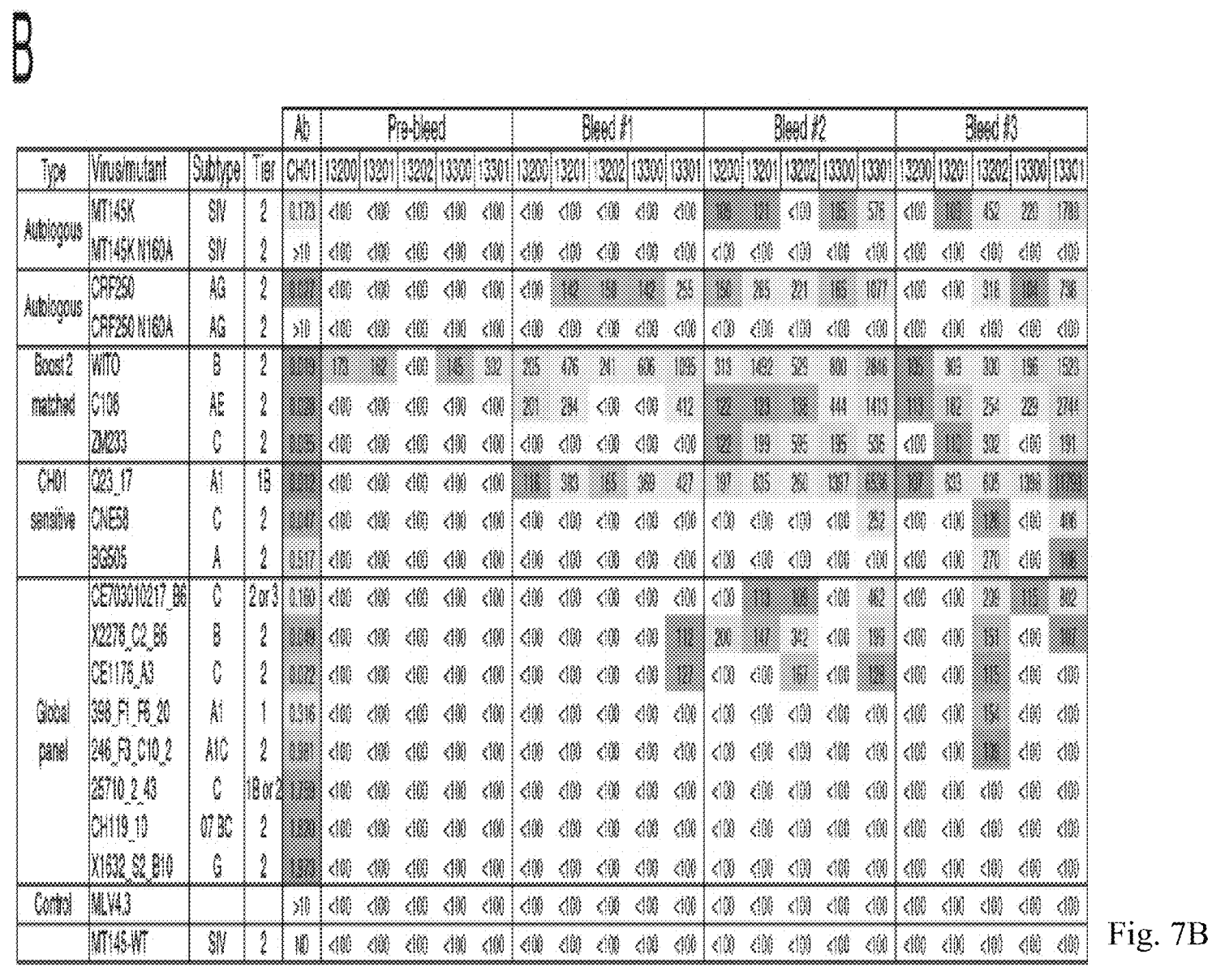
Figure 7C:
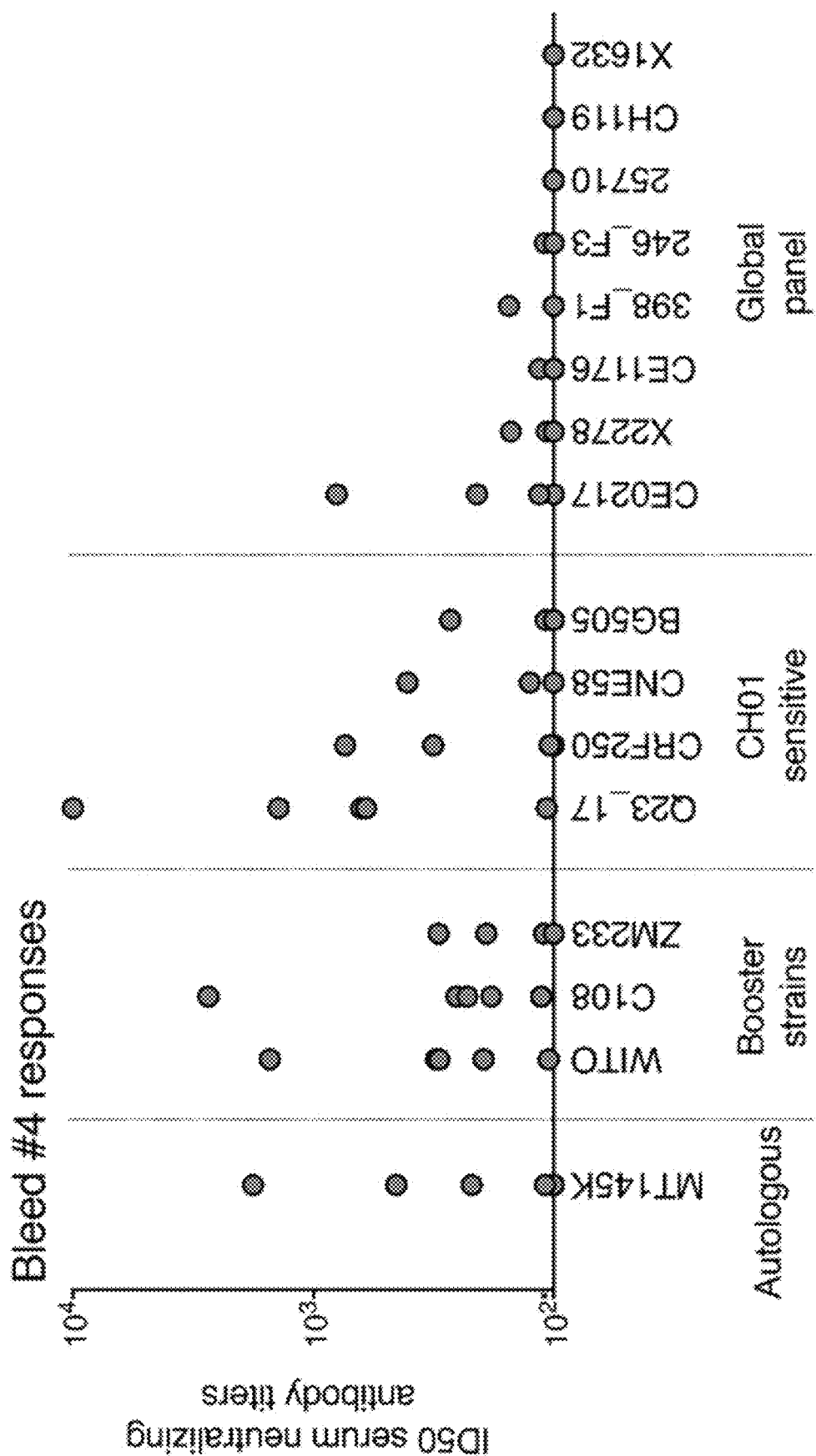

Evaluation of the utility of the MT145K trimer in a sequential HIV immunization regime will be best carried out in humans. Nevertheless, we were interested to investigate the effects of combining the chimpanzee SIV MT145K and HIV Env trimers in a prime-boost immunization in the CH01 UCA "HC only" KI mice. We immunized a group of CH01 UCA KI mice twice with chimpanzee SIV MT145K (as above) and boosted with an HIV Env derived 3-trimer cocktail (C108, WITO and ZM197-ZM233V1V2) (FIG. 7A). NAb titers developed against a few viruses from a global HIV panel that were very sensitive to the mature CH01 bnAb (FIG. 7B). However, viruses that were only somewhat sensitive to CH01 bnAb were not neutralized, suggesting that further affinity maturation would be required for a broad response. The cross-neutralizing responses mapped to the V2 apex bnAb epitope that is shared between HIV and SIV Envs, including to the N160 glycan and the stand C K171 residue.

Overall, the analysis of the immune responses revealed that, due to the extraordinary conservation of the V2 apex bnAb epitope region between HIV and chimpanzee SIV, the MT145K trimer successfully primed human V2 apex bnAb UCA-encoding mouse B cells and induced a V2-focused cross-neutralizing HIV Env specific response that could be further boosted by HIV Env derived trimers.

Example 9: Materials and Methods

Antibodies, expression and purification. HIV-1 envelope specific mAbs to a broad range of epitopes were used, including those that target V2-apex, V3-N332, linear V3, CD4bs, CD4i and gp120-41 Env sites. A dengue antibody (DEN3) was used as control Ab for binding experiments. For PG9 and CH01 V2-apex bnAb inferred germline antibody designs, the heavy and the light chain V-gene of the mature Abs were reverted to their corresponding closest inferred germline gene sequence as determined using the ImMunoGeneTics (IMGT) website (imgt.cines.fr/) (Brochet et al., 2008). The reverted variable heavy and light chain nucleotide sequences were synthesized by Geneart (Life Technologies) and cloned into corresponding Igγ1, Igκ, and Igλ expression vectors as previously described (Tiller et al., 2008), using the Gibson cloning method (NEB, USA). The antibodies were expressed and purified using methods described previously (Sok et al., 2014b). Briefly, the heavy and light chain encoding plasmids were reconstituted (1:1 ratio) in Opti-MEM (Life Technologies), and cotransfected HEK293F cells (Invitrogen) using 293fectin (Invitrogen). The suspension cells were cultured for 4-5 days in a shaker incubator at 8% CO2, 37.0° C., and 125 rpm. The antibody containing supernatants were harvested, filtered through a 0.22 mm Steriflip units (EMD Millipore) and passed over a protein A or protein G affinity column (GE Healthcare). The bound antibody was eluted from the columns in 0.1 M citric acid, pH 3.0. Column fractions containing IgG were neutralized (2M Tris-base), pooled, and dialyzed against phosphate-buffered saline (PBS), pH 7.4. IgG purity was determined by sodium dodecyl sulfate-polyacrylamide gel electrophoresis, and the concentration was determined by measuring the relative absorbance at 280 nm.

Site-directed mutagenesis. The amino-acid point mutations in Env-encoding plasmids were incorporated by using a QuikChange site-directed mutagenesis kit (Agilent Technologies, USA), according to the manufacturer's instructions. All of the mutations were confirmed by DNA sequence analysis (Eton Bioscience, San Diego, CA).

Differential Scanning Calorimetry. Thermal denaturation was analyzed with a differential scanning calorimetry (DSC) using a MicroCal VP-Capillary DSC instrument (Malvern), at a scanning rate of 1 K/min under 3.0 atmospheres of pressure. Samples were dialyzed in PBS pH 7.4 overnight and protein concentration was adjusted to 0.5 mg/mL prior to measurement. DSC data were analyzed after buffer correction, normalization, and baseline subtraction using MicroCal VP-Capillary DSC analysis software provided by the manufacturer.

Negative stain electron microscopy and data treatment. Purified M145K sample was deposited on thin-carbon-coated (Edwards Auto 306 carbon evaporator) a C-flat EM grid (Cu400 mesh, 2 µm hole diameter, 2 m hole spacing) (Protochips, Morrisville, NC, USA) and embedded in 2% (w/V) uranyl formate. The carbon-coated grids were $Ar/O_2$-plasma-cleaned (Gatan Solarus Model 950 Advanced Plasma System; Gatan Inc., Pleasanton, CA, USA) prior to sample deposition. The uranyl-stained EM sample was then inserted into an FEI Tecnai 12 microscope (Thermo Fisher Scientific, Waltham, MA, USA) equipped with a US4000 CMOS detector (Gatan Inc., Pleasanton, CA, USA). The data was collected at 52,000× nominal magnification resulting in a pixel size of 2.05 Å at the object level. Data was binned by a factor of 2 prior to data treatment. Projection image identification in the micrographs was performed with a difference-of-Gaussians implementation (Voss et al., 2009). Projection images subsequently underwent 2D alignment and classification by iterative multi-reference alignment/multivariate statistical analysis (Ogura et al., 2003).

CryoEM sample preparation, data collection, processing and analysis. Purified MT145K sample was deposited on a C-flat EM grid (Cu400 mesh, 2 m hole diameter, 2 m hole spacing) (Protochips, Morrisville, NC, USA) that had been $Ar/O_2$-plasma-cleaned (Gatan Solarus Model 950 Advanced Plasma System; Gatan Inc., Pleasanton, CA, USA) prior to sample deposition. Excess buffer was then blotted away from the grid followed by plunging into and vitrification in liquid ethane cooled by liquid nitrogen using a vitrobot (Thermo Fisher Scientific, Waltham, MA, USA). The resulting cryo-EM specimen was transferred into an FEI Titan Krios microscope (Thermo Fisher Scientific, Waltham, MA, USA) equipped with a Gatan K2 Summit direct electron detector (Gatan Inc., Pleasanton, CA, USA). Dose-fractionated data was collected in electron counting mode at a nominal magnification of 29,000× resulting in a pixel size of 1.02 Å at the object level. Micrograph movie frame exposure time was 200 ms and each movie micrograph was recorded over 10s (50 movie frames) corresponding to a total dose of $94 e^-/Å^2$. Movie micrograph frames were subsequently aligned (MotionCor2; (Zheng et al., 2017)), dose-weighted and signal-integrated resulting in 1,281 micrographs for further data processing. CTF models were determined using GCTF (Zhang, 2016). Candidate projection images of MT145K were identified using a difference-of-Gaussians implementation (Voss et al., 2009). The resulting set of candidate projection images subsequently underwent 2D alignment and classification by use of Relion 2.1b1 (Scheres, 2012). ~95,000 projection images corresponding to well-formed class averages of MT145K were selected for further data processing. This data class was iteratively angularly refined and reconstructed using a B41 unliganded Env trimer map rendered at 60 Å resolution as an initial reference (Ozorowski et al., 2017). The data class then underwent 3D classification into six classes with the initial reconstruction rendered at 60 Å resolution as reference. From 3D classification, a subset of 44,301 projection images was selected for final data processing comprising CTF model adjustment at the projection-image level (Zhang, 2016) and angular refinement and reconstruction (Scheres, 2012).

Model building and refinement. A homology model (Modeller; (Webb and Sali, 2016)) was generated from sequence alignment of MT145K and BG505 and the structure of the latter (PDB: 4TVP). Significant manual rebuilding followed in Coot (Emsley and Cowtan, 2004). A fragment library was then created from the MT145K sequence containing 200 homologous, non-redundant sequences at each MT145K 7-mer position. Library fragment-based, density-guided, real-space rebuilding was then performed (Di-Maio et al., 2015) with 319 decoys. The resulting models were evaluated geometrically (MolProbity; (Chen et al., 2010)) and by fit-to-map (EMRinger; (Barad et al., 2015). The overall best model was selected for further iterations of manual rebuilding and multi-decoy, density-guided, real-space, all-atom Rosetta FastRelax refinement. Finally, glycans were manually built in Coot and restricted, density-guided real-space refinement performed in Phenix 1.12 (Adams et al., 2002) followed by model evaluation by MolProbity, EMRinger and Privateer (Agirre et al., 2015).

Global N-linked glycan analysis. The quantifications and structural characterization of the total glycan pool was achieved by cleaving the N-inked glycans from the surface of the glycoprotein using an in-gel digestion with peptide N-glycosidase F (PNGaseF). The resultant glycans were separated into two aliquots. The first was derivatized with 2-aminobenzoic acid (2-AA) and subjected to HILIC-UPLC analysis using an Acquity UPLC (Waters). To quantify the oligomannose content of the released glycans, the labelled samples were treated with endoglycosidase H (endoH), which selectively cleaves oligomannose glycans. Data analysis and interpretation were performed using Empower software (Waters). The second aliquot of released glycans was subjected to negative ion electrospray ion mobility mass spectrometry using a Synapt G2Si mass spectrometer (Waters). Glycan compositions were determined using collision induced dissociation (CID) fragmentation. Data analysis was performed using Waters Driftscope (version 2.8) software and MassLynx™ (version 4.1). Spectra were interpreted as described previously (Harvey et al., 2009). The glycan compositions were used to generate a sample-specific glycan library that was used to search the glycopeptide data to minimize the number of false-positive assignments in site-specific analysis.

LC-MS glycopeptide analysis. Site-specific N-glycosylation analysis was performed using proteolytic digestion followed by tandem LC-MS. Prior to digestion, trimers were denatured, reduced and alkylated by incubation for 1 h at room temperature (RT) in a 50 mM Tris/HCl, pH 8.0 buffer containing 6 M urea and 5 mM dithiothreitol (DTT), followed by the addition of 20 mM iodacetamide (IAA) for a further 1 h at RT in the dark, and then additional DTT (20 mM) for another 1 h, to eliminate any residual IAA. The alkylated trimers were buffer-exchanged into 50 mM Tris/HCl, pH 8.0 using Vivaspin columns (GE healthcare) and digested separately with trypsin, elastase and chymotrypsin (Mass Spectrometry Grade, Promega) at a ratio of 1:30 (w/w). Glycopeptides were selected from the protease-digested samples using the ProteoExtract Glycopeptide Enrichment Kit (Merck Millipore) following the manufacturer's protocol. Enriched glycopeptides were analyzed by LC-ESI MS on an Orbitrap fusion mass spectrometer (Thermo Fisher Scientific), as previously described (Behrens et al., 2016), using higher energy collisional dissociation (HCD) fragmentation. Data analysis and glycopeptide identification were performed using Byonic™ (Version 2.7) and Byologic™ software (Version 2.3; Protein Metrics Inc.), as previously described (Behrens et al., 2016).

Glycan modeling. $Man_9GlcNAc_2$ oligomannose-type glycans were docked and rigid-body fitted at each of the corresponding Env glycan positions using the MT145K structure presented here or an unliganded BG505 SOSIP.664 structure (PDB: 4ZMJ).

Pseudovirus production. To produce pseudoviruses, Env-encoding plasmids were cotransfected with an Env-deficient backbone plasmid (pSG3ΔEnv) (1:2 ratio) using X-treme-GENE™ 9 (Sigma-Aldrich) DNA transfection reagent. Briefly, $1 \times 10^6$ cells in 10 ml of Dulbecco's Modified Eagle Medium (DMEM) were seeded in a 100 mm×20 mm cell culture dish (Corning) one day prior to transfection. For transfection, 40 μl of X-tremeGENE™ 9 was added to 700 μl of Opti-MEM I reduced serum medium (Thermo Fisher) in tube 1. The Env-encoding plasmid (5 μg) and pSG3ΔEnv (10 μg) were added to tube 2 in 700 μl of Opti-MEM. The tube 1 and tube 2 solutions were mixed together and incubated for 25 min at room temperature. Next, the transfection mixture was added to the media with 293T cells seeded previously and then distributed uniformly. All pseudoviruses were harvested 48-72 h posttransfection, filtered through 0.22 mm Steriflip units (EMD Millipore) and aliquoted for use in neutralization assays.

Neutralization assay. Neutralization was measured by using single-round replication-defective HIV Env-pseudoviruses and TZM-bl target cells (Montefiori, 2005; Seaman et al., 2010). 25 ul of 3-fold serially diluted mAbs or serum samples were pre-incubated at 37° C. for 1 h with 25 ul of tissue culture infective dose-50 (TCID50) Env-pseudotyped virus in a half-area 96-well tissue culture plate. TZM-bl target cells (5,000 cells/well) in 50 μl of DMEM were added and the plates were allowed to grow in humidified incubator at 37° C. and 5% $CO_2$. The luciferase activity of the lysed cells was read on instrument (Biotek) after 2-3 days, by adding lysis buffer followed by Brightglow (Promega). The 50% inhibitory concentration ($IC_{50}$) or 50% inhibitory doses ($ID_{50}$) was reported as the antibody concentration or serum dilution required to reduce infection by half.

ELISA binding assay. ELISA binding experiments were performed as described previously with minor modification (Sanders et al., 2013). ELISA binding with SOSIP.664 trimer proteins with mAbs was carried out by either capturing the trimer proteins onto the anti-His capture antibodies or on the streptavidin coated plates through biotinylated trimers. For trimer biotinylation, the SOSIP.664 proteins were randomly biotinylated using a 2:1 molar ratio of biotin reagent to trimer using the EZ-link-NHS-PEG4-Biotin kit (Thermo Fisher Scientific, 21324). MaxiSorp plates (Thermo Fisher Scientific) were coated overnight at 4C with 2 μg/mL of anti-His Ab (Thermo Fisher Scientific) or 2 μg/mL streptavidin (Thermo Fisher Scientific). Plates were blocked for 1 hr with 3% BSA and washed three times with 0.05% Tween 20-PBS (PBS-T) (pH 7.4). Anti-His or Streptavidin-coated plates were incubated with biotinylated trimers in 1% BSA plus PBST for 1.5 hr and washed three times with PBST. 3-fold serially diluted mAbs or sera were added starting at a maximum concentration of 10 μg/mL (100 ug/ml for iGL Abs) (sera at 1:100 dilution) in 1% BSA plus PBST, and incubated at room temperature (RT) for 1.5 hr. Plates were washed three times with PBST. Alkaline-phosphatase-conjugated goat anti-human IgG Fc secondary antibody (Jackson ImmunoResearch Laboratories) was diluted 1:1000 in 1% BSA PBST and added to plates for 1 hr at RT. Plates were washed three times with PBST and incubated with phosphatase substrate (Sigma) for 15 mins and the absorbance at 405 nm recorded. The 50% binding (EC50) was recorded as the half of the maximum binding activity and was calculated by linear regression method using Prism 6 Software.

Bio Layer Interferometry (BLI) binding assay. The binding experiments of Abs to the affinity purified trimers were performed with an Octet K2 system (ForteBio, Pall Life Sciences). Briefly, the mAbs or IgGs (10 ug/mL in PBST) were immobilizing onto hydrated anti-human IgG-Fc biosensors (AHC: ForteBio) for 60 seconds to achieve a binding response of at least 1.0. After Ab capture, the sensor was placed in a PBST wash buffer to remove the unbound Ab to establish a baseline signal. Next, the IgG immobilized sensor was dipped into a solution containing SOSIP.664 trimer protein as analyte and incubated for 120 seconds at 1000 rpm. Following this, the trimer bound to IgG immobilized sensor was removed from the analyte solution and placed into the PBST buffer for 240 seconds at 1000 rpm. The 2 and 4 minute binding intervals respectively denote the association and dissociation binding curves reported in this study. The sensograms were corrected with the blank reference and fit (1:1 binding kinetics model) with the ForteBio Data Analysis version.9 software using the global fitting function. The data are represented as maximum binding response or the association and dissociation curve fits.

Trimer protein immunizations in CH01 UCA HC-only KI-mice. For the immunization experiments, groups of 5 CH01 UCA HC-only knock-in B cell expressing mice were immunized with 25 ug of the individual trimer protein or 25 ug total protein of the 3-trimer cocktail (Prime, week-0; Boost-1, week-4 and Boost-2, week-8) along with Glucopyranosyl Lipid Adjuvant in stable emulsion (GLA-SE) as adjuvant. Immunizations were administered intramuscular in the leg of each animal with 25 g of total trimer immunogens. Blood samples were collected at pre-bleed, 2-weeks each, post-prime (Bleed #1), post boost-1 (Bleed #2) and post boost-2 (Bleed #3) immunization time-point for the isolation of sera that were tested for presence of neutralizing antibodies in TZM-bl cell based assay. Serum samples were heat inactivated for potential complement activity at 56° C. for 0.5 h. Mice used in this study were approved by Duke University Institutional Animal Care and Use Committee-approved animal protocols.

Data availability. Cryo-EM reconstructions have been deposited in the Electron Microscopy Data Bank.

Example 10: Immunization Strategies and Responses

Sequential MT145K Trimer Boost Following HIV Trimer Prime Recalls "on Target" V2-Apex Specific Memory B Cell Responses and Disfavors Off-Target Responses.

In addition to priming the V2-apex specific B cell responses, the chimpanzee MT145K trimer can be used as a boost to recall HIV trimer induced V2-apex directed memory B cell responses.

Figure 18A:
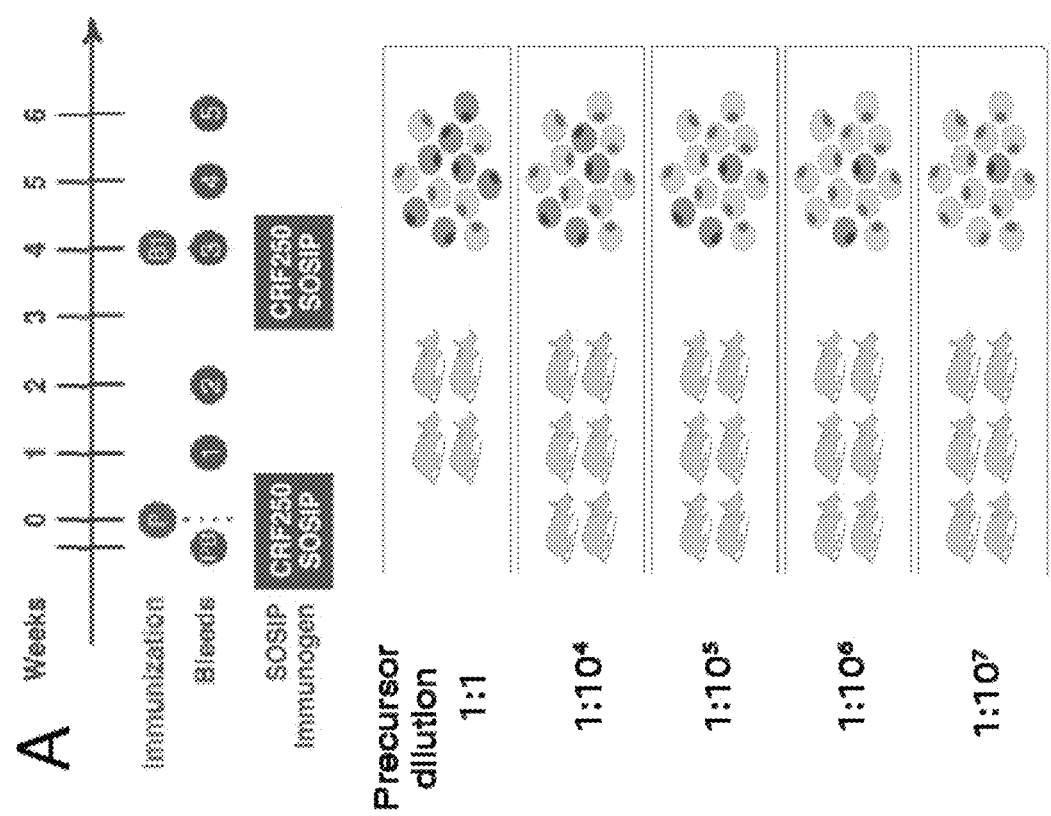
FIG. 18A-18C. Cross-reactivity of CRF250 trimer-induced "on" and "off" target Ab responses with chimpanzee SIV MT145K trimer. A. CD45.2-encoded CH01 UCA B cells were transferred into CD45.1 wild-type (WT) mice at 5 dilutions (1:1, $1:10^4$, $1:10^5$, $1:10^6$ and $1:10^7$). Mice were immunized with CRF250 trimer at week-0 (prime) and boosted at week-4 (boost). A dose of 25 ug of the trimer protein/mouse/immunization was administered with adjuvant GLA-SE. B. Heatmap showing ELISA binding of the CRF250 trimer prime and boosted serum Ab responses of CH01 UCA B cell diluted mice with CRF250 (HIV subtype AG) and MT145K (chimpanzee SIV) Env trimers and their N160K variants. Chimpanzee SIV MT145K trimer shares cross-reactivity only at the V2-apex bnAb epitope with HIV trimers. EC50 binding titers for each serum/protein combination are shown; red color indicates stronger binding; green indicates weaker binding. CRF250 trimer-induced post prime (2 wk) Ab responses exhibit cross-reactive binding with MT 145K trimer almost exclusively through the V2-apex bnAb site; no binding with MT 145K N160K trimer variant. CRF250 trimer-induced post boost (6 wk) Ab responses, in addition cross-reacting at the V2-apex bnAb site, show minimal cross-reactive binding of the CRF250 trimer Env backbone off-target (N160K-dependent) Ab responses with MT145K trimer backbone (2/16 animals). C. Scatter dot plots with bars showing the frequencies of CH01 specific class-switched IgG B cells from CRF250 trimer immunization post-prime and post-boost splenic samples as determined by next generation sequencing (NGS). The CH01 IgG frequencies are derived from Ig sequencing data of the total splenic CH01 specific B cells (IgM+IgG). Each dot represents an individual mouse and the bar height in each dilution groups indicates median CH01 IgG frequencies.
Figure 18B:
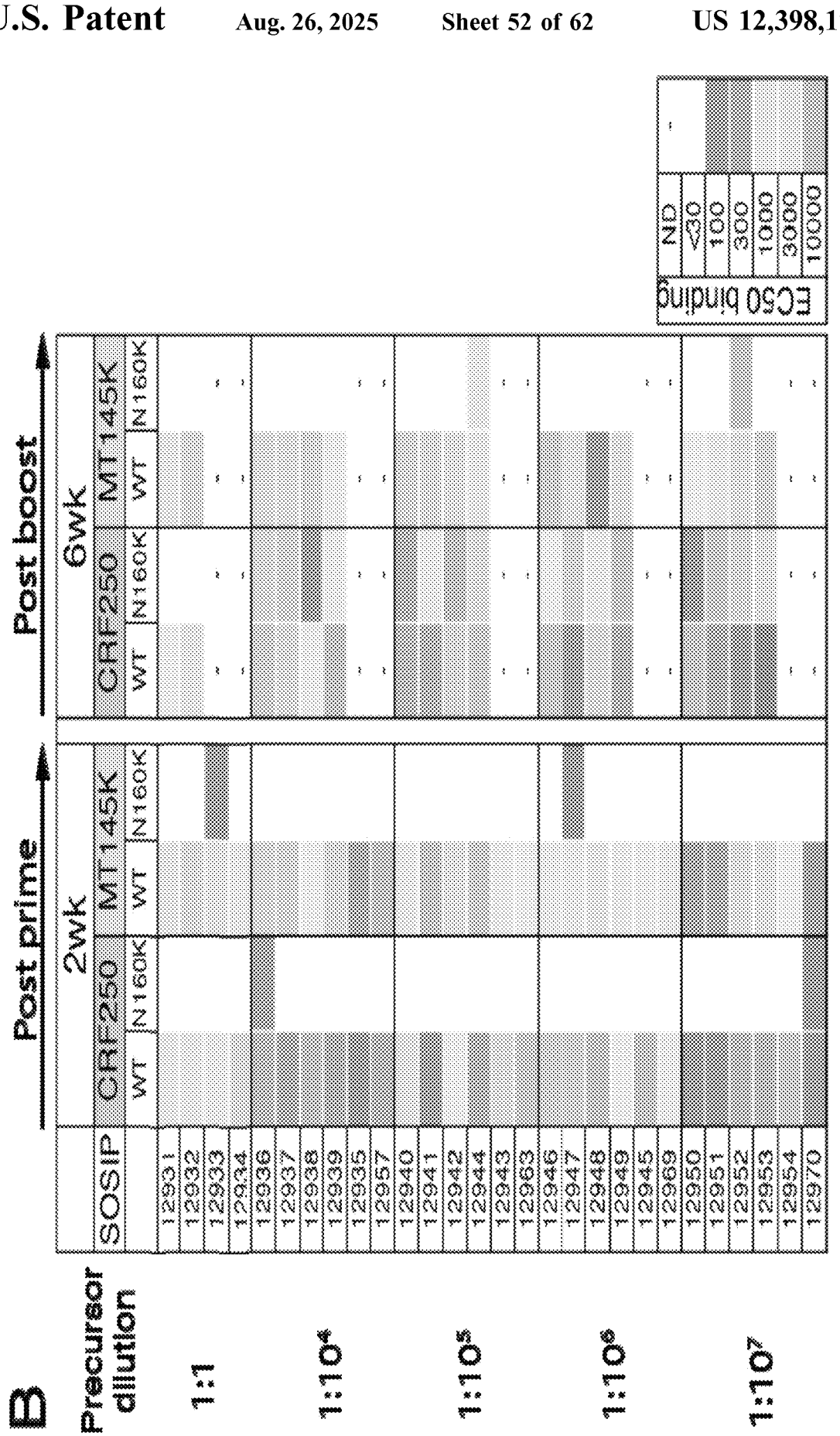
Figure 18C:
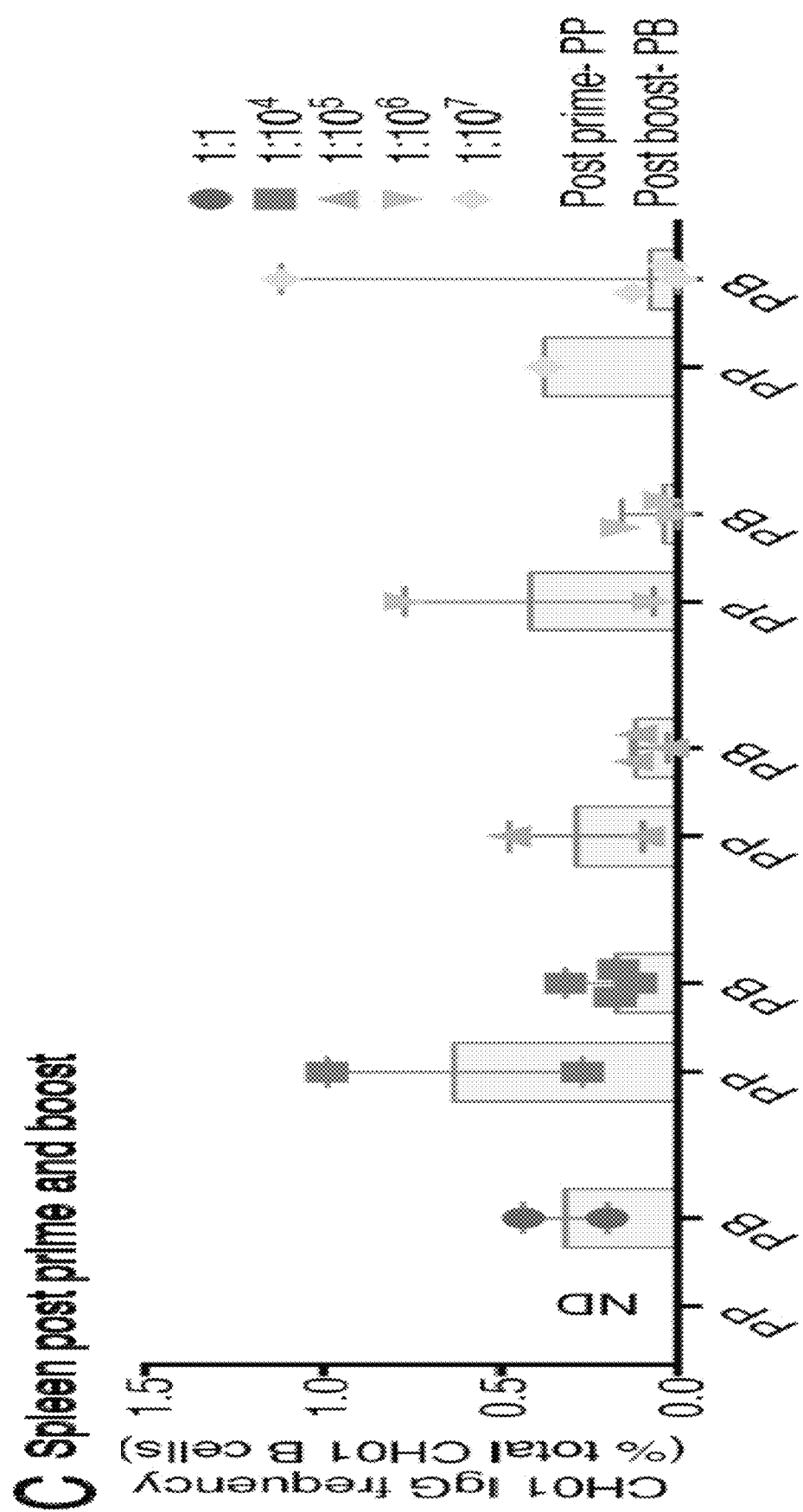
Figure 20A:
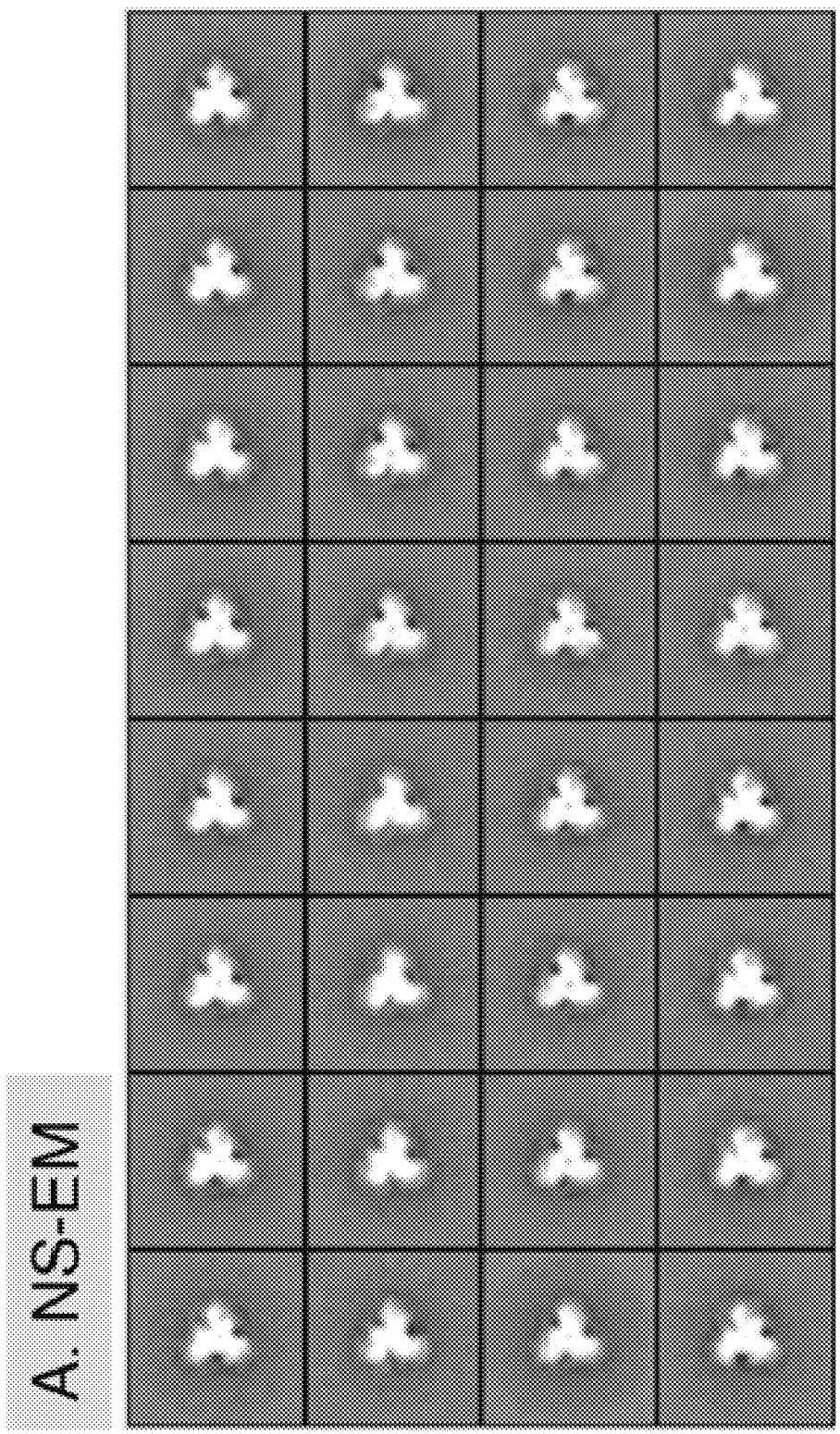
FIG. 20A-20D. Immunogenicity of the MT145KdV5 SOSIP trimer version versus MT145K SOSIP trimer in CH01 HC-only KI mouse model. A. Negative Stain Electron-Microscopy (NS-EM) of MT145KdV5 trimer: 2D class averages show trimers adopting 100% native-like conformations. B. BioLayer Interferometry (BLI) binding responses of the HIV Env specific mAbs and V2-apex bnAb iGLs PG9, CH01, CAP256 UCA to the soluble MT145KdV5 SOSIP trimer. C. Schematic showing immunization schedule of CH01 UCA HC-only KI mice with MT 145KdV5 and MT 145K trimers. The mice were immunized twice with 25 ug of the soluble trimer with glucopyranosyl lipid adjuvant stable emulsion (GLA-SE) as adjuvant. Time points for immunization and bleeds are indicated. D. Neutralizing antibody responses induced by MT145KdV5 and MT145K SOSIP trimer immunogens in CH01 UCA HC-only KI mice. Neutralizing activities of serum samples (pre-bleed; 2 weeks post prime, Bleed #1; and 2 weeks post boost-1, Bleed #2) were tested with MT145K and CH01 Ab sensitive viruses (Q23_17, CRF250 and C108) in TZM-bl reporter cell assay. Each dot in the plots represents virus ID50 neutralization titers that were calculated by a non-linear regression method from the percent neutralizations of serum titrations with the corresponding viruses. The ID50 neutralization titers between MT145KdV5 (red) and MT145K (blue) trimer immunized animal groups were compared by two-tailed unpaired Mann-Whitney test and the P-value for each comparison is indicated. P-values of less than 0.05 are treated as significant. Overall MT145KdV5 SOSIP trimer induced superior nAb responses as compared to the parent MT145K SOSIP trimer.
Figure 20B:
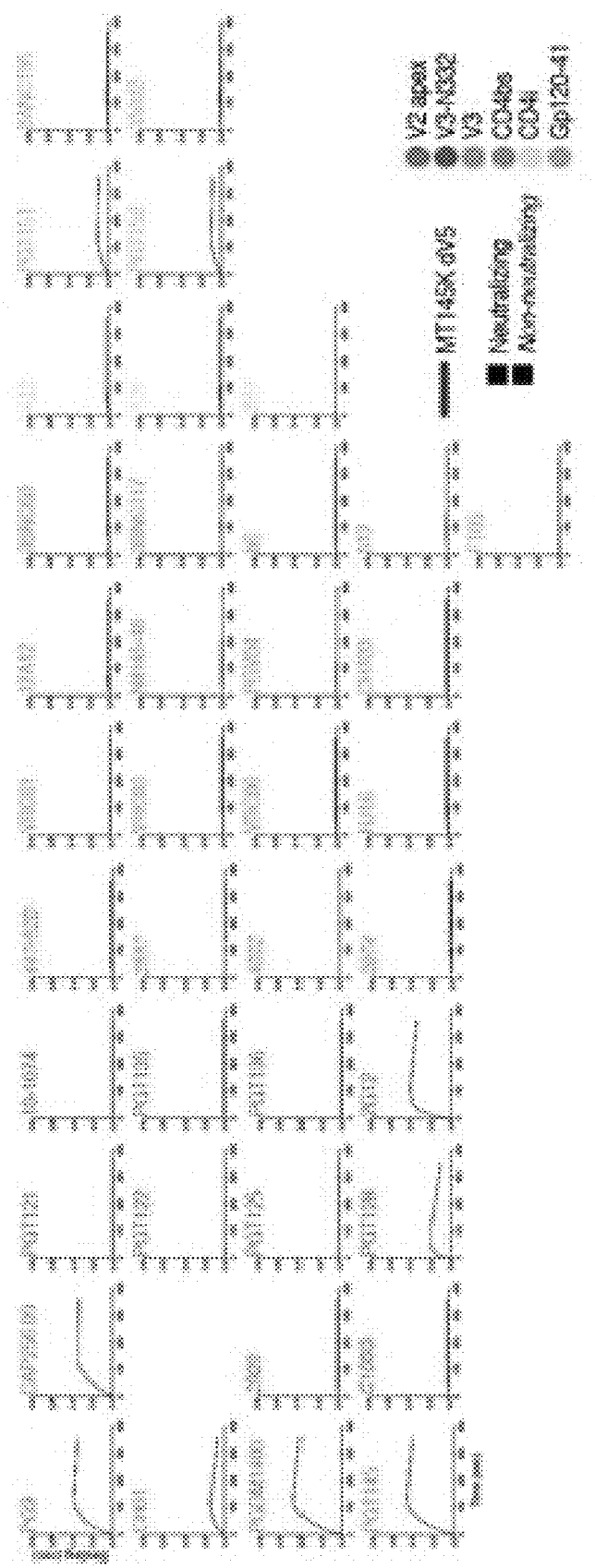
Figure 20B:
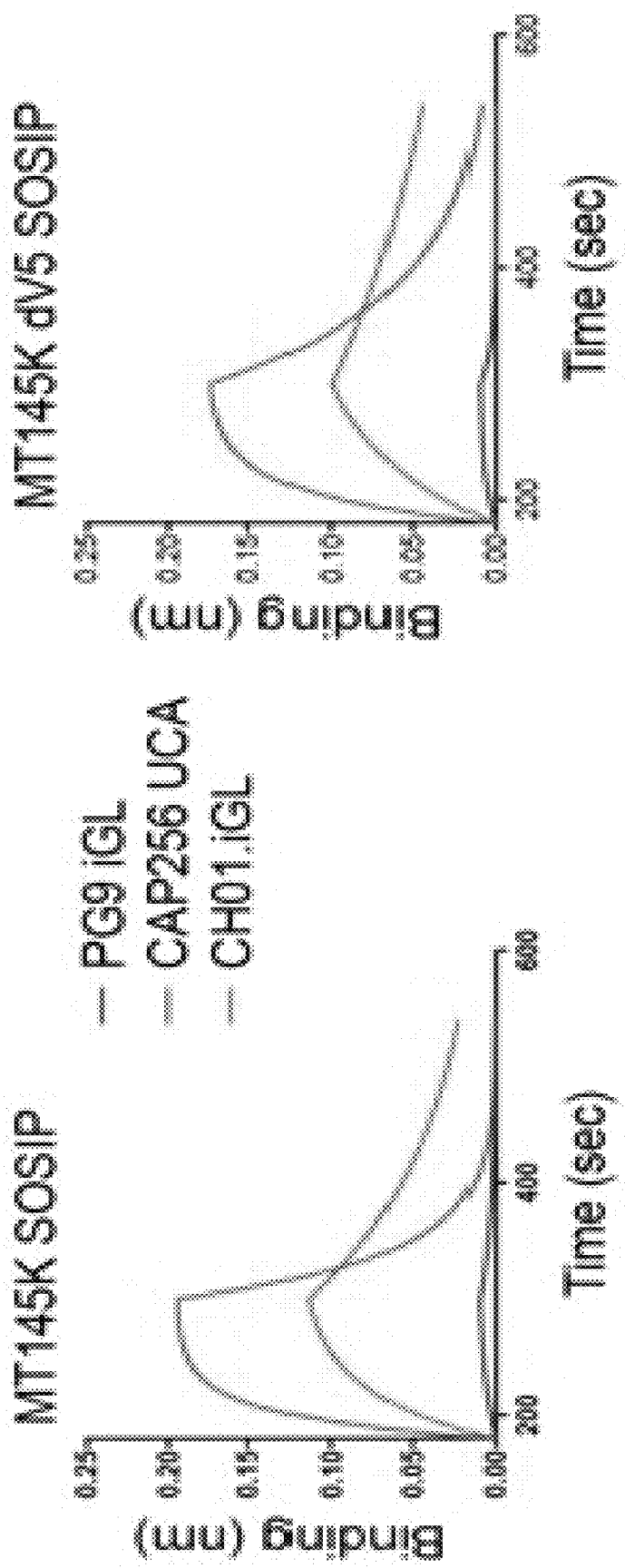
Figure 20C:
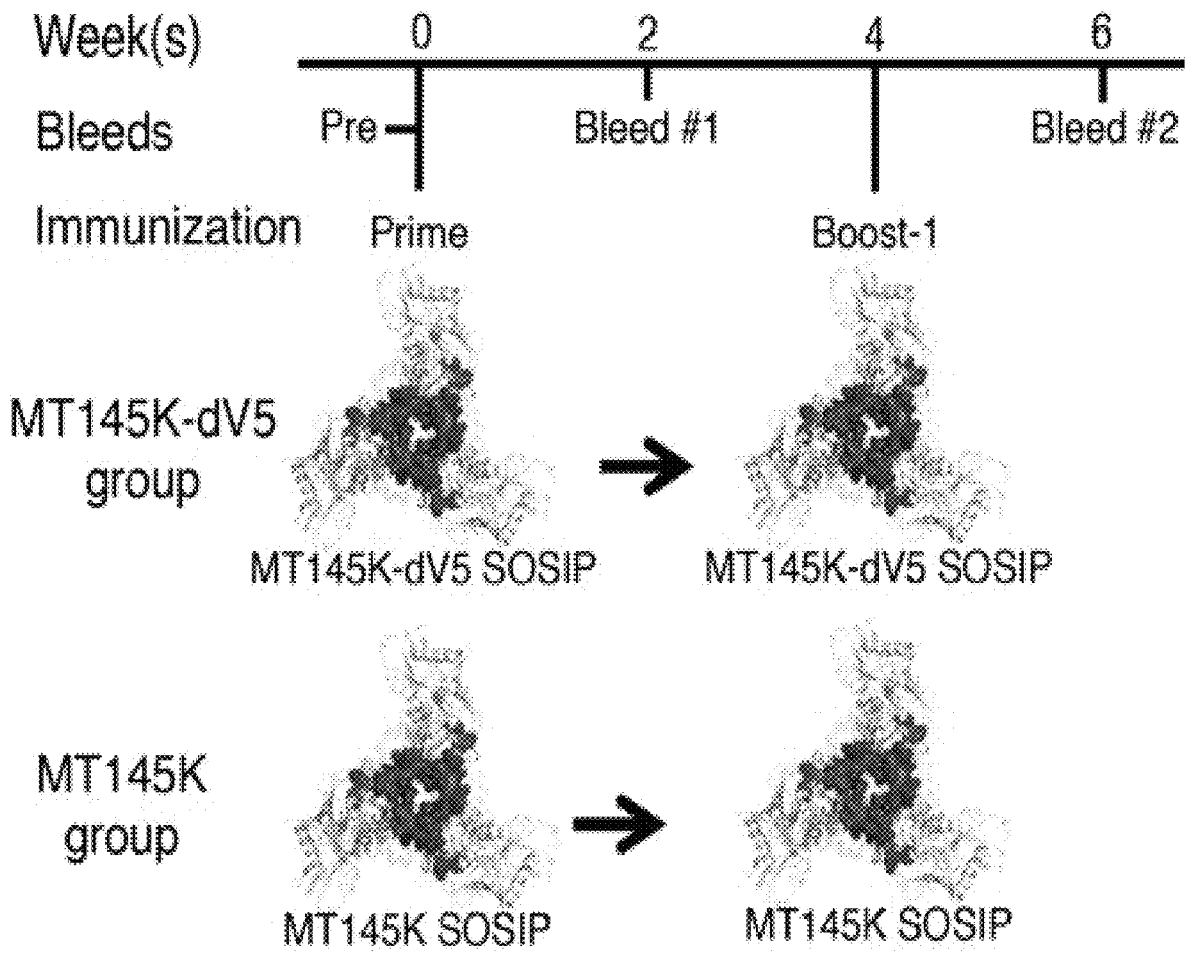
Figure 20D:
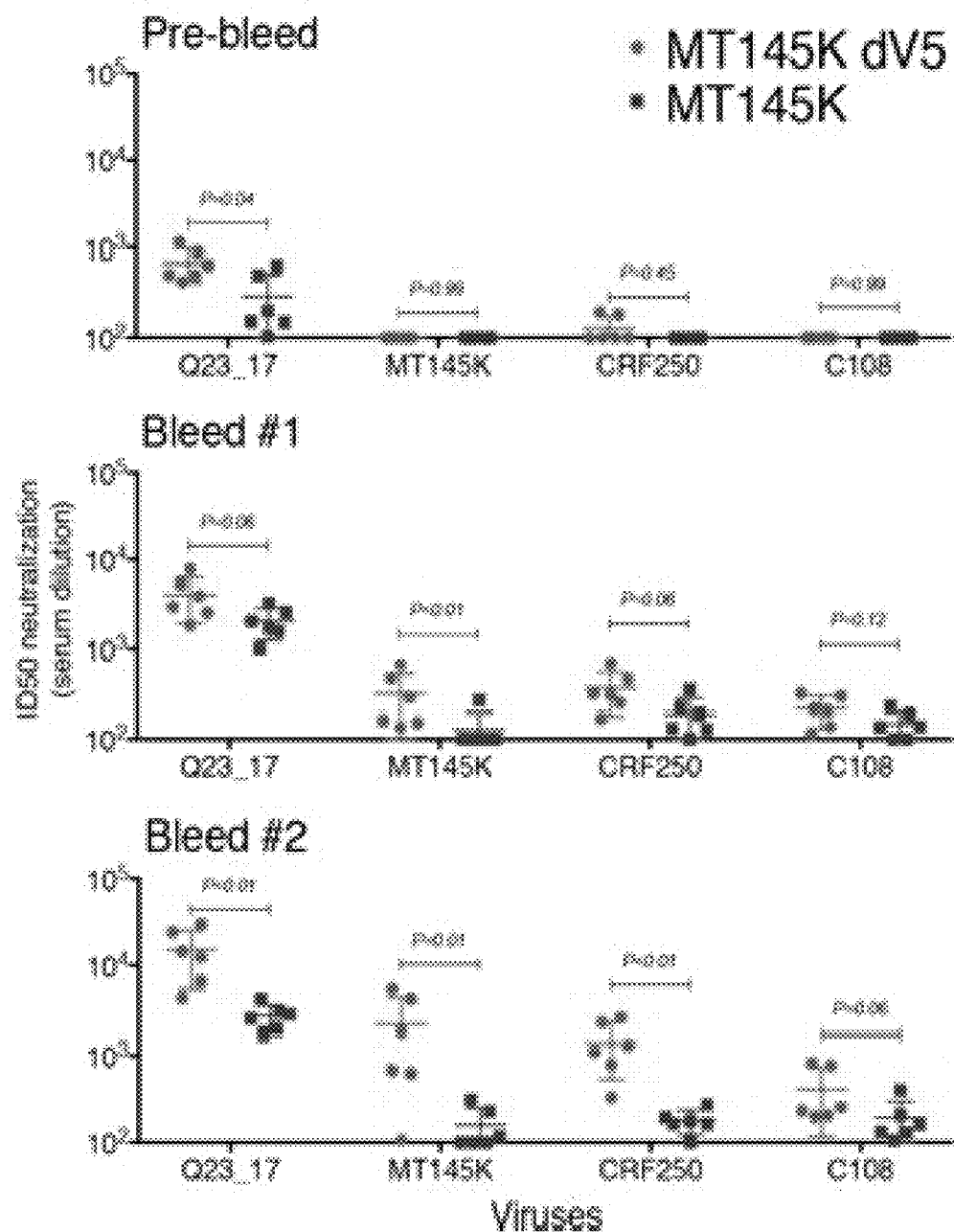
Figure 21A:
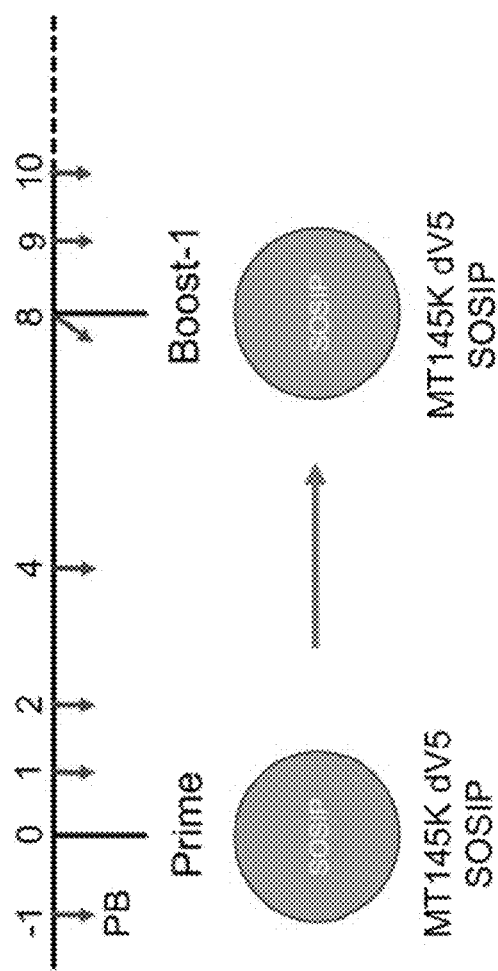
Figure 21C:
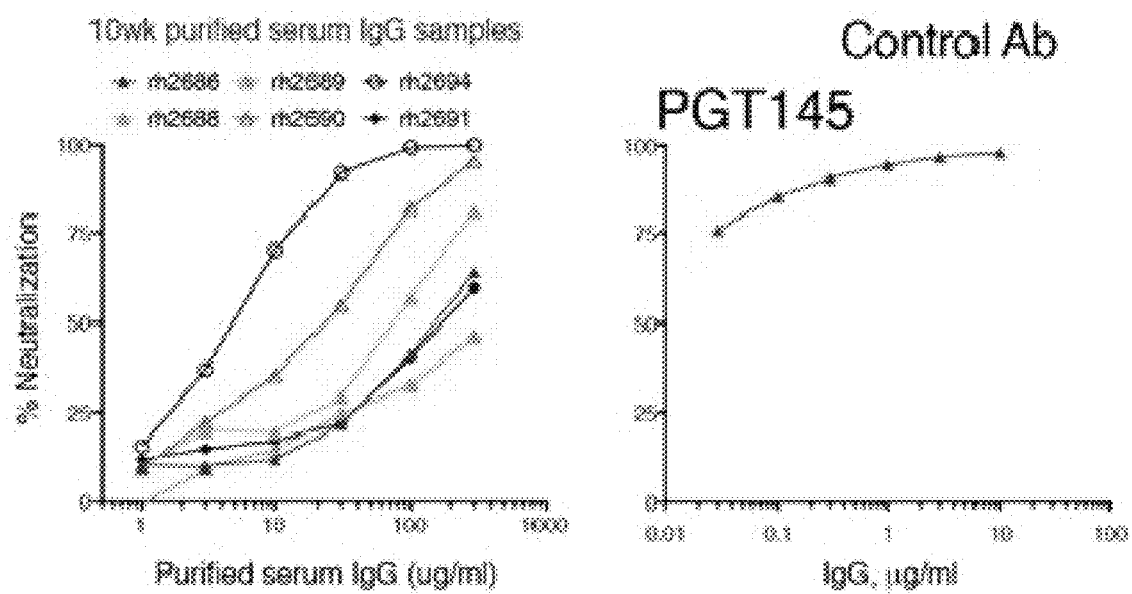

CH01 iGL B cell activation by HIV GT-trimer, CRF250, under rare B cell conditions to mimic their natural circulating frequencies (CH01 iGL B cell diluted up to 1 in $10^7$ cells) was investigated by adoptively transferring CH01 iGL B cells (CD45.2) into WT mice (CD45.1) (FIG. 18A). CRF250 GT-trimer binds CH01 UCA BCR with 100 nM KD affinity and efficiently activated the on-target V2-apex CH01 B cells even at 1 in $10^7$ precursor frequency as determined by ELISA binding of the week-2 (2 wk) post prime Ab responses with CRF250 SOSIP trimer and its N160 glycan-eliminated V2-epitope specific knock-out variant (FIG. 18B). Further boosting with CRF250 trimer recalled the V2-specific Ab responses (6 wk), but also resulted in the development of a strong CRF250 Env-backbone specific off-target B cell responses targeting epitopes outside of the V2-apex bnAb site, as probed by N160 glycan-dependent binding (FIG. 18B). The development of CRF250-specific off-target B cell responses coincided with reduction of CH01-specific class-switched memory B cell responses, as determined by next generation sequencing of B cells from immunized mice (FIG. 18C). Both the CRF250 trimer-elicited post-prime and the post-boost Ab responses displayed strong binding to the chimpanzee SIV MT145K trimer in a V2-apex bnAb epitope-specific manner but largely no binding to the HIV Env backbone-specific off-target Ab responses (FIG. 18B). The results suggest that sequential prime boosting with HIV and SIV trimers that share V2-apex bnAb site can be advantageous, especially in that off-target responses should be disfavored.

MT145KdV5 SOSIP Trimer Version Induces Superior Cross-Neutralizing Ab Responses Compared to the Parent MT145K SOSIP Trimer in CH01 iGL HC-Only KI Mouse Model.

Infection of non-human primates (NHPs) with Simian-Human Immunodeficiency Virus (SHIV)-encoding MT145K envelope induces a rapid and strong autologous neutralizing antibody response largely directed to the immunodominant hypervariable V5-loop of gp120. In response to this early wave of autologous nAb responses, the circulating MT145K SHIV viruses develop multiple escape solutions, including a 9 amino acid deletion in the V5-loop (George Shaw et al, unpublished). Multiple animals developed this common viral escape solution of 9AA V5-loop deletion. Structure of MT145K SOSIP trimer revealed a peripheral positioning of the flexible V5 loop, consistent with its in vivo B cell immunodominance effects.

The MT145K SOSIP trimer was engineered to eliminate this 9AA immunodominant V5-loop (FIG. 19) and the resulting SOSIP trimer, MT145KdV5 with a 9AA V5-deletion showed native-like trimer antigenic and biophysical properties similar to the parent MT 145K SOSIP trimer (FIG. 20). A head-to-head immunogenicity comparison of MT 145dV5 trimer version with MT 145K in CH01 iGL HC-only KI mice showed induction of a more reproducible and superior cross-neutralizing serum antibody response by MT145KdV5 trimer. Deletion of the immunodominant V5-loop in the MT 145KdV5 can reduce the development of non-desired off-target B cell responses and therefore, the modified version of the trimer can be more optimal for human vaccinations to induce V2-apex bnAbs.

Chimpanzee SIV MT145KdV5 SOSIP Trimer Induces Autologous Neutralizing Antibodies in NHPs The immunogenicity of MT145KdV5 trimer was investigated in NHPs, whose B cell repertoires closely resemble to that of humans. A group of 6 NHPs was immunized twice (prime, week 0; boost-1, week 8) with MT145KdV5 SOSIP trimer and monitored the development of antibody responses by ELISA and neutralization assay (FIG. 21). ELISA binding of the post-prime serum antibodies revealed a strong development of autologous trimer immunogen specific binding responses (FIG. 21B). The titers of the Ab binding responses substantially increased post boost immunization indicating a B cell recall response. In addition to stronger Ab binding titers, the post boost (10 wk) serum antibody responses exhibited neutralizing activities against the autologous MT145KdV5 virus (FIG. 21C).

REFERENCES

Adams, P. D., Grosse-Kunstleve, R. W., Hung, L. W., Ioerger, T. R., McCoy, A. J., Moriarty, N. W., Read, R. J., Sacchettini, J. C., Sauter, N. K., and Terwilliger, T. C. (2002). PHENIX: building new software for automated crystallographic structure determination. Acta Crystallogr D Biol Crystallogr 58, 1948-1954.

Agirre, J., Iglesias-Fernandez, J., Rovira, C., Davies, G. J., Wilson, K. S., and Cowtan, K. D. (2015). Privateer: software for the conformational validation of carbohydrate structures. Nature structural & molecular biology 22, 833-834.

Andrabi, R., Pallesen, J., Allen, J. D., Song, G., Zhang, J., de Val, N., Gegg, G., Porter, K., Su, C. Y., Pauthner, M., Newman, A., Bouton-Verville, H., Garces, F., Wilson, I. A., Crispin, M., Hahn, B. H., Haynes, B. F., Verkoczy, L., Ward, A. B., Burton, D. R. (2019) The Chimpanzee SIV Envelope Trimer: Structure and Deployment as an HIV Vaccine Template. Cell Rep. 21, 2426-2441.

Andrabi, R., Su, C. Y., Liang, C. H., Shivatare, S. S., Briney, B., Voss, J. E., Nawazi, S. K., Wu, C. Y., Wong, C. H., and Burton, D. R. (2017). Glycans Function as Anchors for Antibodies and Help Drive HIV Broadly Neutralizing Antibody Development. Immunity 47, 524-537 e523.

Andrabi, R., Voss, J. E., Liang, C. H., Briney, B., McCoy, L. E., Wu, C. Y., Wong, C. H., Poignard, P., and Burton, D. R. (2015). Identification of Common Features in Prototype Broadly Neutralizing Antibodies to HIV Envelope V2 Apex to Facilitate Vaccine Design. Immunity 43, 959-973.

Barad, B. A., Echols, N., Wang, R. Y., Cheng, Y., DiMaio, F., Adams, P. D., and Fraser, J. S. (2015). EMRinger: side chain-directed model and map validation for 3D cryo-electron microscopy. Nature methods 12, 943-946.

Barbian, H. J., Decker, J. M., Bibollet-Ruche, F., Galimidi, R. P., West, A. P., Jr., Learn, G. H., Parrish, N. F., Iyer, S. S., Li, Y., Pace, C. S., et al. (2015). Neutralization properties of simian immunodeficiency viruses infecting chimpanzees and gorillas. mBio 6.

Behrens, A. J., Harvey, D. J., Milne, E., Cupo, A., Kumar, A., Zitzmann, N., Struwe, W. B., Moore, J. P., and Crispin, M. (2017). Molecular Architecture of the Cleavage-Dependent Mannose Patch on a Soluble HIV-1 Envelope Glycoprotein Trimer. Journal of virology 91.

Behrens, A. J., Vasiljevic, S., Pritchard, L. K., Harvey, D. J., Andev, R. S., Krumm, S. A., Struwe, W. B., Cupo, A., Kumar, A., Zitzmann, N., et al. (2016). Composition and Antigenic Effects of Individual Glycan Sites of a Trimeric HIV-1 Envelope Glycoprotein. Cell reports 14, 2695-2706.

Benichou S, Venet A, Beyer C, Tiollais P, and Madaule P. (1993). Characterization of B-cell epitopes in the envelope glycoproteins of simian immunodeficiency virus. Virology 194, 870-874.

Bhiman, J. N., Anthony, C., Doria-Rose, N. A., Karimanzira, O., Schramm, C. A., Khoza, T., Kitchin, D., Botha, G., Gorman, J., Garrett, N.J., et al. (2015). Viral variants that initiate and drive maturation of V1V2-directed HIV-1 broadly neutralizing antibodies. Nature medicine 21, 1332-1336.

Blattner, C., Lee, J. H., Sliepen, K., Derking, R., Falkowska, E., de la Pena, A. T., Cupo, A., Julien, J. P., van Gils, M., Lee, P. S., et al. (2014). Structural delineation of a quaternary, cleavage-dependent epitope at the gp41-gp120 interface on intact HIV-1 Env trimers. Immunity 40, 669-680.

Bonomelli, C., Doores, K. J., Dunlop, D. C., Thaney, V., Dwek, R. A., Burton, D. R., Crispin, M., and Scanlan, C. N. (2011). The glycan shield of HIV is predominantly oligomannose independently of production system or viral clade. PloS one 6, e23521.

Bonsignori, M., Hwang, K. K., Chen, X., Tsao, C. Y., Morris, L., Gray, E., Marshall, D. J., Crump, J. A., Kapiga, S. H., Sam, N. E., et al. (2011). Analysis of a clonal lineage of HIV-1 envelope V2/V3 conformational epitope-specific broadly neutralizing antibodies and their inferred unmutated common ancestors. Journal of virology 85, 9998-10009.

Braibant, M., Gong, E. Y., Plantier, J. C., Moreau, T., Alessandri, E., Simon, F., and Barin, F. (2013). Cross-group neutralization of HIV-1 and evidence for conservation of the PG9/PG16 epitopes within divergent groups. Aids 27, 1239-1244.

Briney, B., Sok, D., Jardine, J. G., Kulp, D. W., Skog, P., Menis, S., Jacak, R., Kalyuzhniy, O., de Val, N., Sesterhenn, F., et al. (2016). Tailored Immunogens Direct Affinity Maturation toward HIV Neutralizing Antibodies. Cell 166, 1459-1470 e1411.

Briney, B. S., Willis, J. R., and Crowe, J. E., Jr. (2012). Human peripheral blood antibodies with long HCDR3s are established primarily at original recombination using a limited subset of germline genes. PloS one 7, e36750.

Brochet, X., Lefranc, M. P., and Giudicelli, V. (2008). IMGT/V-QUEST: the highly customized and integrated system for IG and TR standardized V-J and V-D-J sequence analysis. Nucleic acids research 36, W503-508.

Chen, V. B., Arendall, W. B., 3rd, Headd, J. J., Keedy, D. A., Immormino, R. M., Kapral, G. J., Murray, L. W., Richardson, J. S., and Richardson, D. C. (2010). MolProbity: all-atom structure validation for macromolecular crystallography. Acta Crystallogr D Biol Crystallogr 66, 12-21.

DiMaio, F., Song, Y., Li, X., Brunner, M. J., Xu, C., Conticello, V., Egelman, E., Marlovits, T., Cheng, Y., and Baker, D. (2015). Atomic-accuracy models from 4.5-A cryo-electron microscopy data with density-guided iterative local refinement. Nature methods 12, 361-365.

Doria-Rose, N. A., Schramm, C. A., Gorman, J., Moore, P. L., Bhiman, J. N., DeKosky, B. J., Ernandes, M. J., Georgiev, I. S., Kim, H. J., Pancera, M., et al. (2014). Developmental pathway for potent V1V2-directed HIV-neutralizing antibodies. Nature 509, 55-62.

Dosenovic, P., von Boehmer, L., Escolano, A., Jardine, J., Freund, N. T., Gitlin, A. D., McGuire, A. T., Kulp, D. W., Oliveira, T., Scharf, L., et al. (2015). Immunization for HIV-1 Broadly Neutralizing Antibodies in Human Ig Knockin Mice. Cell 161, 1505-1515.

Emsley, P., and Cowtan, K. (2004). Coot: model-building tools for molecular graphics. Acta Crystallogr D Biol Crystallogr 60, 2126-2132.

Escolano, A., Dosenovic, P., and Nussenzweig, M. C. (2017). Progress toward active or passive HIV-1 vaccination. The Journal of experimental medicine 214, 3-16.

Escolano, A., Steichen, J. M., Dosenovic, P., Kulp, D. W., Golijanin, J., Sok, D., Freund, N. T., Gitlin, A. D., Oliveira, T., Araki, T., et al. (2016). Sequential Immunization Elicits Broadly Neutralizing Anti-HIV-1 Antibodies in Ig Knockin Mice. Cell 166, 1445-1458 e1412.

Falkowska, E., Le, K. M., Ramos, A., Doores, K. J., Lee, J. H., Blattner, C., Ramirez, A., Derking, R., van Gils, M. J., Liang, C. H., et al. (2014). Broadly neutralizing HIV antibodies define a glycan-dependent epitope on the prefusion conformation of gp41 on cleaved envelope trimers. Immunity 40, 657-668.

Gao, F., Bailes, E., Robertson, D. L., Chen, Y., Rodenburg, C. M., Michael, S. F., Cummins, L. B., Arthur, L. O., Peeters, M., Shaw, G. M., et al. (1999). Origin of HIV-1 in the chimpanzee Pan troglodytes troglodytes. Nature 397, 436-441.

Garces, F., Lee, J. H., de Val, N., de la Pena, A. T., Kong, L., Puchades, C., Hua, Y., Stanfield, R. L., Burton, D. R., Moore, J. P., et al. (2015). Affinity Maturation of a Potent Family of HIV Antibodies Is Primarily Focused on Accommodating or Avoiding Glycans. Immunity 43, 1053-1063.

Garces, F., Sok, D., Kong, L., McBride, R., Kim, H. J., Saye-Francisco, K. F., Julien, J. P., Hua, Y., Cupo, A., Moore, J. P., et al. (2014). Structural evolution of glycan recognition by a family of potent HIV antibodies. Cell 159, 69-79.

Georgiev, I. S., Doria-Rose, N. A., Zhou, T., Kwon, Y. D., Staupe, R. P., Moquin, S., Chuang, G. Y., Louder, M. K., Schmidt, S. D., Altae-Tran, H. R., et al. (2013). Delineating antibody recognition in polyclonal sera from patterns of HIV-1 isolate neutralization. Science 340, 751-756.

Gorman, J., Soto, C., Yang, M. M., Davenport, T. M., Guttman, M., Bailer, R. T., Chambers, M., Chuang, G. Y., DeKosky, B. J., Doria-Rose, N. A., et al. (2016). Structures of HIV-1 Env V1V2 with broadly neutralizing antibodies reveal commonalities that enable vaccine design. Nat Struct Mol Biol 23, 81-90.

Harvey, D. J., Baruah, K., and Scanlan, C. N. (2009). Application of negative ion MS/MS to the identification of N-glycans released from carcinoembryonic antigen cell adhesion molecule 1 (CEACAM1). J Mass Spectrom 44, 50-60.

Havenar-Daughton, C., Lee, J. H., and Crotty, S. (2017). Tfh cells and HIV bnAbs, an immunodominance model of the HIV neutralizing antibody generation problem. Immunological reviews 275, 49-61.

Haynes, B. F., Kelsoe, G., Harrison, S. C., and Kepler, T. B. (2012). B-cell-lineage immunogen design in vaccine development with HIV-1 as a case study. Nature biotechnology 30, 423-433.

Haynes, B. F., and Mascola, J. R. (2017). The quest for an antibody-based HIV vaccine. Immunological reviews 275, 5-10.

Jardine, J., Julien, J. P., Menis, S., Ota, T., Kalyuzhniy, O., McGuire, A., Sok, D., Huang, P. S., MacPherson, S., Jones, M., et al. (2013). Rational HIV immunogen design to target specific germline B cell receptors. Science 340, 711-716.

Jardine, J. G., Ota, T., Sok, D., Pauthner, M., Kulp, D. W., Kalyuzhniy, O., Skog, P. D., Thinnes, T. C., Bhullar, D., Briney, B., et al. (2015). HIV-1 VACCINES. Priming a broadly neutralizing antibody response to HIV-1 using a germline-targeting immunogen. Science 349, 156-161.

Julien, J. P., Cupo, A., Sok, D., Stanfield, R. L., Lyumkis, D., Deller, M. C., Klasse, P. J., Burton, D. R., Sanders, R. W., Moore, J. P., et al. (2013a). Crystal structure of a soluble cleaved HIV-1 envelope trimer. Science 342, 1477-1483.

Julien, J. P., Lee, J. H., Cupo, A., Murin, C. D., Derking, R., Hoffenberg, S., Caulfield, M. J., King, C. R., Marozsan, A. J., Klasse, P. J., et al. (2013b). Asymmetric recognition of the HIV-1 trimer by broadly neutralizing antibody PG9. Proceedings of the National Academy of Sciences of the United States of America 110, 4351-4356.

Kepler, T. B., Liao, H. X., Alam, S. M., Bhaskarabhatla, R., Zhang, R., Yandava, C., Stewart, S., Anasti, K., Kelsoe, G., Parks, R., et al. (2014). Immunoglobulin gene insertions and deletions in the affinity maturation of HIV-1 broadly reactive neutralizing antibodies. Cell Host Microbe 16, 304-313.

Klein, F., Diskin, R., Scheid, J. F., Gaebler, C., Mouquet, H., Georgiev, I. S., Pancera, M., Zhou, T., Incesu, R. B., Fu, B. Z., et al. (2013). Somatic mutations of the immunoglobulin framework are generally required for broad and potent HIV-1 neutralization. Cell 153, 126-138.

Korber, B., Muldoon, M., Theiler, J., Gao, F., Gupta, R., Lapedes, A., Hahn, B. H., Wolinsky, S., and Bhattacharya, T. (2000). Timing the ancestor of the HIV-1 pandemic strains. Science 288, 1789-1796.

Kwon, Y. D., Pancera, M., Acharya, P., Georgiev, I. S., Crooks, E. T., Gorman, J., Joyce, M. G., Guttman, M., Ma, X., Narpala, S., et al. (2015). Crystal structure, conformational fixation and entry-related interactions of mature ligand-free HIV-1 Env. Nature structural & molecular biology 22, 522-531.

Landais, E., Huang, X., Havenar-Daughton, C., Murrell, B., Price, M. A., Wickramasinghe, L., Ramos, A., Bian, C. B., Simek, M., Allen, S., et al. (2016). Broadly Neutralizing Antibody Responses in a Large Longitudinal Sub-Saharan HIV Primary Infection Cohort. PLoS pathogens 12, e1005369.

Landais, E., Murrell, B., Briney, B., Murrell, S., Rantalainen, K., Berndsen, Z. T., Ramos, A., Wickramasinghe, L., Smith, M. L., Eren, K., et al. (2017). HIV Envelope Glycoform Heterogeneity and Localized Diversity Govern the Initiation and Maturation of a V2 Apex Broadly Neutralizing Antibody Lineage. Immunity 47, 990-1003 e1009.

Lee, J. H., Andrabi, R., Su, C. Y., Yasmeen, A., Julien, J. P., Kong, L., Wu, N.C., McBride, R., Sok, D., Pauthner, M., et al. (2017). A Broadly Neutralizing Antibody Targets the Dynamic HIV Envelope Trimer Apex via a Long, Rigidified, and Anionic beta-Hairpin Structure. Immunity 46, 690-702.

Lee, J. H., de Val, N., Lyumkis, D., and Ward, A. B. (2015). Model Building and Refinement of a Natively Glycosylated HIV-1 Env Protein by High-Resolution Cryoelectron Microscopy. Structure 23, 1943-1951.

Lee, J. H., Ozorowski, G., and Ward, A. B. (2016). Cryo-EM structure of a native, fully glycosylated, cleaved HIV-1 envelope trimer. Science 351, 1043-1048.

Lyumkis, D., Julien, J. P., de Val, N., Cupo, A., Potter, C. S., Klasse, P. J., Burton, D. R., Sanders, R. W., Moore, J. P., Carragher, B., et al. (2013). Cryo-EM structure of a fully glycosylated soluble cleaved HIV-1 envelope trimer. Science 342, 1484-1490.

McCoy, L. E., and Burton, D. R. (2017). Identification and specificity of broadly neutralizing antibodies against HIV. Immunological reviews 275, 11-20.

McGuire, A. T., Gray, M. D., Dosenovic, P., Gitlin, A. D., Freund, N. T., Petersen, J., Correnti, C., Johnsen, W., Kegel, R., Stuart, A. B., et al. (2016). Specifically modified Env immunogens activate B-cell precursors of broadly neutralizing HIV-1 antibodies in transgenic mice. Nature communications 7, 10618.

McGuire, A. T., Hoot, S., Dreyer, A. M., Lippy, A., Stuart, A., Cohen, K. W., Jardine, J., Menis, S., Scheid, J. F., West, A. P., et al. (2013). Engineering HIV envelope protein to activate germline B cell receptors of broadly neutralizing anti-CD4 binding site antibodies. The Journal of experimental medicine 210, 655-663.

McLellan, J. S., Pancera, M., Carrico, C., Gorman, J., Julien, J. P., Khayat, R., Louder, R., Pejchal, R., Sastry, M., Dai, K., et al. (2011). Structure of HIV-1 gp120 V1/V2 domain with broadly neutralizing antibody PG9. Nature 480, 336-343.

Montefiori, D. C. (2005). Evaluating neutralizing antibodies against HIV, SIV, and SHIV in luciferase reporter gene assays. Current protocols in immunology/edited by John E Coligan [et al] Chapter 12, Unit 12.11.

Moore, P. L., Gray, E. S., Sheward, D., Madiga, M., Ranchobe, N., Lai, Z., Honnen, W. J., Nonyane, M., Tumba, N., Hermanus, T., et al. (2011). Potent and broad neutralization of HIV-1 subtype C by plasma antibodies targeting a quaternary epitope including residues in the V2 loop. Journal of virology 85, 3128-3141.

Morgand, M., Bouvin-Pley, M., Plantier, J. C., Moreau, A., Alessandri, E., Simon, F., Pace, C. S., Pancera, M., Ho, D. D., Poignard, P., et al. (2016). V1/V2 Neutralizing Epitope is Conserved in Divergent Non-M Groups of HIV-1. J Acquir Immune Defic Syndr 71, 237-245.

Ogura, T., Iwasaki, K., and Sato, C. (2003). Topology representing network enables highly accurate classification of protein images taken by cryo electron-microscope without masking. J Struct Biol 143, 185-200.

Ozorowski, G., Pallesen, J., de Val, N., Lyumkis, D., Cottrell, C. A., Torres, J. L., Copps, J., Stanfield, R. L., Cupo, A., Pugach, P., et al. (2017). Open and closed structures reveal allostery and pliability in the HIV-1 envelope spike. Nature 547, 360-363.

Pancera, M., Shahzad-Ul-Hussan, S., Doria-Rose, N. A., McLellan, J. S., Bailer, R. T., Dai, K., Loesgen, S., Louder, M. K., Staupe, R. P., Yang, Y., et al. (2013). Structural basis for diverse N-glycan recognition by HIV-1-neutralizing V1-V2-directed antibody PG16. Nature structural & molecular biology 20, 804-813.

Pancera, M., Zhou, T., Druz, A., Georgiev, I. S., Soto, C., Gorman, J., Huang, J., Acharya, P., Chuang, G. Y., Ofek, G., et al. (2014). Structure and immune recognition of trimeric pre-fusion HIV-1 Env. Nature 514, 455-461.

Panico, M., Bouche, L., Binet, D., O'Connor, M. J., Rahman, D., Pang, P. C., Canis, K., North, S. J., Desrosiers, R. C., Chertova, E., et al. (2016). Mapping the complete glycoproteome of virion-derived HIV-1 gp120 provides insights into broadly neutralizing antibody binding. Sci Rep 6, 32956.

Pejchal, R., Doores, K. J., Walker, L. M., Khayat, R., Huang, P. S., Wang, S. K., Stanfield, R. L., Julien, J. P., Ramos, A., Crispin, M., et al. (2011). A potent and broad neutralizing antibody recognizes and penetrates the HIV glycan shield. Science 334, 1097-1103.

Pritchard, L. K., Harvey, D. J., Bonomelli, C., Crispin, M., and Doores, K. J. (2015). Cell- and Protein-Directed Glycosylation of Native Cleaved HIV-1 Envelope. Journal of virology 89, 8932-8944.

Pugach, P., Ozorowski, G., Cupo, A., Ringe, R., Yasmeen, A., de Val, N., Derking, R., Kim, H. J., Korzun, J., Golabek, M., et al. (2015). A native-like SOSIP.664 trimer based on a HIV-1 subtype B env gene. Journal of virology.

Riedel, S. (2005). Edward Jenner and the history of smallpox and vaccination. Proc (Bayl Univ Med Cent) 18, 21-25.

Sanders, R. W., Derking, R., Cupo, A., Julien, J. P., Yasmeen, A., de Val, N., Kim, H. J., Blattner, C., de la Pena, A. T., Korzun, J., et al. (2013). A next-generation cleaved, soluble HIV-1 Env trimer, BG505 SOSIP.664 gp140, expresses multiple epitopes for broadly neutralizing but not non-neutralizing antibodies. PLoS pathogens 9, e1003618.

Sanders, R. W., van Gils, M. J., Derking, R., Sok, D., Ketas, T. J., Burger, J. A., Ozorowski, G., Cupo, A., Simonich, C., Goo, L., et al. (2015). HIV-1 VACCINES. HIV-1 neutralizing antibodies induced by native-like envelope trimers. Science 349, aac4223.

Saunders, K. O., Verkoczy, L. K., Jiang, C., Zhang, J., Parks, R., Chen, H., Housman, M., Bouton-Verville, H., Shen, X., Trama, A. M., et al. (2017). Vaccine Induction of Heterologous Tier 2 HIV-1 Neutralizing Antibodies in Animal Models. Cell reports 21, 3681-3690.

Scheres, S. H. (2012). RELION: implementation of a Bayesian approach to cryo-EM structure determination. J Struct Biol 180, 519-530.

Seaman, M. S., Janes, H., Hawkins, N., Grandpre, L. E., Devoy, C., Giri, A., Coffey, R. T., Harris, L., Wood, B., Daniels, M. G., et al. (2010). Tiered categorization of a diverse panel of HIV-1 Env pseudoviruses for assessment of neutralizing antibodies. Journal of virology 84, 1439-1452.

Sharma, S. K., de Val, N., Bale, S., Guenaga, J., Tran, K., Feng, Y., Dubrovskaya, V., Ward, A. B., and Wyatt, R. T. (2015). Cleavage-independent HIV-1 Env trimers engineered as soluble native spike mimetics for vaccine design. Cell reports 11, 539-550.

Sharp, P. M., and Hahn, B. H. (2011). Origins of HIV and the AIDS pandemic. Cold Spring Harbor perspectives in medicine 1, a006841.

Sok, D., Briney, B., Jardine, J. G., Kulp, D. W., Menis, S., Pauthner, M., Wood, A., Lee, E. C., Le, K. M., Jones, M., et al. (2016a). Priming HIV-1 broadly neutralizing antibody precursors in human Ig loci transgenic mice. Science.

Sok, D., Doores, K. J., Briney, B., Le, K. M., Saye-Francisco, K. L., Ramos, A., Kulp, D. W., Julien, J. P., Menis, S., Wickramasinghe, L., et al. (2014a). Promiscuous glycan site recognition by antibodies to the high-mannose patch of gp120 broadens neutralization of HIV. Science translational medicine 6, 236ra263.

Sok, D., Pauthner, M., Briney, B., Lee, J. H., Saye-Francisco, K. L., Hsueh, J., Ramos, A., Le, K. M., Jones, M., Jardine, J. G., et al. (2016b). A Prominent Site of Antibody Vulnerability on HIV Envelope Incorporates a Motif Associated with CCR5 Binding and Its Camouflaging Glycans. Immunity 45, 31-45.

Sok, D., van Gils, M. J., Pauthner, M., Julien, J. P., Saye-Francisco, K. L., Hsueh, J., Briney, B., Lee, J. H., Le, K. M., Lee, P. S., et al. (2014b). Recombinant HIV envelope trimer selects for quaternary-dependent antibodies targeting the trimer apex. Proceedings of the National Academy of Sciences of the United States of America 111, 17624-17629.

Steichen, J. M., Kulp, D. W., Tokatlian, T., Escolano, A., Dosenovic, P., Stanfield, R. L., McCoy, L. E., Ozorowski, G., Hu, X., Kalyuzhniy, O., et al. (2016a). HIV Vaccine Design to Target Germline Precursors of Glycan-Dependent Broadly Neutralizing Antibodies. Immunity 45, 483-496.

Steichen, J. M., Kulp, D. W., Tokatlian, T., Escolano, A., Dosenovic, P., Stanfield, R. L., McCoy, L. E., Ozorowski, G., Hu, X., Kalyuzhniy, O., et al. (2016b). HIV Vaccine Design to Target Germline Precursors of Glycan-Dependent Broadly Neutralizing Antibodies. Immunity 45, 483-496.

Tas, J. M., Mesin, L., Pasqual, G., Targ, S., Jacobsen, J. T., Mano, Y. M., Chen, C. S., Weill, J. C., Reynaud, C. A., Browne, E. P., et al. (2016). Visualizing antibody affinity maturation in germinal centers. Science 351, 1048-1054.

Tian, M., Cheng, C., Chen, X., Duan, H., Cheng, H. L., Dao, M., Sheng, Z., Kimble, M., Wang, L., Lin, S., et al. (2016). Induction of HIV Neutralizing Antibody Lineages in Mice with Diverse Precursor Repertoires. Cell 166, 1471-1484 e1418. Tiller, T., Meffre, E., Yurasov, S., Tsuiji, M., Nussenzweig, M. C., and Wardemann, H. (2008).

Efficient generation of monoclonal antibodies from single human B cells by single cell RT-PCR and expression vector cloning. Journal of immunological methods 329, 112-124.

Verkoczy, L., Diaz, M., Holl, T. M., Ouyang, Y. B., Bouton-Verville, H., Alam, S. M., Liao, H. X., Kelsoe, G., and Haynes, B. F. (2010). Autoreactivity in an HIV-1 broadly reactive neutralizing antibody variable region heavy chain induces immunologic tolerance. Proceedings of the National Academy of Sciences of the United States of America 107, 181-186.

Voss, J. E., Andrabi, R., McCoy, L. E., de Val, N., Fuller, R. P., Messmer, T., Su, C. Y., Sok, D., Khan, S. N., Garces, F., et al. (2017). Elicitation of Neutralizing Antibodies Targeting the V2 Apex of the HIV Envelope Trimer in a Wild-Type Animal Model. Cell reports 21, 222-235.

Voss, N. R., Yoshioka, C. K., Radermacher, M., Potter, C. S., and Carragher, B. (2009). DoG Picker and TiltPicker: software tools to facilitate particle selection in single particle electron microscopy. J Struct Biol 166, 205-213.

Walker, L. M., Huber, M., Doores, K. J., Falkowska, E., Pejchal, R., Julien, J. P., Wang, S. K., Ramos, A., Chan-Hui, P. Y., Moyle, M., et al. (2011). Broad neutralization coverage of HIV by multiple highly potent antibodies. Nature 477, 466-470.

Walker, L. M., Phogat, S. K., Chan-Hui, P. Y., Wagner, D., Phung, P., Goss, J. L., Wrin, T., Simek, M. D., Fling, S., Mitcham, J. L., et al. (2009). Broad and potent neutralizing antibodies from an African donor reveal a new HIV-1 vaccine target. Science 326, 285-289.

Wang, S., Mata-Fink, J., Kriegsman, B., Hanson, M., Irvine, D. J., Eisen, H. N., Burton, D. R., Wittrup, K. D., Kardar, M., and Chakraborty, A. K. (2015). Manipulating the Selection Forces during Affinity Maturation to Generate Cross-Reactive HIV Antibodies. Cell 160, 785-797.

Ward, A. B., and Wilson, I. A. (2017). The HIV-1 envelope glycoprotein structure: nailing down a moving target. Immunological reviews 275, 21-32.

Webb, B., and Sali, A. (2016). Comparative Protein Structure Modeling Using MODELLER. Curr Protoc Bioinformatics 54, 561-5637.

Wibmer, C. K., Bhiman, J. N., Gray, E. S., Tumba, N., Abdool Karim, S. S., Williamson, C., Morris, L., and Moore, P. L. (2013). Viral escape from HIV-1 neutralizing antibodies drives increased plasma neutralization breadth through sequential recognition of multiple epitopes and immunotypes. PLoS pathogens 9, e1003738.

Williams, W. B., Zhang, J., Jiang, C., Nicely, N. I., Fera, D., Luo, K., Moody, M. A., Liao, H. X., Alam, S. M., Kepler, T. B., et al. (2017). Initiation of HIV neutralizing B cell lineages with sequential envelope immunizations. Nature communications 8, 1732.

Worobey, M., Gemmel, M., Teuwen, D. E., Haselkorn, T., Kunstman, K., Bunce, M., Muyembe, J. J., Kabongo, J. M., Kalengayi, R. M., Van Marck, E., et al. (2008). Direct evidence of extensive diversity of HIV-1 in Kinshasa by 1960. Nature 455, 661-664.

Wu, X., Yang, Z. Y., Li, Y., Hogerkorp, C. M., Schief, W. R., Seaman, M. S., Zhou, T., Schmidt, S. D., Wu, L., Xu, L., et al. (2010). Rational design of envelope identifies broadly neutralizing human monoclonal antibodies to HIV-1. Science 329, 856-861.

Xiao, X., Chen, W., Feng, Y., Zhu, Z., Prabakaran, P., Wang, Y., Zhang, M. Y., Longo, N. S., and Dimitrov, D. S.

(2009). Germline-like predecessors of broadly neutralizing antibodies lack measurable binding to HIV-1 envelope glycoproteins: implications for evasion of immune responses and design of vaccine immunogens. Biochemical and biophysical research communications 390, 404-409.

Zhang, K. (2016). Gctf Real-time CTF determination and correction. J Struct Biol 193, 1-12.

Zhang, M., Gaschen, B., Blay, W., Foley, B., Haigwood, N., Kuiken, C., and Korber, B. (2004). Tracking global patterns of N-linked glycosylation site variation in highly variable viral glycoproteins: HIV, SIV, and HCV envelopes and influenza hemagglutinin. Glycobiology 14, 1229-1246.

Zheng, S. Q., Palovcak, E., Armache, J. P., Verba, K. A., Cheng, Y., and Agard, D. A. (2017). MotionCor2: anisotropic correction of beam-induced motion for improved cryo-electron microscopy. Nature methods 14, 331-332.

Zhou, T., Georgiev, I., Wu, X., Yang, Z. Y., Dai, K., Finzi, A., Kwon, Y. D., Scheid, J. F., Shi, W., Xu, L., et al. (2010). Structural basis for broad and potent neutralization of HIV-1 by antibody VRC01. Science 329, 811-817.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An engineered or non-naturally occurring molecule that binds to a Human Immunodeficiency Virus (HIV-1) broadly neutralizing antibody (bnAb), wherein the molecule comprises the amino acid sequence of SEQ ID NO: 28.

2. The molecule of claim 1, wherein the HIV-1 bnAb comprises three complementarity determining regions (CDRs) of a heavy chain variable domain, a first CDR of which comprising the amino acid sequence of SEQ ID NO: 33, a second CDR of which comprising the amino acid sequence of SEQ ID NO: 34, and a third CDR of which comprising the amino acid sequence of SEQ ID NO: 35, and three CDRs of a light chain variable domain, a first CDR of which comprising the amino acid sequence of SEO ID NO: 42, a second CDR of which comprising the amino acid sequence of 43, and a third CDR of which comprising the amino acid sequence of SEQ ID NO: 44.

3. The molecule of claim 1, wherein the HIV-1 bnAb comprises three complementarity determining regions (CDRs) of a heavy chain variable domain, a first CDR of which comprising the amino acid sequence of SEQ ID NO: 50, a second CDR of which comprising the amino acid sequence of SEQ ID NO: 51, and a third CDR of which comprising the amino acid sequence of SEQ ID NO: 52, and three CDRs of a light chain variable domain, a first CDR of which comprising the amino acid sequence of SEQ ID NO: 59, a second CDR of which comprising the amino acid sequence of SEQ ID NO: 60, and a third CDR of which comprising the amino acid sequence of SEQ ID NO: 61.

4. An engineered or non-naturally occurring molecule that binds to a Human Immunodeficiency Virus (HIV-1) broadly neutralizing antibody (bnAb), wherein the bnAb binds to the V2 apex region of HIV-1 envelope, wherein the molecule comprises an amino acid sequence comprising SEO ID NO: 28 or an amino acid sequence having at least 95% sequence identity to SEQ ID NO: 28.

5. A nucleic acid encoding the molecule of claim 1.

6. A vector comprising a regulatory element operable in a eukaryotic cell operably linked to the nucleic acid of claim 5, wherein the vector comprises a viral vector.

7. A method of eliciting an immune response in a mammal or stimulating an HIV-1 broadly neutralizing antibody (bnAb) comprising administering the molecule of claim 1.

8. The method of claim 7, wherein the mammal is a mouse, non-human primate, or a human.

9. The engineered or non-naturally occurring molecule of claim 4, wherein the HIV bnAb comprises (i) three complementarity determining regions (CDRs) of a heavy chain variable domain, a first CDR of which comprises an amino acid sequence comprising SEQ ID NO: 33 or an amino acid sequence having at least 95% sequence identity to SEQ ID NO: 33, a second CDR of which comprises an amino acid sequence comprising SEQ ID NO: 34 or an amino acid sequence having at least 95% sequence identity to SEQ ID NO: 34, and a third CDR of which comprises an amino acid sequence comprising SEQ ID NO: 35 or an amino acid sequence having at least 95% sequence identity to SEQ ID NO: 35; and, (ii) three CDRs of a light chain variable domain, a first CDR of which comprises an amino acid sequence comprising SEQ ID NO: 42 or an amino acid sequence having at least 95% sequence identity to SEQ ID NO: 42, a second CDR of which comprises an amino acid sequence comprising SEQ ID NO: 43 or an amino acid sequence having at least 95% sequence identity to SEQ ID NO: 43, and a third of which comprises an amino acid sequence comprising SEQ ID NO: 44 or an amino acid sequence having at least 95% sequence identity to SEQ ID NO: 44.

10. The molecule of claim 1, wherein the HIV-1 bnAb comprises three complementarity determining regions (CDRs) of a heavy chain variable domain, a first CDR of which comprising the amino acid sequence of SEQ ID NO: 50 or an amino acid sequence having at least 95% sequence identity to SEQ ID NO: 50, a second CDR of which comprising the amino acid sequence of SEQ ID NO: 51 or an amino acid sequence having at least 95% sequence identity to SEQ ID NO: 51, and a third CDR of which comprising the amino acid sequence of SEQ ID NO: 52 or an amino acid sequence having at least 95% sequence identity to SEQ ID NO: 52, and three CDRs of a light chain variable domain, a first CDR of which comprising the amino acid sequence of SEQ ID NO: 59 or an amino acid sequence having at least 95% sequence identity to SEQ ID NO: 59, a second CDR of which comprising the amino acid sequence of SEQ ID NO: 60 or an amino acid sequence having at least 95% sequence identity to SEQ ID NO: 60, and a third CDR of which comprising the amino acid sequence of SEQ ID NO: 61 or an amino acid sequence having at least 95% sequence identity to SEQ ID NO: 61.

11. The method of claim 7, wherein the molecule is administered with an adjuvant.

12. The method of claim 11, wherein the adjuvant comprises a lecithin or wherein the adjuvant is an immune stimulating complex-forming adjuvant or a lipid-based vaccine adjuvant.

13. The method of claim 12, wherein the lecithin is (a) combined with an acrylic polymer, (b) in a coated oil droplet in an oil-in-water emulsion or (c) in an acrylic polymer in an oil-in-water emulsion.

14. A method of eliciting an immune response in a mammal or stimulating an HIV-1 broadly neutralizing antibody (bnAb) comprising administering the molecule of claim 1, wherein the molecule is administered in a liposome or in a nanoparticle or wherein the molecule is fixed, wherein the molecule is fixed in glutaraldehyde, or wherein the molecule is quenched with glycine.

15. A method of identifying an HIV-1 binder which comprises contacting a candidate binder with the molecule of claim 1 and identifying a candidate binder that binds to the molecule.

16. A method of identifying a broadly neutralizing antibody (bnAb) against HIV-1 which comprises contacting a candidate antibody with the molecule of claim 1 and identifying an antibody that binds to the molecule as a bnAb, wherein the bnAb is a germline or germline reverted bnAb.

17. The vector of claim 6, wherein the viral vector is selected from the group comprising adenoviruses, adeno-associated viruses (AAV), alphaviruses, herpesviruses, retroviruses, and poxviruses.

18. The vector of claim 17, wherein the viral vector is AAV.

* * * * *